United States Patent
Martin et al.

(10) Patent No.: US 12,157,895 B2
(45) Date of Patent: Dec. 3, 2024

(54) ENHANCED DISEASE RESISTANCE IN PLANTS

(71) Applicants: BOYCE THOMPSON INSTITUTE FOR PLANT RESEARCH, INC., Ithaca, NY (US); Cornell University, Ithaca, NY (US)

(72) Inventors: Gregory B. Martin, Ithaca, NY (US); Ari Feder, Haifa (IL); Samantha Mainiero, Ithaca, NY (US); Sarah Hind, Champaign, IL (US); Diana Carolina Mazo Molina, Ithaca, NY (US)

(73) Assignees: BOYCE THOMPSON INSTITUTE FOR PLANT RESEARCH, INC., Ithaca, NY (US); CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 16/916,757

(22) Filed: Jun. 30, 2020

(65) Prior Publication Data
US 2021/0062216 A1   Mar. 4, 2021

Related U.S. Application Data

(60) Provisional application No. 62/894,234, filed on Aug. 30, 2019.

(51) Int. Cl.
| | | |
|---|---|---|
| A01H 5/08 | (2018.01) | |
| A01H 1/00 | (2006.01) | |
| A01H 6/82 | (2018.01) | |
| C12N 15/00 | (2006.01) | |
| C12N 15/74 | (2006.01) | |
| C12N 15/82 | (2006.01) | |
| C12Q 1/6895 | (2018.01) | |

(52) U.S. Cl.
CPC .......... *C12N 15/8279* (2013.01); *A01H 1/00* (2013.01); *A01H 5/08* (2013.01); *A01H 6/82* (2018.05); *A01H 6/825* (2018.05); *C12N 15/00* (2013.01); *C12N 15/74* (2013.01); *C12N 15/82* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 2016/0242376 A1* | 8/2016 | Jiang | A01H 6/825 |
| 2017/0107531 A1* | 4/2017 | Martin | C12N 15/8281 |

OTHER PUBLICATIONS

Kim et al., Genome Biol., 18:R210.1-R210.11, 2017.*
Kim et al., Database UniProt, Acc. No. A0A2G2XAQ7, Genome Biol., 18:R210.1-R210.11, 2017.*
Mazo-Molina et al., "The Ptr1 Locus of Solanum lycopersicoides Confers Resistance to Race 1 Strains of *Pseudomonas syringae* pv. tomato and to Ralstonia pseudosolanacearum by Recognizing the Type III Effectors AvrRpt2 and RipBN," bioRxiv preprint doi: doi.org/10.1101/518399, bioRxiv (posted Jan. 11, 2019).
Mazo-Molina et al., "The Ptr1 Locus of Solanum lycopersicoides Confers Resistance to Race 1 Strains of *Pseudomonas syringae* pv. tomato and to Ralstonia pseudosolanacearum by Recognizing the Type III Effectors AvrRpt2 and RipBN," Mol. Plant-Microbe Interactions 32(8):949-960, doi: apsjournals.apsnet.org/doi/10.1094/ MPMI-01-19-0018-R (published online Jun. 12, 2019).
Mazo-Molina et al., "Ptr1 Evolved Convergently with RPS2 and Mr5 to Mediate Recognition of AvrRpt2 in Diverse *Solanaceous* Species," bioRxiv preprint doi: doi.org/10.1101/2020.03.05. 979484, bioRxiv (posted Mar. 6, 2020).
Mazo-Molina et al., "Ptr1 Evolved Convergently with RPS2 and Mr5 to Mediate Recognition of AvrRpt2 in Diverse *Solanaceous* Species," with Supplemental Information, The Plant Journal 103:1433-1445 (available online May 11, 2020).
Eckshtain-Levi et al., "The Tomato PTO Gene Confers Resistance to Pseudomonas floridensis, an Emergent Plant Pathogen with just Nine Type III Effectors," with supporting information, Plant Pathology 68:977-984 (published online Feb. 27, 2019).
Kim et al., "Using Decoys to Expand the Recognition Specificity of a Plant Disease Resistance Protein," with Supplementary Materials, Science 351(6274):684-687 (2016).
Oh & Martin, "Effector-Triggered Immunity Mediated by the PTO Kinase," Trends Plant Sci. 16(3):132-140 (2011).

(Continued)

*Primary Examiner* — Phuong T Bui
(74) *Attorney, Agent, or Firm* — Troutman Pepper Hamilton Sanders LLP

(57) ABSTRACT

Embodiments of the disclosure are directed to compositions and methods for enhancing disease resistance in plants. One aspect of embodiments of the disclosure relates to a nucleic acid construct comprising a nucleic acid molecule comprising a *Pseudomonas* tomato race 1 (Ptr1) polynucleotide, a 5' heterologous DNA promoter sequence, and a 3' terminator sequence, wherein the nucleic acid molecule, the DNA promoter sequence, and the terminator sequence are operatively coupled to permit transcription of the nucleic acid molecule. Methods of imparting disease resistance to a plant and methods of identifying a candidate plant suitable for breeding that displays enhanced disease resistance are also disclosed. Embodiments of the disclosure also include plant cells, plants, and plant seeds including a heterologous *Pseudomonas* tomato race 1 (Ptr1) polynucleotide.

40 Claims, 65 Drawing Sheets
Specification includes a Sequence Listing.

(56) References Cited

OTHER PUBLICATIONS

Peralta et al., "Nomenclature for Wild and Cultivated Tomatoes," Tomato Genetics Cooperative Report 56: 6-12 (2006).
Bent et al., "RPS2 of Arabidopsis thaliana: A Leucine-Rich Repeat Class of Plant Disease Resistance Genes," Science 265:1856-1860 (1994).

* cited by examiner

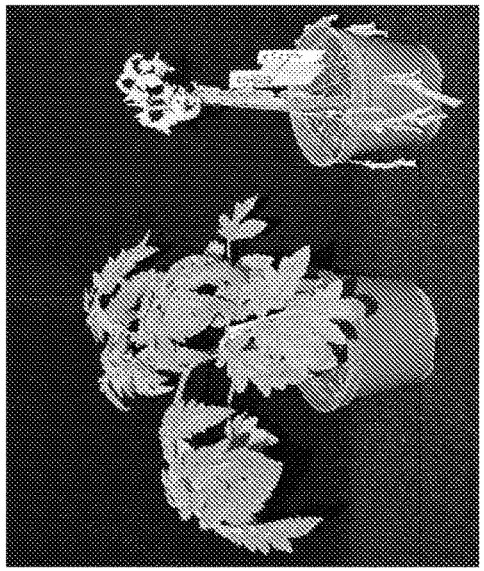
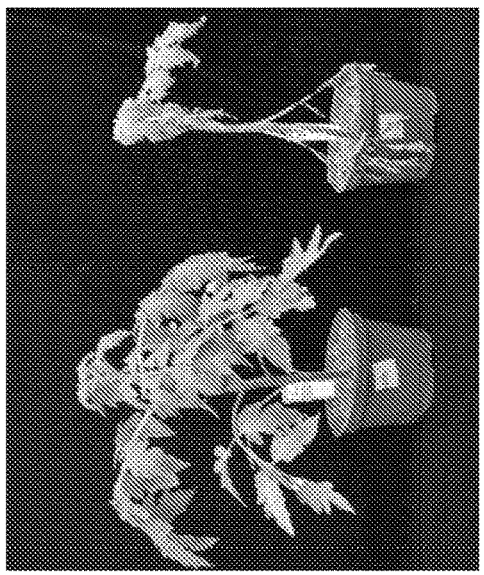
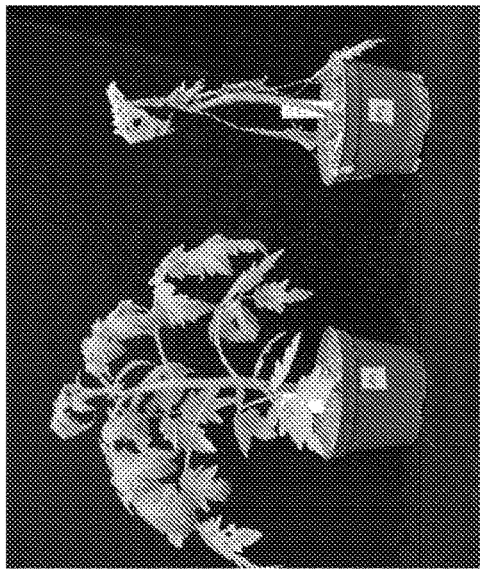
FIG. 5

(a)

(b)

(a)

(b)

| Gene Model | %Similarity to RPS2 | %Similarity to Mr5 | Amino acid | Annotation | | |
|---|---|---|---|---|---|---|
| Solyd04g057440 | 47.8 | 34.7 | 911 | CC | NB-ARC | LRR |
| Solyd04g057510 | 47.3 | 33.9 | 870 |  | NB-ARC | LRR |
| Solyd04g057520 | 47.8 | 34.5 | 908 | CC | NB-ARC | LRR |
| Solyd04g057570 | 52.8 | 56.7 | 452 |  | NB-ARC |  |
| Solyd04g057630 | 49.3 | 44.8 | 718 |  | NB-ARC | LRR |
| Solyd04g057640 | 49.9 | 56.4 | 391 | CC | NB-ARC |  |
| Solyd04g058020 | 43.6 | 39.9 | 655 |  | NB-ARC | LRR |
| Solyd04g059470 | 48.8 | 39.4 | 733 |  | NB-ARC | LRR |
| Solyd04g059610 | 53.8 | 56.4 | 850 | CC | NB-ARC | LRR |
| Solyd04g060430 | 40.6 | 39.3 | 424 | CC | NB-ARC |  |
| Solyd04g060640 | 49.7 | 45.8 | 795 | CC | NB-ARC | LRR |
| Solyd04g061490 | 54.2 | 42.9 | 593 |  | NB-ARC | LRR |
| Solyd04g064750 | 43.4 | 32.4 | 1073 | CC | NB-ARC | LRR |
| Solyd04g067320 | 40.3 | 36.8 | 1159 | TIR | NB-ARC | LRR |
| Solyd04g076500 | 42.7 | 30.7 | 820 |  | NB-ARC | LRR |

CC domains
NB-ARC domain
LRR domain

MAESFLFNIIER**VLAKVSSIAVYEISLAWNVKTELRKLQSTLSTIKAVLLDANEQKA
KNHEVRDWLEKLRDVVYDVDDLMDDLSTQLLLQMHF**QKSFRKKVRRFFSSSNPIIYR
FKIGRKVKEIRELLNEIADDRRNFHFTEHTYVIPAENTSREQTHSFVRASDIIGRDD
DQENIVKQLIDSHDEENISVIPIVGLGGLGKTTLVKLVYNNNRVVQNFDLRMWVSIS
EDFSLSKVIEKILRSATGESFDHLDMDQLQCCLGEVLQQKRYLLVLDDVWNEDQHKW
TDLRELLMNCSRGSKIVVTTRSKMVALITGTVPPYYLGGLANDDCLSLFLKCAFGGQ
DNLFPNLVEIGKEIVKKCGGVPLAVKTLGRLLYMKTDENEWLQIRDNEIWEIEQNKS
DILPILRLSYEQMPSHLRQCFAYCSMLPKGQEIPREDFINRWIAQGFIQSSNRNRKL
EDIGNQYFDELLSRFCFLDVVQAFDGEILACKIHNLVHDLAQSVSGAECLNVKPNAF
VVSERVRHLFFHAEDMSRKHFPRFLLPLQKLRSFSYSFNIGPVNKFFVKTMLSNFKC
LRMLVLNNLDLEELPTSIGHLKELRYLNLSDSGKIKFLPRSMSKLVNLHTLNLINCE
QLKELPRDFRKLISLKTLYLTTHQMSAGIKNQHSFTSLQFLLLFKCCFPKLQPELVQ
HFTALRVLRIYECPSLCSLPSSIRYLTSLEKLWIWNCEELDLIDGEGMSGLTSLQSL
LLMGLPKLVTLPLELKDTAPTTLKYFRIADCPNLVELPEWLPNCSSLQRLYIEDCPV
LASIPQGIYSHNANVHIIDCPLLGG*

FIG. 16

| Gene | Solyc Identifier | Amino acids | Predicted protein mass (kD) | % Similarity to AtRIN4 | PTI | | | | ETI | | | |
|---|---|---|---|---|---|---|---|---|---|---|---|---|
| | | | | | flgII-28 6 hr | mock 6 hr | ratio | p value (FDR) | RG-PtoR DC3000 6 hr | RG-prf3 DC3000 6 hr | ratio | p value (FDR) |
| Rin4-1 | Solyc09g059430 | 254 | 28.5 | 64.1 | 31.3 | 5.5 | 5.7 | 6.73E-19 | 25 | 14.7 | 1.7 | 0.0015 |
| Rin4-2 | Solyc06g083390 | 243 | 26.8 | 60.1 | 95.9 | 34.6 | 2.77 | 4.25E-08 | 90.5 | 27.9 | 3.2 | 6.68E-17 |
| Rin4-3 | Solyc12g098440 | 313 | 34.4 | 50.2 | 49.5 | 46.5 | 1.06 | 1 | 45.8 | 55.6 | 0.8 | 0.8179 |
| Rin4-4 | Solyc11g012010 | 224 | 24.8 | 59.7 | 0 | 0 | NA | NA | 0 | 0 | NA | NA |

NB-ARC: P-loop
Ptr1:      VGLGGLGKTTLVKL
Consensus: VGMGGIGKTTLAKK

NB-ARC: kinase 2
Ptr1:      QQKRYLLVLDDVWNEDQ
Consensus: KGKRYLIVLDDVWDTDQ

NB-ARC: kinase 3a
Ptr1:      SKIVVTTRSKMV
Consensus: SRIIxTTRDxxV

----- CC domain
───── NB-ARC
----- LRR domain

NB-ARC: GLPL
Ptr1:      VKKCGGVPLAVKT
Consensus: VKKCKGLPLALKV

NBR-ARC: MHD
Ptr1:      NLVHDLAQ
Consensus: CRMHDLIR

Leucine-rich repeats:
LRMLV.LNNLDLEEL
LRYLN.LSDSGKIKL
LVNLHTLN.LI
LKELPRDFR
LISLKTLY.L
LQFLL.LFK
LQPELVQHFTALRVL
LCSLPSSIR
LTSLEKLWIWNCEELDL
LTSLQSLLLMGLPK
LVTLP.LELKDTAPTTL
LVELPE.WLPN
LQRLYIEDCPVL

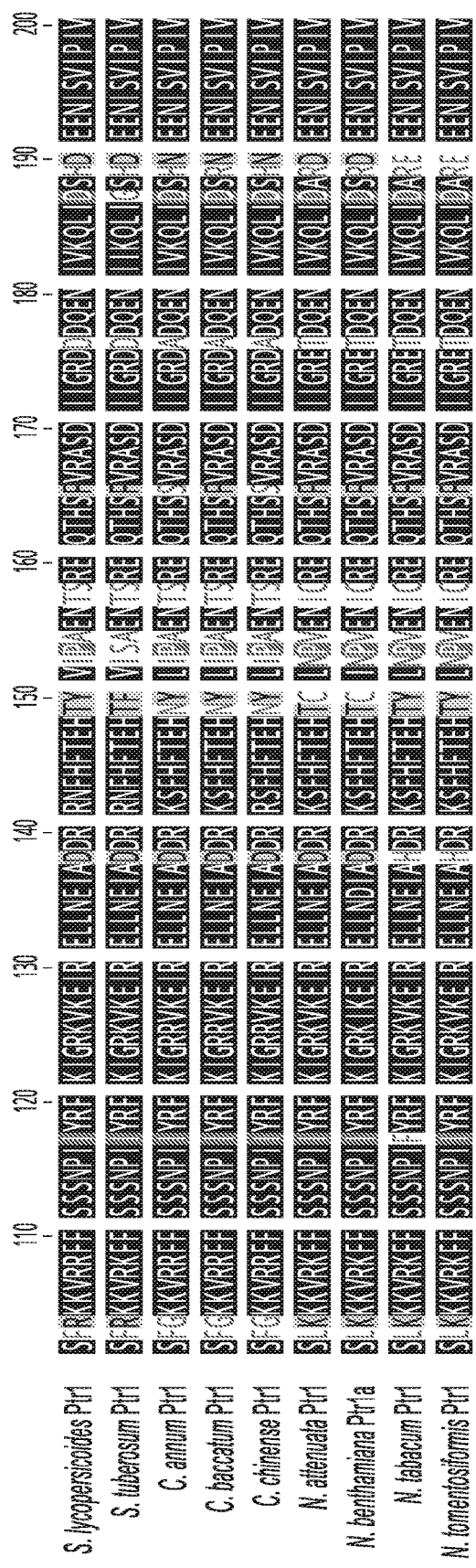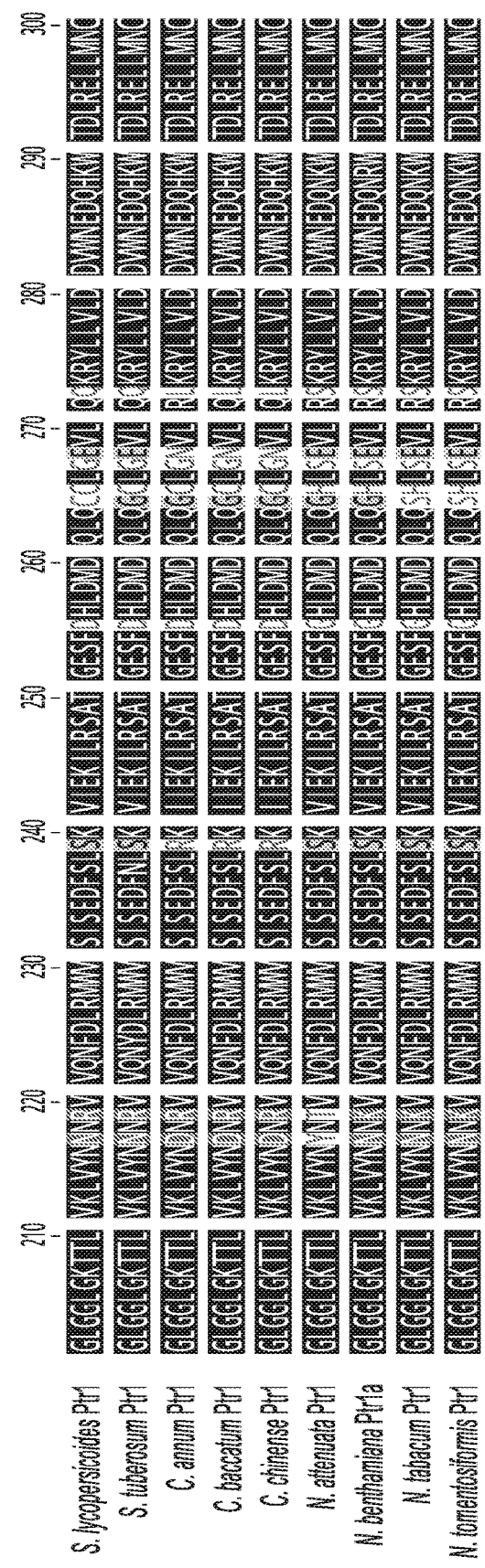
FIG. 29B (cont.)

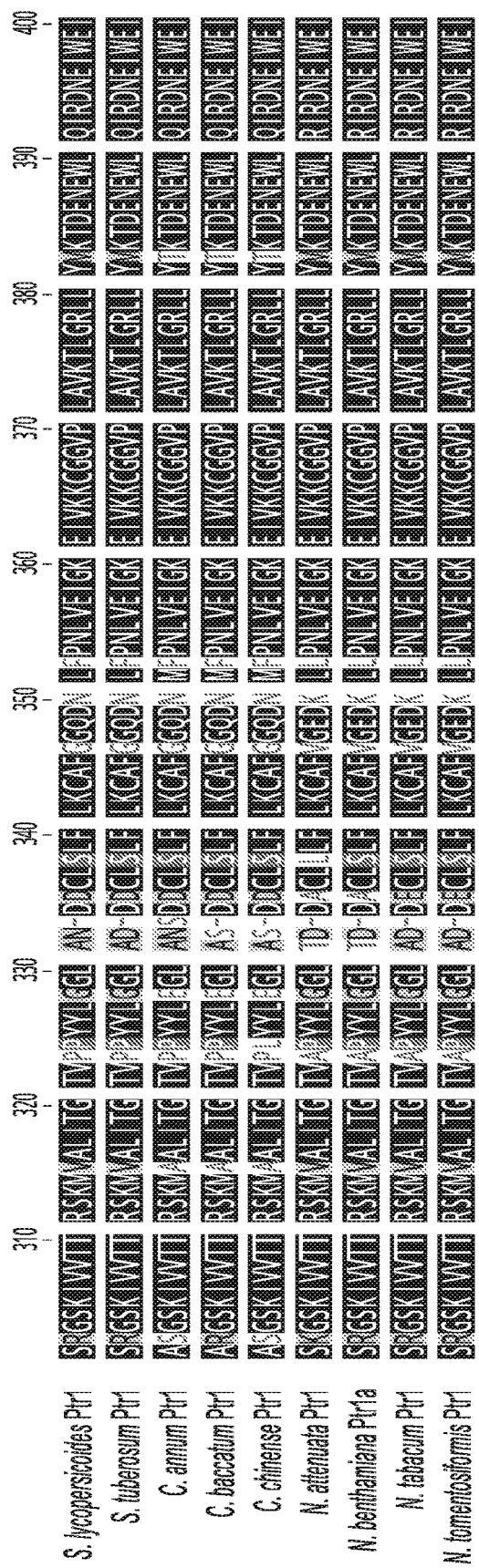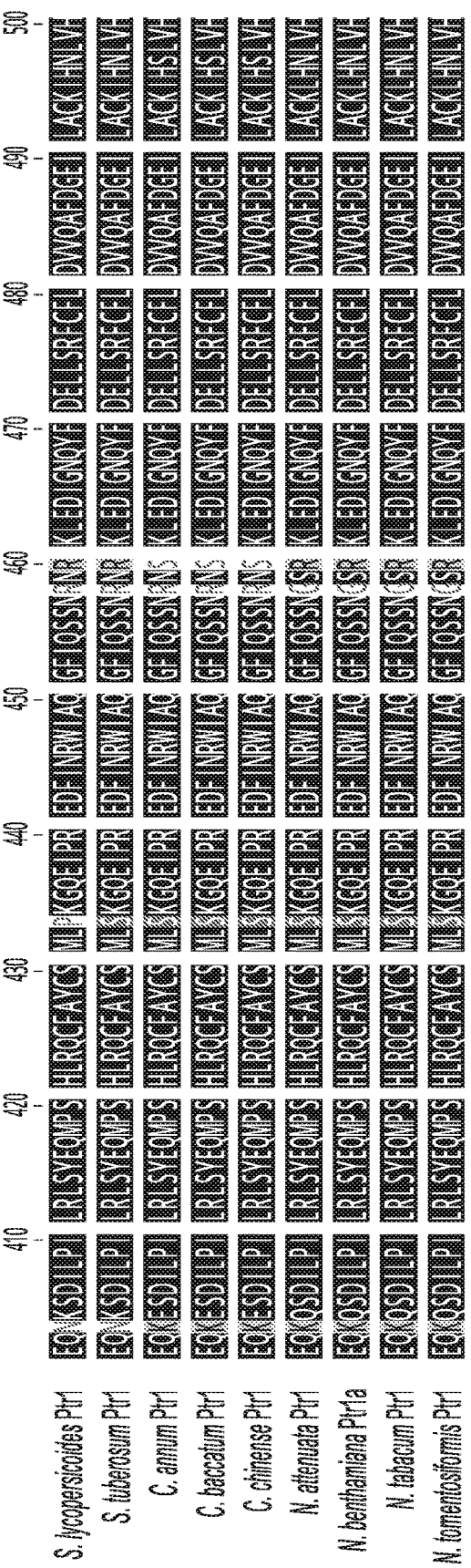
FIG. 29B (cont.)
FIG. 29C

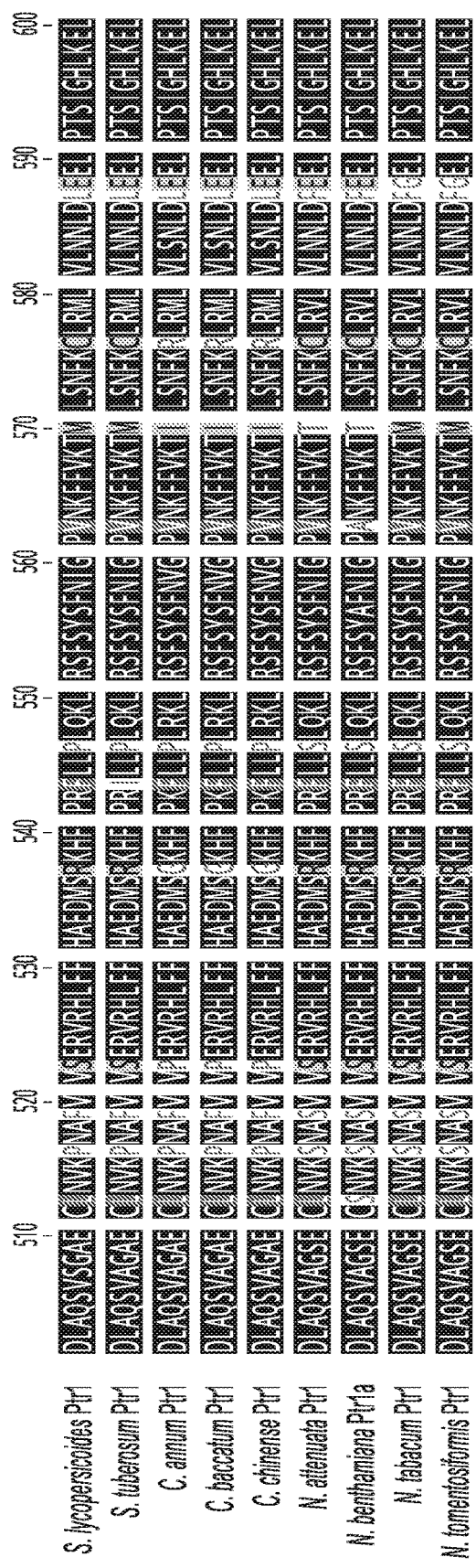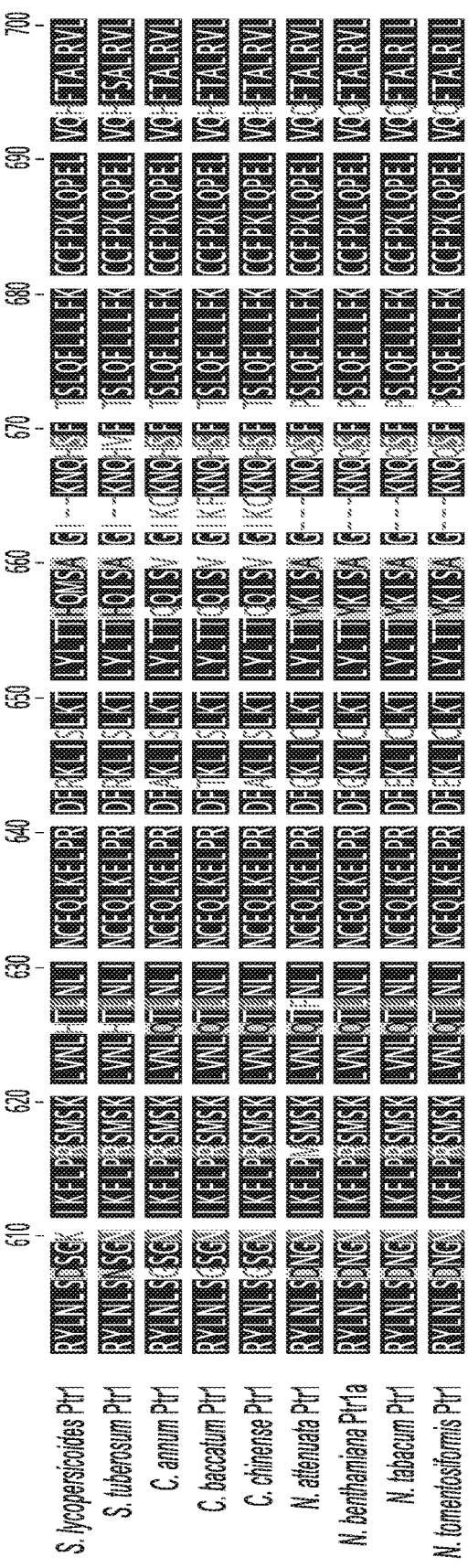
FIG. 29C (cont.)

```
                    P. syringae pv. sesami ICMP763
                    P. syringae pv. sesami HC 1
                    P. syringae pv. sesami ICMP3386
                    P. syringae pv. sesami ICMP4995
                    Pseudomonas amygdali 1
                    P. syringae pv. papulans
                    Pseudomonas syringae 8
                    P. syringae pv. sesami ICMP7459
                    P. syringae pv. castaneae ICMP9421
                    P. syringae pv. castaneae ICMP9420
                    P. syringae pv. castaneae ICMP9419
                99  Pseudomonas syringae 6
                    Pseudomonas syringae 3
                    Pseudomonas amygdali 2
                    P. syringae pv. persicae ICMP5786
           85       P. syringae pv. persicae ICMP3706
                    P. syringae pv. morsprunorum ICMP3897
                    P. syringae pv. tremae ICMP9151
                    Pseudomonas syringae 5
                99  P. syringae pv. zizaniae ICMP8959
```

FIG. 36

```
                    ┌─ Pseudomonas coronafaciens
                 96─┤
                    └─ P. syringae pv. zizaniae ICMP8921
              ┌─────┤
              │  95 ┌─ Pseudomonas syringae 7
              │     └─ P. syringae pv. coriandricola
              │
              │     ┌─ Pseudomonas caricapapayae
              │  95 └─ P. syringae pv. caricapapayae ICMP7496
        ──────┤
              │     ┌─ P. syringae pv. lachrymans 1188 1
              │     │
              │     ├─ Pseudomonas syringae 4
              │     ├─ Pseudomonas syringae 2
              │     ├─ Pseudomonas syringae 1
              │     ├─ P. syringae pv. tomato T1  *
              │     ├─ P. syringae pv. tomato NYS-T1  *
              │     ├─ P. syringae pv. tomato NY15125  *
              │     ├─ P. syringae pv. tomato K40
              │  99 ├─ P. syringae pv. tomato JL1065  *
              └─────┤
                    ├─ P. syringae pv. tomato ICMP7230
                    ├─ P. syringae pv. tomato ICMP4263
                    ├─ P. syringae pv. tomato 1108
                    ├─ P. syringae pv. tagetis ICMP4092
                    ├─ P. syringae pv. spinaceae ICMP16929
                    ├─ P. syringae pv. spinaceae ICMP16928
                    └─ P. syringae pv. maculicola M4a
```

FIG. 36 (cont.)

SEQUENCE LISTING

<160> NUMBER OF SEQ ID NOS: 132

<210> SEQ ID NO 1
<211> LENGTH: 2736
<212> TYPE: DNA
<213> ORGANISM: Solanum lycopersicoides

<400> SEQUENCE: 1

```
atggaggcta caatcgttgc agcgttgagt ccggcggcga caaaagcggt aagctttctg      60
gtggacagtc tatcgcagtt actatcggaa aatgtggaac tgataagagg tgcagataga     120
gatttccagc aattactgga tgaaattaca cccataaatg agttactatc tggagattat     180
gcacaattga aaagcaacaa caacaacgat ttggataaat tgttccagaa tattcaacga     240
acagtatata aagctgaaga tgcgatcgat aaattcctaa ttcaggcgaa aattaacgaa     300
gctaacgtgt tcaataagtt cggtccgttt gtcaagtgga acaacaatag gaaaattaca     360
ccggaattca gaaaaattct cgaacaagtg actgaaattc gccaacagac tcaacaggtt     420
ttggagaaaa ccggtataca gagttctgct ttccagcctg gagaaactac ccggccacag     480
ggtcctgctg aggaggatag cgaagtggtt ggttttaata agcctgcaga agatgtgaaa     540
```

-continued

```
aagcgacttt gtgaaggatc aaaagatctt gatgttatac ctattgtggg tatgccagga     600
cttggaaaga ccacactttc aagaaaagtt tacaatgatt cttccattga ttttttatttt   660
taccataaaa tgtggattta tgttgggaca tcaaagaaac caaaggatat tcttgttgag   720
attgtgaaag atgtcgcgca aagcaatagt aaggaactaa ttaaagacaa ggatgaggac   780
caattagctc atatcatacg tgattttctt gttaaaagag gtaaacatct cattgtcttg   840
gatgatgtgt gggacacaca agttgtagat tttgtcaaga aagctttccc aaacaacaaa   900
tcctggcccc gagggacag aatcatgttg acaactcgcc aacgacgtgt ggctgaagct    960
gtcagcgctc gtcctcacta tctggaaaac ttgtcaaaag aggatagtat aaagttgttg  1020
gaacagagag ttttgccaa taaaaggaca tgtcctattg agttagaagg atatcgagat  1080
gggattgtag ataaatgttg tggtgtacca cttgccatag tggtgatttc aggagctttg  1140
agaggtgtta tggacgaaag tgaatggaga gtagtcgagg aaaatgtggg gaagcacctt  1200
ataaacaagg acgaccataa aagctgcttg aaatttgttg aaacgagtta caatcatttg  1260
ctgcaagaga aaaaggcagc cttcttgtat tttggagtat ttcctcaagg ttttgatatt  1320
cctgcttgga accttattcg cttatgggtt gctgaggggc taataaagtc cgatcataaa  1380
gacagtgaaa tcgagaaggt tgcggagact tacttgagcg actttgctag taggaattta  1440
gtgatggtga tgcaaaagag atcaacggt caaatcaaaa cgtgtcgtct tcatgacatg    1500
ttgcatgagt tctgcattat tgaggctcaa aggataagtc tctttcaaca agtatatctc  1560
caacctggtg ttcgagtttt tccttctata gaagatccaa ataattctcg tcgattatgt  1620
attcaatcct ctattccgta taattttatc cctaaagata gaattgtaca gcacgttagg  1680
tctctcttat gtttttcctc agaccaaaag caaattgact tgtctaatct agatgtccaa  1740
ctcatcccca atgcctttcc actcatcagg gtgttggaca ttcaatccct catatttgaa  1800
ttctccaaga tgttttatgg tctatttcac ttgaggtata ttgccatcaa gggcgacttc  1860
actgtcattc cttcactctt tcgtaatttt tggtatttac aaacccttat acttcgtaat  1920
gatgatacac atacttcaag atccaccctc gagataaaag aggacatatg gaaactgtta  1980
caattgagac atctgcactc cgaccttcat gtgaaattgc ctcctcctcc taccccaaca  2040
agcaatagtc gtacttcttg tctacaaact cttttctaagg ttacaccaga tagttgcaaa  2100
aaaactgtgt ttgcaaaggc ttgtcatctc aaaaaattgg gtattgaagg gcaattggca  2160
cttcttcttg gaaaatctac caagggacgt ggattcgaca gtttccaaga gctaaggtgc  2220
gtcgaaaaat tgaaattgtt gaacaatgat tttagtgaag agcttcacct tcctccacac  2280
tttttcagct tacaaaaaac gctgaacaag ttaactttgt caagtacaag gtttgagtgg  2340
agtgaggcag atatgttggg gaagttggaa tgccttaagg tactaaaatt gaaatataat  2400
gcattcatag ggaagaattg gaagcccaag aaaggaagtt ttagcaagct ccaagtcctg  2460
cacattgtct gggcaggaga ctggcaaact tgggatgcat caaatcgtcc gttccaaagt  2520
cttacacacc ttgttcttat ttcctgtaat catctcaagg ctgtgccaca tgagctggct  2580
gatttacctt atcttcaaga gatgaagctg acgcgcacat acgacgcagt cagttctgcc  2640
atagaaatca aaagaaagat actacaaagg caagatcccg aaagcaacat caaattcaat  2700
ctcattacat ttccccctac ctcgtccaca aattaa                             2736
```

<210> SEQ ID NO 2
<211> LENGTH: 2613
<212> TYPE: DNA

<213> ORGANISM: Solanum lycopersicoides

<400> SEQUENCE: 2

```
atggcggcta cttacggtgc actaacttct gtgttgggaa ccatagagaa ggttttacgg      60
tccaaccata gagaatatgg ttggaccgta aaattgaaat cactgtatgg gttgtttgac     120
actctaattg tgaaatgtga tgtcggagaa gcaattatta gcaaggattt gctaagaaga     180
atcaaagatg ttgcagttta tgcagaagat gaagttgaat cactaatgaa acaacttatt     240
attattggga tgaatgatga atgttgtggt gcgaagcttg ataaagtctc tcaacaggta     300
atacaagtaa ctcattcagt caacaatatt aattgtccaa aaaagttgt ttctccacga      360
ttagatgatg attcaatcca tgagaacttt atggaagggt acaatgaaga aagagtaaat     420
atggttcaaa gacttaccaa aggatcaaat agactgcaag tggtttctgt tgtggggatg     480
gcgggcatag gtaagacaac ttttgccaaa actacattat tacatattaa caaggaggac     540
tttcctattc gtggttggat tacggtgtct aaaaactatg atttaagaaa gttgctccta     600
ctcctccttc atgatgttat tgaaatgaaa ggtaagaatt ttgatggaat ggataatgga     660
caactagctg ctcatctaaa gcaagttttg cagggaaaaa ggtatttgat tgttgtggat     720
gacatatgga gcaaagaaga ttgggatgaa attaaacatt ggtttccaga ttgtggtgac     780
aaaagtcgaa ttttgttgac ttctcgagac aaagaggttg gtgagtatgc tgctaaagaa     840
ggtttggtac tgatgcgtcc tctgacgcaa gatgaaagtc ggaatctgtt ttaccatagg     900
gcatttggga aaaattacac tattcgaggg tcagatattg atgaattcga aaaggttgga     960
gaaaaagtta taacaaattg caaaggatta ccactaatga ttactgcagt tgctggtata    1020
ctccgtagta agagtaaact ggatgagtgg atggaagtag ctcaaagtgt aagctcatta    1080
gtaaatgatg atgattacaa acaatgctta caagttgttg cttttgagcta caataatctt    1140
ccttctctaa tgaaagcttg ctttttgcat ttcggagttt ttccaaaagc ccatgtcatt    1200
tctgtgaaga agttgatcag attatggatt gcagaaggac tcgtaaatct aaagggagtt    1260
gaggaattcg aacaagcagc tgatcgtgtt ttacatgatc ttattggtaa aagtgtagtt    1320
attgttgaca gcgaagttt ggatgggaaa attaagacat gtaggattca tgatcttttt     1380
catgatttct gctccaagga agctgaaagc gagaatcttc tgtatgttgt tggttcagat    1440
tctcaagtac acacaaattt ccgtcaaggt tgtaggtggg tgtcagttca atcaaaactt    1500
gattatcgtc accgcagacg gtatactcct attgaaatat cctcttttta catgctatat    1560
aatattgtta tttttgacaa aaaagttttt catttcaaac tactaagggt attggacttg    1620
gaggtacatg atatcatagg actcagtgaa attactagag accttgtttg tttaaggtat    1680
ttggctgtcg ggattaagta tgtaagtttt gtggatctcc cgattaccaa tctttggaat    1740
ctacacactc tcattttagg taaatctttc actaatagtc ttatacataa agtcttcagt    1800
tttccaaaag atatttggca aatgtcacaa ttaaggcatc tttatgcaaa aggcattat      1860
ctatcttcgc ctggagaaaa ggttctcgaa aacttacaga gtgtttctgg tttgagtcct    1920
tcttgttgta caaggaaat atttgaaggg attaagaatg tgaaaaaatt gatcattcgt     1980
ggaaagaggg aggattatcc tacagatatt aaatggatag ataatcttaa atatttgcaa    2040
catctcgagt cactgagtat tgaaactacc gattttctat ttcataagaa taaaaccagg    2100
ttttttagtc ttacaagtcc agattctttt ccacaaaaac tcaagaaatt gaaacttagc    2160
tacacatatc taccgtggga atacatgtcc attatcagca gttgcccga acttgaggta     2220
ctcaaactga agtgtggttc cttaattggc gacgagtgga aagcaacaga ccagattggg    2280
```

```
ttcccgaagt tgaggttctt gctccttgag aatctcttcc ttggaaaatg ggaaaccacc    2340
acgggctctc atgatcattt ccccagcctt gagcgcttaa ttatcacaaa tttcagtttc    2400
ttaaaagaga ttcctcaagg atttgctgat agcaagaaac tggagctgat tgagttacac    2460
aattgtgacc cttccttggt ggcttttgct aagcagatac aggttgaaca cgaggatttg    2520
gggaggaaca aacttaaagt tactgccttc gatacaggtc gaggatggaa cagaggaatc    2580
ttagcttcaa gaaataacag gatttccagc taa                                 2613

<210> SEQ ID NO 3
<211> LENGTH: 2727
<212> TYPE: DNA
<213> ORGANISM: Solanum lycopersicoides

<400> SEQUENCE: 3
atggaggcta caatcgttgc agcggtgagt ccggcggcga caaaagcggt aagctttctg      60
gtggacagtc tatcgcagct actatcggaa aatgtggaac tgataagagg tgcagataga     120
gatttccagc gattactgga tgaaattaaa cccataaatg agttactagc tggagattat     180
gcacaattga aaagcaacaa caacaacgat ttggataaat tgttccagaa tattcaacga     240
acagtatata agctgaaga tgcgatcgat aaattcctaa ttcaggctaa aattgacgaa      300
gctaacctgt tcaataagtt cggtccgttc gtcaagtgga caacaatcg gaaaattgca      360 ccggaattcg agaaaatttt aaaacaagtg gccggaattc gccaacagac tcaacaggtt     420
ttggacaaaa ccgtatacag gagttctgct ttccagcctg gagaaactac ggggacacag     480
ggtcctgctg aggaggatat cgaagtggtt ggttttaata gcctgcaga agatgtgaaa      540 aagcgactct gtgaaggatc aaaggatgtt gatgttatac ctattgtggg tatgccagga     600
cttggaaaga ccactctgtc aagaaaagtt tacaatgatt gttcccttga ttttattttt      660
taccataaaa tgtggattta tgttgggaca tcaaagaaac caaggatat tcttattgag       720 attgtgaaag aagtcgcgca aagcaatagt aaggaactaa ttatagacaa ggatgaggac     780
caattagctc atatcatacg tggttttctt gttgaaagag gtaaacatct cattgtcttg     840
gatgatgtgt gggacacaca agttgtagat tttgtcaaga aagctttccc aaacaacaaa     900
tcccggcccc gaggggacag aatcatgttg acaactcgcc aacgacgtgt ggctgaagct     960
gtcagcgctc gtcctcacta tctagaaaac ttgtcaaaaa aggatagtat aaagttgttg    1020
gaacagagag tttttgccga taaaaggaca tgtcctattg agttagaagt atatcgagat    1080
gggattgtag ataaatgttg tggtgtacca cttgccatag tggtgatttc aggagctttg    1140
agaggttgta tgggtgtggg agtagtgcaa gaaaatatgg ggaagcacct tataaacaag    1200
gacgaccata aaagctgctt gaaatttgtt gaaacgagtt acaatcattt gccgcaagag    1260
aaaaaggcag ccttcttgta ttttggagta tttcctcaag gttttgatat tcctgcttgg    1320
aaccttattc gctatgggt tgctgagggg ctaataaagt ccagtcataa agacagtgaa     1380
atcgagaagg ttgcggagac ttacttgagc gactttgcta gtaggaattt agtgatggtg    1440
atgcaaaaga gatctaacgg tcaaatcaaa acgtgtcgtc tccatgacat gttgcatgag    1500
ttctgcatta ttgaggctca aaggataagt ctctttcaac aagtatatct ccaacctggt    1560
gttcgagttt tccttctat agaagatcca aatacttctc gccgattatg tattcaatcc    1620
tctattccgt ataattttat cactaaagat agaattgtac agcatgttag gtctctctta    1680 tgttttttcct cagaccaaaa gcaaattgac ttgtctaatc tagatgtcca acttatcccc    1740
```

-continued

```
aatgcctttc cactcatcag ggtgttggac attcaatccc tcatatttga attctccaag   1800
atgttttatg gtctatttca cttgaggtat attgccatca aaggcgactt cactgtcatt   1860
ccttcactct ttcgtaattt ttggtattta caaaccctta tacttcgtaa tgatgataca   1920
catacttcaa gctccaccct tgagataaaa gaggacatat ggaaactgtt acaattgaga   1980
catctgcact ccgaccttcc tgtgaaattg cctccccctc ctaccccaac aagcgagagt   2040
cgtacttctt gtctacaaac tctttctaag gttacgccag atagttgcaa aaaaactgtg   2100
tttgcaaagg cttgtcatct caaaaaattg ggtattgaag ggcaattggc acttcttctt   2160
ggaaaatcta ccaagggaag tggattcgac agtttccaag agctaaggtg cgtcgaaaaa   2220
ttgaaattgt tgaacaatga ttttagtgaa gagcttcacc ttcctccaca ctttttcagc   2280
ttacaaaaaa cactgaacaa gttaactttg tcaagtacaa ggtttgagtg gagtgaggca   2340
gatatgttgg ggaagttgga atgccttaag gtactaaaat tgaaagataa tgcattcata   2400
gggaagaatt ggaagcccaa gaaaggaagt tttagcaagc tccaagtcct gcacattgtc   2460
tgggcaggag actggcaaac ttgggatgca tcaaatcgtc cgttcctaag tcttacacac   2520
cttgttctta tttcctgtta tgatctcaag gctgtgccac acgagctggc tgatttacct   2580
tatcttcaag agatgaagct gacgcgcaca ttccaggcag tcagttctgc catagaaatc   2640
aaaagaaaga tactacaaag gcaagatccc gaaagcagca tcaaattcaa tctcattaca   2700
tttcccccta actcgtccac aaattaa                                       2727
```

<210> SEQ ID NO 4
<211> LENGTH: 1359
<212> TYPE: DNA
<213> ORGANISM: Solanum lycopersicoides

<400> SEQUENCE: 4

```
atggcggcta cttacggtgc actaacttct gtgttgggaa ccatagagaa ggttttacgg     60
tccaaccata gagaatgtgg ttggaccgta aaattgaaat cactgtatga gttatttgac    120
actctacttg gcaaatgtga tgtcggagaa gcaattatta gcaaggattt gctaagaaga    180
atcaaagatg ttgcagttta tgcagaagat gaagttgaat cactaatgaa acaacttatt    240
gttattgggc tgaatgatga atgttgtggt gcgaagcttg ataaagtctc tcaacaggta    300
atacaagtaa ctcattatgt caacaatatt aattgtccaa aaaaaattgt ttctccacga    360
ttagatgatg attcaatcta tgagaacttt atggaagggt acaatgaaga aagagtaaat    420
atggttcaaa gacttaccaa aggatcaaat agactgcaag tggtttctgt tgtggggatg    480
gcgggcatag gtaagacaac ttttgccaaa actatattat ttcatgacca tcttaagaag    540
gaggactttc ctattcgtgg ttggattact gtgtctaaca actatgattt aagaaagttg    600
ctcctactcc tccttcacga tgttattgaa atgaaaggca agaattttga tgaaatggat    660
aatggagaac tatctggtca cgtaaagcaa ggtttgcagg gaaaaaggta tttgattgtt    720
gtggatgaca tatggagcaa taaagattgg gatagtatta aacatttgtt tccagatttt    780
ggtgacagaa gtcgaatttt gttgacttct cgagacaggg aggttggtga gtatgctgct    840
accaatccta aagatggttt ggtactgatg cgtcctctga cgcaagatga aagtcggaat    900
ctgttttacc atagggtatt tgggaaaaat tacactattc gagggtcaga tattgatgaa    960
ttcaaaaagg ttggagaaaa ggttataaca aattgcaaag gattaccact aatgattact   1020
gcagttgctg gtatactccg tagtaagagt aaactggatg agtggatgga agtagctcaa   1080
agtgtaagct cattagtaaa tgatgatgat tacaaacaat gcttacaagt tgttgctttg   1140
```

```
agctacaata atgttccttc tcttatgaaa gcttgctttt tgcatttcgg agtttttcca    1200
aaagcccatg tcatttctgt gaagaagttg atcagattat ggattgcaga aggactcgta    1260
aatctaaagg gagttgagga attcgaacaa gcagctgatc gtgttttaca tgatcttatt    1320
ggtaaaagtg tagttattgt tgacagctgt catgactga                          1359

<210> SEQ ID NO 5
<211> LENGTH: 2157
<212> TYPE: DNA
<213> ORGANISM: Solanum lycopersicoides

<400> SEQUENCE: 5
atggaagggt acaatgaaga aagagtaaat atggttcaaa gacttaccaa aggatcaaat      60
aaactgcaag tggtttctgt tgtggggatg gcgggcatag ttaagacaac ttttgtcaaa     120
actatattat tacatattaa caaggaggac tttcctattc gtggtaggat tactgtgtct     180
aaaaactatg atttaagaaa gttgctccaa ctcctcctcc atgatgttat tgaaatgaaa     240
ggtaagaatt ttgatggaat ggatactgga aaaaggtatt tgattgttgt ggatgacata     300
tggagcaaaa aagattggga tgaaattaaa cattggtttc agattgtgtg tgacagaagt     360
cgaattttgt tgacttctcg agacagggag gttggtgagt atgctgctaa agatggtttg     420
gtaccgatgc gtcctctgac gcaagatgaa agtcggaatc tgttttacca tagggcattt     480
gggaaaaatt acactattcg agggtcagat attgatgaat tcgaaaaggt tggagaaaaa     540
gttataacaa attgcaaagg attaccacta atgattactg cagttgctgg tatactccgt     600
agtaagagta aactggatga gtggatggaa gtagctcaaa gtgtaagctc attagtaaat     660
gatgatgatt acaaacaatg cttacaagtt gttgctttga gctacaataa tcttccttct     720
ctaatgaaag cttgcttttt gcatttcgga gttttccaa aagcccatgt catttctgtg     780
aagaagttga tcagattatg gattgcagaa ggactcgtaa atctaaaggg agttgaggaa     840
ttcgaacaag cagctgatcg tgttttacat gatcttattg gtaaaagtgt agttattgtt     900
gacaagcgaa gtttggatgg gaaaattaag acatgtagga ttcatgatct tttttcatgat    960 ttctgctcca aggaagctga aagcgagaat cttctgtatg ttgttggttc agattctcaa    1020
gtacacacaa atttccgtca aggttgtagg tgggtgtcag ttcaatcaaa acttgattat    1080
cgtcaccgca gacggtatac tcctattgaa atatcctctt tttacatgct atataatatt    1140
gttattttgt acaaaaaagt ttttcatttc aaactactaa gggtattgga cttggaggta    1200
catgatatca taggaatcag tgaaattact agagaccttg tttgtttaag gtatttggct    1260
gtcgggatta agtatgtaga ttttgtggat ctcccaatta ccaatctttg gaatctacac    1320 actctccattt taggtaaata tttattcat aatagtctta tgcataaagt cttcactttt    1380
ccaaaagata tttggcaaat gtcacaatta aggcatcttt atgcaaaagg cattcatcta    1440
tgttcgcctg gagataataa ggttctcgaa aacttactga gtgtttctgg tttgagtcct    1500
tcttgttgta caaaggaaat atttgaaggg attaagaaag tgaaaaaatt ggtcattcgt    1560
ggaacgaggg aggaatgtcc tacagatgtt aaatggatag ataatcttaa atatttgcaa    1620
catctcgagt cactaagtat tgaaaatatc aaatttatat ttcatgagaa tgaaaccagg    1680
ttttttagtc ttacaagtcc agattctttt ccacaaaaac tcaagaagtt gaaacttagc    1740
tacacatatc taccgtggga atacatgtcc attatcagca gttgcccgaa cttgaggta     1800 ctcaaactga agcgtagttc cttaattggc aacgagtgga aagcaacaga acagattggg    1860
```

```
ttcccgaagt tgaggttctt gctccttgag aatctcttcc ttagaaaatg ggaaagcacc    1920
acgggctatc atgatcattt ccccagcctt gagcgcttaa ttatcacaaa tttcaaattc    1980
ttaaaagaga ttcctcaagg atttgctgat agcaagaaac tggagctgat tgagttacac    2040
aattgtgacc cttccttggt ggattttgct aagaaggtgc agcttgaaca cgaggaggtt    2100
ttggggagga acaaacttaa agttactgcc ttcaatacag gtaaatatat ctattag       2157

<210> SEQ ID NO 6
<211> LENGTH: 1176
<212> TYPE: DNA
<213> ORGANISM: Solanum lycopersicoides

<400> SEQUENCE: 6
atggccgcta cttacgctgc actaacttct gtgttgggaa ccatagacaa gcttttacgg      60
tccaacttat tagttggcgt agaagaggtt cataagcaac aattagaatc actcgacaag     120
atgtttggca ctctgcaagt gtctctaatt ggcaaatgtg atggcgaaga agcaattatt     180
agcaaggatt tgcaaagaag aatcaaagat gttgcagttg atgcagaaga tgaagttgaa     240
tcactaatga dacaacttat tattattgag ctgatgatg aatgttgtgg tgcgaagctt     300
gataaagtct ctcaacaggt tatacaagta actcattctg tcaatgaaga gctgatcatc     360
atcaacaata ttaattgtcc agaaaaagct gatgaaaata gtgcttcttc tccacgatta     420
ggtgattcaa tccgtgagaa cgttatggaa gggtacaatg aagaaagaga aggatggtg     480 caaagactta ccaggggctc aggatcaaat agacgggaag tggtctctgt tgtggggatg     540
ccgggcatag gtaagacaac ttttgccaaa actatattat tcgataactc tatcaagagg     600
gtctttcgta ttcgtggttg gattactgtg tctaacaagt atgatttaaa aaagttgctt     660
ctactgctcc ttcatgatgt tattgaaatg aaaggcagca ataattatga tgaaatggat     720
attggacaac tatctggtca cgtaaagcaa ggtttgcagg gacaaaggta tttgattgtt     780
gtggatgaca tatggagcaa taagattgg gatacaattt cacattggtt tccagattgt     840
ggtgacagaa gtcgaatttt gttgacttct cgagactaca aggttggtga gtatgctgca     900
accaatccta aagatggttt ggtactgatg cgtcctctga cgcaagatga aagtcggaat     960
ctgttttacc ataggggcatt tgggaaaaat tacagtattc gagggtcaga tattgatgaa    1020
ttcgagaaag ttggagaaaa agttataaca aattgcaaag gattaccact aatgattact    1080
gcggttgctg gtatactctg tagcaagagt aaactggatg agtggatgga aatagctcaa    1140
agtgtaagct cattagtaaa tgatgatgct tactaa                              1176

<210> SEQ ID NO 7
<211> LENGTH: 1968
<212> TYPE: DNA
<213> ORGANISM: Solanum lycopersicoides

<400> SEQUENCE: 7
atgctgtatg cgacaacaga tgaacggaaa atgaagcatt tcaagattca agtacttgag      60
ggtgttagat ttacgccatt caagattcta ttagcatcta agataggatg ttatggaggc     120
acggattatg atagagggtt agtcgaaaga tatggtacat tgagtcatga ggcagctgag     180
atgcttaaac ttgcttgtta tgatgctgaa caagtcattg acaaggacgt tgatagagat     240
accgttatcg aagcactttt aaaatcagga aatgaagcaa ccctttttgt atatcccatt     300
gttggagttg aaggcattgg aaaaactact cttgccaaat tggtgtataa tgatccaagg     360
atagttagtc agtttcagct gcgtatatgg gttcgtgtgt ctcgtgtgtt taaagtagag     420
```

```
gaagtattag aacaaattgt gaattcagtt agagaagatt tatgtgagaa acttgatatg        480
aatgagctga agaatctagt tcatgagact ttgtatggaa agaattattt gattgtgtta        540
gatgatgtgt ggaatgagga cccagtgaag tgggatgaac ttaagaagtt gttgatggta        600
ggtggttgtg gaagtaagat tcttgtaact actcggaaaa aggaagtagc ttcgataatg        660
gggacggttc ctgcatactg tttggagggt tgttccatg aagatagtct gactttgttc         720
ttgagtaagg catctgaaca aggatcttca ttgcgcaaga aaactgagag acgggagtgg        780
gagatagtta acaatcacag cgggtggaac tcaactcaga atgacgaaat tcatctgca         840 ctaagagtcg cagaaggtct cattagtaag tctaatgaat cagaagatct tgaggacgtt        900
gccattcaac atttccgaga gttattgtcg agatccttct ttcaagacgt tgaagaatat        960
cgttccgttt atacttcaat ctgtacaatg catgaccttg tacatgatct tgcactgtca       1020
gcagcagggg ttgaattctg tacagtaaat tctcacatac aaaacatttc tgatgaggtc       1080
agacatgtgg tgttttctga ctatgattta tcaggcaagg aactgccagc atcccttctc       1140
ggtaaccagg cattaaggac catatccttc tccgttgatg gagtagggcc gatgagtaca       1200
atgttcgttg agaattgctt agcaagattc atgcaactta aggtgctaga tatcagtgat       1260
tcatgtttcg atgagctgcc tagctctgtt ggcgaattga agtatttaag atatcttgat       1320
gtaagttcca atggaagcat taaagaatta cctgattcga ttaacaagtt gctgagctta       1380
cagacacttc gagtttctca ttgtccacaa cttgaaggtc tgcctaaaga tattggaaat       1440
ttgatcagcc taagcacct gtatataacc accaagcaag catgttttcc tgaaaagcaa        1500
ttggctgctt atcatctctt cgttctttgt acattcatag ctgcaacaat ctcgtatctt       1560
tgtctgaagc accttactgc tttaaagaat ctgttgattg ttgactgtaa agagcttaca       1620
ttgttggagt ggcaagatat tgaaggactt aggatgcttc ggtcattggt tatcggaggc       1680
ttacctgaat tggagtcaaa agatgttcac tgcctcggga gccttcagat gttggtactt       1740
gctggtttac cagagttagt tactttgccg cgatggcttg aaggtgctag tgctactcta       1800
caatacctga gggtggaaag gtgcctgaat tttgcagcat tgccaaactg gctggcaaat       1860
cttactgcac ttgaaaaact tgaaatttcc aagtgccgta atcatttttc attgcccgag       1920
ggtatgagtt gcctcacgaa tctgaaggta cttaagaacg acaattga                   1968
```

<210> SEQ ID NO 8  
<211> LENGTH: 2202  
<212> TYPE: DNA  
<213> ORGANISM: Solanum lycopersicoides

<400> SEQUENCE: 8

```
atgcatttcc agaaaagctt taggaagaag gtaagaagat tcttttccag ttcaaatcca         60
attatatatc gattcaagat tggcagaaag gtaaaagaaa tcagggagct gctgaatgag        120
attgcagatg ataggagaaa tttccacttc acggaacata cttatgtaat tccagctgag        180
aatacgagta gagaacaaac acactccttt gtgagggcct cagatatcat tggtagagat        240
gatgatcaag aaaacattgt aaaacagctg atagattctc atgatgagga aaatatttct        300
gtgattccta ttgttggact tggagggctt ggaaaaacca cacttgttaa gttggtttat        360
aacaataata gggttgttca gaattttgac cttagaatgt gggttagtat ttcagaagat       420
ttcagtctga gcaaggtaat tgagaaaatt ctgaggtccg caacaggaga gagttttgac        480
cacctagata tggaccaatt acaatgttgt ttgggagagg ttttgcaaca gaaaaggtat        540
```

-continued

| | |
|---|---|
| ttacttgtgc tggatgatgt ttggaacgaa gatcaacaca agtggacgga tctgagggag | 600 |
| ttgctgatga attgttccag aggtagtaaa attgttgtca ctacacgtag taagatggtt | 660 |
| gctttgatta ctggaacagt tccgccttat tatttgggag gccttgctaa tgatgactgc | 720 |
| ttatctttat ttttgaaatg tgcatttgga ggacaggaca atttgtttcc taatctagta | 780 |
| gaaataggaa agaaattgt gaaaagtgt ggaggagtgc ctttggctgt gaaaaccttg | 840 |
| ggaaggttgt tgtacatgaa aacagacgag aatgaatggt tgcagataag agataatgag | 900 |
| atatgggaaa tcgaacagaa taaatctgac attttaccaa tattgagatt gagctatgaa | 960 |
| cagatgccat cacatctaag acagtgcttt gcctattgct ccatgttacc caaaggtcaa | 1020 |
| gaaattccga gggaggattt tatcaatcgc tggattgctc aaggatttat acagagttcc | 1080 |
| aacagaaaca ggaagctgga agatatcggt aatcagtact ttgatgagtt gctatcaagg | 1140 |
| ttttgcttcc tagatgtggt acaagctttt gatggagaaa tattggcttg taagatacac | 1200 |
| aatcttgtgc atgatcttgc acagtcagta tcaggtgcag agtgcttaaa tgtgaaaccc | 1260 |
| aatgctttcg tggtctctga aagagttcgc cacttatttt tccatgcaga agatatgtct | 1320 |
| aggaaacact tccccagatt tttgcttcct ttgcaaaagt tgaggtcttt ctcttattct | 1380 |
| tttaacattg gacctgtaaa caagttcttt gtcaagacaa tgttgtcaaa tttcaaatgc | 1440 |
| cttcggatgc tagtcttgaa caatctagat cttgaggagt tgccaacttc gataggtcac | 1500 |
| ttgaaggaat taagatacct caaccttagt gacagtggta agatcaagtt tcttccaagg | 1560 |
| tctatgagca aattagtaaa tctgcacacc ctaaacctca ttaactgtga acagcttaag | 1620 |
| gagttgccaa gagattttag aaagttaatc agcctgaaga ccttgtattt gactacacat | 1680 |
| cagatgtcag cagggatcaa gaatcaacat tctttcactt ctcttcaatt tttacttctt | 1740 |
| ttcaaatgtt gtttcccaaa attgcagcca gaactggtgc agcattttac tgcacttcgg | 1800 |
| gttttgcgta tctatgaatg cccaagttta tgttctcttc caagcagtat tagatatctg | 1860 |
| acttcacttg aaaagctatg gatctggaac tgtgaagaac ttgatttgat tgatggagaa | 1920 |
| gggatgtcag gcctaacaag tcttcaatcc ttgcttctaa tggggcttcc taagttggtg | 1980 |
| actctaccat tggaacttaa agatactgct cctacaacat taaagtactt cagaatcgcc | 2040 |
| gattgtccca acctggtgga gcttccagag tggctgccta attgctcctc acttcagaga | 2100 |
| ctctatatag aggattgtcc tgttttggca tcgatacctc aaggaatcta cagccacaat | 2160 |
| gccaacgtcc atataatcga ctgtccattg ctaggtggat ga | 2202 |

<210> SEQ ID NO 9
<211> LENGTH: 2553
<212> TYPE: DNA
<213> ORGANISM: Solanum lycopersicoides

<400> SEQUENCE: 9

| | |
|---|---|
| atggctgatg cctttgtgtc atttgcagtt aaaaaattgg gtgatttcct aatcaacaa | 60 |
| gtttccctga gaaaaaatat gagagatgaa gttacatggc tgagaaatga gctactcttc | 120 |
| atgcagtctt tcctcagaga tgccgaacaa aagcaatatg agatcaaag agttcaacaa | 180 |
| tgggtgtttg agatcaactc tcttgctaat gatgctgtcg ctatactcga gacttacagc | 240 |
| ttcgaggctt gtaaaggtga tgaggatgga tttgctagtc gtctcaaggc ttgcgcttac | 300 |
| atctgtagga aggagaagaa attctacaat gtcgccaagg agattcaatc actcaagcaa | 360 |
| cgaatcatgg atatctctcg caaacgagat acttatggta ttacaaatat caatagtact | 420 |
| aattcaggag aagggccaag taatcagtct gccatggtta aacattgag gagaactacc | 480 |

```
tcctatgtgg atgaccagga ctacatattt gttggacttc aagatgttgt acgaacattg      540
ctagatgaac ttctcaaagc agagcctcgt cgaagtgtcc tctccattta tggcatgggc      600
ggattaggca agaccactct tgcaagaaac ctctacaaca gtcctaacat agtcaatagc      660
ttccctacac gcgcttggat atgtgtttct caagagtaca cacaatggat ctccttagg       720 aatatcataa aatccatcca aggttgcacc aaggaaactt tagatatgtt ggaaaggatg      780
acagaaagag atctagaaat ataccttcgt gatctattaa agaacgcaa ataccttgtg       840 gtggttgatg atgtatggag gagagaagca tgggagagtt tgaaaagagc atttccagat     900
agcaagaatg gaagcagagt tattattacc acgcgcaaag aggatgtcgc tgaaagagca     960
gatgacagag gttttgtcca taaacttcgc ttcctaagcc aagaagaaag ttgggatctc    1020
ttttgtagga aactacttga tgttcaagca atggcctcca caatggagag gctagctaaa   1080
gatatggtgg acaagtgtgg aggcttacct cttgcaattg ttgtactgag cggactactt     1140
tcgcataaaa gggggcaaga cgaatggaaa aaggtgaaag atcacctttg gcagaacatt    1200
gaaaacaact ctattgaaat ctcctacata ctatcattga gctataatga tttgtcaatt    1260
gcactcaagc agtgttttct gtactttggc cttttccag aagatgaaga ggtcgatgct     1320
gaatacataa tatggttgtg gatggccgag ggtttcatac ctaatggaga agaaagaatg    1380
gaagatgtcg ctgaaggctt cttgaatgag ctgataagac gaagcttagt tcaagtggct    1440
ggaacacttt gggagaaagt tattctatgt agggttcatg atgcagttcg tgatctttcc    1500
atacaaaagg caatggaggt aaacttctat gacatttata atccaagaaa ccattccata    1560
tccttcttac ctattagaca tgccattcat agtcaaggag aaaggtacct ctcacttgat    1620 cttttctaatt taaagttgag gtcaattatg ttcttcggtc cagattttcg taacatgaat    1680
cttataaact ttagtagtgc gttccaacat atatatgtgt tgtacttgga taatcgtggt    1740
ggttctatat ctatagtacc tgatgcgata ggaagtttgt accacctcaa gttcttaagc    1800
ttgagaggca tccatgatct tccctcctcc attggcaacc tcaagaattt acagacactt    1860
tctgtcgtga atgaaattgg acacccattc aaactaccct gtgagtcagt tgatctaata    1920
aatctaagac atttagttgc tccgtataca aaaccttgta acgtataag caaactcaaa    1980 aatcttcaag ttcttaaagg cactgcttgt gatcagtgga agatgttgaa ccctgttgat    2040
ttagtcaatc ttcgagaatt aagcatgcat gatattacca aaattacgc cctgaacaac    2100 attagcaact tgaaaaacct tagcacactc agattgtttt gtagaggtgg tgaatcattc    2160
gctgcccttg aatttcttag ttcttgtcaa agctcgaga aattgttgtt aaaagggaga    2220
atagagaaac ttcctttgtt tgtaaattcc atcacaatga tggttttttg gaactcaaaa    2280
ctcatggaag atcccatgcc tatccttgga atgttgccaa acctaaggga tctctattta    2340
gtagcaactt atgaaggaaa agaaataatg tgcggtgaca acagcttcag gcaactcgag    2400
ttccttcgtc ttcatcgtct tgagaaccta gaaacatggc atttagccac aggttccttg    2460
cctctgatta aaggtcttcg tatctatgat tgtccaaagc tgaaggagat tccagataga    2520
ttgaaacatg tgaagctttt caaccatata tga                                  2553
```

<210> SEQ ID NO 10
<211> LENGTH: 1275
<212> TYPE: DNA
<213> ORGANISM: Solanum lycopersicoides

<400> SEQUENCE: 10

-continued

| | |
|---|---|
| atgtcttttg cacttggaaa attgggtgat ttactcttca taaaatcttt cctcaaagat | 60 |
| gcagaactaa agcaatgtgg agatcaaaga gttggagaat gggtatttga gatcaactct | 120 |
| atagctaatg atgttgttgc tacactcgag ccttgcatct ttgaggttgg atgttgtaca | 180 |
| aacattgcta gctcaccttc tcaaagcaga gcctcgtcga agcgtcctct ccatttatgg | 240 |
| tatgggggt taggcaagac cactcttgcc agaaaacttt acattagtcc taatatagcc | 300 |
| tctagtttcc ctacacgtgc ttggatatgt gtttcgcaag agtacaacac cattgatctt | 360 |
| cttaggaata tcatgaaatc cctccaaggt cgcaccaagg aaactctaga tttgttggaa | 420 |
| aggatgatcg aaggagatct agaaatttat cttcgtgatc gattaaaaaa acacaaatgc | 480 |
| cttgtggtgg ttgatgatgt gtggcagaaa gaagcatggg agagtttgaa aagagaattc | 540 |
| ccggatagca agaatggaag cggagtcatt attaccacgc ccaaaaggga agtcgctgaa | 600 |
| agagcagatg acagagaaga tcaagtgctc aaggctgata acataatacg gttgtggacg | 660 |
| gccgagggtt tcatacccag aggagaagaa agaatggagg ataccgctga aggcttcttc | 720 |
| aatgagctta taatacgaag cttggttcaa gtggctaaaa cattttgggg aagagttact | 780 |
| gaatgtaggg ttcatgattt actccatgat cttgcgatac aaaaggcatt ggaggtaaac | 840 |
| atcttttaca tttatgatcc aaaaagccac tccatatcct ctttatgtat cagacatgtc | 900 |
| attcatagtc aaggagaaag gtacccctca cttgatcttt ctaacttaaa gttgaggtca | 960 |
| cttatgttct tcgatccaga ttttcgtaag atgagtctta taaacttcag gagtgtgttc | 1020 |
| caacatctat atgtgttgta cttggagatg cgtgttgaca atatgtctat tgtattagta | 1080 |
| tctgatgcca taggaagttt gtaccacctc aagttcttaa gcttgagagc tccagaaatt | 1140 |
| gaggttagaa ggggtgatag agaaactgcc tcatctgttt ccaaattcca tcacaatgat | 1200 |
| ggttctgagg gactcaagac tgacagaaga tctgatgcct attttggaaa cgttgccaaa | 1260 |
| cttaaggaat catga | 1275 |

<210> SEQ ID NO 11
<211> LENGTH: 2388
<212> TYPE: DNA
<213> ORGANISM: Solanum lycopersicoides

<400> SEQUENCE: 11

| | |
|---|---|
| atgagagatg aagttacatg gctgagaaat gagctactct ttatacaatc tttcctcaaa | 60 |
| gatgcagaac aaaagcaaag tagagatcaa agagttcaac aatgggtatt tgagatcaac | 120 |
| tctattgcta atgatgttgt tgctatactc gagacttata gcattgaggc tggtaaacgt | 180 |
| gctagtcgtc tcaaagcttg cgcttgcata tgtagcaagg agaagaaatt ctacagtgtt | 240 |
| gccgaggaga ttcaatcact caagcaacga atcatggata tctctcgcaa accagagact | 300 |
| tatggtatta caaatatcaa ttataattca ggagaagggc caagtaatca tgattacatt | 360 |
| tttgttggct ttaacgatgt tgtacaaaca ttgctagctc aacttctcaa agcagagcct | 420 |
| cgtcgaagtg tcctctccat ttatggcatg gcggattag gaagaccac tcttgccaga | 480 |
| aacctctaca acagtcatga tatattcaat agcttccata cacgcgcttg gatatgtgtc | 540 |
| tctcaagagt acaacacaat ggatcttctt aggaatacca taaatccatc caaggaaact | 600 |
| ctagatttgt tggaatgggt gacagaagga gatctagaaa tttatcttcg tgatctatta | 660 |
| aaagaacgca aataccttgt ggtggttgat gatgtatgga atagagaagc atgggagcgt | 720 |
| ttgaagagag cattccccgga tagcaagaat ggcagcagag tcattattac cacgcgcaaa | 780 |
| gaggatgtcg ctgaaaagca aacgatagag gtttttcaag aagaaagttg ggatctcttt | 840 |

```
tgtaggaaac tacttgatgt tcgagcaatg gtttcagaaa tgggaagtct agctaaggat      900
atggtggaaa agtgtagagg cttacctctt gcaattgttg tattgagcgg actactttcg      960
cataaaaaag ggctaaacga atggcaaaag gtgaaagacc acctttggaa gaatattaaa     1020
gaaaataaat ctattgaaat ctctaacata ctatctttaa gctacaatga tttgtcaact     1080
gctctcaagc agtttttttct ctactttggt attttttccag aagatcaagt ggtaaaggct    1140
gataacataa tacggttgtg gatggtcgag ggtttcatac ccagaggaga agaaagaatg     1200
gaggatgtcg ctgaaggctt gttgaatgaa ctgataagac gaagcttggt tcaagtggct     1260
aatacatttt ggggaagagt tactgaatgt agtgttcatg atttactcga tcttgcgata     1320
caaaaggcat cggaggtaaa cttctttgac atttatgatc caagaagcca ctccatatcc     1380
tctttatgta tcagacactt cattcatagt caaggagaaa ggtacctctc acttgatctt     1440
tctaacttaa agttgaggtc aattatgttc ttcgatcgag attttttgtaa gacgagtctt    1500
ataaacttca ggagtgtgtt cctacatcta tatgtgtttc acttggatat gaatgttggg     1560
aatatgtcta tagatgtacc tgatgccatt ggaagtttgt accacctcaa gttcttaagc    1620
ttgagaggta tccgtgatct tccctcttcc attggcaacc tcaagaatct acagacactt    1680
gttgtcgatg tgggaggata cactttccaa ctaccccgcg agacagttta cctgataaat    1740
ttaagacatt tagttgctcg gtattcaaaa cctctggtac atataagcaa actaactagt    1800
cttcaagttc ttgaaggtgt tggttgtgat caatggaaag atgttgaccc tgttgattta    1860
gtcaatcttg gagaattaag tatgtttgat attagcaaat cttactccct aaacaacatt    1920
aggagcttga aaaaccttag cactctcaca ttgtcggggg ggtatcggaa ctcatctcca    1980
tttccagacc ttgaatttgt taattgttgt gaaaagctcc agaaattgag gttagaaggg    2040
gtgatagaga aactgcctca tctctttcca aattccatca caatgatgct tctttggaag    2100
tcaagactga cagaagatcc gatgcttatt ttgggaatgt tgccaaacct aaggaatctc    2160
gatttggtta gtgcttatga aggaaaagaa ataaatttgca gtgataacag tttcaatcaa    2220
ctagagttcc ttcaacttga ggatcttcga aatctagaaa gatggtattt aggtacaagt    2280
gccatgcctc taattaaagg tcttggtttc catgactgtc caaatttaaa ggagattcct    2340
atgagaatga agacgtgga gctgctgaag aggaattata tgtggtga                   2388
```

<210> SEQ ID NO 12
<211> LENGTH: 1782
<212> TYPE: DNA
<213> ORGANISM: Solanum lycopersicoides

<400> SEQUENCE: 12

```
atggaaaatg aatatcagaa gctggaggat atcagaattg ggttgcatca aagagcggag       60
gctgatcgga gaaacttact agtcatttca cctaatgttg aggcttggtt tactcgtgtt      120
gatactacta ctgcagatgt ggaagctgta atgcgacgag aggttgaaag atatggctgg      180
tgcccaaaat tgaagtcacg ttactcgctg agcaggaaag ctaaaaaatt tgcactggaa      240
ttgattgaac ttcgaaatca aggcaatgat tatgctgttt ctcctatcc tgcagtcaaa       300
attgaagttc tacctagtaa cagtggtgag gagtttgact ccagaaaatt gcaagaggaa      360
gaggttatgg cagctttgag agatgatggg gtcactatga ttgggatatg tggtatgggt      420
ggttttggta agacaacact ggctgagaaa atcaggcaaa aggcgaaaca aggaagtttg      480
tttgatgagg ttgtcatggt aactatcagt caacaaccag acttgaaaag aattcaaggt      540
```

-continued

```
gaggtagcag ggggtgttgg tctgacgttg caaggggaca atttctggaa tcgtggagat      600
cagctgcgct caaggttaat ggttcagaac agctgtgtcc tagtaatctt ggatgatgtt      660
tgggaggctc ttcatgaact agagaaactt ggaattccca gatgtagcaa ccacaaccaa      720
cgttgtaaag tgacattgac aacgcgattc cgagatgttt tgaagctat  ggaagctcaa      780 aagatcatgg aagttggaac tttacctgaa gaggaagcat ggatccttt  cagggagaaa      840 gttggtaata taatcgacga cgatccttct gtacttgaca tagcaaaagt tgttgccaaa      900
gaatgcaagg ggttgccgct tgcaattatt acagttgcaa gagcacttaa gcgtaaaacc      960
aagccttcgt gggaggatgc ccttgtacaa ttacaaagat caacaccaat aaatattcca     1020
ggagtaatta aaaatgtgta tcaatctctc aaacttagct atgattactt ggaaagtaat     1080
gaagtcaggt ccctgttttt gctttgttcc ttgttcgagg aagatagtaa tatctggact     1140
gaacaattac ttagatatgg aatggggctt gacatctttt cagaaattaa aaacttagaa     1200
gaagcaagga agcgggcgtg tcatctctta gaaacattga agatcgtttt cttcttgtcc     1260
ttaggttcaa cagaaaatta tgtcaaaatg catgatatgg tccgtgatgt ggctataagt     1320
attgcctcta tgggagagta tagctttatg gtaagtcacc atgtgaactc gcaagagctc     1380
ctaagaagaa cttcttacaa gcaatacagt cacatttcaa ttgttgcaaa taaatttgat     1440
gagcttccta acccaatatt ttgcaaaaaa ctgaagcttc taatgttgac tctcgatttt     1500
aaaaatccat ttaaattaca ggaagatttt tttgatgaaa tggctgaact caatgtctta     1560
agtttgagtg gatatggatc cattctgcct tttccaacat ccattgagag ttgtcaagt     1620 ttgaagacat tatgtctgag tcatttaagg ttagatgaca tatccattat tgggatactt     1680
gtcactttag aaattctcag cataagacat tctgacatag aggagctgcc agttgagata     1740
ggaaatttga ccaatctaat tatgttaaga gtttcggaat ag                        1782
```

<210> SEQ ID NO 13
<211> LENGTH: 3219
<212> TYPE: DNA
<213> ORGANISM: Solanum lycopersicoides

<400> SEQUENCE: 13

```
atggatcatc ttatgcctta cctgctgaaa gaaatcaaag attactatta caaggagtat       60
gagatctctc aatgctcttc cgagatctct tctctactta tcgacataat gcctcttgag      120
ctggaggttc tatacatttt tacttctaag ctcatgaaag aatcaaggtc aacagaacta      180
gaagtgtttg ttaagcaaat cctaaaagca ctctccgaaga ttcttcaaaa ttatctgatt     240
cttatgaaag gatgcatgga aggttcagta gctgtcagtt acgctccaat tcaatgcatt      300
aatgtcatga tggagttcct attgatcttt ctcacttata taccaaagcg ctatatccgt      360
cgtgacaaac tgaatgatat gttggcacat gttggagtac ttacaaggaa gatatctatt     420
ctggtgagca agctgatgga ggagagctct gagaataata tcaacgaagc ggactttca      480 gctgcatact tgttgcaaga aattgaacaa atgaagggag atatcagaca gcttttttg      540 aaagccccag agtcatctca aattcgcttt tctatggatg atggtttact cttcatgaat      600
cttctactcg acatttaaa  tgatttgctc atttccaatg cttattcagt tgctctgata      660
aaaaaagaaa ttgggatagt gaagaaagc  cttgaattcc taagatcatc tttcggggaa      720
gtcaggcaaa cattggatga cactagcgga ttagttaaag attgttgggt gcgtgcttta     780
gatgtggcat atgaagcaga acatatcatt aattccattc ttgtcagaga taatgctctc     840
acacatctca tattctcact tccgaatgtc acagataaga tcaagcttat cgtggcagaa      900
```

```
gtcacctgca gtgtacatct ggaggataaa aatggggatg accccttga tgcaaagtct    960
ttcgacgagt caattgagtc aacctcatca tcttttgttg aggtaacagt tggtcatgag   1020
gaagacgaag cctggatcgt tgaccagctc cttgataagc atgaatccaa gcttgatgtc   1080
atttcgattg tcggaatgcc aggagtcggt aaaactactc tagccaacaa agttcatttc   1140
aatgttcatg tttggtgcac tgtttcccaa agtttaaca agtcaaaggt gttgcgggtg    1200
attcttcagc aagttacagg gtcggaagac aagaaacaaa gtaatgaggg tgataaagtt   1260
gttgatcttg ctgaaaagct acgagaagaa ctatacgata aaaggtacct catcgtcttg   1320
gatgatgtgt gggatattgc aacagtggag atgttaatag catgctttcc gagggttgag   1380
agaggaaata gaattatctt aactagccga agtagtgagg taggtttgca agttaaatgt   1440
cgtaatgatc ttctctacct tcaacttcta acacatgaaa aaagttggaa tttatttgaa   1500
aaaaggatca aggaagctgc cctgctgaac tgtcagaagt tggacaccaa atatatagtt   1560
gagaaatgtc aagggcttcc tctggctgtt gtgttgattg ctggagtaat tgttagagga   1620
aagaaaaatg aaaaagattt gtggcttaag attcaacata atatggattc cgttatttct   1680
gccaacaaca atttgcagat gatgaaggtt atgcaattaa gttatgacca cttaccatac   1740
cacctaaagc cgttgttgct ttactttgga agatctcaaa agaacaaact aactccagtc   1800
tctaagttga tgcaattgtg gatggccgaa gggtttgtgg atcattgtat cccgtctaag   1860
agtagtttag aggaaataac ccaaagttac ttggaagctt taatttccag tagcctggta   1920
atggtggatc gtagcgtgtc caagagtagt caccctttt ctgttactat caaggtttgc   1980
tatgtgcatg atgttgtgca tgatttttgt tcagtaaaag caaagaagga aatgtttttc   2040
aagttaatca attcaggtgc tccatttcat gcttcggatt tcatacatcg tcgtctaacc   2100
atttatactg acaaatccca actccacaaa agatgtgttt tgtttaattc taataagtgt   2160
tcagctggta gtaagcatct catatctttg aaagtgaaaa attggcttga tcccttcagt   2220
cacattagac actttggact tgttagagtg ttgcaacttg gtaacattat tctggaagag   2280
tcatcaatgg aagaaatagg ctccctattt catttgaggt ttttgaggtt tcagacatat   2340
gaaaaatctc tcccgctttc gtggttgaac ctccagaatc tggaaactct gtggatccta   2400
aacaggcatt ccaccatggt actactcgac gaactgtcaa agctgaaaca tgtgagcatc   2460
gacgctagat ctttctttga agaggacaag gacaacatta tgcatcagcc aagtagaata   2520
ttggaagctg agtgttcaaa gttagaatac ttgacaactt tatcccgagt tgatatctca   2580
tattctcaag gcacaactga tgctctgggg aagttcccaa atcttcagga ctttgattgc   2640
aacattctgg taccgaatga tcctcctgca aacggcgatt ggtttcccaa gtttgatgtc   2700
cttaataaac ttgaatcact cattctaagt tacagttatg tctggagcag tactgataaa   2760
tgtctggatt attccaagtt tgaaaaaatc cgaaatccca atgaatatca cttccctacc   2820
agtttgcaag agttacggtt gcataggttt cccctgagac ctgctttgtt gttagcaatc   2880
gcgacattgt ctgagcttga aattctggag attatagaat ctaatttcct cgaggatgag   2940
tgggacgcaa gtaaggacat ctatcaaagt ctaaagactt tgcatttagc agatgtcttt   3000
cttacagaat ggcaagttga taagggaact tttcccaagc ttgtggaatt aaaactagaa   3060
cattatcacg ggcttatgga catcccttat gcatttgggg atatagacac tttaaagtcc   3120
attcgagtgg ttcaaacaag ccgtcacctt ggaaattcag ccacaaaaat taaggaagat   3180
gtagaagctt acacgggaaa ggaaagactt aatgtccac                         3219
```

<210> SEQ ID NO 14
<211> LENGTH: 3480
<212> TYPE: DNA
<213> ORGANISM: Solanum lycopersicoides

<400> SEQUENCE: 14

| | | | | | | |
|---|---|---|---|---|---|---|
| atggatggat | tggctgaaac | tggatcttct | tcttcttctt | cttcttcttc | tttgtggcca | 60 |
| tgcacttatg | atgttttctt | aagttttaga | ggagacgatg | tacggaagaa | tttcgtcgat | 120 |
| catctatata | cagctttgca | gcaaagagga | attcacactt | tcaaagatga | tgaaaaactt | 180 |
| gaaagaggga | aatctatttc | accttcactt | ttcaaagcta | tcgaagaatc | gatgatttcc | 240 |
| atcatcatat | tctctcaaaa | ctatgcttct | tcttcgtggt | gtctagatga | gcttgttaag | 300 |
| atcactcaat | gcatgaaact | caggggacag | attgttcttc | ccgtcttcta | tgacgtggat | 360 |
| ccatctgtcg | taagaaaaca | aaaggcaaat | gttggtgagc | tcttcgctaa | acatgagtta | 420 |
| gatttcaaag | atgatgaaga | aagggtgaag | agatggcgta | ctgctatgac | agaagcagca | 480 |
| aatgtatctg | gttgggattt | gccaaatata | gctaacgggc | acgaatcaaa | gtgtatcgat | 540 |
| caagttgtag | aatgtgtcat | ggagatatta | ggtcatactg | cttctgatgc | tactgaaagt | 600 |
| cttattggga | tacgctcaag | aatggggacg | gtgtattcct | tgttgaatct | ggagtctgat | 660 |
| aaagttcaat | tcgttggaat | atggggaatg | agcggaatag | gaaaaacaac | tatagcaaga | 720 |
| gccatctatg | acaagatttt | ccgttacttt | caaggtgcta | cttccttca | tgaagttgga | 780 |
| gaaacttcag | ccaaacatgg | tatccaacat | ttgcagaaga | tacttctttc | tgaactactt | 840 |
| ctgttaaaag | atctaagaat | aaacaacgta | tttgaaggaa | ccagcttgat | aagaagacga | 900 |
| ctaaaaggga | aacgagtcct | aattgttctt | gatgatgtca | atcatggaaa | ccagttagat | 960 |
| gccctagcta | aaagccatga | ctggtttggt | gcaggcagtg | taatcatcat | aacaacaaag | 1020 |
| gataagcagt | tgcttcgtca | atataacgtg | gacaaaatgt | ataaagtgag | tctgttaaac | 1080 |
| actgatgaaa | gtattgaact | ccttagttcg | tatgcattcc | agaatcgtca | tcccaaaagt | 1140 |
| ggatatggag | agattatagc | tgaagttgtt | cggtatgctg | gtggtcttcc | tttagctctt | 1200 |
| aaagttttgg | gttgctctct | gtatggcgga | ggcatgattg | aatggagaga | aacagtggag | 1260 |
| agactaaaac | aaattccaga | aggcgaaatt | gtagaaaagc | tcaaagtaag | tttcaatgga | 1320 |
| ctaagtgaga | ctgaccaaaa | gatcttctta | gatattgcat | gttctttaa | agggaagaag | 1380 |
| aaaggttctg | tcattagaat | tcttcgtagt | ttcagtttta | ctcctgtcgt | tggcataagg | 1440 |
| aatctcatcg | aaaatctct | tgtaactgtt | tcaaaaggta | ggattgtgat | gcatcagttg | 1500 |
| atccaagaga | tgggttggca | tattgttcgc | aaagaagctt | caaacaatct | tggcaagtat | 1560 |
| actaggctct | ggtctaccga | tgatattctt | caggtactat | ctgaaaatac | ggccacagaa | 1620 |
| gctgtggaag | gcatatggtt | gcacttgcct | ataccgaaag | acataaatgt | tggtgcagaa | 1680 |
| gccttcaaac | aaacggacaa | cctgaggctg | ctcaagatac | acaatgcaag | tgtctctgta | 1740 |
| gctccagatt | gtcttcctaa | taattgata | tggcttcatt | ggcatggcta | cccaatgaag | 1800 |
| tcacttccag | caagttttcg | agcagaaagg | cttgtttgtc | tgaaaatgca | gtatagccgc | 1860 |
| gttgtacact | tgtggaaggg | agtaaaattc | ctacacaaac | tgaagtttct | caaccttagt | 1920 |
| cactcccaaa | agctagtcag | ctgtccagat | tcacagggg | tgcccaatct | cgaaaagttg | 1980 |
| gttcttgaag | attgttcgag | tataactgag | atccatcctt | ctgtgggata | tctcaaaaat | 2040 |
| cttgttctac | taaacctgaa | gaactgcaag | aatcttaaga | cccttccaaa | cattattcga | 2100 |
| ttggataatc | ttgagacttt | aattctttct | ggctgcttga | aactcgcgaa | tttcccagaa | 2160 |

```
atcatgagtg acatgaattg cttatctgag gtctacttgg aagctacaga tgtaaaagag    2220
ttgccttcat caattgaacg cctccctggc cttcgattga tgaatctagg ctactgcagg    2280
aatcttacaa atttaccaaa aaccataggt agattaaaat ctcttaggat tcttattctt    2340
tctggatgtt caaagctaga aaagttgcca gaggaactgg gacatataga aatcttggag    2400
gaactctatt gcgacgaaac ttccattcaa agcccaccat catccattac actgttgaag    2460
aaccttaaga ccttatcttt tcatggatgt aaaggcatgg tatctcaatc atggagttca    2520
cttttctatg catggcttca gccaagaaaa cataatcaca agccaacaag tctgatgttt    2580
acttcctttt ctggtttatt ttctttgagg aaattggatc ttagtgactg ttgtatgttg    2640
gatgaaggaa ttcctagtga tcttggatgc ttgtcttctt tggttgagct aaatcttagt    2700
gggaataatt ttgtggatct ctctcaagca agtctcaaca tgcttccgcg gctcagaatc    2760
cttgagctag ttggttgtga gaggcttgaa aggttgccag aacttccaac aacaatagag    2820 gaagttttg cagataattg tacatacctg atgactgata acatgggaat attgaccaac    2880
tacaagatgt tacagcgaat atcgttcact aattgtgttg gactactgca gaatcagcag    2940
acgcgtgaca tggctacctc attgtggctt cacctattca agaagtgcat tgttaaaagt    3000
ggtcacttta gcatttacct acctggagaa caagttccag aatggtttgg ctacaaactc    3060
aacggaactt cagtttcaat gcagctgcca acgattggt acaatgataa attcatggga    3120
tttgccatct gtgttgtgtc tgaacttgaa acaacatggt tatcagttca tgaaggttac    3180
ctacaggaaa tgccaggcat ttcgattgag tttacaatca aaagccacct ccggaggagc    3240
acgagttgcc taatgaacat tggttttgta gggacaaaca agaatgttgc ttcagatcac    3300
acatgccttg cctatgtgcc atttgaagaa tattggtcaa tgtacaaaaa ccacttagac    3360
agcccaaaca attggtatca gatcgatttt tctgcaaact ctttgaggaa acatatattc    3420
ctaaaaagtt ggggaattcg tctcgtgtac actgatgact tacagatttt cacatcttga    3480
```

<210> SEQ ID NO 15
<211> LENGTH: 2463
<212> TYPE: DNA
<213> ORGANISM: Solanum lycopersicoides

<400> SEQUENCE: 15

```
atggcggtga cggactttt cgccggcgaa attaccaccg aactcataaa ataccctgctg     60 ttaatagtta aaaaatccac tttatgccgt tcaagcgcag agaatctcat tgacaatatc    120
aatggtctcc ttccaatcat ccaagaaatc aaacaaaccg tgttgaact tccacagata    180 cggcaaactc agctcgacga tttctccaaa cttctccgag atggctacga actcgccgga    240
aaagttctgc actccggccg ttggaacatg tacaggaacc tacagttggc taggaaaatg    300
gagaggttag agaaaagagt agcgaggttc atgcaagtta caatgcaagc tcatgtacta    360
gctgatgttc atcatgttag gtttaatatg gagcagagat ttgatgtgct tgagcatagg    420
cttaaagcta taaaaatcgg agttgacgat agaagtggtg gaggaggagg gtgtttagga    480
gaagctgtga aaagaatgga agaagatgag aaatggtttg aggatagttt tgtaaattta    540
ggtgctggga ttgaattggg gaagaggaag gtgaaggaga tgctgatggg tgaacaagat    600
aggggtgtgt ttgagatttg tggaattggg ggtagtggca aaactacctt ggctaaggag    660
atttgtaaag atgatcaagt taaaagttat ttcaaggaca agattttctt tttcactgtt    720
tctcaatctc caaatgtgga gcaattaagg aaaatgattt gggaaaagat atcagggtgc    780
```

| | |
|---|---|
| aatctccatg gttatggata cggggagatg tttccccagt ggaacctaca gtaccaatgg | 840 |
| aatacgaaat gtgcatcccc ggtactcttg attcttgatg atgtgtggtc tgcatctgtt | 900 |
| ctagagccac tagttttcaa gatccccgga tgcaagatcc tagttgtatc gcgcatcaag | 960 |
| tttcctctat cgatcattga ctgtatttat gatttagagt tgttaaggaa gatgaagcta | 1020 |
| tgtccttatt ttgccatttt gcttttggac acaattcctt tccgcgtgat gtggatgaa | 1080 |
| tgtgaagggc ttcctttggc tcttaaggtc attggatctt cattgaaggg aaaacctgag | 1140 |
| atgttatgga caagtgcaaa aaacagatta tcacgatgcc aacctgtctg cgagtctcat | 1200 |
| gaactgcagt tgcttgagcg aatgaaattg agtattgact gtttgcctga aaggtgcga | 1260 |
| gagtgtttcc tggacttggg tgctttcccg gaggacaaaa ggattcctgt tgatgttcta | 1320 |
| attaacatgt gggtggagct acatgatatt gatgaggagg aggcttttca cattcttgtt | 1380 |
| gaactttcag acaaaaatct cctaaatcta gtcaaagatg cacgagccgg agacatgtat | 1440 |
| acaagttact atgagatatc ggtgtttcag catgatgtat tacgagacct agcaattcat | 1500 |
| atgagcaact gtgatgatat aaatcagaga aagcgattgg ttatgccgcg agagacaca | 1560 |
| agcttcccaa gagaatggga agaaatgtg gacgaaccTT tccatgcacg agttatctct | 1620 |
| gtgcatacag atgaaatgag agaaatggac tggttcagaa tggattgccc gaaagctgaa | 1680 |
| gtactgattc tcaactttgc ctcatctgag tacttcttgc ctccttttct ggagaacatg | 1740 |
| ccaaagctaa gggcattgat aatcataaac tatagtgctg gcaattcagt tcttcataac | 1800 |
| atgtctgtat tcagtcattt aaccaacttg agaagccttt ggttcgagaa gatatccatc | 1860 |
| actcacttat ctgactccac aaatcctctc aataacctgc gaaagatatc tctagtgctt | 1920 |
| tgtgacatga aaaacagctt cgatgagtca gatgtagacc tccctggttt gttcccacag | 1980 |
| ctctcggagt tcacaatgga tcattgcatc aacttcaaca agctaccatc gagcatttgc | 2040 |
| cggttgcata agctcaacag ccttagtatc actaattgtg atagtctttg tgaacttcca | 2100 |
| tctgatttag gtgaattaca aactctacaa gttttaagga tatatgcctg tccacatctg | 2160 |
| aaaaggcttc ccccgggaat tggtcatctg gtaaagctaa agtaccttga catttcacaa | 2220 |
| tgtgttggtt tgagatgtct ccctgaagca attggttgct gtagaaactt agagaagatt | 2280 |
| gatatgaggg agtgccctca aatcgacagt ttgcctagcg ctctatcctt tcttgaatca | 2340 |
| ttacgttgtg ttatctgtga cgatgaagtt ttttgtcaat ggaaagacgt tgagaaggct | 2400 |
| gtaccaggtc tctgtgtaca ggttgccgag gagtgccata ctcttgactg gctatctcaa | 2460 |
| taa | 2463 |

<210> SEQ ID NO 16
<211> LENGTH: 255
<212> TYPE: PRT
<213> ORGANISM: Solanum lycopersicoides

<400> SEQUENCE: 16

Met Lys Ile Ala Pro Val Ala Ile Asn His Ser Pro Leu Ser Arg Glu
1               5                   10                  15

Val Pro Ser His Ala Ala Pro Thr Gln Ala Lys Gln Thr Asn Leu Gln
            20                  25                  30

Ser Glu Ala Gly Asp Leu Asp Ala Arg Lys Ser Ser Ala Ser Ser Pro
        35                  40                  45

Glu Thr Arg Ala Leu Leu Ala Thr Lys Thr Val Leu Gly Arg His Lys
    50                  55                  60

Ile Glu Val Pro Ala Phe Gly Gly Trp Phe Lys Lys Lys Ser Ser Lys

```
                65                  70                  75                  80
        His Glu Thr Gly Gly Ser Ser Ala Asn Ala Asp Ser Ser Ser Val Ala
                        85                  90                  95

Ser Asp Ser Thr Glu Lys Pro Leu Phe Arg Leu Thr His Val Pro Tyr
                       100                 105                 110

Val Ser Gln Gly Asn Glu Arg Met Gly Cys Trp Tyr Ala Cys Ala Arg
                       115                 120                 125

Met Val Gly His Ser Val Glu Ala Gly Pro Arg Leu Gly Leu Pro Glu
                   130                 135                 140

Leu Tyr Glu Gly Arg Glu Gly Pro Ala Gly Leu Gln Asp Phe Ser Asp
        145                 150                 155                 160

Val Glu Arg Phe Ile His Asn Glu Gly Leu Thr Arg Val Asp Leu Pro
                            165                 170                 175

Asp Asn Glu Arg Phe Thr His Glu Glu Leu Gly Ala Leu Leu Tyr Lys
                        180                 185                 190

His Gly Pro Ile Ile Phe Gly Trp Lys Thr Pro Asn Asp Ser Trp His
                        195                 200                 205

Met Ser Val Leu Thr Gly Val Asp Lys Glu Thr Ser Ser Ile Thr Phe
                    210                 215                 220

His Asp Pro Arg Gln Gly Pro Asp Leu Ala Met Pro Leu Asp Tyr Phe
        225                 230                 235                 240

Asn Gln Arg Leu Ala Trp Gln Val Pro His Ala Met Leu Tyr Arg
                        245                 250                 255

<210> SEQ ID NO 17
<211> LENGTH: 321
<212> TYPE: PRT
<213> ORGANISM: Solanum lycopersicoides

<400> SEQUENCE: 17

Met Gly Ser Lys Tyr Ser Lys Ala Thr Asn Ser Ile Asn Asp Ala Leu
1               5                   10                  15

Ser Ser Ser Tyr Leu Val Pro Phe Glu Ser Tyr Arg Val Pro Leu Val
                20                  25                  30

Asp Leu Glu Glu Ala Thr Asn Asn Phe Asp His Lys Phe Leu Ile Gly
            35                  40                  45

His Gly Val Phe Gly Lys Val Tyr Lys Gly Val Leu Arg Asp Gly Ala
        50                  55                  60

Lys Val Ala Leu Lys Arg Arg Thr Pro Glu Ser Ser Gln Gly Ile Glu
65                  70                  75                  80

Glu Phe Glu Thr Glu Ile Glu Thr Leu Ser Phe Cys Arg His Pro His
                85                  90                  95

Leu Val Ser Leu Ile Gly Phe Cys Asp Glu Arg Asn Glu Met Ile Leu
            100                 105                 110

Ile Tyr Lys Tyr Met Glu Asn Gly Asn Leu Lys Arg His Leu Tyr Gly
        115                 120                 125

Ser Asp Leu Pro Thr Met Ser Met Ser Trp Glu Gln Arg Leu Glu Ile
    130                 135                 140

Cys Ile Gly Ala Ala Arg Gly Leu His Tyr Leu His Thr Arg Ala Ile
145                 150                 155                 160

Ile His Arg Asp Val Lys Ser Ile Asn Ile Leu Leu Asp Glu Asn Phe
                165                 170                 175

Val Pro Lys Ile Thr Asp Phe Gly Ile Ser Lys Lys Gly Thr Glu Leu
            180                 185                 190
```

```
Asp Gln Thr His Leu Ser Thr Val Val Lys Gly Thr Leu Gly Tyr Ile
            195                 200                 205

Asp Pro Glu Tyr Phe Ile Lys Gly Arg Leu Thr Glu Lys Ser Asp Val
210                 215                 220

Tyr Ser Phe Gly Val Val Leu Phe Glu Val Leu Cys Ala Arg Ser Ala
225                 230                 235                 240

Ile Val Gln Ser Leu Pro Arg Glu Met Val Asn Leu Ala Glu Trp Ala
            245                 250                 255

Val Glu Ser His Asn Asn Gly Gln Leu Glu Gln Ile Val Asp Pro Asn
            260                 265                 270

Leu Ala Asp Lys Ile Arg Pro Glu Ser Leu Arg Lys Phe Gly Asp Thr
            275                 280                 285

Ala Val Lys Cys Leu Ala Leu Ser Ser Glu Asp Arg Pro Ser Met Gly
            290                 295                 300

Asp Val Leu Trp Lys Leu Glu Tyr Ala Leu Arg Leu Gln Glu Ser Val
305                 310                 315                 320

Ile

<210> SEQ ID NO 18
<211> LENGTH: 2472
<212> TYPE: DNA
<213> ORGANISM: Solanum lycopersicoides

<400> SEQUENCE: 18
atggcggaat ctttcttgtt caatatcatt gaacgggttt tggctaaagt ttcttcaatt      60
gctgtatatg agatcagtct agcttggaat gttaagacag agctaaggaa actccaaagt     120
actctatcca ccatcaaagc tgtacttcta gatgcaaacg agcaaaaggc aaagaaccat     180
gaagtgagag attggctgga aaagctcaga gatgttgttt atgatgtcga tgatttgatg     240
gatgatttat caacacaact gttgctgcaa atgcatttcc agaaaagctt taggaagaag     300
gtaagaagat tcttttccag ttcaaatcca attatatatc gattcaagat tggcagaaag     360
gtaaaagaaa tcagggagct gctgaatgag attgcagatg ataggagaaa tttccacttc     420
acggaacata cttatgtaat tccagctgag aatacgagta gagaacaaac acactccttt     480
gtgagggcct cagatatcat tggtagagat gatgatcaag aaaacattgt aaaacagctg     540
atagattctc atgatgagga aaatatttct gtgattccta ttgttggact tgagggctt      600
ggaaaaacca cacttgttaa gttggtttat aacaataata gggttgttca gattttgac      660
cttagaatgt gggttagtat ttcagaagat ttcagtctga gcaaggtaat tgagaaaatt     720
ctgaggtccg caacaggaga gagttttgac cacctagata tggaccaatt acaatgttgt     780
ttgggagagg ttttgcaaca gaaaaggtat ttacttgtgc tggatgatgt ttggaacgaa     840
gatcaacaca gtggacgga tctgagggag ttgctgatga attgttccag aggtagtaaa      900
attgttgtca ctacacgtag taagatggtt gctttgatta ctggaacagt tccgccttat     960
tatttgggag gccttgctaa tgatgactgc ttatctttat ttttgaaatg tgcatttgga    1020
ggacaggaca atttgtttcc taatctagta gaaataggaa agaaattgt gaaaaagtgt    1080
ggaggagtgc ctttggctgt gaaaaccttg ggaaggttgt tgtacatgaa acagacgag     1140
aatgaatggt tgcagataag agataatgag atatgggaaa tcgaacagaa taaatctgac    1200
attttaccaa tattgagatt gagctatgaa cagatgccat cacatctaag acagtgcttt    1260
gcctattgct ccatgttacc caaggtcaa gaattccga gggaggattt tatcaatcgc      1320
tggattgctc aaggatttat acagagttcc aacagaaaca ggaagctgga agatatcggt    1380
```

```
aatcagtact tgatgagtt gctatcaagg ttttgcttcc tagatgtggt acaagctttt    1440
gatggagaaa tattggcttg taagatacac aatcttgtgc atgatcttgc acagtcagta    1500
tcaggtgcag agtgcttaaa tgtgaaaccc aatgctttcg tggtctctga agagttcgc    1560 cacttatttt tccatgcaga agatatgtct aggaaacact tccccagatt tttgcttcct    1620
ttgcaaaagt tgaggtcttt ctcttattct tttaacattg gacctgtaaa caagttcttt    1680
gtcaagacaa tgttgtcaaa tttcaaatgc cttcggatgc tagtcttgaa caatctagat    1740
cttgaggagt tgccaacttc gataggtcac ttgaaggaat taagatacct caaccttagt    1800
gacagtggta agatcaagtt tcttccaagg tctatgagca aattagtaaa tctgcacacc    1860
ctaaacctca ttaactgtga acagcttaag gagttgccaa gagattttag aaagttaatc    1920
agcctgaaga ccttgtattt gactacacat cagatgtcag cagggatcaa gaatcaacat    1980
tctttcactt ctcttcaatt tttacttctt ttcaaatgtt gtttcccaaa attgcagcca    2040
gaactggtgc agcattttac ygcacttcgg gttttgcgta tctatgaatg cccaagttta    2100
tgttctcttc caagcagtat tagatatctg acttcacttg aaaagctatg gatctggaac    2160
tgtgaagaac ttgatttgat tgatggagaa gggatgtcag gcctaacaag tcttcaatcc    2220
ttgcttctaa tggggcttcc taagttggtg actctaccat tggaacttaa agatactgct    2280
cctacaacat taaagtactt cagaatcgcc gattgtccca acctggtgga gcttccagag    2340
tggctgccta attgctcctc acttcagaga ctctatatag aggattgtcc tgttttggca    2400
tcgatacctc aaggaatcta cagccacaat gccaacgtcc atataatcga ctgtccattg    2460
ctaggtggat ga    2472
```

<210> SEQ ID NO 19
<211> LENGTH: 823
<212> TYPE: PRT
<213> ORGANISM: Solanum lycopersicoides

<400> SEQUENCE: 19

```
Met Ala Glu Ser Phe Leu Phe Asn Ile Ile Glu Arg Val Leu Ala Lys
1               5                   10                  15

Val Ser Ser Ile Ala Val Tyr Glu Ile Ser Leu Ala Trp Asn Val Lys
            20                  25                  30

Thr Glu Leu Arg Lys Leu Gln Ser Thr Leu Ser Thr Ile Lys Ala Val
        35                  40                  45

Leu Leu Asp Ala Asn Glu Gln Lys Ala Lys Asn His Glu Val Arg Asp
    50                  55                  60

Trp Leu Glu Lys Leu Arg Asp Val Val Tyr Asp Val Asp Asp Leu Met
65                  70                  75                  80

Asp Asp Leu Ser Thr Gln Leu Leu Leu Gln Met His Phe Gln Lys Ser
                85                  90                  95

Phe Arg Lys Lys Val Arg Arg Phe Phe Ser Ser Asn Pro Ile Ile
            100                 105                 110

Tyr Arg Phe Lys Ile Gly Arg Lys Val Lys Glu Ile Arg Glu Leu Leu
        115                 120                 125

Asn Glu Ile Ala Asp Asp Arg Arg Asn Phe His Phe Thr Glu His Thr
    130                 135                 140

Tyr Val Ile Pro Ala Glu Asn Thr Ser Arg Glu Gln Thr His Ser Phe
145                 150                 155                 160

Val Arg Ala Ser Asp Ile Ile Gly Arg Asp Asp Gln Glu Asn Ile
            165                 170                 175
```

```
Val Lys Gln Leu Ile Asp Ser His Asp Glu Asn Ile Ser Val Ile
            180                 185                 190

Pro Ile Val Gly Leu Gly Gly Leu Gly Lys Thr Thr Leu Val Lys Leu
            195                 200                 205

Val Tyr Asn Asn Asn Arg Val Val Gln Asn Phe Asp Leu Arg Met Trp
    210                 215                 220

Val Ser Ile Ser Glu Asp Phe Ser Leu Ser Lys Val Ile Glu Lys Ile
225                 230                 235                 240

Leu Arg Ser Ala Thr Gly Glu Ser Phe Asp His Leu Asp Met Asp Gln
                245                 250                 255

Leu Gln Cys Cys Leu Gly Glu Val Leu Gln Gln Lys Arg Tyr Leu Leu
            260                 265                 270

Val Leu Asp Asp Val Trp Asn Glu Asp Gln His Lys Trp Thr Asp Leu
    275                 280                 285

Arg Glu Leu Leu Met Asn Cys Ser Arg Gly Ser Lys Ile Val Val Thr
            290                 295                 300

Thr Arg Ser Lys Met Val Ala Leu Ile Thr Gly Thr Val Pro Pro Tyr
305                 310                 315                 320

Tyr Leu Gly Gly Leu Ala Asn Asp Asp Cys Leu Ser Leu Phe Leu Lys
                325                 330                 335

Cys Ala Phe Gly Gly Gln Asp Asn Leu Phe Pro Asn Leu Val Glu Ile
            340                 345                 350

Gly Lys Glu Ile Val Lys Lys Cys Gly Gly Val Pro Leu Ala Val Lys
    355                 360                 365

Thr Leu Gly Arg Leu Leu Tyr Met Lys Thr Asp Glu Asn Glu Trp Leu
            370                 375                 380

Gln Ile Arg Asp Asn Glu Ile Trp Glu Ile Glu Gln Asn Lys Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Pro Lys Gly Gln Glu Ile
            420                 425                 430

Pro Arg Glu Asp Phe Ile Asn Arg Trp Ile Ala Gln Gly Phe Ile Gln
    435                 440                 445

Ser Ser Asn Arg Asn Arg Lys Leu Glu Asp Ile Gly Asn Gln Tyr Phe
450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Ile His Asn Leu Val His Asp Leu
                485                 490                 495

Ala Gln Ser Val Ser Gly Ala Glu Cys Leu Asn Val Lys Pro Asn Ala
            500                 505                 510

Phe Val Val Ser Glu Arg Val Arg His Leu Phe Phe His Ala Glu Asp
    515                 520                 525

Met Ser Arg Lys His Phe Pro Arg Phe Leu Pro Leu Gln Lys Leu
            530                 535                 540

Arg Ser Phe Ser Tyr Ser Phe Asn Ile Gly Pro Val Asn Lys Phe Phe
545                 550                 555                 560

Val Lys Thr Met Leu Ser Asn Phe Lys Cys Leu Arg Met Leu Val Leu
                565                 570                 575

Asn Asn Leu Asp Leu Glu Glu Leu Pro Thr Ser Ile Gly His Leu Lys
            580                 585                 590
```

-continued

```
Glu Leu Arg Tyr Leu Asn Leu Ser Asp Ser Gly Lys Ile Lys Phe Leu
            595                 600                 605

Pro Arg Ser Met Ser Lys Leu Val Asn Leu His Thr Leu Asn Leu Ile
610                 615                 620

Asn Cys Glu Gln Leu Lys Glu Leu Pro Arg Asp Phe Arg Lys Leu Ile
625                 630                 635                 640

Ser Leu Lys Thr Leu Tyr Leu Thr Thr His Gln Met Ser Ala Gly Ile
                645                 650                 655

Lys Asn Gln His Ser Phe Thr Ser Leu Gln Phe Leu Leu Leu Phe Lys
            660                 665                 670

Cys Cys Phe Pro Lys Leu Gln Pro Glu Leu Val Gln His Phe Thr Ala
        675                 680                 685

Leu Arg Val Leu Arg Ile Tyr Glu Cys Pro Ser Leu Cys Ser Leu Pro
    690                 695                 700

Ser Ser Ile Arg Tyr Leu Thr Ser Leu Glu Lys Leu Trp Ile Trp Asn
705                 710                 715                 720

Cys Glu Glu Leu Asp Leu Ile Asp Gly Glu Gly Met Ser Gly Leu Thr
                725                 730                 735

Ser Leu Gln Ser Leu Leu Met Gly Leu Pro Lys Leu Val Thr Leu
            740                 745                 750

Pro Leu Glu Leu Lys Asp Thr Ala Pro Thr Thr Leu Lys Tyr Phe Arg
        755                 760                 765

Ile Ala Asp Cys Pro Asn Leu Val Glu Leu Pro Glu Trp Leu Pro Asn
    770                 775                 780

Cys Ser Ser Leu Gln Arg Leu Tyr Ile Glu Asp Cys Pro Val Leu Ala
785                 790                 795                 800

Ser Ile Pro Gln Gly Ile Tyr Ser His Asn Ala Asn Val His Ile Ile
                805                 810                 815

Asp Cys Pro Leu Leu Gly Gly
            820

<210> SEQ ID NO 20
<211> LENGTH: 20
<212> TYPE: DNA
<213> ORGANISM: Artificial
<220> FEATURE:
<223> OTHER INFORMATION: primer Spenn-ch04_541669

<400> SEQUENCE: 20
taatgaggca gagcaagttt                                              20

<210> SEQ ID NO 21
<211> LENGTH: 20
<212> TYPE: DNA
<213> ORGANISM: Artificial
<220> FEATURE:
<223> OTHER INFORMATION: primer Spenn-ch04_5416620

<400> SEQUENCE: 21
ccctcaagaa ccatgaatca                                              20

<210> SEQ ID NO 22
<211> LENGTH: 36
<212> TYPE: DNA
<213> ORGANISM: Artificial
<220> FEATURE:
<223> OTHER INFORMATION: primer oCM26

<400> SEQUENCE: 22
```
caccatgaaa attgctccag ttgccataaa tcacag                               36

<210> SEQ ID NO 23
<211> LENGTH: 20
<212> TYPE: DNA
<213> ORGANISM: Artificial
<220> FEATURE:
<223> OTHER INFORMATION: primer oCM27

<400> SEQUENCE: 23
cacacgcaat gctctaccgc                                                 20

<210> SEQ ID NO 24
<211> LENGTH: 31
<212> TYPE: DNA
<213> ORGANISM: Artificial
<220> FEATURE:
<223> OTHER INFORMATION: primer oCM20

<400> SEQUENCE: 24
atcgggaatt cgtgctgatg gatgctgcag g                                    31

<210> SEQ ID NO 25
<211> LENGTH: 41
<212> TYPE: DNA
<213> ORGANISM: Artificial
<220> FEATURE:
<223> OTHER INFORMATION: primer oCM21

<400> SEQUENCE: 25
ccacgtgaag ataccttgct gcttgttaag tcgtccgttg g                         41

<210> SEQ ID NO 26
<211> LENGTH: 23
<212> TYPE: DNA
<213> ORGANISM: Artificial
<220> FEATURE:
<223> OTHER INFORMATION: primer oCM22

<400> SEQUENCE: 26
agcaaggtat cttcacgtgg cgg                                             23

<210> SEQ ID NO 27
<211> LENGTH: 31
<212> TYPE: DNA
<213> ORGANISM: Artificial
<220> FEATURE:
<223> OTHER INFORMATION: primer oCM23

<400> SEQUENCE: 27
atcggcccgg gttctgcgag cgatttgcgg g                                    31

<210> SEQ ID NO 28
<211> LENGTH: 23
<212> TYPE: DNA
<213> ORGANISM: Artificial
<220> FEATURE:
<223> OTHER INFORMATION: primer oCM38

<400> SEQUENCE: 28
ctgatcatgt gtgccttgac ccc                                             23

<210> SEQ ID NO 29
<211> LENGTH: 22
<212> TYPE: DNA
<213> ORGANISM: Artificial

-continued

```
<220> FEATURE:
<223> OTHER INFORMATION: primer oCM39

<400> SEQUENCE: 29
ggactgcagg gtgtttatcg gg                                              22

<210> SEQ ID NO 30
<211> LENGTH: 21
<212> TYPE: DNA
<213> ORGANISM: Artificial
<220> FEATURE:
<223> OTHER INFORMATION: primer 3719

<400> SEQUENCE: 30
ttagctcact cattaggcac c                                               21

<210> SEQ ID NO 31
<211> LENGTH: 19
<212> TYPE: DNA
<213> ORGANISM: Artificial
<220> FEATURE:
<223> OTHER INFORMATION: primer 3720

<400> SEQUENCE: 31
cctcttcgct attacgcca                                                  19

<210> SEQ ID NO 32
<211> LENGTH: 30
<212> TYPE: DNA
<213> ORGANISM: Artificial
<220> FEATURE:
<223> OTHER INFORMATION: primer oCM28

<400> SEQUENCE: 32
atagaggttc cagcccgtgg agggtggttc                                      30

<210> SEQ ID NO 33
<211> LENGTH: 28
<212> TYPE: DNA
<213> ORGANISM: Artificial
<220> FEATURE:
<223> OTHER INFORMATION: primer oCM29

<400> SEQUENCE: 33
ccctccacgg gctggaacct ctatcttg                                        28

<210> SEQ ID NO 34
<211> LENGTH: 26
<212> TYPE: DNA
<213> ORGANISM: Artificial
<220> FEATURE:
<223> OTHER INFORMATION: primer oCM30

<400> SEQUENCE: 34
gcgaatggga gcttggtatg cctgcg                                          26

<210> SEQ ID NO 35
<211> LENGTH: 27
<212> TYPE: DNA
<213> ORGANISM: Artificial
<220> FEATURE:
<223> OTHER INFORMATION: primer oCM31

<400> SEQUENCE: 35
cataccaagc tcccattcgc tcattac                                         27
```

<210> SEQ ID NO 36
<211> LENGTH: 25
<212> TYPE: DNA
<213> ORGANISM: Artificial
<220> FEATURE:
<223> OTHER INFORMATION: primer oCM74

<400> SEQUENCE: 36
gcgaatggga tattggtatg cctgc                                                25

<210> SEQ ID NO 37
<211> LENGTH: 29
<212> TYPE: DNA
<213> ORGANISM: Artificial
<220> FEATURE:
<223> OTHER INFORMATION: primer oCM75

<400> SEQUENCE: 37
gcataccaat atcccattcg ctcattacc                                            29

<210> SEQ ID NO 38
<211> LENGTH: 26
<212> TYPE: DNA
<213> ORGANISM: Artificial
<220> FEATURE:
<223> OTHER INFORMATION: primer oCM76

<400> SEQUENCE: 38
agaatggttg accattctgt cgaagc                                               26

<210> SEQ ID NO 39
<211> LENGTH: 26
<212> TYPE: DNA
<213> ORGANISM: Artificial
<220> FEATURE:
<223> OTHER INFORMATION: primer oCM77

<400> SEQUENCE: 39
agcttcgaca gaatggtcaa ccattc                                               26

<210> SEQ ID NO 40
<211> LENGTH: 30
<212> TYPE: DNA
<213> ORGANISM: Artificial
<220> FEATURE:
<223> OTHER INFORMATION: primer oCM104

<400> SEQUENCE: 40
cctaagactg ccggagctct atgagggaag                                           30

<210> SEQ ID NO 41
<211> LENGTH: 34
<212> TYPE: DNA
<213> ORGANISM: Artificial
<220> FEATURE:
<223> OTHER INFORMATION: primer oCM105

<400> SEQUENCE: 41
agagctccgg cagtcttagg cgaggcccag cttc                                      34

<210> SEQ ID NO 42
<211> LENGTH: 32
<212> TYPE: DNA
<213> ORGANISM: Artificial
<220> FEATURE:
<223> OTHER INFORMATION: primer oCM86

-continued

<400> SEQUENCE: 42
ctatgaggga aggtcaggcc cagctgggct ac                                32

<210> SEQ ID NO 43
<211> LENGTH: 32
<212> TYPE: DNA
<213> ORGANISM: Artificial
<220> FEATURE:
<223> OTHER INFORMATION: primer oCM87

<400> SEQUENCE: 43
gtagcccagc tgggcctgac cttccctcat ag                                32

<210> SEQ ID NO 44
<211> LENGTH: 26
<212> TYPE: DNA
<213> ORGANISM: Artificial
<220> FEATURE:
<223> OTHER INFORMATION: primer oCM32

<400> SEQUENCE: 44
gtgcactgtt gtgtaagcac gggccg                                       26

<210> SEQ ID NO 45
<211> LENGTH: 29
<212> TYPE: DNA
<213> ORGANISM: Artificial
<220> FEATURE:
<223> OTHER INFORMATION: primer oCM33

<400> SEQUENCE: 45
ccgtgcttac acaacagtgc acccaactc                                    29

<210> SEQ ID NO 46
<211> LENGTH: 26
<212> TYPE: DNA
<213> ORGANISM: Artificial
<220> FEATURE:
<223> OTHER INFORMATION: primer oCM109

<400> SEQUENCE: 46
gttgggtgca ctgttgtcta agcacg                                       26

<210> SEQ ID NO 47
<211> LENGTH: 24
<212> TYPE: DNA
<213> ORGANISM: Artificial
<220> FEATURE:
<223> OTHER INFORMATION: primer oCM110

<400> SEQUENCE: 47
ccgtgcttag acaacagtgc accc                                         24

<210> SEQ ID NO 48
<211> LENGTH: 31
<212> TYPE: DNA
<213> ORGANISM: Artificial
<220> FEATURE:
<223> OTHER INFORMATION: primer oCM80

<400> SEQUENCE: 48
gttgtataag cacaggccga ttatatttgg g                                 31

<210> SEQ ID NO 49

```
<211> LENGTH: 31
<212> TYPE: DNA
<213> ORGANISM: Artificial
<220> FEATURE:
<223> OTHER INFORMATION: primer oCM81

<400> SEQUENCE: 49
cccaaatata atcggcctgt gcttatacaa c                              31

<210> SEQ ID NO 50
<211> LENGTH: 30
<212> TYPE: DNA
<213> ORGANISM: Artificial
<220> FEATURE:
<223> OTHER INFORMATION: primer oCM106

<400> SEQUENCE: 50
gctgggctat gtcggtcctc actggtgtcg                                30

<210> SEQ ID NO 51
<211> LENGTH: 37
<212> TYPE: DNA
<213> ORGANISM: Artificial
<220> FEATURE:
<223> OTHER INFORMATION: primer oCM107

<400> SEQUENCE: 51
gaggaccgac atagcccagc tgtcattcgg agttttc                        37

<210> SEQ ID NO 52
<211> LENGTH: 30
<212> TYPE: DNA
<213> ORGANISM: Artificial
<220> FEATURE:
<223> OTHER INFORMATION: primer oCM34

<400> SEQUENCE: 52
ctcactggtg tcgaaaaaga gacgtcgtcc                                30

<210> SEQ ID NO 53
<211> LENGTH: 30
<212> TYPE: DNA
<213> ORGANISM: Artificial
<220> FEATURE:
<223> OTHER INFORMATION: primer oCM35

<400> SEQUENCE: 53
gacgtctctt tttcgacacc agtgaggacc                                30

<210> SEQ ID NO 54
<211> LENGTH: 20
<212> TYPE: DNA
<213> ORGANISM: Artificial
<220> FEATURE:
<223> OTHER INFORMATION: primer Chr4_4976565F

<400> SEQUENCE: 54
gaagccaatg tctgcagctg                                           20

<210> SEQ ID NO 55
<211> LENGTH: 20
<212> TYPE: DNA
<213> ORGANISM: Artificial
<220> FEATURE:
<223> OTHER INFORMATION: primer Chr4_4976565R

<400> SEQUENCE: 55
```
gccggtcatc agctaggtac                                                  20

<210> SEQ ID NO 56
<211> LENGTH: 20
<212> TYPE: DNA
<213> ORGANISM: Artificial
<220> FEATURE:
<223> OTHER INFORMATION: primer Spennch04_6606838F

<400> SEQUENCE: 56
ctggcctcat tcttatggtt                                                  20

<210> SEQ ID NO 57
<211> LENGTH: 20
<212> TYPE: DNA
<213> ORGANISM: Artificial
<220> FEATURE:
<223> OTHER INFORMATION: primer Spennch04_6606838R

<400> SEQUENCE: 57
taaagggagc tttcgaacaa                                                  20

<210> SEQ ID NO 58
<211> LENGTH: 20
<212> TYPE: DNA
<213> ORGANISM: Artificial
<220> FEATURE:
<223> OTHER INFORMATION: primer Spennch04_7503010F

<400> SEQUENCE: 58
ctaagcatgg attttagcgc                                                  20

<210> SEQ ID NO 59
<211> LENGTH: 20
<212> TYPE: DNA
<213> ORGANISM: Artificial
<220> FEATURE:
<223> OTHER INFORMATION: primer Spennch04_7503010R

<400> SEQUENCE: 59
caacccttga atcatggaga                                                  20

<210> SEQ ID NO 60
<211> LENGTH: 20
<212> TYPE: DNA
<213> ORGANISM: Artificial
<220> FEATURE:
<223> OTHER INFORMATION: primer Spenn-ch04_5416619

<400> SEQUENCE: 60
taatgaggca gagcaagttt                                                  20

<210> SEQ ID NO 61
<211> LENGTH: 20
<212> TYPE: DNA
<213> ORGANISM: Artificial
<220> FEATURE:
<223> OTHER INFORMATION: primer Spenn-ch04_5416620

<400> SEQUENCE: 61
ccctcaagaa ccatgaatca                                                  20

<210> SEQ ID NO 62
<211> LENGTH: 36
<212> TYPE: DNA

```
<213> ORGANISM: Artificial
<220> FEATURE:
<223> OTHER INFORMATION: primer oCM26

<400> SEQUENCE: 62
caccatgaaa attgctccag ttgccataaa tcacag                                36

<210> SEQ ID NO 63
<211> LENGTH: 20
<212> TYPE: DNA
<213> ORGANISM: Artificial
<220> FEATURE:
<223> OTHER INFORMATION: primer oCM27

<400> SEQUENCE: 63
cacacgcaat gctctaccgc                                                  20

<210> SEQ ID NO 64
<211> LENGTH: 20
<212> TYPE: DNA
<213> ORGANISM: Artificial
<220> FEATURE:
<223> OTHER INFORMATION: primer KS12

<400> SEQUENCE: 64
atggctcgtc caaatgtccc                                                  20

<210> SEQ ID NO 65
<211> LENGTH: 20
<212> TYPE: DNA
<213> ORGANISM: Artificial
<220> FEATURE:
<223> OTHER INFORMATION: primer KS13

<400> SEQUENCE: 65
gccagggaca acaacaccac                                                  20

<210> SEQ ID NO 66
<211> LENGTH: 22
<212> TYPE: DNA
<213> ORGANISM: Artificial
<220> FEATURE:
<223> OTHER INFORMATION: primer KS14

<400> SEQUENCE: 66
ttaccaggga caacaacacc ac                                               22

<210> SEQ ID NO 67
<211> LENGTH: 19
<212> TYPE: DNA
<213> ORGANISM: Artificial
<220> FEATURE:
<223> OTHER INFORMATION: primer KS15

<400> SEQUENCE: 67
atggctcgtg caaatgtgc                                                   19

<210> SEQ ID NO 68
<211> LENGTH: 20
<212> TYPE: DNA
<213> ORGANISM: Artificial
<220> FEATURE:
<223> OTHER INFORMATION: primer KS16

<400> SEQUENCE: 68
gccacaaagg aaagcagcag                                                  20
```

<210> SEQ ID NO 69
<211> LENGTH: 22
<212> TYPE: DNA
<213> ORGANISM: Artificial
<220> FEATURE:
<223> OTHER INFORMATION: primer KS17

<400> SEQUENCE: 69
tcaccacaaa ggaaagcagc ag                                              22

<210> SEQ ID NO 70
<211> LENGTH: 23
<212> TYPE: DNA
<213> ORGANISM: Artificial
<220> FEATURE:
<223> OTHER INFORMATION: primer KS18

<400> SEQUENCE: 70
atggcaaaac actcacaagt acc                                             23

<210> SEQ ID NO 71
<211> LENGTH: 20
<212> TYPE: DNA
<213> ORGANISM: Artificial
<220> FEATURE:
<223> OTHER INFORMATION: primer KS19

<400> SEQUENCE: 71
gactccgacc ccatggaaag                                                 20

<210> SEQ ID NO 72
<211> LENGTH: 22
<212> TYPE: DNA
<213> ORGANISM: Artificial
<220> FEATURE:
<223> OTHER INFORMATION: primer KS20

<400> SEQUENCE: 72
tcaactccga ccccatggaa ag                                              22

<210> SEQ ID NO 73
<211> LENGTH: 22
<212> TYPE: DNA
<213> ORGANISM: Artificial
<220> FEATURE:
<223> OTHER INFORMATION: primer KS24

<400> SEQUENCE: 73
atggcacgtt cgaatgtacc aa                                              22

<210> SEQ ID NO 74
<211> LENGTH: 23
<212> TYPE: DNA
<213> ORGANISM: Artificial
<220> FEATURE:
<223> OTHER INFORMATION: primer KS25

<400> SEQUENCE: 74
tcattttcct ccaaagccaa agc                                             23

<210> SEQ ID NO 75
<211> LENGTH: 47
<212> TYPE: DNA
<213> ORGANISM: Artificial
<220> FEATURE:

```
<223> OTHER INFORMATION: primer oCM206

<400> SEQUENCE: 75
tttggagagg acagggtacc atggcggaat ctttcttgtt caatatc            47

<210> SEQ ID NO 76
<211> LENGTH: 36
<212> TYPE: DNA
<213> ORGANISM: Artificial
<220> FEATURE:
<223> OTHER INFORMATION: primer oCM207

<400> SEQUENCE: 76
gtcgtatggg taaggtccac ctagcaatgg acagtc                        36

<210> SEQ ID NO 77
<211> LENGTH: 40
<212> TYPE: DNA
<213> ORGANISM: Artificial
<220> FEATURE:
<223> OTHER INFORMATION: primer oCM208

<400> SEQUENCE: 77
tttggagagg acagggtacc atggctgatg cctttgtgtc                    40

<210> SEQ ID NO 78
<211> LENGTH: 47
<212> TYPE: DNA
<213> ORGANISM: Artificial
<220> FEATURE:
<223> OTHER INFORMATION: primer oCM209

<400> SEQUENCE: 78
gtcgtatggg taagggattg aaacatgtga agcttttcaa ccatata            47

<210> SEQ ID NO 79
<211> LENGTH: 57
<212> TYPE: DNA
<213> ORGANISM: Artificial
<220> FEATURE:
<223> OTHER INFORMATION: primer oSM03

<400> SEQUENCE: 79
ggggacaagt ttgtacaaaa aagcaggctt tgagctatga acagatgcca tcacatc  57

<210> SEQ ID NO 80
<211> LENGTH: 60
<212> TYPE: DNA
<213> ORGANISM: Artificial
<220> FEATURE:
<223> OTHER INFORMATION: primer oSM04

<400> SEQUENCE: 80
ggggaccact ttgtacaaga aagctgggta aagcattggg tttcacattt aagcactctg  60

<210> SEQ ID NO 81
<211> LENGTH: 57
<212> TYPE: DNA
<213> ORGANISM: Artificial
<220> FEATURE:
<223> OTHER INFORMATION: primer oSM15

<400> SEQUENCE: 81
ggggacaagt ttgtacaaaa aagcaggctt tgagctatga acagatgcca tcacatc  57
```

```
<210> SEQ ID NO 82
<211> LENGTH: 60
<212> TYPE: DNA
<213> ORGANISM: Artificial
<220> FEATURE:
<223> OTHER INFORMATION: primer oSM16

<400> SEQUENCE: 82
ggggaccact tgtacaaga aagctgggta aagcattggg tttcacattt aagcactctg     60

<210> SEQ ID NO 83
<211> LENGTH: 47
<212> TYPE: DNA
<213> ORGANISM: Artificial
<220> FEATURE:
<223> OTHER INFORMATION: primer oCM206

<400> SEQUENCE: 83
tttggagagg acagggtacc atggcggaat ctttcttgtt caatatc                  47

<210> SEQ ID NO 84
<211> LENGTH: 36
<212> TYPE: DNA
<213> ORGANISM: Artificial
<220> FEATURE:
<223> OTHER INFORMATION: primer oCM207

<400> SEQUENCE: 84
gtcgtatggg taaggtccac ctagcaatgg acagtc                              36

<210> SEQ ID NO 85
<211> LENGTH: 254
<212> TYPE: PRT
<213> ORGANISM: Solanum lycopersicum

<400> SEQUENCE: 85
```

Met Ala Arg Pro Asn Val Pro Lys Phe Gly Asn Trp Glu Asn Asp Asp
1               5                   10                  15

Asn Thr Pro Tyr Thr Val Tyr Phe Glu Lys Ala Arg Gln Thr Arg Gly
                20                  25                  30

Thr Gly Lys Met Met Asn Pro Asn Asp Pro Glu Glu Asn Pro Asp Met
            35                  40                  45

Phe Arg Asn Leu Ala Pro Pro Glu Val Ala Pro Gln Ser Lys Pro
    50                  55                  60

Lys Arg Gln Thr Glu Glu Pro Pro Ile Gly Arg Gly Pro Ala Arg
65                  70                  75                  80

Gln Thr Arg Asp His Arg Leu Ser Lys Glu Asp Gly Glu Phe Arg Gln
                85                  90                  95

Tyr Ala Asn Ser Pro Ala Arg Lys Glu Ser Val Gly Arg Lys Gly Ala
            100                 105                 110

Asn Glu Pro Ser His Gln Arg Gly Arg Gly Ser Asn Ser Gly Arg Thr
        115                 120                 125

Gly Arg Gln Ser Ile Gly Ser Glu His Ser Phe Asp Lys Ser Pro Leu
    130                 135                 140

His Pro His Tyr Gln Ala Lys Val Ser Asn Ala Gly Arg Gly Val Ala
145                 150                 155                 160

Ser Pro Ala Trp Glu Gly Lys Asn Asn Ser Tyr Asp Ser Ser His Gly
                165                 170                 175

Thr Pro Gly Arg Ser Lys Val Leu Gln Asp Lys Ser Asp Ser Arg Gly Ala
            180                 185                 190

Ala Val Pro Arg Phe Gly Glu Trp Asp Glu Asn Asp Pro Gln Ser Ala
        195                 200                 205

Asp Asn Tyr Thr His Ile Phe Asn Lys Phe Arg Glu Glu Lys Gln Gly
        210                 215                 220

Asn Pro Ser Gly Thr Pro Ser Arg Thr Ser Asn Asn Thr Gln Lys His
225                 230                 235                 240

Asn Ser Glu Glu Lys Gln Arg Lys Trp Cys Cys Cys Pro Trp
                245                 250

<210> SEQ ID NO 86
<211> LENGTH: 243
<212> TYPE: PRT
<213> ORGANISM: Solanum lycopersicum

<400> SEQUENCE: 86

Met Ala Arg Ala Asn Val Pro Lys Phe Gly Asn Trp Gly Asn Glu Asp
1               5                   10                  15

Asn Thr Pro Tyr Thr Val Val Phe Glu Asn Ala Arg Lys Asn Arg Gly
            20                  25                  30

Gly Lys Met Ile Asn Pro Asn Asp Pro Gln Glu Asn Pro Asp Met Phe
        35                  40                  45

Pro Asn Val Ala Pro Ser Ser Arg Pro Lys Thr Pro Pro Thr Glu Glu
    50                  55                  60

Pro Met Gly Met Glu Thr Ala Arg Gln Thr Asn Lys Arg Arg Val Ser
65                  70                  75                  80

Lys Glu Asp Gly Asp Phe Arg Ala Ser Ser Pro Ala Arg Asn Glu Pro
                85                  90                  95

Thr Thr His Gln Arg His Gly Gly Arg Gly Ser Asn Ser Gly Arg
            100                 105                 110

Pro Ser Arg Gln Ser Gly Gly Ser Asp His Ser Ile Ala Lys Ser Pro
        115                 120                 125

Leu His Pro Asn Ser Gln Ala Lys Ile Ser Gly Arg Val Ala Ala Ser
    130                 135                 140

Pro Val Trp Glu Gly Lys Asn Leu Tyr Asp Ser Ser His Gly Thr Pro
145                 150                 155                 160

Gly Arg Ser Phe Glu Ser Ser His Ala Thr Pro Gly Arg His Gln Met
                165                 170                 175

Lys Gln Glu Ser Pro Asp Arg Gly Thr Val Val Pro Lys Phe Gly Gly
            180                 185                 190

Trp Asp Asp Asn Asp Pro Gln Asp Ala Glu Asn Tyr Thr Glu Val Phe
        195                 200                 205

Asn Lys Val Arg Glu Gln Arg His Val Asp Thr Gly Asn Met Pro Ala
    210                 215                 220

Ala Gly Val Arg Thr Ser Tyr Ser Thr Gln Arg Gln Gln Arg Asn Glu
225                 230                 235                 240

Lys Gln Lys

<210> SEQ ID NO 87
<211> LENGTH: 224
<212> TYPE: PRT
<213> ORGANISM: Solanum lycopersicum

<400> SEQUENCE: 87

Met Ala Gly Ser His Val Pro Lys Phe Gly Asn Trp Asp Gly Glu Asn
1               5                   10                  15

Val Pro Tyr Thr Ala Tyr Phe Glu Asn Ala Arg Lys Ser Asn Ser Lys

```
                    20                  25                  30
Gly Gly Lys Met Ile Asn Pro Asn Asp Pro Glu Glu Asn Pro Glu Ala
                35                  40                  45

Phe Ala Tyr Cys Gly Asp Glu Asp Ala Asn Ile Asn Ile Ser Pro Leu
            50                  55                  60

Val Glu Lys His Gln Tyr His Tyr Asp His Arg Asn Pro Ser Val
 65                  70                  75                  80

Glu Ser Gly Gln Asn Lys Ser Ile Gly Pro Thr Asn Ser Asn Ser Glu
                85                  90                  95

Ser Phe Gly Asp Ser Gln Arg Lys Ser Val Ser Gly Phe Ser Val Asn
            100                 105                 110

Gln Pro Thr Arg Arg Arg Thr Ser Asp Val Lys Lys Asn Lys Asn
        115                 120                 125

Asp Arg Gly Asn Gly Phe Val Pro Pro Ser Pro Asn Arg Pro Met Lys
            130                 135                 140

Asn Ser Arg Asn Pro Ser Asp Asp Leu Ser Cys Ser Ser Ala Ala Ser
145                 150                 155                 160

Val Pro Lys Phe Gly Ala Trp Asp Glu Lys Asp Pro Lys Ser Gly Glu
                165                 170                 175

Gly Phe Thr Val Ile Phe Asn Lys Val Lys Glu Lys His Ile Ala
            180                 185                 190

Ala Ala Lys Phe Pro Val Val Gln Pro Gln Ser Asn Met Ser Ser Ser
        195                 200                 205

Asn Asn His Lys Lys Asn Ala Lys Ser Lys Val Phe Cys Cys Leu Phe
210                 215                 220

<210> SEQ ID NO 88
<211> LENGTH: 211
<212> TYPE: PRT
<213> ORGANISM: Arabidopsis thaliana

<400> SEQUENCE: 88

Met Ala Arg Ser Asn Val Pro Lys Phe Gly Asn Trp Glu Ala Glu Glu
 1               5                  10                  15

Asn Val Pro Tyr Thr Ala Tyr Phe Asp Lys Ala Arg Lys Thr Arg Ala
                20                  25                  30

Pro Gly Ser Lys Ile Met Asn Pro Asn Asp Pro Glu Tyr Asn Ser Asp
            35                  40                  45

Ser Gln Ser Gln Ala Pro Pro His Pro Pro Ser Ser Arg Thr Lys Pro
        50                  55                  60

Glu Gln Val Asp Thr Val Arg Arg Ser Arg Glu His Met Arg Ser Arg
 65                  70                  75                  80

Glu Glu Ser Glu Leu Lys Gln Phe Gly Asp Ala Gly Gly Ser Ser Asn
                85                  90                  95

Glu Ala Ala Asn Lys Arg Gln Gly Arg Ala Ser Gln Asn Asn Ser Tyr
            100                 105                 110

Asp Asn Lys Ser Pro Leu His Lys Asn Ser Tyr Asp Gly Thr Gly Lys
        115                 120                 125

Ser Arg Pro Lys Pro Thr Asn Leu Arg Ala Asp Glu Ser Pro Glu Lys
            130                 135                 140

Val Thr Val Val Pro Lys Phe Gly Asp Trp Asp Glu Asn Asn Pro Ser
145                 150                 155                 160

Ser Ala Asp Gly Tyr Thr His Ile Phe Asn Lys Val Arg Glu Glu Arg
                165                 170                 175
```

```
Ser Ser Gly Ala Asn Val Gly Ser Ser Arg Thr Pro Thr His Gln
            180                 185                 190

Ser Ser Arg Asn Pro Asn Asn Thr Ser Ser Cys Cys Cys Phe Gly Phe
        195                 200                 205

Gly Gly Lys
    210

<210> SEQ ID NO 89
<211> LENGTH: 239
<212> TYPE: PRT
<213> ORGANISM: Malus domestica

<400> SEQUENCE: 89

Met Ala Gln Arg Ser His Val Pro Lys Phe Gly Asn Trp Glu Asp Gln
1               5                   10                  15

Glu Ser Val Pro Tyr Thr Ala Tyr Phe Asp Lys Ala Arg Lys Gly Arg
            20                  25                  30

Thr Gly Val Gly Gly Lys Met Ile Asn Pro Asn Asp Pro Glu Glu Asn
        35                  40                  45

Pro Asp Ile Leu Ser Asp Thr Ser Ala Ser Pro Pro Lys Val Arg
50                  55                  60

Pro Glu Pro Gly Lys Pro Val His Glu Arg Arg Ser Arg Glu Asp
65                  70                  75                  80

Asn Asp Leu Arg Phe Ala Asn Ser Pro Ala Gln Arg Arg Ser Ser Gly
                85                  90                  95

Glu His Gln Pro Asn Arg Gly Arg Gly Val Ser Ser Gly Glu Thr His
            100                 105                 110

Arg Arg Ala Ala Arg Pro Ser Ala Gly Ser Glu Asn Ser Val Glu Arg
        115                 120                 125

Ser Pro Leu His Arg Asn Ala Arg Val Ser Gly Arg Asp Ser Pro Ser
    130                 135                 140

Trp Glu Gly Lys Ala Ser Tyr Glu Ser Ser His Gly Thr Pro Ala Arg
145                 150                 155                 160

Ser Arg Leu Lys Pro Arg Asp Glu Ser Pro Glu Lys Gly Ala Ala Val
                165                 170                 175

Pro Lys Phe Gly Glu Trp Asp Glu Asn Asp Pro Ala Ser Ala Asp Gly
            180                 185                 190

Phe Thr His Ile Phe Asn Lys Val Arg Glu Glu Lys Ala Gly Lys Ala
        195                 200                 205

Pro Gly Thr Pro Ser His Pro Ser Tyr Gln Asp Ala Arg Lys Gln Gly
    210                 215                 220

Ser Asn Asp Ser Ala Lys Cys Cys Cys Phe Pro Trp Gly Arg Lys
225                 230                 235

<210> SEQ ID NO 90
<211> LENGTH: 241
<212> TYPE: PRT
<213> ORGANISM: Malus domestica

<400> SEQUENCE: 90

Met Ala Gln Arg Ser His Val Pro Lys Phe Gly Asn Trp Glu Gly Glu
1               5                   10                  15

Glu Ser Val Pro Tyr Thr Ala Tyr Phe Asp Lys Ala Arg Lys Asp Arg
            20                  25                  30

Thr Gly Val Gly Gly Lys Met Ile Asn Pro Asn Asp Pro Gln Glu Asn
        35                  40                  45
```

```
Pro Asp Ile Leu Ser Asp Ile Ser Ala Ser Ser Pro Lys Val Arg
    50              55                  60

Pro Glu Pro Glu Lys Pro Val His Glu Gln Arg Arg Ser Arg Glu Asp
65              70                  75                  80

Asn Asp Leu Arg Phe Ala Asn Ser Pro Ala Gln Arg Arg Asn Ser Gly
                85                  90                  95

Glu Ser Ala His Gln Pro Ser Arg Gly Arg Gly Val Ser Ser Gly Glu
                100                 105                 110

Thr Arg Arg Pro Ala Arg Pro Ser Ala Gly Ser Glu Asn Ser Val
                115                 120                 125

Glu Arg Ser Pro Leu His Arg Asn Ala Arg Val Thr Gly Arg Asp Ser
    130                 135                 140

Pro Ser Trp Glu Gly Lys Ala Ser Tyr Glu Thr Ser His Gly Thr Pro
145                 150                 155                 160

Gly Arg Ser Arg Leu Lys Pro Arg Asp Glu Ser Pro Glu Lys Gly Ala
                165                 170                 175

Ala Val Pro Lys Phe Gly Glu Trp Asp Glu Asn Asp Pro Ala Ser Ala
                180                 185                 190

Asp Gly Phe Thr His Ile Phe Asn Lys Val Arg Glu Glu Arg Ala Gly
                195                 200                 205

Lys Val Pro Gly Thr Pro Ser Gln Pro Ser Tyr Gln Asp Ala Arg Arg
    210                 215                 220

Gln Gly Ser Asn Asp Ser Ala Lys Ser Cys Cys Phe Pro Trp Ser Arg
225                 230                 235                 240

Lys

<210> SEQ ID NO 91
<211> LENGTH: 14
<212> TYPE: PRT
<213> ORGANISM: Solanum lycopersicoides

<400> SEQUENCE: 91

Val Gly Leu Gly Gly Leu Gly Lys Thr Thr Leu Val Lys Leu
1               5                   10

<210> SEQ ID NO 92
<211> LENGTH: 14
<212> TYPE: PRT
<213> ORGANISM: Artificial
<220> FEATURE:
<223> OTHER INFORMATION: Multi Species NB ARC P LOOP Concensus

<400> SEQUENCE: 92

Val Gly Met Gly Gly Ile Gly Lys Thr Thr Leu Ala Lys Lys
1               5                   10

<210> SEQ ID NO 93
<211> LENGTH: 17
<212> TYPE: PRT
<213> ORGANISM: Solanum lycopersicoides

<400> SEQUENCE: 93

Gln Gln Lys Arg Tyr Leu Leu Val Leu Asp Asp Val Trp Asn Glu Asp
1               5                   10                  15

Gln

<210> SEQ ID NO 94
<211> LENGTH: 17
<212> TYPE: PRT
```

```
<213> ORGANISM: Artificial
<220> FEATURE:
<223> OTHER INFORMATION: Multi Species NB ARC Kinase 2 Concensus

<400> SEQUENCE: 94

Lys Gly Lys Arg Tyr Leu Ile Val Leu Asp Asp Val Trp Thr Asp
1               5                   10                  15

Gln

<210> SEQ ID NO 95
<211> LENGTH: 12
<212> TYPE: PRT
<213> ORGANISM: Solanum lycopersicoides

<400> SEQUENCE: 95

Ser Lys Ile Val Val Thr Thr Arg Ser Lys Met Val
1               5                   10

<210> SEQ ID NO 96
<211> LENGTH: 12
<212> TYPE: PRT
<213> ORGANISM: Artificial
<220> FEATURE:
<223> OTHER INFORMATION: Multi Species NB ARC Kinase 3a Concensus
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 96

Ser Arg Ile Ile Xaa Thr Thr Arg Asp Xaa Xaa Val
1               5                   10

<210> SEQ ID NO 97
<211> LENGTH: 13
<212> TYPE: PRT
<213> ORGANISM: Solanum lycopersicoides

<400> SEQUENCE: 97

Val Lys Lys Cys Gly Gly Val Pro Leu Ala Val Lys Thr
1               5                   10

<210> SEQ ID NO 98
<211> LENGTH: 13
<212> TYPE: PRT
<213> ORGANISM: Artificial
<220> FEATURE:
<223> OTHER INFORMATION: Multi Species NB ARC GLPL Concensus

<400> SEQUENCE: 98

Val Lys Lys Cys Lys Gly Leu Pro Leu Ala Leu Lys Val
1               5                   10

<210> SEQ ID NO 99
<211> LENGTH: 8
<212> TYPE: PRT
<213> ORGANISM: Solanum lycopersicoides

<400> SEQUENCE: 99

Asn Leu Val His Asp Leu Ala Gln
1               5
```

```
<210> SEQ ID NO 100
<211> LENGTH: 8
<212> TYPE: PRT
<213> ORGANISM: Artificial
<220> FEATURE:
<223> OTHER INFORMATION: Multi Species NB ARC MHD Concensus

<400> SEQUENCE: 100

Cys Arg Met His Asp Leu Ile Arg
1               5

<210> SEQ ID NO 101
<211> LENGTH: 14
<212> TYPE: PRT
<213> ORGANISM: Solanum lycopersicoides

<400> SEQUENCE: 101

Leu Arg Met Leu Val Leu Asn Asn Leu Asp Leu Glu Glu Leu
1               5                   10

<210> SEQ ID NO 102
<211> LENGTH: 14
<212> TYPE: PRT
<213> ORGANISM: Solanum lycopersicoides

<400> SEQUENCE: 102

Leu Arg Tyr Leu Asn Leu Ser Asp Ser Gly Lys Ile Lys Leu
1               5                   10

<210> SEQ ID NO 103
<211> LENGTH: 10
<212> TYPE: PRT
<213> ORGANISM: Solanum lycopersicoides

<400> SEQUENCE: 103

Leu Val Asn Leu His Thr Leu Asn Leu Ile
1               5                   10

<210> SEQ ID NO 104
<211> LENGTH: 9
<212> TYPE: PRT
<213> ORGANISM: Solanum lycopersicoides

<400> SEQUENCE: 104

Leu Lys Glu Leu Pro Arg Asp Phe Arg
1               5

<210> SEQ ID NO 105
<211> LENGTH: 9
<212> TYPE: PRT
<213> ORGANISM: Solanum lycopersicoides

<400> SEQUENCE: 105

Leu Ile Ser Leu Lys Thr Leu Tyr Leu
1               5

<210> SEQ ID NO 106
<211> LENGTH: 8
<212> TYPE: PRT
<213> ORGANISM: Solanum lycopersicoides

<400> SEQUENCE: 106

Leu Gln Phe Leu Leu Leu Phe Lys
1               5
```

```
<210> SEQ ID NO 107
<211> LENGTH: 15
<212> TYPE: PRT
<213> ORGANISM: Solanum lycopersicoides

<400> SEQUENCE: 107

Leu Gln Pro Glu Leu Val Gln His Phe Thr Ala Leu Arg Val Leu
1               5                   10                  15

<210> SEQ ID NO 108
<211> LENGTH: 9
<212> TYPE: PRT
<213> ORGANISM: Solanum lycopersicoides

<400> SEQUENCE: 108

Leu Cys Ser Leu Pro Ser Ser Ile Arg
1               5

<210> SEQ ID NO 109
<211> LENGTH: 17
<212> TYPE: PRT
<213> ORGANISM: Solanum lycopersicoides

<400> SEQUENCE: 109

Leu Thr Ser Leu Glu Lys Leu Trp Ile Trp Asn Cys Glu Glu Leu Asp
1               5                   10                  15

Leu

<210> SEQ ID NO 110
<211> LENGTH: 14
<212> TYPE: PRT
<213> ORGANISM: Solanum lycopersicoides

<400> SEQUENCE: 110

Leu Thr Ser Leu Gln Ser Leu Leu Leu Met Gly Leu Pro Lys
1               5                   10

<210> SEQ ID NO 111
<211> LENGTH: 16
<212> TYPE: PRT
<213> ORGANISM: Solanum lycopersicoides

<400> SEQUENCE: 111

Leu Val Thr Leu Pro Leu Glu Leu Lys Asp Thr Ala Pro Thr Thr Leu
1               5                   10                  15

<210> SEQ ID NO 112
<211> LENGTH: 10
<212> TYPE: PRT
<213> ORGANISM: Solanum lycopersicoides

<400> SEQUENCE: 112

Leu Val Glu Leu Pro Glu Trp Leu Pro Asn
1               5                   10

<210> SEQ ID NO 113
<211> LENGTH: 12
<212> TYPE: PRT
<213> ORGANISM: Solanum lycopersicoides

<400> SEQUENCE: 113

Leu Gln Arg Leu Tyr Ile Glu Asp Cys Pro Val Leu
1               5                   10
```

<210> SEQ ID NO 114
<211> LENGTH: 2492
<212> TYPE: DNA
<213> ORGANISM: Solanum lycopersicum

<400> SEQUENCE: 114

| | | | | | |
|---|---|---|---|---|---|
| atgtagatcc | ttgaacgtgt | tttggcgaaa | tctttcttgt | tcaatatcat | tgaacgtgtt | 60 |
| ttggctaaag | tttcttcaat | tgctatatat | gagatcagtc | tagcttggaa | tgttaagaca | 120 |
| gagctaagga | aactccaaag | tactctatcc | accatcaaag | ttgtacttct | agatgcaaac | 180 |
| gagcagcagg | cgaagaacca | tgaagtgaga | gattggctgg | aaaagctcag | agatgttgtt | 240 |
| tatgatgtcg | atgatttgat | ggatgattta | tcaacacaac | tgttgctgcg | aatgcatttc | 300 |
| gagtaaagct | ttaggaagaa | ggtaaggaag | ttcttttcag | gttcaaatcc | aattatatat | 360 |
| cgattcaaga | ttggcagaaa | agtaaaagaa | atcaaggagc | tgctgaatga | gattgcagat | 420 |
| gattggagaa | atttccactt | cacggaacat | acttatgtaa | ctccagctga | gaatacgagt | 480 |
| agagaacaaa | cacactcctt | tgtgagggca | tcagatatca | ttggtagaga | tgatgatcaa | 540 |
| gaaaacattg | tataacagct | gatagattct | catgatgagg | aaaatatttt | tgtgattcct | 600 |
| attgttggac | ttagagggct | tggaaaaacc | acacttgtta | agttggttta | taacaataat | 660 |
| agggttgttc | agaatttcaa | ccttagattg | tgggttagta | tttctgaaga | ttttagtctg | 720 |
| agcaaggtaa | ttgagaaaat | tgtgaggtcc | ggaacaggag | agagttttga | ccacctagat | 780 |
| atggaccaat | tacaaggttg | tttgggagag | gttttgcaac | agaaaaggta | tttacttgtg | 840 |
| ctggatgatg | tgtggaatga | agatcaacac | aagtggatag | atatgaggga | gttgccgatg | 900 |
| aattgttcca | gaggtagtaa | aattgttgtc | actacacgta | gtaagatggt | tgctttgatt | 960 |
| actggaacag | ttccgcctta | ttatttgaga | ggccttggta | atgatgactg | cttatcttat | 1020 |
| ttttgaaatg | tgcatttgga | gggcaggaca | atttgtttcc | taatctagta | gaaataggaa | 1080 |
| aagaaattgt | gaaaagtgt | ggaggagtgc | ctttggctgt | gaaaaccttg | ggaaggttgt | 1140 |
| tgtacatgaa | aacagacaag | aacgaatggt | tgcagataag | agacgatgag | atatgggaaa | 1200 |
| tcgaacagaa | taaatctgac | atcttaccaa | tattgaggtt | gagctatgaa | cagatgccat | 1260 |
| cacatctaag | acagtgcttt | gcctattgcc | ccatgttacc | caaaggtcaa | gaaattccgt | 1320 |
| gggaggattt | tatcaatcgc | tgggctcaag | gatttatcca | gagttcaaac | agaaacagga | 1380 |
| agttggaaga | tatcggtaat | cagtactttg | atgagttgct | atcaaggttt | tgcttcctag | 1440 |
| atgtgataca | agcagctttt | gatggagaaa | tattggcttg | taagatacac | aatcttgtgc | 1500 |
| atgatcttgc | acagtcagta | tcaggtgcag | agtgcttaaa | tgtgaaaccc | aatgctttcg | 1560 |
| tggtttctga | gagagttcgc | cacttattct | tccatgcaga | agatatgtct | aggaaatact | 1620 |
| tccccagatt | tttgcttcct | ttgcataagg | tgaggtcttt | tttttattc | gtttaatatt | 1680 |
| ggacctgtaa | acaagttttt | tgtcaagaca | atgttgtcaa | atttcaaatg | ccttcggatg | 1740 |
| ttagtcttga | acaatctaga | tcttgaggag | ttgccaactt | cgataggtaa | cttgaatgaa | 1800 |
| ttaagatacc | ttaaccttag | tgacagtggt | aatatcaagt | ttattccaag | gtctatgagc | 1860 |
| aaattagtaa | atttgcacac | ccttaacctc | attaactgtg | aacagcttaa | ggagttgcca | 1920 |
| agagacttta | gaaagttaat | cagcctgaag | accttgtatt | tgaccacaca | tcagatatta | 1980 |
| gcagggatca | agaatcaaca | ttctttcact | tctcttcaat | ttttgcttct | tttcgaatgt | 2040 |
| tgtttcccaa | aattgcagcc | agaactggtg | cagcattta | ctgaacttcg | gttgttgcgt | 2100 |
| atctacgaat | gccaagttta | tgttctcttc | caagaagtat | tagatatctt | acttcacttg | 2160 |

-continued

| | |
|---|---|
| aaaagctatg gatctggaac tgtgaagaac ttgatttgat tgatagagaa ggaatgtcag | 2220 |
| gcctaacaag tcttcaatcc ttgcttctaa tggggcttcc taagttggtg actctaccat | 2280 |
| tggaactcaa agataccgct cctacaacat tgaagtactt tagaatcgcc gattgtccct | 2340 |
| acctggtgga gcttccagag tggctgccga attgctcctc acttcagaga ctgtatatag | 2400 |
| aggattgtcc tgttttggca tcgatacctc aaggaatcta caaccacaat gccaacgtcc | 2460 |
| atataatcga ctgtccattg ctaggtggat ga | 2492 |

<210> SEQ ID NO 115
<211> LENGTH: 2195
<212> TYPE: DNA
<213> ORGANISM: Solanum pennellii

<400> SEQUENCE: 115

| | |
|---|---|
| atgtagatcc ttgaacgtgt tttggcgaaa tctttcttgt tcaatatcat tgaacgtgtt | 60 |
| ttggctaaag tttcttcaat tgctatatat gagatcagtc tagcttggaa tgttaagaca | 120 |
| gagctaagga aactccaaag tactctatcc accatcaaag ttgtacttct agatgcaaac | 180 |
| gagcagcagg cgaagaacca tgaagtgaga gattggctgg aaaagctcag agatgttgtt | 240 |
| tatgatgtcg atgatttgat gggtgattta tcaacacaac tgttgctgcg aatgcatttc | 300 |
| cagaaaagct ttaggaagaa ggcaaggaag ttcttttcaa gttcaaatcc aattatatat | 360 |
| cgattcaaga ttggcagaaa agtaaaagaa atcaaggagc tgctgaatga gattgcagat | 420 |
| gataggagaa atttccactt cacggaacat acttatgtaa ttccagctga aaatacgagt | 480 |
| agagaacaaa cacactcctt tgtgagggca tcagatatca ttggtagaga tgatgatcaa | 540 |
| gaaacattg tataacagct gatagattct catgatgagg aaaatatttt tgtgattcct | 600 |
| attgttggac ttagagggct tggaaaaacc acacttgtta agttggttta taacaataat | 660 |
| agggttgttc agaatttcaa ccttagattg tgggttagta tttctgaaga ttttagtctg | 720 |
| agcaaggtaa ttgagaaaat tgttaggtcc ggaacaggag agagttttga ccacctagat | 780 |
| atggaccaat tacaaggttg tttgggagag gttttgcaac agaaaaggta tttacttgtg | 840 |
| ctggatgatg tgtggaatga agatcaacac aagtggacag atatgaggga gttgctgatg | 900 |
| aattgttcca gaggtagtaa aattgttgtc actacacgta gtaagatggt tgctttgatt | 960 |
| actggaacag ttccgcctta ttatttgaga ggccttggta atgatgactg cttatcttat | 1020 |
| ttttgaaatg tgcatttgga gggcaggaca atttgtttcc taatctagta gaaataggaa | 1080 |
| aagaaattgt gaaaagtgt ggaggagtgc ctttggctgt gaaaaccttg gaaggttgt | 1140 |
| tgtacatgaa aacagacaag aacgaatggt tgcagataag agacaatgag atatgggaaa | 1200 |
| tcgaacagaa taaatctgac atcttaccaa tattgaggtt gagctatgaa cagatgccat | 1260 |
| cacatctaag acagtgcttt gcctattgcc ccatgttacc caaggtcaa gaaattccga | 1320 |
| gggaggattt tatcaatcgc tgggctcaag gattatccca gagttcaaac agaaacagga | 1380 |
| agttggaaga tatcggtaat cagtactttg atgagttgct atcaaggttt tgcttcctag | 1440 |
| atgtggtaca agcttttgat ggagaaatat tggcttgtaa gatacacaat cttgtgcatg | 1500 |
| atcttgcaca gtcagtatca ggtgcagagt gcttaaatgt gaaacccaat gctttcgtgg | 1560 |
| tttctgagag agttcgccac ttattcttcc atgcagaaga tatgtctagg aaatacttcc | 1620 |
| ccagattttt gcttcctttg cataaggtga ggtcttttc ttattcgttt aacattggac | 1680 |
| ctgtaaacaa gttttttgtc aagacaatgt tgtcaaattt caaatgcctt cggatgttag | 1740 |
| tcttgaacaa tctagatctt gaggagttgc caacttcgat aggtaacttg aatgaattaa | 1800 |

-continued

```
gataccttaa ccttagtgac agtggtaata tcaagtttct tccaaggtct atgagcaaat    1860
tagtaaattt gcacacccct aacctcatta actgtgaaca gcttaaggag ttgccaagag    1920
actttagaaa gttaatcagc ctgaagacct tgtatttgac cacacatcag atatttgcag    1980
ggatcaagaa tcaacattct ttcacttctc ttcaattttg cttcttttca aatgttgttt    2040
cccaaaattg cagccagaac tggtgcagca ttttactgca cttcggttgt tgcgtatcta    2100
cgaatgccca agtttatgtt ctcttccaag cagtattaga tatcttactt cacttgaaaa    2160
gctatggatc tggaactgtg aagaacttga tttga                              2195
```

<210> SEQ ID NO 116
<211> LENGTH: 823
<212> TYPE: PRT
<213> ORGANISM: Solanum tuberosum

<400> SEQUENCE: 116

```
Met Ala Glu Ser Phe Leu Phe Asn Ile Ile Glu Arg Val Leu Ala Lys
1               5                   10                  15

Val Ser Ser Ile Ala Val Tyr Glu Ile Thr Leu Ala Trp Asn Val Lys
            20                  25                  30

Ile Glu Leu Arg Lys Leu Gln Ser Thr Leu Ser Thr Ile Lys Ala Val
        35                  40                  45

Leu Leu Asp Ala Asn Glu Gln Gln Ala Lys Asn His Glu Val Arg Asp
    50                  55                  60

Trp Leu Glu Lys Leu Arg Asp Val Val Tyr Asp Val Asp Asp Leu Met
65                  70                  75                  80

Asp Asp Leu Ser Thr Gln Leu Leu Leu Gln Met His Phe Gln Lys Ser
                85                  90                  95

Phe Arg Lys Lys Val Arg Lys Phe Phe Ser Ser Ser Asn Pro Ile Ile
            100                 105                 110

Tyr Arg Phe Lys Ile Gly Arg Lys Val Lys Glu Ile Arg Glu Leu Leu
        115                 120                 125

Asn Glu Ile Ala Asp Asp Arg Arg Asn Phe His Phe Thr Glu His Thr
    130                 135                 140

Phe Val Ile Ser Ala Glu Asn Thr Ser Arg Glu Gln Thr His Ser Phe
145                 150                 155                 160

Val Arg Ala Ser Asp Ile Ile Gly Arg Asp Asp Gln Glu Asn Ile
                165                 170                 175

Ile Lys Gln Leu Ile Gly Ser His Asp Glu Glu Asn Ile Ser Val Ile
            180                 185                 190

Pro Ile Val Gly Leu Gly Gly Leu Gly Lys Thr Thr Leu Val Lys Leu
        195                 200                 205

Val Tyr Asn Asn Asn Arg Val Val Gln Asn Tyr Asp Leu Arg Met Trp
    210                 215                 220

Val Ser Ile Ser Glu Asp Phe Asn Leu Ser Lys Val Ile Glu Lys Ile
225                 230                 235                 240

Leu Arg Ser Ala Thr Gly Glu Ser Phe Asp His Leu Asp Met Asp Gln
                245                 250                 255

Leu Gln Gly Cys Leu Gly Glu Val Leu Gln Lys Arg Tyr Leu Leu
            260                 265                 270

Val Leu Asp Asp Val Trp Asn Glu Asp Gln His Lys Trp Thr Asp Leu
        275                 280                 285

Arg Glu Leu Leu Met Asn Cys Ser Arg Gly Ser Lys Ile Val Val Thr
    290                 295                 300
```

```
Thr Arg Ser Lys Met Val Ala Leu Ile Thr Gly Thr Val Pro Pro Tyr
305                 310                 315                 320

Tyr Leu Gly Gly Leu Ala Asp Asp Cys Leu Ser Leu Phe Leu Lys
            325                 330                 335

Cys Ala Phe Gly Gly Gln Asp Asn Leu Phe Pro Asn Leu Val Glu Ile
                340                 345                 350

Gly Lys Glu Ile Val Lys Lys Cys Gly Gly Val Pro Leu Ala Val Lys
            355                 360                 365

Thr Leu Gly Arg Leu Leu Tyr Met Lys Thr Asp Glu Asn Glu Trp Leu
370                 375                 380

Gln Ile Arg Asp Asn Glu Ile Trp Glu Ile Gln Asn Lys Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Ser Lys Gly Gln Glu Ile
                420                 425                 430

Pro Arg Glu Asp Phe Ile Asn Arg Trp Ile Ala Gln Gly Phe Ile Gln
            435                 440                 445

Ser Ser Asn Arg Asn Arg Lys Leu Glu Asp Ile Gly Asn Gln Tyr Phe
450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Ile His Asn Leu Val His Asp Leu
                485                 490                 495

Ala Gln Ser Val Ala Gly Ala Glu Cys Leu Asn Val Lys Pro Asn Ala
            500                 505                 510

Phe Val Val Ser Glu Arg Val Arg His Leu Phe Phe His Ala Glu Asp
            515                 520                 525

Met Ser Arg Lys His Phe Pro Arg Ile Leu Leu Pro Leu Gln Lys Leu
530                 535                 540

Arg Ser Phe Ser Tyr Ser Phe Asn Ile Gly Pro Val Asn Lys Phe Phe
545                 550                 555                 560

Val Lys Thr Met Leu Ser Asn Phe Lys Cys Leu Arg Met Leu Val Leu
                565                 570                 575

Asn Asn Leu Asp Leu Glu Glu Leu Pro Thr Ser Ile Gly His Leu Lys
            580                 585                 590

Glu Leu Arg Tyr Leu Asn Leu Ser Asn Ser Gly Asn Ile Lys Phe Leu
            595                 600                 605

Pro Arg Ser Met Ser Lys Leu Val Asn Leu His Thr Leu Asn Leu Ile
            610                 615                 620

Asn Cys Glu Gln Leu Lys Glu Leu Pro Arg Asp Phe Arg Lys Leu Ile
625                 630                 635                 640

Ser Leu Lys Thr Leu Tyr Leu Thr Thr His Gln Ile Ser Ala Gly Ile
                645                 650                 655

Lys Asn Gln His Val Phe Thr Ser Leu Gln Phe Leu Leu Leu Phe Lys
                660                 665                 670

Cys Cys Phe Pro Lys Leu Gln Pro Glu Leu Val Gln His Phe Ser Ala
                675                 680                 685

Leu Arg Val Leu Arg Ile Tyr Glu Cys Pro Ser Leu Cys Ser Leu Pro
            690                 695                 700

Ser Ser Ile Arg Tyr Leu Thr Ser Leu Glu Lys Leu Trp Ile Trp Asn
705                 710                 715                 720
```

-continued

```
Cys Glu Glu Leu Asp Leu Ile Asp Gly Glu Gly Met Ser Gly Leu Thr
                725                 730                 735

Ser Leu His Ser Leu Leu Leu Met Gly Leu Pro Lys Leu Val Thr Leu
            740                 745                 750

Pro Leu Glu Leu Lys Asp Thr Ala Pro Thr Thr Leu Lys Tyr Phe Arg
        755                 760                 765

Ile Ala Asp Cys Pro Asn Leu Met Glu Leu Pro Glu Trp Leu Pro Asn
    770                 775                 780

Cys Ser Ser Leu Gln Arg Leu Tyr Ile Glu Asp Cys Pro Val Leu Ala
785                 790                 795                 800

Ser Ile Pro Gln Gly Ile Tyr Ser His Asn Ala Asn Leu His Ile Ile
                805                 810                 815

Asp Cys Pro Leu Leu Gly Gly
            820

<210> SEQ ID NO 117
<211> LENGTH: 828
<212> TYPE: PRT
<213> ORGANISM: Capsicum annuum

<400> SEQUENCE: 117

Met Ala Glu Ser Phe Leu Phe Asn Ile Ile Glu Arg Val Leu Ala Lys
1               5                   10                  15

Val Ser Ser Ile Ala Val Tyr Glu Ile Ser Leu Ala Trp Asn Val Lys
            20                  25                  30

Thr Asp Leu Arg Lys Leu Gln Ser Thr Leu Ser Thr Ile Lys Ala Val
        35                  40                  45

Leu Leu Asp Ala Asn Glu Lys Gln Ala Lys Asn His Glu Val Arg Asp
    50                  55                  60

Trp Leu Glu Lys Leu Arg Asp Val Val Tyr Asp Val Asp Asp Leu Met
65                  70                  75                  80

Asp Asp Leu Ser Thr Gln Leu Leu Leu Gln Met His Phe Gln Lys Ser
                85                  90                  95

Phe Gly Lys Lys Val Arg Arg Phe Phe Ser Ser Ser Asn Pro Ile Ile
            100                 105                 110

Tyr Arg Phe Lys Ile Gly Arg Val Lys Glu Ile Arg Glu Leu Leu
        115                 120                 125

Asn Glu Ile Ala Asp Asp Arg Lys Ser Phe His Phe Thr Glu His Asn
    130                 135                 140

Tyr Leu Ile Pro Ala Glu Asn Thr Ser Arg Glu Gln Thr His Ser Ser
145                 150                 155                 160

Val Arg Ala Ser Asp Ile Ile Gly Arg Asp Ala Asp Gln Glu Asn Ile
                165                 170                 175

Val Lys Gln Leu Ile Asp Ser His Asn Glu Asn Ile Ser Val Ile
            180                 185                 190

Pro Ile Val Gly Leu Gly Gly Leu Gly Lys Thr Thr Leu Val Lys Leu
        195                 200                 205

Val Tyr Asn Asp Asn Arg Val Val Gln Asn Phe Asp Leu Arg Met Trp
    210                 215                 220

Val Ser Ile Ser Glu Asp Phe Ser Leu Arg Lys Ile Ile Glu Lys Ile
225                 230                 235                 240

Leu Arg Ser Ala Thr Gly Glu Ser Phe Asp His Leu Asp Met Asp Gln
                245                 250                 255

Leu Gln Gly Cys Leu Gly Asn Val Leu Arg Leu Lys Arg Tyr Leu Leu
            260                 265                 270
```

```
Val Leu Asp Asp Val Trp Asn Glu Asp Gln His Lys Trp Thr Asp Leu
            275                 280                 285

Arg Glu Leu Leu Met Asn Cys Ala Ser Gly Ser Lys Ile Val Val Thr
        290                 295                 300

Thr Arg Ser Lys Met Ala Ala Leu Ile Thr Gly Thr Val Pro Pro Tyr
305                 310                 315                 320

Tyr Leu Glu Gly Leu Ala Asn Ser Asp Asp Cys Leu Ser Leu Phe Leu
                325                 330                 335

Lys Cys Ala Phe Gly Gly Gln Asp Asn Met Phe Pro Asn Leu Val Glu
            340                 345                 350

Ile Gly Lys Glu Ile Val Lys Lys Cys Gly Gly Val Pro Leu Ala Val
            355                 360                 365

Lys Thr Leu Gly Arg Leu Leu Tyr Thr Lys Thr Asp Glu Asn Glu Trp
        370                 375                 380

Leu Gln Ile Arg Asp Asn Glu Ile Trp Glu Ile Glu Gln Lys Glu Ser
385                 390                 395                 400

Asp Ile Leu Pro Ile Leu Arg Leu Ser Tyr Glu Gln Met Pro Ser His
                405                 410                 415

Leu Arg Gln Cys Phe Ala Tyr Cys Ser Met Leu Ser Lys Gly Gln Glu
            420                 425                 430

Ile Pro Arg Glu Asp Phe Ile Asn Arg Trp Ile Ala Gln Gly Phe Ile
            435                 440                 445

Gln Ser Ser Asn Arg Asn Ser Lys Leu Glu Asp Ile Gly Asn Gln Tyr
450                 455                 460

Phe Asp Glu Leu Leu Ser Arg Phe Cys Phe Leu Asp Val Val Gln Ala
465                 470                 475                 480

Phe Asp Gly Glu Ile Leu Ala Cys Lys Ile His Ser Leu Val His Asp
            485                 490                 495

Leu Ala Gln Ser Val Ala Gly Ala Glu Cys Leu Asn Val Lys Pro Asn
            500                 505                 510

Ala Phe Val Val Pro Glu Arg Val Arg His Leu Phe Phe His Ala Glu
        515                 520                 525

Asp Met Ser Gly Lys His Phe Pro Lys Phe Leu Leu Pro Leu Arg Lys
        530                 535                 540

Leu Arg Ser Phe Ser Tyr Ser Phe Asn Val Gly Pro Val Asn Lys Phe
545                 550                 555                 560

Phe Val Lys Thr Ile Leu Ser Asn Phe Lys Arg Leu Arg Met Leu Val
                565                 570                 575

Leu Ser Asn Leu Asp Leu Glu Glu Leu Pro Thr Ser Ile Gly His Leu
            580                 585                 590

Lys Glu Leu Arg Tyr Leu Asn Leu Ser Gly Ser Gly Asn Ile Lys Phe
            595                 600                 605

Leu Pro Arg Ser Met Ser Lys Leu Val Asn Leu Gln Thr Leu Asn Leu
        610                 615                 620

Ile Asn Cys Glu Gln Leu Lys Glu Leu Pro Arg Asp Phe Ala Lys Leu
625                 630                 635                 640

Ile Ser Leu Lys Thr Leu Tyr Leu Thr Thr Gln Gln Ile Ser Val Gly
                645                 650                 655

Ile Lys Cys Lys Asn Gln His Ser Phe Thr Ser Leu Gln Phe Leu Leu
            660                 665                 670

Leu Phe Lys Cys Cys Phe Pro Lys Leu Gln Pro Glu Leu Val Gln His
            675                 680                 685
```

```
Phe Thr Ala Leu Arg Val Leu Arg Ile Tyr Glu Cys Pro Ser Leu Cys
    690             695                 700

Ser Leu Pro Ser Ser Ile Arg Tyr Leu Thr Ser Leu Glu Lys Leu Trp
705             710                 715                 720

Ile Trp Asn Cys Glu Glu Leu Asp Leu Met Asp Gly Glu Gly Met Ser
                725                 730                 735

Gly Leu Ser Ser Leu Arg Ser Leu Leu Leu Met Gly Leu Pro Lys Leu
                740                 745                 750

Val Thr Leu Pro Leu Glu Leu Lys Asp Thr Ala Pro Ala Thr Ser Lys
            755                 760                 765

Tyr Phe Arg Ile Ala Asp Cys Pro Asn Leu Val Glu Leu Pro Glu Trp
    770                 775                 780

Leu Gln Asn Tyr Ser Ser Leu Gln Arg Leu Tyr Val Glu Asp Cys Pro
785                 790                 795                 800

Ala Leu Ala Ser Ile Pro Pro Gly Ile Tyr Asn His Asn Val Asn Val
                805                 810                 815

His Ile Ile Asp Cys Pro Leu Leu Ser Gly Gly Cys
                820                 825

<210> SEQ ID NO 118
<211> LENGTH: 827
<212> TYPE: PRT
<213> ORGANISM: Capsicum baccatum

<400> SEQUENCE: 118

Met Ala Glu Ser Phe Leu Phe Asn Ile Ile Glu Arg Val Leu Ala Lys
1               5                   10                  15

Val Ser Ser Ile Ala Val Tyr Glu Ile Ser Leu Ala Trp Asn Val Lys
                20                  25                  30

Thr Asp Leu Arg Lys Leu Gln Ser Thr Leu Ser Thr Ile Lys Ala Val
            35                  40                  45

Leu Leu Asp Ala Asn Glu Lys Gln Ala Lys Asn His Glu Val Arg Asp
        50                  55                  60

Trp Leu Glu Lys Leu Arg Asp Val Val Tyr Asp Val Asp Asp Leu Met
65                  70                  75                  80

Asp Asp Leu Ser Thr Gln Leu Leu Leu Gln Met His Phe Gln Lys Ser
                85                  90                  95

Phe Gly Lys Lys Val Arg Phe Phe Ser Ser Ser Asn Pro Ile Ile
                100                 105                 110

Tyr Arg Phe Lys Ile Gly Arg Val Lys Glu Ile Arg Glu Leu Leu
            115                 120                 125

Asn Glu Ile Ala Asp Asp Arg Lys Ser Phe His Phe Thr Glu His Asn
        130                 135                 140

Tyr Leu Ile Pro Ala Glu Asn Thr Ser Arg Glu Gln Thr His Ser Phe
145                 150                 155                 160

Val Arg Ala Ser Asp Ile Ile Gly Arg Asp Ala Asp Gln Glu Asn Ile
                165                 170                 175

Val Lys Gln Leu Ile Asp Ser Arg Asn Glu Glu Asn Ile Ser Val Ile
            180                 185                 190

Pro Ile Val Gly Leu Gly Gly Leu Gly Lys Thr Thr Leu Val Lys Leu
        195                 200                 205

Val Tyr Asn Asp Asn Arg Val Val Gln Asn Phe Asp Leu Arg Met Trp
    210                 215                 220

Val Ser Ile Ser Glu Asp Phe Ser Leu Arg Lys Ile Ile Glu Lys Ile
225                 230                 235                 240
```

```
Leu Arg Ser Ala Thr Gly Glu Ser Phe Asp His Leu Asp Met Asp Gln
            245                 250                 255

Leu Gln Gly Cys Leu Gly Asn Val Leu Gln Leu Lys Arg Tyr Leu Leu
                260                 265                 270

Val Leu Asp Asp Val Trp Asn Glu Asp Gln His Lys Trp Thr Asp Leu
                275                 280                 285

Arg Glu Leu Leu Met Asn Cys Ala Arg Gly Ser Lys Ile Val Val Thr
            290                 295                 300

Thr Arg Ser Lys Met Ala Ala Leu Ile Thr Gly Thr Val Pro Pro Tyr
305                 310                 315                 320

Tyr Leu Glu Gly Leu Ala Ser Asp Asp Cys Leu Ser Leu Phe Leu Lys
                325                 330                 335

Cys Ala Phe Gly Gly Gln Asp Asn Met Phe Pro Asn Leu Val Glu Ile
                340                 345                 350

Gly Lys Glu Ile Val Lys Lys Cys Gly Gly Val Pro Leu Ala Val Lys
                355                 360                 365

Thr Leu Gly Arg Leu Leu Tyr Thr Lys Thr Asp Glu Asn Glu Trp Leu
            370                 375                 380

Gln Ile Arg Asp Asn Glu Ile Trp Glu Ile Glu Gln Lys Glu Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Ser Lys Gly Gln Glu Ile
                420                 425                 430

Pro Arg Glu Asp Phe Ile Asn Arg Trp Ile Ala Gln Gly Phe Ile Gln
            435                 440                 445

Ser Ser Asn Arg Asn Ser Lys Leu Glu Asp Ile Gly Asn Gln Tyr Phe
450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Ile His Ser Leu Val His Asp Leu
                485                 490                 495

Ala Gln Ser Val Ala Gly Ala Glu Cys Leu Asn Val Lys Pro Asn Ala
            500                 505                 510

Phe Val Val Pro Glu Arg Val Arg His Leu Phe Phe His Ala Glu Asp
            515                 520                 525

Met Ser Gly Lys His Phe Pro Lys Phe Leu Leu Pro Leu Arg Lys Leu
530                 535                 540

Arg Ser Phe Ser Tyr Ser Phe Asn Val Gly Pro Val Asn Lys Phe Phe
545                 550                 555                 560

Val Lys Thr Ile Leu Ser Asn Phe Lys Arg Leu Arg Met Leu Val Leu
                565                 570                 575

Ser Asn Leu Asp Leu Glu Glu Leu Pro Thr Ser Ile Gly His Leu Lys
            580                 585                 590

Glu Leu Arg Tyr Leu Asn Leu Ser Gly Ser Gly Asn Ile Lys Phe Leu
                595                 600                 605

Pro Arg Ser Met Ser Lys Leu Val Asn Leu Gln Thr Leu Asn Leu Ile
            610                 615                 620

Asn Cys Glu Gln Leu Lys Glu Leu Pro Arg Asp Phe Thr Lys Leu Ile
625                 630                 635                 640

Ser Leu Lys Thr Leu Tyr Leu Thr Thr Gln Gln Ile Ser Val Gly Ile
                645                 650                 655
```

```
Lys Phe Lys Asn Gln His Ser Phe Thr Ser Leu Gln Phe Leu Leu Leu
                660                 665                 670

Phe Lys Cys Cys Phe Pro Lys Leu Gln Pro Glu Leu Val Gln His Phe
            675                 680                 685

Thr Ala Leu Arg Val Leu Arg Ile Tyr Glu Cys Pro Ser Leu Cys Ser
        690                 695                 700

Leu Pro Ser Ser Ile Arg Tyr Leu Thr Ser Leu Gln Lys Leu Trp Ile
705                 710                 715                 720

Trp Asn Cys Glu Glu Leu Asp Leu Met Asp Gly Glu Gly Met Ser Gly
                725                 730                 735

Leu Ser Ser Leu Arg Ser Leu Leu Leu Met Gly Leu Pro Lys Leu Val
            740                 745                 750

Thr Leu Pro Leu Glu Leu Lys Asp Thr Ala Pro Ala Thr Ser Lys Tyr
        755                 760                 765

Phe Arg Ile Ala Asp Cys Pro Asn Leu Val Glu Leu Pro Glu Trp Leu
770                 775                 780

Gln Asn Tyr Ser Ser Leu Gln Arg Leu Tyr Ile Glu Asp Cys Pro Ala
785                 790                 795                 800

Leu Ala Ser Ile Pro Pro Gly Ile Tyr Asn His Asn Val Asn Val His
            805                 810                 815

Ile Ile Asp Cys Pro Leu Leu Ser Gly Gly Cys
            820                 825

<210> SEQ ID NO 119
<211> LENGTH: 827
<212> TYPE: PRT
<213> ORGANISM: Capsicum chinense

<400> SEQUENCE: 119

Met Ala Glu Ser Phe Leu Phe Asn Ile Ile Glu Arg Val Leu Ala Lys
1               5                   10                  15

Val Ser Ser Ile Ala Val Tyr Glu Ile Ser Leu Ala Trp Asn Val Lys
            20                  25                  30

Thr Asp Leu Arg Lys Leu Gln Ser Thr Leu Ser Thr Ile Lys Ala Val
        35                  40                  45

Leu Leu Asp Ala Asn Glu Lys Gln Ala Lys Asn His Glu Val Arg Asp
    50                  55                  60

Trp Leu Glu Lys Leu Arg Asp Val Val Tyr Asp Val Asp Asp Leu Met
65                  70                  75                  80

Asp Asp Leu Ser Thr Gln Leu Leu Leu Gln Met His Phe Gln Lys Ser
                85                  90                  95

Phe Gly Lys Lys Val Arg Arg Phe Phe Ser Ser Ser Asn Pro Ile Ile
            100                 105                 110

Tyr Arg Phe Lys Ile Gly Arg Arg Val Lys Glu Ile Arg Glu Leu Leu
        115                 120                 125

Asn Glu Ile Ala Asp Asp Arg Arg Ser Phe His Phe Thr Glu His Asn
    130                 135                 140

Tyr Leu Ile Pro Ala Glu Asn Thr Ser Arg Glu Gln Thr His Ser Ser
145                 150                 155                 160

Val Arg Ala Ser Asp Ile Ile Gly Arg Asp Ala Asp Gln Glu Asn Ile
                165                 170                 175

Val Lys Gln Leu Ile Asp Ser His Asn Glu Glu Asn Ile Ser Val Ile
            180                 185                 190

Pro Ile Val Gly Leu Gly Gly Leu Gly Lys Thr Thr Leu Val Lys Leu
        195                 200                 205
```

```
Val Tyr Asn Asp Asn Arg Val Gln Asn Phe Asp Leu Arg Met Trp
    210                 215                 220
Val Ser Ile Ser Glu Asp Phe Ser Leu Arg Lys Ile Ile Glu Lys Ile
225                 230                 235                 240
Leu Arg Ser Ala Thr Gly Glu Ser Phe Asp His Leu Asp Met Asp Gln
                245                 250                 255
Leu Gln Gly Cys Leu Gly Asn Val Leu Gln Leu Lys Arg Tyr Leu Leu
            260                 265                 270
Val Leu Asp Asp Val Trp Asn Glu Asp Gln His Lys Trp Thr Asp Leu
        275                 280                 285
Arg Glu Leu Leu Met Asn Cys Ala Ser Gly Ser Lys Ile Val Val Thr
    290                 295                 300
Thr Arg Ser Lys Met Ala Ala Leu Ile Thr Gly Thr Val Pro Leu Tyr
305                 310                 315                 320
Tyr Leu Glu Gly Leu Ala Ser Asp Asp Cys Leu Ser Leu Phe Leu Lys
                325                 330                 335
Cys Ala Phe Gly Gly Gln Asp Asn Met Phe Pro Asn Leu Val Glu Ile
            340                 345                 350
Gly Lys Glu Ile Val Lys Cys Gly Gly Val Pro Leu Ala Val Lys
        355                 360                 365
Thr Leu Gly Arg Leu Leu Tyr Thr Lys Thr Asp Glu Asn Glu Trp Leu
    370                 375                 380
Gln Ile Arg Asp Asn Glu Ile Trp Glu Ile Glu Gln Lys Glu Ser Asp
385                 390                 395                 400
Ile Leu Pro Ile Leu Arg Leu Ser Tyr Glu Gln Met Pro Ser His Leu
                405                 410                 415
Arg Gln Cys Phe Ala Tyr Cys Ser Met Leu Ser Lys Gly Gln Glu Ile
            420                 425                 430
Pro Arg Glu Asp Phe Ile Asn Arg Trp Ile Ala Gln Gly Phe Ile Gln
        435                 440                 445
Ser Ser Asn Arg Asn Ser Lys Leu Glu Asp Ile Gly Asn Gln Tyr Phe
    450                 455                 460
Asp Glu Leu Leu Ser Arg Phe Cys Phe Leu Asp Val Val Gln Ala Phe
465                 470                 475                 480
Asp Gly Glu Ile Leu Ala Cys Lys Ile His Ser Leu Val His Asp Leu
                485                 490                 495
Ala Gln Ser Val Ala Gly Ala Glu Cys Leu Asn Val Lys Pro Asn Ala
            500                 505                 510
Phe Val Val Pro Glu Arg Val Arg His Leu Phe His Ala Glu Asp
        515                 520                 525
Met Ser Gly Lys His Phe Pro Lys Phe Leu Pro Leu Arg Lys Leu
    530                 535                 540
Arg Ser Phe Ser Tyr Ser Phe Asn Val Gly Pro Val Asn Lys Phe Phe
545                 550                 555                 560
Val Lys Thr Ile Leu Ser Asn Phe Lys Arg Leu Arg Met Leu Val Leu
                565                 570                 575
Ser Asn Leu Asp Leu Glu Glu Leu Pro Thr Ser Ile Gly His Leu Lys
            580                 585                 590
Glu Leu Arg Tyr Leu Asn Leu Ser Gly Ser Gly Asn Ile Lys Phe Leu
        595                 600                 605
Pro Arg Ser Met Ser Lys Leu Val Asn Leu Gln Thr Leu Asn Leu Ile
    610                 615                 620
```

```
Asn Cys Glu Gln Leu Lys Glu Leu Pro Arg Asp Phe Ala Lys Leu Ile
625                 630                 635                 640

Ser Leu Lys Thr Leu Tyr Leu Thr Thr Gln Gln Ile Ser Val Gly Ile
            645                 650                 655

Lys Cys Lys Asn Gln His Ser Phe Thr Ser Leu Gln Phe Leu Leu Leu
                660                 665                 670

Phe Lys Cys Cys Phe Pro Lys Leu Gln Pro Glu Leu Val Gln His Phe
            675                 680                 685

Thr Ala Leu Arg Val Leu Arg Ile Tyr Glu Cys Pro Ser Leu Cys Ser
        690                 695                 700

Leu Pro Ser Ser Ile Arg Tyr Leu Thr Ser Leu Glu Lys Leu Trp Ile
705                 710                 715                 720

Trp Asn Cys Glu Glu Leu Asp Leu Met Asp Gly Glu Gly Met Ser Gly
            725                 730                 735

Leu Ser Ser Leu Arg Ser Leu Leu Met Gly Leu Pro Lys Leu Val
                740                 745                 750

Thr Leu Pro Leu Glu Leu Lys Asp Thr Ala Pro Ala Thr Ser Lys Tyr
        755                 760                 765

Phe Arg Ile Ala Asp Cys Pro Asn Leu Val Glu Leu Pro Glu Trp Leu
770                 775                 780

Gln Asn Tyr Ser Ser Leu Gln Arg Leu Tyr Ile Glu Asp Cys Pro Ala
785                 790                 795                 800

Leu Ala Ser Ile Pro Pro Gly Ile Tyr Asn His Asn Val Asn Val His
                805                 810                 815

Ile Ile Asp Cys Pro Leu Leu Ser Gly Gly Cys
            820                 825

<210> SEQ ID NO 120
<211> LENGTH: 824
<212> TYPE: PRT
<213> ORGANISM: Nicotiana attenuata

<400> SEQUENCE: 120

Met Ala Glu Ser Phe Leu Phe Asn Ile Ile Glu Arg Val Leu Ala Lys
1               5                   10                  15

Val Ser Ser Val Ala Val Thr Glu Ile Ser Leu Ala Trp Asn Val Lys
            20                  25                  30

Thr Glu Leu Arg Lys Leu Gln Ser Thr Leu Ser Thr Ile Lys Ala Val
        35                  40                  45

Leu Leu Asp Ala Asn Glu Gln Gln Ala Lys Asn His Glu Val Arg Asp
    50                  55                  60

Trp Leu Glu Lys Leu Arg Asp Val Val Tyr Asp Val Asp Asp Val Leu
65                  70                  75                  80

Asp Asp Leu Ser Thr Gln Leu Leu Leu Gln Ile His Phe Gln Lys Ser
                85                  90                  95

Leu Lys Lys Lys Val Arg Lys Phe Phe Ser Ser Ser Asn Pro Ile Ile
            100                 105                 110

Tyr Arg Phe Lys Ile Gly Arg Lys Val Lys Glu Ile Arg Glu Leu Leu
        115                 120                 125

Asn Glu Ile Ala Asp Asp Arg Lys Ser Phe His Phe Thr Glu His Thr
    130                 135                 140

Cys Leu Asn Pro Val Glu Asn Ile Cys Arg Glu Gln Thr His Ser Phe
145                 150                 155                 160

Val Arg Ala Ser Asp Ile Ile Gly Arg Glu Thr Asp Gln Glu Asn Ile
                165                 170                 175
```

```
Val Lys Gln Leu Ile Asp Ala Arg Asp Glu Glu Asn Ile Ser Val Ile
            180                 185                 190

Pro Ile Val Gly Leu Gly Gly Leu Gly Lys Thr Thr Leu Val Lys Leu
            195                 200                 205

Val Tyr Asn Tyr Asn Thr Val Val Gln Asn Phe Asp Leu Arg Met Trp
210                 215                 220

Val Ser Ile Ser Glu Asp Phe Ser Leu Ser Lys Val Ile Glu Lys Ile
225                 230                 235                 240

Leu Arg Ser Ala Thr Gly Glu Ser Phe Gly His Leu Asp Met Asp Gln
                245                 250                 255

Leu Gln Gly His Leu Ser Glu Val Leu Arg Ser Lys Arg Tyr Leu Leu
            260                 265                 270

Val Leu Asp Asp Val Trp Asn Glu Asp Gln Asn Lys Trp Thr Asp Leu
            275                 280                 285

Arg Glu Leu Leu Met Asn Cys Ser Lys Gly Ser Lys Ile Val Val Thr
            290                 295                 300

Thr Arg Ser Lys Met Val Ala Leu Ile Thr Gly Thr Val Ala Pro Tyr
305                 310                 315                 320

Tyr Leu Gly Gly Leu Thr Asp Asp Ala Cys Leu Leu Leu Phe Leu Lys
                325                 330                 335

Cys Ala Phe Val Gly Glu Asp Lys Leu Leu Pro Asn Leu Val Glu Ile
            340                 345                 350

Gly Lys Glu Ile Val Lys Lys Cys Gly Gly Val Pro Leu Ala Val Lys
            355                 360                 365

Thr Leu Gly Arg Leu Leu Tyr Met Lys Thr Asp Glu Asn Glu Trp Leu
            370                 375                 380

Arg Ile Arg Asp Asn Glu Ile Trp Glu Ile Glu Gln Lys Gln Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Ser Lys Gly Gln Glu Ile
            420                 425                 430

Pro Arg Glu Asp Phe Ile Asn Arg Trp Ile Ala Gln Gly Phe Ile Gln
            435                 440                 445

Ser Ser Asn Gly Ser Arg Lys Leu Glu Asp Ile Gly Asn Gln Tyr Phe
450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Leu His Asn Leu Val His Asp Leu
                485                 490                 495

Ala Gln Ser Val Ala Gly Ser Glu Cys Leu Asn Val Lys Ser Asn Ala
            500                 505                 510

Ser Val Val Ser Glu Arg Val Arg His Leu Phe Phe His Ala Glu Asp
            515                 520                 525

Met Ser Arg Lys His Phe Pro Arg Phe Leu Leu Ser Leu Gln Lys Leu
530                 535                 540

Arg Ser Phe Ser Tyr Ser Phe Asn Ile Gly Pro Val Asn Lys Phe Phe
545                 550                 555                 560

Val Lys Thr Thr Leu Ser Asn Phe Lys Cys Leu Arg Val Leu Val Leu
                565                 570                 575

Asn Asn Leu Asp Phe Glu Glu Leu Pro Thr Ser Ile Gly His Leu Lys
            580                 585                 590
```

```
Glu Leu Arg Tyr Leu Asn Leu Ser Asp Asn Gly Asn Ile Lys Phe Leu
            595                 600                 605

Pro Met Ser Met Ser Lys Leu Val Asn Leu Gln Thr Phe Asn Leu Ile
610                 615                 620

Asn Cys Glu Gln Leu Lys Glu Leu Pro Arg Asp Phe Gly Lys Leu Ile
625                 630                 635                 640

Cys Leu Lys Thr Leu Tyr Leu Thr Thr Tyr Lys Ile Ser Ala Gly Lys
                645                 650                 655

Asn Gln Gln Ser Phe Pro Ser Leu Gln Phe Leu Leu Leu Phe Lys Cys
            660                 665                 670

Cys Phe Pro Lys Leu Gln Pro Glu Leu Val Gln Gln Phe Thr Ala Leu
            675                 680                 685

Arg Val Leu Arg Ile Tyr Glu Cys Pro Ser Leu Cys Ser Leu Pro Ser
        690                 695                 700

Ser Ile Arg Tyr Leu Thr Ser Leu Glu Lys Leu Trp Ile Trp Asn Cys
705                 710                 715                 720

Glu Glu Leu Asp Leu Met Asp Gly Glu Gly Met Val Gly Leu Thr Ser
                725                 730                 735

Leu Arg Ser Leu Leu Leu Met Gly Leu Pro Lys Leu Val Thr Leu Pro
            740                 745                 750

Leu Gly Leu Lys Asp Ala Ala His Ala Thr Leu Lys Tyr Phe Arg Val
        755                 760                 765

Ala Asp Cys Pro Asn Leu Val Val Leu Pro Glu Trp Leu Gln Asn Cys
        770                 775                 780

Ser Ser Leu Gln Arg Leu Tyr Ile Glu Asp Cys Pro Val Leu Ala Thr
785                 790                 795                 800

Ile Pro Gln Gly Ile Tyr Asn His Asn Ala Asn Val His Ile Ile Asp
                805                 810                 815

Cys Pro Leu Leu Ser Gly Gly Cys
                820

<210> SEQ ID NO 121
<211> LENGTH: 824
<212> TYPE: PRT
<213> ORGANISM: Nicotiana benthamiana

<400> SEQUENCE: 121

Met Ala Glu Phe Phe Leu Phe Asn Ile Ile Glu Arg Val Leu Ser Lys
1               5                   10                  15

Val Ser Ser Val Ser Val Asn Glu Ile Ser Leu Ala Trp Asn Val Lys
            20                  25                  30

Thr Glu Leu Arg Lys Leu Gln Ser Thr Leu Ser Thr Ile Lys Ala Val
        35                  40                  45

Leu Leu Asp Ala Asn Glu Arg Gln Ala Lys Asn His Glu Val Arg Asp
    50                  55                  60

Trp Leu Glu Lys Leu Arg Asp Val Val Tyr Asp Val Asp Val Leu
65                  70                  75                  80

Asp Asp Leu Ser Thr Gln Leu Leu Gln Ile His Phe Gln Glu Ser
                85                  90                  95

Leu Lys Lys Lys Val Arg Lys Phe Phe Ser Ser Ser Asn Pro Ile Ile
            100                 105                 110

Tyr Arg Phe Lys Ile Gly Arg Lys Ile Lys Glu Ile Arg Glu Leu Leu
        115                 120                 125

Asn Asp Ile Ala Asp Asp Arg Lys Ser Phe His Phe Thr Glu His Thr
    130                 135                 140
```

```
Cys Ile Asn Pro Val Glu Asn Ile Cys Arg Glu Gln Thr His Ser Phe
145                 150                 155                 160

Val Arg Ala Ser Asp Ile Ile Gly Arg Glu Thr Asp Gln Glu Asn Ile
            165                 170                 175

Val Lys Gln Leu Ile Asp Ser Arg Asp Glu Gly Asn Ile Ser Val Ile
            180                 185                 190

Pro Ile Val Gly Leu Gly Gly Leu Gly Lys Thr Thr Leu Val Lys Leu
            195                 200                 205

Val Tyr Asn Asn Lys Val Val Gln Asn Phe Asp Leu Arg Met Trp
210                 215                 220

Val Ser Ile Ser Glu Asp Phe Ser Leu Ser Lys Val Ile Glu Lys Ile
225                 230                 235                 240

Leu Arg Ser Ala Thr Gly Glu Ser Phe Gly His Leu Asp Met Asp Gln
            245                 250                 255

Leu Gln Gly His Leu Ser Glu Val Leu Arg Ser Lys Arg Tyr Leu Leu
            260                 265                 270

Val Leu Asp Asp Val Trp Asn Glu Asp Gln Asn Arg Trp Thr Asp Leu
            275                 280                 285

Arg Glu Leu Leu Met Asn Cys Ser Arg Gly Ser Lys Ile Val Val Thr
            290                 295                 300

Thr Arg Ser Lys Met Val Ala Leu Ile Thr Gly Thr Val Ala Pro Tyr
305                 310                 315                 320

Tyr Leu Gly Gly Leu Thr Asp Asp Ala Cys Leu Ser Leu Phe Leu Lys
                325                 330                 335

Cys Ala Phe Val Gly Glu Asp Lys Leu Pro Asn Leu Val Glu Ile
            340                 345                 350

Gly Lys Glu Ile Val Lys Lys Cys Gly Gly Val Pro Leu Ala Val Lys
            355                 360                 365

Thr Leu Gly Arg Leu Leu Tyr Met Lys Thr Asp Glu Asn Glu Trp Leu
            370                 375                 380

Arg Ile Arg Asp Asn Glu Ile Trp Glu Ile Glu Gln Lys Gln Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Ser Lys Gly Gln Glu Ile
            420                 425                 430

Pro Arg Glu Asp Phe Ile Asn Arg Trp Ile Ala Gln Gly Phe Ile Gln
            435                 440                 445

Ser Ser Asn Gly Ser Arg Lys Leu Glu Asp Ile Gly Asn Gln Tyr Phe
            450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Leu His Asn Leu Val His Asp Leu
            485                 490                 495

Ala Gln Ser Val Ala Gly Ser Glu Cys Ser Asn Val Lys Ser Asn Ala
            500                 505                 510

Ser Val Val Ser Glu Arg Val Arg His Leu Phe Phe His Ala Glu Asp
            515                 520                 525

Met Ser Arg Lys His Phe Pro Arg Phe Leu Ser Leu Gln Lys Leu
            530                 535                 540

Arg Ser Phe Ser Tyr Ala Phe Asn Ile Gly Pro Ala Asn Lys Phe Phe
545                 550                 555                 560
```

-continued

```
Val Lys Thr Thr Leu Ser Asn Phe Lys Cys Leu Arg Val Leu Val Leu
                565                 570                 575

Asn Asn Leu Asp Phe Glu Glu Leu Pro Thr Ser Ile Gly His Leu Lys
            580                 585                 590

Glu Leu Arg Tyr Leu Asn Leu Ser Asp Asn Gly Asn Ile Lys Phe Leu
            595                 600                 605

Pro Arg Ser Met Ser Lys Leu Val Asn Leu Gln Thr Leu Asn Leu Ile
    610                 615                 620

Asn Cys Glu Gln Leu Lys Glu Leu Pro Arg Asp Phe Gly Lys Leu Ile
625                 630                 635                 640

Cys Leu Lys Thr Leu Tyr Leu Thr Thr Tyr Lys Ile Ser Ala Gly Lys
                645                 650                 655

Asn Gln Gln Ser Phe Pro Ser Leu Gln Phe Leu Leu Phe Lys Cys
            660                 665                 670

Cys Phe Pro Lys Leu Gln Pro Glu Leu Val Gln Gln Phe Thr Ala Leu
        675                 680                 685

Arg Val Leu Arg Ile Tyr Glu Cys Pro Ser Leu Cys Ser Leu Pro Ser
    690                 695                 700

Ser Ile Arg Tyr Leu Thr Ser Leu Glu Lys Leu Trp Ile Trp Asn Cys
705                 710                 715                 720

Glu Glu Leu Asp Leu Met Asp Gly Glu Gly Met Val Gly Leu Thr Asn
                725                 730                 735

Leu Arg Ser Leu Leu Met Gly Leu Pro Lys Leu Val Thr Leu Pro
            740                 745                 750

Leu Gly Leu Lys Asp Ala Ala His Ala Thr Leu Asn Tyr Phe Arg Val
        755                 760                 765

Ala Asp Cys Pro Asn Leu Val Val Leu Pro Glu Trp Leu Gln Asp Cys
    770                 775                 780

Ser Ser Leu Gln Arg Leu Tyr Ile Glu Asp Cys Pro Val Leu Ala Thr
785                 790                 795                 800

Val Pro Gln Gly Ile Tyr Asn His Asn Ala Asn Val His Ile Ile Asp
                805                 810                 815

Cys Pro Leu Leu Ser Gly Gly Cys
            820

<210> SEQ ID NO 122
<211> LENGTH: 829
<212> TYPE: PRT
<213> ORGANISM: Nicotiana tabacum

<400> SEQUENCE: 122

Met Leu Leu Gln Ser Met Ala Glu Thr Phe Leu Phe Asn Ile Ile Glu
1               5                   10                  15

Arg Val Leu Ala Lys Val Ser Ser Val Ala Val Tyr Glu Ile Ser Leu
            20                  25                  30

Ala Trp Asn Val Lys Thr Glu Leu Arg Lys Leu Gln Ser Thr Leu Ser
        35                  40                  45

Thr Ile Lys Ala Val Leu Leu Asp Ala Asn Glu Gln Gln Ala Lys Asn
    50                  55                  60

His Glu Val Arg Asp Trp Leu Glu Lys Leu Arg Asp Val Tyr Asp
65                  70                  75                  80

Val Asp Asp Leu Leu Asp Asp Leu Ser Thr Gln Leu Thr Leu Gln Met
                85                  90                  95

His Phe Gln Lys Ser Leu Lys Lys Lys Val Arg Lys Phe Phe Ser Ser
            100                 105                 110
```

```
Ser Asn Pro Ile Phe Tyr Arg Phe Lys Ile Gly Arg Lys Val Lys Glu
            115                 120                 125

Ile Arg Glu Leu Leu Asn Glu Ile Ala His Asp Arg Lys Ser Phe His
    130                 135                 140

Phe Thr Glu His Thr Tyr Leu Asn Pro Val Glu Asn Ile Cys Arg Glu
145                 150                 155                 160

Gln Thr His Ser Phe Val Arg Ala Ser Asp Ile Ile Gly Arg Glu Thr
                165                 170                 175

Asp Gln Glu Asn Ile Val Lys Gln Leu Ile Asp Ala Arg Glu Glu Glu
            180                 185                 190

Asn Ile Ser Val Ile Pro Ile Val Gly Leu Gly Gly Leu Gly Lys Thr
            195                 200                 205

Thr Leu Val Lys Leu Val Tyr Asn Asn Asn Lys Val Val Gln Asn Phe
    210                 215                 220

Asp Leu Arg Met Trp Val Ser Ile Ser Glu Asp Phe Ser Leu Ser Lys
225                 230                 235                 240

Val Ile Glu Lys Ile Leu Arg Ser Ala Thr Gly Glu Ser Phe Gly His
                245                 250                 255

Leu Asp Met Asp Gln Leu Gln Ser His Leu Ser Glu Val Leu Arg Ser
            260                 265                 270

Lys Arg Tyr Leu Leu Val Leu Asp Asp Val Trp Asn Glu Asp Gln Asn
    275                 280                 285

Lys Trp Thr Asp Leu Arg Glu Leu Leu Met Asn Cys Ser Arg Gly Ser
290                 295                 300

Lys Ile Val Val Thr Thr Arg Ser Lys Met Val Ala Leu Ile Thr Gly
305                 310                 315                 320

Thr Val Ala Pro Tyr Tyr Leu Gly Gly Leu Ala Asp Asp Glu Cys Leu
                325                 330                 335

Ser Leu Phe Leu Lys Cys Ala Phe Val Gly Glu Asp Lys Leu Leu Pro
            340                 345                 350

Asn Leu Val Glu Ile Gly Lys Glu Ile Val Lys Lys Cys Gly Gly Val
            355                 360                 365

Pro Leu Ala Val Lys Thr Leu Gly Arg Leu Leu Tyr Met Lys Thr Asp
    370                 375                 380

Glu Asn Glu Trp Leu Arg Ile Arg Asp Asn Glu Ile Trp Glu Ile Glu
385                 390                 395                 400

Gln Lys Gln Ser Asp Ile Leu Pro Ile Leu Arg Leu Ser Tyr Glu Gln
                405                 410                 415

Met Pro Ser His Leu Arg Gln Cys Phe Ala Tyr Cys Ser Met Leu Ser
            420                 425                 430

Lys Gly Gln Glu Ile Pro Arg Glu Asp Phe Ile Asn Arg Trp Ile Ala
            435                 440                 445

Gln Gly Phe Ile Gln Ser Ser Asn Gly Ser Arg Lys Leu Glu Asp Ile
    450                 455                 460

Gly Asn Gln Tyr Phe Asp Glu Leu Leu Ser Arg Phe Cys Phe Leu Asp
465                 470                 475                 480

Val Val Gln Ala Phe Asp Gly Glu Ile Leu Ala Cys Lys Leu His Asn
                485                 490                 495

Leu Val His Asp Leu Ala Gln Ser Val Ala Gly Ser Glu Cys Leu Asn
            500                 505                 510

Val Lys Ser Asn Ala Ser Val Val Ser Glu Arg Val Arg His Leu Phe
    515                 520                 525
```

```
Phe His Ala Glu Asp Met Ser Arg Lys His Phe Pro Arg Phe Leu Leu
    530                 535                 540
Ser Leu Gln Lys Leu Arg Ser Phe Ser Tyr Ser Phe Asn Ile Gly Pro
545                 550                 555                 560
Val Asn Lys Phe Phe Val Lys Thr Met Leu Ser Asn Phe Lys Cys Leu
                565                 570                 575
Arg Val Leu Val Leu Asn Asn Leu Asp Phe Gly Glu Leu Pro Thr Ser
            580                 585                 590
Ile Gly His Leu Lys Glu Leu Arg Tyr Leu Asn Leu Ser Asp Asn Gly
        595                 600                 605
Asn Ile Lys Phe Leu Pro Arg Ser Met Ser Lys Leu Val Asn Leu Gln
    610                 615                 620
Thr Leu Asn Leu Ile Asn Cys Glu Gln Leu Lys Glu Leu Pro Arg Asp
625                 630                 635                 640
Phe Glu Lys Leu Ile Cys Leu Lys Thr Leu Tyr Leu Thr Thr Tyr Lys
                645                 650                 655
Ile Ser Ala Gly Lys Asn Gln Gln Ser Phe Pro Ser Leu Gln Phe Leu
            660                 665                 670
Leu Leu Phe Lys Cys Cys Phe Pro Lys Leu Gln Pro Glu Leu Val Gln
        675                 680                 685
Gln Phe Thr Ala Leu Arg Ile Leu Arg Ile Tyr Glu Cys Arg Ser Leu
    690                 695                 700
Tyr Ser Leu Pro Ser Ser Ile Arg Tyr Leu Thr Ser Leu Glu Lys Leu
705                 710                 715                 720
Trp Ile Trp Asn Cys Glu Glu Leu Asp Leu Met Asp Gly Glu Gly Met
                725                 730                 735
Val Gly Leu Thr Ser Leu Arg Ser Leu Leu Leu Met Gly Leu Pro Lys
            740                 745                 750
Leu Val Thr Leu Pro Leu Gly Leu Lys Asp Thr Ala His Ala Thr Leu
        755                 760                 765
Lys Tyr Phe Arg Val Ala Asp Cys Pro Asn Leu Ala Val Leu Pro Glu
    770                 775                 780
Trp Leu Gln Asn Cys Ser Ser Leu Gln Arg Leu Tyr Ile Glu Asp Cys
785                 790                 795                 800
Pro Val Leu Ala Ser Ile Pro Gln Gly Ile Tyr Asn His Asn Ala Glu
                805                 810                 815
Val His Ile Ile Asp Cys Pro Leu Leu Ser Gly Gly Cys
            820                 825

<210> SEQ ID NO 123
<211> LENGTH: 824
<212> TYPE: PRT
<213> ORGANISM: Nicotiana tomentosiformis

<400> SEQUENCE: 123

Met Ala Glu Thr Phe Leu Phe Asn Ile Ile Glu Arg Val Leu Ala Lys
1               5                   10                  15
Val Ser Ser Val Ala Val Tyr Glu Ile Ser Leu Ala Trp Asn Val Lys
            20                  25                  30
Thr Glu Leu Arg Lys Phe Gln Ser Thr Leu Ser Thr Ile Lys Ala Val
        35                  40                  45
Leu Leu Asp Ala Asn Glu Gln Gln Ala Lys Asn His Glu Val Arg Asp
    50                  55                  60
Trp Leu Glu Lys Leu Arg Asp Val Val Tyr Asp Val Asp Asp Leu Leu
65                  70                  75                  80
```

```
Asp Asp Leu Ser Thr Gln Leu Thr Leu Gln Met His Phe Gln Lys Ser
                85                  90                  95

Leu Lys Lys Lys Val Arg Lys Phe Phe Ser Ser Asn Pro Ile Ile
            100                 105                 110

Tyr Arg Phe Lys Ile Gly Arg Lys Val Lys Glu Ile Arg Glu Leu Leu
            115                 120                 125

Asn Glu Ile Ala His Asp Arg Lys Ser Phe His Phe Thr Glu His Thr
130                 135                 140

Tyr Leu Asn Pro Val Glu Asn Ile Cys Arg Glu Gln Thr His Ser Phe
145                 150                 155                 160

Val Arg Ala Ser Asp Ile Ile Gly Arg Glu Thr Asp Gln Glu Asn Ile
                165                 170                 175

Val Lys Gln Leu Ile Asp Ala Arg Glu Glu Asn Ile Ser Val Ile
            180                 185                 190

Pro Ile Val Gly Leu Gly Gly Leu Gly Lys Thr Thr Leu Val Lys Leu
            195                 200                 205

Val Tyr Asn Asn Lys Val Val Gln Asn Phe Asp Leu Arg Met Trp
210                 215                 220

Val Ser Ile Ser Glu Asp Phe Ser Leu Ser Lys Val Ile Glu Lys Ile
225                 230                 235                 240

Leu Arg Ser Ala Thr Gly Glu Ser Phe Gly His Leu Asp Met Asp Gln
                245                 250                 255

Leu Gln Ser His Leu Ser Glu Val Leu Arg Ser Lys Arg Tyr Leu Leu
            260                 265                 270

Val Leu Asp Asp Val Trp Asn Glu Asp Gln Asn Lys Trp Thr Asp Leu
            275                 280                 285

Arg Glu Leu Leu Met Asn Cys Ser Arg Gly Ser Lys Ile Val Val Thr
290                 295                 300

Thr Arg Ser Lys Met Val Ala Leu Ile Thr Gly Thr Val Ala Pro Tyr
305                 310                 315                 320

Tyr Leu Gly Gly Leu Ala Asp Asp Glu Cys Leu Ser Leu Phe Leu Lys
                325                 330                 335

Cys Ala Phe Val Gly Glu Asp Lys Leu Leu Pro Asn Leu Val Glu Ile
            340                 345                 350

Gly Lys Glu Ile Val Lys Lys Cys Gly Gly Val Pro Leu Ala Val Lys
            355                 360                 365

Thr Leu Gly Arg Leu Leu Tyr Met Lys Thr Asp Glu Asn Glu Trp Leu
370                 375                 380

Arg Ile Arg Asp Asn Glu Ile Trp Glu Ile Glu Gln Lys Gln Ser Asp
385                 390                 395                 400

Ile Leu Pro Ile Leu Arg Leu Ser Tyr Glu Gln Met Pro Ser His Leu
                405                 410                 415

Arg Gln Cys Phe Ala Tyr Cys Ser Met Leu Ser Lys Gly Gln Glu Ile
            420                 425                 430

Pro Arg Glu Asp Phe Ile Asn Arg Trp Ile Ala Gln Gly Phe Ile Gln
            435                 440                 445

Ser Ser Asn Gly Ser Arg Lys Leu Glu Asp Ile Gly Asn Gln Tyr Phe
450                 455                 460

Asp Glu Leu Leu Ser Arg Phe Cys Phe Leu Asp Val Val Gln Ala Phe
465                 470                 475                 480

Asp Gly Glu Ile Leu Ala Cys Lys Leu His Asn Leu Val His Asp Leu
                485                 490                 495
```

```
Ala Gln Ser Val Ala Gly Ser Glu Cys Leu Asn Val Lys Ser Asn Ala
            500                 505                 510

Ser Val Val Ser Glu Arg Val Arg His Leu Phe Phe His Ala Glu Asp
            515                 520                 525

Met Ser Arg Lys His Phe Pro Arg Phe Leu Leu Ser Leu Gln Lys Leu
            530                 535                 540

Arg Ser Phe Ser Tyr Ser Phe Asn Ile Gly Pro Val Asn Lys Phe Phe
545                 550                 555                 560

Val Lys Thr Met Leu Ser Asn Phe Lys Cys Leu Arg Val Leu Val Leu
            565                 570                 575

Asn Asn Leu Asp Phe Gly Glu Leu Pro Thr Ser Ile Gly His Leu Lys
            580                 585                 590

Glu Leu Arg Tyr Leu Asn Leu Ser Asp Asn Gly Asn Ile Lys Phe Leu
            595                 600                 605

Pro Arg Ser Met Ser Lys Leu Val Asn Leu Gln Thr Leu Asn Leu Ile
            610                 615                 620

Asn Cys Glu Gln Leu Lys Glu Leu Pro Arg Asp Phe Glu Lys Leu Ile
625                 630                 635                 640

Cys Leu Lys Thr Leu Tyr Leu Thr Thr Tyr Lys Ile Ser Ala Gly Lys
            645                 650                 655

Asn Gln Gln Ser Phe Pro Ser Leu Gln Phe Leu Leu Phe Lys Cys
            660                 665                 670

Cys Phe Pro Lys Leu Gln Pro Glu Leu Val Gln Phe Thr Ala Leu
            675                 680                 685

Arg Ile Leu Arg Ile Tyr Glu Cys Arg Ser Leu Tyr Ser Leu Pro Ser
            690                 695                 700

Ser Ile Arg Tyr Leu Thr Ser Leu Glu Lys Leu Trp Ile Trp Asn Cys
705                 710                 715                 720

Glu Glu Leu Asp Leu Met Asp Gly Glu Gly Met Val Gly Leu Thr Ser
            725                 730                 735

Leu Arg Ser Leu Leu Leu Met Gly Leu Pro Lys Leu Val Thr Leu Pro
            740                 745                 750

Leu Gly Leu Lys Asp Thr Ala His Ala Thr Leu Lys Tyr Phe Arg Val
            755                 760                 765

Ala Asp Cys Pro Asn Leu Ala Val Leu Pro Glu Trp Leu Gln Asn Cys
            770                 775                 780

Ser Ser Leu Gln Arg Leu Tyr Ile Glu Asp Cys Pro Val Leu Ala Ser
785                 790                 795                 800

Ile Thr Gln Gly Ile Tyr Asn His Asn Ala Glu Val His Ile Ile Asp
            805                 810                 815

Cys Pro Leu Leu Ser Gly Gly Cys
            820
```

<210> SEQ ID NO 124
<211> LENGTH: 2475
<212> TYPE: DNA
<213> ORGANISM: Nicotiana benthamiana

<400> SEQUENCE: 124

| | |
|---|---|
| atggcagaat ttttcttgtt caacatcatt gaaagagttt tgtcaaaagt ttcttcagtt | 60 |
| tctgtaaatg agatcagttt agcgtggaat gttaaaacag agttaagaaa actccagagc | 120 |
| actttatcca caatcaaagc tgtacttttta gatgcaaatg agcggcaggc aaagaaccat | 180 |
| gaagtgagag attggctgga aaagctaaga gatgttgttt atgatgtcga tgatgtgctc | 240 |

```
gatgatttgt caacacagct attactacaa atacattttc aggaaagcct taagaagaag       300
gtaagaaaat tcttttcaag ttcaaatcca attatttata gattcaagat tggtagaaag       360
ataaaagaga ttagggaact attgaatgat attgcagatg atcggaaaag tttccacttt       420
actgaacata cttgtataaa tccagttgaa aatatttgta gagaacaaac acattccttt       480
gtaagggcct ctgatattat tggtagagaa actgatcaag aaaacatagt aaaacagctc       540
atagattctc gcgatgagga aaatatttct gtgattccta ttgttggact tggagggctt       600
ggaaaaacca cacttgttaa gttggtttat aacaataata aggttgttca gaattttgac       660
ctgagaatgt gggtgagtat ttcagaagat tttagtctga gtaaggtaat tgagaaaatt       720
ctgcgatctg caacaggaga gagttttggc cacctagata tggaccaatt acaaggtcat       780
ttgagtgagg ttttgcgatc gaaaaggtat ttacttgtac tggatgatgt gtggaatgaa       840
gatcaaaaca ggtggacgga cttgagggag ttgctgatga attgttctag aggtagtaag       900
attgttgtca ctacacgcag taagatggtt gctttgatta ctggaacagt tgcaccttac       960
tatttgggtg gtcttaccga tgatgcgtgc ttatcgttat ttttgaaatg tgcatttgta      1020
ggggaggaca aattgttgcc taatctagta gaaataggaa aagagattgt gaaaaagtgt      1080
ggaggagtgc ctttggctgt gaaaaccttg ggaaggttat tgtatatgaa aacagacgaa      1140
aatgaatggt tgcggataag agataatgag atatgggaga tcgaacagaa acaatcagac      1200
attttaccaa tattgagatt gagctatgaa cagatgccat ctcatctaag acagtgctTT      1260
gcctattgct ccatgttatc caaaggtcaa gaaattccga gagaggactt catcaaccgg      1320
tggattgctc aaggatttat acagagttct aacggatcca ggaagttgga agatattggt      1380
aatcagtact tgatgagtt gctatcaagg ttttgcttcc ttgatgtggt acaagcattt      1440
gatggagaaa tattggcttg taagttacac aatcttgtgc atgatcttgc acagtcagtg      1500
gcaggttctg aatgttcaaa tgtgaaatct aatgcttctg tggtttctga aagagttcgc      1560
cacttatttt tcatgcaga agatatgtct aggaaacact tcccaagatt tttacttct      1620 ttgcaaaagt tgaggtctTT tcttacgca tttaacattg gacctgcaaa caagttctTT      1680
gtcaagacga cattatcaaa tttcaaatgc cttcgggtgt tagtcttgaa caatttagat      1740
tttgaggagt tgccaacttc gataggtcac ttgaaggaac taagatatct taacctcagt      1800
gacaatggta acatcaagtt tctcccaagg tctatgagca aattagtaaa tctgcagact      1860
cttaacctca ttaattgtga acagcttaag gagttgccga gagactttgg aaagttaatc      1920
tgcttgaaga ccttgtattt gactacatat aagatatcag cagggaagaa tcaacaatct      1980
ttcccttctc ttcaatttt gcttcttttc aagtgttgtt tcccaaaatt gcagccagaa      2040
ctggtgcagc agtttactgc acttcgggtt ttgcgtatct atgaatgccc gagtttatgt      2100
tctcttccaa gcagtattag atacctgact tcacttgaaa agctatggat ttggaactgt      2160
gaagaacttg atttgatgga tggagaggga atggtaggcc taacaaattt acggtcgttg      2220
cttctaatgg gactccctaa gttggtgact ctaccattgg gacttaaaga tgctgctcat      2280
gcaacactga actactttag agttgccgat tgtcccaacc tagtggtgct tccagaatgg      2340
ctgcaggatt gctcttccct tcagaggctg tatatagagg attgtcctgt attggcaact      2400
gtacctcaag gaatctacaa ccataatgcc aatgtccata taatcgactg tccattgcta      2460
agtggaggat gctaa                                                       2475

<210> SEQ ID NO 125
<211> LENGTH: 2324
```

```
<212> TYPE: DNA
<213> ORGANISM: Nicotiana benthamiana

<400> SEQUENCE: 125
atggcagaat ctttcttgtt caacatcatt gaaagagttt tggcaaaagt ctcttcagtt     60
gctgtaaatg agatcagttt agcttggatt gttaaaatta agaaaactcc agagcacttt    120
atccacaatc aaagctgtac ttttagatgc aaatgagcag taggcaaaga accatgaagt    180
gagagattgg ctggaaaagc taagacatat tgtttatgat gtcgatgatc tgctcgatga    240
tttgtctaca cagttattac tacaaataca ttttcagaaa agccttaaga agaaggtaag    300
aaaattcttt tcaagttcaa atccaattat ttatagattc aagattggta gaaaggtaaa    360
agagattagg gaactattga atgagattgc agatgatagg agaactttcc actttactga    420
acatacttgt ctaaatccag ttgagaatat tgtagagaa caaacacatt cctttgtaag     480
ggcctccgat attattagta gagaaactga tcaagaaaac atagtaaaac agctcataga    540
tgctcgtgac gaggaaaata tttctgtgat tcctgttgtt ggacttggtg ggcttggaaa    600
aaccacactt gttaagttgg tttataacaa taataaggtt gttcagaatt ttgacctgag    660
aatgtgggtt agtatttcag aggattttag tctgagtaag gtaattgaga aaattctgcg    720
gtctgcaaca ggagagagtt ttggccacct tgatatggat caattacaag gtcatttaag    780
tgaggttttg cgatcaaaat ggtatttact tgtactggat gatgtgtgga atgaagatca    840
aaacaggtgg acggacttga gggagttgct gatgaattgt tctagaggta gtacgattgt    900
tgtcactaca cgcaataaga tggttgcttt gattactgga acagttgcac cttactattt    960
gggtggtctt actgatgtgc gtgcttatcg ttattttga aatgtgcatt gtagggtg     1020
gaaaaattgt tgcctaatct agtagaaata ggaaaagaaa ttgtgaaaaa gtgtggagga   1080
gtgcctttgg ctgtgaaaac cttgggaagg ttgctgtaca tgaaaacaga cgaaaatgaa   1140
tggttgcgga tacgagataa tgagatatgg gagatcgaac agaaacaatc tgacattttg   1200
ccaatattga gattgagcta tgaacagatg ccatcacatc taagacagtg ctttgcctat   1260
tgctccatgt tatccaaagg tcaagaaatt ccgagagagg acttcatcaa ccggtggatt   1320
gctcaaggat ttatacagag ttcaaacgga tccaggaagt tggaagatat tggtaatcag   1380
tactttgatg agttactatc gaggttttgc ttccttgatg tggtacaagc ttttgatgga   1440
gaaatattgg cttgtaagtt acacaatctt gtgcatgatc ttgcacagtc agtggcaggt   1500
tctgaatgtt taaatgtgaa atctaatgct tctgtggttt ctgaaagagt tcgccactta   1560
tttttttcatg cagaagatat gtctaggaaa cacttcccaa tatttttact ttctttgcaa   1620
aagttgaggt ctttttctta ctcatttaac attggacctg taaacaagtt ctttgtcaaa   1680
acgacgttat caaatttcaa atgccttcgg gtgttagtct tgaacaattt agattttgag   1740
gagttgccaa cttcgatagg tcacttgaag gaattaagat atcttaacct tagtgacaat   1800
ggcaacatca gtttctcccc aaggtctatg agcaaattag taaatctgca gacttttaac   1860
ctcattagtt gggaacagct taaggagttg ccaagaggct ttggaaagtt aatctgtttg   1920
aagaccttgt atttgactac atataagata cggaaaagag tcatatgttc tactagtcaa   1980
aataagctac atttgtcctc cgttatacta tttggccata tatgtcccta ccgttcacat   2040
ctctggccat atatgtccct ctgacgttaa cttttttaaa aaataattaa aaagccacgt   2100
gtcatagtcc tattggttaa actaaaccca cttcttttt  ttaatattaa aacgaaaata   2160
tttgtaaaaa atgtaaaaaa acttgtaaaa aatgtgtcaa aaataatttt gtcaaaaata   2220
```

| | |
|---|---|
| aaaatatttt attaaaaaaa ttttattttt gttttacaa gaagaaaatc agttcatttt | 2280 |
| caaatttgaa aaatatttcc aaaatgtgtt ttttgttttt aaaa | 2324 |

<210> SEQ ID NO 126
<211> LENGTH: 2472
<212> TYPE: DNA
<213> ORGANISM: Artificial
<220> FEATURE:
<223> OTHER INFORMATION: Synthetic Ptr1

<400> SEQUENCE: 126

| | |
|---|---|
| atggcagaat cattccttt caacattatt gagagggttc ttgctaaggt ttcatcaatc | 60 |
| gctgtgtatg aaatctcact agcatggaac gttaaaacag aactaagaaa acttcaatct | 120 |
| actctttcca ctatcaaggc tgttcttctt gatgctaacg aacaaaaagc aaaaaaccac | 180 |
| gaagttagag actggcttga aaaactcagg gatgtggttt acgatgttga tgaccttatg | 240 |
| gacgatcttt caactcaact tttgcttcag atgcacttcc aaaaatcttt tagaaagaaa | 300 |
| gtaaggagat tttttctag ttctaatcct attatttata gattcaaaat tggaagaaaa | 360 |
| gtaaaggaaa ttagggaact gcttaatgaa attgctgatg acaggaggaa ttttcacttt | 420 |
| acggagcata catatgttat tcctgctgag aatactagta gggaacagac acattccttc | 480 |
| gtgagagcct ctgatattat tggaagagac gatgaccaag agaacatcgt aaagcagctt | 540 |
| atagactctc acgatgaaga aaacatttca gtgatcccta tcgttggtct tggtgggttg | 600 |
| ggaaagacca ctcttgtgaa gcttgtttac aacaacaata gagttgtgca gaactttgat | 660 |
| cttaggatgt gggtgagtat ctcagaggat tttagtctta gcaaagtaat cgagaagatt | 720 |
| cttaggtctg caactggaga agtttcgac catctagaca tggatcaact tcaatgctgt | 780 |
| cttggagaag ttcttcaaca aaaagatat cttcttgttc tggacgatgt gtggaatgaa | 840 |
| gaccaacata gtggacaga tcttagagag cttcttatga actgttctag aggaagtaag | 900 |
| attgtggtca caacaagaag taaaatggtg gctcttatta caggaactgt tccaccttac | 960 |
| tatcttggag acttgcaaa tgacgactgt ttatcattat tcttgaagtg tgcttttggt | 1020 |
| ggacaagaca acttgttccc taacctagtt gaaattggaa aggaaatcgt gaagaagtgc | 1080 |
| ggaggtgtgc cattggcagt gaagacccct tggaagattg ctttatatga gacagatgag | 1140 |
| aacgagtggt tgcaaataag ggataacgag atttgggaga tcgagcagaa caaatcagac | 1200 |
| atcttaccta tacttagact tagctacgaa caaatgcctt cacacctaag gcagtgtttt | 1260 |
| gcttattgtt ctatgttgcc caagggtcag gaaatcccga gagggactt tattaataga | 1320 |
| tggatcgctc agggattcat acaaagttct aacaggaaca gaaagcttga agacatcgga | 1380 |
| aatcaatact tcgatgaatt gctttcaaga ttttgtttcc ttgatgttgt acaggctttc | 1440 |
| gatggtgaaa ttttggcatg taaaatacat aatttggtgc acgatttggc acaatcagtt | 1500 |
| tcaggagcag aatgccttaa tgttaaacct aatgcattcg ttgtctcaga aagggttaga | 1560 |
| cacctttttt ttcatgctga agacatgtca aggaagcact ttcccaggtt tcttcttcca | 1620 |
| ttgcagaagc ttaggtcatt ctcatattca tttaatattg gtcctgttaa caaattcttc | 1680 |
| gtcaaaacta tgctttcaaa cttcaagtgc ttgagaatgc ttgtccttaa caacctagac | 1740 |
| cttgaagagc ttccaacatc gattggtcat ttgaaagaac ttagatatct caatctttct | 1800 |
| gactctggta aaatcaaatt tttgccaaga tcaatgtcta acttgtaaa cctgcatacc | 1860 |
| ctaaatctca tcaactgcga acaacttaaa gagcttccaa gggatttcag aaaattaatt | 1920 |
| agccttaaga ctttgtactt gacaacacac caaatgtctg caggtatcaa aaatcagcat | 1980 |

| | |
|---|---|
| tcattcacat ctttgcaatt cttattgctt tttaaatgct gttttccaaa gttgcaacca | 2040 |
| gagctggttc agcactttac tgcattgcgg gtgttgagaa tctacgaatg tccatcatta | 2100 |
| tgctctttgc catctagtat cagatacctg acatcattgg aaaaactttg gatttggaat | 2160 |
| tgtgaggaat tggatcttat tgacggagag ggaatgtctg gccttacatc tcttcagtcc | 2220 |
| cttcttctta tgggacttcc aaagcttgtg acactacctt tggagcttaa ggatacagct | 2280 |
| ccaacaactt taaaatactt tagaattgcc gactgtccta accttgtgga acttcctgaa | 2340 |
| tggcttccta actgctcttc attgcagagg ctctacatag aagattgccc tgtgttggct | 2400 |
| tcgattcctc agggaattta ctctcacaac gccaatgtcc acataattga ctgcccactt | 2460 |
| ctaggaggat aa | 2472 |

<210> SEQ ID NO 127
<211> LENGTH: 2730
<212> TYPE: DNA
<213> ORGANISM: Arabidopsis thaliana

<400> SEQUENCE: 127

| | |
|---|---|
| atggatttca tctcatctct tatcgttggc tgtgctcagg tgttgtgtga atctatgaat | 60 |
| atggcggaga gaagaggaca taagactgat cttagacaag ccatcactga tcttgaaaca | 120 |
| gccatcggtg acttgaaggc catacgtgat gacctgactt tacgGatcca acaagacggt | 180 |
| ctagagggac gaagctgctc aaatcgtgcc agagagtggc ttagtgcggt gcaagtaacg | 240 |
| gagactaaaa cagccctact tttagtgagg tttaggcgtc gggaacagag gacgcgaatg | 300 |
| aggaggagat acctcagttg tttcggttgt gccgactaca aactgtgcaa gaaggtttct | 360 |
| gccatattga agagcattgg tgagctgaga gaacgctctg aagctatcaa acagatggc | 420 |
| gggtcaattc aagtaacttg tagagagata cccatcaagt ccgttgtcgg aaataccacg | 480 |
| atgatgaaac aggttttgga atttctcagt gaagaagaag aaagaggaat cattggtgtt | 540 |
| tatggacctg gtggggttgg aagacaacg ttaatgcaga gcattaacaa cgagctgatc | 600 |
| acaaaaggac atcagtatga tgtactgatt tgggttcaaa tgtccagaga attcggcgag | 660 |
| tgtacaattc agcaagccgt tggagcacgg ttgggtttat cttgggacga aaggagacc | 720 |
| ggcgaaaaca gagcttttgaa gatatacaga gctttgagac agaaacgttt cttgttgttg | 780 |
| ctagatgatg tctgggaaga gatagacttg agaaaactg gagttcctcg acctgacagg | 840 |
| gaaaacaaat gcaaggtgat gttcacgaca cggtctatag cattatgcaa caatatgggt | 900 |
| gcggaataca agttgagagt ggagtttctg gagaagaaac acgcgtggga gctgttctgt | 960 |
| agtaaggtat ggagaaaaga tcttttagag tcatcatcaa ttcgccggct cgcggagatt | 1020 |
| atagtgagta atgtggagg attgccacta gcgttgatca ctttaggagg agccatggct | 1080 |
| catagagaga cagaagaaga gtggatccat gctagtgaag ttctgactag atttccagca | 1140 |
| gagatgaagg gtatgaacta tgtatttgcc cttttgaaat tcagctacga caacctcgag | 1200 |
| agtgatctgc ttcggtcttg tttcttgtac tgcgctttat tcccagaaga acattctata | 1260 |
| gagatcgagc agcttgttga gtactgggtc ggcgaagggt ttctcaccag ctcccatggc | 1320 |
| gttaacacca tttacaaggg atattttctc attggggatc tgaaagcggc atgtttgttg | 1380 |
| gaaaccggag atgagaaaac acaggtgaag atgcataatg tggtcagaag ctttgcattg | 1440 |
| tggatggcat ctgaacaggg gacttataag gagctgatcc tagttgagcc tagcatggga | 1500 |
| catactgaag ctccctaaagc agaaaactgg cgacaagcgt tggtgatctc attgttagat | 1560 |

-continued

```
aacagaatcc agaccttgcc tgaaaaactc atatgcccga aactgacaac actgatgctc      1620
caacagaaca gctctttgaa gaagattcca cagggtttt tcatgcatat gcctgttctc       1680
agagtcttgg acttgtcgtt cacaagtatc actgagattc cgttgtctat caagtatttg      1740
gtggagttgt atcatctgtc tatgtcagga acaaagataa gtgtattgcc acaggagctt      1800
gggaatctta gaaaactgaa gcatctggac ctacaaagaa ctcagtttct tcagacgatc      1860
ccacgagatg ccatatgttg gctgagcaag ctcgaggttc tgaacttgta ctacagttac      1920
gccggttggg aactgcagag cttggagaa gatgaagcag aagaactcgg attcgctgac       1980
ttggaatact ggaaaaacct aaccacactc ggtatcactg ttctctcatt ggagaccta       2040
aaaactctct tcgagttcgg tgctttgcat aaacatatac agcatctcca cgttgaagag      2100
tgcaatgaac cctctactt caatctccca tcactcacta accatggcag gaacctgaga       2160
agacttagca ttaaaagttg ccatgacttg gagtacctgg tcacacccgc agattttgaa      2220
aatgattggc ttccgagtct agaggttctg acgttacaca gccttcacaa cttaaccaga      2280
gtgtgggaa attctgtaag ccaagattgt ctgcggaata tccgttgcat aaacatttca       2340
cactgcaaca agctgaagaa tgtctcatgg gttcagaaac tcccaaagct agaggtgatt      2400
gaactgttcg actgcagaga gatagaggaa ttgataagcg aacacgagag tccatccgtc      2460
gaagatccaa cattgttccc aagcctgaag accttgagaa ctagggatct gccagaacta     2520
aacagcatcc tcccatctcg attttcattc caaaagttg aaacattagt catcacaaat      2580
tgccccagag ttaagaaact gccgtttcag gagaggagga cccagatgaa cttgccaaca     2640
gtttattgtg aggagaaatg gtggaaagca ctggaaaaag atcaaccaaa cgaagagctt     2700
tgttatttac cgcgctttgt tccaaattga                                       2730
```

<210> SEQ ID NO 128
<211> LENGTH: 4167
<212> TYPE: DNA
<213> ORGANISM: Malus domestica

<400> SEQUENCE: 128

```
atggggggag aggcttttct tgtggcattc ctccaagtgc tggttgacaa gttggcgcat        60
cgcgaggtct tcaagtactt tggacttgta aagggcgtag atcaaaaact gaagaaatgg       120
agtgccacct tgtctgcgat ggagcgcgtg ctgaatgacg cagaggagag gcaactgacg       180
gctaagaaca cacactgaa gctctggctc gaagatctca gggacttggc ttttgatgtg        240
gaagacgtgt tggacaaata tgctactaaa atgttgaaac gtcagataca acatgctcat       300
tcccgcacaa caagcaaact atggaactca attcctgatg gtgttttcaa cttcaacatg       360
aactcggaaa tacagaagat tagtgagcga ttacaagaga tatctgaaca aaaagaccag       420
cttaatttga aaattgatac tggggcgttg actacaaggg cacgccgaaa catatcacct       480
agttccagtc aaccagatgg acctgtgatt ggaagggatg aggacaaaag aaagattgtt       540
gagctgctgt cgaaacaaga gcatcgtact gtcaatttcg atgtagttgc aattgttggt       600
atggctggag tcggaaagac aacacttgct ggacaagtac tcaatgatat ggttgcaacc       660
caaacgtttc aaccagctgt ttgggcatgc gtatctgacg acttcaacct tgaaagagtg       720
acaaagcaaa ttcttgaatc aatcacatct cggcaatgca ccacagaaga ttacaataag       780
gttcaagatt atctgcataa ggagttagcg gggaagaagt ttttaattgt tttagatgat       840
gtgtggaaaa cgtgtagcta cggtgaatgg atgaagttgc agtcccettt tcgtgacgga       900
gcacaaggaa gcaagataat tgtgacaaca cgtgatacag atgtttcaaa aatgatggga       960
```

```
gctgccacgc tcgttcacaa tttggagcct atggaaagta gtgtttgttt gcaagtattt    1020
gagcagcatg cattcttaaa ttctaatgac gacaaaccac caaattacga gttacttaag    1080
gaaaaaattg ctgccaagtg taggggattg cctttggccg caaggaccct tggtggtgtt    1140
ctacttcgta aagatacata cgaatgggaa gacatattga caacaaact gtggagtcta     1200 tcaaatgagc acgacatact tccagtactg agattaacct acttttatct tccttcacat    1260
ttgaaaagat gctttgccta ttgctcaata cttccaaatg actatgaatt tgaagagaag    1320
caaatgatcc ttctatggat ggccgagggg tttattcttc cacgaccaga agataagaag    1380
caaattgaag atttaggtgc tgattatttt cgggatctcg tatcaaggtc attgtttcaa    1440
aaatcaacca aatgtatttc aaaatatgtg atgcatgacc ttattggtga tttagcacgg    1500
tgggcagcag gagaaatttg ttttagattg gaggataagc aaaatgatga tggtgaacaa    1560
cttagatgtt ttcccaaggc acgccattcg tcttacatca ggggtctgtc tgatggggtc    1620
aaaagatttg aggtattttc tgaactgaaa tatttgcgaa ccttcttgcc actaagaaag    1680 gattcttct ggaattattt aagtcgtcag gttgcttttg atttattgcc gaaattgcaa     1740
tatttgcggg tgctctcttt caattgctat aaaataactg agcttccaga ctcaatcggt    1800
gatttaaggt atctacggta tctcgacctt tcctacacag atataacaag tttacctaaa    1860
tcaacaagca ctcttacaa cttgcagacg ttgatattgg aaggctgttc taaattgaag    1920
gcattgccta tagacatgag taatctagtt aatttgcgtc atctcaacaa ctcaaatgta    1980
tctttgttgg aagacatgcc tccacaacta ggtcgattgg tgaatctcca gtcattgact    2040
aagtttgtgg tgagtggtgg tggtggtggt gatcgatcag ggatacgaga gctggagttc    2100
ctaatgcatc tccgaggaac attgtgcatc tcaagattgg agaatgtgac tgatgtcgag    2160
gatgctcaga gggccaactt aaactgcaaa gagaggcttg attcgttggt gctagaatgg    2220
tctcattcaa gcgacacaag agaaacagaa tccgctgtgc ttgacatgtt acagcctcat    2280
acaaagctta aggagctcac catcaagagt tatgcaggaa aagaattttc atcatgggtt    2340
ggagttccat tgttctctaa tatggtgctc gtgcgcttag aggaatgtaa caattgtcta    2400
tctctaccac ctctcggaaa attgcctcat ctcaaagaac tttatattag aggaatgaat    2460
gcagtggaaa gtgttggagc tgagttttat ggagagtgct ccttgccttt tccgctatta    2520
gagactcttg agtttgtgga tatgcaacat tggaaagtat ggcttccatt tcaaacggat    2580
cacagaggta gtgttttccc ttgcctgaaa acactcttag tcagaaaatg ttctaaactg    2640
gagggtaagc tgccagagaa ccttgattcg ctggcatcgc ttgaaattgt taaatgtgaa    2700
gaattattgg tttcaattgc caattacaaa caacttcgtc agttaaacat tgacggttgt    2760
aaaggggtgg tgcatacagc tgctaaggtt gagtttgagt tattagagtc cttgtaccct    2820 tcaaatatt cggagctgac gtctctacaa acaggagaat tgtgcagaaa tggattaaac    2880
atggtcagag atttgaagat taatggatgt gaggagctga cgtcttcatt gaagaatgag    2940
gcaatattat tgcaacagtt gatttctctt ggccgtttag agattgaaga caactctctc    3000
ctagttgaag aactaggaaa agaagcagat gagttgttgc aattgcaaat attggggtgt    3060
aagcttgaat ttctgaagtt aaagaagtgc aaaaatcttt tgaagctacc agaagggtta    3120
aatcagttgt cgtcacttca agagcttcgc atacatgaat gttcaagtct agtttctttt    3180
ccagatgttg gtttgccacc ttctcttaaa gacatcgaga ttacagagtg ccactcgttg    3240
atatattttg caaaatccca gattcccaa aatctcagaa gaatacagat aagagattgc     3300
```

```
agaagtttga gatcactagt agacaatgag gctgttggtt cttgttcttc gtcttctcac    3360
aattgtcttg agtacttgaa tatcgagaga tgtcaatctc taacgttgtt atcattgagt    3420
gaccagcttg tcagggcact tagagaactt gacatatatg attgtgaaca actggagttt    3480
ctcgcaccgg acgggttgtt ctgcaacaac actaattact ttctcgaaaa ttttaggata    3540
cggaggtgcc aaaatctgaa atccttaccg agactgagtg ggggataag gggctctaac     3600
ctgagagaga tccggatcac cgattgcgac agattggagg ccttgcccga agacatgcac    3660
aatttcaact ctcttgagaa attgattatc gactaccgtg aaggtttgac ttgctccttt    3720
cccgccaacc taacatcact tatgatttgg aaggtcaaga gctgtaagtc attgtgggag    3780
ttggagtggg ggttacacag actcacctct cttagatact tgtggatcgg tggtgaagac    3840
ccggatatgg tatcgtttcc accggacatg gtccgaatgg agacgttgct ccccaaatct    3900
ctcactgaac tctcaattgg tggcttcccg aatctgaaga aactgagcag caagggcttt    3960
caattcctaa cctcccttga atctttggaa ctctgggatt gtccaaagct agcatccatt    4020
ccaaaggagg gactgcctct ttcacttacg gaactttgca tctatgggtg tcctgttcta    4080
aaagagagat gtcaaccagg aaaaggacgc tactggcaca aaatatccca catcccttac    4140
atagatatag attggaagat gatttga                                        4167
```

<210> SEQ ID NO 129
<211> LENGTH: 909
<212> TYPE: PRT
<213> ORGANISM: Arabidopsis thaliana

<400> SEQUENCE: 129

```
Met Asp Phe Ile Ser Ser Leu Ile Val Gly Cys Ala Gln Val Leu Cys
1               5                   10                  15

Glu Ser Met Asn Met Ala Glu Arg Arg Gly His Lys Thr Asp Leu Arg
            20                  25                  30

Gln Ala Ile Thr Asp Leu Glu Thr Ala Ile Gly Asp Leu Lys Ala Ile
        35                  40                  45

Arg Asp Asp Leu Thr Leu Arg Ile Gln Gln Asp Gly Leu Glu Gly Arg
    50                  55                  60

Ser Cys Ser Asn Arg Ala Arg Glu Trp Leu Ser Ala Val Gln Val Thr
65                  70                  75                  80

Glu Thr Lys Thr Ala Leu Leu Leu Val Arg Phe Arg Arg Glu Gln
            85                  90                  95

Arg Thr Arg Met Arg Arg Arg Tyr Leu Ser Cys Phe Gly Cys Ala Asp
            100                 105                 110

Tyr Lys Leu Cys Lys Lys Val Ser Ala Ile Leu Lys Ser Ile Gly Glu
        115                 120                 125

Leu Arg Glu Arg Ser Glu Ala Ile Lys Thr Asp Gly Gly Ser Ile Gln
    130                 135                 140

Val Thr Cys Arg Glu Ile Pro Ile Lys Ser Val Val Gly Asn Thr Thr
145                 150                 155                 160

Met Met Glu Gln Val Leu Glu Phe Leu Ser Glu Glu Glu Arg Gly
            165                 170                 175

Ile Ile Gly Val Tyr Gly Pro Gly Gly Val Gly Lys Thr Thr Leu Met
            180                 185                 190

Gln Ser Ile Asn Asn Glu Leu Ile Thr Lys Gly His Gln Tyr Asp Val
        195                 200                 205

Leu Ile Trp Val Gln Met Ser Arg Glu Phe Gly Glu Cys Thr Ile Gln
    210                 215                 220
```

```
Gln Ala Val Gly Ala Arg Leu Gly Leu Ser Trp Asp Glu Lys Glu Thr
225                 230                 235                 240

Gly Glu Asn Arg Ala Leu Lys Ile Tyr Arg Ala Leu Arg Gln Lys Arg
            245                 250                 255

Phe Leu Leu Leu Leu Asp Asp Val Trp Glu Ile Asp Leu Glu Lys
            260                 265                 270

Thr Gly Val Pro Arg Pro Asp Arg Glu Asn Lys Cys Lys Val Met Phe
        275                 280                 285

Thr Thr Arg Ser Ile Ala Leu Cys Asn Asn Met Gly Ala Glu Tyr Lys
        290                 295                 300

Leu Arg Val Glu Phe Leu Glu Lys Lys His Ala Trp Glu Leu Phe Cys
305                 310                 315                 320

Ser Lys Val Trp Arg Lys Asp Leu Leu Glu Ser Ser Ile Arg Arg
                325                 330                 335

Leu Ala Glu Ile Ile Val Ser Lys Cys Gly Gly Leu Pro Leu Ala Leu
                340                 345                 350

Ile Thr Leu Gly Gly Ala Met Ala His Arg Glu Thr Glu Glu Glu Trp
            355                 360                 365

Ile His Ala Ser Glu Val Leu Thr Arg Phe Pro Ala Glu Met Lys Gly
    370                 375                 380

Met Asn Tyr Val Phe Ala Leu Leu Lys Phe Ser Tyr Asp Asn Leu Glu
385                 390                 395                 400

Ser Asp Leu Leu Arg Ser Cys Phe Leu Tyr Cys Ala Leu Phe Pro Glu
                405                 410                 415

Glu His Ser Ile Glu Ile Glu Gln Leu Val Glu Tyr Trp Val Gly Glu
                420                 425                 430

Gly Phe Leu Thr Ser Ser His Gly Val Asn Thr Ile Tyr Lys Gly Tyr
            435                 440                 445

Phe Leu Ile Gly Asp Leu Lys Ala Ala Cys Leu Leu Glu Thr Gly Asp
    450                 455                 460

Glu Lys Thr Gln Val Lys Met His Asn Val Val Arg Ser Phe Ala Leu
465                 470                 475                 480

Trp Met Ala Ser Glu Gln Gly Thr Tyr Lys Leu Ile Leu Val Glu
                485                 490                 495

Pro Ser Met Gly His Thr Glu Ala Pro Lys Ala Glu Asn Trp Arg Gln
                500                 505                 510

Ala Leu Val Ile Ser Leu Leu Asp Asn Arg Ile Gln Thr Leu Pro Glu
            515                 520                 525

Lys Leu Ile Cys Pro Lys Leu Thr Thr Leu Met Leu Gln Gln Asn Ser
            530                 535                 540

Ser Leu Lys Lys Ile Pro Thr Gly Phe Phe Met His Met Pro Val Leu
545                 550                 555                 560

Arg Val Leu Asp Leu Ser Phe Thr Ser Ile Thr Glu Ile Pro Leu Ser
                565                 570                 575

Ile Lys Tyr Leu Val Glu Leu Tyr His Leu Ser Met Ser Gly Thr Lys
            580                 585                 590

Ile Ser Val Leu Pro Gln Glu Leu Gly Asn Leu Arg Lys Leu Lys His
        595                 600                 605

Leu Asp Leu Gln Arg Thr Gln Phe Leu Gln Thr Ile Pro Arg Asp Ala
    610                 615                 620

Ile Cys Trp Leu Ser Lys Leu Glu Val Leu Asn Leu Tyr Tyr Ser Tyr
625                 630                 635                 640
```

```
Ala Gly Trp Glu Leu Gln Ser Phe Gly Glu Asp Glu Ala Glu Leu
            645                 650                 655

Gly Phe Ala Asp Leu Glu Tyr Leu Glu Asn Leu Thr Thr Leu Gly Ile
        660                 665                 670

Thr Val Leu Ser Leu Glu Thr Leu Lys Thr Leu Phe Glu Phe Gly Ala
            675                 680                 685

Leu His Lys His Ile Gln His Leu His Val Glu Glu Cys Asn Glu Leu
        690                 695                 700

Leu Tyr Phe Asn Leu Pro Ser Leu Thr Asn His Gly Arg Asn Leu Arg
705                 710                 715                 720

Arg Leu Ser Ile Lys Ser Cys His Asp Leu Glu Tyr Leu Val Thr Pro
            725                 730                 735

Ala Asp Phe Glu Asn Asp Trp Leu Pro Ser Leu Glu Val Leu Thr Leu
            740                 745                 750

His Ser Leu His Asn Leu Thr Arg Val Trp Gly Asn Ser Val Ser Gln
            755                 760                 765

Asp Cys Leu Arg Asn Ile Arg Cys Ile Asn Ile Ser His Cys Asn Lys
            770                 775                 780

Leu Lys Asn Val Ser Trp Val Gln Lys Leu Pro Lys Leu Glu Val Ile
785                 790                 795                 800

Glu Leu Phe Asp Cys Arg Glu Ile Glu Glu Leu Ile Ser Glu His Glu
            805                 810                 815

Ser Pro Ser Val Glu Asp Pro Thr Leu Phe Pro Ser Leu Lys Thr Leu
            820                 825                 830

Arg Thr Arg Asp Leu Pro Glu Leu Asn Ser Ile Leu Pro Ser Arg Phe
            835                 840                 845

Ser Phe Gln Lys Val Glu Thr Leu Val Ile Thr Asn Cys Pro Arg Val
        850                 855                 860

Lys Lys Leu Pro Phe Gln Glu Arg Arg Thr Gln Met Asn Leu Pro Thr
865                 870                 875                 880

Val Tyr Cys Glu Glu Lys Trp Trp Lys Ala Leu Glu Lys Asp Gln Pro
            885                 890                 895

Asn Glu Glu Leu Cys Tyr Leu Pro Arg Phe Val Pro Asn
            900                 905

<210> SEQ ID NO 130
<211> LENGTH: 1388
<212> TYPE: PRT
<213> ORGANISM: Malus domestica

<400> SEQUENCE: 130

Met Gly Gly Glu Ala Phe Leu Val Ala Phe Leu Gln Val Leu Val Asp
1               5                   10                  15

Lys Leu Ala His Arg Glu Val Phe Lys Tyr Phe Gly Leu Val Lys Gly
            20                  25                  30

Val Asp Gln Lys Leu Lys Lys Trp Ser Ala Thr Leu Ser Ala Ile Gly
        35                  40                  45

Ala Val Leu Asn Asp Ala Glu Glu Arg Gln Leu Thr Ala Lys Asn Asn
    50                  55                  60

Thr Leu Lys Leu Trp Leu Glu Asp Leu Arg Asp Leu Ala Phe Asp Val
65                  70                  75                  80

Glu Asp Val Leu Asp Lys Tyr Ala Thr Lys Met Leu Lys Arg Gln Ile
            85                  90                  95

Gln His Ala His Ser Arg Thr Thr Ser Lys Leu Trp Asn Ser Ile Pro
            100                 105                 110
```

```
Asp Gly Val Phe Asn Phe Asn Met Asn Ser Glu Ile Gln Lys Ile Ser
        115                 120                 125
Glu Arg Leu Gln Glu Ile Ser Glu Gln Lys Asp Gln Leu Asn Leu Lys
        130                 135                 140
Ile Asp Thr Gly Ala Leu Thr Thr Arg Ala Arg Arg Asn Ile Ser Pro
145                 150                 155                 160
Ser Ser Ser Gln Pro Asp Gly Pro Val Ile Gly Arg Asp Glu Asp Lys
                165                 170                 175
Arg Lys Ile Val Glu Leu Leu Ser Lys Gln Glu His Arg Thr Val Asn
                180                 185                 190
Phe Asp Val Val Ala Ile Val Gly Met Ala Gly Val Gly Lys Thr Thr
            195                 200                 205
Leu Ala Gly Gln Val Leu Asn Asp Met Val Ala Thr Gln Thr Phe Gln
        210                 215                 220
Pro Ala Val Trp Ala Cys Val Ser Asp Asp Phe Asn Leu Glu Arg Val
225                 230                 235                 240
Thr Lys Gln Ile Leu Glu Ser Ile Thr Ser Arg Gln Cys Thr Thr Glu
                245                 250                 255
Asp Tyr Asn Lys Val Gln Asp Tyr Leu His Lys Glu Leu Ala Gly Lys
                260                 265                 270
Lys Phe Leu Ile Val Leu Asp Asp Val Trp Lys Thr Cys Ser Tyr Gly
        275                 280                 285
Glu Trp Met Lys Leu Gln Ser Pro Phe Arg Asp Gly Ala Gln Gly Ser
        290                 295                 300
Lys Ile Ile Val Thr Thr Arg Asp Thr Asp Val Ser Lys Met Met Gly
305                 310                 315                 320
Ala Ala Thr Leu Val His Asn Leu Glu Pro Met Glu Ser Ser Val Cys
                325                 330                 335
Leu Gln Val Phe Glu Gln His Ala Phe Leu Asn Ser Asn Asp Asp Lys
                340                 345                 350
Pro Pro Asn Tyr Glu Leu Leu Lys Glu Lys Ile Ala Ala Lys Cys Arg
            355                 360                 365
Gly Leu Pro Leu Ala Ala Arg Thr Leu Gly Gly Val Leu Leu Arg Lys
        370                 375                 380
Asp Thr Tyr Glu Trp Glu Asp Ile Leu Asn Asn Lys Leu Trp Ser Leu
385                 390                 395                 400
Ser Asn Glu His Asp Ile Leu Pro Val Leu Arg Leu Thr Tyr Phe Tyr
                405                 410                 415
Leu Pro Ser His Leu Lys Arg Cys Phe Ala Tyr Cys Ser Ile Leu Pro
                420                 425                 430
Asn Asp Tyr Glu Phe Glu Glu Lys Gln Met Ile Leu Leu Trp Met Ala
            435                 440                 445
Glu Gly Phe Ile Leu Pro Arg Pro Glu Asp Lys Lys Gln Ile Glu Asp
        450                 455                 460
Leu Gly Ala Asp Tyr Phe Arg Asp Leu Val Ser Arg Ser Leu Phe Gln
465                 470                 475                 480
Lys Ser Thr Lys Cys Ile Ser Lys Tyr Val Met His Asp Leu Ile Gly
                485                 490                 495
Asp Leu Ala Arg Trp Ala Ala Gly Glu Ile Cys Phe Arg Leu Glu Asp
                500                 505                 510
Lys Gln Asn Asp Asp Gly Glu Gln Leu Arg Cys Phe Pro Lys Ala Arg
            515                 520                 525
```

His Ser Ser Tyr Ile Arg Gly Leu Ser Asp Gly Val Lys Arg Phe Glu
    530                 535                 540

Val Phe Ser Glu Leu Lys Tyr Leu Arg Thr Phe Leu Pro Leu Arg Lys
545                 550                 555                 560

Asp Ser Phe Trp Asn Tyr Leu Ser Arg Gln Val Ala Phe Asp Leu Leu
                565                 570                 575

Pro Lys Leu Gln Tyr Leu Arg Val Leu Ser Phe Asn Cys Tyr Lys Ile
                580                 585                 590

Thr Glu Leu Pro Asp Ser Ile Gly Asp Leu Arg Tyr Leu Arg Tyr Leu
            595                 600                 605

Asp Leu Ser Tyr Thr Asp Ile Thr Ser Leu Pro Lys Ser Thr Ser Thr
    610                 615                 620

Leu Tyr Asn Leu Gln Thr Leu Ile Leu Glu Gly Cys Ser Lys Leu Lys
625                 630                 635                 640

Ala Leu Pro Ile Asp Met Ser Asn Leu Val Asn Leu Arg His Leu Asn
                645                 650                 655

Asn Ser Asn Val Ser Leu Leu Glu Asp Met Pro Pro Gln Leu Gly Arg
                660                 665                 670

Leu Val Asn Leu Gln Ser Leu Thr Lys Phe Val Val Ser Gly Gly Gly
            675                 680                 685

Gly Gly Asp Arg Ser Gly Ile Arg Glu Leu Glu Phe Leu Met His Leu
    690                 695                 700

Arg Gly Thr Leu Cys Ile Ser Arg Leu Glu Asn Val Thr Asp Val Glu
705                 710                 715                 720

Asp Ala Gln Arg Ala Asn Leu Asn Cys Lys Glu Arg Leu Asp Ser Leu
                725                 730                 735

Val Leu Glu Trp Ser His Ser Ser Asp Thr Arg Glu Thr Glu Ser Ala
                740                 745                 750

Val Leu Asp Met Leu Gln Pro His Thr Lys Leu Lys Glu Leu Thr Ile
            755                 760                 765

Lys Ser Tyr Ala Gly Lys Glu Phe Ser Ser Trp Val Gly Val Pro Leu
    770                 775                 780

Phe Ser Asn Met Val Leu Val Arg Leu Glu Glu Cys Asn Asn Cys Leu
785                 790                 795                 800

Ser Leu Pro Pro Leu Gly Lys Leu Pro His Leu Lys Glu Leu Tyr Ile
                805                 810                 815

Arg Gly Met Asn Ala Val Glu Ser Val Gly Ala Glu Phe Tyr Gly Glu
                820                 825                 830

Cys Ser Leu Pro Phe Pro Leu Leu Glu Thr Leu Glu Phe Val Asp Met
            835                 840                 845

Gln His Trp Lys Val Trp Leu Pro Phe Gln Thr Asp His Arg Gly Ser
    850                 855                 860

Val Phe Pro Cys Leu Lys Thr Leu Leu Val Arg Lys Cys Ser Lys Leu
865                 870                 875                 880

Glu Gly Lys Leu Pro Glu Asn Leu Asp Ser Leu Ala Ser Leu Glu Ile
                885                 890                 895

Val Lys Cys Glu Glu Leu Leu Val Ser Ile Ala Asn Tyr Lys Gln Leu
            900                 905                 910

Arg Gln Leu Asn Ile Asp Gly Cys Lys Gly Val Val His Thr Ala Ala
    915                 920                 925

Lys Val Glu Phe Glu Leu Leu Glu Ser Leu Tyr Leu Ser Asn Ile Ser
    930                 935                 940

Glu Leu Thr Ser Leu Gln Thr Gly Glu Leu Cys Arg Asn Gly Leu Asn

```
                945                 950                 955                 960
            Met Val Arg Asp Leu Lys Ile Asn Gly Cys Glu Glu Leu Thr Ser Ser
                        965                 970                 975
            Leu Lys Asn Glu Ala Ile Leu Leu Gln Gln Leu Ile Ser Leu Gly Arg
                        980                 985                 990
            Leu Glu Ile Glu Asp Asn Ser Leu Leu Val Glu Glu Leu Gly Lys Glu
                        995                 1000                1005
            Ala Asp Glu Leu Leu Gln Leu Gln Ile Leu Gly Cys Lys Leu Glu
                1010                1015                1020
            Phe Leu Lys Leu Lys Lys Cys Lys Asn Leu Leu Lys Leu Pro Glu
                1025                1030                1035
            Gly Leu Asn Gln Leu Ser Ser Leu Gln Glu Leu Arg Ile His Glu
                1040                1045                1050
            Cys Ser Ser Leu Val Ser Phe Pro Asp Val Gly Leu Pro Pro Ser
                1055                1060                1065
            Leu Lys Asp Ile Glu Ile Thr Glu Cys His Ser Leu Ile Tyr Phe
                1070                1075                1080
            Ala Lys Ser Gln Ile Pro Gln Asn Leu Arg Arg Ile Gln Ile Arg
                1085                1090                1095
            Asp Cys Arg Ser Leu Arg Ser Leu Val Asp Asn Glu Ala Val Gly
                1100                1105                1110
            Ser Cys Ser Ser Ser Ser His Asn Cys Leu Glu Tyr Leu Asn Ile
                1115                1120                1125
            Glu Arg Cys Gln Ser Leu Thr Leu Leu Ser Leu Ser Asp Gln Leu
                1130                1135                1140
            Val Arg Ala Leu Arg Glu Leu Asp Ile Tyr Asp Cys Glu Gln Leu
                1145                1150                1155
            Glu Phe Leu Ala Pro Asp Gly Leu Phe Cys Asn Asn Thr Asn Tyr
                1160                1165                1170
            Phe Leu Glu Asn Phe Arg Ile Arg Arg Cys Gln Asn Leu Lys Ser
                1175                1180                1185
            Leu Pro Arg Leu Ser Gly Gly Ile Arg Gly Ser Asn Leu Arg Glu
                1190                1195                1200
            Ile Arg Ile Thr Asp Cys Asp Arg Leu Glu Ala Leu Pro Glu Asp
                1205                1210                1215
            Met His Asn Phe Asn Ser Leu Glu Lys Leu Ile Ile Asp Tyr Arg
                1220                1225                1230
            Glu Gly Leu Thr Cys Ser Phe Pro Ala Asn Leu Thr Ser Leu Met
                1235                1240                1245
            Ile Trp Lys Val Lys Ser Cys Lys Ser Leu Trp Glu Leu Glu Trp
                1250                1255                1260
            Gly Leu His Arg Leu Thr Ser Leu Arg Tyr Leu Trp Ile Gly Gly
                1265                1270                1275
            Glu Asp Pro Asp Met Val Ser Phe Pro Pro Asp Met Val Arg Met
                1280                1285                1290
            Glu Thr Leu Leu Pro Lys Ser Leu Thr Glu Leu Ser Ile Gly Gly
                1295                1300                1305
            Phe Pro Asn Leu Lys Lys Leu Ser Ser Lys Gly Phe Gln Phe Leu
                1310                1315                1320
            Thr Ser Leu Glu Ser Leu Glu Leu Trp Asp Cys Pro Lys Leu Ala
                1325                1330                1335
            Ser Ile Pro Lys Glu Gly Leu Pro Leu Ser Leu Thr Glu Leu Cys
                1340                1345                1350
```

Ile Tyr Gly Cys Pro Val Leu Lys Glu Arg Cys Gln Pro Gly Lys
    1355                1360                1365

Gly Arg Tyr Trp His Lys Ile Ser His Ile Pro Tyr Ile Asp Ile
    1370                1375                1380

Asp Trp Lys Met Ile
    1385

<210> SEQ ID NO 131
<211> LENGTH: 823
<212> TYPE: PRT
<213> ORGANISM: Solanum tuberosum

<400> SEQUENCE: 131

Met Ala Glu Ser Phe Leu Phe Asn Ile Ile Glu Arg Val Leu Ala Lys
1               5                   10                  15

Val Ser Ser Ile Ala Val Tyr Glu Ile Thr Leu Ala Trp Asn Val Lys
            20                  25                  30

Ile Glu Leu Arg Lys Leu Gln Ser Thr Leu Ser Thr Ile Lys Ala Val
        35                  40                  45

Leu Leu Asp Ala Asn Glu Gln Gln Ala Lys Asn His Glu Val Arg Asp
    50                  55                  60

Trp Leu Glu Lys Leu Arg Asp Val Val Tyr Asp Val Asp Asp Leu Met
65              70                  75                  80

Asp Asp Leu Ser Thr Gln Leu Leu Leu Gln Met His Phe Gln Lys Ser
                85                  90                  95

Phe Arg Lys Lys Val Arg Lys Phe Phe Ser Ser Ser Asn Pro Ile Ile
            100                 105                 110

Tyr Arg Phe Lys Ile Gly Arg Lys Val Lys Glu Ile Arg Glu Leu Leu
        115                 120                 125

Asn Glu Ile Ala Asp Asp Arg Arg Asn Phe His Phe Thr Glu His Thr
    130                 135                 140

Tyr Val Ile Pro Ala Glu Asn Thr Ser Arg Glu Gln Thr His Ser Phe
145                 150                 155                 160

Val Arg Ala Ser Asp Ile Ile Gly Arg Asp Asp Asp Gln Glu Asn Ile
                165                 170                 175

Val Lys Gln Leu Ile Asp Ser His Asp Glu Glu Asn Ile Ser Val Ile
            180                 185                 190

Pro Ile Val Gly Leu Gly Gly Leu Gly Lys Thr Thr Leu Val Lys Leu
        195                 200                 205

Val Tyr Asn Asn Arg Val Val Gln Asn Phe Asp Leu Arg Met Trp
    210                 215                 220

Val Ser Ile Ser Glu Asp Phe Ser Leu Ser Lys Val Ile Glu Lys Ile
225                 230                 235                 240

Leu Arg Ser Ala Thr Gly Glu Ser Phe Asp His Leu Asp Met Asp Gln
                245                 250                 255

Leu Gln Gly Cys Leu Gly Glu Val Leu Gln Lys Tyr Arg Tyr Leu Leu
            260                 265                 270

Val Leu Asp Asp Val Trp Asn Glu Asp Gln His Lys Trp Thr Asp Leu
        275                 280                 285

Arg Glu Leu Leu Met Asn Cys Ser Arg Gly Ser Lys Ile Val Val Thr
    290                 295                 300

Thr Arg Ser Lys Met Ala Ala Leu Ile Thr Gly Thr Val Pro Pro Tyr
305                 310                 315                 320

Tyr Leu Glu Gly Leu Ala Asp Asp Asp Cys Leu Ser Leu Phe Leu Lys

```
                    325                 330                 335
Cys Ala Phe Gly Gly Gln Asp Asn Leu Phe Pro Asn Leu Val Glu Ile
                340                 345                 350
Gly Lys Glu Ile Val Lys Lys Cys Gly Gly Val Pro Leu Ala Val Lys
                355                 360                 365
Thr Leu Gly Arg Leu Leu Tyr Met Lys Thr Asp Glu Asn Glu Trp Leu
                370                 375                 380
Gln Ile Arg Asp Asn Glu Ile Trp Glu Ile Glu Gln Asn Lys Ser Asp
385                 390                 395                 400
Ile Leu Pro Ile Leu Arg Leu Ser Tyr Glu Gln Met Pro Ser His Leu
                405                 410                 415
Arg Gln Cys Phe Ala Tyr Cys Ser Met Leu Ser Lys Gly Gln Glu Ile
                420                 425                 430
Pro Arg Glu Asp Phe Ile Asn Arg Trp Ile Ala Gln Gly Phe Ile Gln
                435                 440                 445
Ser Ser Asn Arg Asn Arg Lys Leu Glu Asp Ile Gly Asn Gln Tyr Phe
                450                 455                 460
Asp Glu Leu Leu Ser Arg Phe Cys Phe Leu Asp Val Val Gln Ala Phe
465                 470                 475                 480
Asp Gly Glu Ile Leu Ala Cys Lys Ile His Asn Leu Val His Asp Leu
                485                 490                 495
Ala Gln Ser Val Ala Gly Ala Glu Cys Leu Asn Val Lys Pro Asn Ala
                500                 505                 510
Phe Val Val Ser Glu Arg Val Arg His Leu Phe Phe His Ala Glu Asp
                515                 520                 525
Met Ser Arg Lys His Phe Pro Arg Phe Leu Leu Pro Leu Gln Lys Leu
                530                 535                 540
Arg Ser Phe Ser Tyr Ser Phe Asn Ile Gly Pro Val Asn Lys Phe Phe
545                 550                 555                 560
Val Lys Thr Met Leu Ser Asn Phe Lys Cys Leu Arg Met Leu Val Leu
                565                 570                 575
Asn Asn Leu Asp Leu Glu Glu Leu Pro Thr Ser Ile Gly His Leu Lys
                580                 585                 590
Glu Leu Arg Tyr Leu Asn Leu Ser Asn Ser Gly Asn Ile Lys Phe Leu
                595                 600                 605
Pro Arg Ser Met Ser Lys Leu Val Asn Leu His Thr Leu Asn Leu Ile
                610                 615                 620
Asn Cys Glu Gln Leu Lys Glu Leu Pro Arg Asp Phe Arg Lys Leu Ile
625                 630                 635                 640
Ser Leu Lys Thr Leu Tyr Leu Thr Thr His Gln Ile Ser Glu Gly Ile
                645                 650                 655
Lys Asn Gln His Ser Phe Thr Ser Leu Gln Phe Leu Leu Leu Phe Lys
                660                 665                 670
Cys Cys Phe Pro Lys Leu Gln Pro Glu Leu Val Gln His Phe Thr Ala
                675                 680                 685
Leu Arg Val Leu Arg Ile Tyr Glu Cys Pro Ser Leu Cys Ser Leu Pro
                690                 695                 700
Ser Ser Ile Arg Tyr Leu Thr Ser Leu Glu Lys Leu Trp Ile Trp Asn
705                 710                 715                 720
Cys Glu Glu Leu Asp Leu Ile Asp Gly Glu Gly Met Ser Gly Leu Thr
                725                 730                 735
Ser Leu Gln Ser Leu Leu Leu Met Gly Leu Pro Lys Leu Val Thr Leu
                740                 745                 750
```

```
Pro Leu Glu Leu Lys Asp Thr Ala Pro Thr Thr Leu Lys Tyr Phe Arg
        755                 760                 765

Ile Ala Asp Cys Pro Asn Leu Met Glu Leu Pro Glu Trp Leu Pro Asn
        770                 775                 780

Cys Ser Ser Leu Gln Arg Leu Tyr Ile Glu Asp Cys Pro Val Leu Ala
785                 790                 795                 800

Ser Ile Pro Gln Gly Ile Tyr Ser His Asn Ala Asn Leu His Ile Ile
                805                 810                 815

Asp Cys Pro Leu Leu Gly Gly
            820

<210> SEQ ID NO 132
<211> LENGTH: 2472
<212> TYPE: DNA
<213> ORGANISM: Solanum tuberosum

<400> SEQUENCE: 132
```

| | |
|---|---|
| atggcggaat ctttcttgtt caatatcatt gaacgagttt tggctaaagt ttcttcaatt | 60 |
| gctgtatatg agatcactct agcttggaat gttaagatag agctaaggaa actccaaagt | 120 |
| actctatcca ccatcaaagc tgtacttcta gatgcaaacg agcaacaggc aaagaaccat | 180 |
| gaagtgagag attggctgga aaagctcaga gatgttgttt atgatgtcga tgatttgatg | 240 |
| gatgatttat caacacaact gttgctgcaa atgcatttcc agaaaagctt taggaagaag | 300 |
| gtaagaaaat tcttttcaag ttcaaatcca attatatatc gattcaagat ggcagaaag | 360 |
| gtaaagaaa tcagggagct actgaatgag attgcagatg ataggagaaa tttccacttc | 420 |
| acggaacata cgtatgtaat tccagctgag aatacgagta gagaacaaac acactccttt | 480 |
| gtgagggcat cagatatcat tggtagagat gatgatcaag aaaacattgt aaaacagctg | 540 |
| atagattctc atgatgagga aaatatttct gtgattccta ttgttggact tggagggctt | 600 |
| ggaaaaacca cacttgttaa gttggtttat aacaataata gggttgttca gaattttgac | 660 |
| cttagaatgt gggttagtat ttcagaagat tttagtctga gcaaggtaat tgagaaaatt | 720 |
| ctgaggtctg caacgggaga gagttttgac cacctagata tggaccaatt acaaggttgt | 780 |
| ttgggagagg ttttgcaaca gaaaaggtat ttacttgtgc tggatgatgt gtggaatgaa | 840 |
| gatcaacaca gtggacaga tctgagggag ttgctgatga attgttccag aggtagtaaa | 900 |
| attgttgtca ctacacgtag taagatggct gctttgatta ctggaacagt tccgccttat | 960 |
| tatttggaag gccttgctga tgatgactgc ttatctttat ttttgaaatg tgcatttgga | 1020 |
| gggcaggaca atttgtttcc taatctagta gaaataggaa aagaaattgt gaaaaagtgt | 1080 |
| ggaggagtgc ctttggctgt gaaaaccttg gaaggttat tgtacatgaa acagacgag | 1140 |
| aatgaatggt tgcaaataag agataatgag atatgggaaa tcgaacagaa taaatctgac | 1200 |
| attttaccaa tattgagatt gagctatgaa cagatgccat cacatctaag acagtgcttt | 1260 |
| gcctattgct ccatgttatc caaaggtcaa gaaattccga gggaggattt tatcaatcgg | 1320 |
| tggattgctc aaggatttat acagagttca aacagaaaca ggaagctgga agatataggt | 1380 |
| aatcagtact tgatgagtt gctatcaagg ttttgcttcc tagatgtggt acaagctttt | 1440 |
| gatggagaaa tattggcttg taagatacac aatcttgtgc atgatcttgc acagtcagta | 1500 |
| gcaggtgcag aatgcttaaa tgtgaaaccc aatgctttcg tggttctga agagttcgc | 1560 |
| cacttattct tccatgcaga agatatgtct aggaaaacact tccccagatt tttgcttcct | 1620 |
| ttgcaaaagt tgaggtcttt ctcttattct tttaacattg gacctgtaaa caagttcttt | 1680 |

```
gtcaagacaa tgttgtcaaa tttcaaatgc cttcggatgt tagtcttgaa caatctagat    1740
cttgaggagt tgccaacttc gataggtcac ttgaaggaat taagatacct taaccttagc    1800
aacagtggta atatcaagtt tcttccaagg tctatgagca aattagtaaa tctgcacacc    1860
ctaaacctca ttaactgtga acagcttaag gagttgccaa gagactttag aaagttaatc    1920
agcctaaaga ccttgtattt gactacacat cagatatcag aagggatcaa gaatcaacat    1980
tctttcactt ctcttcaatt tttgcttctt ttcaaatgtt gtttcccaaa attgcagcca    2040
gaactggtgc agcattttac tgcacttcgg gttttgcgta tctatgaatg cccaagttta    2100
tgttctcttc caagcagtat tagatatctg acttcacttg aaaagctatg gatctggaac    2160
tgtgaagaac ttgatttgat agatggagaa ggaatgtcag gcctaacaag tcttcaatcc    2220
ttgcttctaa tggggcttcc taagttggtg actctaccat tggaacttaa agatactgct    2280
cctacaacat taaagtactt cagaatcgcc gattgtccca acctgatgga gcttccagag    2340
tggctgccca attgctcctc acttcagaga ctgtatatag aggactgtcc tgttttggca    2400
tcgataccct aaggaatcta cagccacaat gccaatctcc atataatcga ctgtccattg    2460
ctaggtggat ga                                                        2472
```

ENHANCED DISEASE RESISTANCE IN PLANTS

This application claims the benefit of U.S. Provisional Patent Application Ser. No. 62/894,234, filed Aug. 30, 2019, which is hereby incorporated by reference in its entirety.

This invention was made with government support under grant number 1546625 awarded by the National Science Foundation. The government has certain rights in the invention.

FIELD

Embodiments of the disclosure relate generally to disease resistance in plants.

BACKGROUND

Bacterial speck disease of tomato, caused by *Pseudomonas syringae* pv. tomato (Pst), occurs in cool, wet environments that favor bacterial spreading and leaf colonization through stomata (Pedley et al., "Molecular Basis of Pto-Mediated Resistance to Bacterial Speck Disease in Tomato," *Ann. Rev. Phytopathol.* 41:215-43 (2003)). The disease causes necrotic lesions (specks) on different parts of the plant including leaves, stems, flowers, and fruits. As a result, it can affect both fruit yield and quality, leading to significant economic losses (Jones et al., "Bacterial speck," in *COMPENDIUM OF TOMATO DISEASES* 26-27 (J. B. Jones et al. eds, 1991). Two races of Pst are currently defined which differ in their ability to cause disease on tomato varieties expressing the resistance gene Pto. Race 0 strains express the type III effectors AvrPto or AvrPtoB, are recognized by Pto, and consequently are unable to cause disease on Pto-expressing tomato varieties. Race 1 strains do not have the avrPto or avrPtoB genes or do not express these effector proteins and are therefore not recognized by Pto (Lin et al., "Diverse AvrPtoB Homologs from Several *Pseudomonas syringae* Pathovars Elicit Pto-Dependent Resistance and Have Similar Virulence Activities," *Appl. Environ. Microbiol.* 72(1):702-12 (2006); Kunkeaw et al., "Molecular and Evolutionary Analyses of *Pseudomonas syringae* pv. tomato Race 1," *Mol. Plant-Microbe. Interact.* 23:415-24 (2010)). Recently, strains with virulence attributes intermediate between race 0 and race 1 strains have been discovered (Kraus et al, "*Pseudomonas syringae* pv. tomato strains from New York Exhibit Virulence Attributes Intermediate Between Typical race 0 and race 1 Strains," *Plant Dis.* 101:1442-8 (2017)). These strains express AvrPto but nevertheless multiply to levels intermediate between race 0 and race 1 strains in tomato plants that express Pto.

In order to combat pathogens, plants have evolved a two-layered immune system. In an initial defense response, plants use extracellular pattern recognition receptors (PRRs) to detect the presence of microbe-associated molecular patterns (MAMPS) (Dangl et al., "Pivoting the Plant Immune System from Dissection to Deployment," *Science* 341(6147):746-51 (2013)). In the second immune response, plants use intracellular proteins (R proteins or nucleotide-binding oligomerization domain-like (NOD-like) receptors, NLRs) to detect pathogen effector proteins translocated inside the host cell during the infection process. NLR-triggered immunity (NTI) is typically associated with programed cell death and significant inhibition of pathogen multiplication (Jones et al., "The Plant Immune System," *Nature* 444(7117):323-29 (2006); Buttner, "Behind the Lines-Actions of Bacterial type III Effector Proteins in Plant Cells," *FEMS Microbiol. Rev.* 40(6):894-937 (2016)).

Genetic resistance to Pst is conferred by the Pto and Prf genes which encode a serine/threonine cytoplasmic kinase and a nucleotide-binding leucine-rich repeat (NLR) protein, respectively (Pedley and Martin, "Molecular Basis of Pto-Mediated Resistance to Bacterial Speck Disease in Tomato," *Ann Rev Phytopathol* 41:215-243 (2003)). The Pto/Prf proteins form a complex that recognizes the type III effectors AvrPto or AvrPtoB expressed by race 0 Pst strains (Kim et al, "Two Distinct *Pseudomonas* Effector Proteins Interact With the Pto Kinase and Activate Plant Immunity," *Cell* 109:589-598 (2002); Mucyn et al., "Regulation of Tomato Prf by Pto-like Protein Kinases," *Mol Plant-Microbe Interact* 22:391-401 (2009); Martin, "Suppression and Activation of the Plant Immune System by *Pseudomonas syringae* Effectors AvrPto and AvrPtoB," in EFFECTORS IN PLANT-MICROBE INTERACTIONS 123-154 (F. Martin and S. Kamoun eds, 2012); Ntoukakis et al., "The Tomato Prf Complex is a Molecular Trap for Bacterial Effectors Based on Pto Trans-phosphorylation," *PLoS Pathog,* 9:e1003123 (2013); and Saur et al., "The N-terminal Domain of the Tomato Immune Protein Prf Contains Multiple Homotypic and Pto Kinase Interaction Sites," *J Biol Chem,* 290:11258-11267 (2015)). After translocation of AvrPto or AvrPtoB into the plant cell, Pto, which encodes a serine/threonine protein kinase, physically interacts with either one of these effectors and acts in concert with Prf, an NLR, to activate NTI (Salmeron et al., "Tomato Prf is a Member of the Leucine-Rich Repeat Class of Plant Disease Resistance Genes and Lies Embedded Within the Pto Kinase Gene Cluster," *Cell* 86(1):123-33 (1996); Pedley et al., "Molecular Basis of Pto-Mediated Resistance to Bacterial Speck Disease in Tomato," *Ann. Rev. Phytopathol.* 41:215-43 (2003)). Pto was originally identified in a wild relative of tomato, *Solanum pimpinellifolium*, and it has been introgressed into many processing-type tomato varieties. For over 30 years, the gene has provided effective control of speck disease caused by Pst race 0 strains (Pitblado et al., "Resistance to Bacterial Speck (*Pseudomonas tomato*) in Tomato," *Acta Hort.* 100:379-82 (1980)). The widespread use of the Pto/Prf genes since the 1980s appears to have exerted selection pressure on the pathogen and race 0 Pst strains are becoming less common. Instead, strains of race 1 Pst, which lack AvrPto and AvrPtoB, are becoming more prevalent and represent a new threat in tomato growing areas (Kunkeaw et al., "Molecular and Evolutionary Analyses of *Pseudomonas syringae* pv. tomato Race 1," *Mol Plant-Microbe Interact* 23:415-424 (2010) and Thapa and Coaker, "Genome Sequences of Two *Pseudomonas syringae* pv. tomato Race 1 Strains, Isolated From Tomato Fields in California," *Genome Announc* 4: e01671-01615 (2016). The increasing prevalence of race 1 Pst strains able to overcome Pto/Prf-mediated NTI has led to the search for sources of resistance to these virulent strains. Since no race 1 resistance has been identified in cultivated tomato, wild relatives of tomato are likely to be the best potential source for this trait (Peralta et al., "Taxonomy of Wild Tomatoes and Their Relatives (Solanum sect. Lycopersicoides, sect. Juglandifolia, sect. Lycopersicon; Solanaceaea)," *Syst. Bot. Mon.* 84:1-186 (2008)).

Wild relatives of tomato have been screened previously to identify resistance against race 1 Pst strains. One study reported a screen of introgression lines (ILs) derived from *S. habrochaites* LA1777 using the race 1 strain A9 from California (Thapa et al., "Identification of QTLs Controlling Resistance to *Pseudomonas syringae* pv. Tomato Race 1 Strains From the Wild Tomato, *Solanum habrochaites*

LA1777," *Theor. Appl. Genet.* 128: 681-92 (2015)). The detection of four QTLs, on chromosomes 1, 2, and 12 (2 loci), explained the moderate resistance to this strain, however, overall they accounted for a small percentage of the variability observed (10.5-12.5% of the phenotypic variation) (Thapa et al., "Identification of QTLs Controlling Resistance to *Pseudomonas syringae* pv. Tomato Race 1 Strains From the Wild Tomato, *Solanum habrochaites* LA1777," *Theor. Appl. Genet.* 128: 681-92 (2015)). A second study identified two QTLs, on chromosomes 2 and 8, in *S. habrochaites* accession LA2109 that contributed to resistance to race 1 strain T1, which accounted for 24% and 26% of the phenotypic variability, respectively (Bao Z et al., "Identification of a Candidate Gene in *Solanum habrochaites* for Resistance to a Race 1 Strain of *Pseudomonas syringae* pv. tomato," *The Plant Genome* 8:10.3835/plantgenome2015.3802.0006 (2015)). Recently, another study reported a screen of 96 wild accessions and identified two accessions that display resistance toward race 1 strain T1, *S. neorickii* LA1329 and *S. habrochaites* LA1253. Resistance in LA1253 appears to be a complex genetic trait and its inheritance remains unclear (Hassan et al., "A Rapid Seedling Resistance Assay Identifies Wild Tomato Lines that Aae Resistant to *Pseudomonas syringae* pv. tomato Race 1," *Mol. Plant Microbe. Interact.* 30:701-9 (2017)). Although together these QTLs might contribute to the breeding of enhanced race 1 Pst resistance in tomato, their quantitative nature and relatively weak race 1 resistance limits their usefulness.

Embodiments of the disclosure are directed to overcoming these and other deficiencies in the art.

SUMMARY

One aspect of embodiments of the disclosure is a nucleic acid construct comprising a nucleic acid molecule comprising a *Pseudomonas* tomato race 1 (Ptr1) polynucleotide, a 5' heterologous DNA promoter sequence, and a 3' terminator sequence, wherein the nucleic acid molecule, the DNA promoter sequence, and the terminator sequence are operatively coupled to permit transcription of the nucleic acid molecule.

Another aspect of embodiments of the disclosure relates to a plant or plant seed transformed with one or more nucleic acid constructs described herein.

Another aspect of embodiments of the disclosure is a method of expressing a nucleic acid molecule in a plant. The method involves providing a transgenic plant or transgenic plant cell transformed with a nucleic acid construct comprising a nucleic acid molecule comprising a *Pseudomonas* tomato race 1 (Ptr1) polynucleotide, a 5' heterologous DNA promoter sequence, and a 3' terminator sequence, wherein the nucleic acid molecule, the DNA promoter sequence, and the terminator sequence are operatively coupled to permit transcription of the nucleic acid molecule, and growing the transgenic plant or a plant grown from the transgenic plant seed under conditions effective to express the nucleic acid molecule in said transgenic plant or said plant grown from the transgenic plant seed.

Yet another aspect of embodiments of the disclosure is a method of imparting disease resistance to a plant. The method involves transforming a plant or a plant cell with a nucleic acid molecule that increases expression of Ptr1, wherein said expression is effective in imparting disease resistance to the transformed plant or to a transgenic plant produced from the transformed plant cell.

A further aspect of embodiments of the disclosure is a method of identifying the presence of a putative Ptr1 sequence based on sequence homology to one or more polynucleotide sequences set forth herein.

A further aspect of embodiments of the disclosure a method of identifying a candidate plant suitable for breeding that displays enhanced disease resistance. The method involves providing a candidate plant; analyzing the candidate plant for the presence, in its genome, of a Ptr1 polynucleotide; identifying, based on said analyzing, a candidate plant suitable for breeding that includes in its genome, a Ptr1 polynucleotide; and breeding the identified plant with at least one other plant.

A further aspect of embodiments of the disclosure a method of identifying a candidate plant suitable for breeding that comprises a putative Ptr1 polynucleotide sequence.

A further aspect of embodiments of the disclosure is a plant cell comprising a nucleic acid molecule comprising a heterologous *Pseudomonas* tomato race 1 (Ptr1) polynucleotide.

As described herein, it was surprisingly shown that *Pseudomonas syringae* pv. tomato race 1 resistance in a distantly-related relative of tomato, *Solanum lycopersicoides*. Experimental results indicate that the resistance is due to a single locus referred to here as *Pseudomonas* tomato race 1 (Ptr1). Ptr1 confers resistance to several race 1 Pst strains but not to the race 0 strain DC3000. A test of type III effectors that are present in race 1 strains but lacking in DC3000 identified AvrRpt2 as the effector recognized by Ptr1. AvrRpt2 is a cysteine protease that has been intensively studied because it cleaves RIN4 leading to activation of the *Arabidopsis* NLR protein RPS2 (Axtell et al., "Genetic and Molecular Evidence that the *Pseudomonas syringae* Type III Effector Protein AvrRpt2 is a Cysteine Protease," *Mol. Microbiol.* 49(6):1537-46 (2003); Mackey et al., "*Arabidopsis* RIN4 is a Target of the Type III Virulence Effector AvrRpt2 and Modulates RPS2-Mediated Resistance," *Cell* 112(3):379-89 (2003), which are hereby incorporated by reference in their entirety). By using site-directed mutagenesis of AvrRpt2 it was discovered that, like RPS2, Ptr1 detects the proteolytic activities of this effector. Ptr1 also detects the activity of AvrRpt2 variants expressed by diverse bacterial phytopathogens and this recognition correlates with ability of the variants to cleave the *Arabidopsis* RIN4 protein. Notably, Ptr1 conferred strong resistance to a *Ralstonia pseudosolanacearum* strain that expresses an AvrRpt2 homolog (RipBN); no resistance gene that gives protection against this important pathogen, causative agent of bacterial wilt disease, has been reported previously.

Also described herein is the identification and phylogenetic analysis of the Ptr1 gene. A single recombinant among 585 F2 plants segregating for the Ptr1 locus was discovered that narrowed the Ptr1 candidates to eight nucleotide-binding leucine-rich repeat protein (NLR)-encoding genes. From analysis of the gene models in the *S. lycopersicoides* genome sequence and RNA-Seq data, two of the eight genes emerged as the strongest candidates for Ptr1. One of these two candidates was found to encode Ptr1 based on its ability to mediate recognition of AvrRpt2 and RipBN when it was transiently expressed with these effectors in leaves of *Nicotiana glutinosa*. The ortholog of Ptr1 in tomato and in *Solanum pennellii* is a pseudogene. However, a functional Ptr1 ortholog exists in *N. benthamiana* and potato and both mediate recognition of AvrRpt2 and RipBN. In apple and *Arabidopsis*, recognition of AvrRpt2 is mediated by the Mr5 and RPS2 proteins, respectively. Phylogenetic analysis places Ptr1 in a distinct clade compared to Mr5 and RPS2 and it therefore appears to have arisen by convergent evolution for recognition of AvrRpt2.

These findings are a significant advance in disease resistance in plants.

BRIEF DESCRIPTION OF THE DRAWINGS

FIG. 1A shows disease symptoms of LA4245-R and LA4245-S leaves vacuum infiltrated with T1, NY15125 or DC3000 at $3\times10^4$ cfu/mL and photographed five days later. FIG. 1B is a graph showing bacterial populations measured two days after inoculation with the Pst strains indicated. Significance was determined by a pair wise t-test and indicated as: *P<0.02, **P<0.0001, not significant (n.s.) at P>0.05. Bars indicate the mean of three plants and error bars represent +/−SEM. Results shown are representative of three independent experiments.

FIG. 2A shows measures of bacterial populations two days after LA4245-R and LA4245-S plants were vacuum infiltrated with DC3000 carrying avrRpt2$_{NY15125}$ or an empty vector (EV) at $5\times10^4$ cfu/mL. FIG. 2B shows measures of bacterial populations two days after LA4245-R and LA4245-S plants were inoculated with NY15125 wild-type, NY15125ΔavrRpt2, a complemented strain, or an empty vector (EV) at $5\times10^4$ cfu/mL. Significance was determined by a pair wise t-test and is indicated as: *P<0.05, not significant (n.s.) at P>0.05. Bars indicate the mean of three plants and error bars represent +/−SEM. Both FIG. 5A and FIG. 5B are representative of three independent experiments.

FIG. 5 provides results that demonstrate that Ptr1 confers resistance to several race 1 *Pseudomonas syringae* pv. tomato strains. Disease symptoms of LA4245-R and LA4245-S plants vacuum infiltrated with Pst strains CA-A9, CA-407 and NYT1 at $1\times10^4$ cfu/mL and photographed eight days later.

FIG. 7A depicts symptoms of LA4245-R plants vacuum infiltrated with DC3000 expressing avrRpt2 wild-type (WT), avrRpt2 variants or an empty vector (EV) at $5\times10^4$ CFU/ml. Photographs were taken five days after inoculation. FIG. 7B shows bacterial populations measured two days after LA4245-R plants were inoculated with DC3000 expressing avrRpt2 wild-type (WT), avrRpt2 variants and empty vector (EV). Significance was determined using ANOVA with a Tukey's post hoc multiple comparison test, and different letters indicate significant differences between treatments (P<0.001). Bars indicate the mean of three plants and error bars represent +/−SEM. Results shown are representative of three independent experiments.

FIG. 8A shows whole-plant symptoms of LA4245-S plants inoculated with DC3000 carrying avrRpt2 wild-type (WT), avrRpt2 variants or an empty vector (EV) at $5\times10^4$ CFU/ml five days after inoculation. FIG. 8B shows bacterial populations in leaves of LA4245-S plants inoculated with DC3000 expressing avrRpt2 wild-type (WT), avrRpt2 variants or an empty vector (EV), 2 days after inoculation. Significance was determined using ANOVA with a Tukey's post hoc multiple comparison test, and different letters indicate significant differences between treatments (P<0.001). Bars indicate the mean of three plants and error bars represent +/−SEM. Data are representative of three independent experiments.

FIG. 10A shows degradation of the endogenous tomato Rin4 proteins after vacuum infiltration of LA4245-S leaves with DC3000 strains carrying avrRpt2 wild-type (WT), avrRpt2 variants or an empty vector (EV). Plant tissue was harvested 0 and 6 hours post infiltration (hpi). Total protein extracted from infiltrated plants was subjected to immunoblotting using an ∝-RIN4 antibody. Locations of SlRin4-1, Rin4-2, and Rin4-3 are shown. The asterisk indicates an unknown cross-reacting protein. FIG. 10B shows total protein extracted from infiltrated leaves and subjected to immunoblotting using an ∝-RIN4 antibody. *Arabidopsis* Col-0 rps2 leaves were syringe-infiltrated with DC3000 carrying avrRpt2 wild-type (WT), avrRpt2 variants or an empty vector (EV). Leaf tissue was harvested four hours after infiltration. Total protein extracted from infiltrated leaves was subjected to immunoblotting using an α-RIN4 antibody. Ponceau staining shows amount of protein loaded in each lane.

FIG. 13A shows disease symptoms of LA4245-R and LA4245-S plants four days after inoculation with DC3000 expressing avrRpt2(Y191S), avrRpt2 wild-type (WT) or an empty vector (EV) at $5 \times 10^4$ CFU/ml. FIG. 13B shows bacterial populations measured in LA4245-R plants two days after inoculation. Significance was determined using ANOVA with a Tukey's post hoc multiple comparison test, and different letters indicate significant differences between treatments (P<0.001). Bars indicate the mean of three plants and error bars represent +/−SD. Results shown are representative of three independent experiments.

FIG. 14A shows LA4245-R plants (n=25) and LA4245-S plants (n=30) were soil drench-inoculated with 50 mL of $10^8$ cfu/mL of Ralstonia pseudosolanaceraum CMR15. The percentage of plants surviving (showing no wilt symptoms) or dying (showing severe wilting) 1 to 13 days post-inoculation (DPI) is shown. The two survival curves are significantly different at P<0.0001 using the Mantel-Cox test. FIG. 14B is photographs taken 13 days after inoculation show extreme wilting of a LA4245-S (left) plant and no wilting of a LA4245-R plant (right). Results shown are representative of three independent experiments.

FIG. 15A is a scheme of the introgression segments present in LA4245-R. Coordinates (in megabases, Mb) are based on SNP density mapped to S. lycopersicum Heinz 1706 SL2.50. FIG. 15B shows predicted NRL-like genes present in the large introgression segment of LA4245-R (no NLR genes are present in the small introgression segment). Shading indicates absence of this domain.

FIG. 16 shows an annotation of the amino acid sequence of Ptr1 (SEQ ID NO:19). Coiled-coil (CC) domains are shown in bold; nucleotide binding (NB-ARC) domains are shown in underline; leucine-rich repeat (LRR) domains are shaded.

FIGS. 19A and 19B each illustrate four boxed regions—three leftmost boxed regions that are individually shaded (respectively referred to herein as box 1, box 2, and box 3, from left to right) and one rightmost boxed region that appears unshaded or white (referred to herein as box 4). FIG. 19A is a schematic of S. lycopersicoides introgression on chromosome 4 in LA4245-R (box 2 and box 3) and LA4277-R (box 1, box 2, and box 3). The rightmost boxed region shown in white (box 4) is derived from the tomato parent VF36. Distribution of NLR-encoding genes unique to LA4277-R (dots above box 1, representing ~50 NLR genes) and those shared with LA4245-R (dots above box 2 and box 3) is shown. Indicated are the locations of the DNA markers (megabases, Mb) used to identify recombinants. FIG. 19B depicts that LA4277-159 derived from a selfed LA4277-R plant has a recombination event between markers at 9.15 and 9.94 Mb (box 3). LA4277-R, LA4277-S, and LA4277-159 plants were vacuum infiltrated with Pst JL1065 or Pst JL1065ΔavrRpt2. Photos were taken 6 days after inoculation and are representative of three independent experiments. R, resistant; S, susceptible. FIG. 19C depicts the region defined as containing Ptr1 contains eight NLR gene models, A-H. Their positions and orientations within the Ptr1 region are shown with the coordinates (Mb) corresponding to the start codon of each gene model. Transcripts were not detectable in leaves from genes C, E, F, G, and H; candidate D is a pseudogene.

FIG. 20A shows *N. glutinosa* leaves that were syringe-infiltrated with *Agrobacterium* strains carrying either A:HA or B:HA ($OD_{600}$=0.025), and AvrRpt2:Myc, AvrRpt2(C122A):Myc or RipBN:Myc ($OD_{600}$=0.05). Photographs were taken 48 hr after infiltration. FIG. 20B shows *N. glutinosa* leaves that were syringe-infiltrated with *Agrobacterium* strains expressing A:HA or B:HA ($OD_{600}$=0.1), Prf(D1416V):HA ($OD_{600}$=0.1) or Myc:SlRin4 ($OD_{600}$=0.2). Photographs for candidates A and B were taken 48 hr after infiltration and 4 days after infiltration for Prf(D1416V). FIG. 20C shows *N. glutinosa* leaves that were syringe-infiltrated with *Agrobacterium* strains carrying either A:HA ($OD_{600}$=0.1), AvrRpt2:Myc ($OD_{600}$=0.05), RipBN:Myc ($OD_{600}$=0.05), YFP:Myc ($OD_{600}$=0.05) or Myc:SlRin4-3 ($OD_{600}$=0.2). Photographs were taken 48 hr after infiltration. FIG. 20D shows immunoblot analysis of protein extracts isolated from *N. benthamiana* leaves agroinfiltrated with A:HA ($OD_{600}$=0.1), SlRin4-3:Myc ($OD_{600}$=0.2), AvrRpt2:Myc ($OD_{600}$=0.05), RipBN:Myc ($OD_{600}$=0.05), or YFP:Myc ($OD_{600}$=0.05). Samples were collected 28 hr after infiltration. Total proteins extracted from infiltrated leaves were subjected to immunoblotting using an ∝-HA antibody to detect candidate A and c-Myc antibody to detect SlRin4-3, AvrRpt2, RipBN, and YFP. +, construct was included in the experiment. Protein masses are indicated at the left of the blot. Ponceau staining shows amount of protein loaded in each lane. The asterisk indicates a nonspecific band across the immunoblot. All genes were expressed from the CaMV 35S promoter. Data shown are representative of three independent experiments, using three biological replicates and infiltrating two leaves per plant.

FIG. 21A is a schematic of Ptr1 gene structure in *S. lycoperiscoides* (Ptr1), *S. lycoperiscum* (SlPtr1), and *S. pennellii* (SpPtr1). Ptr1 has a single exon of 2,472 base pairs. SlPtr1 and SpPtr1 are pseudogenes that lack a start codon (asterisk) and have other nonsense mutations (dotted bars) and frameshift mutations (solid bars). The position of each mutation is indicated relative to the Ptr1 base pair (bp) position. FIG. 21B shows that Ptr1 is conserved in many species in the Solanaceae family. Maximum likelihood tree generated from the amino acid sequences of *S. lycopersicoides* Ptr1 and homologs from *S. tuberosum* (St), *Capsicum chinense* (Cc), *Capsicum baccatum* (Cb), *Capsicum annuum* (Ca), *Nicotiana tomentosiformis* (Ntom), *Nicotiana tabacum* (Ntab), *Nicotiana benthamiana* (Nb), and *Nicotiana attenuata* (Na). Bootstrapping 1000 replicates, with bootstrap values over 75 shown. The tree is drawn to scale, with branch lengths measured in the number of substitutions per site.

FIG. 22A shows *Agrobacterium* strains carrying AvrRpt2:Myc ($OD_{600}$=0.2), AvrRpt2(C122A):Myc ($OD_{600}$=0.2), RipBN:Myc ($OD_{600}$=0.2), YFP:Myc ($OD_{600}$=0.2), or 35S:Prf(D1416V):HA ($OD_{600}$=0.2) were infiltrated into leaves of *N. benthamiana* (Nb 1) or Nb1 plants silenced with either TRV:Ptr1 (Ptr1 VIGS) or TRV:EC1 (EC1 VIGS). Photographs were taken 48 hr after agroinfiltration (except 35S:Prf(D1416V):HA) in Nb1 leaves and after 72 hr for VIGS leaves. 35S:Prf(D1416V):HA treatment was photographed 4 days after infiltration for both Nb1 and VIGS plants. See FIGS. 30A-30B for details of NbPtr1 VIGS construct. Photographs are representative of three independent experiments. For FIG. 22B, Ptr1 gene was synthesized (synPtr1) with a divergent nucleotide sequence to avoid silencing but retaining the same amino acid sequence (FIGS. 31A-31B). *Agrobacterium* strains harboring AvrRpt2, AvrRpt2(C122A), RipBN, and YFP were infiltrated into leaves at $OD_{600}$=0.05 co-expressed with either 35S:Ptr1:HA or 35S:synPtr1:HA (both at $OD_{600}$=0.025). Photographs were taken 6 days after infiltration and are representative of three independent experiments. All genes were expressed from the CaMV 35S promoter.

FIG. 23A shows *Nicotiana glutinosa* leaves that were syringe-infiltrated with *Agrobacterium* strains carrying the potato Ptr1 ortholog ($OD_{600}$=0.1) and Myc:SlRin4-3 ($OD_{600}$=0.2) both expressed from the CaMV 35S promoter. Photographs were taken 48 hr after agroinfiltration. FIG. 23B shows *N. glutinosa* leaves that were syringe-infiltrated with *Agrobacterium* strains carrying the potato Ptr1 ortholog ($OD_{600}$=0.025), AvrRpt2:Myc ($OD_{600}$=0.05), RipBN:Myc ($OD_{600}$=0.025), and YFP:Myc ($OD_{600}$=0.05) with all genes expressed from the CaMV 35S promoter. Photographs were taken 41 hr after agroinfiltration. Data shown are representative of three independent experiments, using three biological replicates and infiltrating two leaves per plant.

FIG. 25A is an amino acid sequence alignment of Rin4 proteins from tomato (*Solanum lycopersicum* (Sl)); *Arabidopsis thaliana* (At); and *Malus domestica* (Md) (SlRin4-1, SEQ ID NO:85; SlRin4-2, SEQ ID NO:86; SlRin4-2, SEQ ID NO:87; AtRIN4, SEQ ID NO:88; MdRIN4-1, SEQ ID NO:89, MdRIN4-2, SEQ ID NO:90) (Table 13). Black background indicates identical amino acid residues; grey background indicate similar amino acid residues; boxed regions RCS1 and RCS2 indicate regions cleaved by AvrRpt2 cysteine protease activity with arrows marking the exact cleavage site. AvrRpt2 cleavage products (ACP) are indicated. Boxed region PS2 indicates the palmitoylation (PS). The polymorphic residues in AtRIN4 and the two MdRIN4 proteins are shown. FIG. 25B shows *N. glutinosa* leaves that were syringe-infiltrated with *Agrobacterium* strains carrying A:HA ($OD_{600}$=0.1) and SlRin4:Myc ($OD_{600}$=0.2) with both being expressed by the CaMV 35S promoter. Tomato Rin4 proteins were c-Myc tagged at the N- or C-terminal as indicated. Photographs were taken 48 hr after agroinfiltration. Data shown are representative of three independent experiments, using three biological replicates and infiltrating two leaves per plant.

FIG. 26A shows *N. glutinosa* leaves that were syringe-infiltrated with *Agrobacterium* strains carrying either B:HA ($OD_{600}$=0.1), AvrRpt2:Myc ($OD_{600}$=0.05), RipBN:Myc ($OD_{600}$=0.05), YFP:Myc ($OD_{600}$=0.05) or Myc:SlRin4-3 ($OD_{600}$=0.2). Photographs were taken 48 hr after agroinfiltration. FIG. 26B shows immunoblot analysis of protein extracts isolated from *N. benthamiana* leaves agroinfiltrated with B:HA ($OD_{600}$=0.1), Myc:SlRin4-3 ($OD_{600}$=0.2), AvrRpt2:Myc ($OD_{600}$=0.05) or YFP:Myc ($OD_{600}$=0.05). Samples were collected 28 hr after agroinfiltration. Total proteins extracted from infiltrated leaves were subjected to immunoblotting using an ∝-HA antibody to detect candidate B or a c-Myc antibody to detect SlRin4-3, AvrRpt2, RipBN and YFP. Protein masses are indicated at the left of the blot. Ponceau staining shows amount of protein loaded in each lane. +, candidate B protein; *, a nonspecific bands across the immunoblot. All genes in this figure were expressed from the CaMV 35S promoter. Data shown are representative of three independent experiments, using three biological replicates and infiltrating two leaves per plant.

FIG. 28A and FIG. 28B show that the ortholog of Ptr1 is a pseudogene in tomato and *S. pennellii*. FIG. 28A and FIG. 28B show a ClustalW alignment of the nucleotide sequence (including 20 nucleotides upstream of start codon) of candidate A (Ptr1, SEQ ID NO:19) and its ortholog in *S. lycopersicum* (SlPtr1, SEQ ID NO:114) and *S. pennellii* (SpPtr1, SEQ ID NO:115) (Table 13). The asterisk denotes the start codon unique to *S. lycopersicoides* Ptr1. Numbers on right correspond to the sequence of Ptr1. FIG. 28A shows positions 1-1,260 of the alignment. FIG. 28B shows positions 1,261-2,500 of the alignment.

FIG. 29A shows a comparison of Ptr1 nucleotide and amino acid sequences with its orthologs in potato and *Nicotiana benthamiana*. FIG. 29B and FIG. 29C show an amino acid sequence alignment of Ptr1 proteins from various Solanaceae species. *S. lycopersicoides* Ptr1 (Ptr1, SEQ ID NO:19), *S. tuberosum* Ptr1 (SEQ ID NO:116), *C. anuum* Ptr1 (SEQ ID NO:117), *C. baccatum* Ptr1 (SEQ ID NO:118), *C. chinense* Ptr1 (SEQ ID NO:119), *N. attenuata* Ptr1 (SEQ ID NO:120), *N. benthamiana* Ptr1a (SEQ ID NO:121), *N. tabacum* Ptr1 (SEQ ID NO:122), *N. tomentosiformis* Ptr1 (SEQ ID NO:123) (Table 13). FIG. 29B shows positions 1-400 of the alignment. FIG. 29C shows positions 401-833 of the alignment.

FIG. 30A and FIG. 30B show that Ptr1 has extensive sequence similarity with the two Ptr1 homologs in *N. benthamiana*. Nucleotide alignment of Ptr1 (SEQ ID NO:18), NbPtr1a 15 (SEQ ID NO:124) and NbPtr1b (SEQ ID NO:125) (Table 13). FIG. 30A shows positions 1-1,170 of the alignment. FIG. 30B shows positions 1,171-2,482 of the alignment. A five base pair deletion in NbPtr1b (box at positions 98-102) leads to a premature stop codon (box at positions 166-168), although the nucleotide sequence remains conserved at the region targeted by VIGS (line above positions 1,213-1,538).

FIG. 31A shows positions 1-1,236 of the alignment. FIG. 31B shows positions 1,237-2,472 of the alignment. Identical nucleotides are shown in black. The amino acid sequence is identical for both Ptr1 and synPtr1.

Figure 33A:
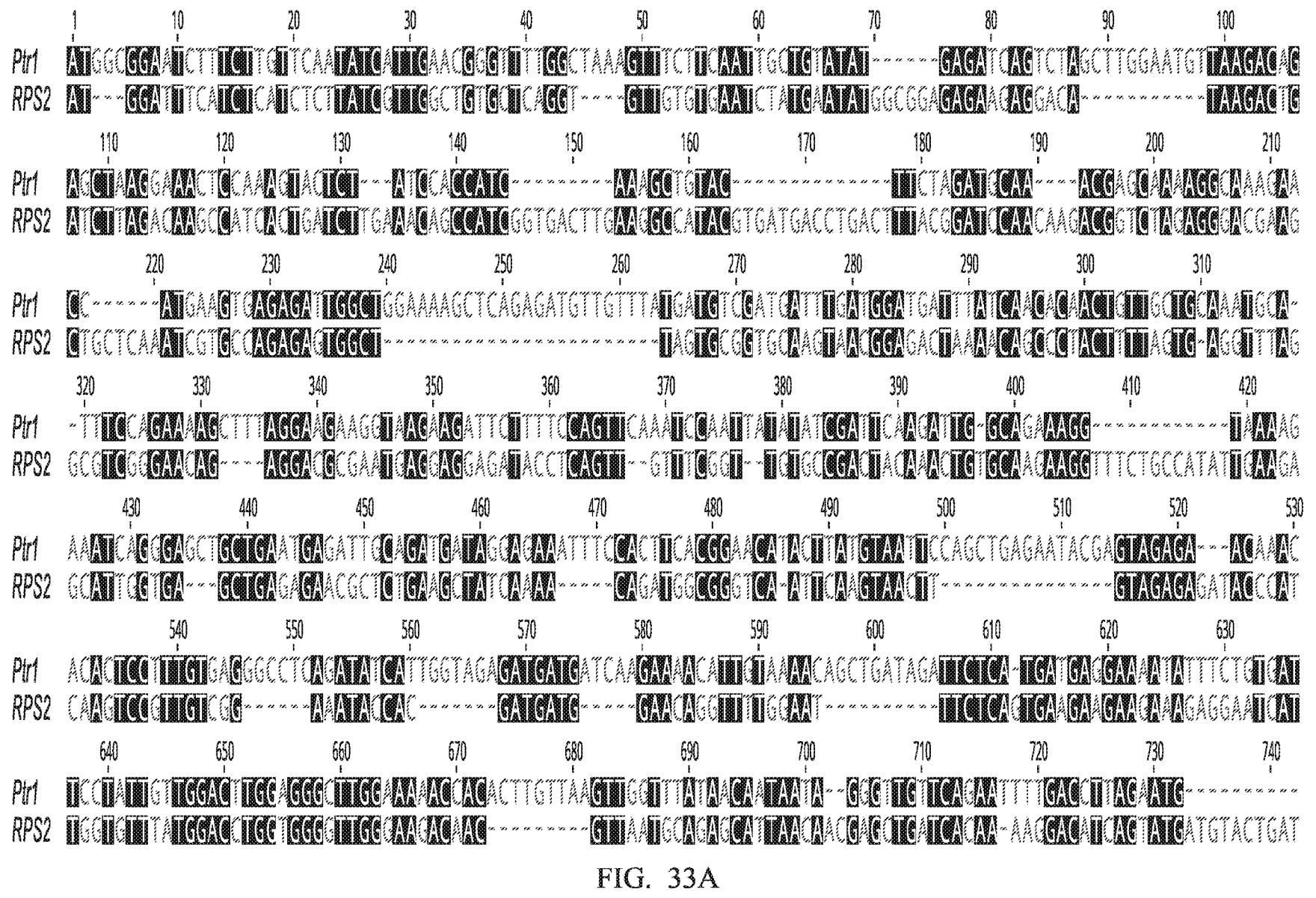
Figure 33A:
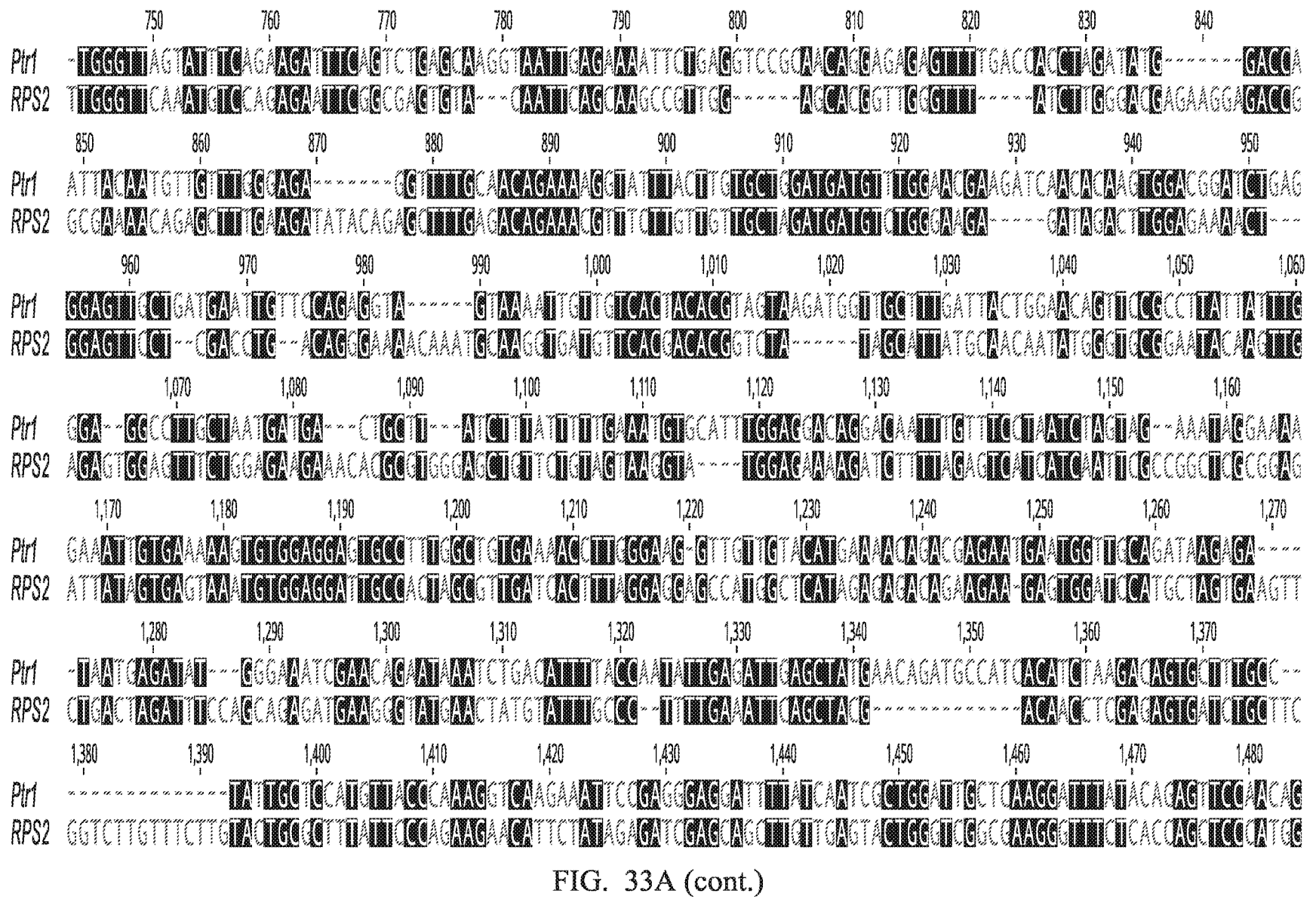

FIG. 33A, FIG. 33B, FIG. 33C, and FIG. 33D show that Ptr1 has little nucleotide similarity with RPS2 or Mr5. FIGS. 33A-33B show an alignment of the nucleotide sequences of Ptr1 (SEQ ID NO:18) and RPS2 (SEQ ID NO:127 (*Arabidopsis thaliana*)) (Table 13) generated using MUSCLE. FIG. 33A shows positions 1-1,484 of the alignment. FIG. 33B shows positions 1,485-2,966 of the alignment. Identical nucleotides are shown in black. FIGS. 33C-33D show an alignment of the nucleotide sequences of Ptr1 (SEQ ID NO:18) and Mr5 (SEQ ID NO:128 (*Malus domestica*)) (Table 13) generated using MUSCLE. FIG. 33C shows positions 1-2,144 of the alignment. FIG. 33D shows positions 2,145-4,265 of the alignment. Identical nucleotides are shown in black.

Figure 34A:
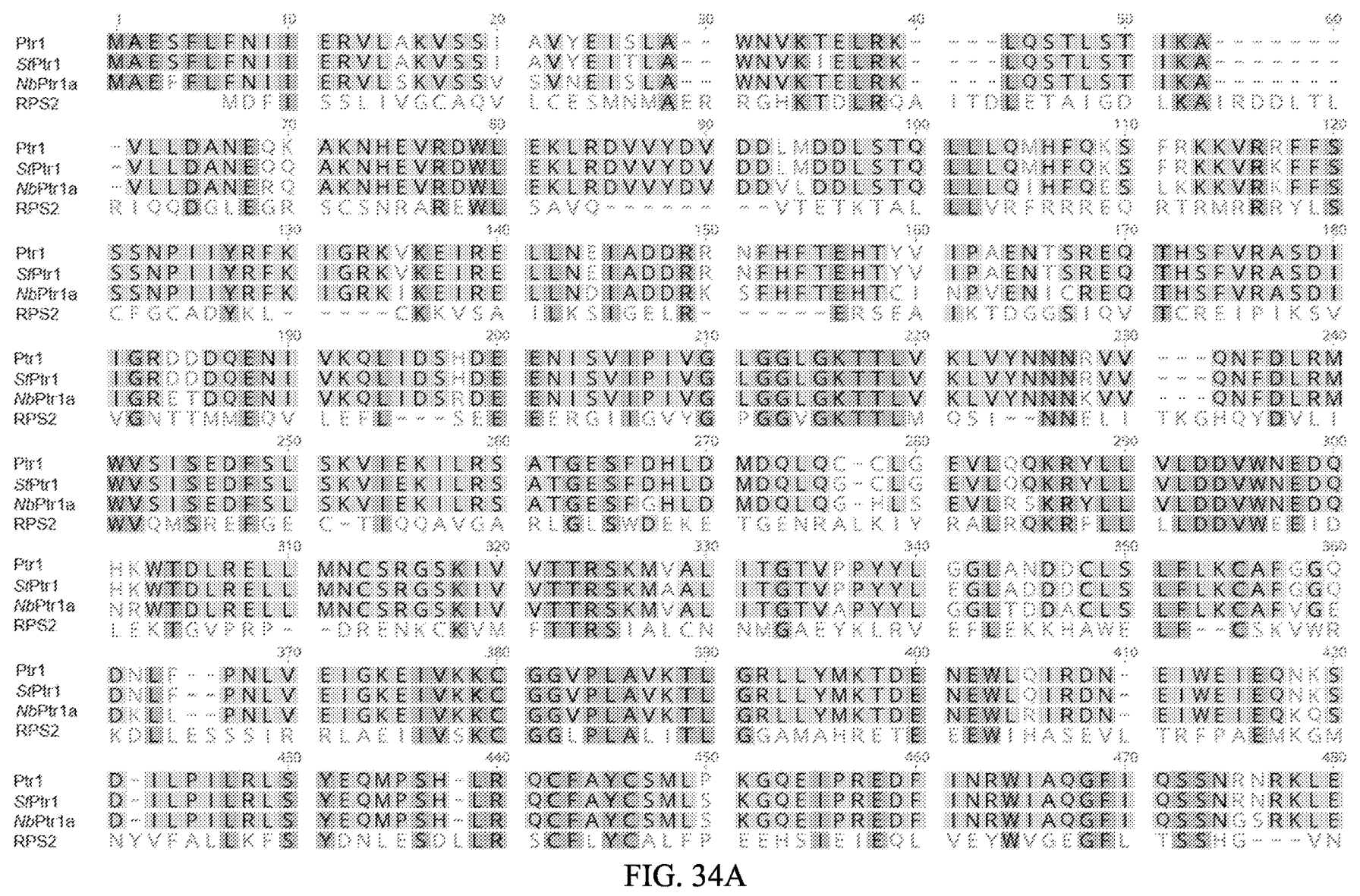
Figure 34B:
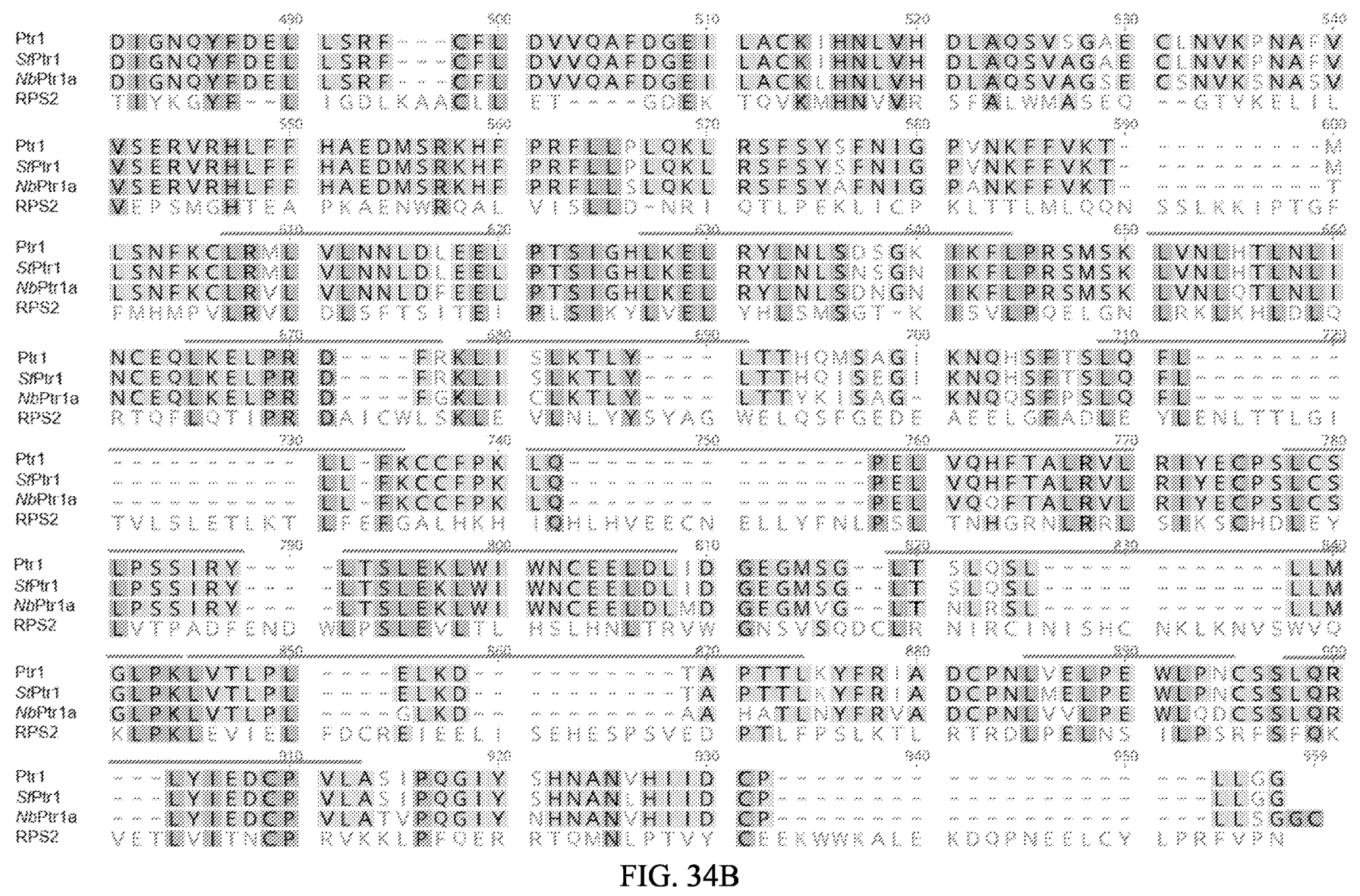

FIG. 34A, FIG. 34B, FIG. 34C, and FIG. 34D show that Ptr1, StPtr1, and NbPtr1 share little amino acid sequence similarity with RPS2 (FIGS. 34A-34B) or Mr5 (FIGS. 34C-34D). FIGS. 34A-34B show an amino acid alignment of the Ptr1 protein (SEQ ID NO:19) with StPtr1 (GenBank Accession No. XP_006340095.1, which is hereby incorporated by reference in its entirety) (SEQ ID NO:131), NbPtr1a (SEQ ID NO:121), and RPS2 (SEQ ID NO:129 (*Arabidopsis thaliana*)) (Table 13). FIG. 34A shows positions 1-480 of the alignment. FIG. 34B shows positions 481-959 of the alignment. FIGS. 34C-34D show an amino acid alignment of the Ptr1 protein (SEQ ID NO:19) with StPtr1 (SEQ ID NO:131), NbPtr1a (SEQ ID NO:121), and Mr5 (SEQ ID NO:130 (*Malus domestica*)) (Table 13). FIG. 34C shows positions 1-720 of the alignment. FIG. 34D shows positions 721-1,402 of the alignment. Darker shading indicates all four of the proteins have the same residue at that position, lighter shading indicates that three of the four proteins have the same residue at that position. Lines indicates leucine-rich repeats (LRRs).

Figure 35A:
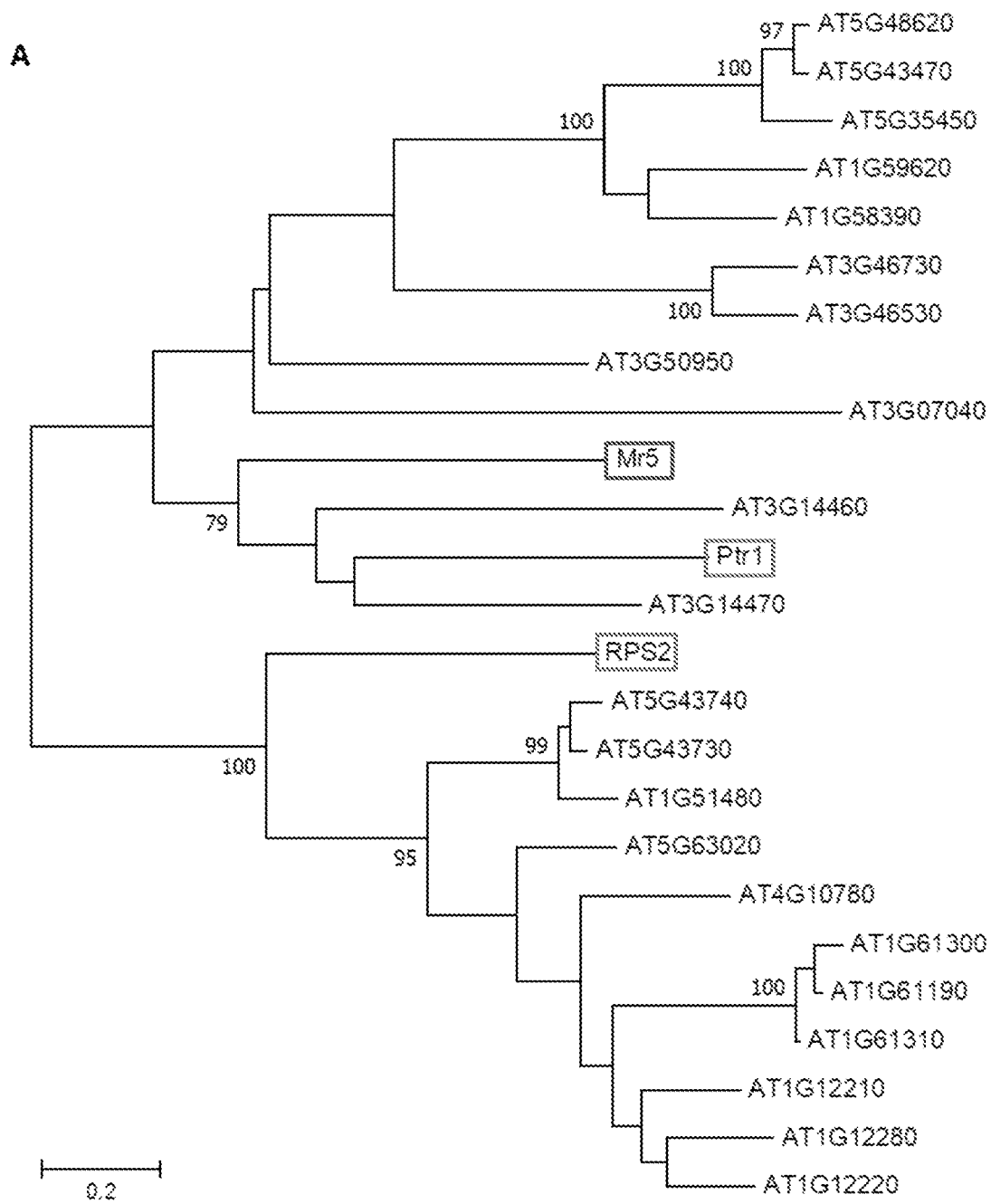
Figure 35B:
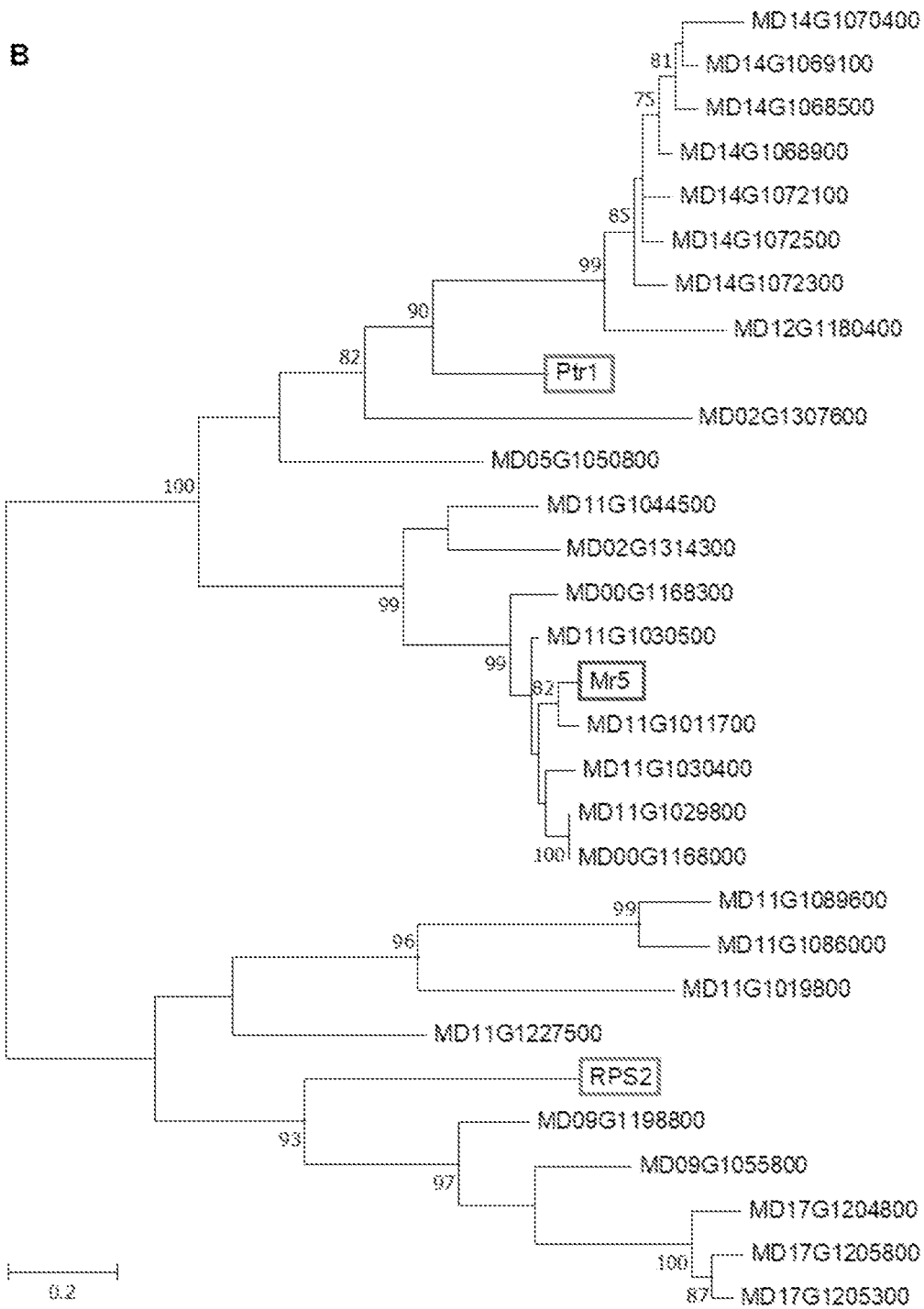

FIG. 35A and FIG. 35B show phylogenetic trees of Ptr1, Mr5, and RPS2 with their most closely related proteins in *Arabidopsis* and apple. Maximum likelihood trees of top BLAST hits of Ptr1, Mr5, and RPS2 NB-ARC domains from: *Arabidopsis* (AT; Araport 11 protein database) (FIG. 35A) and *Malus domestica* (MD; GDDH13 V1.1 protein database) (FIG. 35B). Only hits with an intact NB-ARC domain, including the P-loop, kinase 2, kinase 3a, and GLPL motifs were included in the analysis. Bootstrapping 1000 replicates, with bootstraps over 75 shown. The tree is drawn to scale, with branch lengths measured in the number of substitutions per site.

Figure 36:
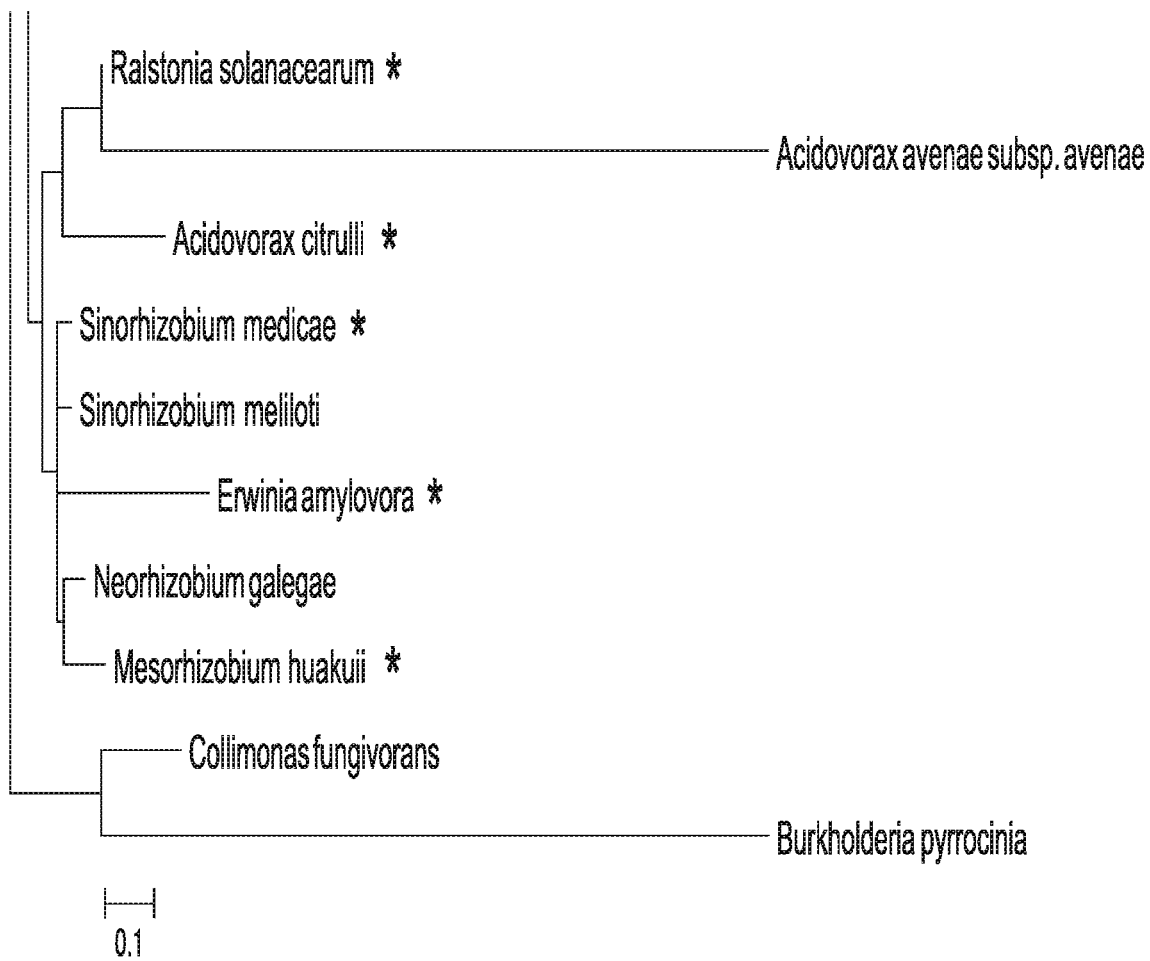

FIG. 36 shows a maximum likelihood phylogenetic tree of AvrRpt2 homologs in GenBank. Ptr1 is known to mediate recognition of AvrRpt2 proteins indicated with asterisks (all are cysteine protease-active). Bootstrapping 1000 replicates, with bootstraps over 75 shown. The tree is drawn to scale, with branch lengths measured in the number of substitutions per site.

DETAILED DESCRIPTION

Unless otherwise indicated, the definitions and embodiments described in this and other sections are intended to be applicable to all embodiments and aspects of the present application herein described for which they are suitable as would be understood by a person skilled in the art.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

Terms of degree such as "substantially", "about" and "approximately" as used herein mean a reasonable amount of deviation of the modified term such that the end result is not significantly changed. These terms of degree should be construed as including a deviation of at least +/−5% of the modified term if this deviation would not negate the meaning of the word it modifies.

Where a range of values is provided, it is intended that each intervening value between the upper and lower limit of that range and any other stated or intervening value in that stated range is encompassed within the disclosure.

As used herein, the terms "nucleic acid", "polynucleotide", and "DNA" are used interchangeably, unless indicated otherwise by context. In some embodiments, a nucleic acid or protein of the invention is "isolated". As used herein, the term "isolated" refers to a synthesized, cloned, and/or truncated sequence from the naturally-occurring sequence.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "comprising" and its derivatives, as used herein, are intended to encompass "consisting of" and "consisting essentially of". The term "consisting of" and its derivatives are intended to be closed terms that specify the presence of the stated features, elements, components, groups, integers, and/or steps, but exclude the presence of other unstated features, elements, components, groups, integers and/or steps. The term "consisting essentially of" is intended to specify the presence of the stated features, elements, components, groups, integers, and/or steps as well as those that do not materially affect the basic and novel characteristic(s) of features, elements, components, groups, integers, and/or steps.

Preferences and options for a given aspect, feature, embodiment, or parameter of the disclosure should, unless the context indicates otherwise, be regarded as having been disclosed in combination with any and all preferences and options for all other aspects, features, embodiments, and parameters of the disclosure.

Embodiments of the disclosure relate to disease resistance in plants and compositions useful in imparting or enhancing disease resistance in plants.

Accordingly, a first aspect of embodiments of the disclosure is a nucleic acid construct comprising a nucleic acid molecule comprising a *Pseudomonas* tomato race 1 (Ptr1) polynucleotide, a 5' heterologous DNA promoter sequence, and a 3' terminator sequence, wherein the nucleic acid molecule, the DNA promoter sequence, and the terminator sequence are operatively coupled to permit transcription of the nucleic acid molecule.

In some embodiments, the nucleic acid molecule comprises the nucleotide sequence of SEQ ID NO:18, as set forth below:

ATGGCGGAATCTTTCTTGTTCAATATCATTGAACGGGTTTTGGCTAAAGT

TTCTTCAATTGCTGTATATGAGATCAGTCTAGCTTGGAATGTTAAGACAG

AGCTAAGGAAACTCCAAAGTACTCTATCCACCATCAAAGCTGTACTTCTA

GATGCAAACGAGCAAAAGGCAAAGAACCATGAAGTGAGAGATTGGCTGGA

AAAGCTCAGAGATGTTGTTTATGATGTCGATGATTTGATGGATGATTTAT

CAACACAACTGTTGCTGCAAATGCATTTCCAGAAAAGCTTTAGGAAGAAG

GTAAGAAGATTCTTTTCCAGTTCAAATCCAATTATATATCGATTCAAGAT

TGGCAGAAAGGTAAAAGAAATCAGGGAGCTGCTGAATGAGATTGCAGATG

ATAGGAGAAATTTCCACTTCACGGAACATACTTATGTAATTCCAGCTGAG

AATACGAGTAGAGAACAAACACACTCCTTTGTGAGGGCCTCAGATATCAT

TGGTAGAGATGATGATCAAGAAAACATTGTAAAACAGCTGATAGATTCTC

ATGATGAGGAAAATATTTCTGTGATTCCTATTGTTGGACTTGGAGGGCTT

GGAAAAACCACACTTGTTAAGTTGGTTTATAACAATAATAGGGTTGTTCA

GAATTTTGACCTTAGAATGTGGGTTAGTATTTCAGAAGATTTCAGTCTGA

GCAAGGTAATTGAGAAAATTCTGAGGTCCGCAACAGGAGAGAGTTTTGAC

CACCTAGATATGGACCAATTACAATGTTGTTTGGGAGAGGTTTTGCAACA

GAAAAGGTATTTACTTGTGCTGGATGATGTTTGGAACGAAGATCAACACA

AGTGGACGGATCTGAGGGAGTTGCTGATGAATTGTTCCAGAGGTAGTAAA

ATTGTTGTCACTACACGTAGTAAGATGGTTGCTTTGATTACTGGAACAGT

TCCGCCTTATTATTTGGGAGGCCTTGCTAATGATGACTGCTTATCTTTAT

TTTTGAAATGTGCATTTGGAGGACAGGACAATTTGTTTCCTAATCTAGTA

GAAATAGGAAAAGAAATTGTGAAAAAGTGTGGAGGAGTGCCTTTGGCTGT

-continued

```
GAAAACCTTGGGAAGGTTGTTGTACATGAAAACAGACGAGAATGAATGGT
TGCAGATAAGAGATAATGAGATATGGGAAATCGAACAGAATAAATCTGAC
ATTTTACCAATATTGAGATTGAGCTATGAACAGATGCCATCACATCTAAG
ACAGTGCTTTGCCTATTGCTCCATGTTACCCAAAGGTCAAGAAATTCCGA
GGGAGGATTTTATCAATCGCTGGATTGCTCAAGGATTTATACAGAGTTCC
AACAGAAACAGGAAGCTGGAAGATATCGGTAATCAGTACTTTGATGAGTT
GCTATCAAGGTTTTGCTTCCTAGATGTGGTACAAGCTTTTGATGGAGAAA
TATTGGCTTGTAAGATACACAATCTTGTGCATGATCTTGCACAGTCAGTA
TCAGGTGCAGAGTGCTTAAATGTGAAACCCAATGCTTTCGTGGTCTCTGA
AAGAGTTCGCCACTTATTTTTCCATGCAGAAGATATGTCTAGGAAACACT
TCCCCAGATTTTTGCTTCCTTTGCAAAAGTTGAGGTCTTTCTCTTATTCT
TTTAACATTGGACCTGTAAACAAGTTCTTTGTCAAGACAATGTTGTCAAA
TTTCAAATGCCTTCGGATGCTAGTCTTGAACAATCTAGATCTTGAGGAGT
TGCCAACTTCGATAGGTCACTTGAAGGAATTAAGATACCTCAACCTTAGT
GACAGTGGTAAGATCAAGTTTCTTCCAAGGTCTATGAGCAAATTAGTAAA
TCTGCACACCCTAAACCTCATTAACTGTGAACAGCTTAAGGAGTTGCCAA
GAGATTTTAGAAAGTTAATCAGCCTGAAGACCTTGTATTTGACTACACAT
CAGATGTCAGCAGGGATCAAGAATCAACATTCTTTCACTTCTCTTCAATT
TTTACTTCTTTTCAAATGTTGTTTCCCAAAATTGCAGCCAGAACTGGTGC
AGCATTTTACYGCACTTCGGGTTTTGCGTATCTATGAATGCCCAAGTTTA
TGTTCTCTTCCAAGCAGTATTAGATATCTGACTTCACTTGAAAAGCTATG
GATCTGGAACTGTGAAGAACTTGATTTGATTGATGGAGAAGGGATGTCAG
GCCTAACAAGTCTTCAATCCTTGCTTCTAATGGGCTTCCTAAGTTGGTG
ACTCTACCATTGGAACTTAAAGATACTGCTCCTACAACATTAAAGTACTT
CAGAATCGCCGATTGTCCCAACCTGGTGGAGCTTCCAGAGTGGCTGCCTA
ATTGCTCCTCACTTCAGAGACTCTATATAGAGGATTGTCCTGTTTTGGCA
TCGATACCTCAAGGAATCTACAGCCACAATGCCAACGTCCATATAATCGA
CTGTCCATTGCTAGGTGGATGA
```

In some embodiments, the nucleic acid molecule may include the nucleotide sequence of SEQ ID NO:18. Also encompassed are nucleic acid molecules at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identical with the entire sequence of SEQ ID NO:18.

In some embodiments, the invention provides nucleic acids capable of improving disease resistance in a plant. A person of ordinary skill in the art would be readily able to predict a resulting protein sequence based on the nucleic acid molecules of embodiments of the disclosure. Thus, where protein coding nucleic acid sequences are disclosed, the resulting amino acid sequence or sequences (i.e. a polypeptide or protein sequence) are also contemplated as embodiments of the disclosure.

Accordingly, polypeptides or protein sequences of embodiments of the disclosure include SEQ ID NO:19, as set forth below:

```
MAESFLFNIIERVLAKVSSIAVYEISLAWNVKTELRKLQSTLSTIKAVLL
DANEQKAKNHEVRDWLEKLRDVVYDVDDLMDDLSTQLLLQMHFQKSFRKK
VRRFFSSSNPIIYRFKIGRKVKEIRELLNEIADDRRNFHFTEHTYVIPAE
NTSREQTHSFVRASDIIGRDDDQENIVKQLIDSHDEENISVIPIVGLGGL
GKTTLVKLVYNNNRVVQNFDLRMWVSISEDFSLSKVIEKILRSATGESFD
HLDMDQLQCCLGEVLQQKRYLLVLDDVWNEDQHKWTDLRELLMNCSRGSK
IVVTTRSKMVALITGTVPPYYLGGLANDDCLSLFLKCAFGGQDNLFPNLV
EIGKEIVKKCGGVPLAVKTLGRLLYMKTDENEWLQIRDNEIWEIEQNKSD
ILPILRLSYEQMPSHLRQCFAYCSMLPKGQEIPREDFINRWIAQGFIQSS
NRNRKLEDIGNQYFDELLSRFCFLDVVQAFDGEILACKIHNLVHDLAQSV
SGAECLNVKPNAFVVSERVRHLFFHAEDMSRKHFPRFLLPLQKLRSFSYS
FNIGPVNKFFVKTMLSNFKCLRMLVLNNLDLEELPTSIGHLKELRYLNLS
DSGKIKFLPRSMSKLVNLHTLNLINCEQLKELPRDFRKLISLKTLYLTTH
QMSAGIKNQHSFTSLQFLLLFKCCFPKLQPELVQHFTALRVLRIYECPSL
CSLPSSIRYLTSLEKLWIWNCEELDLIDGEGMSGLTSLQSLLLMGLPKLV
TLPLELKDTAPTTLKYFRIADCPNLVELPEWLPNCSSLQRLYIEDCPVLA
SIPQGIYSHNANVHIIDCPLLGG*.
```

In some embodiments, the polypeptides or proteins according to this or any other embodiment described herein comprise one or more (e.g., 1, 2, 3, 4, 5 or more) amino acid insertions, deletions, or modifications (e.g., substitution of one amino acid for another) compared to SEQ ID NO:19, or are otherwise substantially identical (e.g., having a sequence at least 80%, 81%, 82%, 83%, 84%, 85%, 86%, 87%, 88%, 89%, 90%, 91%, 92%, 93%, 94%, 95%, 96%, 97%, 98%, 99% or more identical) with the entire sequence of SEQ ID NO:19. It is contemplated that such variants retain the function of, for example, SEQ ID NO:19 (e.g., in imparting or enhancing disease resistance). For example, polypeptides or proteins comprising an amino acid sequence having one or more (e.g., 1, 2, 3, 4, 5, or more) conservative amino acid substitutions relative to SEQ ID NO:19, but retaining the function of SEQ ID NO:19 (e.g., in imparting or enhancing disease resistance) are encompassed. Nucleic acid molecules encoding such variants of the polypeptides of embodiments of the disclosure are also contemplated. Such nucleic acid molecules may have, for example, a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identical with the entire sequence of SEQ ID NO:18.

In some embodiments, the polynucleotide, polypeptide, or protein (or a fragment or variant thereof) of embodiments of the disclosure confers resistance to an organism expressing the bacterial effector AvrRpt2 (or fragments or variants thereof) or a homolog of AvrRpt2 (or fragments or variants thereof), the sequence of which (SEQ ID NO:16) is as follows:

```
MKIAPVAINHSPLSREVPSHAAPTQAKQTNLQSEAGDLDARKSSASSPET
RALLATKTVLGRHKIEVPAFGGWFKKKSSKHETGGSSANADSSSVASDST
EKPLFRLTHVPYVSQGNERMGCWYACARMVGHSVEAGPRLGLPELYEGRE
```

```
-continued
GPAGLQDFSDVERFIHNEGLTRVDLPDNERFTHEELGALLYKHGPIIFGW

KTPNDSWHMSVLTGVDKETSSITFHDPRQGPDLAMPLDYFNQRLAWQVPH

AMLYR
```

Thus, it is contemplated that such a polynucleotide, polypeptide, or protein (or fragment or variant thereof) confers resistance to an organism expressing the effector encoded by SEQ ID NO:16. In some embodiments, the polynucleotide or protein (or fragment or variant thereof) confers resistance to a fragment or variant of SEQ ID NO:16, including those that comprise one or more (e.g., 1, 2, 3, 4, 5 or more) amino acid insertions, deletions, or modifications (e.g., substitution of one amino acid for another) compared to SEQ ID NO:16, or are otherwise substantially identical (e.g., having a sequence at least 80%, 85%, 90%, 95%, 96%, 97%, 98%, 99% or more identical) with the entire sequence of SEQ ID NO:16).

In some embodiments, a polynucleotide, polypeptide, or protein (or fragment or variant thereof) of embodiments of the disclosure confers resistance to an organism expressing the bacterial effector AvrRpt2 (SEQ ID NO:16) comprising mutations selected from F70R, E150S, Y191C, D216E, and combinations thereof.

In some embodiments, a polynucleotide, polypeptide, or protein (or fragment or variant thereof) of embodiments of the disclosure confers resistance to an organism expressing a pathogen effector protein (e.g., AvrRpt2 as described herein) capable of degrading a RIN4 expressed by the cell (e.g., host cell) or plant of embodiments of the disclosure. Accordingly, in some embodiments, a polynucleotide (e.g., Ptr1 or a variant or ortholog thereof as described herein) or polypeptide or protein (e.g., encoded by a polynucleotide described herein or fragment or variant thereof) of embodiments of the disclosure confers resistance to an organism by responding to degradation of a target (e.g., RIN4) by a pathogen-associated protease (e.g., AvrRpt2). In some embodiments, the response to degradation is a conformational change in the polynucleotide, polypeptide, or protein. In some embodiments, the method involves co-expressing one or more RIN4 proteins and Ptr1 (or a variant or ortholog thereof) as described herein. Accordingly, in some embodiments of the disclosure, the nucleic acid molecule described herein further comprises one or more RIN4 polynucleotides. See Kim et al., "Using Decoys to Expand the Recognition Specificity of a Plant Disease Resistance Protein," *Research Reports* 351 (6274): 684-687 (2016), which is hereby incorporated by reference in its entirety. In some embodiments, RIN4 is *Arabidopsis thaliana* RIN4 (see Mackey et al., "*Arabidopsis* RIN4 is a Target of the Type III Virulence Effector AvrRpt2 and Modulates RPS2-Mediated Resistance," *Cell* 112(3):379-89 (2003), which is hereby incorporated by reference in its entirety) or a variant or ortholog thereof. Exemplary RIN4 proteins are described in the Examples below. For example, in some embodiments, RIN4 is encoded by RIN4-1, RIN4-2, RIN4-3, and/or RIN4-4 (corresponding, respectively, to Solyc identifiers Solyc09g059430, Solyc06g083390, Solyc12g098440, and Solyc11g012010, each of which are hereby incorporated by reference in its entirety (see FIG. 18) or a variant or ortholog thereof. Accordingly, another aspect of the disclosure is a method of imparting or enhancing disease resistance in plants expressing a pathogen effector protein (e.g., AvrRpt2 as described herein) capable of degrading a RIN4 expressed by the plant.

In some embodiments, the nucleic acid molecule further comprises a *Pseudomonas* tomato race (Pto) polynucleotide, the amino acid sequence of which (SEQ ID NO:17) is as follows:

```
MGSKYSKATNSINDALSSSYLVPFESYRVPLVDLEEATNNFDHKFLIGHG

VFGKVYKGVLRDGAKVALKRRTPESSQGIEEFETEIETLSFCRHPHLVSL

IGFCDERNEMILIYKYMENGNLKRHLYGSDLPTMSMSWEQRLEICIGAAR

GLHYLHTRAIIHRDVKSINILLDENFVPKITDFGISKKGTELDQTHLSTV

VKGTLGYIDPEYFIKGRLTEKSDVYSFGVVLFEVLCARSAIVQSLPREMV

NLAEWAVESHNNGQLEQIVDPNLADKIRPESLRKFGDTAVKCLALSSEDR

PSMGDVLWKLEYALRLQESVI
```

The Ptr1 nucleic acid molecules of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire Ptr1 sequences set forth herein or to variants and fragments thereof are encompassed by embodiments of the disclosure. Accordingly, another aspect of embodiments of the disclosure is a method of identifying the presence of a putative Ptr1 sequence based on sequence homology to the sequences set forth herein by, for example, using next generation sequencing, TaqMan assays, UniTaq assays, real-time PCR assays, digital PCR, microarray, hybridization or other detection methods. Accordingly, a further aspect of embodiments of the disclosure a method of identifying a candidate plant suitable for breeding that comprises a putative Ptr1 sequence. The method involves providing a candidate plant; analyzing the candidate plant for the presence, in its genome, of a putative Ptr1 polynucleotide; identifying, based on said analyzing, a candidate plant suitable for breeding that includes in its genome, a Ptr1 polynucleotide; and breeding the identified plant with at least one other plant.

Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an Ptr1 protein or polypeptide and which hybridize under stringent conditions to at least one of the Ptr1 nucleic acid molecules disclosed herein, or to variants or fragments thereof, are encompassed by embodiments of the disclosure. In some embodiments, the orthologous Ptr1 to those described herein may be from a member of the Solanaceae family. Plants that are members of the Solanaceae family include, but not limited to, tomato, potato, pepper, tobacco, eggplant, tomatillo, and petunia.

Accordingly, in embodiments, the polynucleotide, polypeptide, or protein (or a fragment or variant thereof) of embodiments of the disclosure is an ortholog of Ptr1. In some embodiments, the polynucleotide, polypeptide, or protein (or a fragment or variant thereof) of embodiments of the disclosure is a modified form of an ortholog of Ptr1.

In some embodiments, the ortholog of Ptr1 is from a species of *Solanum, Capsicum,* or *Nicotiana.* In some embodiments, the ortholog of Ptr1 is from *S. lycopersicum, S. pennellii, S. tuberosum, C. annuum, C. baccatum, C. chinense, N. attenuata, N. benthamiana, N. tabacum,* or *N. tomentosiformis.*

In some embodiments, the ortholog of Ptr1 is RGA1 of *Solanum tuberosum* (St). For example, in some embodiments the ortholog of Ptr1 has the amino acid sequence of SEQ ID NO: 131 (GenBank Accession No. XP_006340095.1). In some embodiments the ortholog of Ptr1 has the polynucleotide sequence of SEQ ID NO:132 (coding sequence from GenBank Accession No. XM_006340033.2).

In some embodiments, the ortholog of Ptr1 is selected from *S. lycopersicum* (SlPtr1, SEQ ID NO:114), *S. pennellii* (SpPtr1, SEQ ID NO:115), *S. tuberosum* Ptr1 (SEQ ID NO:116), *C. anuum* Ptr1 (SEQ ID NO:117), *C. baccatum* Ptr1 (SEQ ID NO:118), *C. chinense* Ptr1 (SEQ ID NO:119), *N. attenuata* Ptr1 (SEQ ID NO:120), *N. benthamiana* Ptr1a (SEQ ID NO:121), *N. tabacum* Ptr1 (SEQ ID NO:122), or *N. tomentosiformis* Ptr1 (SEQ ID NO:123).

In some embodiments, the ortholog of Ptr1 is selected from *S. lycopersicum* (SlPtr1, SEQ ID NO:114) or *S. pennellii* (SpPtr1, SEQ ID NO:115).

In some embodiments, the ortholog of Ptr1 is *S. lycopersicum* (SlPtr1, SEQ ID NO:114).

Components of the plant cells and nucleic acid constructs according to embodiments of the disclosure may be heterologous. A polynucleotide sequence is "heterologous to" an organism or a second polynucleotide sequence if it is synthetic or originates from a different organism, or, if from the same organism, is modified from its original form. For example, a promoter operably linked to a heterologous coding sequence (or vice versa) refers to a coding sequence from an organism or species different from that from which the promoter was derived, or, if from the same organism or species, a coding sequence which is not naturally associated with the promoter (e.g., a genetically engineered coding sequence or an allele from a different ecotype or variety).

In some embodiments, a plant or cell provided by the invention incorporates a heterologous polynucleotide sequence not native to the plant or cell, e.g., an exogenous nucleic acid derived from another plant, strain, or cultivar. In some embodiments, a plant or cell of the invention incorporates modifications to its own native polynucleotide sequence (e.g., by genome modification as described herein) resulting in a heterologous polynucleotide sequence. The resulting heterologous polynucleotide sequence may result in a change in the expression or functionality of the gene product of the modified polynucleotide sequence or of another native polynucleotide sequence. Modifications can be incorporated, for example, by genome modification. The specific mutations can be based on information such as the use of known techniques to identify variations in the gene that correlate with improved function. In some embodiments, modifications may be introduced to produce a heterologous polynucleotide that encodes a protein that imparts or enhances disease resistance in a plant as described herein. Such modifications include modifications of the native polynucleotide sequence to increase sequence similarity to SEQ ID NO:18 or to produce an expression product with similarity (or increased similarity) to SEQ ID NO:19. For example, in comparing the native polynucleotide sequence to that of SEQ ID NO:18, differences (or mutations) in the native polynucleotide sequence versus SEQ ID NO:18 may be identified. For example, functional start and/or stop codons, missense mutations, nonsense mutations, splice junction mutations, insertion mutations, deletion mutations, or frameshift mutations may be identified in the native polynucleotide sequence as compared to SEQ ID NO: 18. See Example 15. Accordingly, in some embodiments, modifications to a native polynucleotide sequence to produce a heterologous polynucleotide include modifications made to introduce or repair a start and/or stop codon or modifications to repair missense mutations, nonsense mutations, splice junction mutations, insertion mutations, deletion mutations, or frameshift mutations to correspond to, e.g., the polynucleotide sequence of SEQ ID NO:18.

Genome modification can be achieved, for example, by use of known techniques or systems for site directed mutagenesis or genome editing. Such techniques or systems include, for example, zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems and variants thereof) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7):397-405 (2013); Chen et al., "CRISPR/Cas Genome Editing and Precision Plant Breeding in Agriculture," *Ann. Rev. Plant Biol.* 70:667-97 (2019), each of which is hereby incorporated by reference in its entirety), or DNA free genome editing (Metje-Sprink et al., "DNA-Free Genome Editing: Past, Present, and Future," *Front. Plant. Sci.* 9:1957 (2019), which is hereby incorporated by reference in its entirety).

The polypeptide or protein sequences, fragments, and variants thereof as described herein include, for example, modified forms of native polynucleotide sequences naturally present in the organism or species prior to modification. For example, in some embodiments, the native polynucleotide sequence naturally present in the organism or species prior to modification is that of an ortholog of Ptr1 as described herein. In some embodiments, the native polynucleotide sequence is from a species of *Solanum, Capsicum,* or *Nicotiana.* In some embodiments, the native polynucleotide sequence naturally present in the organism or species prior to modification is from *S. lycopersicum, S. pennellii, S. tuberosum, C. annuum, C. baccatum, C. chinense, N. attenuata, N. benthamiana, N. tabacum,* or *N. tomentosiformis.*

In embodiments, the polynucleotide, polypeptide, or protein (or a fragment or variant thereof) of embodiments of the disclosure is a modified form of the RGA1 gene of *Solanum tuberosum.* In some embodiments, the RGA1 gene of *Solanum tuberosum* encodes a protein having the amino acid sequence of SEQ ID NO: 131. In some embodiments, the RGA1 gene of *Solanum tuberosum* has the polynucleotide coding sequence of SEQ ID NO:132.

In some embodiments, the polynucleotide, polypeptide, or protein (or a fragment or variant thereof) of embodiments of the disclosure is a modified form of *S. lycopersicum* (SlPtr1, SEQ ID NO:114), *S. pennellii* (SpPtr1, SEQ ID NO:115), *S. tuberosum* Ptr1 (SEQ ID NO:116), *C. anuum* Ptr1 (SEQ ID NO:117), *C. baccatum* Ptr1 (SEQ ID NO:118), *C. chinense*

Ptr1 (SEQ ID NO:119), *N. attenuata* Ptr1 (SEQ ID NO:120), *N. benthamiana* Ptr1a (SEQ ID NO:121), *N. tabacum* Ptr1 (SEQ ID NO:122), or *N. tomentosiformis* Ptr1 (SEQ ID NO:123).

In some embodiments, the polynucleotide, polypeptide, or protein (or a fragment or variant thereof) of embodiments of the disclosure is a modified form of *S. lycopersicum* (SlPtr1, SEQ ID NO:114) or *S. pennellii* (SpPtr1, SEQ ID NO:115). In some embodiments, the polynucleotide, polypeptide, or protein (or a fragment or variant thereof) of embodiments of the disclosure is a modified form of *S. lycopersicum* (SlPtr1, SEQ ID NO:114).

Heterologous polynucleotides may be introduced into the cells of embodiments of the disclosure by use of known techniques or systems. For example, by traditional breeding, transgenic methods, or direct editing. A person of skill in the art will recognize that some of these techniques or systems will produce transgenic cells, while others produce non-transgenic cells. Thus, both transgenic and non-transgenic cells and plants comprising the heterologous polynucleotide sequences of embodiments of the disclosure are contemplated.

Methods of producing recombinant nucleic acids for purposes of, e.g., making transgenic plants are well-known. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, NY, Cold Spring Harbor Press (1989), and Ausubel et al., *Current Protocols in Molecular Biology*, New York, NY, John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with embodiments of the disclosure.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known by those of ordinary skill in the art (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters Used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the Chrysanthemum UEP1 Promoter and Comparative Expression in Florets and Leaves of *Dendranthema grandiflora*," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimeric Granule-Bound Starch Synthase-GUS Gene in Transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

Nucleic acid constructs of embodiments of the disclosure include an operable 3' regulatory region, selected from among those which are capable of providing correct transcription termination and polyadenylation of mRNA for expression in the host cell of choice, operably linked to a nucleic acid molecule configured to silence BBTV. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would be suitable for use in conjunction with embodiments of the disclosure.

The different components described supra can be ligated together to produce the expression systems which contain the nucleic acid constructs of embodiments of the disclosure, using well known molecular cloning techniques as described in Sambrook et al., *Molecular Cloning: A Laboratory Manual*, Second Edition Cold Spring Harbor, NY, Cold Spring Harbor Press (1989), and Ausubel et al. *Current Protocols in Molecular Biology*, New York, NY, John Wiley & Sons (1989), which are hereby incorporated by reference in their entirety.

Once the nucleic acid construct of embodiments of the disclosure has been prepared, it is ready to be incorporated into a host cell. Accordingly, another aspect of embodiments of the disclosure relates to a recombinant host cell containing one or more of the nucleic acid constructs of embodiments of the disclosure. Basically, this method is carried out by transforming a host cell with a nucleic acid construct of embodiments of the disclosure under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, NY (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of embodiments of the disclosure is stably inserted into the genome of the recombinant plant cell as a result of the transformation, although transient expression can serve an important purpose.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of embodiments of the disclosure. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of embodiments of the disclosure. Any method that results in efficient transformation of the host cell of choice is appropriate for practicing embodiments of the disclosure.

After transformation, the transformed plant cells must be regenerated. Plant regeneration from cultured protoplasts is described in Evans et al., *Handbook of Plant Cell Cultures*, Vol. 1, New York, NY, MacMillan Publishing Co. (1983); Vasil, ed., *Cell Culture and Somatic Cell Genetics of Plants*, Vol. I (1984) and Vol. III (1986), Orlando, Acad. Press; and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of embodiments of the disclosure. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of embodiments of the disclosure. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, NY, Cold Spring Harbor Press (1989), which is hereby incorporated by reference in its entirety).

Accordingly, another aspect of embodiments of the disclosure relates to a plant or plant seed transformed with one or more nucleic acid constructs described herein. Embodiments of the disclosure also encompasses the whole plant, or a component part of a plant, including shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same.

In some embodiments, a transgenic plant or cell of embodiments of the disclosure is modified, for example by outcrossing, to remove the transgene (e.g., removal of Cas9 following genomic introduction of heterologous polynucleotide sequences). Thus, also contemplated are non-transgenic cells and plants comprising heterologous polynucleotide sequences of embodiments of the disclosure, derived from transgenic cells and plants comprising heterologous polynucleotide sequences of embodiments of the disclosure.

Suitable plants for use in accordance with embodiments of the disclosure include both monocots and dicots. Suitable plants for use in accordance with embodiments of the disclosure also include both crop plants and ornamentals. For example, suitable plants include rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana*, *Saintpaulia*, petunia, pelargonium, poinsettia, chrysanthemum, carnation, crocus, marigold, daffodil, pine, *Medicago truncatula*, *Sandersonia aurantiaca*, and zinnia.

In embodiments, the plant is a *Solanum* spp. In embodiments, the plant is *Solanum lycopersicum*. In other embodiments, the plant is *Solanum tuberosum*.

In embodiments, the plant is a *Cucurbita* spp. In embodiments, the plant is *Cucurbita argyrosperma*, *Cucurbita ficifolia*, *Cucurbita moschata*, *Cucurbita maxima*, or *Cucurbita pepo*.

In embodiments, the plant is a *Pyrus* spp. In embodiments, the plant is *Pyrus communis*, *Pyris pyrifolia*, *Pyris bretschneideri*, *Pyrus sinkiangensis*, or *Pyrus ussuriensis*.

Another aspect of embodiments of the disclosure is a method of expressing a nucleic acid molecule in a plant. The method involves providing a transgenic plant or transgenic plant cell transformed with a nucleic acid construct comprising a nucleic acid molecule comprising a *Pseudomonas* tomato race 1 (Ptr1) polynucleotide, a 5' heterologous DNA promoter sequence, and a 3' terminator sequence, wherein the nucleic acid molecule, the DNA promoter sequence, and the terminator sequence are operatively coupled to permit transcription of the nucleic acid molecule, and growing the transgenic plant or a plant grown from the transgenic plant seed under conditions effective to express the nucleic acid molecule in said transgenic plant or said plant grown from the transgenic plant seed. Suitable nucleic acid molecules are described above.

In some embodiments a transgenic plant is provided. In some embodiments, a transgenic plant cell is provided. In some embodiments, a transgenic plant seed comprising a transgenic plant cell is provided.

In some embodiments, providing a transgenic plant, plant cell, or plant seed involves transforming a non-transgenic plant, non-transgenic plant cell, or a non-transgenic plant seed with the nucleic acid construct to yield the transgenic plant or plant seed. Transformation is described above and may include *Agrobacterium*-mediated transformation, whisker method transformation, vacuum infiltration, biolistic transformation, electroporation, micro-injection, polyethylene-mediated transformation, or laser-beam transformation.

Another aspect of embodiments of the disclosure is a method of imparting disease resistance to a plant. The method involves transforming a plant or a plant cell with a nucleic acid molecule that increases expression of Ptr1, wherein the expression is effective in imparting disease resistance to the transformed plant or to a transgenic plant produced from the transformed plant cell.

In some embodiments, a plant is transformed. In another embodiment, a plant seed is transformed and the method also involves planting the transformed plant seed under conditions effective for a plant to grow from the planted plant seed. Suitable nucleic acid molecules and are described above.

Imparting disease resistance also includes enhancing disease resistance in a plant. Imparting disease resistance or enhancing disease resistance refers to an increase in the ability of a plant to prevent pathogen infection or pathogen-induced symptoms. In some embodiments, disease resistance is increased compared to a control plant (for example, an unmodified or non-transgenic plant). In some embodiments, the level of resistance in a non-naturally occurring transgenic plant of the invention is at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the resistance exhibited by a control plant. The level of resistance may be measured using conventional methods. For example, the level of resistance to a pathogen may be determined by comparing physical features and characteristics (for example, plant height and weight) or by comparing disease symptoms (for example, delayed lesion development, reduced lesion size, leaf wilting and curling, water-soaked spots, amount of pathogen growth, and discoloration of cells) of the non-naturally occurring plant (e.g., a modified plant or transgenic plant).

Disease resistance can be increased or enhanced resistance to a particular pathogen species or genus or can be increased or enhanced resistance to a broad range of pathogens (e.g., pattern-triggered immunity, systemic acquired resistance, etc.). In some embodiments, the pathogen is a bacterial plant pathogen. By way of example, bacterial pathogens may belong to *Acidovorax, Agrobacterium, Burkholderia, Candidatus* Liberibacter, *Clavibacter, Curtobacterium, Dickeya, Envinia, Pantoea, Pectobacterium, Phytoplasma, Pseudomonas, Ralstonia, Spiroplasma, Streptomyces, Xanthomonas*, and *Xylella*. See PLANT PATHOGENIC BACTERIA: GENOMICS AND MOLECULAR BIOLOGY, Robert W. Jackson Ed., Norfolk, UK, Caister Academic Press (2009), which is hereby incorporated by reference in its entirety. By way of example, the bacterial parasite may belong to *Pseudomonas syringae* pv. tomato. In some embodiments, the pathogen is a fungal parasite. By way of example, the fungal parasite may be to *Collimonas fungivorans.*

In some embodiments, the pathogen expresses an AvrRpt2 protein (or a variant, homolog, or ortholog thereof). In some embodiments, the AvrRpt2 protein is one of those identified in Table 10.

In some embodiments, disease resistance to a *Pseudomonas, Ralstonia, Acidovoraxavenae, Acidovorax, Sinorhizobium, Erwinia, Neorhizobium, Meshorhizobium, Collimonas*, or *Burkholderia* species, such as those identified in FIG. 36 and Table 10 is increased.

In some embodiments, disease resistance to one or more of *Erwinia amylovora, Ralstonia pseudosolanacearum, Acidovorax citrulli, Acidovorax avenae, Burkholderia pyrrocinia, Collimonas fungivorans, Mezorhizobium huakuii*, and *Sinorhizobium medicae* is increased.

Another aspect of embodiments of the disclosure is a method of imparting disease resistance to a plant. The method involves providing a plant, plant cell, or plant seed. The plant, plant cell, or plant seed comprises a heterologous Ptr1 as described herein. The expression of the heterologous Ptr1 is effective in imparting or enhancing disease resistance in the plant or plant produced from the plant cell or plant seed.

Suitable heterologous Ptr1 polynucleotides are described herein above.

For example, in some embodiments, the heterologous Ptr1 polynucleotide is a heterologous polynucleotide sequence not native to the plant or cell. In some embodiments, the heterologous Ptr1 polynucleotide incorporates modifications to its own native polynucleotide sequence (e.g., by genome modification as described herein) resulting in a heterologous polynucleotide sequence, as described herein above.

In some embodiments, the heterologous Ptr1 polynucleotide is a transgene. Accordingly, in some embodiments, providing the plant includes transforming a plant, plant cell, or plant seed with a nucleic acid molecule that increases expression of an Ptr1 protein or polypeptide according to embodiments of the disclosure. Suitable nucleic acid molecules are described above.

Another aspect of embodiments of the disclosure is a method of identifying a candidate plant suitable for breeding that displays enhanced disease resistance. The method involves providing a candidate plant; analyzing the candidate plant for the presence, in its genome, of a Ptr1 polynucleotide (or a variant or ortholog thereof); identifying, based on said analyzing, a candidate plant suitable for breeding that includes in its genome, a Ptr1 polynucleotide (or a variant or ortholog thereof); and breeding the identified plant with at least one other plant. In some embodiments, identifying the presence of a Ptr1 sequence is achieved based on sequence homology to the sequences set forth herein by, for example, using next generation sequencing, TaqMan assays, UniTaq assays, real-time PCR assays, digital PCR, microarray, hybridization or other detection methods.

In some embodiments, analyzing the candidate plant for the presence, in its genome, of a gene encoding an Ptr1 polynucleotide involves isolating genomic DNA from the plant, germplasm, pollen, or seed of the plant; analyzing genomic DNA from the plant, germplasm, pollen, or seed of the plant for the presence of the gene encoding the Ptr1 polynucleotide; and detecting the gene encoding the Ptr1 polynucleotide.

In some embodiments, the breeding involves crossing, making hybrids, backcrossing, self-crossing, double haploid breeding, and/or combinations thereof.

In some embodiments, a transgenic plant transformed with a nucleic acid molecule that encodes a Ptr1 polynucleotide is provided as the candidate plant. In some embodiments, providing the transgenic plant involves transforming a plant or plant cell with a nucleic acid construct according to embodiments of the disclosure and growing the transgenic plant or a plant grown from the transgenic plant cell under conditions effective to express the nucleic acid molecule in the transgenic plant or a plant grown from the transgenic plant cell.

Another aspect of embodiments of the disclosure is a plant cell comprising a nucleic acid molecule comprising a heterologous *Pseudomonas* tomato race 1 (Ptr1) polynucleotide.

In embodiments, the plant cell comprising a nucleic acid molecule comprising a heterologous *Pseudomonas* tomato race 1 (Ptr1) polynucleotide is transgenic; in other embodiments the plant cell comprising a nucleic acid molecule comprising a heterologous *Pseudomonas* tomato race 1 (Ptr1) polynucleotide is non-transgenic.

The following examples are provided to illustrate embodiments of the present disclosure but are by no means intended to limit its scope.

EXAMPLES

Example 1: Materials and Methods for Examples 2-11

Bacterial Strains and Plasmids

*Pseudomonas syringae* pv. tomato strains DC3000 (Buell et al., "The Complete Genome Sequence of the *Arabidopsis* and Tomato Pathogen *Pseudomonas syringae* pv. Tomato DC3000," PNAS 100(18):10181-6 (2003), which is hereby incorporated by reference in its entirety), NY15125 (Kraus et al, "*Pseudomonas syringae* pv. tomato strains from New York Exhibit Virulence Attributes Intermediate Between Typical race 0 and race 1 Strains," *Plant Dis.* 101:1442-8 (2017), which is hereby incorporated by reference in its entirety), T1 (Almeida et al., "A Draft Genome Sequence of *Pseudomonas syringae* pv. Tomato T1 Reveals a Type III Effector Repertoire Significantly Divergent from that of *Pseudomonas syringae* pv. tomato DC3000," *Mol. Plant-Microbe Interact.* 22(1): 52-62 (2009), which is hereby incorporated by reference in its entirety), JL1065 (Whalen et al., "Identification of *Pseudomonas syringae* Pathogens of *Arabidopsis* and a Bacterial Locus Determining Avirulence on Both *Arabidopsis* and Soybean," *Plant Cell* 3:49-59 (1991), which is hereby incorporated by reference in its entirety), NYT1 (Jones et al., "Genome-Assisted Development of a Diagnostic Protocol for Distinguishing High Virulence *Pseudomonas syringae* pv. tomato Strains," *Plant Disease* 99:527-34 (2015), which is hereby incorporated by reference in its entirety), CA-A9, and CA-407 (Kunkeaw et al., "Molecular and Evolutionary Analyses of *Pseudomonas syringae* pv. tomato Race 1," *Mol. Plant-Microbe. Interact.* 23:415-24 (2010), which is hereby incorporated by reference in its entirety) were grown on King's B (KB) (King et al., "Two Simple Media for the Demonstration of Pycocyanin and Fluorescin," *J. Lab. Clin. Med.* 44:301-7 (1954), which is hereby incorporated by reference in its entirety) semi-selective media at 30° C. (Table 1). *Ralstonia pseudosolanacearum* CMR15 (Remenant et al., "Genomes of Three Tomato Pathogens Within the *Ralstonia solanacearum* Species Complex Reveal Significant Evolutionary Divergence," *BMC Genomics* 11:379 (2010), which is hereby incorporated by reference in its entirety) was grown on rich B medium (27.7 mM glucose, 10 g $l^{-1}$ bacto-peptone, 1 g $l^{-1}$ yeast extract, 1 g $l^{-1}$ casamino acids). Plasmids pCPP5372 (Oh et al., "*Pseudomonas syringae* Lytic Transglycosylases Coregulated with the Type III Secretion System Contribute to the Translocation of Effector Proteins into Plant Cells," *J. Bacteriol.* 189: 8277-89 (2007), which is hereby incorporated by reference in its entirety) carrying wildtype avrRpt2$_{NY15125}$, avrRpt2 variants or the empty vector were introduced into DC3000 by electroporation (Tables 2 and 3). All *P. syringae* pv. tomato strains were stored in 20% glycerol+60 mM sucrose at −80° C. *Escherichia coli* TOP10 was used for plasmid maintenance and grown in LB medium at 37° C.

TABLE 1

Bacterial strains used in this study.

| Name | Genotype | Race | Source | Relevant efectors |
|---|---|---|---|---|
| *P. syringae* pv. tomato DC3000 | Wild type | 0 | Beull et al., 2003[a] | AvrPto |
| *P. syringae* pv. tomato NY15125 | Wild type | 0 | Kraus et al., 2017[b] | AvrPto, AvrRpt2 |
| *P. syringae* pv. tomato JL1065 | Wild type | 0 | Whalen et al., 1991[c] | AvrPto, AvrRpt2 |
| *P. syringae* pv. tomato T1 | Wild type | 1 | Almeida et al., 2009[d] | AvrRpt2 |

TABLE 1-continued

Bacterial strains used in this study.

| Name | Genotype | Race | Source | Relevant efectors |
|---|---|---|---|---|
| *P. syringae* pv. tomato NYT1 | Wild type | 1 | Jones et al., 2015[e] | AvrRpt2 |
| *P. syringae* pv. tomato CA-A9 | Wild type | 1 | Kunkeaw et al., 2010[f] | AvrRpt2 |
| *P. syringae* pv. tomato CA-407 | Wild type | 1 | Kunkeaw et al., 2010[f] | AvrRpt2 |
| *P. pseudosolanacearum* CMR15 | Wild type | — | Mahbou Somo Toukam et al., 2009[g] | RipBN |
| *A. tumefaciens* 1D1249 | Wild type | — | Wroblewski et al., 2005[h] | — |
| *E. coli* TOP 10 | Wild type | — | Thermo Fisher Co. | — |
| *E. coli* S17-1 | Wild type | — | A. Collmer, Cornell University | — |

Table 1 source references include:
[a]Buell et al., "The Complete Genome Sequence of the *Arabidopsis* and Tomato Pathogen *Pseudomonas Syringae* pv. Tomato DC3000," PNAS 100(18):10181-6 (2003);
[b]Kraus et al, "*Pseudomonas syringae*" pv. *tomato* strains from New York Exhibit Virulence Attributes Intermediate Between Typical race 0 and race 1 Strains," *Plant Dis.* 101:1442-8 (2017);
[c]Whalen et al., "Identification of *Pseudomonas syringae* Pathogens of *Arabidopsis* and a Bacterial Locus Determining Avirulence on Both *Arabidopsis* and Soybean," *Plant Cell* 3;49-59 (1991);
[d]Almeida et al., "A Draft Genome Sequence of *Pseudomonas Syringae* pv. Tomato T1 Reveals a Type III Effector Repertoire Significantly Divergent from that of *Pseudomonas syringae* pv. tomato DC3000," *Mol. Plant-Microbe Interact.* 22(1): 52-62 (2009);
[e]Jones et al., "Genome-Assisted Development of a Diagnostic Protocol for Distinguishing High Virulence *Pseudomonas Syringae* pv. *tomato* Strains," *Plant Disease* 99:527-34 (2015);
[f]Kunkeaw et al., "Molecular and Evolutionary Analyses of *Pseudomonas syringae* pv. *tomato* Race 1," *Mol. Plant-Microbe. Interact.* 23:415-24 (2010);
[g]Mahbou et al., "Broad Diversity of *Ralstonia solanacearum* Strains in Cameroon," *Plant Dis.* 93:1123-30 (2009); and [h]Wroblewski et al., "Optimization of *Agrobacterium*-Mediated Transient Assays of Gene Expression in Lettuce, Tomato, and *Arabidopsis*," *Plant Biotech. J.* 3:259-73 (2005), each of which is hereby incorporated by reference in its entirety.

TABLE 2

Vectors and plasmids used in this study.

| Vector | Insert | Identifier | Purpose | Source |
|---|---|---|---|---|
| pK18mobsac | — | — | Biparental Mating | Kvitko et al., 2011[a] |
| pk18mobsac | ΔavrRpt2 | pCM3 | For deletion of avrRpt2 in NY15125 biparental mating | This work |
| pENTR SD TOPO | — | — | Gateway entry vector | ThermoFisher |
| pENTR SD TOPO | avrRpt2 (no stop) | 7208 | For LR recombination into destination vector | This work |
| pENTR SD TOPO | avrRpt2 F70R (no stop) | pCM4 | For LR recombination into destination vector | This work |
| pENTR SD TOPO | avrRpt2 C122A (no stop) | pCM5 | For LR recombination into destination vector | This work |
| pENTR SD TOPO | avrRpt2 C122Y (no stop) | pCM17 | For LR recombination into destination vector | This work |
| pENTR SD TOPO | avrRpt2 G131D (no stop) | pCM18 | For LR recombination into destination vector | This work |
| pENTR SD TOPO | avrRpt2 G141R (no stop) | pCM30 | For LR recombination into destination vector | This work |
| pENTR SD TOPO | avrRpt2 E150S (no stop) | pCM27 | For LR recombination into destination vector | This work |
| pENTR SD TOPO | avrRpt2 Y191C (no stop) | pCM6 | For LR recombination into destination vector | This work |
| pENTR SD TOPO | avrRpt2 Y191S (no stop) | pCM53 | For LR recombination into destination vector | This work |
| pENTR SD TOPO | avrRpt2 G194R (no stop) | pCM19 | For LR recombination into destination vector | This work |
| pENTR SD TOPO | avrRpt2 H208A (no stop) | pCM31 | For LR recombination into destination vector | This work |
| pENTR SD TOPO | avrRpt2 D216E (no stop) | pCM7 | For LR recombination into destination vector | This work |
| pCPP5372 | — | — | Binary Gateway destination vector for type three effector protein expression with C-terminal HA-tag | Oh et al., 2007[b] |
| pCPP5372 | avrRpt2 | 7200 | Generating hrp protein fusion with C-terminal HA-tag | This work |
| pCPP5372 | avrRpt2 F70R | pCM9 | Generating hrp protein fusion with C-terminal HA-tag | This work |
| pCPP5372 | avrRpt2 C122A | pCM10 | Generating hrp protein fusion with C-terminal HA-tag | This work |

TABLE 2-continued

Vectors and plasmids used in this study.

| Vector | Insert | Identifier | Purpose | Source |
|---|---|---|---|---|
| pCPP5372 | avrRpt2 C122Y | pCM20 | Generating hrp protein fusion with C-terminal HA-tag | This work |
| pCPP5372 | avrRpt2 G131D | pCM21 | Generating hrp protein fusion with C-terminal HA-tag | This work |
| pCPP5372 | avrRpt2 G141R | pCM32 | Generating hrp protein fusion with C-terminal HA-tag | This work |
| pCPP5372 | avrRpt2 E150S | pCM28 | Generating hrp protein fusion with C-terminal HA-tag | This work |
| pCPP5372 | avrRpt2 Y191C | pCM11 | Generating hrp protein fusion with C-terminal HA-tag | This work |
| pCPP5372 | avrRpt2 Y191S | pCM55 | Generating hrp protein fusion with C-terminal HA-tag | This work |
| pCPP5372 | avrRpt2 G194R | pCM22 | Generating hrp protein fusion with C-terminal HA-tag | This work |
| pCPP5372 | avrRpt2 H208A | pCM33 | Generating hrp protein fusion with C-terminal HA-tag | This work |
| pCPP5372 | avrRpt2 D216E | pCM33 | Generating hrp protein fusion with C-terminal HA-tag | This work |
| pGWB417 | — | — | Binary Gateway destination vector for plant transformation with C-terminal Myc-tag | Nakagawa et al., 2007[c] |
| pGWB417 | avrRpt2_Acidovorax avenae subsp. avenae ATCC 19860 | pTK187 | Generating C-terminal Myc-tag fusion | Eschen-Lippold et al., 2016[d] |
| pGWB417 | avrRpt2_Acidovorax citrulli tw6 | pTK188 | Generating C-terminal Myc-tag fusion | Eschen-Lippold et al., 2016[d] |
| pGWB417 | avrRpt2_Burkholderia pyrrocinia Lyc2 | pTK189 | Generating C-terminal Myc-tag fusion | Eschen-Lippold et al., 2016[d] |
| pGWB417 | avrRpt2_Collimonas fungivorans | pTK190 | Generating C-terminal Myc-tag fusion | Eschen-Lippold et al., 2016[d] |
| pGWB417 | avrRpt2_Erwinia amylovora ATCC 49946 | pTK191 | Generating C-terminal Myc-tag fusion | Eschen-Lippold et al., 2016[d] |
| pGWB417 | avrRpt2_Mesorhizobium huakuii 7653R | pTK192 | Generating C-terminal Myc-tag fusion | Eschen-Lippold et al., 2016[d] |
| pGWB417 | avrRpt2_Pseudomonas syringae pv. tomato NY15125 | pCM1 | Generating C-terminal Myc-tag fusion | This work |
| pGWB417 | avrRpt2_Ralstonia solanacearum CMR15 | pTK194 | Generating C-terminal Myc-tag fusion | Eschen-Lippold et al., 2016[d] |
| pGWB417 | avrRpt2_Sinorhizobium medicae WSM1369 | pTK195 | Generating C-terminal Myc-tag fusion | Eschen-Lippold et al., 2016[d] |

Table 2 source references include:

[a]Kvitko et al., "Construction of *Pseudomonas syringae* pv. tomato DC3000 Mutant and Polymutant Strains," *Methods Mol. Biol.* 712:109-28 (2011);
[b]Oh et al., "*Pseudomonas syringae* Lytic Transglycosylases Coregulated with the Type III Secretion System Contribute to the Translocation of Effector Proteins into Plant Cells," *J. Bacteriol.* 189: 8277-89 (2007);
[c]Nakagawa et al., "Improved Gateway Binary Vectors: High-Performance Vectors for Creation of Fusion Constructs in Transgenic Analysis of Plants," *Biosci. Biotechnol. Biochem.* 71:2095-100 (2007); and
[d]Eschen-Lippold et al., "Bacterial AvrRpt2-Like Cysteine Proteases Block Activation of the *Arabidopsis* Mitogen-Activated Protein Kinases, MPK4 and MPK11," *Plant Physiol.* 171:2223-8 (2016), each of which is herey incorporated by reference in its entirety.

TABLE 3

Oligonucleotides used in this study.

| Gene | Direction | Identifier | Sequence (5'-3') | SEQ ID NO: | Source |
|---|---|---|---|---|---|
| Introgressed region in Chr4 | Forward | Spenn-ch04_541669 | taatgaggcagagcaagttt | 20 | This work |
| Introgressed region in Chr4 | Reverse | Spenn-ch04_5416620 | ccctcaagaaccatgaatca | 21 | |
| avrRpt2 | Forward | oCM26 | CACCatgaaaattgctccagttgccataaatcacag | 22 | This work |
| avrRpt2 | Reverse | oCM27 | cacacgcaatgctctaccgc | 23 | |
| 5'UTR avrRpt2 | Forward | oCM20 | atcggGAATTCgtgctgatggatgctgcagg | 24 | |
| 5'UTR avrRpt2 | Reverse | oCM21 | ccacgtgaagatacctgctgcttgttaagtcgtccgttgg | 25 | |
| 3'UTR avrRpt2 | Forward | oCM22 | agcaaggtatcttcacgtggcgg | 26 | |
| 3'UTR avrRpt2 | Reverse | oCM23 | atcggCCCGGGttctgcgagcgatttgcggg | 27 | |
| UTR avrRpt2 | Forward | oCM38 | CTGATCATGTGTGCCTTGACCCC | 28 | |
| UTR avrRpt2 | Reverse | oCM39 | GGACTGCAGGGTGTTTATCGGG | 29 | |
| UTR avrRpt2 | Forward | 3719 | TTAGCTCACTCATTAGGCACC | 30 | Kraus et al., 2017[a] |
| UTR avrRpt2 | Reverse | 3720 | CCTCTTCGCTATTACGCCA | 31 | |
| avrRpt2 F70R | Forward | oCM28 | atagaggttccagccCGTggagggtggttc | 32 | This work |
| avrRpt2 F70R | Reverse | oCM29 | ccctccACGggctggaacctctatcttg | 33 | |
| avrRpt2 C122A | Forward | oCM30 | gcgaatgggaGCTtggtatgcctgcg | 34 | This work |
| avrRpt2 C122A | Reverse | oCM31 | cataccaAGCtcccattcgctcattac | 35 | |
| avrRpt2 C122Y | Forward | oCM74 | gcgaatgggaTATtggtatgcctgc | 36 | This work |
| avrRpt2 C122Y | Reverse | oCM75 | gcataccaATAtcccattcgctcattacc | 37 | |
| avrRpt2 G131D | Forward | oCM76 | agaatggttGACcattctgtcgaagc | 38 | This work |
| avrRpt2 G131D | Reverse | oCM77 | agcttcgacagaatgGTCaaccattc | 39 | |
| avrRpt2 G141R | Forward | oCM104 | cctaAGActgccggagctctatgagggaag | 40 | This work |
| avrRpt2 G141R | Reverse | oCM105 | agagctccggcagTCTtaggcgaggcccagcttc | 41 | |
| avrRpt2 E150S | Forward | oCM86 | ctatgagggaaggTCAggcccagctgggctac | 42 | This work |
| avrRpt2 E150S | Reverse | oCM87 | gtagcccagctgggccTGAccttccctcatag | 43 | |
| avrRpt2 Y191C | Forward | oCM32 | gtgcactgttgTGTaagcacgggccg | 44 | This work |
| avrRpt2 Y191C | Reverse | oCM33 | ccgtgatACAaacagtgcacccaactc | 45 | |
| avrRpt2 Y191C | Forward | oCM109 | gttgggtgcactgttgTCTaagcacg | 46 | This work |
| avrRpt2 Y191C | Reverse | oCM110 | ccgtgatAGAaacagtgcaccc | 47 | |
| avrRpt2 G194R | Forward | oCM80 | gttgtataagcacAGGccgattatatttggg | 48 | This work |
| avrRpt2 G194R | Reverse | oCM81 | cccaaatataatcggCCTgtgatatacaac | 49 | |
| avrRpt2 H208A | Forward | oCM106 | gctggGCTatgtcggtcctcactggtgtcg | 50 | This work |
| avrRpt2 H208A | Reverse | oCM107 | gaggaccgacatAGCccagctgtcattcggagttttc | 51 | |

TABLE 3-continued

Oligonucleotides used in this study.

| Gene | Direction | Identifier | Sequence (5'-3') | SEQ ID NO: | Source |
|---|---|---|---|---|---|
| avrRpt2 D216E | Forward | oCM34 | ctcactggtgtcGAAaaagagacgtcgtcc | 52 | This work |
| avrRpt2 D216E | Reverse | oCM35 | gacgtctattTTCgacaccagtgaggacc | 53 | |

Table 3 source references include:
[a] Kraus et al, "*Pseudomonas syringae* pv. tomato strains from New York Exhibit Virulence Attributes Intermediate Between Typical race 0 and race 1 Strains," *Plant Dis.* 101:1442-8 (2017), which is hereby incorporated by reference in its entirety.

Plant Material

Solanum lycopersicoides introgression lines (ILs) seeds of LA4245 and LA4277 were obtained from the Tomato Genetics Resource Center (tgrc.ucdavis.edu/lycopersicoides_ils.aspx). The genotype of LA4245 can be heterozygous for the presence of Ptr1 (Ptr1/ptr1) (LA4245-R) or homozygous for the lack of the gene (ptr1/ptr1) (LA4245-S). *S. lycopersicoides* introgression lines were grown in a greenhouse at 24° C. during daylight and 22° C. at night. *Nicotiana benthamiana* Nb-1 (Bombarely et al., "A Draft Genome Sequence of *Nicotiana benthamiana* to Enhance Molecular Plant-Microbe Biology Research," *Mol. Plant Microbe Interact.* 25(12):1523-30 (2012), which is hereby incorporated by reference in its entirety) was maintained in a growth chamber with 16 h:8 h, light:dark at 24° C. with light and 20° C. in the dark and 50% humidity. Tomatoes and *N. benthamiana* plants were grown in Cornell Osmocote Mix soil (0.16 m$^3$ peat moss, 0.34 m$^3$ vermiculite, 2.27 kg lime, 2.27 kg Osmocote Plus 15-9-12 and 0.54 kg Uni-Mix 11-5-11; Everris, Israeli Chemicals Ltd). After pathogen inoculation, plants were moved to a growth chamber with 25° C., 50% humidity, and 16 h light. *Arabidopsis thaliana* accession Columbia (Col-0) seeds were ethanol-sterilized, suspended in 1 ml of water and cold stratified for 2 days at 4° C. *A. thaliana* was grown in Fafard Mix (Sungro Horticulture) in a growth chamber under fluorescent lighting (100 µmol m$^{-2}$s$^{-1}$) with a 12 h:12 h; light:dark cycle at 21° C. and 40% humidity.

Genome Sequencing, Assembly, and Type III Effector Annotation of NY 15125

The NY15125 genome was sequenced to 163× coverage with long reads from the Pacbio RSII platform. A Canu assembly was performed with a stringent error rate (corrected Error Rate=0.035) (Koren et al., "Canu: Scalable and Accurate Long-Read Assembly via Adaptive k-mer Weighting and Repeat Separation," *Genome Res.* 27(5):722-36 (2017), which is hereby incorporated by reference in its entirety). Illumina sequencing was also done to generate paired-end reads for a coverage of 114×. Adapter clipping and quality filtering of the Illumina reads was done with Trimmomatic (Bolger et al., "Trimmomatic: a Flexible Trimmer for Illumina Sequence Data," *Bioinformatics* 30(15):2114-20 (2014), which is hereby incorporated by reference in its entirety). Concordant read mapping of the Illumina paired-end reads was used to evaluate the quality of the assembly. Two rounds of base level error corrections were done with Pacbio reads using Arrow (github.com/PacificBiosciences/pbbioconda), followed by two rounds of error correction with Illumina reads using Pilon (Walker et al., "Pilon: an Integrated Tool for Comprehensive Microbial Variant Detection and Genome Assembly Improvement," *PloS ONE* 9(11):e112963 (2014), which is hereby incorporated by reference in its entirety).

The polished assembly includes a 6.2 Mb chromosome and three putative plasmids (88 Kb, 116 Kb, 122 Kb). It was annotated with Prokka (Seemann, "Prokka: Rapid Prokaryotic Genome Annotation," *Bioinformatics* 30(14):2068-9 (2014), which is hereby incorporated by reference in its entirety) using proteins from the T1 genome (Almeida et al., "A Draft Genome Sequence of *Pseudomonas syringae* pv. Tomato T1 Reveals a Type III Effector Repertoire Significantly Divergent from that of *Pseudomonas syringae* pv. tomato DC3000," *Mol. Plant-Microbe Interact.* 22(1): 52-62 (2009), which is hereby incorporated by reference in its entirety) as supporting evidence. The NY15125 chromosome was compared with the DC3000 and T1 genomes using BRIGG (Alikhan et al., "BLAST Ring Image Generator (BRIG): Simple Prokaryote Genome Comparisons," *BMC Genomics* 12:402 (2011), which is hereby incorporated by reference in its entirety). Pseudomolecules were constructed from the deposited contigs for *P. syringae* pv. tomato NY15125 and annotated using MG-RAST (Meyer et al., "The Metagenomics RAST Server—a Public Resource for the Automatic Phylogenetic and Functional Analysis of Metagenomes," *BMC Bioinf.* 9:386 (2008), which is hereby incorporated by reference in its entirety). Effector genes were identified from the MG-RAST annotation, by alignment with other *P. syringae* pv. tomato sequences, and based on proximity to HrpL binding sites, predicted using the methods described previously (Saha et al., "Bound to Succeed: Transcription Factor Binding-Site Prediction and its Contribution to Understanding Virulence and Environmental Adaptation in Bacterial Plant Pathogens," *Mol. Plant Microbe. Interact.* 26(10):1123-30 (2013), which is hereby incorporated by reference in its entirety). The NY15125 genome sequence and plasmid sequences are available from GenBank (accession numbers: CP034558-CP034561).

Development of a *P. syringae* pv. Tomato NY15125ΔavrRpt2 Strain

A 1,024-bp promoter fragment and a 841-bp fragment downstream of the avrRpt2 gene sequence were PCR amplified and EcoRI or XmaI restriction sites were added, respectively. Fusion of both DNA fragments was cloned into the suicide vector pK18mobsacB and transformed into *E. coli* S17-1. Deletion of avrRpt2 in NY15125 was performed by biparental mating as described previously (Kraus et al, "*Pseudomonas syringae* pv. tomato strains from New York Exhibit Virulence Attributes Intermediate Between Typical race 0 and race 1 Strains," *Plant Dis.* 101:1442-8 (2017), which is hereby incorporated by reference in its entirety) with modifications (Kvitko et al., "Construction of *Pseudomonas syringae* pv. tomato DC3000 Mutant and Polymutant Strains," *Methods Mol. Biol.* 712:109-28 (2011), which is hereby incorporated by reference in its entirety).

*P. syringae* pv. Tomato Inoculation and Population Assays in Tomato

*P. syringae* pv. tomato strains were grown on KB plates for 2 days at 30° C. Strains were diluted in 10 mM $MgCl_2$+0.002% Silwet L-77 at a final concentration of $5\times10^4$ cfu $ml^{-1}$. Four-week-old plants were vacuum infiltrated, and three leaf disk samples (7 mm in diameter) were collected at 2 h (day 0) and 2 days post inoculation (dpi) to quantify bacterial populations. The experiments were repeated three times. Results shown are the mean of three independent experiments using three biological replicates per strain, including standard error of the mean. Photographs for each technical replicate were taken 7 dpi. Statistical analyses were performed using Prism 6.0 (GraphPad Software).

*P. syringae* pv. Tomato Inoculation and Population Assays in *Arabidopsis thaliana*

Five-week-old plants were dip inoculated for 20 seconds in a bacterial suspension ($1\times10^8$ cfu $ml^{-1}$ of Pst) containing 10 mM $MgCl_2$+0.02% Silwet L-77. Bacterial populations were measured 3 dpi by submerging the aerial plant tissue in 10 mM $MgCl_2$+0.2% Silwet L-77 for 2 h at 28° C. The bathing solution was serially diluted and plated (Tornero et al., "A high-Throughput Method for Quantifying Growth of Phytopathogenic Bacteria in *Arabidopsis thaliana*," *Plant J.* 28(4):475-81 (2001), which is hereby incorporated by reference in its entirety).The experiments were repeated three times. Results shown are the mean of three independent experiments using three biological replicates per strain, including standard error of the mean. Statistical analyses were performed using Prism 6.0 (GraphPad Software).

Immunodetection of AvrRpt2 Proteins in *P. syringae* pv. Tomato

Strains of *P. syringae* pv. tomato grown on KB plates for 2 days at 30° C. were resuspended in hrp-inducing liquid minimal media (50 mM KH2PO4, 7.6 mM (NH4)2SO4, 1.7 mM NaCl, 1.7 mM $MgCl_2$, 10 mM fructose, pH 5.7) or KB liquid media containing the appropriate antibiotics at an $OD_{600}$ of 0.4 and 0.1 respectively. Bacterial cultures were grown at 28° C. for 16 hours shaking at 220 RPM and $OD_{600}$ was adjusted to a final concentration of 0.5. One ml of each bacterial culture was washed with water and centrifuged. Bacterial pellets were resuspended in 100 µl of Laemmli buffer (20 mM Tris, 1% sodium dodecyl sulfate [SDS], 0.05% bromphenol blue, and 10% glycerol, pH 6.8), boiled for 5 minutes, and 5 µl of each was used for immunoblot analysis. To detect AvrRpt2 proteins, membranes were probed with ∝-HA antibody (Roche, Indianapolis, IN) conjugated with HRP.

*Agrobacterium*-mediated Transient Protein Expression in Leaves

*Agrobacterium tumefaciens* 1D1249 (Wroblewski et al., "Optimization of *Agrobacterium*-Mediated Transient Assays of Gene Expression in Lettuce, Tomato, and *Arabidopsis*," *Plant Biotech. J* 3:259-73 (2005), which is hereby incorporated by reference in its entirety) harboring the various expression vectors were grown on LB media with the appropriate antibiotics for 2 days at 30° C. Bacteria were scraped from the plate, resuspended in infiltration buffer (10 mM $MgCl_2$, 10 mM MES [pH 5.6], and 200 mM acetosyringone) and maintained for 4 h in the dark at room temperature on a nutator rocker. Bacterial cultures were then washed, centrifuged, and the pellet was resuspended in fresh infiltration buffer before diluting cultures at a final $OD_{600}$ of 0.15. Tomato or *N. benthamiana* leaves were infiltrated using a needle-less syringe and placed to a growth chamber (24° C. day and 22° C. night). Leaf samples for protein expression were taken 32 hours later.

Immunoblot Detection of Plant-Expressed Proteins

Protein samples were analyzed by grinding three leaf disks (9 mm in diameter) in protein sample buffer (50 mM Tris HCl [pH 7.5], 10% glycerol, 2% SDS, 2 mM EDTA, 1 mM DTT and 1% protease inhibitor [Sigma-Aldrich]). Samples were separated by SDS-PAGE on 4-20% gradient polyacrylamide gels and transferred to Immobilon-P PVDF membranes (Millipore) according to standard procedures (Taylor, "Using Antibodies: A Laboratory Manual," *Quarterly Rev. Biol.* 74:1-374 (2015), which is hereby incorporated by reference in its entirety). To detect AvrRpt2 proteins, membranes were probed with ∝-c-Myc (GeneScript, Piscataway, NJ) antibody conjugated with HRP. For tomato Rin4 detection, AtRin4 polyclonal antiserum (G. Coaker, UC-Davis) was used at a concentration of 1:2.000. Secondary goat anti-rabbit IgG conjugated with HRP was used at a dilution of 1:10,000 (Promega, Madison, WI).

*Ralstonia pseudosolanacearum* Disease Assays

For survival assays with *R. pseudosolanacearum* CMR15, 4-week-old tomato plants (grown in peat pots) were transferred in potting mixture in 3-liter pots to the Toulouse Plant-Microbe Phenotyping facility, (28° C., 16 hours light). Each tomato plant was soil-drench inoculated with 50 ml of 108 cfu $ml^{-1}$. Disease scoring was performed daily using a visual index in which the numbers 1, 2, 3 and 4 corresponded to 25%, 50%, 75% and 100% wilted leaves, respectively. Disease scores were transformed into binary data for the purpose of statistical comparison between disease curves (Remigi et al., "Functional Diversification of the GALA Type III Effector Family Contributes to *Ralstonia solanacearum* Adaptation on Different Plant Hosts," *New Phytol.* 192(4):976-87 (2011), which is hereby incorporated by reference in its entirety).

Tomato Genome Sequencing

Genomic DNA was extracted from a single LA4245-R plant using a DNeasy Plant Mini Kit (QIAGEN). DNA was mechanically sheared using the Covaris S2 Adaptative Focused Acoustic Disruptor (Covaris, Inc., Woburn, MA, USA) to an average size of 500-600 bp, and used to prepare a library. Single-end 100 bp DNA reads were sequenced using the Illumina HiSeq 2000 platform. The reads from LA4245-R were mapped to the *S. lycopersicum* Heinz 1706 genome sequence SL2.50 (Tomato Genome Consortium, 2012) using hisat2 version 2.1.0 (Kim et al., "HISAT: a Fast Spliced Aligner with Low Memory Requirements," *Nat. Methods* 12(4):357-60 (2015), which is hereby incorporated by reference in its entirety), and SNPs were called using GATK version 4.0. (McKenna et al., "The Genome Analysis Toolkit: a MapReduce Framework for Analyzing Next-Generation DNA Sequencing Data," *Genome Res.* 20(9): 1297-303 (2010), which is hereby incorporated by reference in its entirety). SNPs were plotted in 10 kb bins using R. Synteny between SL2.50 and LA2951 version 0.6 was determined using SynMap at CoGe: genomevolution.org/coge/SynMap.pl. Protein similarity for RPS2 and MR5 were calculated with Geneious R11: geneious.com. The genome sequence of LA4245 is available at NCBI SRA under BioProject ID PRJNA516877 and is hereby incorporated by reference in its entirety. The genome sequence of LA2951 is available at: solgenomics.net/organism/*Solanum_lycopersicoides*/genome and is hereby incorporated by reference in its entirety.

Example 2: A Locus on Chromosome 4 from *S. lycopersicoides* LA2951 Confers Resistance to Pst Race 1 Strains During the summer of 2015 in upstate New York, a research plot of 110 *S. lycopersicum* VF36×*S. lycopersicoides* LA2951 introgression lines (ILs; (Canady et al., "A Library of *Solanum lycopersicoides* Introgression Lines in Cultivated Tomato," *Genome* 48(4):685-97 (2005), which is hereby incorporated by reference in its entirety) became naturally infected by *Pseudomonas syringae* pv. tomato (Pst) resulting in severe symptoms of bacterial speck disease. However, two ILs, LA4245 and LA4277, remained essentially free of disease. LA4245 and LA4277 have large overlapping introgressed segments from chromosome 4 of *S. lycopersicoides* (Canady et al., "A Library of *Solanum lycopersicoides* Introgression Lines in Cultivated Tomato," *Genome* 48(4):685-97 (2005), which is hereby incorporated by reference in its entirety). The introgression in LA4245 is smaller and so that line was further characterized. In order to determine the race and other characteristics of the Pst strain involved in the outbreak, isolates were collected from the field and analyzed. The presence of both avrPto and avrPtoB genes, immunoblot detection of the AvrPto protein, and subsequent inoculation of tomato plants with and without the Pto gene indicated the field isolates were race 0 Pst strains (Kraus et al, "*Pseudomonas syringae* pv. tomato strains from New York Exhibit Virulence Attributes Intermediate Between Typical race 0 and race 1 Strains," *Plant Dis.* 101:1442-8 (2017), which is hereby incorporated by reference in its entirety). One Pst strain, referred to as NY15125, was chosen for further analysis.

Figure 1A:
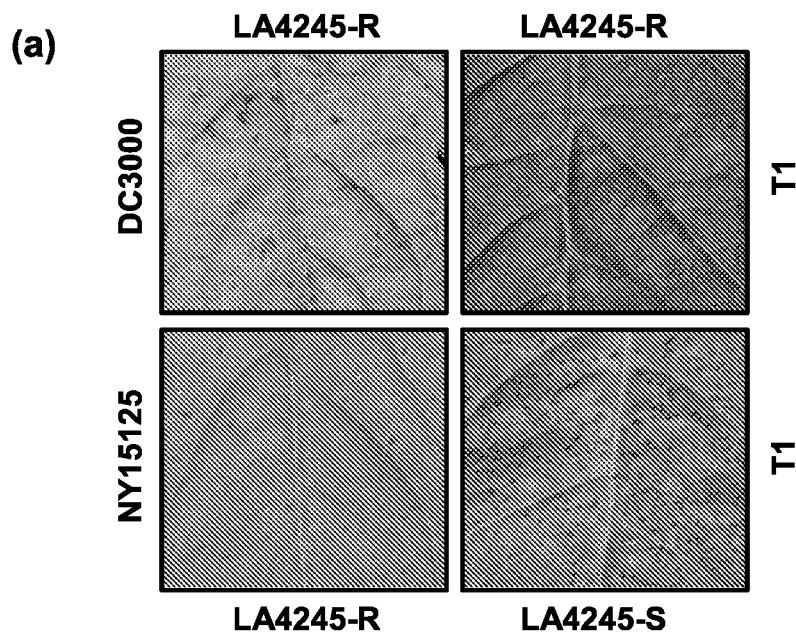
FIG. 1A and FIG. 1B provide results that demonstrate that LA4245-R confers resistance to certain strains of *Pseudomonas syringae* pv. tomato.
Figure 1B:
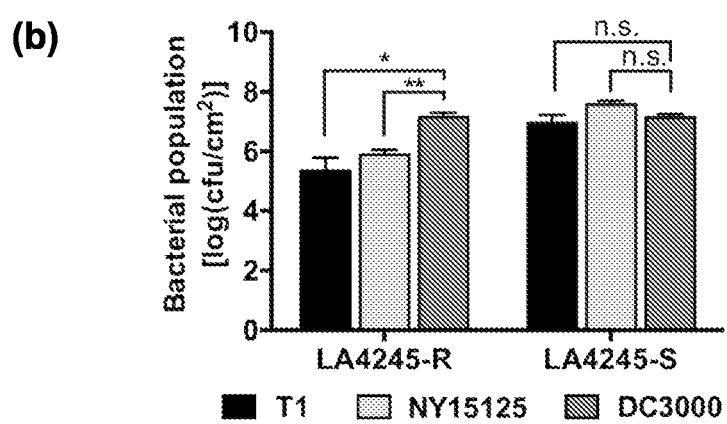

The chromosome 4 introgression segment in LA4245 is maintained in heterozygous condition because homozygotes are very rarely obtained, as noted previously (Canady et al., "A Library of *Solanum lycopersicoides* Introgression Lines in Cultivated Tomato," *Genome* 48(4):685-97 (2005), which is hereby incorporated by reference in its entirety). The putative LA4245 resistance locus was named Ptr1 (*Pseudomonas* s. pv. tomato race 1) and a nomenclature was used in which its presence or absence is denoted as LA4245-R (Ptr1/ptr1) or LA4245-S (ptr1/ptr1), respectively. To follow up the field observations, LA4245 plants were inoculated with Pst strains DC3000, NY15125 and T1 in the greenhouse. Pathogen assays showed that DC3000 caused severe symptoms on LA4245-R plants, whereas NY15125 and T1 caused the appearance of few or no specks on LA4245-R, respectively (FIG. 1A). All of the Pst strains caused more disease on LA4245-S plants. Consistent with these observations, bacterial population assays showed that T1 attained levels ~65-fold lower than DC3000 on LA4245-R plants (FIG. 1B). NY15125 grew to a level intermediate between T1 and DC3000 on LA4245-R. Such intermediate growth was observed previously for NY15125 on Pto-expressing plants (Kraus et al, "*Pseudomonas syringae* pv. tomato strains from New York Exhibit Virulence Attributes Intermediate Between Typical race 0 and race 1 Strains," *Plant Dis.* 101:1442-8 (2017), which is hereby incorporated by reference in its entirety). The three Pst strains all attained similar population levels on LA4245-S plants (FIG. 1B). Therefore, the putative Ptr1 locus from *S. lycopersicoides* LA2951 confers resistance to Pst strains NY15125 and notably T1, which is a race 1 strain.

Example 3: Pst Resistance in LA4245-R Plants is Due to Recognition of the Bacterial Effector AvrRpt2

Figure 2A:
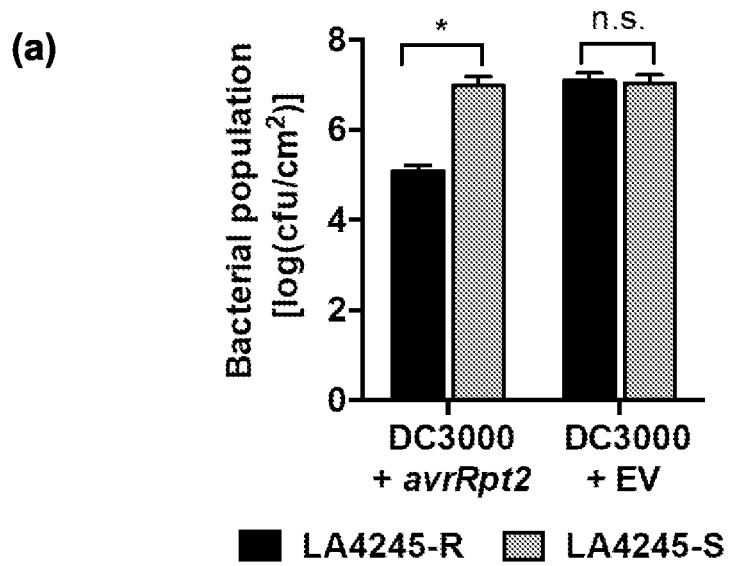
FIG. 2A and FIG. 2B provide results that demonstrate that Pst race 1 resistance in LA4245-R plants is due to the recognition of the bacterial effector AvrRpt2.

A comparison of the type III effector genes in DC3000 and T1 identified eight that are present exclusively in T1 (avrA1, avrRpt2, hopAE1, hopAG1, hopAI 1, hopAS1, hopS1, and hopW1) (Jones et al., "Genome-Assisted Development of a Diagnostic Protocol for Distinguishing High Virulence *Pseudomonas syringae* pv. tomato Strains," *Plant Disease* 99:527-34 (2015), which is hereby incorporated by reference in its entirety). To determine whether LA4245-R resistance involves the recognition of any of these effectors, T1-specific effectors were individually cloned into the expression vector pCPP5372, the plasmids were introduced via electroporation into DC3000 ΔavrPtoΔavrPtoB and the strains were inoculated onto LA4245-R plants. All of the strains, except the one expressing AvrRpt2, caused disease on LA4245-R plants. Subsequent experiments showed that the DC3000 strain expressing AvrRpt2 reached a population size 80-fold less in leaves of LA4245-R plants compared to LA4245-S plants; a DC3000 strain carrying an empty vector grew to the same level in the two plant lines (FIG. 2A).

Figure 2B:
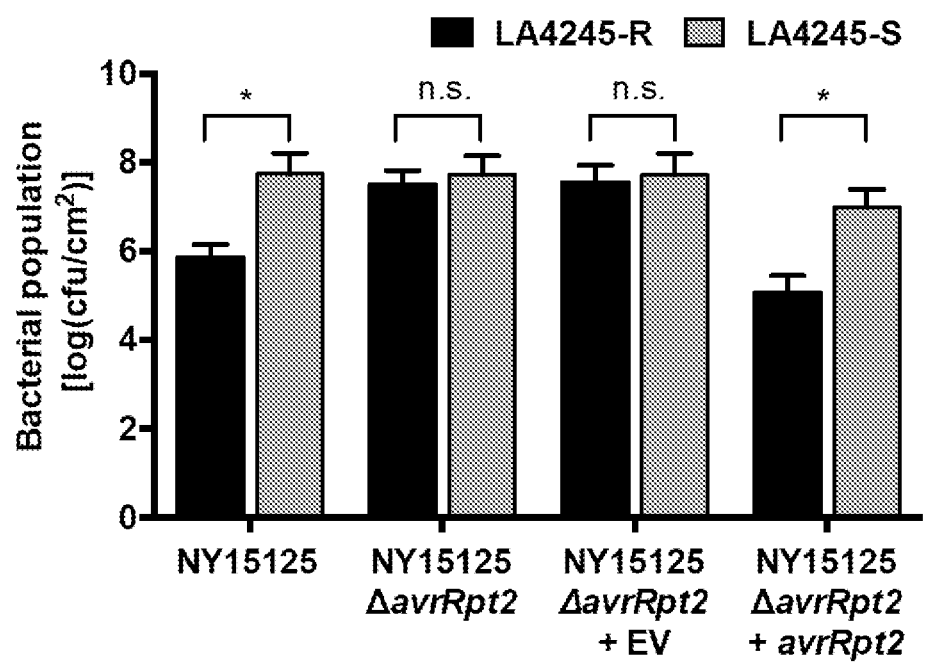
Figure 3:
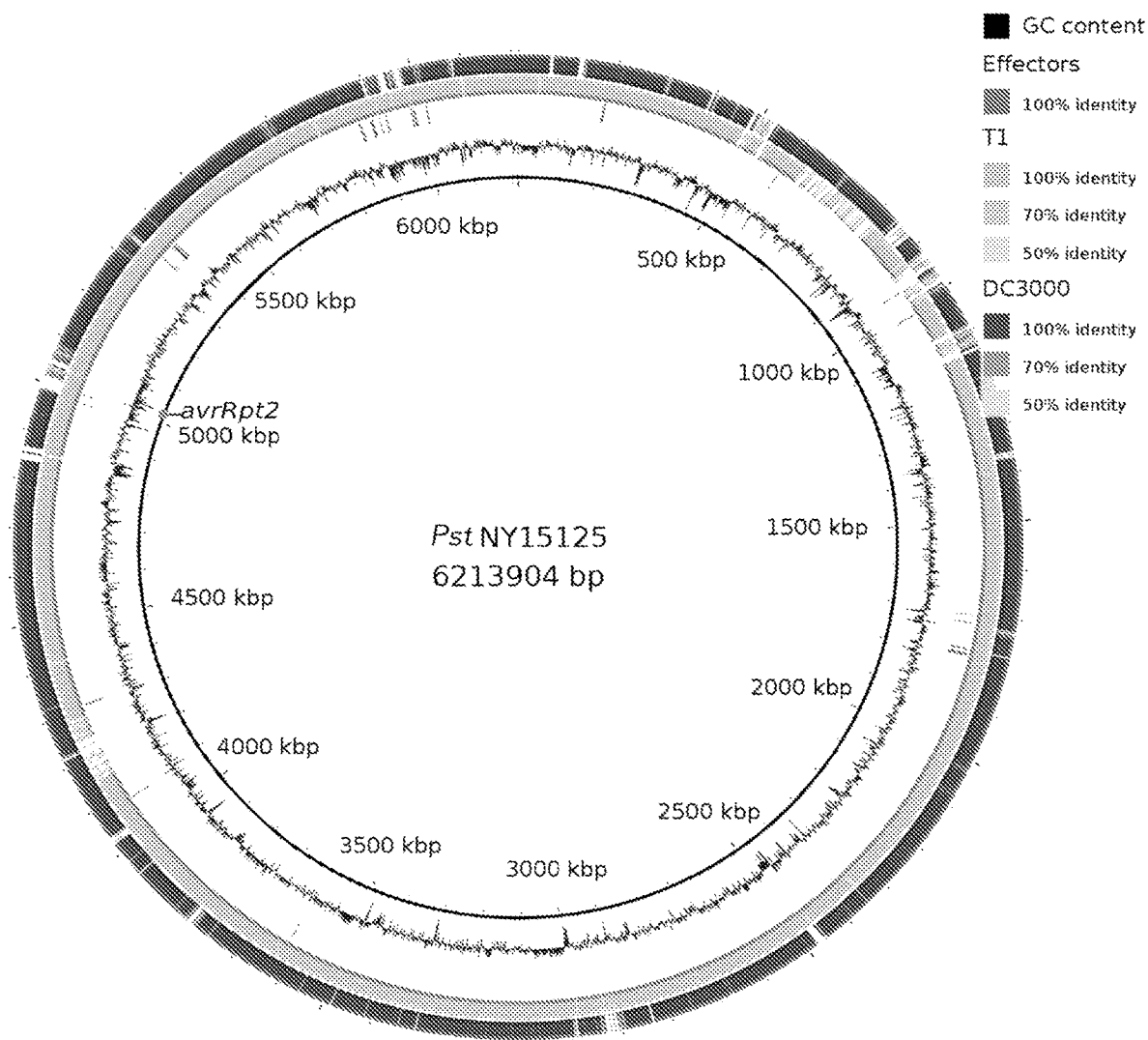
FIG. 3 shows a comparison of the Pst NY15125 chromosome with the chromosomes of Pst strains DC3000 and T1. The innermost ring (solid line) represents the NY15125 chromosome; the next outermost ring (jagged line) represents GC percentage. The next outermost ring (short lines) represent the locations of the type III effectors. The final two most outermost rings (short lines) represent genome comparisons between NY15123 and T1 (second to outermost ring) or DC3000 (outermost ring), respectively. The location of avrRpt2 is shown with a dot on the innermost ring (solid line). Ring image was generated using the BLAST Ring Image Generator (BRIG) sourceforge.net/projects/brig/.
Figures 17, 18:
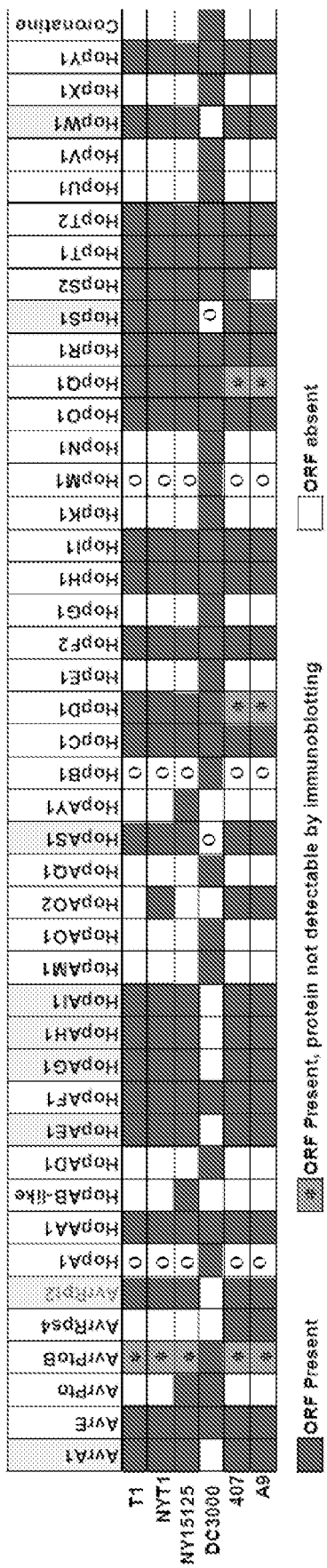
FIG. 17 shows a summary of the type III effectors present in the P. syringae strains T1, NYT1, NY15125, DC3000, CA-407, and CA-A9. The type III effector genes are listed across the top and the P. syringae strains are listed at the left edge. "ORF Present" indicates presence of a full length open-reading frame (ORF). "ORF Present, protein not detectable by immunoblotting" indicates the gene is present but protein is not detectable by immunoblotting. "Partial ORF" indicates the genes has an ORF truncated by an insertion sequence element or the presence of a premature stop codon. "ORF absent" indicates the gene is not present in that strain. "Present in T1 and NY15125, but absent in DC3000" indicates the effectors that are present in T1, NYT1, NY15125, CA-407, and CA-A9 but absent in DC3000. AvrRpt2 is highlighted. DC3000 is the only strain that produce coronatine. References: Jones et al., "Genome-Assisted Development of a Diagnostic Protocol for Distinguishing High Virulence Pseudomonas syringae pv. tomato Strains," Plant Disease 99:527-34 (2015); Kraus et al, "Pseudomonas syringae pv. tomato strains from New York Exhibit Virulence Attributes Intermediate Between Typical race 0 and race 1 Strains," Plant Dis. 101:1442-8 (2017); Kunkeaw et al., "Molecular and Evolutionary Analyses of Pseudomonas syringae pv. tomato Race 1," Mol. Plant-Microbe. Interact. 23:415-24 (2010); Saha et al., "Bound to Succeed: Transcription Factor Binding-Site Prediction and its Contribution to Understanding Virulence and Environmental Adaptation in Bacterial Plant Pathogens," Mol. Plant Microbe. Interact. 26(10):1123-30 (2013); and Thapa et al., "Identification of QTLs Controlling Resistance to Pseudomonas syringae pv. Tomato Race 1 Strains From the Wild Tomato, Solanum habrochaites LA1777," Theor. Appl. Genet. 128: 681-92 (2015), each of which is hereby incorporated by reference in its entirety.
FIG. 18 shows features and expression patterns of the four genes in tomato that encode proteins with similarity to Arabidopsis RIN4. The predicted protein mass is shown along with the percentage similarity to the Arabidopsis RIN4 protein (AtRIN4). RNA-Seq data for PTI (pattern-triggered immunity) are from Pombo et al., "Transcriptomic Analysis Reveals Tomato Genes Whose Expression is Induced Specifically During Effector-Triggered Immunity and Identifies the Epk1 Protein Kinase Which is Required for the Host Response to Three Bacterial Effector Proteins," Genome Biology 15:492 (2014), which is hereby incorporated by reference in its entirety, and for effector-triggered immunity (ETI) are from Rosli et al., "Transcriptomics-Based Screen for Genes Induced by Flagellin and Repressed by Pathogen Effectors Identifies a cell wall-associated Kinase Involved in Plant Immunity," Genome Biology 14:R139 (2013), which is hereby incorporated by reference in its entirety. Numbers under PTI and ETI are RPKMs (reads per kilobase of transcript per million mapped reads). FDR, false discovery rate. Data are available on the Tomato Functional Genomics Database (TGFD; ted.bti.cornell.edu/cgi-bin/TFGD/digital/home.cgi).

Next, it was determined whether Pst isolate NY15125, which was collected from the naturally-infected tomato field, has the avrRpt2 gene. Genome sequencing and PCR analysis confirmed the presence of avrRpt2 in this isolate (FIG. 3, FIG. 17). A comparison of AvrRpt2 protein sequences from NY15125 and T1 showed they are 100% identical. To investigate the activity of avrRpt2 in NY15125, a NY15125ΔavrRpt2 deletion mutant was generated and tested with regard to whether the strain was altered in its ability to grow on LA4245-R or LA4245-S plants. LA4245-R plants inoculated with the NY15125 wild-type strain supported a ~60-fold lower bacterial population compared to LA4245-S plants (FIG. 2B). In contrast, this difference was not observed when LA4245-R and LA4245-S plants were inoculated with NY15125ΔavrRpt2. Importantly, complementation of the mutant strain with avrRpt2 restored the wild-type growth difference in LA4245-R plants (FIG. 2B).

Figure 4:
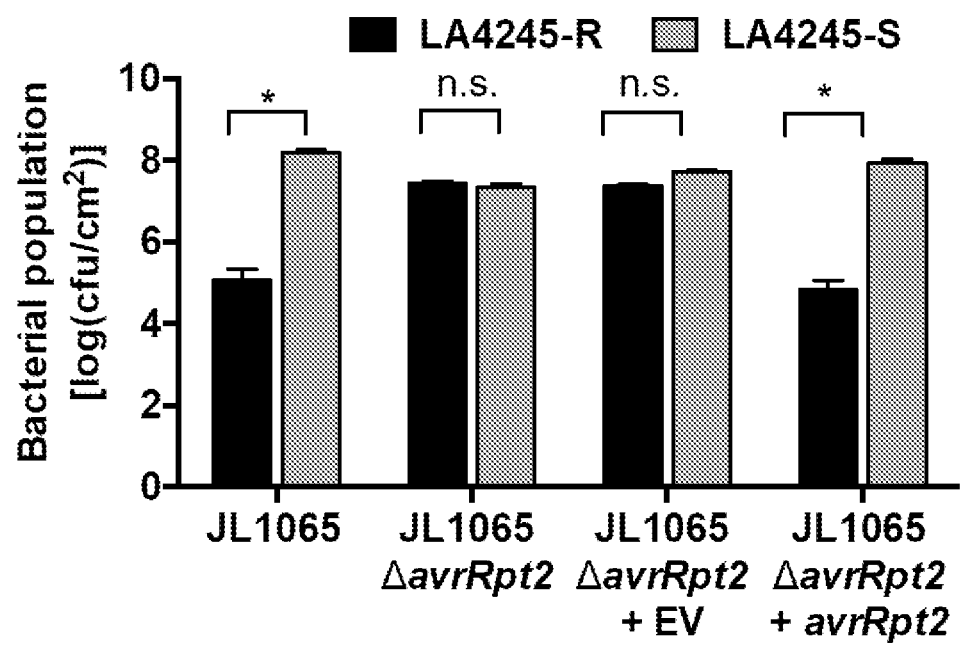
FIG. 4 provides results that demonstrate that deletion of avrRpt2 from Pst strain JL1065 abolishes recognition by Ptr1. LA4245-R and LA4245-S plants inoculated with JL1065 wild-type, JL106ΔavrRpt2, a complemented strain, or an empty vector (EV) strain at $1\times10^4$ cfu/mL. Bacterial populations were measured four days after inoculation. Significance was determined by a pair wise t-test and is indicated as: * P<0.05 or not significant (n.s.) at P>0.05. Bars indicate the mean of three plants and error bars represent +/−SEM. Data are representative of three independent experiments.

AvrRpt2 was originally identified in Pst JL1065 (Whalen et al., "Identification of *Pseudomonas syringae* Pathogens of *Arabidopsis* and a Bacterial Locus Determining Avirulence on Both *Arabidopsis* and Soybean," *Plant Cell* 3:49-59 (1991), which is hereby incorporated by reference in its entirety). A comparison between the AvrRpt2 protein sequences from JL1065 and NY15125 showed that the proteins have just two divergent amino acids: proline-24 and alanine-152 in AvrRpt2$_{JL1065}$ are replaced by threonine and glycine, respectively in AvrRpt2$_{NY15125}$. Difference in effector recognition on LA4245-R plants when infected with JL1065 wild-type and JL1065ΔavrRpt2 strains (Lim et al. "The *Pseudomonas syringae* avrRpt2 Gene Contributes to Virulence on Tomato," *Mol. Plant Microbe. Interact.* 18:626-33 (2005), which is hereby incorporated by reference in its entirety) was investigated. Bacterial population assays indicated that AvrRpt2$_{JL1065}$ is also recognized by LA4245-R (FIG. 4). Finally, three additional race 1 Pst strains which all carry the avrRpt2 gene (NYT1, CA-A9, and CA-407) were tested; it was found that LA4245-R is resistant to all of them, whereas LA4245-S was susceptible to these strains (FIG. 5). Thus, Ptr1 confers AvrRpt2-mediated resistance to multiple Pst race 1 strains.

Example 4: The Ptr1 Locus and RPS2 Detect the Same Variants of AvrRpt2

Figure 6:
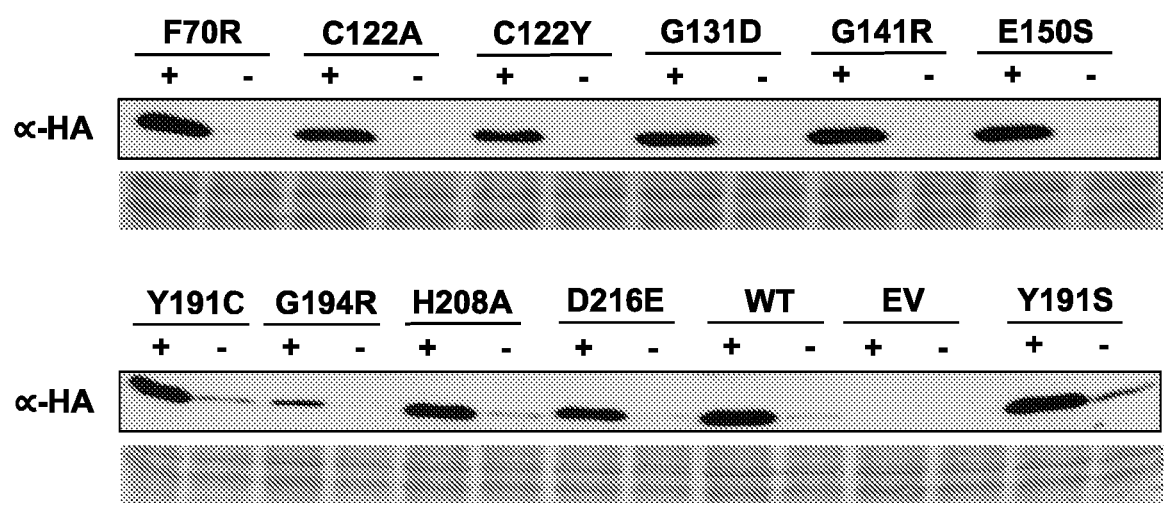
FIG. 6 provides results of immunoblotting that confirms expression of each AvrRpt2 variant in Pst DC3000. Detection of protein accumulation of each AvrRpt2 variant by immunoblotting using ∝-HA. Bacteria were grown in Hrp-inducing minimal media (+) or KB media (−) to detect each effector protein. As expected, proteins were detectable only when the strains were grown in Hrp-inducing medium (+). Ponceau staining shows amount of protein loaded in each lane.
Figure 7A:
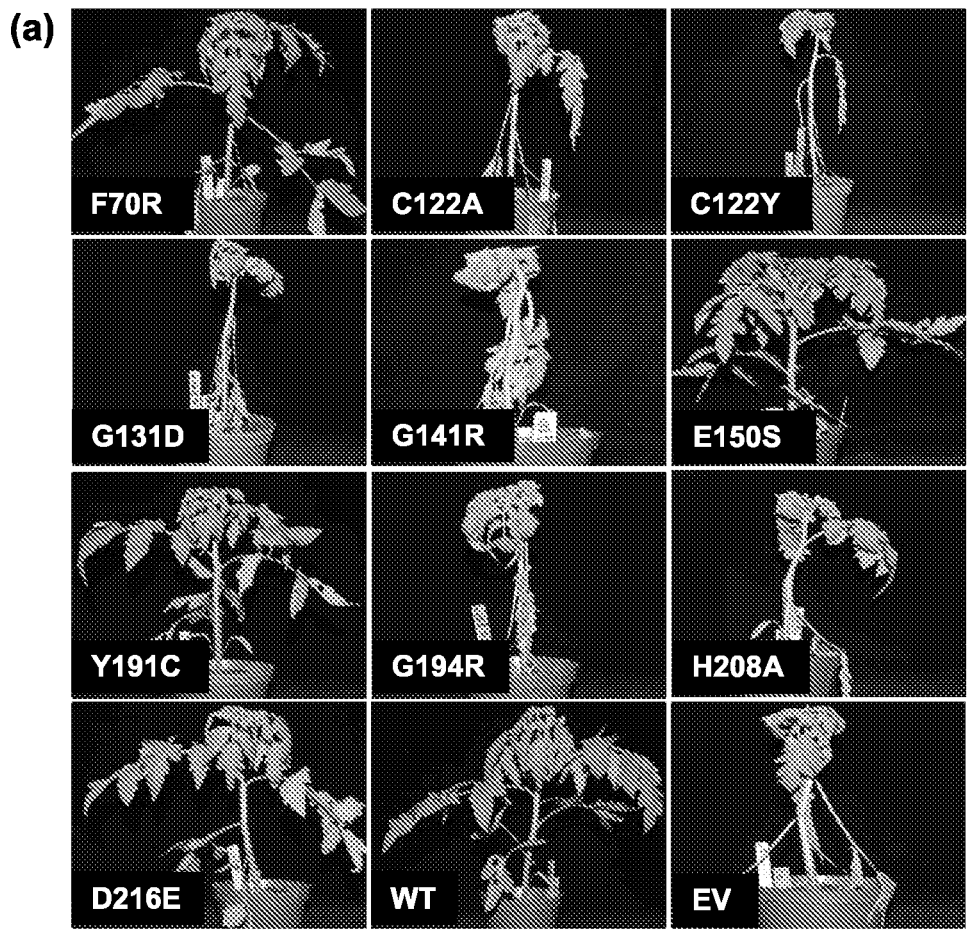
FIG. 7A and FIG. 7B demonstrate that Ptr1 detects the same features of AvrRpt2 as does RPS2.
Figure 7B:
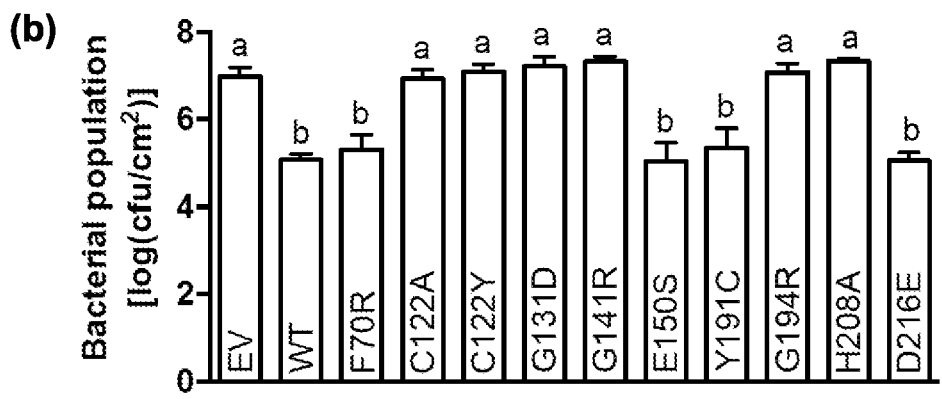
Figure 8A:
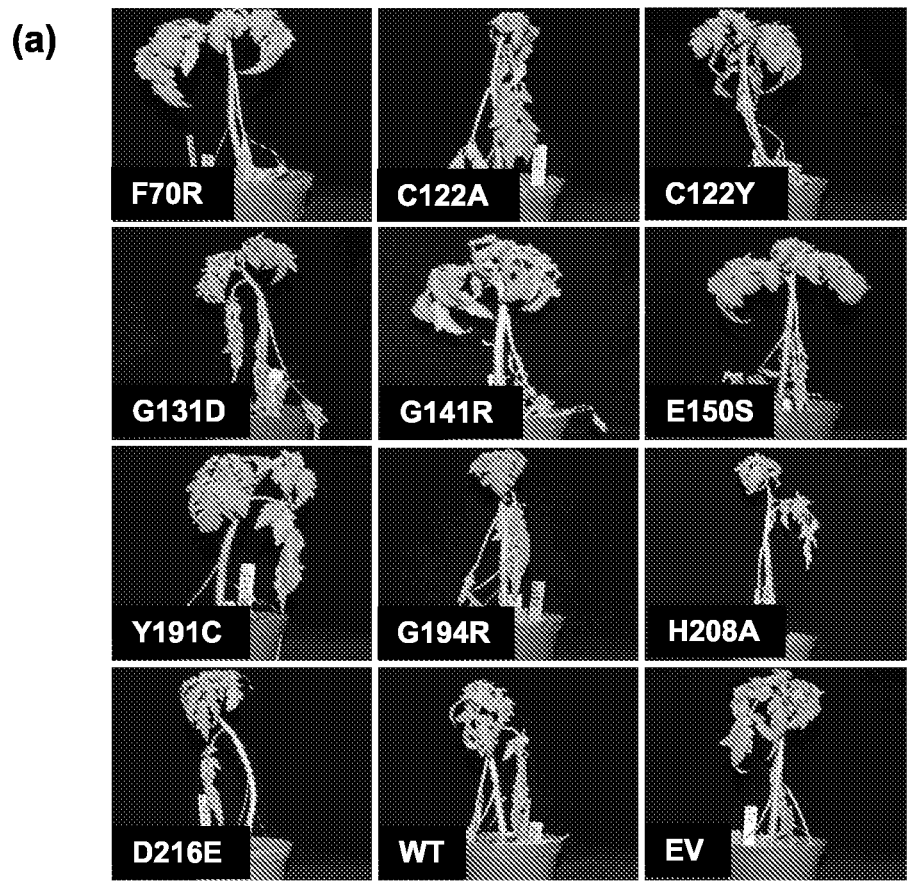
FIG. 8A and FIG. 8B provide results demonstrating that DC3000 strains expressing AvrRpt2 or the AvrRpt2 variants cause similar disease symptoms and grow to the same levels in LA4245-S plants.
Figure 8B:
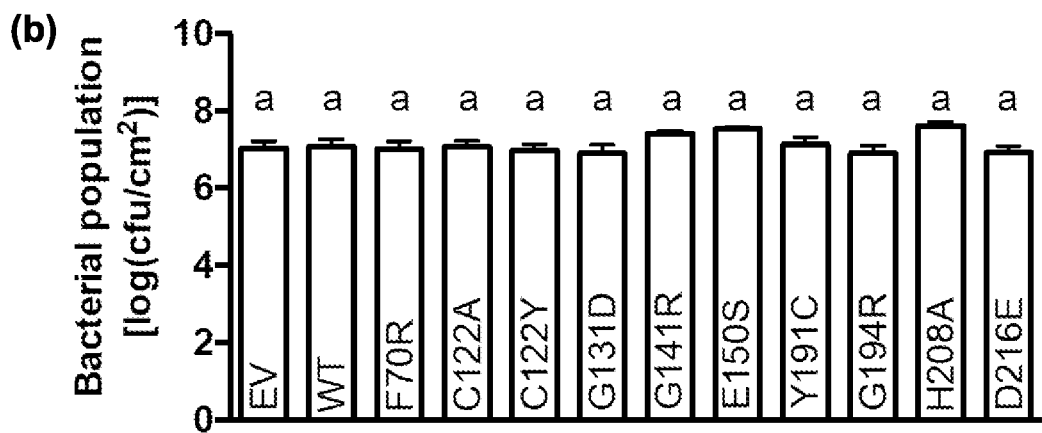

To gain insight into the mechanism of Ptr1 recognition of AvrRpt2, site-directed mutagenesis was performed to alter amino acids in the effector that have been reported to be essential for its recognition by RPS2 in *Arabidopsis* (Jin et al., "Cleavage of the *Pseudomonas syringae* Type III Effector AvrRpt2 Requires a Host Factor(s) Common Among Eukaryotes and is Important for AvrRpt2 Localization in the Host Cell," *Plant Physiol.* 133(3):1072-82 (2003); Lim et al., "The *Pseudomonas syringae* Type III Effector AvrRpt2 Promotes Virulence Independently of RIN4, a Predicted Virulence Target in *Arabidopsis thaliana*," *Plant* 40(5): 790-8 (2004); Lim et al., "Mutations in the *Pseudomonas syringae* avrRpt2 gene that Dissociate its Virulence and Avirulence Activities Lead to Decreased Efficiency in AvrRpt2-Induced Disappearance of RIN4," *Mol. Plant Microbe. Interact.* 17(3):313-21 (2004); Chisholm et al., "Molecular Characterization of Proteolytic Cleavage Sites of the *Pseudomonas syringae* Effector AvrRpt2," *PNAS* 102:2087-92 (2005), which are hereby incorporated by reference in their entirety). Ten AvrRpt2 variants were generated, of which eight have been reported to abolish recognition by RPS2 (Axtell et al., "Mutational Analysis of the *Arabidopsis* RPS2 Disease Resistance Gene and the Corresponding *Pseudomonas syringae* avrRpt2 Avirulence Gene," *Mol. Plant-Microbe Interact.* 14(2):181-8 (2001); Axtell et al., "Genetic and Molecular Evidence that the *Pseudomonas syringae* Type III Effector Protein AvrRpt2 is a Cysteine Protease," *Mol. Microbiol.* 49(6):1537-46 (2003); Jin et al., "Cleavage of the *Pseudomonas syringae* Type III Effector AvrRpt2 Requires a Host Factor(s) Common Among Eukaryotes and is Important for AvrRpt2 Localization in the Host Cell," *Plant Physiol.* 133(3):1072-82 (2003); Lim et al., "The *Pseudomonas syringae* Type III Effector AvrRpt2 Promotes Virulence Independently of RIN4, a Predicted Virulence Target in *Arabidopsis thaliana*," *Plant J.* 40(5):790-8 (2004), which are hereby incorporated by reference in their entirety); two variants, F70R, which disrupts the AvrRpt2 autocleavage site, and E150S are still recognized by RPS2 (Jin et al., "Cleavage of the *Pseudomonas syringae* Type III Effector AvrRpt2 Requires a Host Factor(s) Common Among Eukaryotes and is Important for AvrRpt2 Localization in the Host Cell," *Plant Physiol.* 133(3):1072-82 (2003); Chisholm et al., "Molecular Characterization of Proteolytic Cleavage Sites of the *Pseudomonas syringae* Effector AvrRpt2," *PNAS* 102:2087-92 (2005), which are hereby incorporated by reference in their entirety). Each AvrRpt2 variant was introduced into DC3000 on a plasmid and shown to be expressed by immunoblotting (FIG. 6). The strains were then vacuum infiltrated into LA4245-R and LA4245-S plants and bacterial populations in leaves were measured and plants scored for disease symptoms. It was observed that DC3000 expressing AvrRpt2 variants with the substitutions C122A, C122Y, G131D, G141D, G194R or H208A grew to high levels and caused severe disease on LA4245-R plants, indicating a loss of Ptr1 recognition (FIGS. 7A and 7B). In contrast, similar to wild-type AvrRpt2, strains with variants F70R, E150S, Y191C or D216E reached population levels on average ~60-fold lower than the empty vector control strain and did not cause any disease symptoms on LA4245-R plants (FIGS. 7A and 7B). All of the DC3000 strains caused disease and reached similar population levels in LA4245-S plants (FIGS. 8A-8B).

Figure 9:
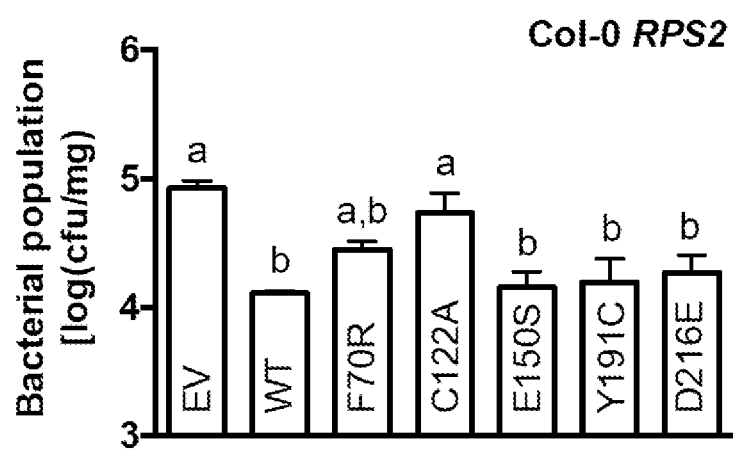
FIG. 9 shows results demonstrating that AvrRpt2 variants F70R, E150S, Y191C and D216E are recognized by RPS2. Five week-old *Arabidopsis* Col-0 RPS2 plants were dip inoculated with DC3000 carrying avrRpt2 wild-type (WT), avrRpt2 variants or an empty vector (EV) at $3\times10^8$ CFU/ml. Bacterial populations were measured three days after inoculation. Significance was determined using ANOVA with a Tukey's post hoc multiple comparison test, and different letters indicate significant differences between treatments (P<0.1). Bars indicate the mean of three plants and error bars represent +/−SEM. Data are representative of three independent experiments.

Interestingly, AvrRpt2 variants with the substitutions Y191C and D216E were recognized by Ptr1 but have been reported earlier not to be recognized by RPS2 and to be unable to induce *Arabidopsis* RIN4 degradation (Lim et al., "Mutations in the *Pseudomonas syringae* avrRpt2 gene that Dissociate its Virulence and Avirulence Activities Lead to Decreased Efficiency in AvrRpt2-Induced Disappearance of RIN4," *Mol. Plant Microbe. Interact.* 17(3):313-21 (2004), which is hereby incorporated by reference in its entirety). However, recently it was shown that *Arabidopsis* RIN4 is cleaved by variants AvrRpt2(Y191C) and AvrRpt2(D216E) (Eschen-Lippold et al., "Bacterial AvrRpt2-like Cysteine Proteases Block Activation of the *Arabidopsis* Mitogen-Activated Protein Kinases, MPK4 and MPK11," *Plant Physiol.* 171: 2223-38 (2016), which is hereby incorpoated by reference in its entirety). To investigate this discrepancy, *Arabidopsis* Col-0 RPS2 plants were inoculated with DC3000 expressing AvrRpt2 and several of the variants, including Y191C and D216E, and bacterial population were measured three days later. A significant reduction in bacterial growth and an absence of disease symptoms was observed in Col-0 RPS2 plants inoculated with DC3000 carrying AvrRpt2 and the variants E150S, Y191C, and D216E; the F70R variant appeared to be weakly detected by RPS2 (FIG. 9). Thus Ptr1 and RPS2 detect the same variants of AvrRpt2.

Figure 10A:
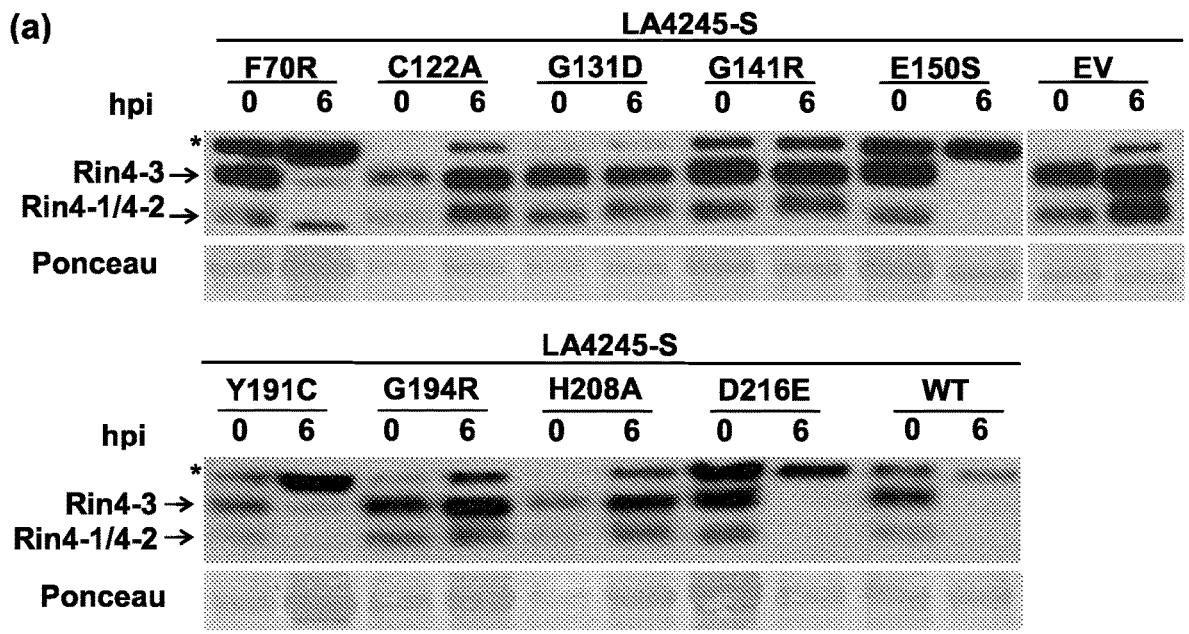
FIG. 10A and FIG. 10B provide results demonstrating that AvrRpt2 variants F70R, E150S, Y191C, D216E and AvrRpt2 wild-type which are recognized by Ptr1 are able to degrade tomato Rin4 proteins.
Figure 10B:
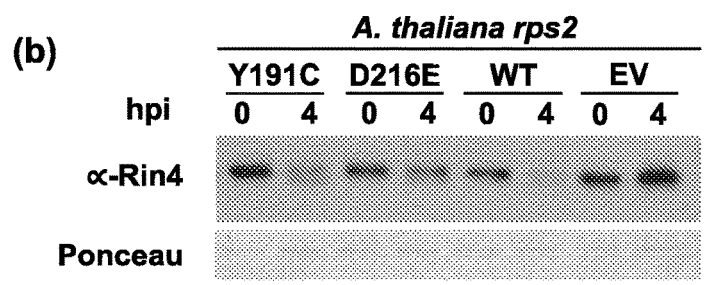

Example 5: Ptr1 Recognition of the AvrRpt2 Variants Correlates with the Effector's Ability to Cleave Tomato RIN4 Proteins In *Arabidopsis*, AvrRpt2-mediated degradation of RIN4 leads to the activation of RPS2 (Mackey et al., "*Arabidopsis* RIN4 is a Target of the Type III Virulence Effector AvrRpt2 and Modulates RPS2-Mediated Resistance," *Cell* 112(3): 379-89 (2003), which is hereby incorporated by reference in its entirety). Accordingly, it was hypothesized that AvrRpt2 variants that are recognized by Ptr1 will also be capable of degrading RIN4 in tomato. Tomato has three genes with similarity to AtRIN4 that are expressed in leaves and two of these are induced during Pto-mediated NTI (SlRin4-1, SlRin4-2, and SlRin4-3; FIG. 18). To avoid the Ptr1-mediated defense response, LA4245-S plants with the DC3000 strains expressing each AvrRpt2 variant and wildtype AvrRpt2 were vacuum infiltrated and SlRin4 abundance was detected by immunoblotting 6 hours later. Wild-type AvrRpt2 and the variants F70R, E150S, Y191S and, D216A each induced a reduction in tomato RIN4 abundance which correlates with Ptr1 recognition of these proteins in LA4245-R plants (FIG. 10A). DC3000 strains with AvrRpt2 variants C122A, G131D, G141D, G194R, H208A, or an empty vector, all of which caused disease on LA4245-R plants, failed to induce tomato Rin4 elimination (FIG. 10A). Similar experiments in *Arabidopsis*, supported our earlier observations in that both AvrRpt2(Y191C) and AvrRpt2 (D216E) were able to degrade RIN4 in rps2 plants (FIG. 10B). Therefore, there is a perfect correlation between the recognition of each AvrRpt2 variant by Ptr1 and the effector's ability to induce tomato Rin4 disappearance.

Example 6: AvrRpt2 Proteins from Different Bacterial Species are Recognized by Ptr1

Figure 11:
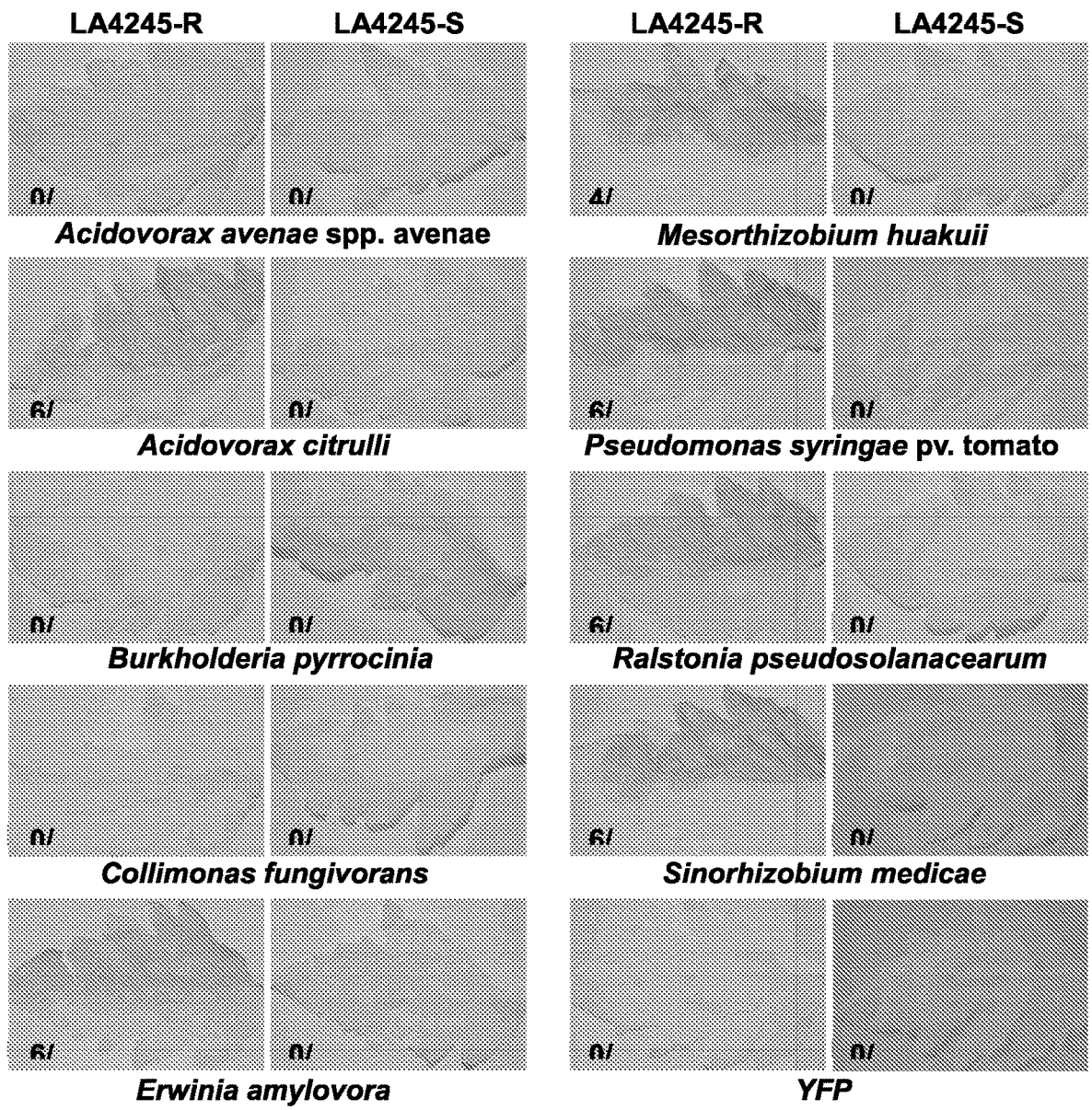
FIG. 11 shows results demonstrating that AvrRpt2 homologs from diverse bacteria are recognized by Ptr1. Agroinfiltration of each avrRpt2 homolog and a yellow fluorescent protein (YFP) control into leaves of LA4245-R and LA4245-S plants. Detached leaves were cleared with ethanol to better visualize cell death associated with AvrRpt2 recognition. Photographs were taken four days after infiltration. Shown are the number of times cell death was observed over the total number of agroinfiltrations performed.
Figure 12:
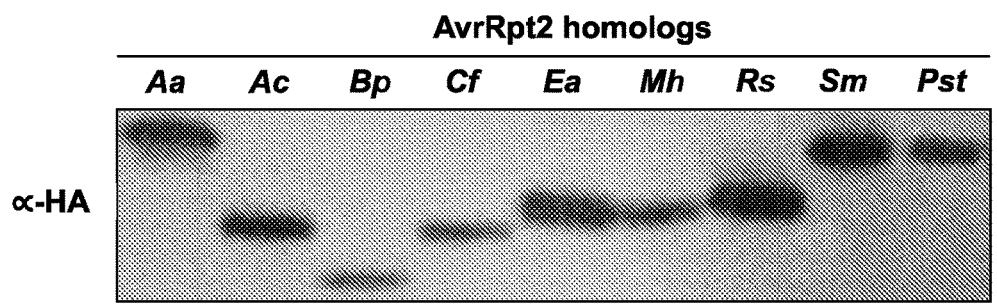
FIG. 12 depicts Agrobacterium-mediated transient expression of AvrRpt2 homologs in leaves of Nicotiana benthamiana. Agroinfiltration of AvrRpt2 homologs (Aa, A. avenae; Ac, A. citrulli; Bp, B. pyrrocinia; Cf, C. fungivorans; Ea, E. amylovora; Mh, M huakuii; Rs, R. pseudosolanacearum; Sm, S. medicae; Pst, P. syringae pv tomato) at an $OD_{600}$ of 0.3 into N. benthamiana leaves. Samples were taken 43 hours after infiltration. Total proteins extracted from infiltrated leaves were subjected to immunoblotting using an α-HA antibody.

Homologs of AvrRpt2 are found in diverse bacterial species including the plant pathogens *Erwinia amylovora, Ralstonia pseudosolanacearum, Acidovorax citrulli* and *Acidovorax avenae*, the soil bacterium *Burkholderia pyrrocinia*, the fungal parasite *Collimonas fungivorans*, and the symbiotic bacteria *Mezorhizobium huakuii* and *Sinorhizobium medicae* (Zhao et al., "The *Erwinia amylovora* avrRpt2EA Gene Contributes to Virulence on Pear and AvrRpt2EA is Recognized by *Arabidopsis* RPS2 When Expressed in *Pseudomonas syringae*," *Mol. Plant Microbe. Interact.* 19(6):644-54 (2006); Eschen-Lippold et al., "Bacterial AvrRpt2-like Cysteine Proteases Block Activation of the *Arabidopsis* Mitogen-Activated Protein Kinases, MPK4 and MPK11," *Plant Physiol.* 171: 2223-38 (2016), which are hereby incorporated by reference in their entirety). Some of these AvrRpt2 proteins have very divergent amino acid sequences or are truncated in comparison to Pst AvrRpt2, and it was investigated whether Ptr1 would recognize them. *Agrobacterium*-mediated expression (agroinfiltration) was used to express each AvrRpt2 protein or a YFP control in leaves of LA4245-R and LA4245-S. The AvrRpt2 homologs from five of the eight bacterial species induced cell death in LA4245-R leaves but not in LA4245-S leaves indicating their activity is recognized by Ptr1 (FIG. 11). Detection of protein expression of each AvrRpt2 homolog was done via agroinfiltration in LA4245-S leaves (FIG. 12).

Example 7: An Amino Acid Substitution in AvrRpt2 that Abolishes its Recognition by the Apple Mr5 NLR Resistance Protein Does Not Affect Recognition by Ptr1

Figure 13A:
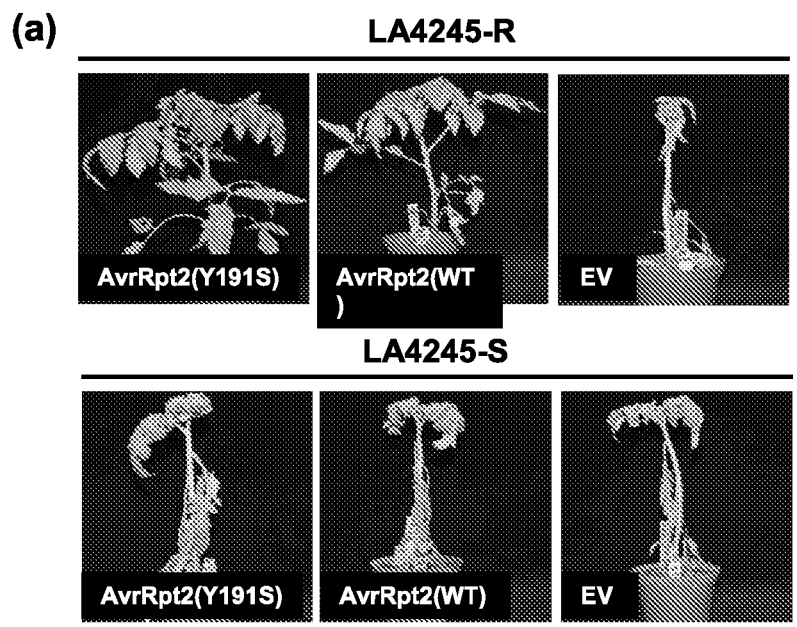
FIG. 13A and FIG. 13B show results demonstrating that Pst AvrRpt2(Y191S) variant, analog of the E. amylovora AvrRpt2(C156S) virulent variant, is recognized by Ptr1.
Figure 13B:
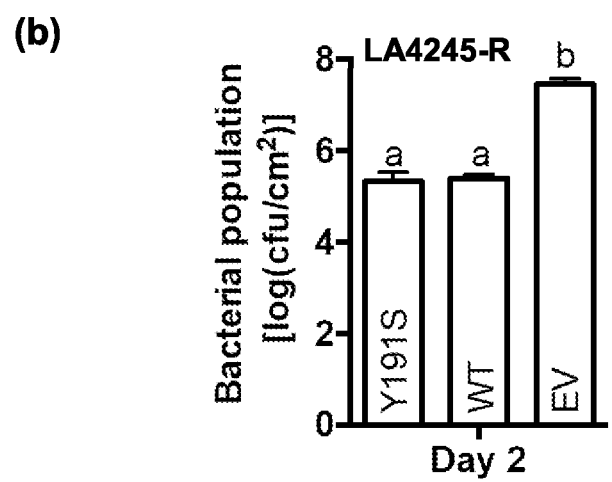

Mr5 is an NLR fire blight resistance protein in apple that recognizes strains of *Erwinia amylovora* that express AvrRpt2 (Fahrentrapp et al., "A Candidate Gene for Fire Blight Resistance in Malus×Robusta 5 is Coding for a CC-NBS-LRR," *Tree Genet. Genomes* 9:237-51 (2012); Vogt et al., "Gene-for-Gene Relationship in the Host-Pathogen System Malus×Robusta 5-*Erwinia amylovora*," *New Phytol.* 197:1262-75 (2013), which are hereby incorporated by reference in their entirety). A single amino acid substitution in AvrRpt2 at position 156 (cysteine-to-serine) abolishes recognition of the effector by Mr5. In AvrRpt2$_{NY15125}$ the comparable residue is tyrosine-191. Since a Y191C substitution in AvrRpt2 was shown previously to be recognized by Ptr1 (FIGS. 7A-7B), it was investigated whether a Y191S substitution in AvrRpt2 would abolish Ptr1 recognition as it does for Mr5 recognition. Inoculation of LA4245-R plants with a DC3000 strain expressing AvrRpt2(Y191S) revealed this variant is recognized by Ptr1, as it induced disease resistance and reduced bacterial growth compared to an empty vector DC3000 control strain (FIGS. 13A-13B). Mr5 and Ptr1 therefore appear to use different mechanisms to detect AvrRpt2.

Example 8: Ptr1 Confers Resistance to Bacterial Wilt Disease Caused by *Ralstonia pseudosolanacearum*

Figure 14A:
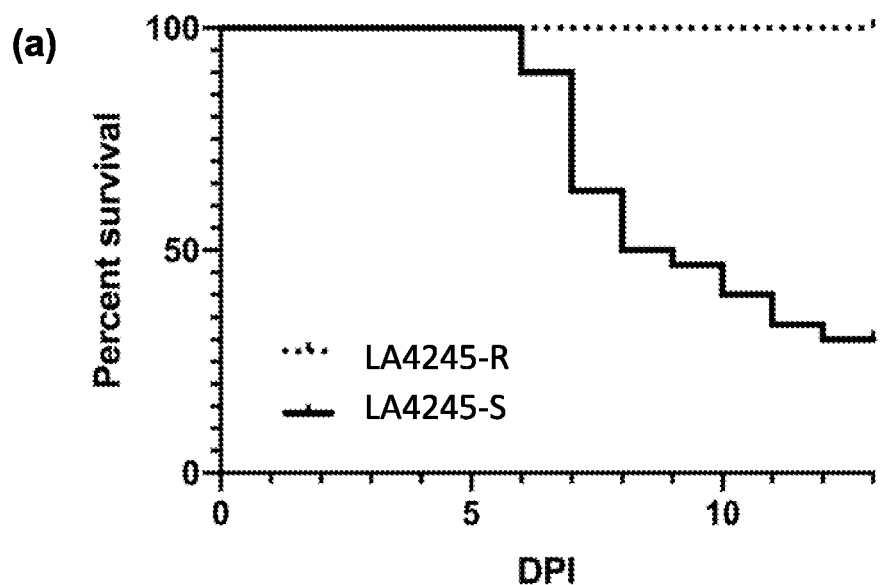
FIG. 14A and FIG. 14B show results that demonstrate that Ptr1 confers resistance to Ralstonia pseudosolanacearum strain CMR15 expressing AvrRpt2 homolog RipBN.
Figure 14B:
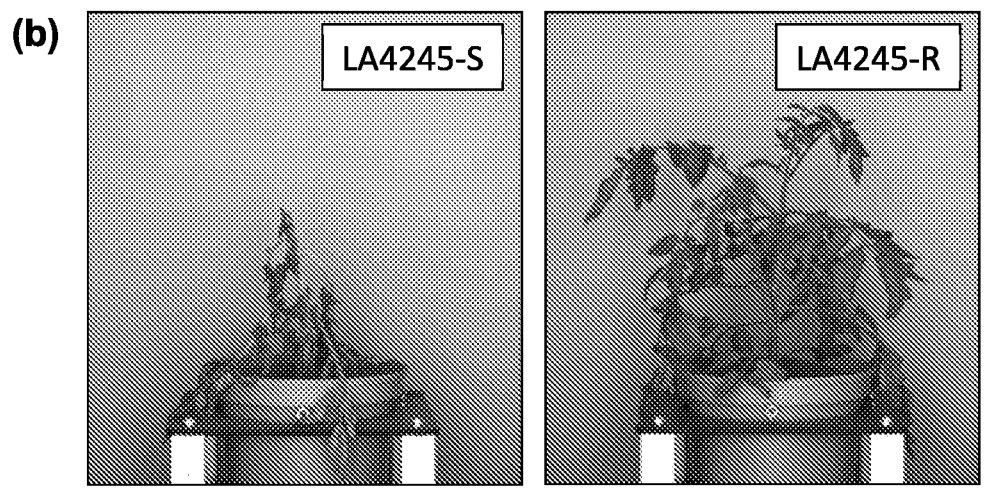

The agroinfiltration experiments indicated that RipBN, the AvrRpt2 homolog from *R. pseudosolanacearum*, is recognized by Ptr1 (FIG. 11). The ripBN gene is present in a strain of *R. pseudosolanacearum*, CMR15, which was collected from tomato in Cameroon in 2009 (Mahbou et al., "Broad Diversity of *Ralstonia solanacearum* Strains in Cameroon," *Plant Dis.* 93:1123-30 (2009), which is hereby incorporated by reference in its entirety) and later sequenced (Remenant et al., "Genomes of Three Tomato Pathogens Within the *Ralstonia Solanacearum* Species Complex Reveal Significant Evolutionary Divergence," *BMC Genomics* 11:379 (2010), which is hereby incorporated by reference in its entirety). Bacterial wilt, caused by *R. pseudosolanacearum*, is a devastating disease for which no NLR-mediated resistance in tomato has been reported (Huet, "Breeding for Resistances to *Ralstonia solanacearum*," *Frontiers Plant Sci.* 5:715 (2014), which is hereby incorporated by reference in its entirety). LA4245-R and LA4245-S plants with CMR15 were soil-drench inoculated and the number of plants showing symptoms of bacterial wilt over a 13-day time period were scored. Beginning at 6 days after inoculation LA4245-S plants started to wilt, and 13 days after inoculation ~70% of the plants were dead (FIGS. 14A-14B). Remarkably, at this timepoint there was 100% survival of the LA4245-R plants. Ptr1-mediated resistance therefore can be effective against bacterial wilt and might be useful for controlling bacterial wilt disease in tomato-growing areas that have *R. pseudosolanacearum* strains expressing RipBN.

Figures 15A, 15B:
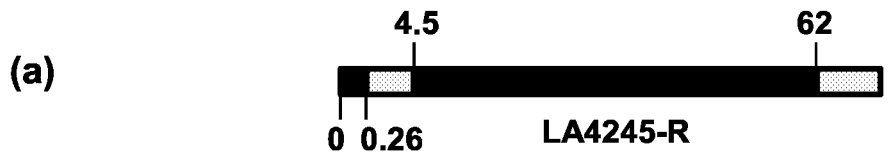
FIGS. 15A and 15B show results that demonstrate that the predicted proteins of the 14 NLR-encoding genes in the introgression segment of LA4245 bear little similarity to RPS2 or MrS.

Example 9: No RPS2, Mr5 or RIN4 Orthologs are Present in the *S. lycopersicoides* Chromosome 4 Introgression Segments of LA4245-R To initiate the map-based cloning of Ptr1, sequence data was generated at 14× coverage of the Heinz 1706 reference genome from genomic DNA of LA4245-R using an Illumina HiSeq2000. The reads were mapped to the *S. lycopersicum* Heinz 1706 genome sequence to identify areas of high sequence polymorphism. This analysis revealed that LA4245-R contains two *S. lycopersicoides* introgression segments on chromosome 4 in the background of the tomato parent VF36. One small segment lies within coordinates 1-260,000 bp (260 kb) and the other lies between coordinates 4,480,000 bp and 62,030,000 bp (~57.5 mb) (FIG. 15A). A high-quality genome sequence of *S. lycopersicoides* LA2951, a parent of the introgression lines, has been generated recently (see Example 1). Synteny between Heinz 1706 and LA2951 was determined and gene models predicted to be in the introgressed regions of LA4245-R were identified in the *S. lycopersicoides* annotation. Ptr1 recognition of AvrRpt2 suggests it likely encodes an NLR protein or possibly a guardee such as Rin4. No NLR-encoding genes are annotated within the small introgression segment and just 15 NLR genes are annotated within the large *S. lycopersicoides* introgression segment. Interestingly, none of these 15 genes encode a predicted protein with similarity to RPS2 or Mr5 (FIG. 15B). In fact, the *S. lycopersicoides* genes with predicted proteins having the highest similarity to RPS2 and Mr5 are all located on other chromosomes (Table 4). None of the four Rin4 genes in tomato are located on chromosome 4 (FIG. 18).

The sequences of the predicted NRL-like genes present in the large introgression segment of LA4245-R are as follows:

The coding sequence for Solyd04g057440.1, which is hereby incorporated by reference in its entirety, (SEQ ID NO: 1) is as follows:

```
ATGGAGGCTACAATCGTTGCAGCGTTGAGTCCGGCGGCGACAAAAGCGGT

AAGCTTTCTGGTGGACAGTCTATCGCAGTTACTATCGGAAAATGTGGAAC

TGATAAGAGGTGCAGATAGAGATTTCCAGCAATTACTGGATGAAATTACA

CCCATAAATGAGTTACTATCTGGAGATTATGCACAATTGAAAAGCAACAA

CAACAACGATTTGGATAAATTGTTCCAGAATATTCAACGAACAGTATATA

AAGCTGAAGATGCGATCGATAAATTCCTAATTCAGGCGAAAATTAACGAA

GCTAACGTGTTCAATAAGTTCGGTCCGTTTGTCAAGTGGAACAACAATAG

GAAAATTACACCGGAATTCAGAAAAATTCTCGAACAAGTGACTGAAATTC

GCCAACAGACTCAACAGGTTTTGGAGAAAACCGGTATACAGAGTTCTGCT

TTCCAGCCTGGAGAAACTACCCGGCCACAGGGTCCTGCTGAGGAGGATAG

CGAAGTGGTTGGTTTTAATAAGCCTGCAGAAGATGTGAAAAAGCGACTTT
```

```
GTGAAGGATCAAAAGATCTTGATGTTATACCTATTGTGGGTATGCCAGGA
CTTGGAAAGACCACACTTTCAAGAAAAGTTTACAATGATTCTTCCATTGA
TTTTTATTTTTACCATAAAATGTGGATTTATGTTGGGACATCAAAGAAAC
CAAAGGATATTCTTGTTGAGATTGTGAAAGATGTCGCGCAAAGCAATAGT
AAGGAACTAATTAAAGACAAGGATGAGGACCAATTAGCTCATATCATACG
TGATTTTCTTGTTAAAAGAGGTAAACATCTCATTGTCTTGGATGATGTGT
GGGACACACAAGTTGTAGATTTTGTCAAGAAAGCTTTCCCAAACAACAAA
TCCTGGCCCCGAGGGGACAGAATCATGTTGACAACTCGCCAACGACGTGT
GGCTGAAGCTGTCAGCGCTCGTCCTCACTATCTGGAAAACTTGTCAAAAG
AGGATAGTATAAAGTTGTTGGAACAGAGAGTTTTTGCCAATAAAAGGACA
TGTCCTATTGAGTTAGAAGGATATCGAGATGGGATTGTAGATAAATGTTG
TGGTGTACCACTTGCCATAGTGGTGATTTCAGGAGCTTTGAGAGGTGTTA
TGGACGAAAGTGAATGGAGAGTAGTCGAGGAAAATGTGGGGAAGCACCTT
ATAAACAAGGACGACCATAAAAGCTGCTTGAAATTTGTTGAAACGAGTTA
CAATCATTTGCTGCAAGAGAAAAAGGCAGCCTTCTTGTATTTTGGAGTAT
TTCCTCAAGGTTTTGATATTCCTGCTTGGAACCTTATTCGCTTATGGGTT
GCTGAGGGGCTAATAAAGTCCGATCATAAAGACAGTGAAATCGAGAAGGT
TGCGGAGACTTACTTGAGCGACTTTGCTAGTAGGAATTTAGTGATGGTGA
TGCAAAAGAGATCTAACGGTCAAATCAAAACGTGTCGTCTTCATGACATG
TTGCATGAGTTCTGCATTATTGAGGCTCAAAGGATAAGTCTCTTTCAACA
AGTATATCTCCAACCTGGTGTTCGAGTTTTTCCTTCTATAGAAGATCCAA
ATAATTCTCGTCGATTATGTATTCAATCCTCTATTCCGTATAATTTTATC
CCTAAAGATAGAATTGTACAGCACGTTAGGTCTCTCTTATGTTTTTCCTC
AGACCAAAAGCAAATTGACTTGTCTAATCTAGATGTCCAACTCATCCCCA
ATGCCTTTCCACTCATCAGGGTGTTGGACATTCAATCCCTCATATTTGAA
TTCTCCAAGATGTTTTATGGTCTATTTCACTTGAGGTATATTGCCATCAA
GGGCGACTTCACTGTCATTCCTTCACTCTTTCGTAATTTTTGGTATTTAC
AAACCCTTATACTTCGTAATGATGATACACATACTTCAAGATCCACCCTC
GAGATAAAAGAGGACATATGGAAACTGTTACAATTGAGACATCTGCACTC
CGACCTTCATGTGAAATTGCCTCCTCCTCCTACCCCAACAAGCAATAGTC
GTACTTCTTGTCTACAAACTCTTTCTAAGGTTACACCAGATAGTTGCAAA
AAAACTGTGTTTGCAAAGGCTTGTCATCTCAAAAAATTGGGTATTGAAGG
GCAATTGGCACTTCTTCTTGGAAAATCTACCAAGGGACGTGGATTCGACA
GTTTCCAAGAGCTAAGGTGCGTCGAAAAATTGAAATTGTTGAACAATGAT
TTTAGTGAAGAGCTTCACCTTCCTCCACACTTTTTCAGCTTACAAAAAAC
GCTGAACAAGTTAACTTTGTCAAGTACAAGGTTTGAGTGGAGTGAGGCAG
ATATGTTGGGGAAGTTGGAATGCCTTAAGGTACTAAAATTGAAATATAAT
GCATTCATAGGGAAGAATTGGAAGCCCAAGAAAGGAAGTTTTAGCAAGCT
CCAAGTCCTGCACATTGTCTGGGCAGGAGACTGGCAAACTTGGGATGCAT
CAAATCGTCCGTTCCAAAGTCTTACACACCTTGTTCTTATTTCCTGTAAT
CATCTCAAGGCTGTGCCACATGAGCTGGCTGATTTACCTTATCTTCAAGA
GATGAAGCTGACGCGCACATACGACGCAGTCAGTTCTGCCATAGAAATCA
AAAGAAAGATACTACAAAGGCAAGATCCCGAAAGCAACATCAAATTCAAT
CTCATTACATTTCCCCCTACCTCGTCCACAAATTAA
```

The coding sequence for Solyd04g057510.1, which is hereby incorporated by reference in its entirety, (SEQ ID NO: 2) is as follows:

```
ATGGCGGCTACTTACGGTGCACTAACTTCTGTGTTGGGAACCATAGAGAA
GGTTTTACGGTCCAACCATAGAGAATATGGTTGGACCGTAAAATTGAAAT
CACTGTATGGGTTGTTTGACACTCTAATTGTGAAATGTGATGTCGGAGAA
GCAATTATTAGCAAGGATTTGCTAAGAAGAATCAAAGATGTTGCAGTTTA
TGCAGAAGATGAAGTTGAATCACTAATGAAACAACTTATTATTATTGGGA
TGAATGATGAATGTTGTGGTGCGAAGCTTGATAAAGTCTCTCAACAGGTA
ATACAAGTAACTCATTCAGTCAACAATATTAATTGTCCAAAAAAAGTTGT
TTCTCCACGATTAGATGATGATTCAATCCATGAGAACTTTATGGAAGGGT
ACAATGAAGAAAGAGTAAATATGGTTCAAAGACTTACCAAAGGATCAAAT
AGACTGCAAGTGGTTTCTGTTGTGGGGATGGCGGGCATAGGTAAGACAAC
TTTTGCCAAAACTACATTATTACATATTAACAAGGAGGACTTTCCTATTC
GTGGTTGGATTACGGTGTCTAAAAACTATGATTTAAGAAAGTTGCTCCTA
CTCCTCCTTCATGATGTTATTGAAATGAAAGGTAAGAATTTTGATGGAAT
GGATAATGGACAACTAGCTGCTCATCTAAAGCAAGTTTTGCAGGGAAAAA
GGTATTTGATTGTTGTGGATGACATATGGAGCAAAGAAGATTGGGATGAA
ATTAAACATTGGTTTCCAGATTGTGGTGACAAAAGTCGAATTTTGTTGAC
TTCTCGAGACAAAGAGGTTGGTGAGTATGCTGCTAAAGAAGGTTTGGTAC
TGATGCGTCCTCTGACGCAAGATGAAAGTCGGAATCTGTTTTACCATAGG
GCATTTGGGAAAAATTACACTATTCGAGGGTCAGATATTGATGAATTCGA
AAAGGTTGGAGAAAAAGTTATAACAAATTGCAAAGGATTACCACTAATGA
TTACTGCAGTTGCTGGTATACTCCGTAGTAAGAGTAAACTGGATGAGTGG
ATGGAAGTAGCTCAAAGTGTAAGCTCATTAGTAAATGATGATGATTACAA
ACAATGCTTACAAGTTGTTGCTTTGAGCTACAATAATCTTCCTTCTCTAA
TGAAAGCTTGCTTTTTGCATTTCGGAGTTTTTCCAAAAGCCCATGTCATT
TCTGTGAAGAAGTTGATCAGATTATGGATTCAGAAGGACTCGTAAATCT
AAAGGGAGTTGAGGAATTCGAACAAGCAGCTGATCGTGTTTTACATGATC
TTATTGGTAAAGTGTAGTTATTGTTGACAAGCGAAGTTGGATGGGAAA
ATTAAGACATGTAGGATTCATGATCTTTTTCATGATTTCTGCTCCAAGGA
AGCTGAAAGCGAGAATCTTCTGTATGTTGTTGGTTCAGATTCTCAAGTAC
ACACAAATTTCCGTCAAGGTTGTAGGTGGGTGTCAGTTCAATCAAAACTT
GATTATCGTCACCGCAGACGGTATACTCCTATTGAAATATCCTCTTTTTA
CATGCTATATAATATTGTTATTTTTGACAAAAAAGTTTTTCATTTCAAAC
TACTAAGGGTATTGGACTTGGAGGTACATGATATCATAGGACTCAGTGAA
ATTACTAGAGACCTTGTTTGTTTAAGGTATTTGGCTGTCGGGATTAAGTA
```

```
TGTAAGTTTTGTGGATCTCCCGATTACCAATCTTTGGAATCTACACACTC

TCATTTTAGGTAAATCTTTCACTAATAGTCTTATACATAAAGTCTTCAGT

TTTCCAAAAGATATTTGGCAAATGTCACAATTAAGGCATCTTTATGCAAA

AGGCATTTATCTATCTTCGCCTGGAGAAAAGGTTCTCGAAAACTTACAGA

GTGTTTCTGGTTTGAGTCCTTCTTGTTGTACAAAGGAAATATTTGAAGGG

ATTAAGAATGTGAAAAAATTGATCATTCGTGGAAAGAGGGAGGATTATCC

TACAGATATTAAATGGATAGATAATCTTAAATATTTGCAACATCTCGAGT

CACTGAGTATTGAAACTACCGATTTTCTATTTCATAAGAATAAAACCAGG

TTTTTTAGTCTTACAAGTCCAGATTCTTTTCCACAAAAACTCAAGAAATT

GAAACTTAGCTACACATATCTACCGTGGGAATACATGTCCATTATCAGCA

AGTTGCCCGAACTTGAGGTACTCAAACTGAAGTGTGGTTCCTTAATTGGC

GACGAGTGGAAAGCAACAGACCAGATTGGGTTCCCGAAGTTGAGGTTCTT

GCTCCTTGAGAATCTCTTCCTTGGAAAATGGGAAACCACCACGGGCTCTC

ATGATCATTTCCCCAGCCTTGAGCGCTTAATTATCACAAATTTCAGTTTC

TTAAAAGAGATTCCTCAAGGATTTGCTGATAGCAAGAAACTGGAGCTGAT

TGAGTTACACAATTGTGACCCTTCCTTGGTGGCTTTTGCTAAGCAGATAC

AGGTTGAACACGAGGATTTGGGGAGGAACAAACTTAAAGTTACTGCCTTC

GATACAGGTCGAGGATGGAACAGAGGAATCTTAGCTTCAAGAAATAACAG

GATTTCCAGCTAA
```

The coding sequence for Solyd04g057520.1, which is hereby incorporated by reference in its entirety, (SEQ ID NO: 3) is as follows:

```
ATGGAGGCTACAATCGTTGCAGCGGTGAGTCCGGCGGCGACAAAAGCGGT

AAGCTTTCTGGTGGACAGTCTATCGCAGCTACTATCGGAAAATGTGGAAC

TGATAAGAGGTGCAGATAGAGATTTCCAGCGATTACTGGATGAAATTAAA

CCCATAAATGAGTTACTAGCTGGAGATTATGCACAATTGAAAAGCAACAA

CAACAACGATTTGGATAAATTGTTCCAGAATATTCAACGAACAGTATATA

AAGCTGAAGATGCGATCGATAAATTCCTAATTCAGGCTAAAATTGACGAA

GCTAACCTGTTCAATAAGTTCGGTCCGTTCGTCAAGTGGAACAACAATCG

GAAAATTGCACCGGAATTCGAGAAAATTTTAAAACAAGTGGCCGGAATTC

GCCAACAGACTCAACAGGTTTTGGACAAAACCGGTATACAGAGTTCTGCT

TTCCAGCCTGGAGAAACTACGGGGACACAGGGTCCTGCTGAGGAGGATAT

CGAAGTGGTTGGTTTTAATAAGCCTGCAGAAGATGTGAAAAAGCGACTCT

GTGAAGGATCAAAGGATGTTGATGTTATACCTATTGTGGGTATGCCAGGA

CTTGGAAAGACCACTCTGTCAAGAAAAGTTTACAATGATTGTTCCCTTGA

TTTTTATTTTTACCATAAAATGTGGATTTATGTTGGGACATCAAAGAAAC

CAAAGGATATTCTTATTGAGATTGTGAAGAAGTCGCGCAAAGCAATAGT

AAGGAACTAATTATAGACAAGGATGAGGACCAATTAGCTCATATCATACG

TGGTTTTCTTGTTGAAAGAGGTAAACATCTCATTGTCTTGGATGATGTGT

GGGACACACAAGTTGTAGATTTTGTCAAGAAAGCTTTCCCAAACAACAAA

TCCCGGCCCCGAGGGGACAGAATCATGTTGACAACTCGCCAACGACGTGT
```

```
GGCTGAAGCTGTCAGCGCTCGTCCTCACTATCTAGAAAACTTGTCAAAAA

AGGATAGTATAAAGTTGTTGGAACAGAGAGTTTTTGCCGATAAAAGGACA

TGTCCTATTGAGTTAGAAGTATATCGAGATGGGATTGTAGATAAATGTTG

TGGTGTACCACTTGCCATAGTGGTGATTTCAGGAGCTTTGAGAGGTTGTA

TGGGTGTGGGAGTAGTGCAAGAAAATATGGGGAAGCACCTTATAAACAAG

GACGACCATAAAAGCTGCTTGAAATTTGTTGAAACGAGTTACAATCATTT

GCCGCAAGAGAAAAAGGCAGCCTTCTTGTATTTTGGAGTATTTCCTCAAG

GTTTTGATATTCCTGCTTGGAACCTTATTCGCTTATGGGTTGCTGAGGGG

CTAATAAAGTCCAGTCATAAAGACAGTGAAATCGAGAAGGTTGCGGAGAC

TTACTTGAGCGACTTTGCTAGTAGGAATTTAGTGATGGTGATGCAAAAGA

GATCTAACGGTCAAATCAAAACGTGTCGTCTCCATGACATGTTGCATGAG

TTCTGCATTATTGAGGCTCAAAGGATAAGTCTCTTTCAACAAGTATATCT

CCAACCTGGTGTTCGAGTTTTTCCTTCTATAGAAGATCCAAATACTTCTC

GCCGATTATGTATTCAATCCTCTATTCCGTATAATTTTATCACTAAAGAT

AGAATTGTACAGCATGTTAGGTCTCTCTTATGTTTTTCCTCAGACCAAAA

GCAAATTGACTTGTCTAATCTAGATGTCCAACTTATCCCCAATGCCTTTC

CACTCATCAGGGTGTTGGACATTCAATCCCTCATATTTGAATTCTCCAAG

ATGTTTTATGGTCTATTTCACTTGAGGTATATTGCCATCAAAGGCGACTT

CACTGTCATTCCTTCACTCTTTCGTAATTTTTGGTATTTACAAACCCTTA

TACTTCGTAATGATGATACACATACTTCAAGCTCCACCCTTGAGATAAAA

GAGGACATATGGAAACTGTTACAATTGAGACATCTGCACTCCGACCTTCC

TGTGAAATTGCCTCCCCCTCCTACCCCAACAAGCGAGAGTCGTACTTCTT

GTCTACAAACTCTTTCTAAGGTTACGCCAGATAGTTGCAAAAAAACTGTG

TTTGCAAAGGCTTGTCATCTCAAAAAATTGGGTATTGAAGGGCAATTGGC

ACTTCTTCTTGGAAAATCTACCAAGGGAAGTGGATTCGACAGTTTCCAAG

AGCTAAGGTGCGTCGAAAAATTGAAATTGTTGAACAATGATTTTAGTGAA

GAGCTTCACCTTCCTCCACACTTTTTCAGCTTACAAAAAACACTGAACAA

GTTAACTTTGTCAAGTACAAGGTTTGAGTGGAGTGAGGCAGATATGTTGG

GGAAGTTGGAATGCCTTAAGGTACTAAAATTGAAAGATAATGCATTCATA

GGGAAGAATTGGAAGCCCAAGAAAGGAAGTTTTAGCAAGCTCCAAGTCCT

GCACATTGTCTGGGCAGGAGACTGGCAAACTTGGGATGCATCAAATCGTC

CGTTCCTAAGTCTTACACACCTTGTTCTTATTTCCTGTTATGATCTCAAG

GCTGTGCCACACGAGCTGGCTGATTTACCTTATCTTCAAGAGATGAAGCT

GACGCGCACATTCCAGGCAGTCAGTTCTGCCATAGAAATCAAAAGAAAGA

TACTACAAAGGCAAGATCCCGAAAGCAGCATCAAATTCAATCTCATTACA

TTTCCCCCTAACTCGTCCACAAATTAA
```

The coding sequence for Solyd04g057570.1, which is hereby incorporated by reference in its entirety, (SEQ ID NO: 4) is as follows:

```
ATGGCGGCTACTTACGGTGCACTAACTTCTGTGTTGGGAACCATAGAGAA

GGTTTTACGGTCCAACCATAGAGAATGTGGTTGGACCGTAAAATTGAAAT
```

```
CACTGTATGAGTTATTTGACACTCTACTTGGCAAATGTGATGTCGGAGAA
GCAATTATTAGCAAGGATTTGCTAAGAAGAATCAAAGATGTTGCAGTTTA
TGCAGAAGATGAAGTTGAATCACTAATGAAACAACTTATTGTTATTGGGC
TGAATGATGAATGTTGTGGTGCGAAGCTTGATAAAGTCTCTCAACAGGTA
ATACAAGTAACTCATTATGTCAACAATATTAATTGTCCAAAAAAAATTGT
TTCTCCACGATTAGATGATGATTCAATCTATGAGAACTTTATGGAAGGGT
ACAATGAAGAAAGAGTAAATATGGTTCAAAGACTTACCAAAGGATCAAAT
AGACTGCAAGTGGTTTCTGTTGTGGGGATGGCGGGCATAGGTAAGACAAC
TTTTGCCAAAACTATATTATTTCATGACCATCTTAAGAAGGAGGACTTTC
CTATTCGTGGTTGGATTACTGTGTCTAACAACTATGATTTAAGAAAGTTG
CTCCTACTCCTCCTTCACGATGTTATTGAAATGAAAGGCAAGAATTTTGA
TGAAATGGATAATGGAGAACTATCTGGTCACGTAAAGCAAGGTTTGCAGG
GAAAAAGGTATTTGATTGTTGTGGATGACATATGGAGCAATAAAGATTGG
GATAGTATTAAACATTTGTTTCCAGATTTTGGTGACAGAAGTCGAATTTT
GTTGACTTCTCGAGACAGGGAGGTTGGTGAGTATGCTGCTACCAATCCTA
AAGATGGTTTGGTACTGATGCGTCCTCTGACGCAAGATGAAAGTCGGAAT
CTGTTTTACCATAGGGTATTTGGGAAAAATTACACTATTCGAGGGTCAGA
TATTGATGAATTCAAAAAGGTTGGAGAAAAGGTTATAACAAATTGCAAAG
GATTACCACTAATGATTACTGCAGTTGCTGGTATACTCCGTAGTAAGAGT
AAACTGGATGAGTGGATGGAAGTAGCTCAAAGTGTAAGCTCATTAGTAAA
TGATGATGATTACAAACAATGCTTACAAGTTGTTGCTTTGAGCTACAATA
ATGTTCCTTCTCTTATGAAAGCTTGCTTTTTGCATTTCGGAGTTTTTCCA
AAAGCCCATGTCATTTCTGTGAAGAAGTTGATCAGATTATGGATTGCAGA
AGGACTCGTAAATCTAAAGGGAGTTGAGGAATTCGAACAAGCAGCTGATC
GTGTTTTACATGATCTTATTGGTAAAAGTGTAGTTATTGTTGACAGCTGT
CATGACTGA
```

The coding sequence for Solyd04g057630.1, which is hereby incorporated by reference in its entirety, (SEQ ID NO: 5) is as follows:

```
ATGGAAGGGTACAATGAAGAAAGAGTAAATATGGTTCAAAGACTTACCAA
AGGATCAAATAAACTGCAAGTGGTTTCTGTTGTGGGGATGGCGGGCATAG
TTAAGACAACTTTTGTCAAAACTATATTATTACATATTAACAAGGAGGAC
TTTCCTATTCGTGGTAGGATTACTGTGTCTAAAAACTATGATTTAAGAAA
GTTGCTCCAACTCCTCCTCCATGATGTTATTGAAATGAAAGGTAAGAATT
TTGATGGAATGGATACTGGAAAAAGGTATTTGATTGTTGTGGATGACATA
TGGAGCAAAAAGATTGGGATGAAATTAAACATTGGTTTCCAGATTGTGG
TGACAGAAGTCGAATTTTGTTGACTTCTCGAGACAGGGAGGTTGGTGAGT
ATGCTGCTAAAGATGGTTTGGTACCGATGCGTCCTCTGACGCAAGATGAA
AGTCGGAATCTGTTTTACCATAGGGCATTTGGGAAAAATTACACTATTCG
AGGGTCAGATATTGATGAATTCGAAAAGGTTGGAGAAAAAGTTATAACAA
ATTGCAAAGGATTACCACTAATGATTACTGCAGTTGCTGGTATACTCCGT
AGTAAGAGTAAACTGGATGAGTGGATGGAAGTAGCTCAAAGTGTAAGCTC
ATTAGTAAATGATGATGATTACAAACAATGCTTACAAGTTGTTGCTTTGA
GCTACAATAATCTTCCTTCTCTAATGAAAGCTTGCTTTTTGCATTTCGGA
GTTTTTCCAAAAGCCCATGTCATTTCTGTGAAGAAGTTGATCAGATTATG
GATTGCAGAAGGACTCGTAAATCTAAAGGGAGTTGAGGAATTCGAACAAG
CAGCTGATCGTGTTTTACATGATCTTATTGGTAAAAGTGTAGTTATTGTT
GACAAGCGAAGTTTGGATGGGAAAATTAAGACATGTAGGATTCATGATCT
TTTTCATGATTTCTGCTCCAAGGAAGCTGAAAGCGAGAATCTTCTGTATG
TTGTTGGTTCAGATTCTCAAGTACACACAAATTTCCGTCAAGGTTGTAGG
TGGGTGTCAGTTCAATCAAAACTTGATTATCGTCACCGCAGACGGTATAC
TCCTATTGAAATATCCTCTTTTTACATGCTATATAATATTGTTATTTTG
ACAAAAAAGTTTTTCATTTCAAACTACTAAGGGTATTGGACTTGGAGGTA
CATGATATCATAGGAATCAGTGAAATTACTAGAGACCTTGTTTGTTTAAG
GTATTTGGCTGTCGGGATTAAGTATGTAGATTTTGTGGATCTCCCAATTA
CCAATCTTTGGAATCTACACACTCTCATTTTAGGTAAATATTTTATTCAT
AATAGTCTTATGCATAAAGTCTTCACTTTTCCAAAAGATATTTGGCAAAT
GTCACAATTAAGGCATCTTTATGCAAAAGGCATTCATCTATGTTCGCCTG
GAGATAATAAGGTTCTCGAAAACTTACTGAGTGTTTCTGGTTTGAGTCCT
TCTTGTTGTACAAAGGAAATATTTGAAGGGATTAAGAAAGTGAAAAAATT
GGTCATTCGTGGAACGAGGGAGGAATGTCCTACAGATGTTAAATGGATAG
ATAATCTTAAATATTTGCAACATCTCGAGTCACTAAGTATTGAAAATATC
AAATTTATATTTCATGAGAATGAAACCAGGTTTTTTAGTCTTACAAGTCC
AGATTCTTTTCCACAAAAACTCAAGAAGTTGAAACTTAGCTACACATATC
TACCGTGGGAATACATGTCCATTATCAGCAAGTTGCCCGAACTTGAGGTA
CTCAAACTGAAGCGTAGTTCCTTAATTGGCAACGAGTGGAAAGCAACAGA
ACAGATTGGGTTCCCGAAGTTGAGGTTCTTGCTCCTTGAGAATCTCTTCC
TTAGAAAATGGGAAAGCACCACGGGCTATCATGATCATTTCCCCAGCCTT
GAGCGCTTAATTATCACAAATTTCAAATTCTTAAAAGAGATTCCTCAAGG
ATTTGCTGATAGCAAGAAACTGGAGCTGATTGAGTTACACAATTGTGACC
CTTCCTTGGTGGATTTTGCTAAGAAGGTGCAGCTTGAACACGAGGAGGTT
TTGGGGAGGAACAAACTTAAAGTTACTGCCTTCAATACAGGTAAATATAT
CTATTAG
```

The coding sequence for Solyd04g057640.1, which is hereby incorporated by reference in its entirety, (SEQ ID NO: 6) is as follows:

```
ATGGCCGCTACTTACGCTGCACTAACTTCTGTGTTGGGAACCATAGACAA
GCTTTTACGGTCCAACTTATTAGTTGGCGTAGAAGAGGTTCATAAGCAAC
AATTAGAATCACTCGACAAGATGTTTGGCACTCTGCAAGTGTCTCTAATT
GGCAAATGTGATGGCGAAGAAGCAATTATTAGCAAGGATTTGCAAAGAAG
AATCAAAGATGTTGCAGTTGATGCAGAAGATGAAGTTGAATCACTAATGA
```

```
GACAACTTATTATTATTGAGCTGAATGATGAATGTTGTGGTGCGAAGCTT

GATAAAGTCTCTCAACAGGTTATACAAGTAACTCATTCTGTCAATGAAGA

GCTGATCATCATCAACAATATTAATTGTCCAGAAAAAGCTGATGAAAATA

GTGCTTCTTCTCCACGATTAGGTGATTCAATCCGTGAGAACGTTATGGAA

GGGTACAATGAAGAAAGAGAAAGGATGGTGCAAAGACTTACCAGGGGCTC

AGGATCAAATAGACGGGAAGTGGTCTCTGTTGTGGGGATGCCGGGCATAG

GTAAGACAACTTTTGCCAAAACTATATTATTCGATAACTCTATCAAGAGG

GTCTTTCGTATTCGTGGTTGGATTACTGTGTCTAACAAGTATGATTTAAA

AAAGTTGCTTCTACTGCTCCTTCATGATGTTATTGAAATGAAAGGCAGCA

ATAATTATGATGAAATGGATATTGGACAACTATCTGGTCACGTAAAGCAA

GGTTTGCAGGGACAAAGGTATTTGATTGTTGTGGATGACATATGGAGCAA

TAAAGATTGGGATACAATTTCACATTGGTTTCCAGATTGTGGTGACAGAA

GTCGAATTTTGTTGACTTCTCGAGACTACAAGGTTGGTGAGTATGCTGCA

ACCAATCCTAAAGATGGTTTGGTACTGATGCGTCCTCTGACGCAAGATGA

AAGTCGGAATCTGTTTTACCATAGGGCATTTGGGAAAAATTACAGTATTC

GAGGGTCAGATATTGATGAATTCGAGAAAGTTGGAGAAAAAGTTATAACA

AATTGCAAAGGATTACCACTAATGATTACTGCGGTTGCTGGTATACTCTG

TAGCAAGAGTAAACTGGATGAGTGGATGGAAATAGCTCAAAGTGTAAGCT

CATTAGTAAATGATGATGCTTACTAA
```

The coding sequence for Solyd04g058020.1, which is hereby incorporated by reference in its entirety, (SEQ ID NO: 7) is as follows:

```
ATGCTGTATGCGACAACAGATGAACGGAAAATGAAGCATTTCAAGATTCA

AGTACTTGAGGGTGTTAGATTTACGCCATTCAAGATTCTATTAGCATCTA

AGATAGGATGTTATGGAGGCACGGATTATGATAGAGGGTTAGTCGAAAGA

TATGGTACATTGAGTCATGAGGCAGCTGAGATGCTTAAACTTGCTTGTTA

TGATGCTGAACAAGTCATTGACAAGGACGTTGATAGAGATACCGTTATCG

AAGCACTTTTAAAATCAGGAAATGAAGCAACCCTTTTTGTATATCCCATT

GTTGGAGTTGAAGGCATTGGAAAAACTACTCTTGCCAAATTGGTGTATAA

TGATCCAAGGATAGTTAGTCAGTTTCAGCTGCGTATATGGGTTCGTGTGT

CTCGTGTGTTTAAAGTAGAGGAAGTATTAGAACAAATTGTGATTCAGTTA

GAGAAGATTTATGTGAGAAACTTGATATGAATGAGCTGAAGAATCTAGTT

CATGAGACTTTGTATGGAAAGAATTATTTGATTGTGTTAGATGATGTGTG

GAATGAGGACCCAGTGAAGTGGGATGAACTTAAGAAGTTGTTGATGGTAG

GTGGTTGTGGAAGTAAGATTCTTGTAACTACTCGGAAAAAGGAAGTAGCT

TCGATAATGGGACGGTTCCTGCATACTGTTTGGAGGGTTTGTTCCATGA

AGATAGTCTGACTTTGTTCTTGAGTAAGGCATCTGAACAAGGATCTTCAT

TGCGCAAGAAAACTGAGAGACGGGAGTGGGAGATAGTTAACAATCACAGC

GGGTGGAACTCAACTCAGAATGACGAAATTTCATCTGCACTAAGAGTCGC

AGAAGGTCTCATTAGTAAGTCTAATGAATCAGAAGATCTTGAGGACGTTG
```

```
CCATTCAACATTTCCGAGAGTTATTGTCGAGATCCTTCTTTCAAGACGTT

GAAGAATATCGTTCCGTTTATACTTCAATCTGTACAATGCATGACCTTGT

ACATGATCTTGCACTGTCAGCAGCAGGGGTTGAATTCTGTACAGTAAATT

CTCACATACAAAACATTTCTGATGAGGTCAGACATGTGGTGTTTTCTGAC

TATGATTTATCAGGCAAGGAACTGCCAGCATCCCTTCTCGGTAACCAGGC

ATTAAGGACCATATCCTTCTCCGTTGATGGAGTAGGGCCGATGAGTACAA

TGTTCGTTGAGAATTGCTTAGCAAGATTCATGCAACTTAAGGTGCTAGAT

ATCAGTGATTCATGTTTCGATGAGCTGCCTAGCTCTGTTGGCGAATTGAA

GTATTTAAGATATCTTGATGTAAGTTCCAATGGAAGCATTAAAGAATTAC

CTGATTCGATTAACAAGTTGCTGAGCTTACAGACACTTCGAGTTTCTCAT

TGTCCACAACTTGAAGGTCTGCCTAAAGATATTGGAAATTTGATCAGCCT

AAGACACCTGTATATAACCACCAAGCAAGCATGTTTTCCTGAAAAGCAAT

TGGCTGCTTATCATCTCTTCGTTCTTTGTACATTCATAGCTGCAACAATC

TCGTATCTTTGTCTGAAGCACCTTACTGCTTTAAAGAATCTGTTGATTGT

TGACTGTAAAGAGCTTACATTGTTGGAGTGGCAAGATATTGAAGGACTTA

GGATGCTTCGGTCATTGGTTATCGGAGGCTTACCTGAATTGGAGTCAAAA

GATGTTCACTGCCTCGGGAGCCTTCAGATGTTGGTACTTGCTGGTTTACC

AGAGTTAGTTACTTTGCCGCGATGGCTTGAAGGTGCTAGTGCTACTCTAC

AATACCTGAGGGTGGAAAGGTGCCTGAATTTTGCAGCATTGCCAAACTGG

CTGGCAAATCTTACTGCACTTGAAAAACTTGAAATTTCCAAGTGCCGTAA

ATCATTTTCATTGCCCGAGGGTATGAGTTGCCTCACGAATCTGAAGGTAC

TTAAGAACGACAATTGA
```

The coding sequence for Solyd04g059470.1, which is hereby incorporated by reference in its entirety, (SEQ ID NO: 8) is as follows:

```
ATGCATTTCCAGAAAAGCTTTAGGAAGAAGGTAAGAAGATTCTTTTCCAG

TTCAAATCCAATTATATATCGATTCAAGATTGGCAGAAAGGTAAAAGAAA

TCAGGGAGCTGCTGAATGAGATTGCAGATGATAGGAGAAATTTCCACTTC

ACGGAACATACTTATGTAATTCCAGCTGAGAATACGAGTAGAGAACAAAC

ACACTCCTTTGTGAGGGCCTCAGATATCATTGGTAGAGATGATGATCAAG

AAAACATTGTAAAACAGCTGATAGATTCTCATGATGAGGAAAATATTTCT

GTGATTCCTATTGTTGGACTTGGAGGGCTTGGAAAAACCACACTTGTTAA

GTTGGTTTATAACAATAATAGGGTTGTTCAGAATTTTGACCTTAGAATGT

GGGTTAGTATTTCAGAAGATTTCAGTCTGAGCAAGGTAATTGAGAAAATT

CTGAGGTCCGCAACAGGAGAGAGTTTTGACCACCTAGATATGGACCAATT

ACAATGTTGTTGGGAGAGGTTTTGCAACAGAAAAGGTATTTACTTGTGC

TGGATGATGTTTGGAACGAAGATCAACACAAGTGGACGGATCTGAGGGAG

TTGCTGATGAATTGTTCCAGAGGTAGTAAAATTGTTGTCACTACACGTAG

TAAGATGGTTGCTTTGATTACTGGAACAGTTCCGCCTTATTATTTGGGAG

GCCTTGCTAATGATGACTGCTTATCTTTATTTTTGAAATGTGCATTTGGA

GGACAGGACAATTTGTTTCCTAATCTAGTAGAAATAGGAAAAGAAATTGT
```

-continued

```
GAAAAAGTGTGGAGGAGTGCCTTTGGCTGTGAAAACCTTGGGAAGGTTGT
TGTACATGAAAACAGACGAGAATGAATGGTTGCAGATAAGAGATAATGAG
ATATGGGAAATCGAACAGAATAAATCTGACATTTTACCAATATTGAGATT
GAGCTATGAACAGATGCCATCACATCTAAGACAGTGCTTTGCCTATTGCT
CCATGTTACCCAAAGGTCAAGAAATTCCGAGGGAGGATTTTATCAATCGC
TGGATTGCTCAAGGATTTATACAGAGTTCCAACAGAAACAGGAAGCTGGA
AGATATCGGTAATCAGTACTTTGATGAGTTGCTATCAAGGTTTTGCTTCC
TAGATGTGGTACAAGCTTTTGATGGAGAAATATTGGCTTGTAAGATACAC
AATCTTGTGCATGATCTTGCACAGTCAGTATCAGGTGCAGAGTGCTTAAA
TGTGAAACCCAATGCTTTCGTGGTCTCTGAAAGAGTTCGCCACTTATTTT
TCCATGCAGAAGATATGTCTAGGAAACACTTCCCCAGATTTTTGCTTCCT
TTGCAAAAGTTGAGGTCTTTCTCTTATTCTTTTAACATTGGACCTGTAAA
CAAGTTCTTTGTCAAGACAATGTTGTCAAATTTCAAATGCCTTCGGATGC
TAGTCTTGAACAATCTAGATCTTGAGGAGTTGCCAACTTCGATAGGTCAC
TTGAAGGAATTAAGATACCTCAACCTTAGTGACAGTGGTAAGATCAAGTT
TCTTCCAAGGTCTATGAGCAAATTAGTAAATCTGCACACCCTAAACCTCA
TTAACTGTGAACAGCTTAAGGAGTTGCCAAGAGATTTTAGAAAGTTAATC
AGCCTGAAGACCTTGTATTTGACTACACATCAGATGTCAGCAGGGATCAA
GAATCAACATTCTTTCACTTCTCTTCAATTTTTACTTCTTTTCAAATGTT
GTTTCCCAAAATTGCAGCCAGAACTGGTGCAGCATTTTACTGCACTTCGG
GTTTTGCGTATCTATGAATGCCCAAGTTTATGTTCTCTTCCAAGCAGTAT
TAGATATCTGACTTCACTTGAAAAGCTATGGATCTGGAACTGTGAAGAAC
TTGATTTGATTGATGGAGAAGGGATGTCAGGCCTAACAAGTCTTCAATCC
TTGCTTCTAATGGGGCTTCCTAAGTTGGTGACTCTACCATTGGAACTTAA
AGATACTGCTCCTACAACATTAAAGTACTTCAGAATCGCCGATTGTCCCA
ACCTGGTGGAGCTTCCAGAGTGGCTGCCTAATTGCTCCTCACTTCAGAGA
CTCTATATAGAGGATTGTCCTGTTTTGGCATCGATACCTCAAGGAATCTA
CAGCCACAATGCCAACGTCCATATAATCGACTGTCCATTGCTAGGTGGAT
GA
```

The coding sequence for Solyd04g059610.1, which is hereby incorporated by reference in its entirety, (SEQ ID NO: 9) is as follows:

```
ATGGCTGATGCCTTTGTGTCATTTGCAGTTAAAAAATTGGGTGATTTCCT
AATACAACAAGTTTCCCTGAGAAAAAATATGAGAGATGAAGTTACATGGC
TGAGAAATGAGCTACTCTTCATGCAGTCTTTCCTCAGAGATGCCGAACAA
AAGCAATATGGAGATCAAAGAGTTCAACAATGGGTGTTTGAGATCAACTC
TCTTGCTAATGATGCTGTCGCTATACTCGAGACTTACAGCTTCGAGGCTT
GTAAAGGTGATGAGGATGGATTTGCTAGTCGTCTCAAGGCTTGCGCTTAC
ATCTGTAGGAAGGAAGAAATTCTACAATGTCGCCAAGGAGATTCAATC
ACTCAAGCAACGAATCATGGATATCTCTCGCAAACGAGATACTTATGGTA
TTACAAATATCAATAGTACTAATTCAGGAGAAGGGCCAAGTAATCAGTCT
GCCATGGTTAGAACATTGAGGAGAACTACCTCCTATGTGGATGACCAGGA
CTACATATTTGTTGGACTTCAAGATGTTGTACGAACATTGCTAGATGAAC
TTCTCAAAGCAGAGCCTCGTCGAAGTGTCCTCTCCATTTATGGCATGGGC
GGATTAGGCAAGACCACTCTTGCAAGAAACCTCTACAACAGTCCTAACAT
AGTCAATAGCTTCCCTACACGCGCTTGGATATGTGTTTCTCAAGAGTACA
ACACAATGGATCTCCTTAGGAATATCATAAAATCCATCCAAGGTTGCACC
AAGGAAACTTTAGATATGTTGGAAAGGATGACAGAAAGAGATCTAGAAAT
ATACCTTCGTGATCTATTAAAAGAACGCAAATACCTTGTGGTGGTTGATG
ATGTATGGAGGAGAGAAGCATGGGAGAGTTTGAAAAGAGCATTTCCAGAT
AGCAAGAATGGAAGCAGAGTTATTATTACCACGCGCAAAGAGGATGTCGC
TGAAAGAGCAGATGACAGAGGTTTTGTCCATAAACTTCGCTTCCTAAGCC
AAGAAGAAAGTTGGGATCTCTTTTGTAGGAAACTACTTGATGTTCAAGCA
ATGGCCTCCACAATGGAGAGGCTAGCTAAAGATATGGTGGACAAGTGTGG
AGGCTTACCTCTTGCAATTGTTGTACTGAGCGGACTACTTTCGCATAAAA
GGGGGCAAGACGAATGGAAAAAGGTGAAAGATCACCTTTGGCAGAACATT
GAAAACAACTCTATTGAAATCTCCTACATACTATCATTGAGCTATAATGA
TTTGTCAATTGCACTCAAGCAGTGTTTTCTGTACTTTGGCCTTTTTCCAG
AAGATGAAGAGGTCGATGCTGAATACATAATATGGTTGTGGATGGCCGAG
GGTTTCATACCTAATGGAGAAGAAAGAATGGAAGATGTCGCTGAAGGCTT
CTTGAATGAGCTGATAAGACGAAGCTTAGTTCAAGTGGCTGGAACACTTT
GGGAGAAAGTTATTCTATGTAGGGTTCATGATGCAGTTCGTGATCTTTCC
ATACAAAAGGCAATGGAGGTAAACTTCTATGACATTTATAATCCAAGAAA
CCATTCCATATCCTTCTTACCTATTAGACATGCCATTCATAGTCAAGGAG
AAAGGTACCTCTCACTTGATCTTTCTAATTTAAAGTTGAGGTCAATTATG
TTCTTCGGTCCAGATTTTCGTAACATGAATCTTATAAACTTTAGTAGTGC
GTTCCAACATATATATGTGTTGTACTTGGATAATCGTGGTGGTTCTATAT
CTATAGTACCTGATGCGATAGGAAGTTTGTACCACCTCAAGTTCTTAAGC
TTGAGAGGCATCCATGATCTTCCCTCCTCCATTGGCAACCTCAAGAATTT
ACAGACACTTTCTGTCGTGAATGAAATTGGACACCCATTCAAACTACCCT
GTGAGTCAGTTGATCTAATAAATCTAAGACATTTAGTTGCTCCGTATACA
AAACCTTTGAAACGTATAAGCAAACTCAAAAATCTTCAAGTTCTTAAAGG
CACTGCTTGTGATCAGTGGAAAGATGTTGACCCTGTTGATTTAGTCAATC
TTCGAGAATTAAGCATGCATGATATTACCAAAATTTACGCCCTGAACAAC
ATTAGCAACTTGAAAAACCTTAGCACACTCAGATTGTTTTGTAGAGGTGG
TGAATCATTCGCTGCCCTTGAATTTCTTAGTTCTTGTCAAAAGCTCGAGA
AATTGTTGTTAAAAGGGAGAATAGAGAAACTTCCTTTGTTTGTAAATTCC
ATCACAATGATGGTTTTTTGGAACTCAAAACTCATGGAAGATCCCATGCC
TATCTTGGGAATGTTGCCAAACCTAAGGGATCTCTATTTAGTAGCAACTT
ATGAAGGAAAAGAAATAATGTGCGGTGACAACAGCTTCAGGCAACTCGAG
TTCCTTCGTCTTCATCGTCTTGAGAACCTAGAAACATGGCATTTAGCCAC
```

-continued

```
AGGTTCCTTGCCTCTGATTAAAGGTCTTCGTATCTATGATTGTCCAAAGC
TGAAGGAGATTCCAGATAGATTGAAACATGTGAAGCTTTTCAACCATATA
TGA
```

The coding sequence for Solyd04g060430.1, which is hereby incorporated by reference in its entirety, (SEQ ID NO: 10) is as follows:

```
ATGTCTTTTGCACTTGGAAAATTGGGTGATTTACTCTTCATAAATCTTT
CCTCAAAGATGCAGAACTAAAGCAATGTGGAGATCAAAGAGTTGGAGAAT
GGGTATTTGAGATCAACTCTATAGCTAATGATGTTGTTGCTACACTCGAG
CCTTGCATCTTTGAGGTTGGATGTTGTACAAACATTGCTAGCTCACCTTC
TCAAAGCAGAGCCTCGTCGAAGCGTCCTCTCCATTTATGGTATGGGGGT
TAGGCAAGACCACTCTTGCCAGAAAACTTTACATTAGTCCTAATATAGCC
TCTAGTTTCCCTACACGTGCTTGGATATGTGTTTCGCAAGAGTACAACAC
CATTGATCTTCTTAGGAATATCATGAAATCCCTCCAAGGTCGCACCAAGG
AAACTCTAGATTTGTTGGAAAGGATGATCGAAGGAGATCTAGAAATTTAT
CTTCGTGATCGATTAAAAAAACACAAATGCCTTGTGGTGGTTGATGATGT
GTGGCAGAAAGAAGCATGGGAGAGTTTGAAAAGAGAATTCCCGGATAGCA
AGAATGGAAGCGGAGTCATTATTACCACGCCCAAAAGGGAAGTCGCTGAA
AGAGCAGATGACAGAGAAGATCAAGTGCTCAAGGCTGATAACATAATACG
GTTGTGGACGGCCGAGGGTTTCATACCCAGAGGAGAAGAAAGAATGGAGG
ATACCGCTGAAGGCTTCTTCAATGAGCTTATAATACGAAGCTTGGTTCAA
GTGGCTAAAACATTTTGGGGAAGAGTTACTGAATGTAGGGTTCATGATTT
ACTCCATGATCTTGCGATACAAAAGGCATTGGAGGTAAACATCTTTTACA
TTTATGATCCAAAAAGCCACTCCATATCCTCTTTATGTATCAGACATGTC
ATTCATAGTCAAGGAGAAAGGTACCCCTCACTTGATCTTTCTAACTTAAA
GTTGAGGTCACTTATGTTCTTCGATCCAGATTTTCGTAAGATGAGTCTTA
TAAACTTCAGGAGTGTGTTCCAACATCTATATGTGTTGTACTTGGAGATG
CGTGTTGACAATATGTCTATTGTATTAGTATCTGATGCCATAGGAAGTTT
GTACCACCTCAAGTTCTTAAGCTTGAGAGCTCCAGAAATTGAGGTTAGAA
GGGGTGATAGAGAAACTGCCTCATCTGTTTCCAAATTCCATCACAATGAT
GGTTCTGAGGGACTCAAGACTGACAGAAGATCTGATGCCTATTTTGGAAA
CGTTGCCAAACTTAAGGAATCATGA
```

The coding sequence for Solyd04g060640.1, which is hereby incorporated by reference in its entirety, (SEQ ID NO: 11) is as follows:

```
ATGAGAGATGAAGTTACATGGCTGAGAAATGAGCTACTCTTTATACAATC
TTTCCTCAAAGATGCAGAACAAAGCAAAGTAGAGATCAAAGAGTTCAAC
AATGGGTATTTGAGATCAACTCTATTGCTAATGATGTTGTTGCTATACTC
GAGACTTATAGCATTGAGGCTGGTAAACGTGCTAGTCGTCTCAAAGCTTG
CGCTTGCATATGTAGCAAGGAGAAGAAATTCTACAGTGTTGCCGAGGAGA
TTCAATCACTCAAGCAACGAATCATGGATATCTCTCGCAAACCAGAGACT
TATGGTATTACAAATATCAATTATAATTCAGGAGAAGGGCCAAGTAATCA
TGATTACATTTTTGTTGGCTTTAACGATGTTGTACAAACATTGCTAGCTC
AACTTCTCAAAGCAGAGCCTCGTCGAAGTGTCCTCTCCATTTATGGCATG
GGCGGATTAGGGAAGACCACTCTTGCCAGAAACCTCTACAACAGTCATGA
TATATTCAATAGCTTCCATACACGCGCTTGGATATGTGTCTCTCAAGAGT
ACAACACAATGGATCTTCTTAGGAATACCATAAATCCATCCAAGGAAACT
CTAGATTTGTTGGAATGGGTGACAGAAGGAGATCTAGAAATTTATCTTCG
TGATCTATTAAAAGAACGCAAATACCTTGTGGTGGTTGATGATGTATGGA
ATAGAGAAGCATGGGAGCGTTTGAAGAGAGCATTCCCGGATAGCAAGAAT
GGCAGCAGAGTCATTATTACCACGCGCAAAGAGGATGTCGCTGAAAAGCA
AACGATAGAGGTTTTTCAAGAAGAAAGTTGGGATCTCTTTTGTAGGAAAC
TACTTGATGTTCGAGCAATGGTTTCAGAAATGGGAAGTCTAGCTAAGGAT
ATGGTGGAAAAGTGTAGAGGCTTACCTCTTGCAATTGTTGTATTGAGCGG
ACTACTTTCGCATAAAAAAGGGCTAAACGAATGGCAAAAGGTGAAAGACC
ACCTTTGGAAGAATATTAAAGAAAATAAATCTATTGAAATCTCTAACATA
CTATCTTTAAGCTACAATGATTTGTCAACTGCTCTCAAGCAGTTTTTTCT
CTACTTTGGTATTTTTCCAGAAGATCAAGTGGTAAAGGCTGATAACATAA
TACGGTTGTGGATGGTCGAGGGTTTCATACCCAGAGGAGAAGAAAGAATG
GAGGATGTCGCTGAAGGCTTGTTGAATGAACTGATAAGACGAAGCTTGGT
TCAAGTGGCTAATACATTTTGGGGAAGAGTTACTGAATGTAGTGTTCATG
ATTTACTCGATCTTGCGATACAAAAGGCATCGGAGGTAAACTTCTTTGAC
ATTTATGATCCAAGAAGCCACTCCATATCCTCTTTATGTATCAGACACTT
CATTCATAGTCAAGGAGAAAGGTACCTCTCACTTGATCTTTCTAACTTAA
AGTTGAGGTCAATTATGTTCTTCGATCGAGATTTTGTAAGACGAGTCTT
ATAAACTTCAGGAGTGTGTTCCTACATCTATATGTGTTTCACTTGGATAT
GAATGTTGGGAATATGTCTATAGATGTACCTGATGCCATTGGAAGTTTGT
ACCACCTCAAGTTCTTAAGCTTGAGAGGTATCCGTGATCTTCCCTCTTCC
ATTGGCAACCTCAAGAATCTACAGACACTTGTTGTCGATGTGGGAGGATA
CACTTTCCAACTACCCCGCGAGACAGTTTACCTGATAAATTTAAGACATT
TAGTTGCTCGGTATTCAAAACCTCTGGTACATATAAGCAAACTAACTAGT
CTTCAAGTTCTTGAAGGTGTTGGTTGTGATCAATGGAAAGATGTTGACCC
TGTTGATTAGTCAATCTTGGAGAATTAAGTATGTTTGATATTAGCAAAT
CTTACTCCCTAAACAACATTAGGAGCTTGAAAAACCTTAGCACTCTCACA
TTGTCGGGGGGGTATCGGAACTCATCTCCATTTCCAGACCTTGAATTTGT
TAATTGTTGTGAAAAGCTCCAGAAATTGAGGTTAGAGGGGGTGATAGAGA
AACTGCCTCATCTCTTTCCAAATTCCATCACAATGATGCTTCTTTGGAAG
TCAAGACTGACAGAAGATCCGATGCTTATTTTGGGAATGTTGCCAAACCT
AAGGAATCTCGATTTGGTTAGTGCTTATGAAGGAAAAGAAATAATTTGCA
GTGATAACAGTTTCAATCAACTAGAGTTCCTTCAACTTGAGGATCTTCGA
AATCTAGAAAGATGGTATTTAGGTACAAGTGCCATGCCTCTAATTAAAGG
```

TCTTGGTTTCCATGACTGTCCAAATTTAAAGGAGATTCCTATGAGAATGA

AAGACGTGGAGCTGCTGAAGAGGAATTATATGTGGTGA

The coding sequence for Solyd04g061490.1, which is hereby incorporated by reference in its entirety, (SEQ ID NO: 12) is as follows:

ATGGAAAATGAATATCAGAAGCTGGAGGATATCAGAATTGGGTTGCATCA

AAGAGCGGAGGCTGATCGGAGAAACTTACTAGTCATTTCACCTAATGTTG

AGGCTTGGTTTACTCGTGTTGATACTACTACTGCAGATGTGGAAGCTGTA

ATGCGACGAGAGGTTGAAAGATATGGCTGGTGCCCAAAATTGAAGTCACG

TTACTCGCTGAGCAGGAAAGCTAAAAAATTTGCACTGGAATTGATTGAAC

TTCGAAATCAAGGCAATGATTATGCTGTTTTCTCCTATCCTGCAGTCAAA

ATTGAAGTTCTACCTAGTAACAGTGGTGAGGAGTTTGACTCCAGAAAATT

GCAAGAGGAAGAGGTTATGGCAGCTTTGAGAGATGATGGGGTCACTATGA

TTGGGATATGTGGTATGGGTGGTTTTGGTAAGACAACACTGGCTGAGAAA

ATCAGGCAAAAGGCGAAACAAGGAAGTTTGTTTGATGAGGTTGTCATGGT

AACTATCAGTCAACAACCAGACTTGAAAAGAATTCAAGGTGAGGTAGCAG

GGGGTGTTGGTCTGACGTTGCAAGGGACAATTTCTGGAATCGTGGAGAT

CAGCTGCGCTCAAGGTTAATGGTTCAGAACAGCTGTGTCCTAGTAATCTT

GGATGATGTTTGGGAGGCTCTTCATGAACTAGAGAAACTTGGAATTCCCA

GATGTAGCAACCACAACCAACGTTGTAAAGTGACATTGACAACGCGATTC

CGAGATGTTTGTGAAGCTATGGAAGCTCAAAAGATCATGGAAGTTGGAAC

TTTACCTGAAGAGGAAGCATGGATCCTTTTCAGGGAGAAAGTTGGTAATA

TAATCGACGACGATCCTTCTGTACTTGACATAGCAAAAGTTGTTGCCAAA

GAATGCAAGGGGTTGCCGCTTGCAATTATTACAGTTGCAAGAGCACTTAA

GCGTAAAACCAAGCCTTCGTGGGAGGATGCCCTTGTACAATTACAAAGAT

CAACACCAATAAATATTCCAGGAGTAATTAAAAATGTGTATCAATCTCTC

AAACTTAGCTATGATTACTTGGAAAGTAATGAAGTCAGGTCCCTGTTTTT

GCTTTGTTCCTTGTTCGAGGAAGATAGTAATATCTGGACTGAACAATTAC

TTAGATATGGAATGGGCTTGACATCTTTTCAGAAATTAAAAACTTAGAA

GAAGCAAGGAAGCGGGCGTGTCATCTCTTAGAAACATTGAAAGATCGTTT

CTTCTTGTCCTTAGGTTCAACAGAAAATTATGTCAAAATGCATGATATGG

TCCGTGATGTGGCTATAAGTATTGCCTCTATGGGAGAGTATAGCTTTATG

GTAAGTCACCATGTGAACTCGCAAGAGCTCCTAAGAAGAACTTCTTACAA

GCAATACAGTCACATTTCAATTGTTGCAAATAAATTTGATGAGCTTCCTA

ACCCAATATTTTGCAAAAAACTGAAGCTTCTAATGTTGACTCTCGATTTT

AAAAATCCATTTAAATTACAGGAAGATTTTTTTGATGAAATGGCTGAACT

CAATGTCTTAAGTTTGAGTGGATATGGATCCATTCTGCCTTTTCCAACAT

CCATTGAGAGGTTGTCAAGTTTGAAGACATTATGTCTGAGTCATTTAAGG

TTAGATGACATATCCATTATTGGGATACTTGTCACTTTAGAAATTCTCAG

CATAAGACATTCTGACATAGAGGAGCTGCCAGTTGAGATAGGAAATTTGA

CCAATCTAATTATGTTAAGAGTTTCGGAATAG

The coding sequence for Solyd04g064750.1, which is hereby incorporated by reference in its entirety, (SEQ ID NO: 13) is as follows:

ATGGATCATCTTATGCCTTACCTGCTGAAAGAAATCAAAGATTACTATTA

CAAGGAGTATGAGATCTCTCAATGCTCTTCCGAGATCTCTTCTCTACTTA

TCGACATAATGCCTCTTGAGCTGGAGGTTCTATACATTTTTACTTCTAAG

CTCATGAAAGAATCAAGGTCAACAGAACTAGAAGTGTTTGTTAAGCAAAT

CCTAAAAGCATCTCCGAAGATTCTTCAAAATTATCTGATTCTTATGAAAG

GATGCATGGAAGGTTCAGTAGCTGTCAGTTACGCTCCAATTCAATGCATT

AATGTCATGATGGAGTTCCTATTGATCTTTCTCACTTATATACCAAAGCG

CTATATCCGTCGTGACAAACTGAATGATATGTTGGCACATGTTGGAGTAC

TTACAAGGAAGATATCTATTCTGGTGAGCAAGCTGATGGAGGAGAGCTCT

GAGAATAATATCAACGAAGCGGACTTTTCAGCTGCATACTTGTTGCAAGA

AATTGAACAAATGAAGGGAGATATCAGACAGCTTTTTTTGAAAGCCCCAG

AGTCATCTCAAATTCGCTTTTCTATGGATGATGGTTTACTCTTCATGAAT

CTTCTACTCGGACATTTAAATGATTTGCTCATTTCCAATGCTTATTCAGT

TGCTCTGATAAAAAAAGAAATTGGGATAGTGAAAGAAAGCCTTGAATTCC

TAAGATCATCTTTCGGGGAAGTCAGGCAAACATTGGATGACACTAGCGGA

TTAGTTAAAGATTGTTGGGTGCGTGCTTTAGATGTGGCATATGAAGCAGA

ACATATCATTAATTCCATTCTTGTCAGAGATAATGCTCTCACACATCTCA

TATTCTCACTTCCGAATGTCACAGATAAGATCAAGCTTATCGTGGCAGAA

GTCACCTGCAGTGTACATCTGGAGGATAAAAATGGGGATGACCCCCTTGA

TGCAAAGTCTTTCGACGAGTCAATTGAGTCAACCTCATCATCTTTTGTTG

AGGTAACAGTTGGTCATGAGGAAGACGAAGCCTGGATCGTTGACCAGCTC

CTTGATAAGCATGAATCCAAGCTTGATGTCATTTCGATTGTCGGAATGCC

AGGAGTCGGTAAAACTACTCTAGCCAACAAAGTTCATTTCAATGTTCATG

TTTGGTGCACTGTTTCCCAAAAGTTTAACAAGTCAAAGGTGTTGCGGGTG

ATTCTTCAGCAAGTTACAGGGTCGGAAGACAAGAAACAAAGTAATGAGGG

TGATAAAGTTGTTGATCTTGCTGAAAAGCTACGAGAAGAACTATACGATA

AAAGGTACCTCATCGTCTTGGATGATGTGTGGGATATTGCAACAGTGGAG

ATGTTAATAGCATGCTTTCCGAGGGTTGAGAGAGGGAAATAGAATTATCTT

AACTAGCCGAAGTAGTGAGGTAGGTTTGCAAGTTAAATGTCGTAATGATC

TTCTCTACCTTCAACTTCTAACACATGAAAAAAGTTGGAATTTATTTGAA

AAAAGGATCAAGGAAGCTGCCCTGCTGAACTGTCAGAAGTTGGACACCAA

ATATATAGTTGAGAAATGTCAAGGGCTTCCTCTGGCTGTTGTGTTGATTG

CTGGAGTAATTGTTAGAGGAAAGAAAAATGAAAAAGATTTGTGGCTTAAG

ATTCAACATAATATGGATTCCGTTATTTCTGCCAACAACAATTTGCAGAT

```
GATGAAGGTTATGCAATTAAGTTATGACCACTTACCATACCACCTAAAGC
CGTTGTTGCTTTACTTTGGAAGATCTCAAAAGAACAAACTAACTCCAGTC
TCTAAGTTGATGCAATTGTGGATGGCCGAAGGGTTTGTGGATCATTGTAT
CCCGTCTAAGAGTAGTTTAGAGGAAATAACCCAAAGTTACTTGGAAGCTT
TAATTTCCAGTAGCCTGGTAATGGTGGATCGTAGCGTGTCCAAGAGTAGT
CACCCTTTTTCTGTTACTATCAAGGTTTGCTATGTGCATGATGTTGTGCA
TGATTTTTGTTCAGTAAAAGCAAAGAAGGAAATGTTTTTCAAGTTAATCA
ATTCAGGTGCTCCATTTCATGCTTCGGATTTCATACATCGTCGTCTAACC
ATTTATACTGACAAATCCCAACTCCACAAAAGATGTGTTTTGTTTAATTC
TAATAAGTGTTCAGCTGGTAGTAAGCATCTCATATCTTTGAAAGTGAAAA
ATTGGCTTGATCCCTTCAGTCACATTAGACACTTTGGACTTGTTAGAGTG
TTGCAACTTGGTAACATTATTCTGGAAGAGTCATCAATGGAAGAAATAGG
CTCCCTATTTCATTTGAGGTTTTTGAGGTTTCAGACATATGAAAAATCTC
TCCCGCTTTCGTGGTTGAACCTCCAGAATCTGGAAACTCTGTGGATCCTA
AACAGGCATTCCACCATGGTACTACTCGACGAACTGTCAAAGCTGAAACA
TGTGAGCATCGACGCTAGATCTTTCTTTGAAGAGGACAAGGACAACATTA
TGCATCAGCCAAGTAGAATATTGGAAGCTGAGTGTTCAAAGTTAGAATAC
TTGACAACTTTATCCCGAGTTGATATCTCATATTCTCAAGGCACAACTGA
TGCTCTGGGGAAGTTCCCAAATCTTCAGGACTTTGATTGCAACATTCTGG
TACCGAATGATCCTCCTGCAAACGGCGATTGGTTTCCCAAGTTTGATGTC
CTTAATAAACTTGAATCACTCATTCTAAGTTACAGTTATGTCTGGAGCAG
TACTGATAAATGTCTGGATTATTCCAAGTTTGAAAAAATCCGAAATCCCA
ATGAATATCACTTCCCTACCAGTTTGCAAGAGTTACGGTTGCATAGGTTT
CCCCTGAGACCTGCTTTGTTGTTAGCAATCGCGACATTGTCTGAGCTTGA
AATTCTGGAGATTATAGAATCTAATTTCCTCGAGGATGAGTGGGACGAA
GTAAGGACATCTATCAAAGTCTAAAGACTTTGCATTTAGCAGATGTCTTT
CTTACAGAATGGCAAGTTGATAAGGGAACTTTTCCCAAGCTTGTGGAATT
AAAACTAGAACATTATCACGGGCTTATGGACATCCCTTATGCATTTGGGG
ATATAGACACTTTAAAGTCCATTCGAGTGGTTCAAACAAGCCGTCACCTT
GGAAATTCAGCCACAAAAATTAAGGAAGATGTAGAAGCTTACACGGGAAA
GGAAAGACTTAATGTCCAC
```

The coding sequence for Solyd04g067320.1, which is hereby incorporated by reference in its entirety, (SEQ ID NO: 14) is as follows:

```
ATGGATGGATTGGCTGAAACTGGATCTTCTTCTTCTTCTTCTTCTTCTTC
TTTGTGGCCATGCACTTATGATGTTTTCTTAAGTTTTAGAGGAGACGATG
TACGGAAGAATTTCGTCGATCATCTATATACAGCTTTGCAGCAAAGAGGA
ATTCACACTTTCAAAGATGATGAAAAACTTGAAAGAGGGAAATCTATTTC
ACCTTCACTTTTCAAAGCTATCGAAGAATCGATGATTTCCATCATCATAT
TCTCTCAAAACTATGCTTCTTCTTCGTGGTGTCTAGATGAGCTTGTTAAG
ATCACTCAATGCATGAAACTCAGGGGACAGATTGTTCTTCCCGTCTTCTA
TGACGTGGATCCATCTGTCGTAAGAAAACAAAAGGCAAATGTTGGTGAGC
TCTTCGCTAAACATGAGTTAGATTTCAAAGATGATGAAGAAAGGGTGAAG
AGATGGCGTACTGCTATGACAGAAGCAGCAAATGTATCTGGTTGGGATTT
GCCAAATATAGCTAACGGGCACGAATCAAAGTGTATCGATCAAGTTGTAG
AATGTGTCATGGAGATATTAGGTCATACTGCTTCTGATGCTACTGAAAGT
CTTATTGGGATACGCTCAAGAATGGGACGGTGTATTCCTTGTTGAATCT
GGAGTCTGATAAAGTTCAATTCGTTGGAATATGGGGAATGAGCGGAATAG
GAAAAACAACTATAGCAAGAGCCATCTATGACAAGATTTTCCGTTACTTT
CAAGGTGCTACTTTCCTTCATGAAGTTGGAGAAACTTCAGCCAAACATGG
TATCCAACATTTGCAGAAGATACTTCTTTCTGAACTACTTCTGTTAAAAG
ATCTAAGAATAAACAACGTATTTGAAGGAACCAGCTTGATAAGAAGACGA
CTAAAAGGGAAACGAGTCCTAATTGTTCTTGATGATGTCAATCATGGAAA
CCAGTTAGATGCCCTAGCTAAAAGCCATGACTGGTTTGGTGCAGGCAGTG
TAATCATCATAACAACAAAGGATAAGCAGTTGCTTCGTCAATATAACGTG
GACAAATGTATAAAGTGAGTCTGTTAAACACTGATGAAAGTATTGAACT
CCTTAGTTCGTATGCATTCCAGAATCGTCATCCCAAAAGTGGATATGGAG
AGATTATAGCTGAAGTTGTTCGGTATGCTGGTGGTCTTCCTTTAGCTCTT
AAAGTTTTGGGTTGCTCTCTGTATGGCGGAGGCATGATTGAATGGAGAGA
AACAGTGGAGAGACTAAAACAAATTCCAGAAGGCGAAATTGTAGAAAAGC
TCAAAGTAAGTTTCAATGGACTAAGTGAGACTGACCAAAAGATCTTCTTA
GATATTGCATGTTTCTTTAAAGGGAAGAAGAAAGGTTCTGTCATTAGAAT
TCTTCGTAGTTTCAGTTTTACTCCTGTCGTTGGCATAAGGAATCTCATCG
AAAAATCTCTTGTAACTGTTTCAAAAGGTAGGATTGTGATGCATCAGTTG
ATCCAAGAGATGGGTTGGCATATTGTTCGCAAAGAAGCTTCAAACAATCT
TGGCAAGTATACTAGGCTCTGGTCTACCGATGATATTCTTCAGGTACTAT
CTGAAAATACGGCCACAGAAGCTGTGGAAGGCATATGGTTGCACTTGCCT
ATACCGAAAGACATAAATGTTGGTGCAGAAGCCTTCAAACAAACGGACAA
CCTGAGGCTGCTCAAGATACACAATGCAAGTGTCTCTGTAGCTCCAGATT
GTCTTCCTAATAAATTGATATGGCTTCATTGGCATGGCTACCCAATGAAG
TCACTTCCAGCAAGTTTTCGAGCAGAAAGGCTTGTTTGTCTGAAAATGCA
GTATAGCCGCGTTGTACACTTGTGGAAGGGAGTAAAATTCCTACACAAAC
TGAAGTTTCTCAACCTTAGTCACTCCCAAAAGCTAGTCAGCTGTCCAGAT
TTCACAGGGGTGCCCAATCTCGAAAAGTTGGTTCTTGAAGATTGTTCGAG
TATAACTGAGATCCATCCTTCTGTGGGATATCTCAAAAATCTTGTTCTAC
TAAACCTGAAGAACTGCAAGAATCTTAAGACCCTTCCAAACATTATTCGA
TTGGATAATCTTGAGACTTTAATTCTTTCTGGCTGCTTGAAACTCGCGAA
TTTCCCAGAAATCATGAGTGACATGAATTGCTTATCTGAGGTCTACTTGG
AAGCTACAGATGTAAAAGAGTTGCCTTCATCAATTGAACGCCTCCCTGGC
CTTCGATTGATGAATCTAGGCTACTGCAGGAATCTTACAAATTTACCAAA
AACCATAGGTAGATTAAAATCTCTTAGGATTCTTATTCTTTCTGGATGTT
```

```
CAAAGCTAGAAAAGTTGCCAGAGGAACTGGGACATATAGAAATCTTGGAG

GAACTCTATTGCGACGAAACTTCCATTCAAAGCCCACCATCATCCATTAC

ACTGTTGAAGAACCTTAAGACCTTATCTTTTCATGGATGTAAAGGCATGG

TATCTCAATCATGGAGTTCACTTTTCTATGCATGGCTTCAGCCAAGAAAA

CATAATCACAAGCCAACAAGTCTGATGTTTACTTCCTTTTCTGGTTTATT

TTCTTTGAGGAAATTGGATCTTAGTGACTGTTGTATGTTGGATGAAGGAA

TTCCTAGTGATCTTGGATGCTTGTCTTCTTTGGTTGAGCTAAATCTTAGT

GGGAATAATTTTGTGGATCTCTCTCAAGCAAGTCTCAACATGCTTCCGCG

GCTCAGAATCCTTGAGCTAGTTGGTTGTGAGAGGCTTGAAAGGTTGCCAG

AACTTCCAACAACAATAGAGGAAGTTTTTGCAGATAATTGTACATACCTG

ATGACTGATAACATGGGAATATTGACCAACTACAAGATGTTACAGCGAAT

ATCGTTCACTAATTGTGTTGGACTACTGCAGAATCAGCAGACGCGTGACA

TGGCTACCTCATTGTGGCTTCACCTATTCAAGAAGTGCATTGTTAAAAGT

GGTCACTTTAGCATTTACCTACCTGGAGAACAAGTTCCAGAATGGTTTGG

CTACAAACTCAACGGAACTTCAGTTTCAATGCAGCTGCCAAACGATTGGT

ACAATGATAAATTCATGGGATTTGCCATCTGTGTTGTGTCTGAACTTGAA

ACAACATGGTTATCAGTTCATGAAGGTTACCTACAGGAAATGCCAGGCAT

TTCGATTGAGTTTACAATCAAAAGCCACCTCCGGAGGAGCACGAGTTGCC

TAATGAACATTGGTTTTGTAGGGACAAACAAGAATGTTGCTTCAGATCAC

ACATGCCTTGCCTATGTGCCATTTGAAGAATATTGGTCAATGTACAAAAA

CCACTTAGACAGCCCAAACAATTGGTATCAGATCGATTTTTCTGCAAACT

CTTTGAGGAAACATATATTCCTAAAAAGTTGGGGAATTCGTCTCGTGTAC

ACTGATGACTTACAGATTTTCACATCTTGA
```

The coding sequence for Solyd04g076500.1, which is hereby incorporated by reference in its entirety, (SEQ ID NO: 15) is as follows:

```
ATGGCGGTGACGGACTTTTTCGCCGGCGAAATTACCACCGAACTCATAAA

ATACCTGCTGTTAATAGTTAAAAAATCCACTTTATGCCGTTCAAGCGCAG

AGAATCTCATTGACAATATCAATGGTCTCCTTCCAATCATCCAAGAAATC

AAACAAACCGGTGTTGAACTTCCACAGATACGGCAAACTCAGCTCGACGA

TTTCTCCAAACTTCTCCGAGATGGCTACGAACTCGCCGGAAAAGTTCTGC

ACTCCGGCCGTTGGAACATGTACAGGAACCTACAGTTGGCTAGGAAAATG

GAGAGGTTAGAGAAAAGAGTAGCGAGGTTCATGCAAGTTACAATGCAAGC

TCATGTACTAGCTGATGTTCATCATGTTAGGTTTAATATGGAGCAGAGAT

TTGATGTGCTTGAGCATAGGCTTAAAGCTATAAAAATCGGAGTTGACGAT

AGAAGTGGTGGAGGAGGAGGGTGTTTAGGAGAAGCTGTGAAAAGAATGGA

AGAAGATGAGAAATGGTTTGAGGATAGTTTTGTAAATTTAGGTGCTGGGA

TTGAATTGGGGAAGAGGAAGGTGAAGGAGATGCTGATGGGTGAACAAGAT

AGGGGTGTGTTTGAGATTTGTGGAATTGGGGGTAGTGGCAAAACTACCTT

GGCTAAGGAGATTTGTAAAGATGATCAAGTTAAAAGTTATTTCAAGGACA

AGATTTTCTTTTTCACTGTTTCTCAATCTCCAAATGTGGAGCAATTAAGG

AAAATGATTTGGGAAAAGATATCAGGGTGCAATCTCCATGGTTATGGATA

CGGGGAGATGTTTCCCCAGTGGAACCTACAGTACCAATGGAATACGAAAT

GTGCATCCCCGGTACTCTTGATTCTTGATGATGTGTGGTCTGCATCTGTT

CTAGAGCCACTAGTTTTCAAGATCCCCGGATGCAAGATCCTAGTTGTATC

GCGCATCAAGTTTCCTCTATCGATCATTGACTGTATTTATGATTTAGAGT

TGTTAAGGAAGATGAAGCTATGTCCTTATTTTGCCATTTGCTTTTGGAC

ACAATTCCTTTCCGCGTGATTGTGGATGAATGTGAAGGGCTTCCTTTGGC

TCTTAAGGTCATTGGATCTTCATTGAAGGGAAAACCTGAGATGTTATGGA

CAAGTGCAAAAAACAGATTATCACGATGCCAACCTGTCTGCGAGTCTCAT

GAACTGCAGTTGCTTGAGCGAATGAAATTGAGTATTGACTGTTTGCCTGA

GAAGGTGCGAGAGTGTTTCCTGGACTTGGGTGCTTTCCCGGAGGACAAAA

GGATTCCTGTTGATGTTCTAATTAACATGTGGGTGGAGCTACATGATATT

GATGAGGAGGAGGCTTTTCACATTCTTGTTGAACTTTCAGACAAAAATCT

CCTAAATCTAGTCAAAGATGCACGAGCCGGAGACATGTATACAAGTTACT

ATGAGATATCGGTGTTTCAGCATGATGTATTACGAGACCTAGCAATTCAT

ATGAGCAACTGTGATGATATAAATCAGAGAAAGCGATTGGTTATGCCGCG

GAGAGACACAAGCTTCCCAAGAGAATGGGAAAGAAATGTGGACGAACCTT

TCCATGCACGAGTTATCTCTGTGCATACAGATGAAATGAGAGAAATGGAC

TGGTTCAGAATGGATTGCCCGAAAGCTGAAGTACTGATTCTCAACTTTGC

CTCATCTGAGTACTTCTTGCCTCCTTTTCTGGAGAACATGCCAAAGCTAA

GGGCATTGATAATCATAAACTATAGTGCTGGCAATTCAGTTCTTCATAAC

ATGTCTGTATTCAGTCATTTAACCAACTTGAGAAGCCTTTGGTTCGAGAA

GATATCCATCACTCACTTATCTGACTCCACAAATCCTCTCAATAACCTGC

GAAAGATATCTCTAGTGCTTTGTGACATGAAAAACAGCTTCGATGAGTCA

GATGTAGACCTCCCTGGTTTGTTCCCACAGCTCTCGGAGTTCACAATGGA

TCATTGCATCAACTTCAACAAGCTACCATCGAGCATTTGCCGGTTGCATA

AGCTCAACAGCCTTAGTATCACTAATTGTGATAGTCTTTGTGAACTTCCA

TCTGATTTAGGTGAATTACAAACTCTACAAGTTTTAAGGATATATGCCTG

TCCACATCTGAAAAGGCTTCCCCCGGGAATTGGTCATCTGGTAAAGCTAA

AGTACCTTGACATTTCACAATGTGTTGGTTTGAGATGTCTCCCTGAAGCA

ATTGGTTGCTGTAGAAACTTAGAGAAGATTGATATGAGGGAGTGCCCTCA

AATCGACAGTTTGCCTAGCGCTCTATCCTTTCTTGAATCATTACGTTGTG

TTATCTGTGACGATGAAGTTTTTTGTCAATGGAAAGACGTTGAGAAGGCT

GTACCAGGTCTCTGTGTACAGGTTGCCGAGGAGTGCCATACTCTTGACTG

GCTATCTCAATAA
```

TABLE 4

Gene models with the highest similarity to RPS2 and Mr5 in *S. lycopersicoides*. A genome-wide comparison between all proteins from *S. lycopersicoides* LA2951 and the amino acid sequences from RPS2 and Mr5 was performed to identify the most similar proteins present in this tomato accession. A pairwise alignment between each gene model and RPS2 (a) or Mr5 (b) amino acids sequences was done to calculate the percentage of similarity. References: Fahrentrapp et al., "A Candidate Gene for Fire Blight Resistance in Malus × Robusta 5 is Coding for a CC-NBS-LRR," *Tree Genet. Genomes* 9:237-51 (2012); Bent et al., "RPS2 of *Arabidopsis thaliana*: a leucine-rich repeat class of plant disease resistance genes," *Science* 265:1856-60 (1994), which are hereby incorporated by reference in their entirety.

| Gene Model | % Similarity RPS2 | Amino Acid Residues | Annotation | |
|---|---|---|---|---|
| Solyd08g052660 | 56.7 | 1,314 | NB-ARC | LRR |
| Solyd11g052900 | 56.1 | 743 | NB-ARC | LRR |
| Solyd10g073720 | 56.1 | 996 | NB-ARC | LRR |
| Solyd06g059160 | 54.8 | 740 | NB-ARC | LRR |
| Solyd02g054510 | 54.6 | 1027 | NB-ARC | LRR |

| Gene Model | % Similarity Mr5 | Amino Acid Residues | Annotation | |
|---|---|---|---|---|
| Solyd11g070490 | 69.3 | 916 | NB-ARC | LRR |
| Solyd11g069520 | 62.5 | 1329 | NB-ARC | LRR |
| Solyd03g059570 | 62.3 | 1226 | NB-ARC | LRR |
| Solyd11g069260 | 62.3 | 1431 | NB-ARC | LRR |
| Solyd11g070530 | 61.9 | 1244 | NB-ARC | LRR |

Example 10: Identification of Ptr1

Further analysis confirmed that the gene conferring AvrRpt2-mediated Pst race 1 resistance (Ptr1) is Solyd04g059470, the coding sequence of which (SEQ ID NO:18) and amino acid sequence of which (SEQ ID NO:19) are as follows:

```
>Solyd04g059470 (2472 bp nucleotide)
(SEQ ID NO: 18):
ATGGCGGAATCTTTCTTGTTCAATATCATTGAACGGGTTTTGGCTAAAGT

TTCTTCAATTGCTGTATATGAGATCAGTCTAGCTTGGAATGTTAAGACAG

AGCTAAGGAAACTCCAAAGTACTCTATCCACCATCAAAGCTGTACTTCTA

GATGCAAACGAGCAAAAGGCAAAGAACCATGAAGTGAGAGATTGGCTGGA

AAAGCTCAGAGATGTTGTTTATGATGTCGATGATTTGATGGATGATTTAT

CAACACAACTGTTGCTGCAAATGCATTTCCAGAAAAGCTTTAGGAAGAAG

GTAAGAAGATTCTTTTCCAGTTCAAATCCAATTATATATCGATTCAAGAT

TGGCAGAAAGGTAAAAGAAATCAGGGAGCTGCTGAATGAGATTGCAGATG

ATAGGAGAAATTTCCACTTCACGGAACATACTTATGTAATTCCAGCTGAG

AATACGAGTAGAGAACAAACACACTCCTTTGTGAGGGCCTCAGATATCAT

TGGTAGAGATGATGATCAAGAAAACATTGTAAAACAGCTGATAGATTCTC

ATGATGAGGAAAATATTTCTGTGATTCCTATTGTTGGACTTGGAGGGCTT

GGAAAAACCACACTTGTTAAGTTGGTTTATAACAATAATAGGGTTGTTCA

GAATTTTGACCTTAGAATGTGGGTTAGTATTTCAGAAGATTTCAGTCTGA

GCAAGGTAATTGAGAAAATTCTGAGGTCCGCAACAGGAGAGAGTTTTGAC

CACCTAGATATGGACCAATTACAATGTTGTTTGGGAGAGGTTTTGCAACA

GAAAAGGTATTTACTTGTGCTGGATGATGTTTGGAACGAAGATCAACACA

AGTGGACGGATCTGAGGGAGTTGCTGATGAATTGTTCCAGAGGTAGTAAA

ATTGTTGTCACTACACGTAGTAAGATGGTTGCTTTGATTACTGGAACAGT

TCCGCCTTATTATTTGGGAGGCCTTGCTAATGATGACTGCTTATCTTTAT

TTTTGAAATGTGCATTTGGAGGACAGGACAATTTGTTTCCTAATCTAGTA

GAAATAGGAAAAGAAATTGTGAAAAAGTGTGGAGGAGTGCCTTTGGCTGT

GAAAACCTTGGGAAGGTTGTTGTACATGAAAACAGACGAGAATGAATGGT

TGCAGATAAGAGATAATGAGATATGGGAAATCGAACAGAATAAATCTGAC

ATTTTACCAATATTGAGATTGAGCTATGAACAGATGCCATCACATCTAAG

ACAGTGCTTTGCCTATTGCTCCATGTTACCCAAAGGTCAAGAAATTCCGA

GGGAGGATTTTATCAATCGCTGGATTGCTCAAGGATTTATACAGAGTTCC

AACAGAAACAGGAAGCTGGAAGATATCGGTAATCAGTACTTTGATGAGTT

GCTATCAAGGTTTTGCTTCCTAGATGTGGTACAAGCTTTTGATGGAGAAA

TATTGGCTTGTAAGATACACAATCTTGTGCATGATCTTGCACAGTCAGTA

TCAGGTGCAGAGTGCTTAAATGTGAAACCCAATGCTTTCGTGGTCTCTGA

AAGAGTTCGCCACTTATTTTTCCATGCAGAAGATATGTCTAGGAAACACT

TCCCCAGATTTTTGCTTCCTTTGCAAAAGTTGAGGTCTTTCTCTTATTCT

TTTAACATTGGACCTGTAAACAAGTTCTTTGTCAAGACAATGTTGTCAAA

TTTCAAATGCCTTCGGATGCTAGTCTTGAACAATCTAGATCTTGAGGAGT

TGCCAACTTCGATAGGTCACTTGAAGGAATTAAGATACCTCAACCTTAGT

GACAGTGGTAAGATCAAGTTTCTTCCAAGGTCTATGAGCAAATTAGTAAA

TCTGCACACCCTAAACCTCATTAACTGTGAACAGCTTAAGGAGTTGCCAA

GAGATTTTAGAAAGTTAATCAGCCTGAAGACCTTGTATTTGACTACACAT

CAGATGTCAGCAGGGATCAAGAATCAACATTCTTTCACTTCTCTTCAATT

TTTACTTCTTTTCAAATGTTGTTTCCCAAAATTGCAGCCAGAACTGGTGC

AGCATTTTACYGCACTTCGGGTTTTGCGTATCTATGAATGCCCAAGTTTA

TGTTCTCTTCCAAGCAGTATTAGATATCTGACTTCACTTGAAAAGCTATG

GATCTGGAACTGTGAAGAACTTGATTTGATTGATGGAGAAGGGATGTCAG

GCCTAACAAGTCTTCAATCCTTGCTTCTAATGGGGCTTCCTAAGTTGGTG

ACTCTACCATTGGAACTTAAAGATACTGCTCCTACAACATTAAAGTACTT

CAGAATCGCCGATTGTCCCAACCTGGTGGAGCTTCCAGAGTGGCTGCCTA

ATTGCTCCTCACTTCAGAGACTCTATATAGAGGATTGTCCTGTTTTGGCA

TCGATACCTCAAGGAATCTACAGCCACAATGCCAACGTCCATATAATCGA

CTGTCCATTGCTAGGTGGATGA

>Solyd04g059470 (823 amino acid 94.9 kDa)
(SEQ ID NO: 19):
MAESFLFNIIERVLAKVSSIAVYEISLAWNVKTELRKLQSTLSTIKAVLL

DANEQKAKNHEVRDWLEKLRDVVYDVDDLMDDLSTQLLLQMHFQKSFRKK

VRRFFSSSNPIIYRFKIGRKVKEIRELLNEIADDRRNFHFTEHTYVIPAE

NTSREQTHSFVRASDIIGRDDDQENIVKQLIDSHDEENISVIPIVGLGGL

GKTTLVKLVYNNNRVVQNFDLRMWVSISEDFSLSKVIEKILRSATGESFD

HLDMDQLQCCLGEVLQQKRYLLVLDDVWNEDQHKWTDLRELLMNCSRGSK
```

```
                        -continued
IVVTTRSKMVALITGTVPPYYLGGLANDDCLSLFLKCAFGGQDNLFPNLV

EIGKEIVKKCGGVPLAVKTLGRLLYMKTDENEWLQIRDNEIWEIEQNKSD

ILPILRLSYEQMPSHLRQCFAYCSMLPKGQEIPREDFINRWIAQGFIQSS

NRNRKLEDIGNQYFDELLSRFCFLDVVQAFDGEILACKIHNLVHDLAQSV

SGAECLNVKPNAFVVSERVRHLFFHAEDMSRKHFPRFLLPLQKLRSFSYS

FNIGPVNKFFVKTMLSNFKCLRMLVLNNLDLEELPTSIGHLKELRYLNLS

DSGKIKFLPRSMSKLVNLHTLNLINCEQLKELPRDFRKLISLKTLYLTTH

QMSAGIKNQHSFTSLQFLLLFKCCFPKLQPELVQHFTALRVLRIYECPSL

CSLPSSIRYLTSLEKLWIWNCEELDLIDGEGMSGLTSLQSLLLMGLPKLV

TLPLELKDTAPTTLKYFRIADCPNLVELPEWLPNCSSLQRLYIEDCPVLA

SIPQGIYSHNANVHIIDCPLLGG*
```

An annotation of SEQ ID NO:19, showing the location of coiled-coil (CC), nucleotide binding (NB-ARC), and leucine-rich repeat (LRR) domains is depicted in FIG. 16.

Example 11: Discussion of Examples 1-10

From a serendipitous observation during a natural occurrence of bacterial speck disease two *S. lycopersicoides* introgression lines (ILs) that have strong resistance to multiple race 1 strains of Pst were identified and further characterized. Such resistance is important since race 1 Pst strains are becoming increasingly common throughout the world and yet no simply-inherited genetic resistance to these strains is known. The two ILs contain a large overlapping introgression segment from *S. lycopersicoides* chromosome 4 which carries the locus which is referred to here as *Pseudomonas* tomato race 1 (Ptr1), that recognizes the effector AvrRpt2.

This effector is present in Pst strains collected from diverse tomato-growing regions including all race 1 Pst strains for which a genome sequence is available (T1, K40, NY-T1, CA-A9, CA-407) and some race 0 Pst strains (JL1065, NY15125). The Ptr1 locus, if combined with Pto in the same tomato variety, has the potential to become an important component of bacterial speck disease control. Here the activity of Ptr1 to *Arabidopsis* RPS2 and apple Mr5, two genes that also detect AvrRpt2, was compared, the potential utility of Ptr1 and approaches to identifying the Ptr1 gene was discussed, and the definition of additional Pst races to account for the fact that two NTI loci are now known to confer resistance to bacterial speck disease was proposed.

Cleavage of Rin4 by AvrRpt2 in *Arabidopsis* leads to activation of RPS2 and resistance to *P. syringae* pv. tomato, although the specific mechanism by which Rin4 degradation activates RPS2 is unknown (Day et al., "Molecular Basis for the RIN4 Negative Regulation of RPS2 Disease Resistance," *Plant Cell* 17(4):1292-1305 (2005); Toruño et al., "Regulated Disorder: Posttranslational Modifications Control the RIN4 Plant Immune Signaling Hub," *Mol. Plant Microbe. Interact.* 32(1):56-64 (2018), which are hereby incorporated by reference in their entirety). Our analysis of AvrRpt2 variants revealed a perfect correlation between the ability of a variant to degrade tomato Rin4 proteins and its recognition by Ptr1 and RPS2; AvrRpt2 variants that do not degrade Rin4 are not recognized by Ptr1 or RPS2. It is possible therefore that the Ptr1 and RPS2 proteins are activated via the same mechanism subsequent to Rin4 degradation, although the possibility that a mechanism specific to tomato or *Arabidopsis* exists cannot currently be ruled out. The apple Mr5 protein detects activity of AvrRpt2 from *Erwinia amylovora* (Ea). The AvrRpt2$_{Ea}$ effector does not induce *Arabidopsis* Rin4 degradation when the proteins are transiently co-overexpressed in *N. benthamiana*, although it is possible that this method masks moderate degradation; whether Rin4 degradation in apple is correlated with Mr5 activation has not been reported (Vogt et al., "Gene-for-Gene Relationship in the Host-Pathogen System Malus×Robusta 5-*Erwinia amylovora*," *New Phytol.* 197: 1262-75 (2013), which is hereby incorporated by reference in its entirety). Interestingly, an AvrRpt2$_{Ea}$ variant that is not detected by Mr5 is detected by Ptr1 and is able to degrade *Arabidopsis* RIN4, suggesting that the recognition mechanism of these two proteins is different.

Using an anti-AtRin4 antibody, it was observed that all three tomato Rin4-like proteins that are expressed in leaves were degraded in the presence of AvrRpt2. Soybean also has four Rin4 proteins and virus-induced gene silencing experiments showed that just two of them, GmRIN4a and GmRIN4b, play a role in the HR induced by AvrB and the NLR protein Rpg1b (Selote and Kachroo, 2010). A subsequent study showed that over-expression of any one of the four soybean RIN4s with Rpg1b/AvrB in leaves of *Nicotiana glutinosa* caused an HR; the authors concluded that the expression level differences in these two studies might account for these different observations (Kessens et al., "Determining the GmRIN4 Requirements of the soybean Disease Resistance Proteins Rpg1b and Rpg1r Using a *Nicotiana Glutinosa*-Based Agroinfiltration System," *PloS ONE* 9(9):e108159 (2014), which is hereby incorporated by reference in its entierty). Apple contains two Rin4-like genes although, as noted above, any specific roles they might have in activation of Mr5 have not been reported yet (Fahrentrapp et al., "A Candidate Gene for Fire Blight Resistance in Malus×Robusta 5 is Coding for a CC-NBS-LRR," *Tree Genet. Genomes* 9:237-51 (2012); Vogt et al., "Gene-for-Gene Relationship in the Host-Pathogen System Malus× Robusta 5-*Erwinia amylovora*," *New Phytol.* 197:1262-75 (2013), which are hereby incorporated by reference in their entirety). The requirement of the three tomato Rin4 proteins for activation of Ptr1 using both CRISPR-generated mutations in the corresponding genes and transient co-expression in *N. benthamiana* will be investigated.

Ptr1 is able to recognize AvrRpt2 homologs from a diverse array of different bacteria including several plant pathogens. Each of the AvrRpt2 proteins recognized by Ptr1 had been previously shown to also to induce AtRin4 degradation in *Arabidopsis*, although their ability to activate RPS2-mediated resistance was not reported (Eschen-Lippold et al., "Bacterial AvrRpt2-like Cysteine Proteases Block Activation of the *Arabidopsis* Mitogen-Activated Protein Kinases, MPK4 and MPK11," *Plant Physiol.* 171: 2223-38 (2016), which is hereby incorporated by reference in its entirety). If avrRpt2 homologs are widespread in field isolates of *Acidovorax citrulli* and *Erwinia amylovora* then our results suggest that Ptr1 might be useful if expressed transgenically in cucurbits to control bacterial fruit blotch caused by *A. citrulli* and in apple or pear to confer resistance to fire blight caused by *E. amylovora*. Despite extensive screening of tomato germplasm, no single R gene has been identified which confers resistance to bacterial wilt disease caused by *R. pseudosolanacearum* (Huet, "Breeding for Resistances to *Ralstonia solanacearum*," *Frontiers Plant*

Sci. 5:715 (2014), which is hereby incorporated by reference in its entirety). It was found that Ptr1 was remarkably effective in preventing symptoms of bacterial wilt in a growth chamber assay using strain CMR15. Unfortunately, CMR15 seems to be a rare example of a *R. pseudosolanacearum* strain that expresses an AvrRpt2 homolog (RipBN) (Peeters et al., "Repertoire, Unified Nomenclature and Evolution of the Type III Effector Gene set in the *Ralstonia solanacearum* Species Complex," *BMC Genomics* 14:859 (2013); (iant.toulouse.inra.fr//bacteria/annotation/site/prj/T3Ev3/), each of which are hereby incorporated by reference in their entirety), and Ptr1 will therefore likely not be of broad utility for controlling bacterial wilt disease. Nevertheless, further study of interaction between CMR15 and LA4245-R might provide some useful insights into the molecular basis of the NTI response against *R. pseudosolanacearum* that is induced by Ptr1.

Considering that Ptr1 plays a role in detecting the type III effector AvrRpt2 it seems most likely that it encodes an NLR, although it could encode a decoy or guardee protein which is monitored by an NLR. In either case, one of these genes must be located in the introgression segments although the other one may or may not lie in the introgressions. Examples of each possibility are known: the Pto (decoy) and Prf (NLR) genes are located in a 20 kb region of chromosome 5, whereas the RIN4 (guardee) and RPS2 (NLR) genes are located on different chromosome in *Arabidopsis*. In the Heinz 1706 tomato reference genome sequence chromosome 4 has 56 NLR-encoding genes, the most of any chromosome; 43 of these genes are clustered tightly within a 100-kilobase region with the other 13 located throughout the rest of the chromosome. *S. lycopersicoides* has 66 NLR-encoding genes on chromosome 4 with a similar distribution as seen in Heinz 1706-58 are tightly clustered at one end and 8 are distributed along the chromosome. One boundary of the large introgression segment occurs in the middle of the large NLR cluster which potentially eliminates as Ptr1 candidates 51 NLR-encoding genes. Each of the remaining 15 NLR genes is a candidate for Ptr1. None of these candidates encode proteins with obvious similarity to RPS2 or Mr5, and if one of these is Ptr1, it will be just the third known example of convergent evolution in different plant species for recognition of the same effector (Ashfield et al., "Convergent Evolution of Disease Resistance Gene Specificity in Two Flowering Plant Families," *Plant Cell* 16:309-18 (2004); Carter et al., "Convergent Evolution of Effector Protease Recognition by *Arabidopsis* and Barley," *Mol. Plant Microbe. Interact.* 32(5):550-65 (2019), which are hereby incorporated by reference in their entirety). The obvious decoy/guardee proteins that might be involved with AvrRpt2 recognition in tomato are the three Rin4-like proteins expressed in leaves. None of these genes are located on chromosome 4 of tomato or *S. lycopersicoides*. Another, perhaps less likely, scenario that should be considered is that a gene in the introgression segment encodes a novel host protein that acts with Rin4 to activate an NLR located on another chromosome in VF36. All of these possibilities will be investigated in the future to identify the genes involved in AvrRpt2 recognition and understand the associated molecular mechanisms.

Although LA4245-R plants are morphologically very similar to VF36, the IL line has two introgression segments on chromosome 4, including one large (~57.5 mb) segment encompassing the majority of the 66.56 mb chromosome; however, this IL line cannot be maintained in a homozygous condition. If Ptr1 is to be useful for control of speck disease, it will need to be introgressed into other tomato breeding lines and it will be necessary to reduce the size of the introgressed segment in order to reduce 'linkage drag' (i.e., deleterious alleles). However, recombination is often severely suppressed in plants carrying chromosomal regions from a wild relative of tomato, and *S. lycopersicoides* is particularly distant from cultivated tomato (Grandillo et al., "*Solanum* sect. *Lycopersicon*," in Ch. 9 Wild Crop Relatives: Genomics and Breeding Resources, Vegetables 129-215 (Chittaranjan Kole ed., 2011), each of which is hereby incorporated by reference in its entirety). One approach that might be used in this case is to cross LA4245-R with a species which is phylogenetically intermediate between tomato and *S. lycopersicoides*. A good candidate for such a 'bridge' species is *S. pennellii* which has been shown previously to be useful in increasing recombination frequency in *S. lycopersicoides* introgression regions (Canady et al., "Homeologous Recombination in *Solanum lycopersicoides* Introgression Lines of Cultivated Tomato," *Genetics* 174(4):1775-88 (2006), which is hereby incorporated by reference in its entirety). Importantly, Ptr1 and Pto are located on different chromosomes (4 and 5, respectively) which will facilitate introgressing them both into advanced breeding lines.

The identification of a second R gene that confers resistance to bacterial speck disease presents the opportunity to extend the currently defined race structure of *P. syringae* pv. tomato. The two current races were defined based on the Pto gene in which race 0 strains express either or both of the type III effectors AvrPto and AvrPtoB and race 1 strains evade Pto detection by either losing or mutating these effector genes, or in the case of AvrPtoB suppressing its protein accumulation (Pedley et al., "Molecular Basis of Pto-Mediated Resistance to Bacterial Speck Disease in Tomato," *Ann. Rev. Phytopathol.* 41:215-43 (2003); Lin et al., "Diverse AvrPtoB Homologs from Several *Pseudomonas syringae* Pathovars Elicit Pto-Dependent Resistance and Have Similar Virulence Activities," *Appl. Environ. Microbiol.* 72(1):702-12 (2006); Kunkeaw et al., "Molecular and Evolutionary Analyses of *Pseudomonas syringae* pv. tomato Race 1," *Mol. Plant-Microbe. Interact.* 23:415-24 (2010), which are hereby incorporated by reference in their entirety). Based on the discovery of Ptr1, and focusing on Pst strains related to T1, it is proposed that race 0 strains might be considered the original state of the pathogen and refer to those strains that express avrPto or avrPtoB along with avrRpt2 (Table 5). Race 1 can then refer to strains that express avrRpt2, but lack avrPto or avrPtoB. A newly defined race 2 would refer to strains that have avrPto or avrPtoB, but lack avrRpt2. Finally, a hypothetical strain that lacks all three of these effectors would be defined as race 3. Examples of race 0, 1, and 2 Pst strains are provided in Table 5 along with the ability of Ptr1 and/or Pto to recognize them.

TABLE 5

Proposed races for *P. syringae* pv. tomato based on the Pto and Ptr1 genes.

| Pst race | Example | References | Relevant effectors | R gene present Pto | Ptr1 | none |
|---|---|---|---|---|---|---|
| 0 | JL1065 NY15125 | Whalen et al., 1991; Kraus et al., 2017 | AvrPto and/or AvrPtoB, AvrRpt2 | R | R | S |
| 1 | aT1 NYT1 CA-A9 CA-407 | Almeida et al., 2009; Jones et al., 2015; Kunkeaw et al., 2010 | AvrRpt2 | S | R | S |
| 2 | Max13 | | AvrPto and/or AvrPtoB | R | S | S |
| 3 | unknown | | No AvrPto, AvrPtoB, or AvrRpt2 | S | S | S |

Resistance and susceptibility are denoted as R and S, respectively.
[a]Race 1 strains T1, NYT1, CA-A9 and CA-407 are positive for the presence of the avrPtoB gene, but AvrPtoB protein does not accumulate for unknown reasons.

References cited in Table 5 include: Almeida et al., "A Draft Genome Sequence of *Pseudomonas Syringae* pv. Tomato T1 Reveals a Type III Effector Repertoire Significantly Divergent from that of *Pseudomonas syringae* pv. tomato DC3000," *Mol. Plant-Microbe Interact.* 22(1): 52-62 (2009);[e] Jones et al., "Genome-Assisted Development of a Diagnostic Protocol for Distinguishing High Virulence *Pseudomonas syringae* pv. tomato Strains," *Plant Disease* 99:527-34 (2015); and Kunkeaw et al., "Molecular and Evolutionary Analyses of *Pseudomonas syringae* pv. tomato Race 1," *Mol. Plant-Microbe. Interact.* 23:415-24 (2010), each of which is hereby incorporated by reference in its entirety.

In addition, the DNA sequence and predicted amino acid sequence for the Ptr1 gene from *Solanum lycopersicoides* have been confirmed as SEQ ID Nos 18 and 19, respectively. Evidence confirms that this gene confers AvrRpt2-mediated Pst race 1 resistance. In summary, Ptr1 has the potential to become an important component (along with Pto) for the control of bacterial speck disease in tomato.

Example 12: Materials and Methods for Examples 13-18

Bacterial Strains

*Pseudomonas syringae* pv. tomato strains JL1065 (Whalen et al., "Identification of *Pseudomonas syringae* Pathogens of *Arabidopsis* and a Bacterial Locus Determining Avirulence on Both *Arabidopsis* and Soybean," *Plant Cell* 3:49-59 (1991), which is hereby incorporated by reference in its entirety) and JL10654ΔavrRpt2 (Lim et al., "The *Pseudomonas syringae* avrRpt2 Gene Contributes to Virulence on Tomato," *Mol. Plant Microbe. Interact.* 18:626-33 (2005), which is hereby incorporated by reference in its entirety) were grown on King's B (KB) semi-selective media at 30° C. *Agrobacterium tumefaciens* strains GV3101 and GV2260 (Holsters et al., "The Functional Organization of the Nopaline *A. tumefaciens* Plasmid pTiC58," *Plasmid* 3:212-30 (1980), which is hereby incorporated by reference in its entirety) were grown on LB with appropriate antibiotics at 30° C. (Table 6). All strains were stored in 20% glycerol+60 mM sucrose at −80° C. *Escherichia coli* was used for plasmid maintenance and grown in LB medium at 37° C.

TABLE 6

Bacterial strains used in this study

| Strain | Genotype | Source | Selection |
|---|---|---|---|
| *P. syringae* pv. tomato JL1065 | Wild type | Whalen et al. (1991)[a] | Rifampicin |
| *P. syringae* pv. tomato JL1065 | ΔavrRpt2 | Lim et al. (2005)[b] | Rifampicin Spectinomycin |
| *A. tumefaciens* GV3101 + pMP90 | Wild type | Holsters et al. (1980)[c] | Rifampicin Gentamycin |
| *A. tumefaciens* GV2260 | Wild type | | Rifampicin |
| *E. coli* Stellar | Wild type | Clontech | — |

Table 6 source references include:
[a]Whalen et al., "Identification of *Pseudomonas syringae* Pathogens of *Arabidopsis* and a Bacterial Locus Determining Avirulence on Both *Arabidopsis* and Soybean," *Plant Cell* 3:49-59 (1991);
[b]Lim et al., "The *Pseudomonas syringae* avrRpt2 Gene Contributes to Virulence on Tomato," *Mol. Plant Microbe. Interact.* 18:626-33 (2005); and
[c]Holsters et al., "The Functional Organization of the Nopaline *A. Tumefaciens* Plasmid pTiC58. Plasmid," 3:212-30 (1980), each of which is hereby incorporated by reference in its entirety.

Plant Materials

Seeds of *Solanum lycopersicoides* introgression lines were obtained from the Tomato Genetics Resource Center (tgrc.ucdavis.edu/lycopersicoides_ils.aspx). LA4245-R and LA4277-R are maintained as heterozygotes (Ptr1/ptr1). Progeny derived from selfing these plants are rarely homozygous Ptr1/Ptr1 (around 3% of the progeny) and such plants grow more slowly than Ptr1/ptr1 or ptr1/ptr1 plants. Tomato plants were grown in a greenhouse at 24° C. during daylight and 22° C. at night. *Nicotiana benthamiana* Nb1 (Bombarely et al, "A draft Genome Sequence of *Nicotiana benthamiana* to Enhance Molecular Plant-Microbe Biology Research," *Mol. Plant-Microbe Interact.* 25:1523-30 (2012), which is hereby incorporated by reference in its entirety) and *Nicotiana glutinosa* plants were maintained in a growth chamber with 16 hr:8 hr, light:dark at 24° C. with light and 20° C. in the dark and 50% humidity. Tomato and *Nicotiana* plants were grown in Cornell Osmocote Mix soil (0.16 m³ peat moss, 0.34 m³ vermiculite, 2.27 kg lime, 2.27 kg Osmocote Plus15-9-12 and 0.54 kg Uni-Mix 11-5-11; Everris, Israeli Chemicals Ltd). After pathogen inoculation, tomato plants were moved to a growth chamber with 25° C., 50% humidity, and 16 hr light.

Mapping of Ptr1

DNA from progeny of selfed LA4277-R (Ptr1/ptr1) plants was isolated with DNA extraction buffer (200 mM Tris-HCI pH 8.0, 250 mM NaCl, 25 mM EDTA pH 8, 0.5% w/v sodium dodecyl sulfate) and resuspended in distilled water. Simple sequence repeat (SSR) markers were designed by mapping the *S. lycopersicoides* genome to *S. lycopersicum*

Heinz 1706 v 3.0 using nucmer 4.0.0beta (Delcher et al., "Alignment of Whole Genomes," *Nucleic Acids Res.* 27:2369-76 (1999); and Marcais et al., "MUMmer4: A Fast and Versatile Genome Alignment System," *PLoS Comput. Biol.* 14:e1005944 (2018), which are hereby incorporated by reference in their entirety). A pipeline was developed to identify indels between 30-200 bp and develop flanking primers in order to amplify PCR products of different sizes based on insertions or deletions (Untergasser et al., "Primer3: New Capabilities and Interfaces," *Nucleic Acids Res.* 40(15):e115 (2012), which is hereby incorporated by reference in its entirety) (Table 7). Potential recombinants were selfed and the resulting progeny were genotyped to confirm the segregating recombination event. Recombinant progeny were phenotyped by vacuum infiltration with Pst JL1065 or Pst JL1065ΔavrRpt2 as described previously (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia Pseudosolanacearum* by Recognizing the Type III effectors AvrRpt2 and RipBN,"*Mol. Plant-Microbe. Interact.* 32:949-60 (2019), which is hereby incorporated by reference in its entirety) and visually monitored for the absence or presence of disease symptoms.

TABLE 7

Oligonucleotides used in this study

| Gene | Direction | Identifier | Sequence (5'→3') | SEQ ID NO: | Source |
|---|---|---|---|---|---|
| Introgressed region in Chr4 7.14 Mb | Forward | Chr4_4976565F | gaagccaatgtctgcagctg | 54 | This work |
| Introgressed region in Chr4 7.14 Mb | Reverse | Chr4_4976565R | gccggtcatcagctaggtac | 55 | This work |
| Introgressed region in Chr4 9.15 Mb | Forward | Spennch04_6606838F | ctggcctcattcttatggtt | 56 | This work |
| Introgressed region in Chr4 9.15 Mb | Reverse | Spennch04_6606838R | taaagggagctttcgaacaa | 57 | This work |
| Introgressed region in Chr4 9.94 Mb | Forward | Spennch04_7503010F | ctaagcatggattttagcgc | 58 | This work |
| Introgressed region in Chr4 9.94 Mb | Reverse | Spennch04_7503010R | caacccttgaatcatggaga | 59 | This work |
| Introgressed region in Chr4 69.13 Mb | Forward | Spennch04_5416619 | taatgaggcagagcaagttt | 60 | Examples 1-11; Mazo-Molina et al. (2019)[a] |
| Introgressed region in Chr4 69.13 Mb | Reverse | Spennch04_5416620 | ccctcaagaaccatgaatca | 61 | |
| avrRpt2 | Forward | oCM26 | caccatgaaaattgctccagttgccataaatcacag | 62 | This work |
| avrRpt2 | Reverse | oCM27 | cacacgcaatgctctaccgc | 63 | This work |
| S/Rin4-1_Solyc09g059430 | Forward | KS12 | atggctcgtccaaatgtccc | 64 | This work |
| S/Rin4-1_Solyc09g059430 [no stop] | Reverse | KS13 | gccagggacaacaacaccac | 65 | This work |
| S/Rin4-1_Solyc09g059430 | Reverse | KS14 | ttaccagggacaacaacaccac | 66 | This work |
| S/Rin4-2_Solyc06g083390 | Forward | KS15 | atggctcgtgcaaatgtgc | 67 | This work |
| S/Rin4-2_Solyc06g083390 [no stop] | Reverse | KS16 | gccacaaaggaaagcagcag | 68 | This work |
| S/Rin4-2_Solyc06g083390 | Reverse | KS17 | tcaccacaaaggaaagcagcag | 69 | This work |
| S/Rin4-3_Solyc12g098440 | Forward | KS18 | atggcaaaacactcacaagtacc | 70 | This work |

TABLE 7-continued

Oligonucleotides used in this study

| Gene | Direction | Identifier | Sequence (5'→3') | SEQ ID NO: | Source |
|---|---|---|---|---|---|
| S/Rin4-3_Solyc12g098440 [no stop] | Reverse | KS19 | gactccgacccatggaaag | 71 | This work |
| S/Rin4-3_Solyc12g098440 | Reverse | KS20 | tcaactccgacccatggaaag | 72 | This work |
| AtRIN4_At3G25070.1 | Forward | KS24 | atggcacgttcgaatgtaccaa | 73 | This work |
| AtRIN4_At3G25070.1 | Reverse | KS25 | tcattttcctccaaagccaaagc | 74 | This work |
| Ptr1_Solyd04g059470 | Forward | oCM206 | tttggagaggacagggtaccat ggcggaatctttcttgttcaatatc | 75 | This work |
| Ptr1_Solyd04g059470 | Reverse | oCM207 | gtcgtatgggtaaggtccaccta gcaatggacagtc | 76 | This work |
| Candidate B_Solyd04g059610 | Forward | oCM208 | tttggagaggacagggtaccat ggctgatgcctttgtgtc | 77 | This work |
| Candidate-B_Solyd04g059610 | Reverse | oCM209 | gtcgtatgggtaagggattgaaa catgtgaagcttttcaaccatata | 78 | This work |
| Ptr1-VIGS1 | Forward | oSM03 | ggggacaagtttgtacaaaaaa gcaggctttgagctatgaacaga tgccatcacatc | 79 | This work |
| Ptr1-VIGS1 | Reverse | oSM04 | ggggaccactttgtacaagaaa gctgggtaaagcattgggtttcac atttaagcactctg | 80 | This work |
| synPtr1 | Forward | oSM15 | ggggacaagtttgtacaaaaaa gcaggctttgagctatgaacaga tgccatcacatc | 81 | This work |
| synPtr1 | Reverse | oSM16 | ggggaccactttgtacaagaaa gctgggtaaagcattgggtttcac atttaagcactctg | 82 | This work |
| StPtr1 | Forward | oCM206 | tttggagaggacagggtaccat ggcggaatctttcttgttcaatatc | 83 | This work |
| StPtr1 | Reverse | oCM207 | gtcgtatgggtaaggtccaccta gcaatggacagtc | 84 | This work |

[a]Mazo-Molina et al., "The Ptr1 Locus of Solanum lycopersicoides Confers Resistance to Race 1 Strains of *Pseudomonas syringae* pv. Tomato and to *Ralstonia Pseudosolanacearum* by Recognizing the Type III effectors AvrRpt2 and RipBN," *Mol. Plant-Microbe. Interact.* 32:949-60 (2019), which is hereby incorporated by reference in its entirety. See Examples 1-11.

RNA-Seq

Seven-week-old LA4277-Ro (Ptr1/Ptr1) plants were identified by markers and vacuum-infiltrated with a suspension of Pst JL1065 at $2 \times 10^7$ cfu/mL. Four biological replicates were performed for each treatment. Tissue samples were collected at 5 hr after infiltration. Total RNA was isolated using RNeasy Plant Mini Kit (Qiagen) with additional in-column DNase digestion using the RNase-Free DNase Kit (Qiagen). Libraries for 3' RNA-Seq were prepared by the Cornell Biotechnology Resource Center's Genomics Facility using the Quantseq FWD kit (Lexogen). Raw RNA-Seq reads were processed, removing adaptors and low-quality sequences using Trimmomatic (Bolger et al., "Trimmomatic: A Flexible Trimmer for Illumina Sequence Data," *Bioinf* 30:2114-20 (2014), which is hereby incorporated by reference in its entirety). Low quality sequences were removed from leading and trailing read ends, and trimmed reads shorter than 10 bases were discarded. Clean reads were then aligned to the SILVA rRNA database (Quast et al., "The SILVA Ribosomal RNA Gene Database Project: Improved Data Processing and Web-Based Tools," *Nucleic Acids Res.* 41:D590-96 (2013), which is hereby incorporated by reference in its entirety) using Bowtie (Langmead et al., "Fast Gapped-Read Alignment with Bowtie 2," *Nat. Methods* 9:357-9 (2012), which is hereby incorporated by reference in its entirety) allowing for up to three mismatches. Reads that mapped to rRNA sequence were discarded. The final high-quality reads for each library were aligned to the *S. lycopersicoides* LA2951 reference genome (solgenomics.net/organism/Solanum_lycopersicoides/genome) using STAR default parameters (Dobin et al., "STAR: Ultrafast Universal RNA-Seq Aligner," *Bioinformatics* 29:15-21 (2013), which is hereby incorporated by reference in its entirety). Raw counts for each LA2951 gene model were generated by counting the total number of reads that mapped between the gene region and 500 bp downstream of its stop codon. Reads were normalized to reads per million (RPM).

Cloning of Ptr1 Candidates and Tomato Rin4 Genes

Ptr1 candidate genes were cloned from LA4277-Ro (Ptr1/Ptr1) cDNA into pBTEX (Table 8) using the In-fusion cloning kit manufacturer's instructions (Takara). StPtr1 was cloned from Dakota Crisp potato plants (*Solanum tubero-* sum) into pBTEX via the In-fusion cloning kit (Takara). Nucleotide and amino acid sequences have been deposited in GenBank for Ptr1 from *S. lycopersicoides* (GenBank accession no. MT134103, which is hereby incorporated by reference in its entirety), *N. benthamiana*, NbPtr1a (MT134102, which is hereby incorporated by reference in its entirety) and potato StPtr1 (MT134101, which is hereby incorporated by reference in its entirety) (Table 9).

TABLE 8

Vectors and plasmids used in this study

| Vector | Insert | Identifier | Purpose | Source |
|---|---|---|---|---|
| pBTEX | — | — | Binary expression vector with N-terminal HA-tag | R. Bressan, Purdue University |
| pBTEX | Ptr1-A_Solyd04g059470 | pCM64 | Generating N-terminal HA-tag fusion | This work |
| pBTEX | Ptr1-B_Solyd04g059610 | pCM66 | Generating N-terminal HA-tag fusion | This work |
| | RPS2_At4g26090 | — | N-terminal HA-tagged RPS2 gene | B. Staskawicz, UC Berkeley |
| pJLSmart | — | — | Binary Gateway entry vector | Mathieu et al. (2014)[a] |
| pJLSmart | SlRin4-1_Solyc09g059430 | 10347 | Entry clone for N-terminal Myc-tag fusion | This work |
| pJLSmart | SlRin4-1_Solyc09g059430 [no stop] | 10346 | Entry clone for C-terminal Myc-tag fusion | This work |
| pJLSmart | SlRin4-2_Solyc06g083390 | 10352 | Entry clone for N-terminal Myc-tag fusion | This work |
| pJLSmart | SlRin4-2_Solyc06g083390 [no stop] | 10348 | Entry clone for C-terminal Myc-tag fusion | This work |
| pJLSmart | SlRin4-3_Solyc12g098440 | 10350 | Entry clone for N-terminal Myc-tag fusion | This work |
| pJLSmart | SlRin4-3_Solyc12g098440 [no stop] | 10349 | Entry clone for C-terminal Myc-tag fusion | This work |
| pGWB417 | — | — | Binary Gateway destination vector for plant expression with C-terminal Myc-tag. | Nakagawa et al. (2007)[b] |
| pGWB518 | — | — | Binary Gateway destination vector for plant expression with C-terminal Myc-tag. | Nakagawa et al. (2007)[b] |
| pGWB518 | SlRin4-1_Solyc09g059430 | pKS13 | Generating N-terminal Myc-tag fusion | This work |
| pGWB518 | SlRin4-2_Solyc06g083390 | pKS15 | Generating N-terminal Myc-tag fusion | This work |
| pGWB518 | SlRin4-3_Solyc12g098440 | pKS17 | Generating N-terminal Myc-tag fusion | This work |
| pGWB518 | AtRIN4_At3G25070.1 | pKS18 | Generating N-terminal Myc-tag fusion | This work |
| pGWB417 | SlRin4-1_Solyc09g059430 | pKS12 | Generating C-terminal Myc-tag fusion | This work |
| pGWB417 | SlRin4-2_Solyc06g083390 | pKS14 | Generating C-terminal Myc-tag fusion | This work |
| pGWB417 | SlRin4-3_Solyc12g098440 | pKS16 | Generating C-terminal Myc-tag fusion | This work |
| pGWB417 | avrRpt2_*Pseudomonas syringae* pv. tomato NY15125 | pCM1 | Generating C-terminal Myc-tag fusion | Examples 1-11; Mazo-Molina et al. (2019)[c] |
| pGWB417 | AvrRpt2(C122A) | — | Generating C-terminal Myc-tag fusion | Examples 1-11; Mazo-Molina et al. (2019)[c] |
| pGWB417 | RipBN | — | Generating C-terminal Myc-tag fusion | Examples 1-11; Mazo-Molina et al. (2019)[c] |
| pGWB417 | YFP | — | Generating C-terminal Myc-tag fusion | Roberts et al. (2019)[d] |
| pBTEX | Prf(D1416V) | — | Generating N-terminal HA-tag fusion | Du et al. (2012)[e] |
| pDONR/Zeo | — | — | Binary Gateway entry vector | Invitrogen |
| pDONR/Zeo | Ptr1-TRV2 | pSM1 | Entry clone for Ptr1-TRV2 construct | This work |
| pQ11 | TRV1 | — | VIGS TRV1 construct | Liu et at. (2002)[f] |
| pQ11 | — | — | empty TRV2 constrcut | Liu et al. (2002)[f] |
| pQ11 | EC1-TRV2 | — | VIGS TRV2 construct to silence EC1 | Rosli et at. (2013)[g] |
| pQ11 | Ptr1-TRV2 | pSM2 | VIGS TRV2 construct to silence Ptr1 | This work |

TABLE 8-continued

Vectors and plasmids used in this study

| Vector | Insert | Identifier | Purpose | Source |
|---|---|---|---|---|
| pBTEX | synPtr1 | pSM3 | Generating N-terminal HA-tag fusion | This work |
| pBTEX | StPtr1/RGA1 | pCM68 | Generating N-terminal HA-tag fusion | This work |

Table 8 source references include:
[a]Mathieu et al., "Pto Kinase Binds two Domains of AvrPtoB and its Proximity to the Effector E3 Ligase Determines if it Evades Degradation and Activates Plant Immunity," *PLoS Pathog.* 10:e1004227 (2014);
[b]Nakagawa et al., "Improved Gateway Binary Vectors: High-Performance Vectors for Creation of Fusion Constructs in Transgenic Analysis of Plants," *Biosci. Biotechnol. Biochem.* 71:2095-100 (2007);
[c]Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," *Mol. Plant Microbe. Interact.* 32:949-60 (2019);
[d]Roberts et al., "Mai1 Protein Acts Between Host Recognition of Pathogen Effectors and Mitogen-Activated Protein Kinase Signaling," *Mol. Plant-Microbe. Interact.* 32:1496-507 (2019);
[e]Du et al., "Plant Programmed Cell Death Caused by an Autoactive Form of Prf is Suppressed by Co-Expression of the Prf LRR Domain," *Mol. Plant* 5:1058-67 (2012);
[f]Du et al., "Plant Programmed Cell Death Caused by an Autoactive Form of Prf is Suppressed by Co-Expression of the Prf LRR Domain," *Mol. Plant* 5:1058-67 (2012); and
[g]Rosli et al., "Transcriptomics-Based Screen for Genes Induced by Flagellin and Repressed by Pathogen Effectors Identifies a Cell Wall-Associated Kinase Involved in Plant Immunity," *Genome Biol.* 14:R139 (2013), each of which is hereby incorporated by reference in its entirety.

TABLE 9

Details of each Ptr1 gene in various *solanaceous* species. Each sequence identified in Table 9 is hereby incorporated by reference in its entirety.

| Species | Gene ID | GenBank ID/ NCBI reference sequence | Comments |
|---|---|---|---|
| S. lycopersicoides | Solyd04g059470 | MT134103 | Ptr1 |
| S. tuberosum | | MT134101 | StrPtr1; cv. Dakota Crisp |
| S. lycopersicum | Solyc04g039980/ Solyc04g039990 | | no open reading frame |
| S. pennellii | Sopen04g016200 | | no open reading frame |
| C. annuum | CA05g00030 | PHT80575.1 | cv. CM334; annotated previously as RGA1 |
| N. tabacum | Nitab4.5_0002085g0050.1 | XP_016435110.1 | gene misannotated. Intron should be exon; correct in GenBank; annotated previously as RGA3 |
| N. attenuata | NIATv7_g26201.t1 | O1T07149.1 | annotated previously as RGA3 |
| N. tomentosiformis | mRNA_17526 | XP_018629570.1 | annotated previously as RGA3 |
| C. chinense | | PHU16668.1 | hypothetical protein |
| C. baccatum | | PHT54558.1 | hypothetical protein |
| N. benthamiana | Niben101Scf07061g00004.1 | MT134102 | NbPtr1a; gene misannotated in Nb1 genome sequence. Intron should be exon |
| N. benthamiana | Niben101Scf00597g00011.1/ Niben101Scf00597g00010.1 | | NbPtr1b; no open reading frame |
| S. melongena | SMEL011g377860 | | missing NB-ARC domain; annotated previously as RPP13-like |
| P. axillaris | Peaxi162Scf00970g00162.1 | | no open reading frame |
| P. inflata | Peinf101 Scf01668g00022.1 | | no open reading frame |
| P. inflata | Peinf101Scf14222g00007.1 | | no open reading frame |

SlRin4 genes were cloned from LA4245 cDNA into pJLSmart (Mathieu et al., "Pto Kinase Binds two Domains of AvrPtoB and its Proximity to the Effector E3 Ligase Determines if it Evades Degradation and Activates Plant Immunity," *PLoS Pathog.* 10:e1004227 (2014), which is hereby incorporated by reference in its entirety) and recombined into the Gateway expression vectors pGWB518 and pGWB417 (Nakagawa et al., "Improved Gateway Binary Vectors: High-Performance Vectors for Creation of Fusion Constructs in Transgenic Analysis of Plants," *Biosci. Biotechnol. Biochem.* 71:2095-100 (2007), which is hereby incorporated by reference in its entirety) using LR Clonase II according to the manufacturer's instructions (Thermo Fisher Scientific) to generate N-tagged and C-tagged proteins, respectively.

Constructs were transformed into *E. coli* Stellar competent cells (Clontech). Inserts of all plasmids were sequenced from *E. coli* and then transformed into *Agrobacterium tumefaciens* GV2260. See Table 7 and Table 8 for a list of all oligo and constructs used in this study.

LA4277 Genomic DNA Library Preparation and Oxford Nanopore Sequencing

The LA4277 genome sequence data are available at NCBI as BioProject No. PRJNA610286. To extract high molecular weight DNA, nuclei were enriched from 2 g of LA4277-Ro (Ptr1/Ptr1) leaves using a method modified from (Gendrel et al., "Profiling Histone Modification Patterns in Plants Using Genomic Tiling Microarrays," *Nat. Methods* 2:213-8 (2005), which is hereby incorporated by reference in its entirety). Two g of leaf tissue was harvested and ground in liquid nitrogen and incubated with 90 mL of 0.4 M sucrose, 10 mM Tris-HCl pH 8, 10 mM $MgCl_2$, 5 mM BME (β-mercaptoethanol) for 10 min on ice with shaking. Large leaf debris was removed by filtering through 8 layers of filter paper (Fisher Scientific) and one layer of miracloth (Fisher Scientific). The solution was centrifuged at 3000×g at 4° C. for 20 min. The resulting pellet was resuspended in 500 uL of 0.25 M sucrose, 10 mM Tris-HCl pH 8, 10 mM $MgCl_2$, 1% Triton X-100, 5 mM BME. The suspension was then centrifuged at 12,000×g at 4° C. for 10 min. The pellet was resuspended in 300 uL 0.25 sucrose, 20 mM Tris-HCl pH 8, 4 mM $MgCl_2$, 0.3% Triton X-100 and 500 uL of 2.5 M sucrose was then mixed with the nuclei suspension. This mixture was then overlayed on top of 800 uL of 1.7 M sucrose, 10 mM Tris-HCl pH 8, 2 mM $MgCl_2$, 0.15% Triton X-100, 5 mM BME and centrifuged at 16,000×g at 4° C. for 1 hr. The pelleted nuclei were washed 2× in 500 uL of 25% glycerol, 20 mM Tris-HCl pH 7.4, 2.5 mM $MgCl_2$, 0.2% Triton X-100. DNA was isolated from the enriched nuclei suspension as described previously (Bernatzky et al., "Genetics of Actin-Related Sequences in Tomato," *Theory Appl. Genet.* 72:314-21 (1986), which is hereby incorporated by reference in its entirety).

Covaris g-tube was used in accordance with the manufacturer's protocol to shear 8 ug DNA to 20 kb fragments. Following shearing, small fragments were removed with a size-selection step using 1×AMPure XP (Beckman Coulter, Brea, CA, USA) in NaCl/PEG buffer (10 mM Tris-HCl, mM EDTA pH 8, 1.6 M NaCl, 0.25% Tween-20, 11% PEG-800) (Nagar et al., "DNA Size Selection (>3-4 kb) and Purification of DNA Using an Improved Homemade Spribeads Solution," Protocols.iodoi.org/10.17504/protocols.io.n7hdhj6 (2018), which is hereby incorporated by reference in its entirety). Large fragments were eluted from beads in 50 uL $H_2O$. A library was prepared using 1 ug of DNA as input using the SQK-LSK109 kit (Oxford Nanopore Technologies, Oxford, UK) according to manufacturer's protocol, except incubation times were increased to 30 min for DNA repair, end-prep and 1 hr for adapter ligation, and 10 min for all elutions from beads. The finished library was loaded on to a single FLO-Min106D R9 Spot-ON flowcell (Oxford Nanopore Technologies, Oxford, UK). MinION sequencing was performed using the standard script for a 60 hr run.

LA4277 Genomic DNA Library Preparation and Illumina Sequencing

Illumina libraries for whole genome sequencing of LA4277-Ro were prepared as described previously (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant Microbe. Interact. 32:949-60 (2019), which is hereby incorporated by reference in its entirety) using nuclear-enriched DNA. Paired-end 150-bp DNA reads were sequenced using the Illumina HiSeq 2000 platform by Genewiz (South Plainfield, NJ).

LA4277 Genome Assembly

Nanopore sequence was base-called using Guppy v 2.3.5+ 53a111f (Wick et al., "Performance Of Neural Network Basecalling Tools for Oxford Nanopore Sequencing," *Genome Biol.* 20:129 (2019), which is hereby incorporated by reference in its entirety). A hybrid approach implemented in MaSuRCA v3.3.2 (Zimin et al., "The MaSuRCA Genome Assembler," *Bioinformatics* 29:2669-77 (2013), which is hereby incorporated by reference in its entirety) was used to de novo assemble the LA4277 Nanopore and Illumina genome sequence. The assembly was polished with Illumina reads and 3 rounds of Pilon correction. The assembly had a total length of 840.2 Mbp, N50 of 1.3 Mbp, and captured over 97% of the BUSCO set.

Agrobacterium-mediated Transient Protein Expression

Cell death assays in five-week-old *N. benthamiana* and *N. glutinosa* plants were performed as described previously (Oh et al., "Tomato 14-3-3 Protein 7 Positively Regulates Immunity-Associated Programmed Cell Death by Enhancing Protein Abundance and Signaling Ability of MAPKKKα," *Plant Cell* 22:260-72 (2010), which is hereby incorporated by reference in its entirety), after dilution of the *Agrobacterium* strains to a final $OD_{600}$ of 0.025 or 0.1 as indicated in the figure legend for Ptr1, 0.05 for AvrRpt2, 0.2 for Rin4, and 0.1 for Prf. For all of the *Agrobacterium* assays, cell death in the infiltrated areas, when it occurred, was strong and reproducible and was documented as plus (100% cell death) or minus (no cell death). Cell death started to appear 2 days after *Agrobacterium* infiltration, except for Prf where it started 4 days after infiltration. To detect protein expression in *N. benthamiana*, a final $OD_{600}$ of 0.1 for Ptr1, 0.05 for AvrRpt2, and 0.2 for Rin4 was used and leaf tissue was sampled 28 hr after infiltration.

For the VIGS experiments, *Agrobacterium* strains were diluted to a final $OD_{600}$ of 0.2 for AvrRpt2, AvrRpt2 (C122A), RipBN, YFP, and Prf(D1416V). Cell death started to appear 2 days after infiltration at which time the Nb 1 plants were scored and photographed. TRV:EC1 and TRV: Ptr1 silenced plants were scored for cell death and photographed 72 hr after infiltration for all constructs except Prf(D1416V), which was scored and photographed 4 days after infiltration. The experiment was repeated three times, using six TRV:EC1 and TRV:Ptr1 plants in each experiment and infiltrating two leaves per plant.

For the synPtr1 complementation assays, *Agrobacterium* containing the Ptr1 and synPtr1 constructs were infiltrated into TRV:EC1 and TRV:Ptr1 silenced plants at a final $OD_{600}$ of 0.025 and co-infiltrated with *Agrobacterium* strains carrying AvrRpt2, AvrRpt2(C122A), RipBN, or YFP at a final $OD_{600}$ of 0.05. Cell death started to appear 48 hr after infiltration. Plants were scored for cell death and photographed 6 days after infiltration. The complementation experiment was repeated three times, using 3-6 TRV:EC1 and TRV:Ptr1 plants in each experiment and infiltrating two leaves per plant. Photos shown in the figures are representative of all replicates. To detect protein expression of Ptr1 and synPtr1 in silenced plants, *Agrobacterium* strains were infiltrated at a final $OD_{600}$ of 0.1. Leaf samples for protein expression were collected 46 hr after infiltration.

Immunoblot Detection of Plant-expressed Proteins

To detect protein expression in *N. benthamiana*, total proteins were extracted as previously described (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia Pseudosolanacearum* by Recognizing the Type III effectors AvrRpt2 and RipBN," *Mol. Plant-Microbe. Interact.* 32:949-60 (2019), which is hereby incorporated by reference in its entirety). To detect AvrRpt2 and Rin4, membranes were probed with anti-c-Myc (GeneScript) antibody at a concentration of 1/7000. Secondary α-mouse-HRP was used at a dilution of 1/10,000 (Sigma-Aldrich). For detection of Ptr1, synPtr1, and RPS2 proteins, membranes were probed with anti-HA antibody at a concentration of 1/2,000 (Roche). Secondary ∝-rat-HRP was used at a dilution of 1/10,000 (Cell Signaling Technology).

Phylogenetic Analyses

Alignments were generated using MUSCLE except where noted otherwise. Phylogenetic trees were constructed in MEGA7 (Kumar et al., "MEGA7: Molecular Evolutionary Genetics Analysis Version 7.0 for Bigger Datasets," *Mol. Biol. Evol.* 33:1870-4 (2016), which is hereby incorporated by reference in its entirety) using the maximum likelihood with a JTT matrix-based model method (Jones et al., "The Rapid Generation of Mutation Data Matrices From Protein Sequences," *Comput. Appl. Biosci.* 8:275-82 (1992), which is hereby incorporated by reference in its entirety). Positions containing gaps and missing data were eliminated. A bootstrap analysis with 1,000 replicates was used to determine the confidence probability of each branch (Felsenstein, "Confidence Limits on Phylogenies: An Approach Using the Bootstrap," *Evolution* 39:783-91 (1985), which is hereby incorporated by reference in its entirety). Data on which AvrRpt2-like proteins are recognized by Ptr1 are from Examples 1-11, Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," *Mol. Plant Microbe. Interact.* 32:949-60 (2019), which is hereby incorporated by reference in its entirety, and the current study.

The top 10 BLASTp hits of the Ptr1, Mr5, and RPS2 NB-ARC domains were identified in the *S. lycopersicoides* v.0.6 genome sequence (Powell et al., "A *Solanum lycopersicoides* Reference Genome Facilitates Biological Discovery in Tomato," *bioRxiv* 2020.2004.2016.039636 (2020), which is hereby incorporated by reference in its entirety), *M domestica* (GDR GDDH13 V1.1) (Jung et al., "15 years of GDR: New Data and Functionality in the Genome Database for Rosaceae," *Nucleic Acids Res.* 47:D1137-45 (2019), which is hereby incorporated by reference in its entirety), and *A. thaliana* (TAIR Araport 11) genome protein databases. The NB-ARC domain of each protein hit was determined using Interpro scan and the amino acid sequences of the NB-ARC domain for each species were aligned to check for the presence of the NB-ARC conserved motifs. To ensure alignment of the sequences, NB-ARC domains missing any of the motifs were removed from further analysis. AvrRpt2 homologs in GenBank were identified through NCBI BLAST, and were aligned with MUSCLE, along with sequences of avrRpt2 homologs from Examples 1-11 and recent papers (Eschen-Lippold et al., "Bacterial AvrRpt2-like Cysteine Proteases Block Activation of the *Arabidopsis* Mitogen-Activated Protein Kinases, MPK4 and MPK11," *Plant Physiol* 171:2223-8 (2016); Dillon et al., "Molecular Evolution of *Pseudomonas syringae* Type III Secreted Effector Proteins," *Front Plant Sci.* 10(418):10.3389/fpls.2019.00418 (2019); and Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant Microbe. Interact. 32:949-60 (2019), which are hereby incorporated by reference in their entirety) (Table 10).

TABLE 10

| AvrRpt2 sequences used in the phylogenetic tree in FIG. 36. | | | |
|---|---|---|---|
| Species | Annotation | ID | Reference |
| *Acidovorax avenae* subsp. *avenae* ATCC 19860 | AvrRpt2 | ADX44172.1 | Eschen-Lippold et al. (2016)[a] |
| *Acidovorax citrulli* | hypothetical protein | WP_082091296.1 | |
| *Burkholderia pyrrocinia* Lyc2 | AvrRpt2 | KFL50402.1 | Eschen-Lippold et al. (2016)[a] |
| *Collimonas fungivorans* | cysteine protease | WP_082814589.1 | |
| *Erwinia amylovora* ATCC 49946 | AvrRpt2 | CBJ45097.1 | Eschen-Lippold et al. (2016)[a] |
| *Mesorhizobium huakuii* 7653R | AvrRpt2 | AID34449.1 | Eschen-Lippold et al. (2016)[a] |
| *Neorhizobium galegae* | cysteine protease | WP_151045106.1 | |
| *P syringae* pv. *castaneae* | AvrRpt2 | PcsICMP9421 | Dillon et al. (2019)[b] |
| *P syringae* pv. *morsprunorum* | AvrRpt2 | PmpICMP3897 | Dillon et al. (2019)[b] |
| *P. syringae* pv. *castaneae* | AvrRpt2 | PcsICMP9419 | Dillon et al. (2019)[b] |
| *P. syringae* pv. *castaneae* | AvrRpt2 | PcsICMP9420 | Dillon et al. (2019)[b] |
| *P. syringae* pv. *caricapapayae* | AvrRpt2 | PcaICMP7496 | Dillon et al. (2019)[b] |
| *P. syringae* pv. *lachrymans* | AvrRpt2 | Pla1188_1 | Dillon et al. (2019)[b] |
| *P. syringae* pv. *maculicola* | AvrRpt2 | PmaM4a | Dillon et al. (2019)[b] |
| *P. syringae* pv. *persicae* | AvrRpt2 | PpeICMP3706 | Dillon et al. (2019)[b] |
| *P. syringae* pv. *persicae* | AvrRpt2 | PpeICMP5786 | Dillon et al. (2019)[b] |
| *P. syringae* pv. *sesami* | AvrRpt2 | PseHC_1 | Dillon et al. (2019)[b] |
| *P. syringae* pv. *sesami* | AvrRpt2 | PseICMP3386 | Dillon et al. (2019)[b] |
| *P. syringae* pv. *sesami* | AvrRpt2 | PseICMP4995 | Dillon et al. (2019)[b] |
| *P. syringae* pv. *sesami* | AvrRpt2 | PseICMP7459 | Dillon et al. (2019)[b] |
| *P. syringae* pv. *sesami* | AvrRpt2 | PseICMP763 | Dillon et al. (2019)[b] |
| *P. syringae* pv. *spinaceae* | AvrRpt2 | PspICMP16928 | Dillon et al. (2019)[b] |
| *P. syringae* pv. *spinaceae* | AvrRpt2 | PspICMP16929 | Dillon et al. (2019)[b] |
| *P. syringae* pv. *tagetis* | AvrRpt2 | PtgICMP4092 | Dillon et al. (2019)[b] |
| *P. syringae* pv. *tremae* | AvrRpt2 | PtrICMP9151 | Dillon et al. (2019)[b] |
| *P. syringae* pv. *zizaniae* | AvrRpt2 | PziICMP8959 | Dillon et al. (2019)[b] |
| *P. syringae* pv. *zizaniae* | AvrRpt2 | PziICMP8921 | Dillon et al. (2019)[b] |
| *Pseudomonas amygdali* | cysteine protease avirulence protein AvrRpt2 | WP_103379467.1 | |

TABLE 10-continued

AvrRpt2 sequences used in the phylogenetic tree in FIG. 36.

| Species | Annotation | ID | Reference |
|---|---|---|---|
| *Pseudomonas amygdali* | cysteine protease avirulence protein AvrRpt2 | WP_081003941.1 | |
| *Pseudomonas caricapapayae* | cysteine protease | WP_122340504.1 | |
| *Pseudomonas coronafaciens* | cysteine protease avirulence protein AvrRpt2 | WP_081021999.1 | |
| *Pseudomonas syringae* | cysteine protease avirulence protein AvrRpt2 | WP_080397204.1 | |
| *Pseudomonas syringae* group | cysteine protease avirulence protein AvrRpt2 | WP_081012136.1 | |
| *Pseudomonas syringae* group | peptidase C70 | WP_007247525.1 | |
| *Pseudomonas syringae* group | cysteine protease avirulence protein AvrRpt2 | WP_083492254.1 | |
| *Pseudomonas syringae* group | cysteine protease avirulence protein AvrRpt2 | WP_080392394.1 | |
| *Pseudomonas syringae* group | cysteine protease avirulence protein AvrRpt2 | WP_099264889.1 | |
| *Pseudomonas syringae* group | cysteine protease | WP_080378320.1 | |
| *Pseudomonas syringae* group genomosp. 3 | cysteine protease, partial | WP_122290586.1 | |
| *Pseudomonas syringae* pv. *coriandricola* | cysteine protease avirulence protein AvrRpt2 | KPW75402.1 | |
| *Pseudomonas syringae* pv. *papulans* | hypothetical protein ALQ56_200124 | RMN57113.1 | Dillon et al. (2019)[b] |
| *Pseudomonas syringae* pv. *tomato* | AvrRpt2 | Pto1108 | Dillon et al. (2019)[b] |
| *Pseudomonas syringae* pv. *tomato* | AvrRpt2 | PtoICMP4263 | Dillon et at. (2019)[b] |
| *Pseudomonas syringae* pv. *tomato* | AvrRpt2 | PtoICMP7230 | Dillon et al. (2019)[b] |
| *Pseudomonas syringae* pv. *tomato* | AvrRpt2 | PtoK40 | Dillon et al. (2019)[b] |
| *Pseudomonas syringae* pv. *tomato* | AvrRpt2 | PtoT1 | Dillon et al. (2019)[b] |
| *Pseudomonas syringae* pv. *tomato* JL1065 | AvrRpt2 | CAA79815.2 | Eschen-Lippold et al. (2016)[a] |
| *Pseudomonas syringae* pv. *tomato* NY 15125 | AvrRpt2 | | Examples 1-11; Mazo-Molina et al. (2019)[c] |
| *Pseudomonas syringae* pv. *tomato* NYS-T1 | cysteine protease | KGK92417.1 | |
| *Ralstonia solanacearum* CMR15 | hypothetical protein | WP_080658778.1 | |
| *Sinorhizobium medicae* WSM1369 | AvrRpt2 | NZ_AQUS01000051.1 | Eschen-Lippold et al. (2016)[a] |
| *Sinorhizobium meliloti* | cysteine protease avirulence protein AvrRpt2 | WP_146722358.1 | |

Table 10 references include:
[a]Eschen-Lippold et al., "Bacterial AvrRpt2-like Cysteine Proteases Block Activation of the *Arabidopsis* Mitogen-Activated Protein Kinases, MPK4 and MPK11," *Plant Physiol* 171:2223-8 (2016);
[b]Dillon et al., "Molecular Evolution of *Pseudomonas syringae* Type III Secreted Effector Proteins," *Front Plant Sci.* 10(418):10.3389/fpls.2019.00418 (2019); and
[c]Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant Microbe. Interact. 32:949-60 (2019), each of which is hereby incorporated by reference in its entirety. Each sequence identified in Table 10 is hereby incorporated by reference in its entirety.

Virus-Induced Gene Silencing (VIGS)

The Ptr1-targeting VIGS sequence was selected using the SGN VIGS Tool (Fernandez-Pozo, et al., "The SGN VIGS Tool: User-friendly Software to Design Virus-Induced Gene Silencing (VIGS) Constructs for Functional Genomics," *Mol. Plant* 8:486-88 (2015), which is hereby incorporated by reference in its entirety). The fragment was cloned into pDONR/Zeo (Invitrogen) followed by an LR reaction (Invitrogen) into pQ11 (Liu et al., "Virus-Induced Gene Silencing in Tomato," *Plant J.* 31:777-86 (2002), which is hereby incorporated by reference in its entirety). The resulting pQ11:Ptr1 (TRV:Ptr1) construct was transformed into *A. tumefaciens* GV2260. The control, pQ11:EC1 (TRV:EC1), contains a small DNA fragment from *E. coli* and was described previously (Rosli et al., "Transcriptomics-Based Screen for Genes Induced by Flagellin and Repressed by Pathogen Effectors Identifies a Cell Wall-Associated Kinase Involved in Plant Immunity," *Genome Biol.* 14:R139 (2013), which is hereby incorporated by reference in its entirety). VIGS constructs were prepared for infections in *N. benthamiana* as described previously (Chakravarthy et al., "Identification of *Nicotiana benthamiana* Genes Involved in Pathogen-Associated Molecular Pattern-Triggered Immunity," *Mol. Plant-Microbe. Interact.* 23:715-26 (2010), which is hereby incorporated by reference in its entirety). Cell death assays were performed five-to-six weeks after agroinfiltration with the VIGS constructs.

Generation of Synthetic Ptr1

Figure 31A:
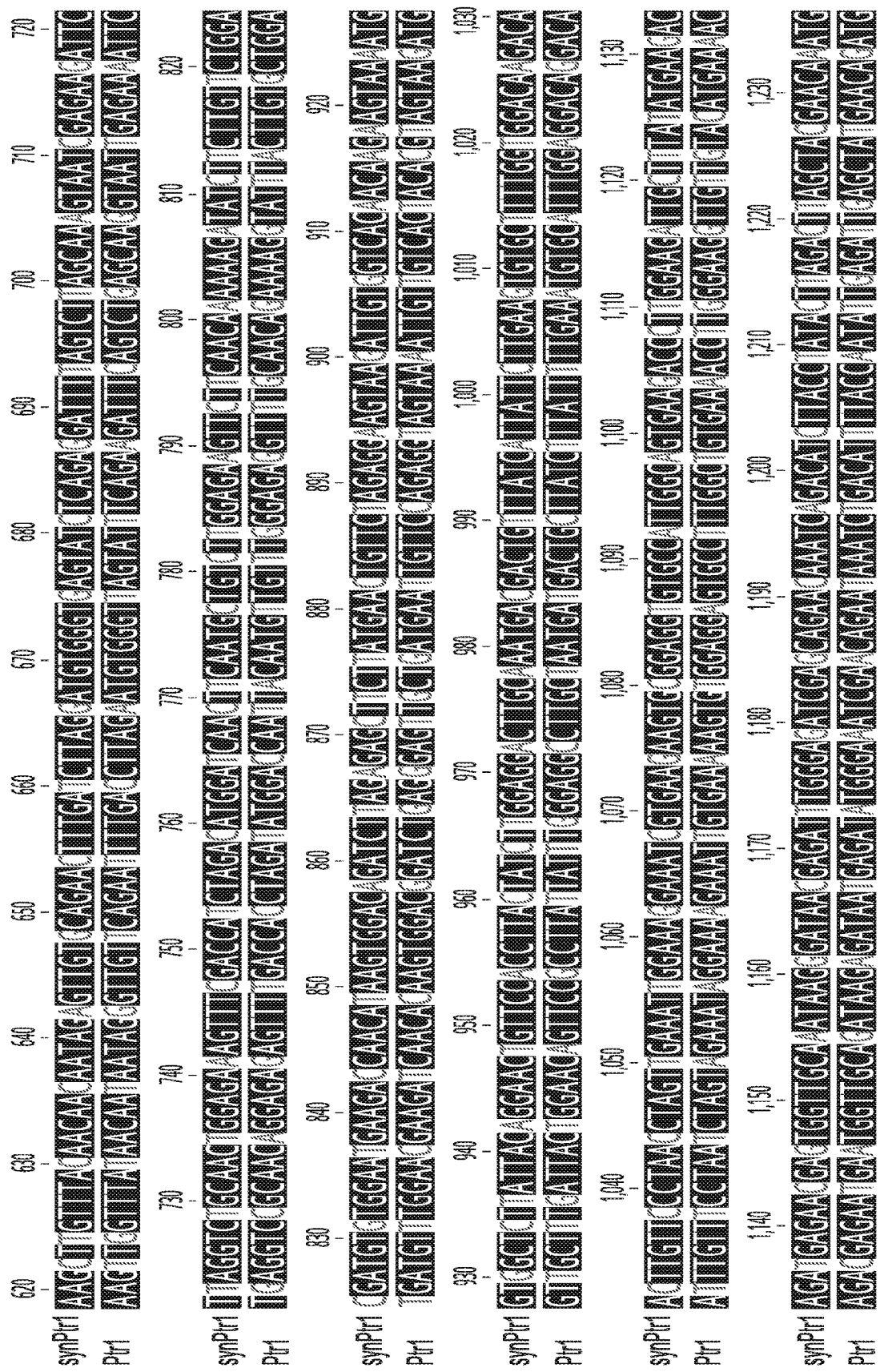
FIG. 31A and FIG. 31B show a nucleotide alignment of Ptr1 (SEQ ID NO:18) and synthetic Ptr1 (synPtr1, SEQ ID NO:126) (Table 13).
Figure 31B:
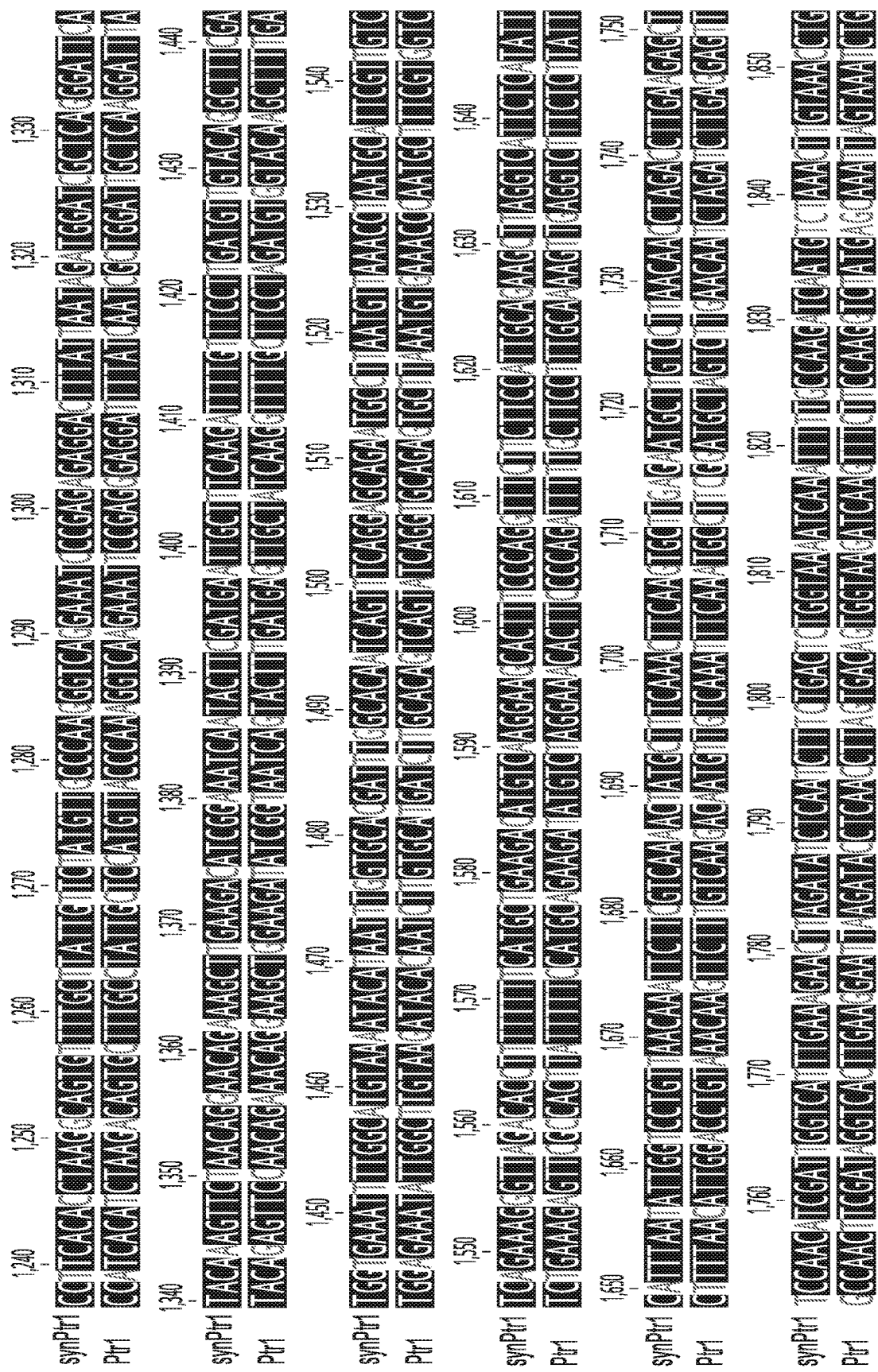
Figure 31B:
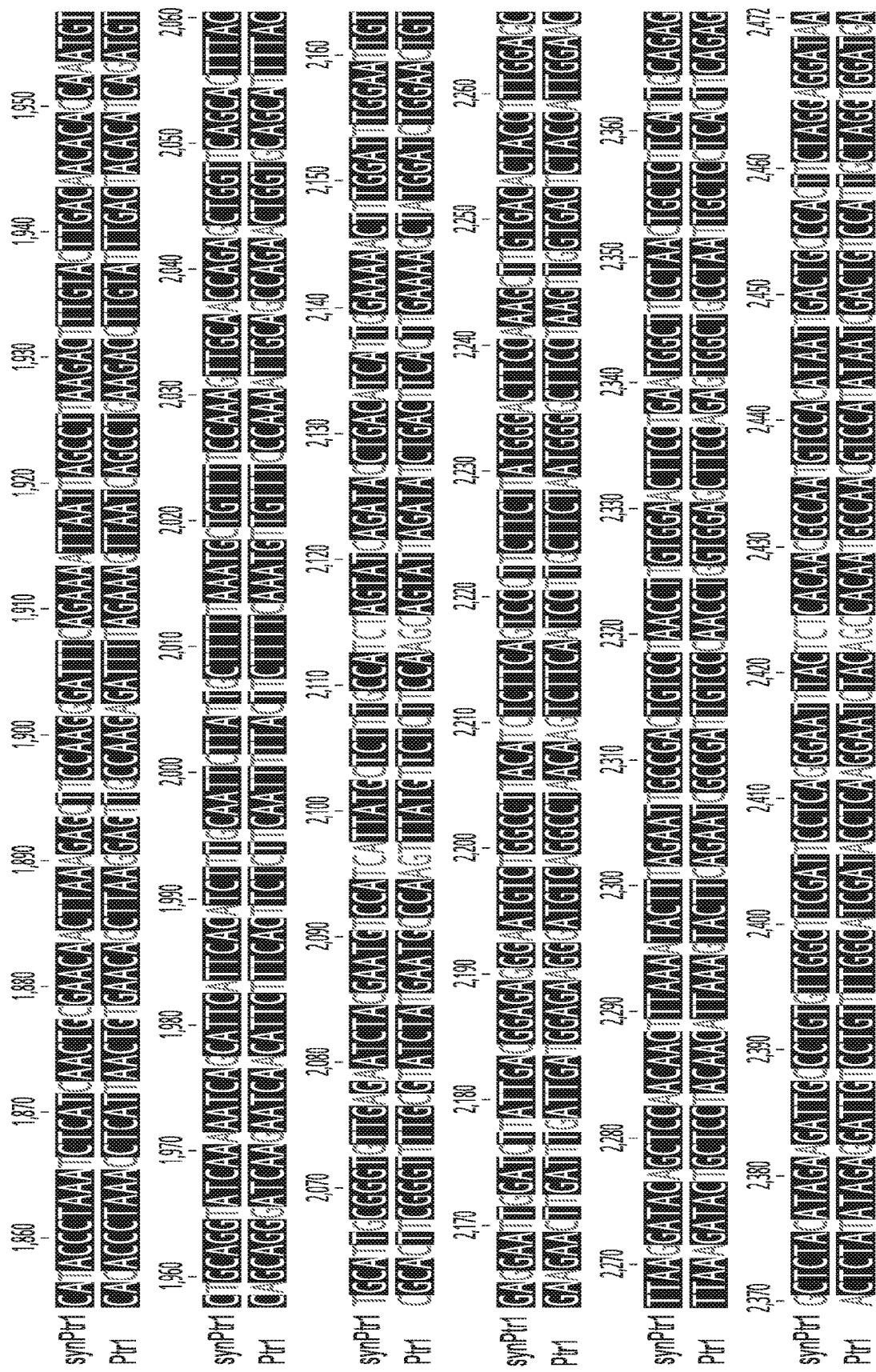

The synthetic Ptr1 (synPtr1) sequence was designed using the Integrated DNA Technologies (IDT) Codon Optimization Tool as previously described (Roberts et al., "Mai1 Protein Acts Between Host Recognition of Pathogen Effectors and Mitogen-Activated Protein Kinase Signaling," *Mol. Plant-Microbe. Interact.* 32:1496-507 (2019), which is hereby incorporated by reference in its entirety) (FIGS. 31A-31B). The stop codon was removed in order to generate a C-terminal HA-tag and KpnI and StuI restriction sites were added to the 5' and 3' end, respectively, for cloning into pBTEX. The synPtr1 was synthesized by IDT (Skokie, IL, USA) as a gBlocks fragment and cloned into pBTEX using the In-fusion cloning kit following the manufacturer's instructions.

Data Availability

Nucleotide and amino acid sequences have been deposited in GenBank for Ptr1 from *S. lycopersicoides* (GenBank accession no. MT134103), *N. benthamiana*, NbPtr1a (MT134102) and potato StPtr1 (MT134101), each of which is hereby incorporated by reference in its entirety.

Example 13: Identifying Candidates for the Ptr1 Gene

Figure 19A:
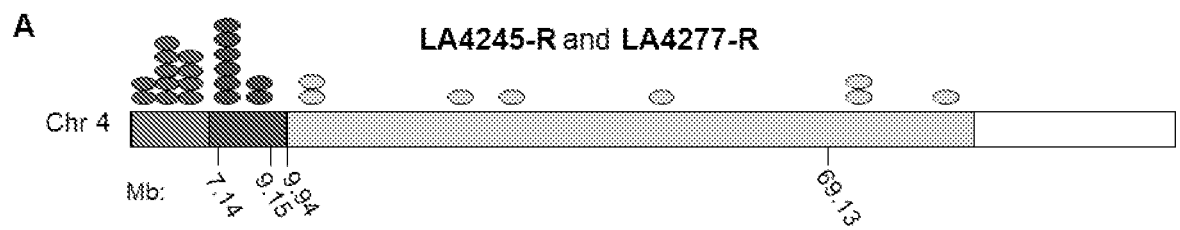
FIG. 19A, FIG. 19B, and FIG. 19C depict delimiting the region containing Ptr1 using progeny of selfed LA4277-R (Ptr1/ptr1) plants.
Figure 19B:
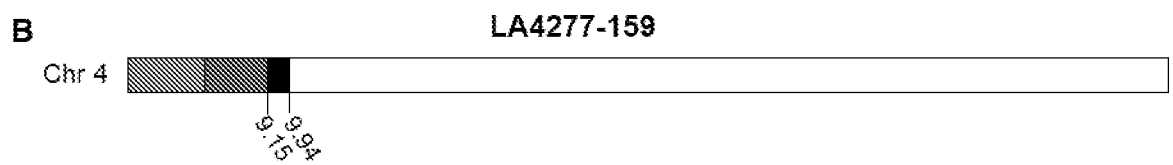

The introgression on chromosome 4 containing the Ptr1 locus is maintained in heterozygous condition and such Ptr1/ptr1 plants are referred to as LA4245-R and LA4277-R. Homozygous Ptr1/Ptr1 plants are referred to as LA4245-Ro and LA4277-Ro and ptr1/ptr1 plants are referred to as LA4245-S and LA4277-S (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN,"*Mol. Plant Microbe. Interact.* 32:949-60 (2019), which is hereby incorporated by reference in its entirety). The introgression region shared by LA4245-R and LA4277-R contains 16 annotated NLR-encoding genes in the current assembly of the *S. lycopersicoides* genome sequence (Powell et al., "A *Solanum lycopersicoides* Reference Genome Facilitates Biological Discovery in Tomato," bioRxiv 2020.2004.2016.039636 (2020), which is hereby incorporated by reference in its entirety). An additional ~50 NLR genes occur only in LA4277-R; the latter genes were not considered as candidates for Ptr1 (FIG. 19A). To identify candidates for the Ptr1 gene, F2 progeny from a selfed LA4277-R plant were screened for recombinants. Plants were genotyped for the presence of the *S. lycopersicoides* introgression using DNA markers at 7.14, 9.94, and 69.13 megabases (Mb) (FIG. 19A). From 585 F2 plants, one plant, LA4277-159, was identified with a recombination between markers 7.14 and 9.94. An additional marker at 9.15 Mb further delimited the region of the recombination and indicated this plant retained just a small portion of the *S. lycopersicoides* segment shared by both LA4245-R and LA4277-R (FIG. 19B). This segment contains eight NLR-encoding genes.

Figure 19C:
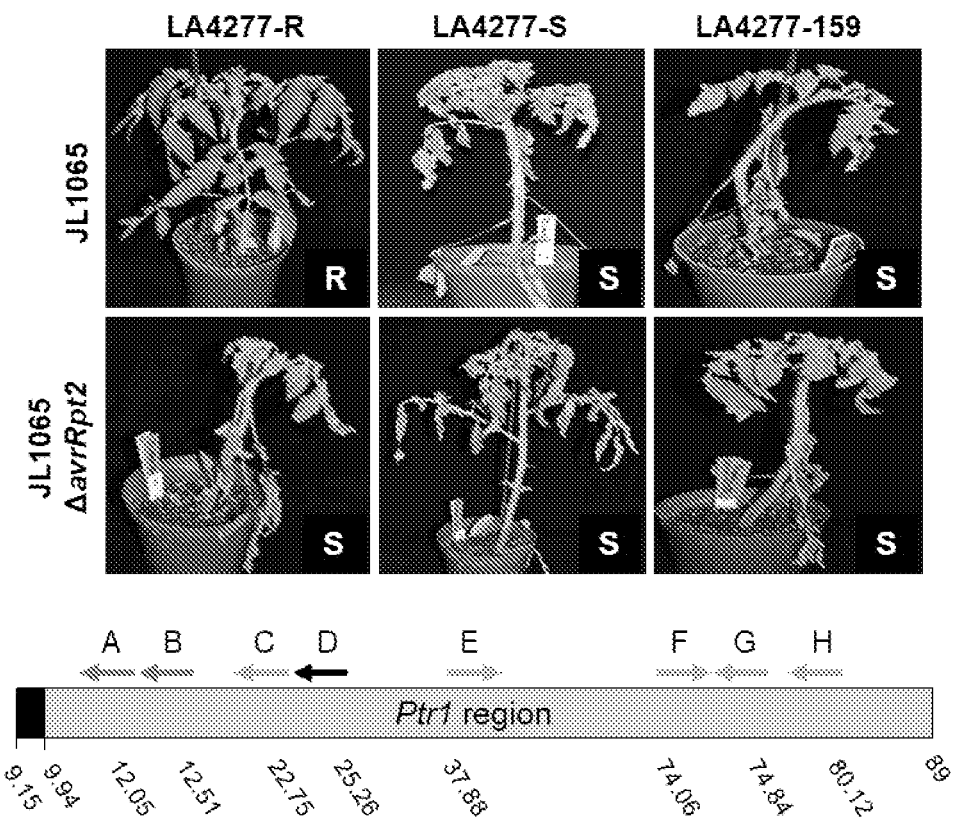

To determine if LA4277-159 contained the Ptr1 locus, selfed progeny of the recombinant plant that contain the *S. lycopersicoides*0-9.94 Mb segment were identified by using DNA markers. These plants, and controls, were then vacuum infiltrated with Pst JL1065 (which has avrRpt2) and JL1065ΔavrRpt2, which lacks avrRpt2. As expected, LA4277-R, LA4277-S, and the LA4277-159 progeny all developed extensive disease upon inoculation with JL1065ΔavrRpt2 (FIG. 19B). However, when infiltrated with JL1065, LA4277-159 progeny and LA4277-S developed disease whereas LA4277-R plants remained disease-free. Considering the location of the recombination event in LA4277-159 this susceptible phenotype eliminated the eight NLR genes in the LA4277-159 *S. lycopersicoides* segment as candidates for Ptr1 and indicated Ptr1 is one of the eight NLR genes lying between marker 9.94 and the end of the introgression at 89 Mb (FIG. 19C). These genes were named A, B, C, D, E, F, G, and H based on their sequential location on chromosome 4 (FIG. 19C; Table 11).

TABLE 11

Predicted gene models for the Ptr1 candidates in the *S. lycopersicoides* genome sequence. The start and stop of each gene model corresponds to the genomic coordinates along the chromosome. The number of nucleotides and amino acids correspond to the gene models. Candidate D has a nonsense mutation at base pair 391 which terminates its open reading frame.

| Candidate | Gene ID | Start | Stop | No. Nucleotides | No. Amino Acids |
|---|---|---|---|---|---|
| A | Solyd04g059470 | 12054434 | 12051962 | 2472 | 823 |
| B | Solyd04g059610 | 12505909 | 12503356 | 2553 | 850 |
| C | Solyd04g060430 | 22745706 | 22743765 | 1275 | 424 |
| D | Solyd04g060640 | 25255273 | 25252810 | 2464 | pseudogene |
| E | Solyd04g061490 | 37884585 | 37886367 | 1782 | 593 |
| F | Solyd04g064510 | 74057098 | 74064935 | 2457 | 818 |
| G | Solyd04g064750 | 74838450 | 74834836 | 3276 | 1091 |
| H | Solyd04g067320 | 80119015 | 80115223 | 3480 | 1159 |

Next, RNA-Seq analysis was used to determine which of the eight Ptr1 candidates is expressed in leaves of a LA4277-Ro (Ptr1/Ptr1) plant (Table 12). Seven-week-old plants were vacuum infiltrated with JL1065 and the abundance of transcripts was determined by 3' RNA-Seq. Transcripts of only three candidates, A, B and D were detectable by this method (Table 11). Each of these genes was PCR amplified from cDNA derived from a LA4277-Ro plant and sequenced to determine whether they were the same as annotated in the *S. lycopersicoides* LA2951 genome sequence. In addition, an LA4277 genome sequence was generated and assembled as a comparison. Candidate D was found to be a pseudogene as it contained multiple mutations disrupting the reading frame. The sequence of candidate A was identical between LA2951 and LA4277 whereas one SNP occurred in candidate B which changes an alanine at position 647 in LA2951 to a valine in LA4277 (GCT>GTT).

TABLE 12

Transcripts of three of the Ptr1 candidates are detectable in leaves. 3' RNA-Seq data (normalized reads per million, RPMs) of the eight Ptr1 candidates in LA4277-Ro (Ptr1/Ptr1) plants that were vacuum infiltrated with Pst JL1065 and sampled 5 hr later.

| Candidate | Gene ID | Rep 1 | Rep 2 | Rep 3 | Rep 4 | Mean | Standard Deviation |
|---|---|---|---|---|---|---|---|
| A | Solyd04g059470 | 5.89 | 4.87 | 3.61 | 2.74 | 4.28 | 1.386 |
| B | Solyd04g059610 | 0.34 | 1.26 | 0.87 | 0 | 0.62 | 0.558 |
| C | Solyd04g060430 | 0 | 0 | 0 | 0 | 0 | 0.000 |
| D | Solyd04g060640 | 1.01 | 0.94 | 1.88 | 1.31 | 1.29 | 0.428 |
| E | Solyd04g061490 | 0 | 0 | 0 | 0 | 0 | 0.000 |
| F | Solyd04g064510 | 0 | 0 | 0 | 0 | 0 | 0.000 |
| G | Solyd04g064750 | 0 | 0 | 0 | 0 | 0 | 0.000 |
| H | Solyd04g067320 | 0 | 0 | 0 | 0 | 0 | 0.000 |

Example 14: Candidate A Mediates Recognition of AvrRpt2 and RipBN in *Nicotiana glutinosa*

Candidates A and B were cloned into a binary vector under control of the CaMV 35S promoter and tested by *Agrobacterium*-mediated transient transformation (agroinfiltration'). *Nicotiana glutinosa* was used in these experiments because it was reported previously that AvrRpt2 does not cause cell death in this species whereas it does in *N. benthamiana* and this would have interfered with the assays (Mudgett et al., "Characterization of the *Pseudomonas syringae* pv. Tomato AvrRpt2 Protein: Demonstration of Secretion and Processing During Bacterial Pathogenesis," *Mol. Microbiol.* 32:927-41 (1999); Day et al., "Molecular Basis for the RIN4 Negative Regulation of RPS2 Disease Resistance," *Plant Cell* 17:1292-305 (2005); and Kessens et al., "Determining the GmRIN4 Requirements of the Soybean Disease Resistance Proteins Rpg1b and Rpg1r Using a *Nicotiana glutinosa*-Based Agroinfiltration System," *PLoS One* 9:e108159 (2014), which are hereby incorporated by reference in their entirety).

Figures 20A, 20B:
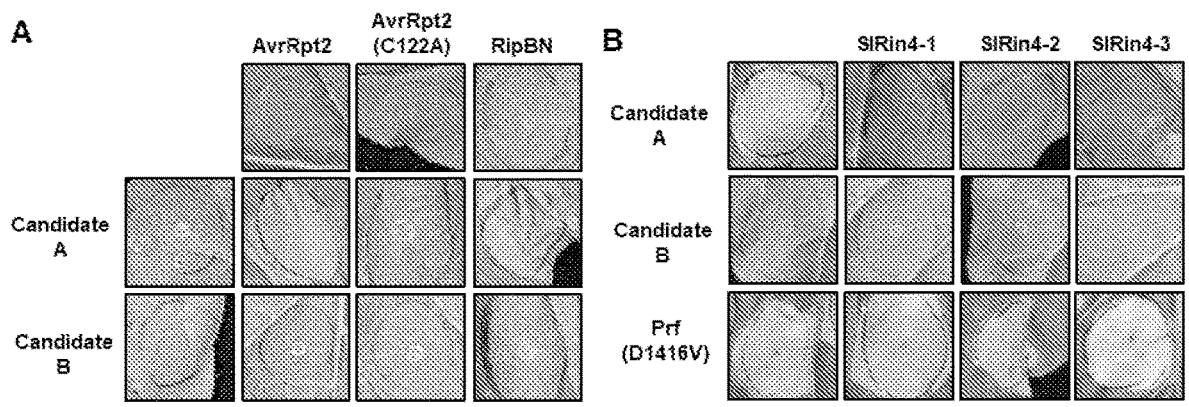
FIG. 20A, FIG. 20B, FIG. 20C, and FIG. 20D show that candidate A mediates recognition of AvrRpt2 and RipBN in *Nicotiana glutinosa*.

Syringe infiltration into leaves of *N. glutinosa* of a relatively low titer ($OD_{600}$=0.025) of *Agrobacterium* carrying constructs of candidate A or B expressed from the CaMV 35S promoter caused no observable host response (FIG. 20A). However, co-expression of candidate A with either AvrRpt2 or RipBN induced cell death two days after infiltration. No cell death was observed when candidate A was co-expressed with the protease-inactive protein AvrRpt2 (C122A). Candidate B did not induce cell death when co-expressed with any of the effector proteins (FIG. 20A).

Figure 25A:
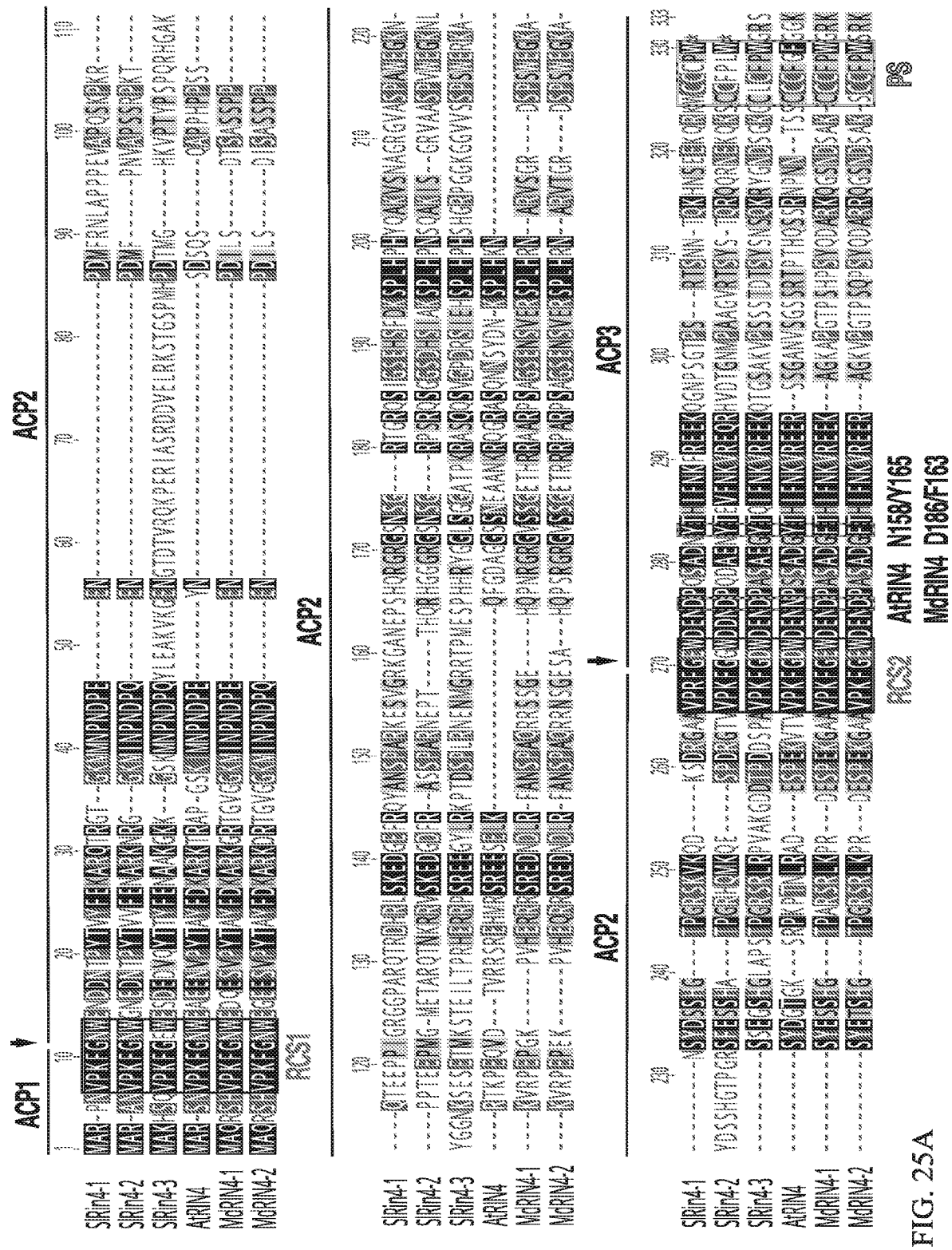
FIG. 25A and FIG. 25B show the amino acid sequences of Rin4 proteins in (among others) tomato and *Arabidopsis* and suppression of candidate A-mediated cell death by N- or C-terminal Myc-tagged tomato Rin4 proteins.
Figure 25B:
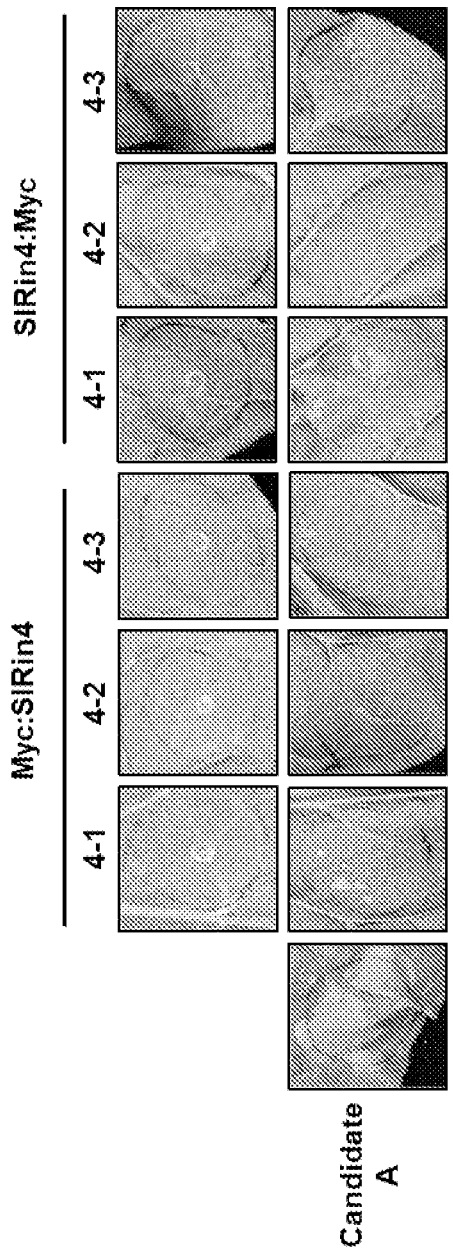
Figure 26B:
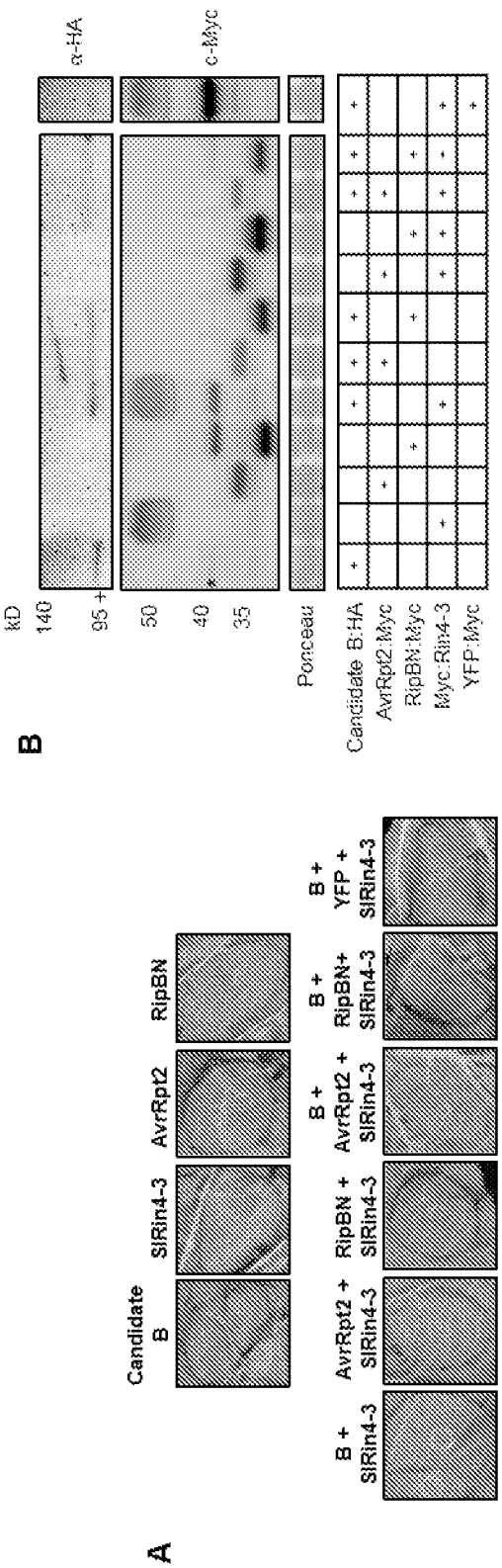
FIG. 26A and FIG. 26B show that candidate B does not mediate recognition of AvrRpt2 or RipBN in *N. glutinosa*.
Figure 26A:
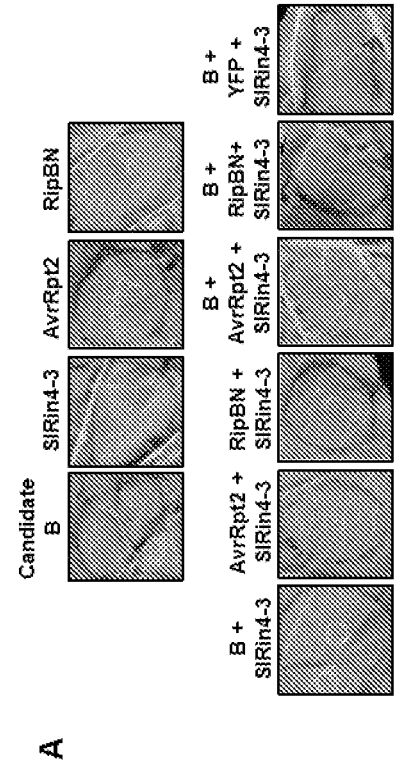

RPS2 can cause cell death on its own when overexpressed in *N. benthamiana* leaves and this cell death is suppressed by co-expression of AtRIN4 (Day et al., "Molecular Basis for the RIN4 Negative Regulation of RPS2 Disease Resistance," *Plant Cell* 17:1292-305 (2005), which is hereby incorporated by reference in its entirety). Therefore *Agrobacterium* strains carrying the candidate A and B constructs were syringe infiltrated at a four-fold higher titer ($OD_{600}$=0.1). At this titer, candidate A, but not candidate B, induced strong cell death on its own. Tomato has three Rin4 genes that are expressed in leaves (SlRin4-1, SlRin4-2, and SlRin4-3) (FIG. 25A; (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," *Mol. Plant Microbe. Interact.* 32:949-60 (2019), which is hereby incorporated by reference in its entirety). To test whether the tomato Rin4 proteins can suppress cell death caused by candidate A, SlRin4-1, SlRin4-2 and SlRin 4-3 were expressed with candidate A in *N. glutinosa* leaves. Each of these proteins suppressed candidate A-mediated cell death (FIG. 20B; FIG. 25B). This observation indicated that the tomato Rin4 proteins are functionally equivalent and we therefore chose one, SlRin4-3, as representative of these proteins for some of the subsequent experiments. Candidate B did not cause cell death even at higher *Agrobacterium* titers nor was it affected by co-expression of SlRin4-3 or either of the effectors (FIG. 20B; FIGS. 26A-26B). A constitutively-active version of Prf was used as a positive control for cell death in these experiments and this response was not suppressed by co-expression with the tomato SlRin4 proteins (FIG. 20B).

Figure 20C:
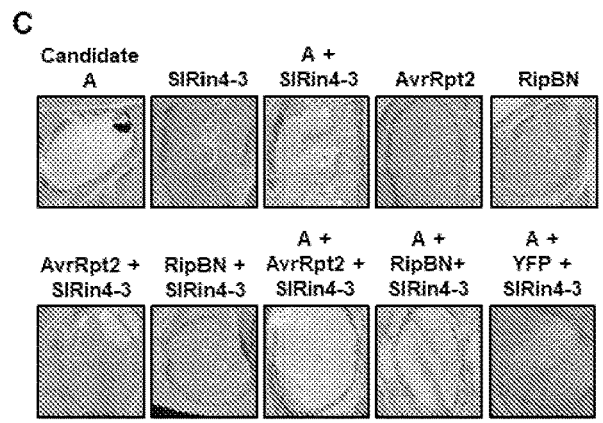
Figure 20D:
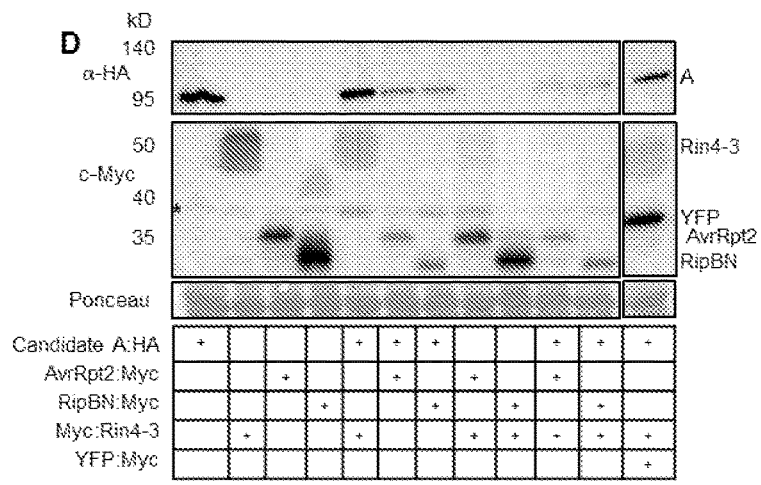
Figure 27:
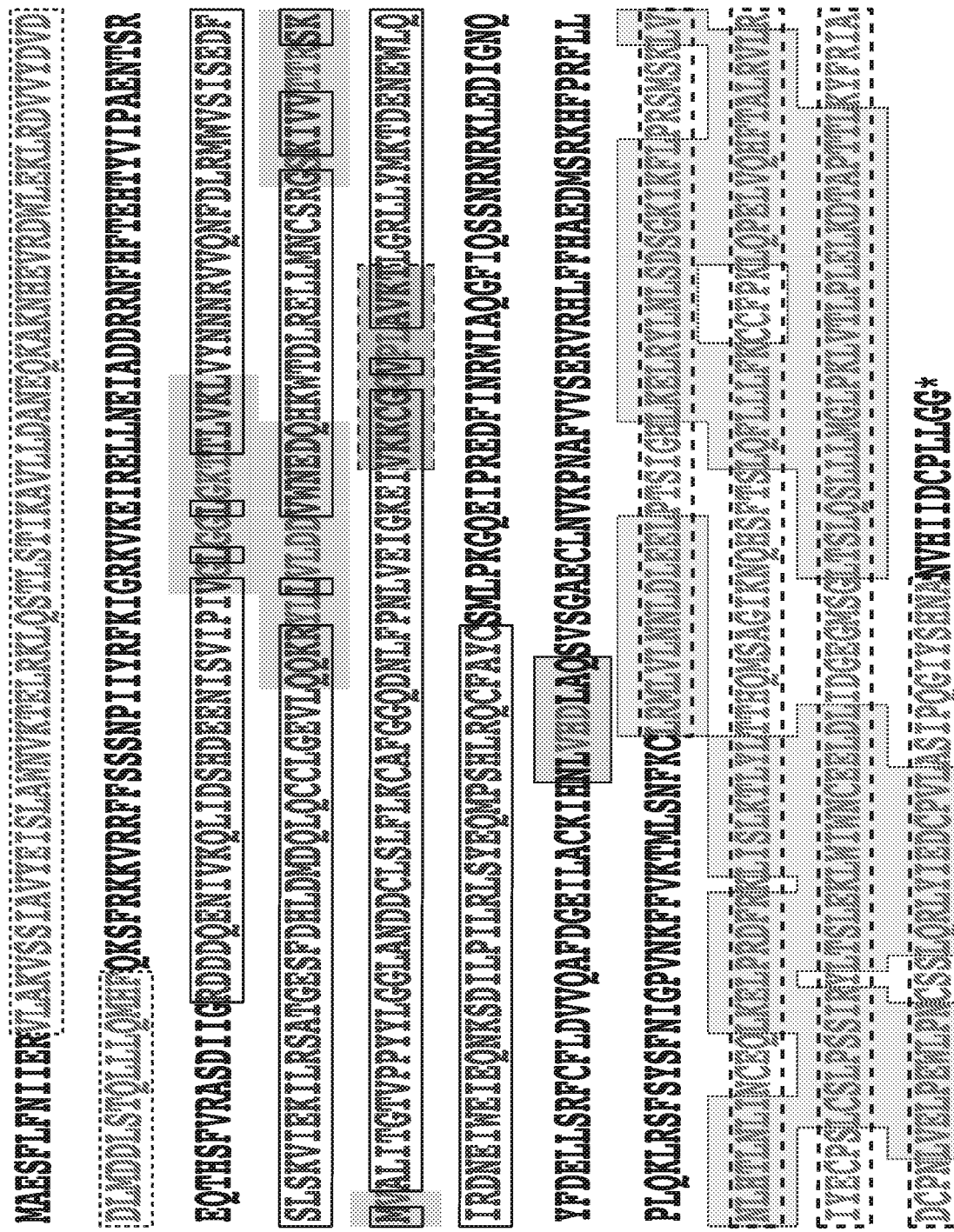
FIG. 27 shows the amino acid sequence of the predicted Ptr1 protein showing motifs characteristic of NLR immune receptors. The full sequence of Ptr1 (SEQ ID NO:19) is shown with annotations, and motifs are set forth below the full sequence: NB-ARC P-loop (Ptr1, SEQ ID NO:91; Consensus, SEQ ID NO:92); NB-ARC kinase 2 (Ptr1, SEQ ID NO:93; Consensus, SEQ ID NO:94); NB-ARC kinase 3a (Ptr1, SEQ ID NO:95; Consensus, SEQ ID NO:96); NB-ARC GLPL (Ptr1, SEQ ID NO:97; Consensus, SEQ ID NO:98); NBR-ARC MHD (Ptr1, SEQ ID NO:99; Consensus, SEQ ID NO: 100); Leucine-rich repeats (SEQ ID NOs:101-113) (Table 13). The LRR repeats (LxxLxxLxxLxLxxLxx motif) were identified using the LRRSearch Tool (Bej et al., "LRRsearch: An Asynchronous Server-Based Application for the Prediction of Leucine-Rich Repeat Motifs and an Integrative Database of NOD-like Receptors," *Comp. Biol. Med.* 53:164-70 (2014), which is hereby incorporated by reference in its entirety) and adjusted manually.

In *Arabidopsis*, AvrRpt2 cleaves AtRIN4 resulting in the activation of RPS2 (Axtell et al., "Initiation of RPS2-Specified Disease Resistance in *Arabidopsis* is Coupled to the AvrRpt2-Directed Elimination of RIN4," *Cell* 112:369-77 (2003); and Mackey et al., "*Arabidopsis* RIN4 is a Target of the Type III Virulence Effector AvrRpt2 and Modulates RPS2-Mediated Resistance," Cell 112:379-89 (2003), which are hereby incorporated by reference in their entirety). To test whether this is the case for candidate A, we co-expressed candidate A with SlRin4-3 with or without the effectors AvrRpt2 and RipBN (FIG. 20C). Co-expression of either one of the effectors with candidate A and SlRin4-3 restored candidate A-induced cell death and this was correlated with a decrease in the abundance of Rin4 protein (FIG. 20D). All proteins were found to be expressed as expected by immunoblotting (FIG. 20D). These experiments demonstrate that candidate A is the Ptr1 gene. The predicted Ptr1 protein is a coiled-coil NLR with 13 leucine-rich repeats and all of the other hallmark motifs of this class of protein (FIG. 27).

Figure 21A:
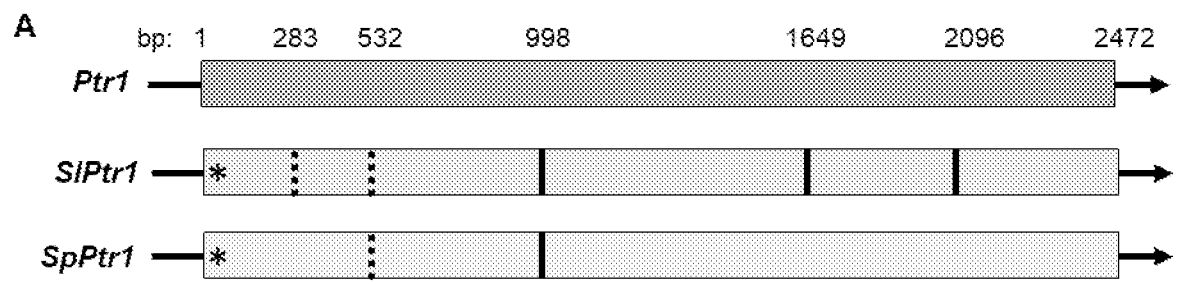
FIG. 21A and FIG. 21B depict Ptr1 orthologs in various solanaceous species.
Figure 28A:
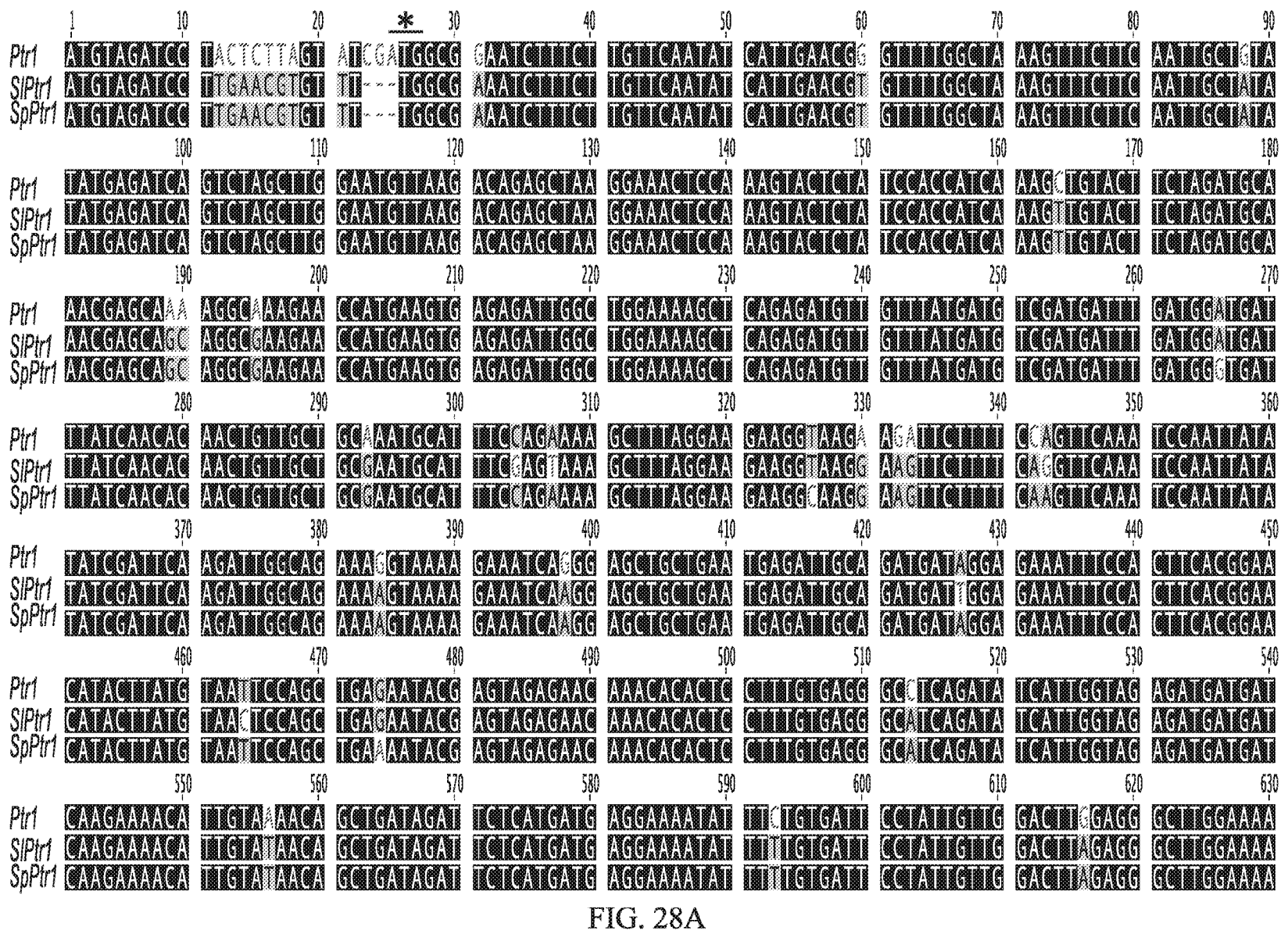
Figure 28A:
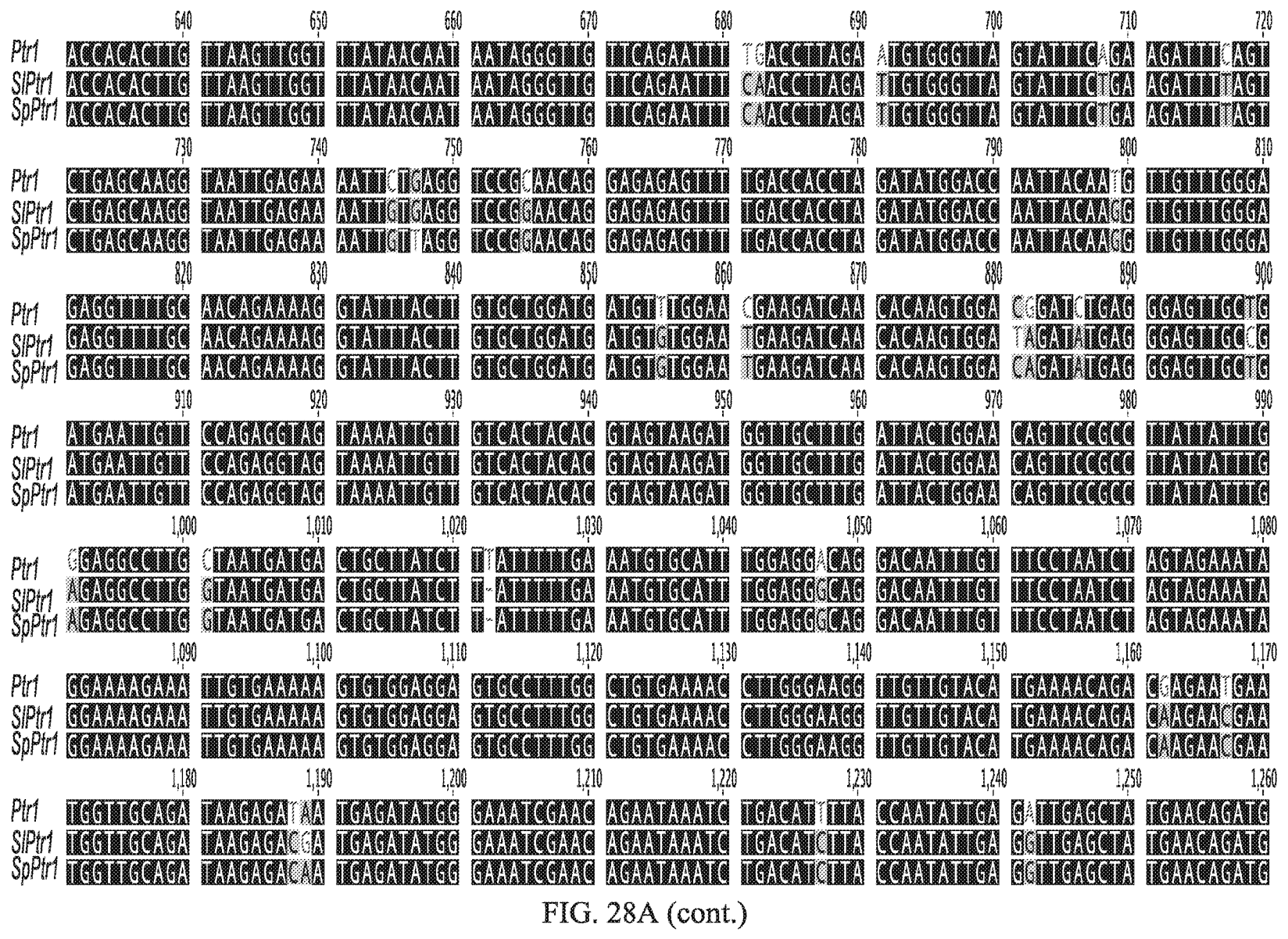
Figure 28B:
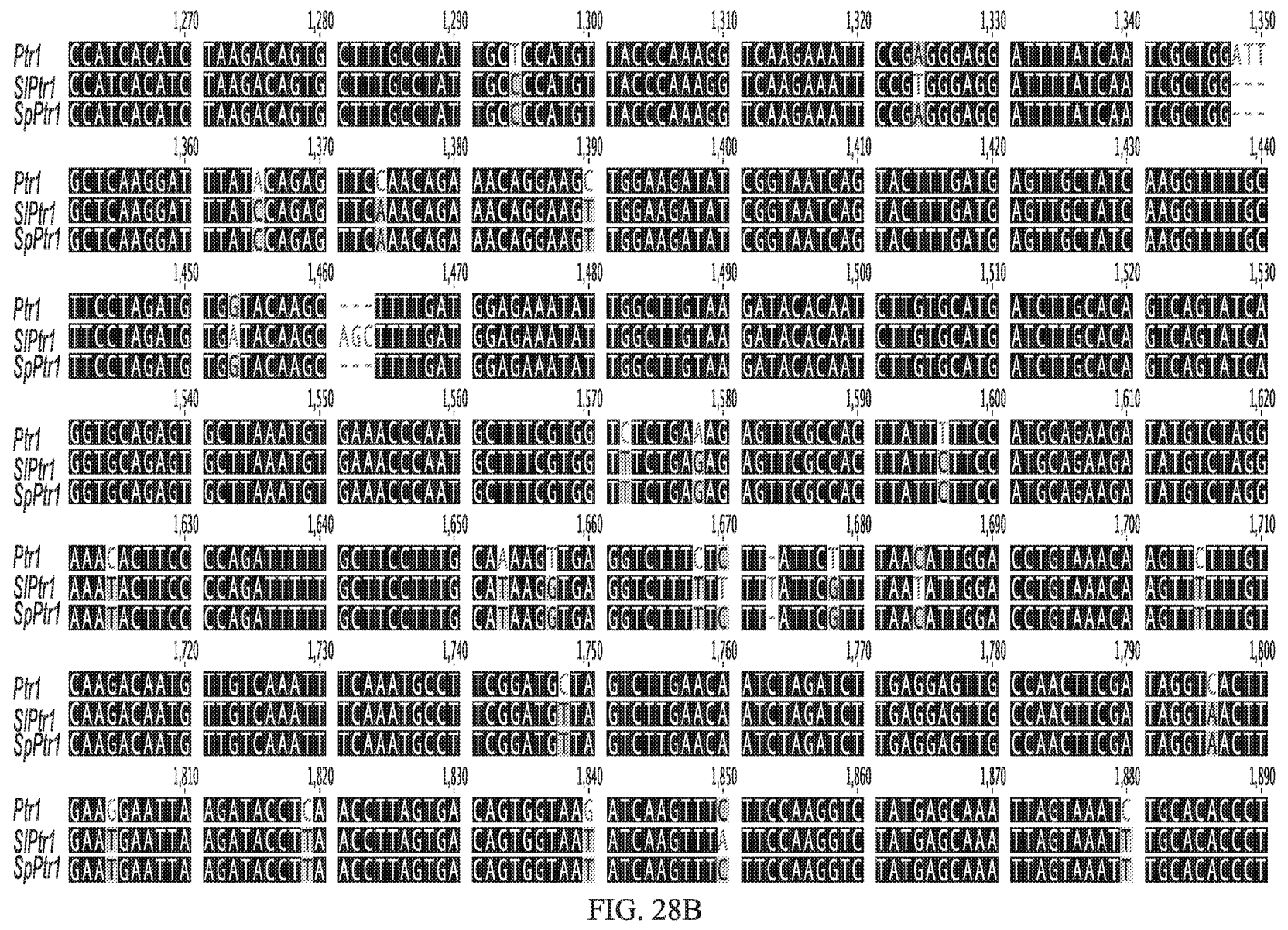
Figure 28B:
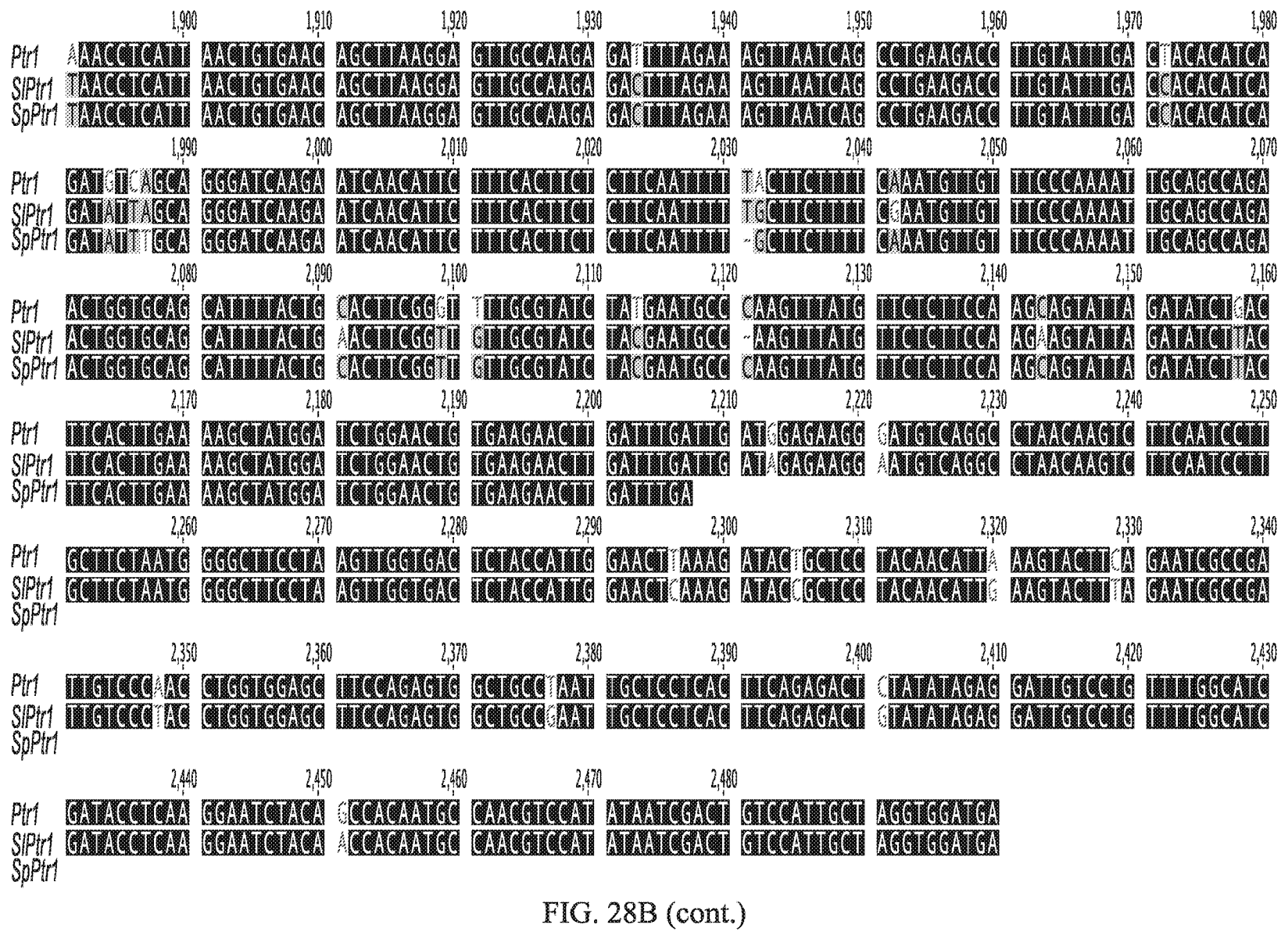

Example 15: Ptr1 is a Pseudogene in Tomato and *S. pennellii*, but Intact Ptr1 Genes Occur in Other Solanaceous Species No accessions of tomato or its close wild relatives are known that recognize AvrRpt2. The genome sequences of the tomato reference genome (Heinz 1706) and its wild relative *S. pennellii* (LA0716; Bolger et al., "The Genome of the Stress-Tolerant Wild Tomato Species *Solanum pennellii*," *Nat. Genet.* 46:1034-8 (2014), which is hereby incorporated by reference in its entirety) were searched, and it was found that, while both have a clear ortholog of Ptr1 (with greater than 95% identical nucleotide sequences) which occurs at a syntenous location compared with *S. lycopersicoides*, a small deletion abolishes the Ptr1 start codon in both species and multiple other nonsense and frameshift mutations disrupt the reading frames of these Ptr1 genes (FIG. 21A; FIGS. 28A-28B).

Figure 21B:
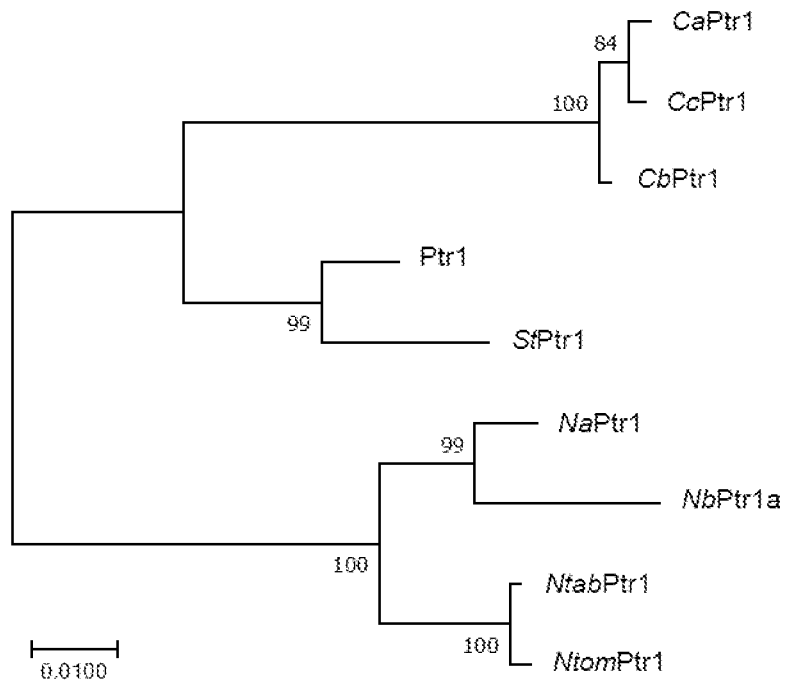

A broader search identified intact Ptr1 orthologs in a variety of other solanaceous plants, including potato, three species of pepper, and four species of tobacco including *N. benthamiana* (FIG. 21B). In all of these species the predicted amino acid similarity between Ptr1 and that encoded by the orthologs is greater than 95% (FIGS. 29A-29C; Table 9). Ptr1 occurs at syntenous locations in potato and pepper compared with *S. lycopersicoides*; it was not possible to make this determination in other species based on current genome sequence assemblies.

Figure 22A:
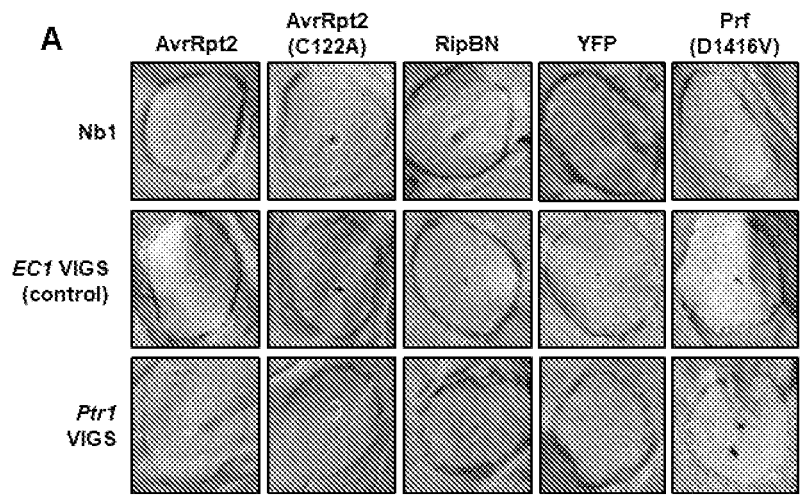
FIG. 22A and FIG. 22B show that the Ptr1 homolog in *N. benthamiana* mediates cell death response to AvrRpt2 and RipBN.
Figure 30A:
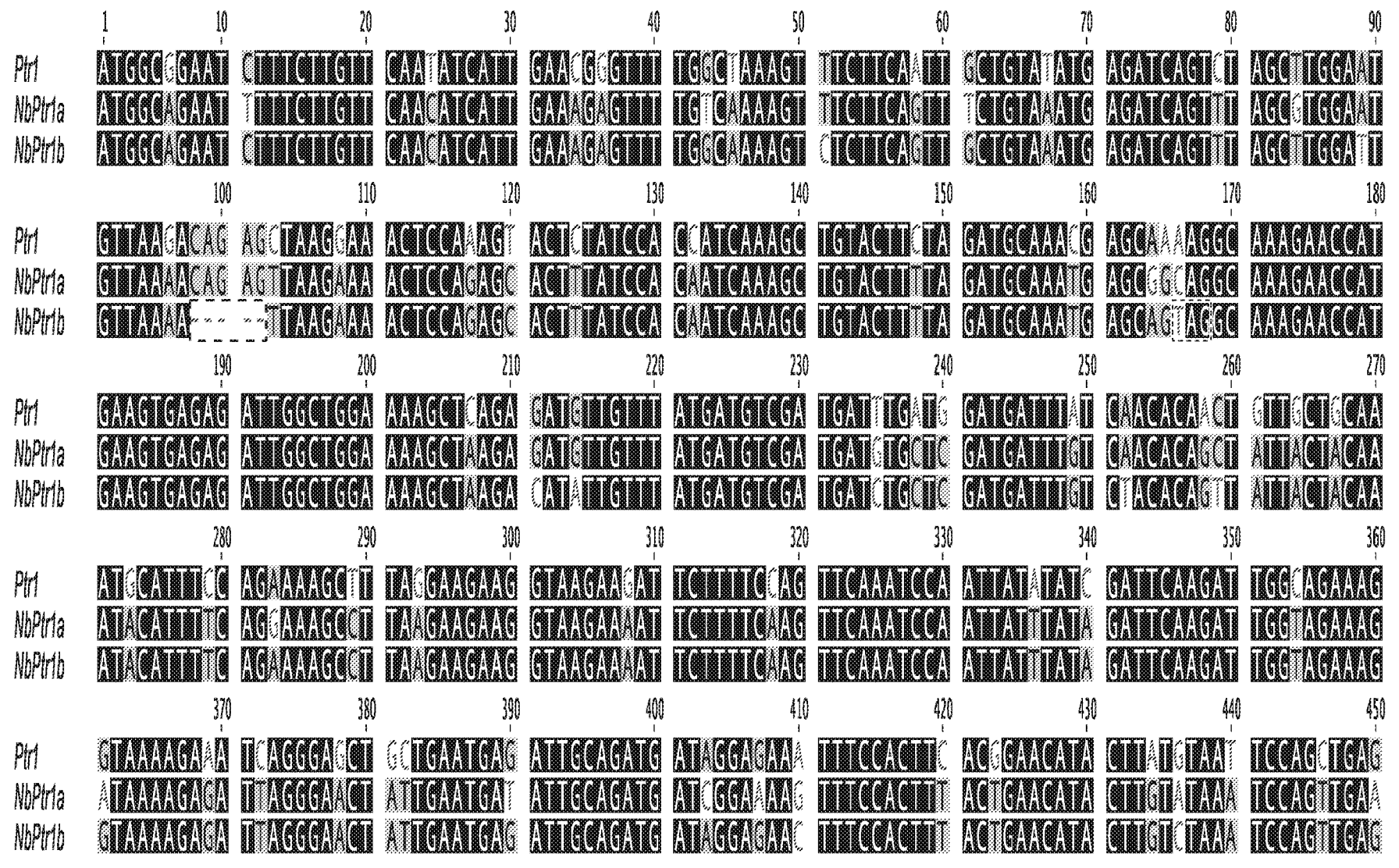
Figure 30A:
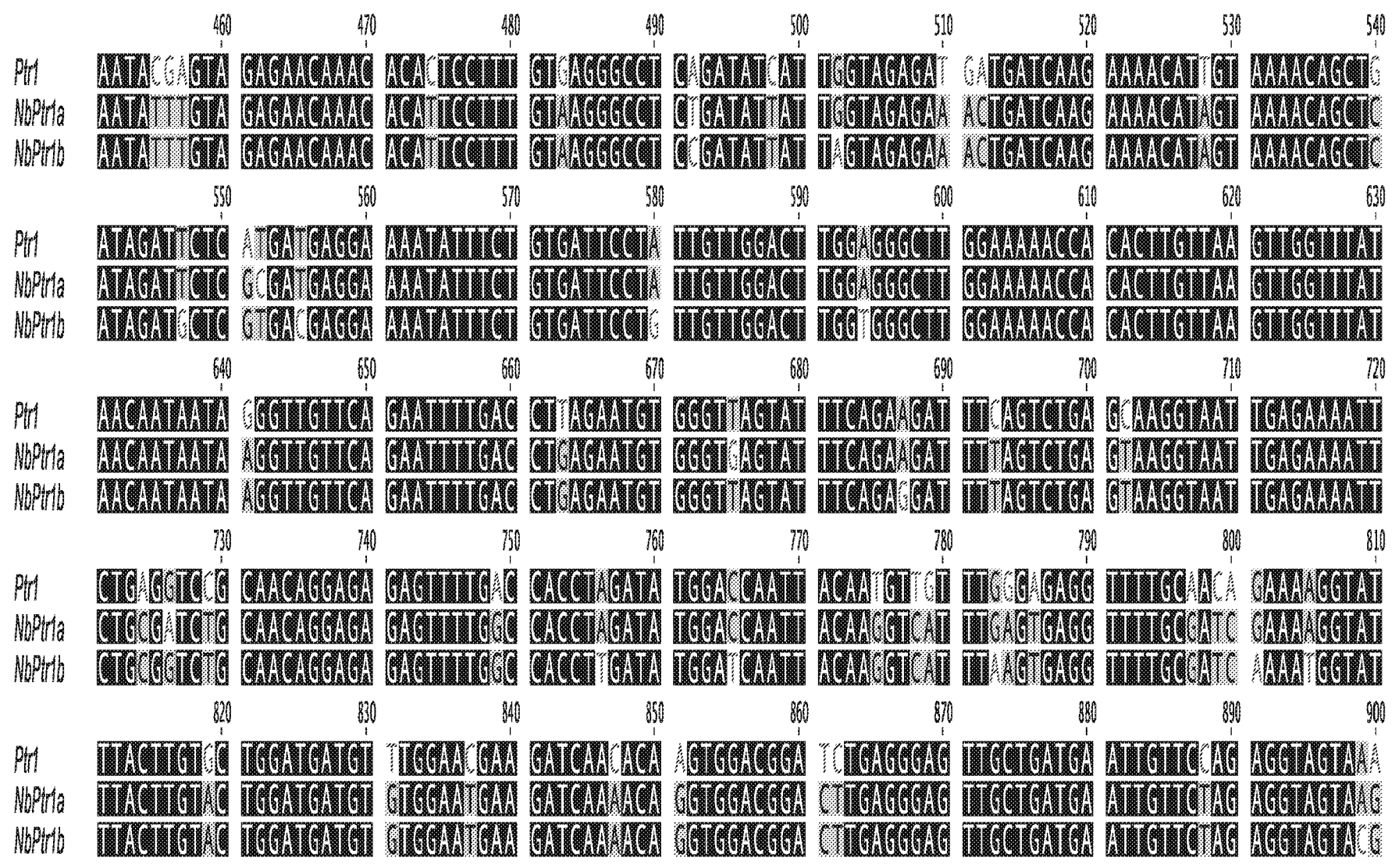
Figure 30B:
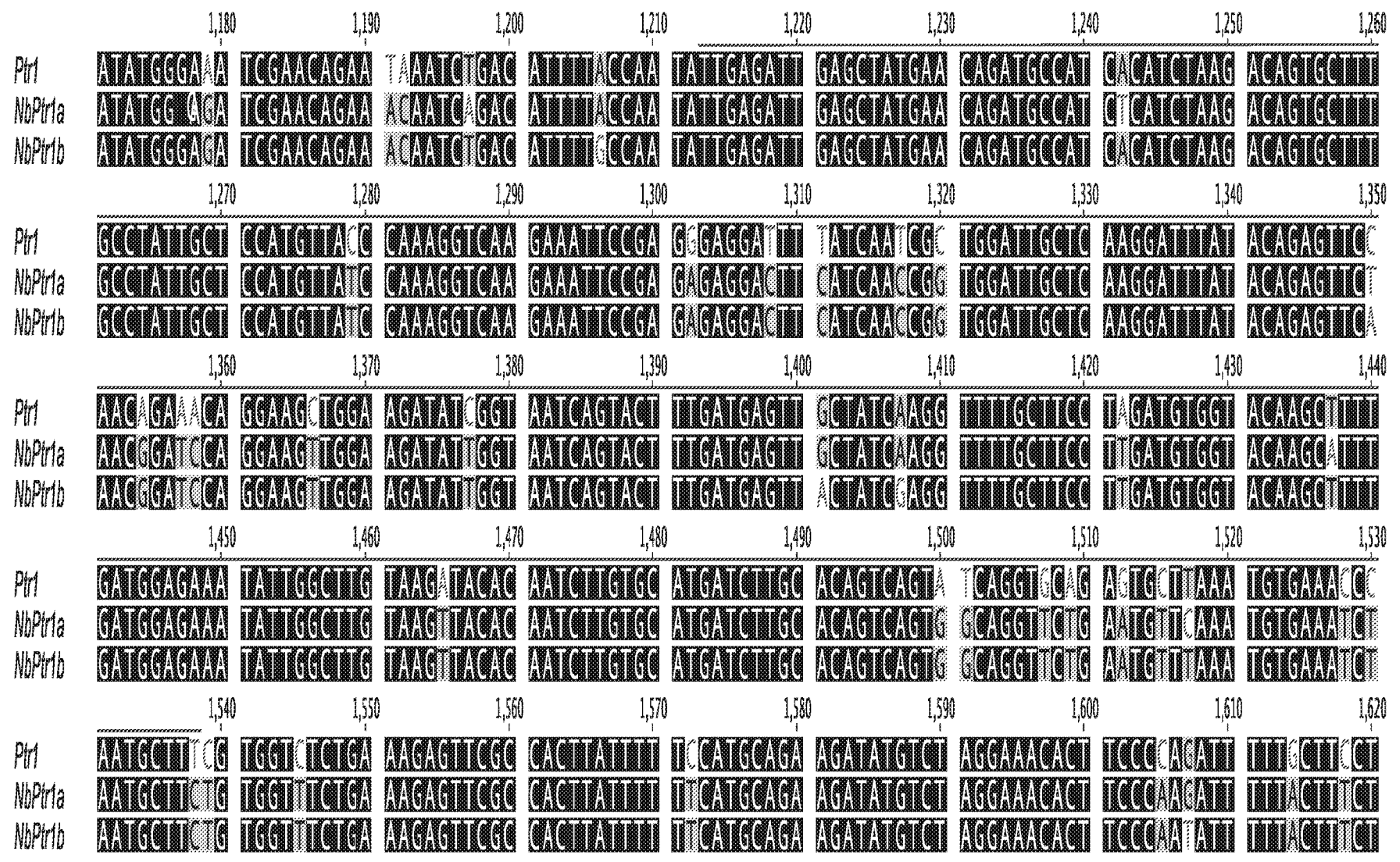
Figure 30B:
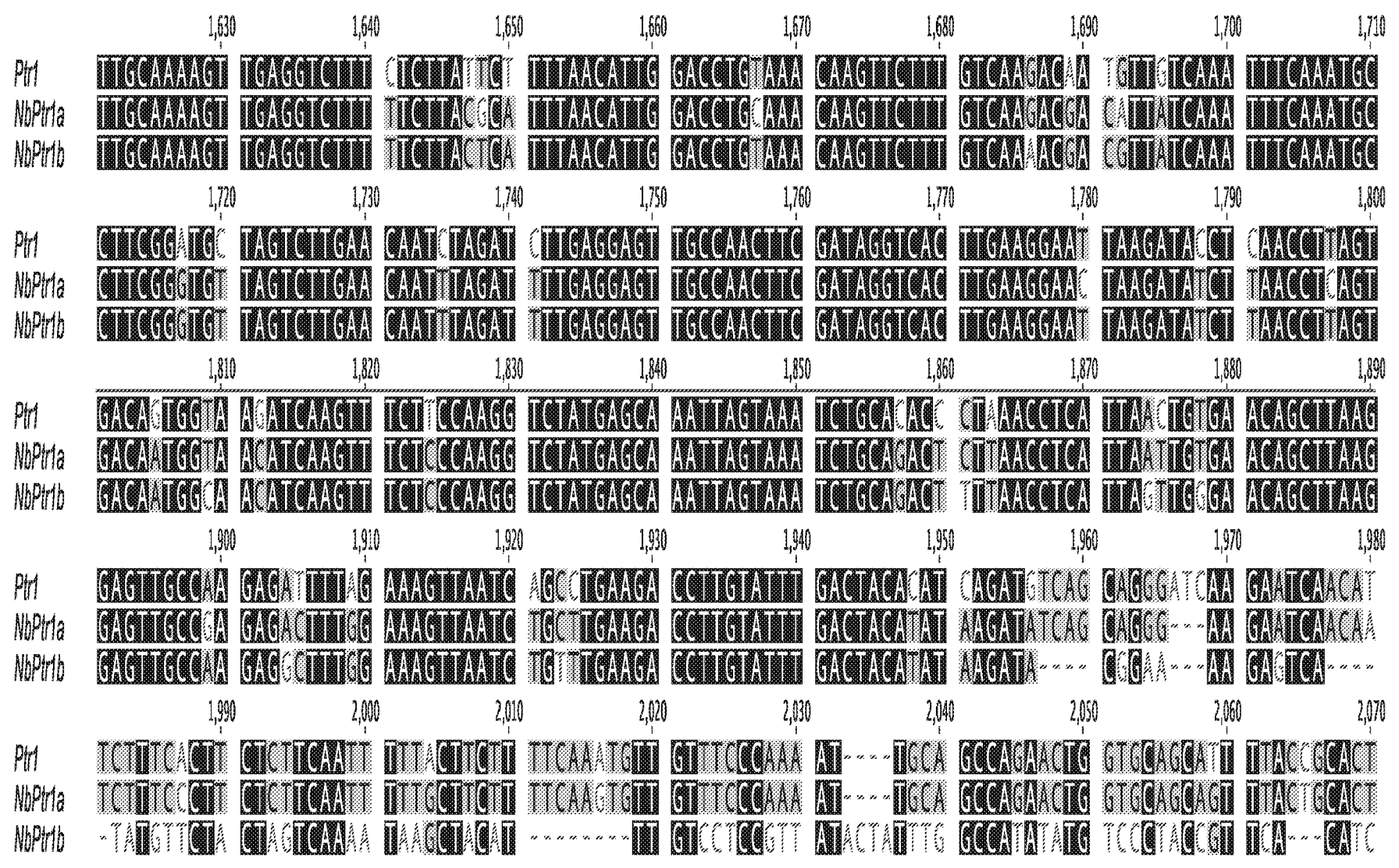
Figure 30B:
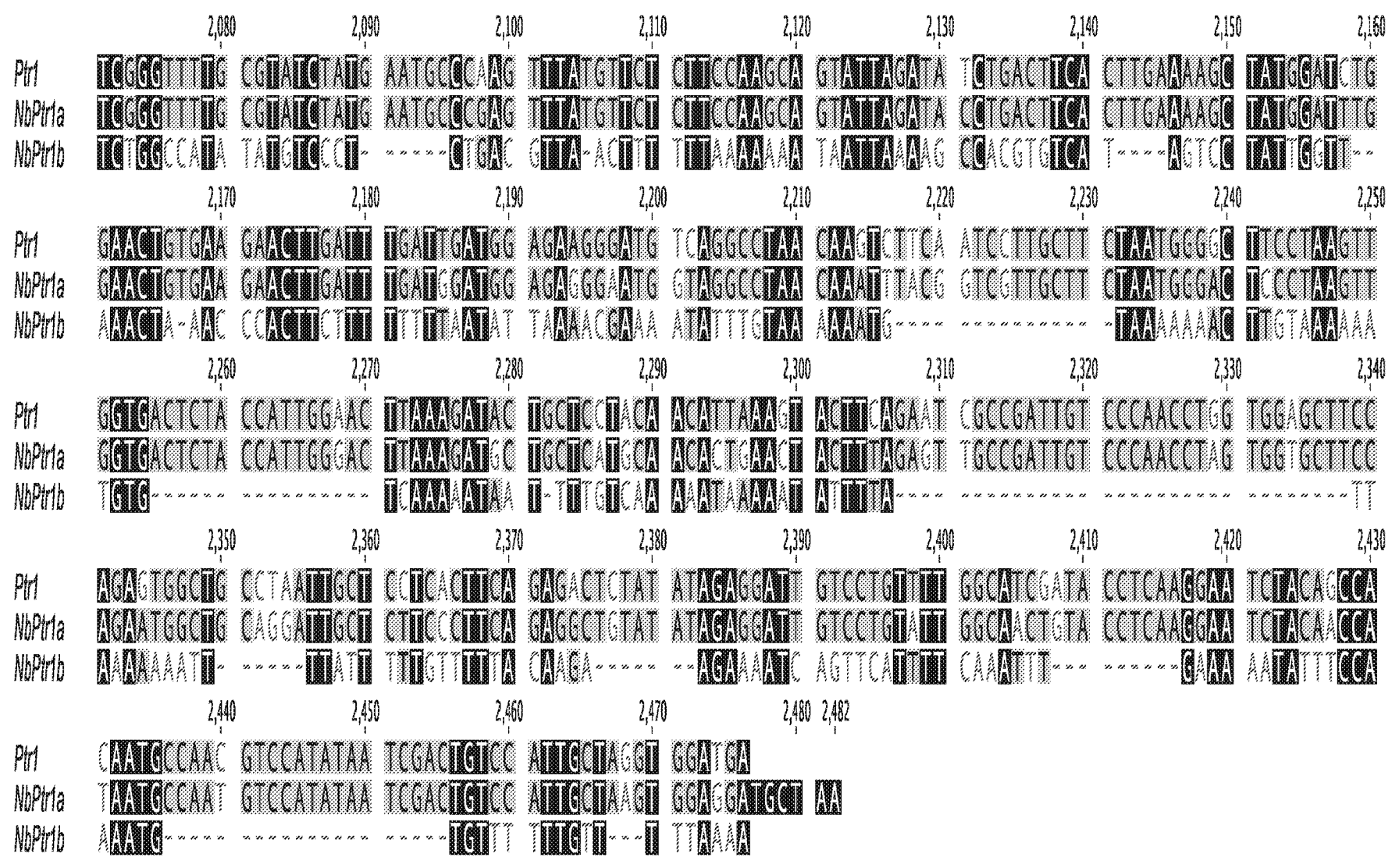

Example 16: The Ptr1 Ortholog in *N. benthamiana* and in Potato Mediates Recognition of AvrRpt2 and RipBN The observation that expression of AvrRpt2 alone in *N. benthamiana* leaves causes cell death raised the possibility that the Ptr1 ortholog in this species is responsible for this response. As expected for an allotetraploid, *N. benthamiana* has two Ptr1 orthologs (NbPtr1a and NbPtr1b), although a 5-base pair deletion in NbPtr1b leads to a premature stop codon (FIGS. 30A-30B). To test whether NbPtr1a plays a role in AvrRpt2-mediated cell death in *N. benthamiana*, a 325-bp fragment of this gene was selected for use in tobacco rattle virus (TRV)-induced gene silencing (VIGS; FIGS. 30A-30B). *N. benthamiana* (Nb1; Bombarely et al, "A draft Genome Sequence of *Nicotiana benthamiana* to Enhance Molecular Plant-Microbe Biology Research," *Mol. Plant-Microbe Interact.* 25:1523-30 (2012), which is hereby incorporated by reference in its entirety) plants were infected with TRV:Ptr1 or a control, TRV:EC1, containing a small fragment of *E. coli* DNA (Rosli et al., "Transcriptomics-Based Screen for Genes Induced by Flagellin and Repressed by Pathogen Effectors Identifies a Cell Wall-Associated Kinase Involved in Plant Immunity," *Genome Biol.* 14:R139 (2013), which is hereby incorporated by reference in its entirety). Expression of AvrRpt2 or RipBN, but not of the controls AvrRpt2(C122A) or YFP, induced strong cell death in uninfected Nb 1 leaves, as well as those infected with TRV:EC1 (FIG. 22A). No cell death was observed in NbPtr1-silenced plants, indicating the Ptr1 ortholog mediates AvrRpt2 recognition in *N. benthamiana*. The constitutively-active Prf protein induced cell death in all the plants as expected.

Figure 22B:
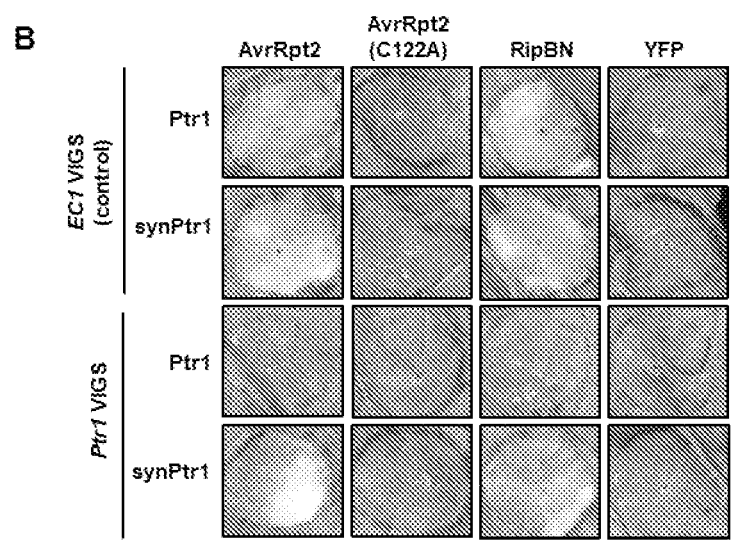
Figure 32:
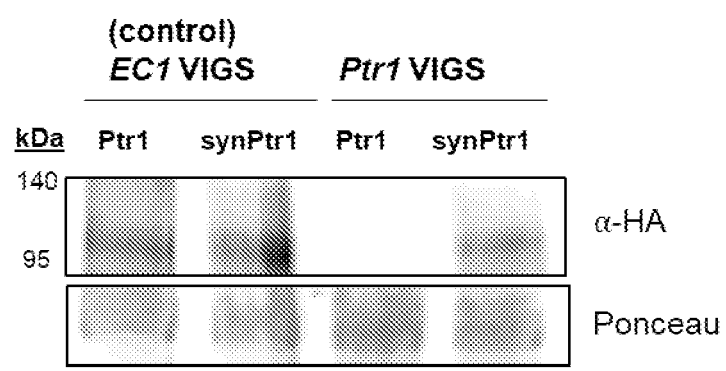
FIG. 32 shows immunoblot analysis of protein extracts isolated from *N. benthamiana* leaves transiently expressing 35S:Ptr1:HA or 35S:synPtr1:HA. Proteins were extracted from leaves collected 46 hr after *Agrobacterium*-mediated transient transformation of Ptr1 and synPtr1 (agroinfiltration; $OD_{600}$=0.1) and subjected to immunoblotting using an ∝-HA antibody to detect Ptr1 and synPtr1. Protein masses are indicated at the left of each blot. Ponceau staining shows amount of protein loaded in each lane.
Figure 33B:
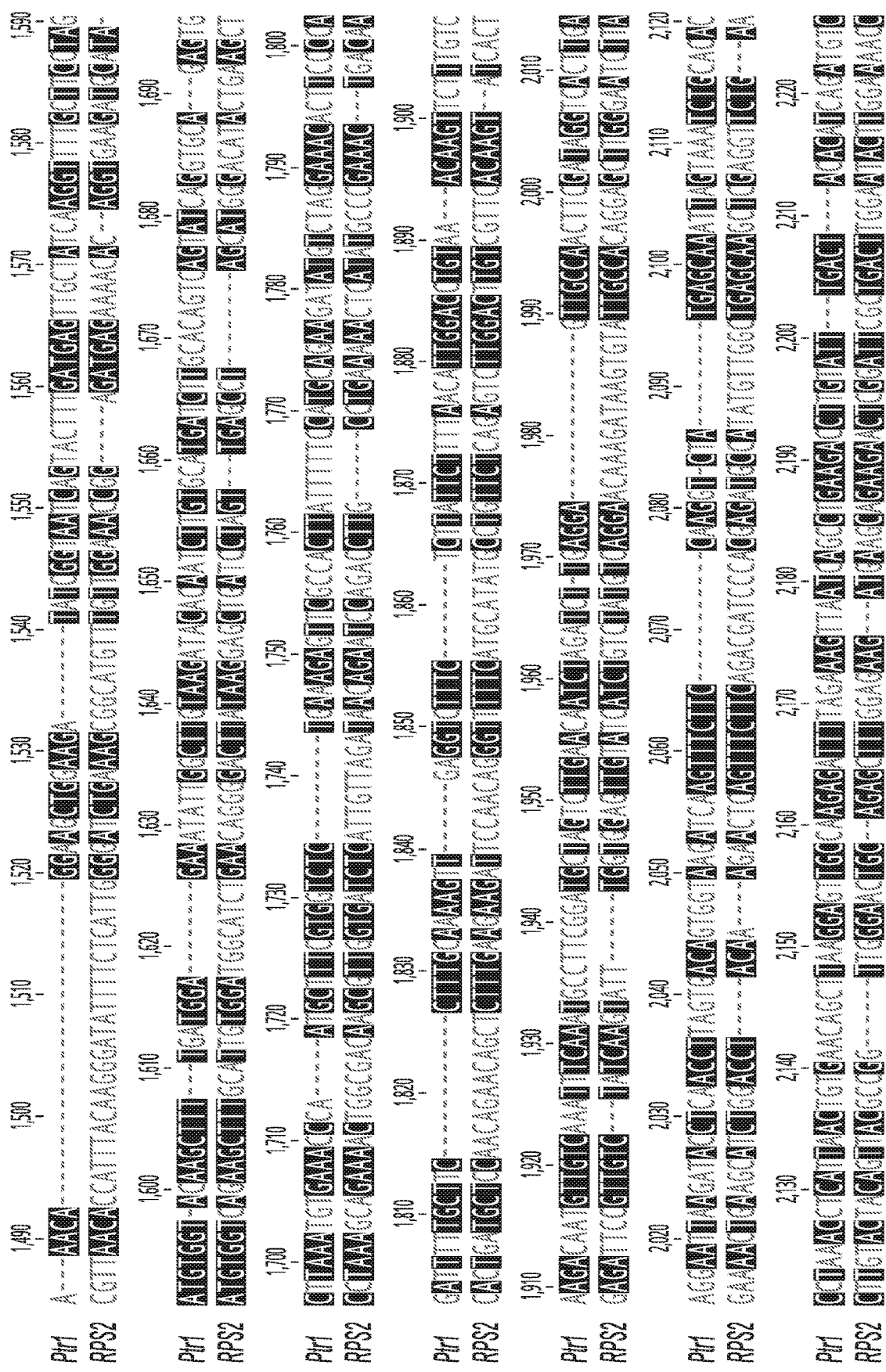
Figure 33B:
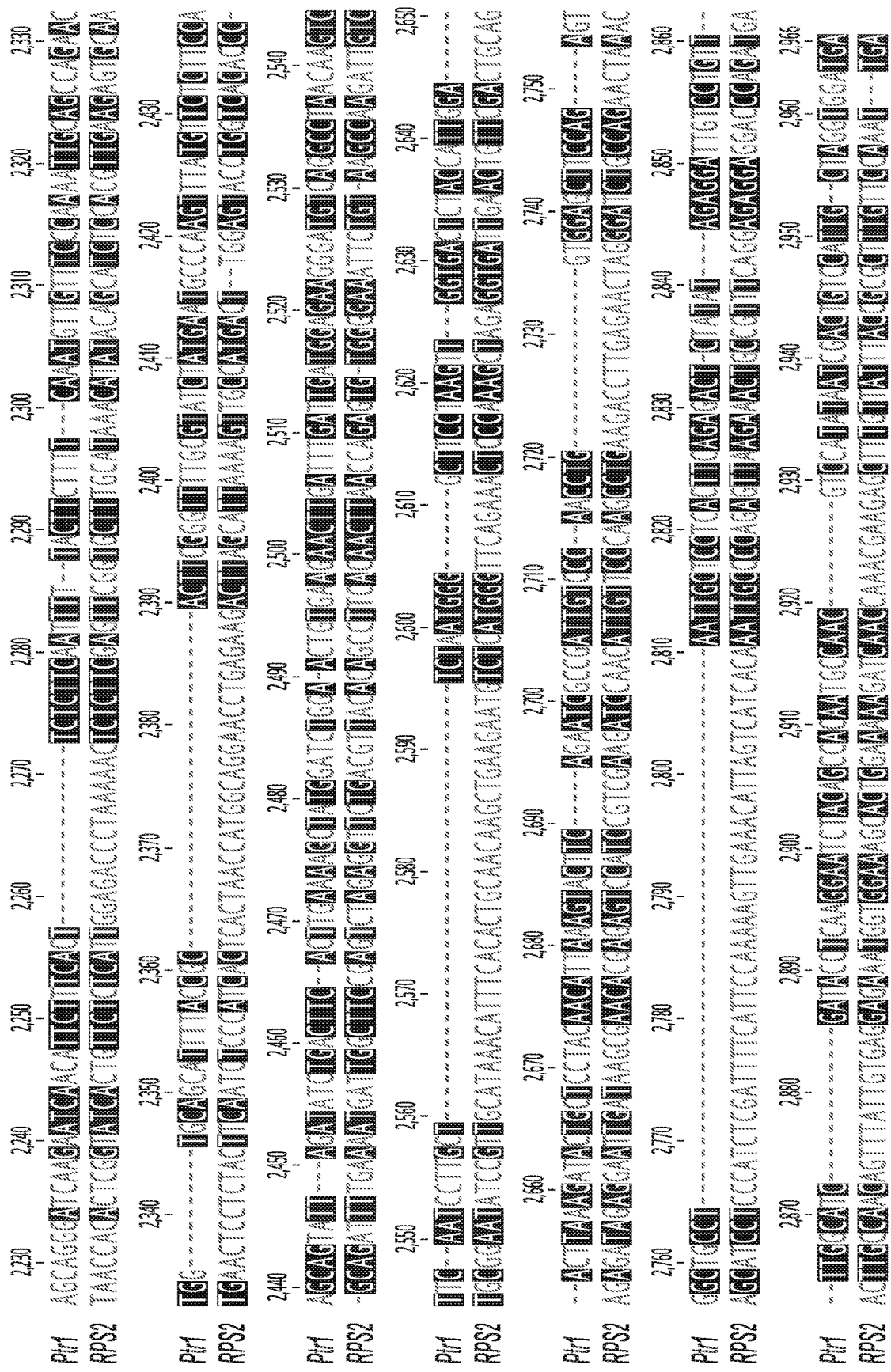
Figure 33C:
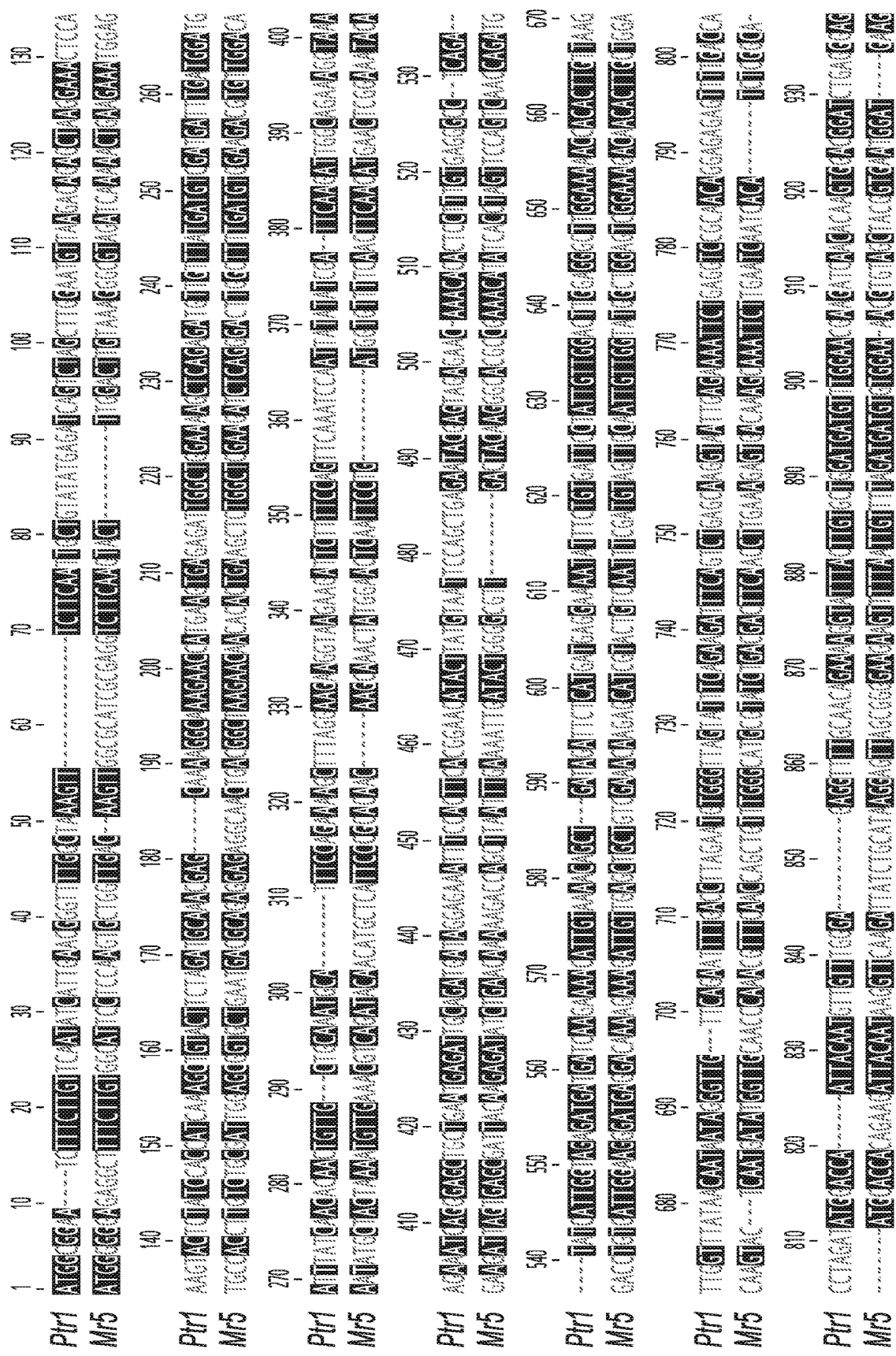
Figure 33C:
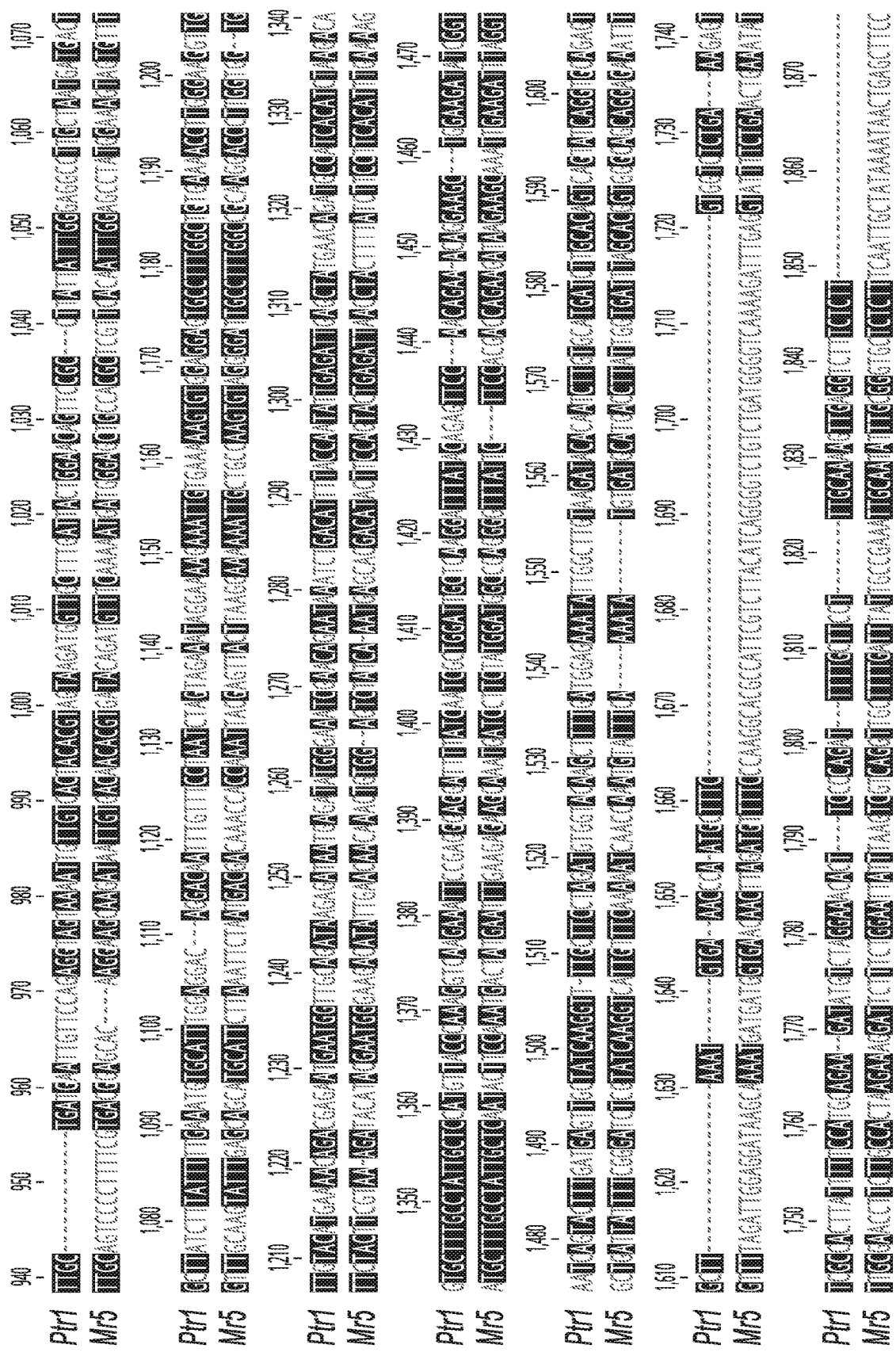
Figure 33C:
Figure 33D:
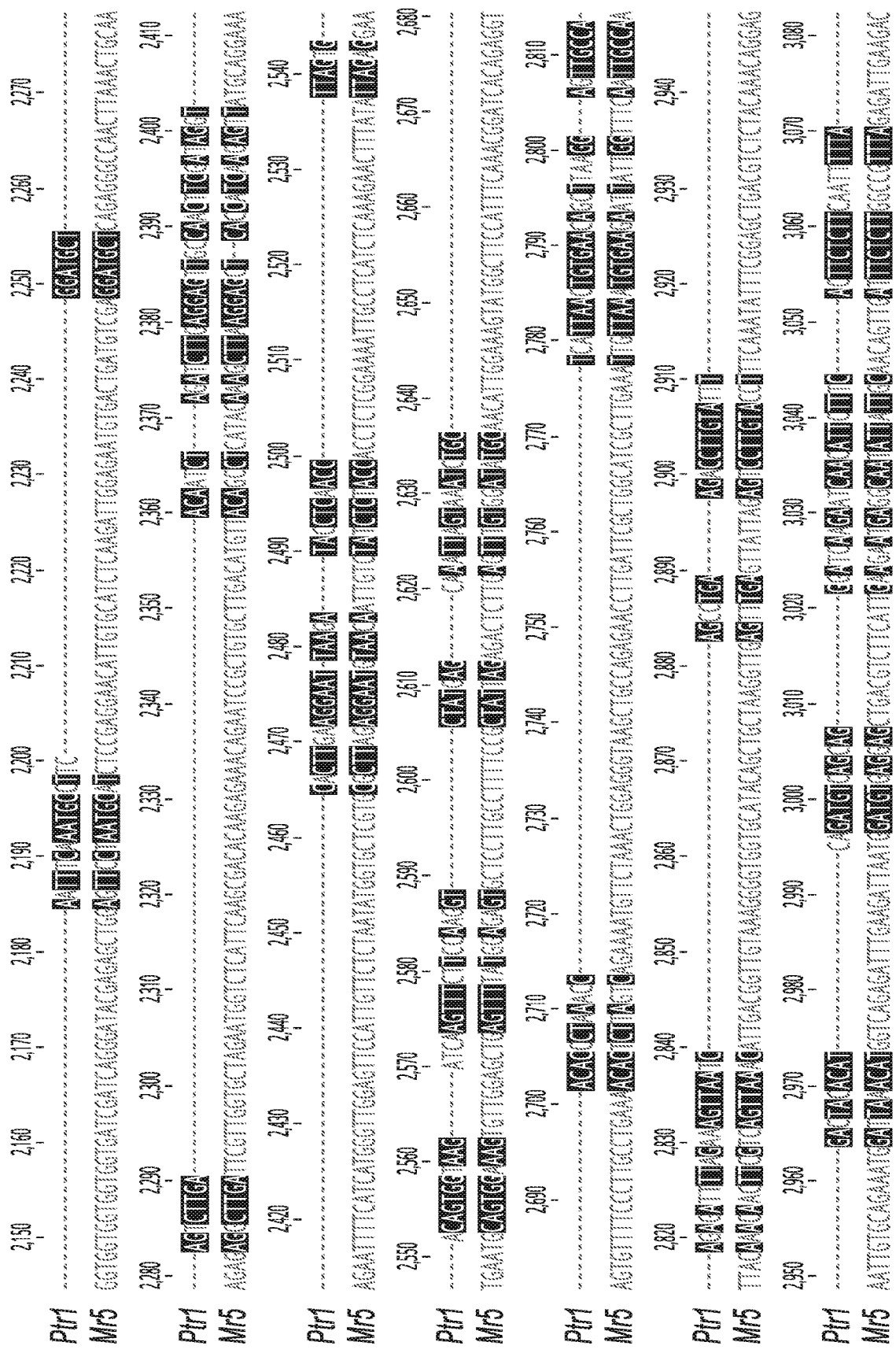
Figure 33D:
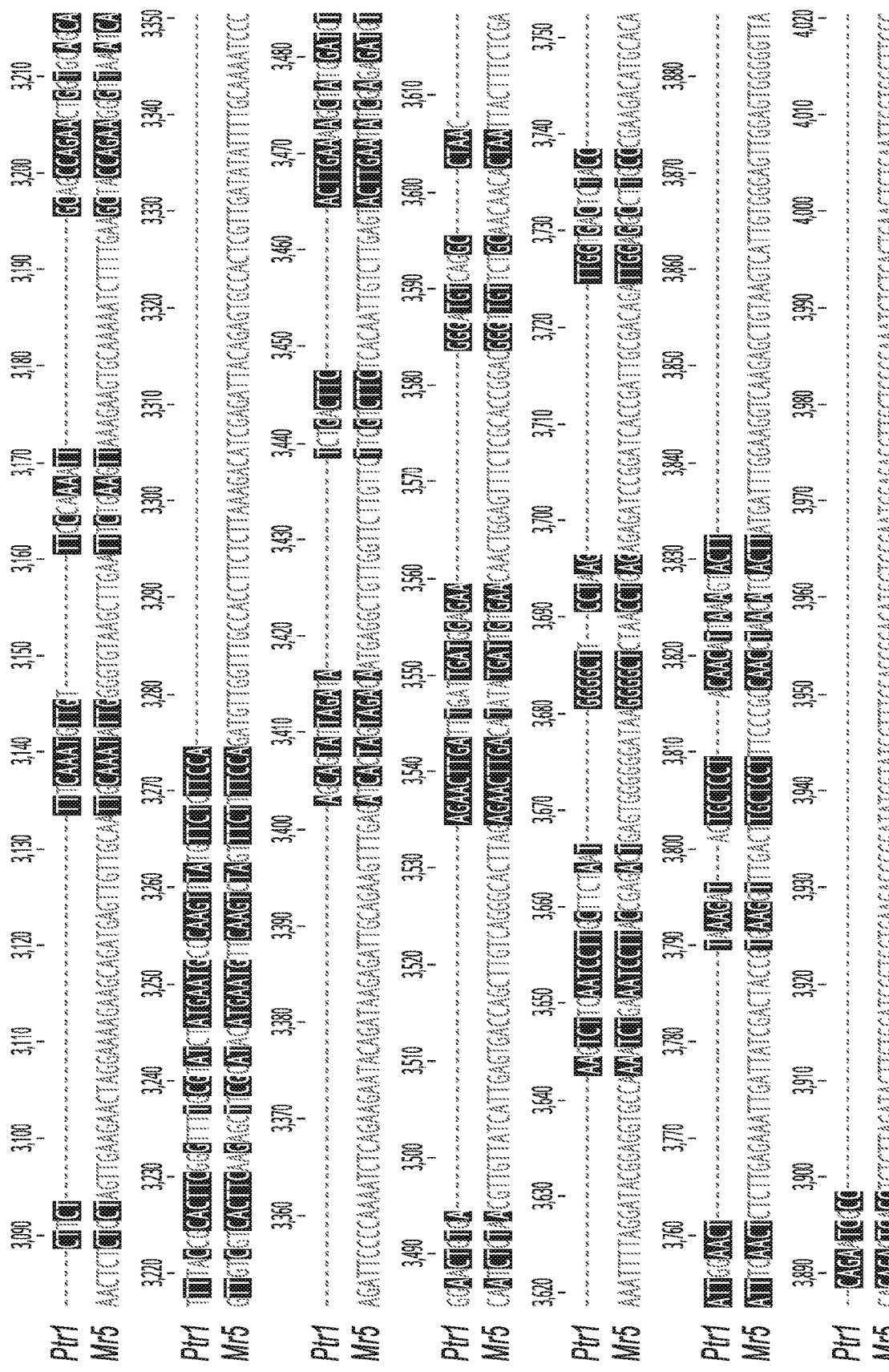
Figure 34D:
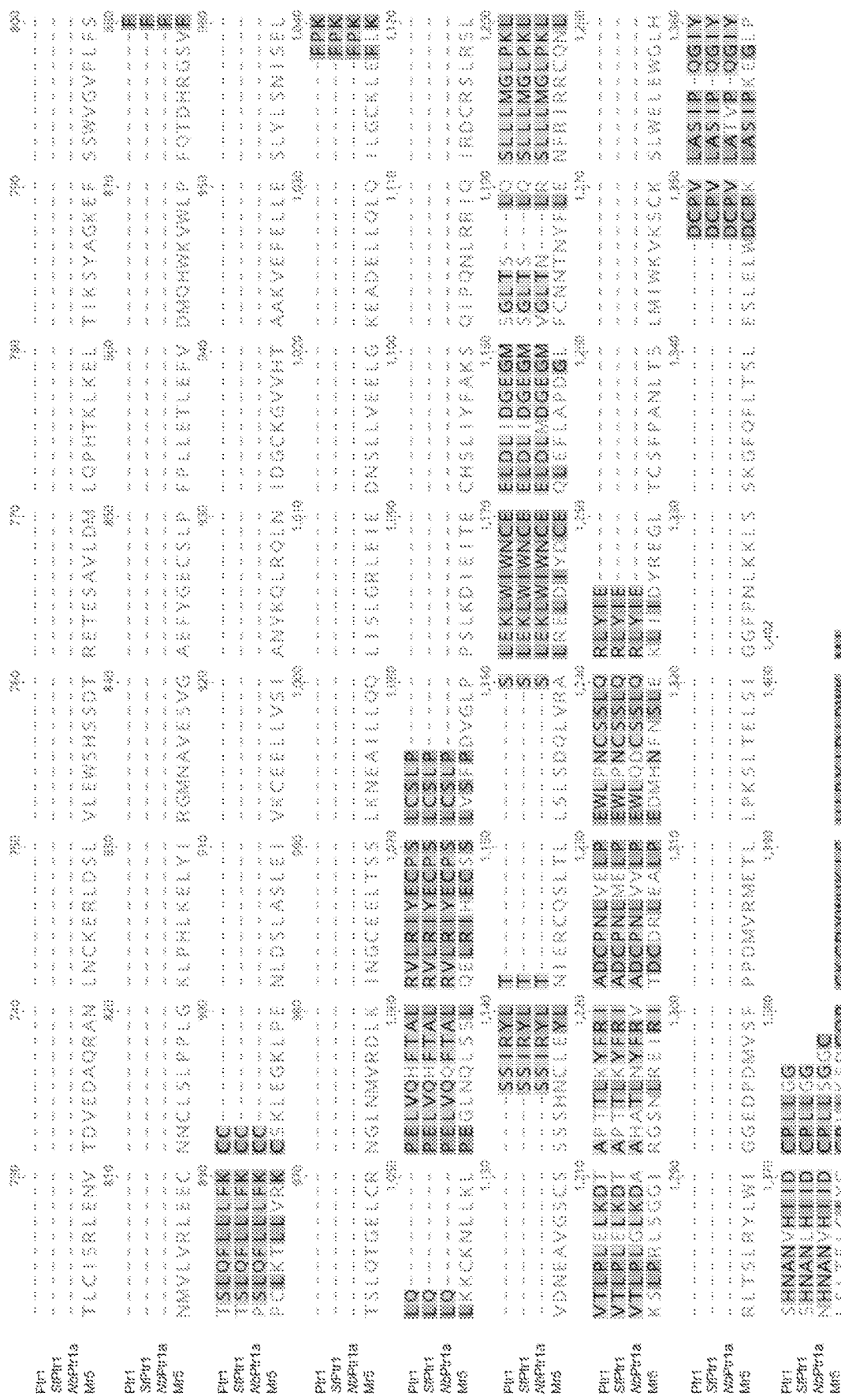

To assure that the loss of AvrRpt2-induced cell death observed in the Ptr1-silenced plants was not due to silencing of an 'off-target' gene, a synthetic version of Ptr1 (synPtr1) was developed with a divergent DNA sequence that would make it resistant to silencing, yet encode an identical amino acid sequence (FIGS. 31A-31B). Immunoblotting showed that both Ptr1 and synPtr1 proteins accumulated in the TRV:EC1 control plants, whereas in Ptr1-silenced plants only the protein encoded by synPtr1 accumulated (FIG. 32). Co-expression in Ptr1-silenced plants of synPtr1 with either AvrRpt2 or RipBN induced cell death whereas cell death did not occur in silenced plants co-expressing Ptr1 with the effectors (FIG. 22B). No cell death occurred in any plants in response to AvrRpt2(C122A). These experiments demonstrate that Ptr1 and its function in mediating recognition of proteolytically-active AvrRpt2 is conserved in *N. benthamiana*.

Figure 23A:
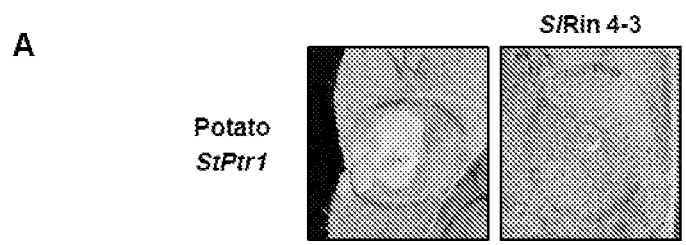
FIG. 23A and FIG. 23B show that the Ptr1 ortholog in potato (StPtr1) mediates recognition of AvrRpt2 and RipBN.
Figure 23B:
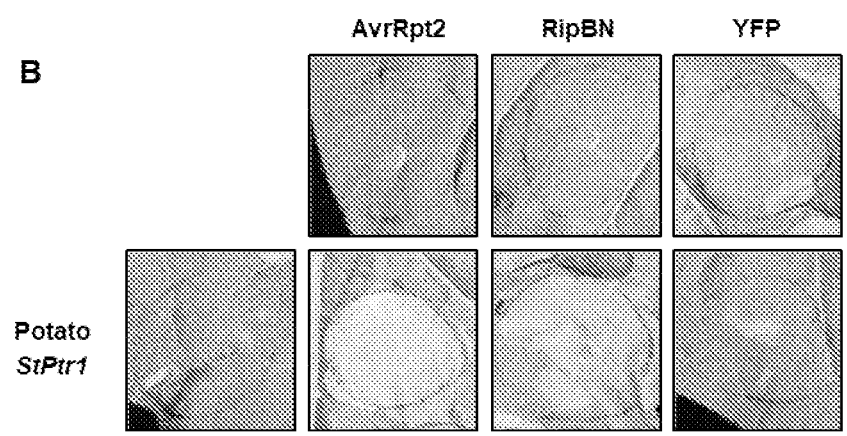
Figures 29A, 29B:
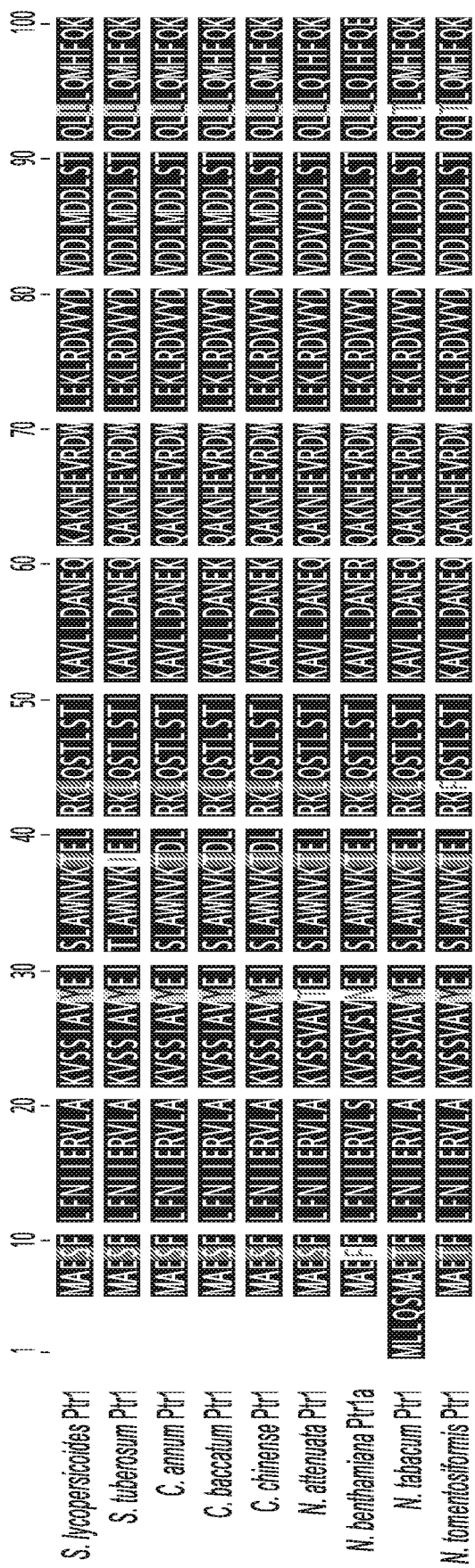
FIG. 29A, FIG. 29B, and FIG. 29C show Ptr1 orthologs in various Solanaceae species.
Figure 29C:
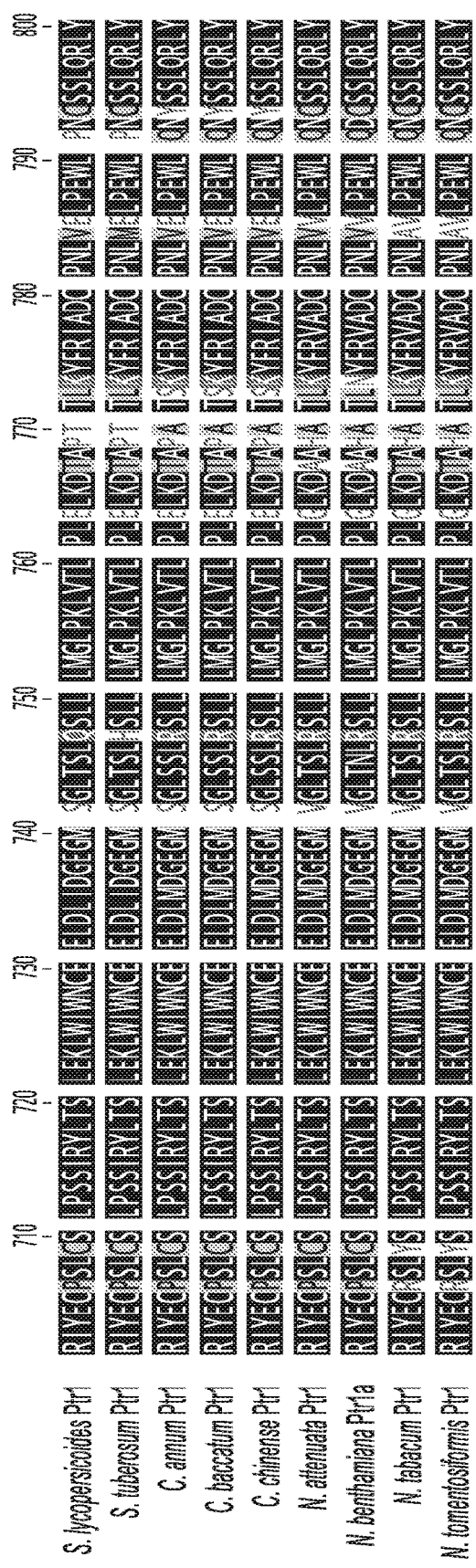
Figure 29C:
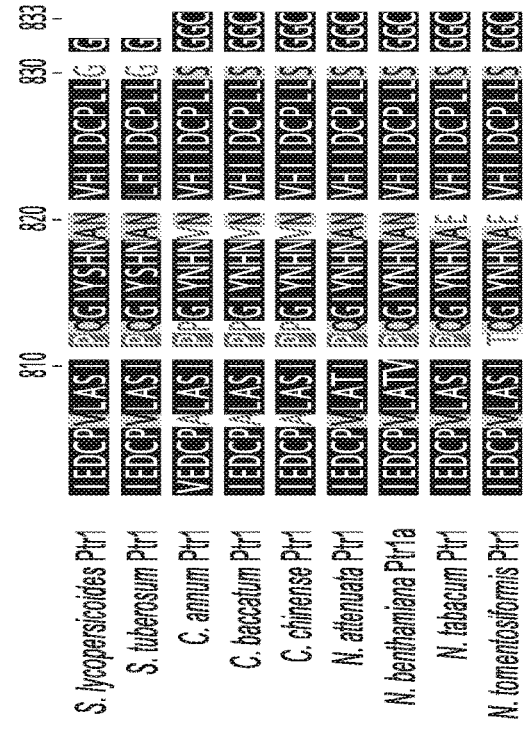

The protein predicted to be encoded by the Ptr1 ortholog in potato (StPtr1) is 97% identical to the Ptr1 protein and it seemed likely that it might also mediate recognition of AvrRpt2 and RipBN (FIGS. 29A-29C). Attempted use of *Agrobacterium*-infiltration to transiently express AvrRpt2 or RipBN in potato leaves did not cause cell death possibly due to the inefficiency of this method in this species. The StPtr1 ortholog from potato variety Dakota Crisp was cloned and expressed using a high titer of *Agrobacterium* in *N. glutinosa* leaves. StPtr1 caused cell death on its own at this titer which was inhibited by co-expression of SlRin4-3 just as observed for Ptr1 (FIG. 23A). As with Ptr1, using a lower titer of *Agrobacterium* prevented StPtr1-induced cell death and co-expression of AvrRpt2 or RipBN in this condition induced cell death (FIG. 23B). Ptr1 is therefore conserved in diverse solanaceous species, but is a pseudogene in tomato and *S. pennellii*.

Example 17: Ptr1 is not Orthologous to Mr5 or RPS2

Figure 24:
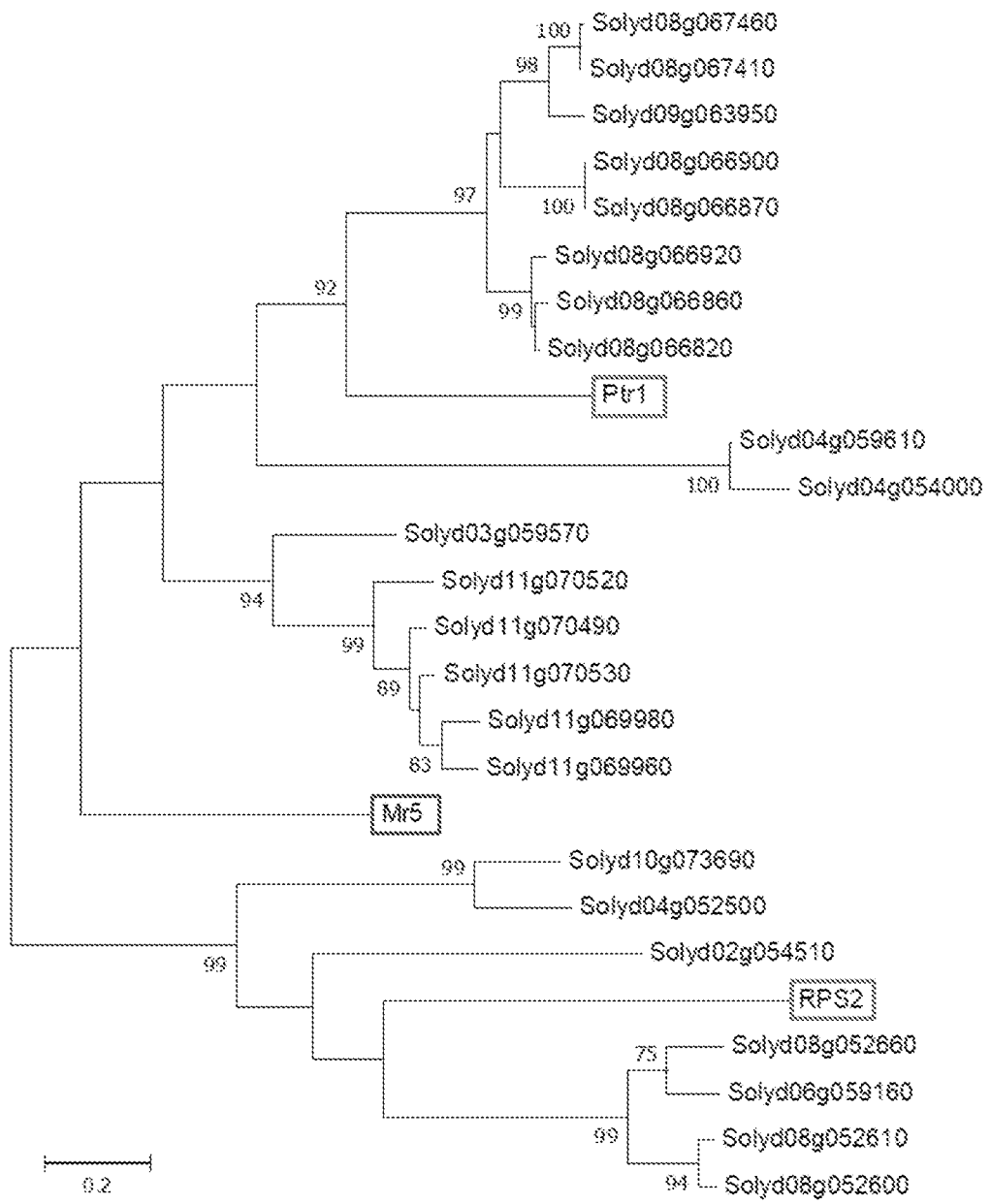
FIG. 24 is a phylogenetic tree of Ptr1, Mr5, RPS2 with their most closely related proteins in *S. lycopersicoides*. Maximum likelihood tree of the amino acid sequence of the NB-ARC domain only of Ptr1, Mr5, and RPS2 top BLAST hits with an intact NB-ARC domain, including the P-loop, kinase 2, kinase 3a, and GLPL motifs, from the *S. lycopersicoides* genome protein database. 1000 bootstrap replicates, with bootstraps 75 or above shown. The tree is drawn to scale, with branch lengths measured in the number of substitutions per site.

The nucleotide sequence of the Ptr1 gene is 39% identical to RPS2 and 34% identical to Mr5, which mediate recognition of AvrRpt2 in *Arabidopsis* and apple, respectively (FIGS. 33A-33D). The amino acid sequence identity is similarly low (~20% identity of the Ptr1 protein with either RPS2 or Mr5) with many of the identical residues being in conserved NLR motifs (FIGS. 34A-34D). To understand the broader relationships of the Ptr1, RPS2, and Mr5 genes the *S. lycopersicoides* genome sequence was searched to find the most closely related genes for each of them. The NB-ARC domains encoded by these genes were then used in a phylogenetic analysis. This revealed that multiple *S. lycopersicoides* proteins are more similar to RPS2 and Mr5 than to Ptr1 with each of the proteins belonging to a distinct clade (FIG. 24). A similar analysis looking for the most closely related genes in *Arabidopsis* and in apple confirmed that multiple genes occur in these two species which are closer to Ptr1 than to either RPS2 or Mr5 (FIGS. 34A-35B).

Example 18: Discussion of Examples 12-17

A natural outbreak of bacterial speck disease led to the serendipitous discovery of the Ptr1 locus which confers resistance to Pst strains that express the effector AvrRpt2 (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant Microbe. Interact. 32:949-60 (2019), which is hereby incorporated by reference in its entirety). The current annotation of the *S. lycopersicoides* genome sequence indicated there are 16 NLR-encoding genes in the large introgression segment shared between LA4245-R and LA4277-R and it was hypothesized that one of them is Ptr1. Eight of these NLR-encoding genes are clustered within a ~2 Mb region while the other eight are dispersed in an almost 80 Mb segment of chromosome 4. As expected when working with a wild relative of tomato, little overall recombination involving the introgressed region was observed. However, a single recombinant among the 585 F2 plants screened eliminated the eight clustered NLR-encoding genes as being candidates for Ptr1. Inspection of the gene models for the remaining eight genes revealed one of them to be a pseudogene and no transcripts were detectable in leaves of five of the remaining genes, leaving just two candidates. *Agrobacterium*-mediated transient expression assays revealed that one of these two genes is Ptr1 and showed that it mediated recognition of proteolytically-active AvrRpt2 and RipBN. Discussed herein is the use of *N. glutinosa*, the discovery of Ptr1 homologs in various solanaceous species, and potential use of Ptr1 in breeding programs and the process of convergent evolution which apparently is responsible for the ability of three diverse NLR-encoding genes to mediate recognition of AvrRpt2.

It was reported previously that AvrRpt2 does not induce cell death in *N. glutinosa* (Kessens et al., "Determining the GmRIN4 Requirements of the Soybean Disease Resistance Proteins Rpg1b and Rpg1r Using a *Nicotiana glutinosa*-Based Agroinfiltration System," *PLoS One* 9:e108159 (2014), which is hereby incorporated by reference in its entirety). Therefore, this species was used for *Agrobacterium*-mediated transient expression of the Ptr1 candidates because in our conditions AvrRpt2 induces strong cell death in *N. benthamiana*, the typical species used for agroinfiltration. No genome sequence is currently available for *N. glutinosa* but it appears to lack a functional Ptr1 gene since these experiments show that the Ptr1 pathway is otherwise intact in this species. *N. glutinosa* does appear to have one or more functional Rin4 proteins because at a lower titer Ptr1

-induced cell death does not occur, whereas co-expression of AvrRpt2 at this low titer (likely leading to cleavage of Rin4) induces cell death. Higher expression of Ptr1 by using higher titers of *Agrobacterium* causes cell death without AvrRpt2 likely because it disrupts the stoichiometric levels of Ptr1 and Rin4 needed to negatively regulate Ptr1. Indeed, similar to observations with RPS2 and AtRIN4, it was found that co-overexpression of Ptr1 and SlRin4-3 suppressed the ectopic activation of Ptr1.

*Arabidopsis* RIN4 has two sites (RCS1 and RCS2) each with a consensus sequence which is proteolytically cleaved by AvrRpt2, resulting in three AvrRpt2-cleavage products: ACP1, ACP2, and ACP3 (Coaker et al, "Activation of a Phytopathogenic Bacterial Effector Protein by a Eukaryotic Cyclophilin," *Science* 308:548-50 (2005), which is hereby incorporated by reference in its entirety). The C-terminal half of AtRIN4 is necessary and sufficient for the negative regulation of RPS2, but none of the individual cleavage products can alone negatively regulate RPS2. This supports a model that cleavage of RIN4 specifically at RCS2 leads directly to RPS2 activation via loss of suppression by RIN4 (Day et al., "Molecular Basis for the RIN4 Negative Regulation of RPS2 Disease Resistance," *Plant Cell* 17:1292-305 (2005); and Kim et al., "The *Pseudomonas syringae* Effector AvrRpt2 Cleaves its C-Terminally Acylated Target, RIN4, from *Arabidopsis* Membranes to Block RPM1 Activation," *PNAS* 102:6496-501 (2005), which are hereby incorporated by reference in their entirety). Interestingly, different from AtRIN4, apple MdRIN4 does not suppress NLR-dependent autoactivity. Instead, ACP3 released upon cleavage of MdRIN4 is sufficient to activate Mr5 (Prokchorchik et al., "A Host Target of a Bacterial Cysteine Protease Virulence Effector Plays a Key Role in Convergent Evolution of Plant Innate Immune System Receptors," *New Phytol.* 225:1327-42 (2019), which is hereby incorporated by reference in its entirety). Investigation of the mechanism by which ACP3 from MdRIN4, and not AtRIN4, activates Mr5 revealed two polymorphic amino acid residues in the N-terminal sequences of ACP3 in AtRIN4 (N158/Y165) and MdRIN4 (D186/F193) (Prokchorchik et al., "A Host Target of a Bacterial Cysteine Protease Virulence Effector Plays a Key Role in Convergent Evolution of Plant Innate Immune System Receptors," *New Phytol.* 225:1327-42 (2019), which is hereby incorporated by reference in its entirety). The three tomato Rin4 proteins that are expressed in leaves each have a hybrid of these polymorphisms. That is, instead of having an asparagine (N) as occurs in *Arabidopsis*, SlRin4-1, 4-2, and 4-3 have an aspartic acid (D) like apple. Moreover, the tomato Rin4 proteins have a tyrosine (Y) like AtRIN4 instead of a phenylalanine (F) as occurs in MdRIN4 (FIG. 25A). Whether or not these differences play a role in activation or suppression of Ptr1 is unknown and their future investigation may shed light on how the SlRin4 proteins regulate Ptr1.

Despite much effort, by many researchers, no source of simply-inherited resistance to race 1 strains of Pst has been discovered among accessions of cultivated tomato or its wild relatives (although some QTLs contributing to race 1 resistance have been reported; (Bao et al., "Identification of a Candidate Gene in *Solanum habrochaites* for Resistance to a Race 1 Strain of *Pseudomonas syringae* pv. Tomato," *The Plant Genome* 8(3):10.3835/plantgenome2015.02.0006 (2015); Thapa et al., "Identification of QTLs Controlling Resistance to *Pseudomonas syringae* pv. Tomato Race 1 Strains From the Wild Tomato, *Solanum habrochaites* LA1777," *Theor. Appl. Genet.* 128:681-92 (2015); and Hassan et al., "A Rapid Seedling Resistance Assay Identifies Wild Tomato Lines that are Resistant to *Pseudomonas syringae* pv. Tomato Race 1," *Mol. Plant-Microbe Interact.* 30:701-9 (2017), which are hereby incorporated by reference in their entirety). The discovery that the Ptr1 ortholog in both tomato and *S. pennellii* has multiple mutations including one that disrupts the start codon explains why race 1 resistance involving recognition of AvrRpt2 was never found. This observation suggests that strains of Pst expressing AvrRpt2 were not serious pathogens in the environment where wild relatives of tomato evolved and that there was no selection pressure to retain Ptr1. It will be interesting in the future to determine if all or just some of the accessions of the 12 wild relatives of tomato have nonfunctional versions of Ptr1 and possibly correlate this feature with the regions in which the accessions were originally collected.

The Ptr1 ortholog from potato was able to mediate recognition of AvrRpt2 and RipBN when transiently expressed in *N. glutinosa* leaves. This ortholog was cloned from the variety Dakota Crisp and has a sequence (i.e., SEQ ID NO: 116) that is 98% similar to a gene annotated in the potato genome sequence as resistance gene analog 1 (RGA1; GenBank No. XP_006340095.1, SEQ ID NO: 131). No function for the RGA1 gene has been reported and we have therefore named it StPtr1. Potato, tomato, and *S. lycopersicoides* originated in South America and *N. benthamiana* originated in Australia. The fact that these four diverse species all have highly conserved Ptr1 sequences suggests Ptr1 is ancestral in the Solanaceae and that its function was lost in some clades, such as the tomato clade. The observations described herein also support the hypothesis that bacterial pathogens of potato, *N. benthamiana* and *S. lycopersicoides* and likely their progenitors have, over evolutionary time, expressed an AvrRpt2-like protein. This is consistent with the importance of this effector for bacterial virulence and with its presence in many bacterial species and multiple pathovars of *P. syringae* (FIG. 36).

The observation that expression of AvrRpt2 or RipBN alone causes cell death in *N. benthamiana* leaves and the discovery of an intact Ptr1 ortholog (NbPtr1a) in this tobacco species raised the possibility that the effector-induced cell death involves Ptr1. Virus-induced gene silencing of the NbPtr1a gene in *N. benthamiana* and complementation with a synthetic Ptr1 gene that is recalcitrant to silencing confirmed this is the case. *N. benthamiana* has been used extensively to characterize biochemical aspects of the Pto/Prf complex and to identify and study host proteins that play a role in the Pto/Prf pathway such as 0110, Cpk6, Epk1, Hsp90, Mai1, Nrc2/3, MAPKKKα, MKK2, Sgt1, TFT7 (Ekengren et al., "Two MAPK Cascades, NPR1, and TGA Transcription Factors Play a Role in Pto-Mediated Disease Resistance in Tomato," *Plant J.* 36:905-17 (2003); Lu et al., "High throughput Virus-Induced Gene Silencing Implicates Heat Shock Protein 90 in Plant Disease Resistance," *EMBO J.* 22:5690-9 (2003); del Pozo et al., "MAPKKKα is a Positive Regulator of Cell Death Associated with both Plant Immunity and Disease," *EMBO J.* 23:3072-82 (2004); Mucyn et al., "Regulation of Tomato Prf by Pto-like Protein Kinases," *Mol. Plant-Microbe. Interact.* 22:391-401 (2009); Oh et al., "Tomato 14-3-3 Protein 7 Positively Regulates Immunity-Associated Programmed Cell Death by Enhancing Protein Abundance and Signaling Ability of MAPKKKα," *Plant Cell* 22:260-72 (2010); Oh et al., "Tomato 14-3-3 Protein TFT7 Interacts with a MAP Kinase Kinase to Regulate Immunity-Associated Programmed Cell Death Mediated by Diverse Disease Resistance Proteins," *J. Biol. Chem.* 286:14129-36 (2011); de la Torre et al., "The Tomato Calcium Sensor Cbl10 and its Interacting Protein Kinase Cipk6 Define a Signaling Pathway in Plant Immunity," *Plant Cell* 25:2748-64 (2013); Kud et al., "SGT1 Interacts with the Prf Resistance Protein and is Required for Prf Accumulation and Prf-Mediated Defense Signaling," *Biochem. Biophys. Res. Comm.* 431:501-5 (2013); Ntoukakis et al., "The Tomato Prf Complex is a Molecular Trap for Bacterial Effectors Based on Pto Transphosphorylation," *PLoS Pathog.* 9:e1003123 (2013); Saur et al., "The N-Terminal Domain of the Tomato Immune Protein Prf Contains Multiple Homotypic and Pto Kinase Interaction Sites," *J. Biol. Chem.* 290:11258-67 (2015); Wu et al., "NLR Network Mediates Immunity to Diverse Plant Pathogens," *PNAS* 114:8113-8 (2017); Roberts et al., "Mai1 Protein Acts Between Host Recognition of Pathogen Effectors and Mitogen-Activated Protein Kinase Signaling," *Mol. Plant-Microbe. Interact.* 32:1496-507 (2019); and Wu et al., "Tomato Prf requires NLR Helpers NRC2 and NRC3 to Confer Resistance Against the Bacterial Speck Pathogen *Pseudomonas syringae* pv. Tomato," *bioRxiv*, doi:10.1101/595744 (2019), which are hereby incorporated by reference in their entirety). It will be interesting in the future to determine if all of these proteins play a role in the Ptr1 pathway or if the Pto/Prf and Ptr1 pathways use some divergent host components.

It was considered previously how the Ptr1 locus could play an important role in protection of tomato against bacterial speck disease (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant Microbe. Interact. 32:949-60 (2019), which is hereby incorporated by reference in its entirety). The identification of the Ptr1 gene will now allow it to be efficiently tracked as it is backcrossed into various breeding lines. Ptr1 and Pto are located on different chromosomes (4 and 5, respectively) which will facilitate the development of tomato varieties containing both genes. Such varieties would confer resistance to all currently known races of Pst. The low rate of recombination between *S. lycopersicoides* and tomato DNA could interfere with introgression of a small segment of *S. lycopersicoides* carrying the Ptr1 gene. Methods are available to address low recombination such as using a bridge species as discussed previously (Examples 1-11; Mazo-Molina et al., "The Ptr1 Locus of *Solanum lycopersicoides* Confers Resistance to Race 1 Strains of *Pseudomonas syringae* pv. Tomato and to *Ralstonia pseudosolanacearum* by Recognizing the Type III Effectors AvrRpt2 and RipBN," Mol. Plant. Microbe. Interact. 32:949-60 (2019), which is hereby incorporated by reference in its entirety). Finally, if the new method of CRISPR 'Prime editing' proves to be feasible in tomato then it might be employed to 'repair' the Ptr1 pseudogene present in tomato (Anzalone et al., "Search-and-Replace Genome Editing Without Double-Strand Breaks or Donor DNA," *Nature* 576:149-57 (2019), which is hereby incorporated by reference in its entirety). Such an approach would greatly simplify the introgression of the modified gene into advanced breeding lines for use in development of speck-resistant tomato varieties.

By using a phylogenetic analysis, it was found that the most similar genes to RPS2 and Mr5 in *S. lycopersicoides* fall into distinct clades which are distantly related to Ptr1. The same conclusion came from phylogenetic trees of the most closely related genes to Ptr1 in the apple and *Arabidopsis* genomes. These observations indicate that Ptr1, which is present in at least three solanaceous species, is not orthologous to either RPS2 or Mr5 and likely arose by convergent evolution to mediate recognition of AvrRpt2. Ptr1, RPS2 and Mr5 represent just the third case where non-orthologous NLR-encoding genes in different plant species have been reported to mediate recognition of the same effector. In soybean, the R genes Rpg1b and Rpg1r recognize AvrB and AvrRpm1, respectively, whereas in *Arabidopsis* RPM1 recognizes both of these effectors. Although all of these genes encode CC-NLR proteins, which detect alteration of RIN4, the Rpg1 genes are not orthologous to RPM1 (Ashfield et al., "Convergent Evolution of Disease Resistance Gene Specificity in two Flowering Plant Families," *Plant Cell* 16:309-18 (2004), which is hereby incorporated by reference in its entirety). The other example is the recent discovery of an NLR-encoding gene in barley, Pbr1, whose protein detects AvrPphB-directed cleavage of PBS1 as does the *Arabidopsis* RPS5 protein; the RPS5 and Pbr1 genes are not orthologous (Carter et al., "Convergent Evolution of Effector Protease Recognition by *Arabidopsis* and Barley," *Mol. Plant-Microbe. Interact.* 32:550-65 (2018), which is hereby incorporated by reference in its entirety). These three examples demonstrate the remarkable plasticity inherent in the modular structure of NLR proteins which facilitates the generation of common resistance specificities from highly divergent genes.

The specific mechanisms by which RPS2 and Mr5 are activated upon cleavage of Rin4 are unknown (Prokchorchik et al., "A Host Target of a Bacterial Cysteine Protease Virulence Effector Plays a Key Role in Convergent Evolution of Plant Innate Immune System Receptors," *New Phytol.* 225:1327-42 (2019); and Toruño et al., "Regulated disorder: Posttranslational modifications control the RIN4 plant immune signaling hub," *Mol. Plant Microbe. Interact.* 32:56-64 (2019), which are hereby incorporated by reference in their entirety). The availability now of amino acid sequences of three diverse proteins that mediate recognition of AvrRpt2 might provide insights into subdomains of the proteins that are involved in the response to AvrRpt2 (and to Rin4 cleavage products). As expected, there are a number of residues in common between the Ptr1, StPtr1, NbPtr1a, RPS2, and Mr5 proteins in the NB-ARC domain (FIGS. 34A-34D). More interesting perhaps is the presence of some conserved residues in the LRR domain which is typically more divergent among NLR proteins. Whether these conserved residues play a role in mediating the response to AvrRpt2 will be a focus of future work using the *Agrobacterium* infiltration assay in *N. glutinosa*.

TABLE 13

Additional Sequences.

| Description | SEQ ID NO: | Sequence |
|---|---|---|
| SlRin4-1 | 85 | MARPNVPKFGNWENDDNTPYTVYFEKARQTRGTGKMMNPNDP EENPDMFRNLAPPPEVAPQSKPKRQTEEPPIGRGGPARQTRDHRL SKEDGEFRQYANSPARKESVGRKGANEPSHQRGRGSNSGRTGR |

TABLE 13-continued

Additional Sequences.

| Description | SEQ ID NO: | Sequence |
|---|---|---|
| | | QSIGSEHSFDKSPLHPHYQAKVSNAGRGVASPAWEGKNNSYDSS HGTPGRSKVKQDKSDRGAAVPRFGEWDENDPQSADNYTHIFNK FREEKQGNPSGTPSRTSNNTQKHNSEEKQRKWCCCPW |
| SlRin4-2 | 86 | MARANVPKFGNWGNEDNTPYTVVFENARKNRGGKMINPNDPQ ENPDMFPNVAPSSRPKTPPTEEPMGMETARQTNKRRVSKEDGDF RASSPARNEPTTHQRHGGGRGSNSGRPSRQSGGSDHSIAKSPLHP NSQAKISGRVAASPVWEGKNLYDSSHGTPGRSFESSHATPGRHQ MKQESPDRGTVVPKFGGWDDNDPQDAENYTEVFNKVREQRHV DTGNMPAAGVRTSYSTQRQQRNEKQK |
| SlRin4-3 | 87 | MAGSHVPKFGNWDGENVPYTAYFENARKSNSKGGKMINPNDP EENPEAFAYCGDEDANINISPLVEKHQYHYDHRRNPSVESGQNK SIGPTNSNSESFGDSQRKSVSGFSVNQPTRRRRTSDVKKNKNDRG NGFVPPSPNRPMKNSRNPSDDLSCSSAASVPKFGAWDEKDPKSG EGFTVIFNKVKEEKHIAAAKFPVVQPQSNMSSSNNHKKNAKSKV FCCLF |
| AtRin4 | 88 | MARSNVPKFGNWEAEENVPYTAYFDKARKTRAPGSKIMNPNDP EYNSDSQSQAPPHPPSSRTKPEQVDTVRRSREHMRSREESELKQF GDAGGSSNEAANKRQGRASQNNSYDNKSPLHKNSYDGTGKSRP KPTNLRADESPEKVTVVPKFGDWDENNPSSADGYTHIFNKVREE RSSGANVSGSSRTPTHQSSRNPNNTSSCCCFGFGGK |
| MdRin4-1 | 89 | MAQRSHVPKFGNWEDQESVPYTAYFDKARKGRTGVGGKMINP NDPEENPDILSDTSASSPPKVRPEPGKPVHERRRSREDNDLRFAN SPAQRRSSGEHQPNRGRGVSSGETHRRAARPSAGSENSVERSPL HRNARVSGRDSPSWEGKASYESSHGTPARSRLKPRDESPEKGAA VPKFGEWDENDPASADGFTHIFNKVREEKAGKAPGTPSHPSYQD ARKQGSNDSAKCCCFPWGRK |
| MdRin4-2 | 90 | MAQRSHVPKFGNWEGEESVPYTAYFDKARKDRTGVGGKMINP NDPQENPDILSDISASSPPKVRPEPEKPVHEQRRSREDNDLRFANS PAQRRNSGESAHQPSRGRGVSSGETRRRPARPSAGSENSVERSPL HRNARVTGRDSPSWEGKASYETSHGTPGRSRLKPRDESPEKGAA VPKFGEWDENDPASADGFTHIFNKVREERAGKVPGTPSQPSYQD ARRQGSNDSAKSCCFPWSRK |
| NB-ARC: P-loop, Ptr1 | 91 | VGLGGLGKTTLVKL |
| NB-ARC: P-loop, Consensus | 92 | VGMGGIGKTTLAKK |
| NB-ARC: kinase 2, Ptr1 | 93 | QQKRYLLVLDDVWNEDQ |
| NB-ARC: kinase 2, Consensus | 94 | KGKRYLIVLDDVWDTDQ |
| NB-ARC: kinase 3a, Ptr1 | 95 | SKIVVTTRSKMV |
| NB-ARC: kinase 3a, Consensus | 96 | SRIIXTTRDXXV |
| NB-ARC: GLPL, Ptr1 | 97 | VKKCGGVPLAVKT |
| NB-ARC: GLPL, Consensus | 98 | VKKCKGLPLALKV |
| NB-ARC: MHD, Ptr1 | 99 | NLVHDLAQ |
| NB-ARC: MHD, Consensus | 100 | CRMHDLIR |
| Leucine-rich repeat | 101 | LRMLVLNNLDLEEL |
| Leucine-rich repeat | 102 | LRYLNLSDSGKIKL |

TABLE 13-continued

Additional Sequences.

| Description | SEQ ID NO: | Sequence |
|---|---|---|
| Leucine-rich repeat | 103 | LVNLHTLNLI |
| Leucine-rich repeat | 104 | LKELPRDFR |
| Leucine-rich repeat | 105 | LISLKTLYL |
| Leucine-rich repeat | 106 | LQFLLLFK |
| Leucine-rich repeat | 107 | LQPELVQHFTALRVL |
| Leucine-rich repeat | 108 | LCSLPSSIR |
| Leucine-rich repeat | 109 | LTSLEKLWIWNCEELDL |
| Leucine-rich repeat | 110 | LTSLQSLLLMGLPK |
| Leucine-rich repeat | 111 | LVTLPLELKDTAPTTL |
| Leucine-rich repeat | 112 | LVELPEWLPN |
| Leucine-rich repeat | 113 | LQRLYIEDCPVL |
| SlPtr1 | 114 | ATGTAGATCCTTGAACGTGTTTTGGCGAAATCTTTCTTGTTCA ATATCATTGAACGTGTTTTGGCTAAAGTTTCTTCAATTGCTAT ATATGAGATCAGTCTAGCTTGGAATGTTAAGACAGAGCTAAG GAAACTCCAAAGTACTCTATCCACCATCAAAGTTGTACTTCTA GATGCAAACGAGCAGCAGGCGAAGAACCATGAAGTGAGAGA TTGGCTGGAAAAGCTCAGAGATGTTGTTTATGATGTCGATGAT TTGATGGATGATTTATCAACACAACTGTTGCTGCGAATGCATT TCGAGTAAAGCTTTAGGAAGAAGGTAAGGAAGTTCTTTTCAG GTTCAAATCCAATTATATATCGATTCAAGATTGGCAGAAAAG TAAAAGAAATCAAGGAGCTGCTGAATGAGATTGCAGATGATT GGAGAAATTTCCACTTCACGGAACATACTTATGTAACTCCAG CTGAGAATACGAGTAGAGAACAAACACACTCCTTTGTGAGGG CATCAGATATCATTGGTAGAGATGATGATCAAGAAAACATTG TATAACAGCTGATAGATTCTCATGATGAGGAAAATATTTTTGT GATTCCTATTGTTGGACTTAGAGGGCTTGGAAAAACCACACTT GTTAAGTTGGTTTATAACAATAATAGGGTTGTTCAGAATTTCA ACCTTAGATTGTGGGTTAGTATTTCTGAAGATTTTAGTCTGAG CAAGGTAATTGAGAAATTGTGAGGTCCGGAACAGGAGAGA GTTTTGACCACCTAGATATGGACCAATTACAAGGTTGTTTGGG AGAGGTTTTGCAACAGAAAAGGTATTTACTTGTGCTGATGA TGTGTGGAATGAAGATCAACACAAGTGGATAGATATGAGGGA GTTGCCGATGAATTGTTCCAGAGGTAGTAAAATTGTTGTCACT ACACGTAGTAAGATGGTTGCTTTGATTACTGGAACAGTTCCGC CTTATTATTTGAGAGGCCTTGGTAATGATGACTGCTTATCTTA TTTTTGAAATGTGCATTTGGAGGGCAGGACAATTTGTTTCCTA ATCTAGTAGAAATAGGAAAAGAAATTGTGAAAAAGTGTGGA GGAGTGCCTTTGGCTGTGAAAACCTTGGGAAGGTTGTTGTAC ATGAAAACAGACAAGAACGAATGGTTGCAGATAAGAGACGA TGAGATATGGGAAATCGAACAGAATAAATCTGACATCTTACC AATATTGAGGTTGAGCTATGAACAGATGCCATCACATCTAAG ACAGTGCTTTGCCTATTGCCCCATGTTACCCAAAGGTCAAGAA ATTCCGTGGGAGGATTTTATCAATCGCTGGGCTCAAGGATTTA TCCAGAGTTCAAACAGAAACAGGAAGTTGGAAGATATCGGTA ATCAGTACTTTGATGAGTTGCTATCAAGGTTTTGCTTCCTAGA TGTGATACAAGCAGCTTTTGATGGAGAAATATTGGCTTGTAA GATACACAATCTTGTGCATGATCTTGCACAGTCAGTATCAGGT GCAGAGTGCTTAAATGTGAAACCCAATGCTTTCGTGGTTTCTG AGAGAGTTCGCCACTTATTCTTCCATGCAGAAGATATGTCTAG GAAATACTTCCCCAGATTTTTGCTTCCTTTGCATAAGGTGAGG TCTTTTTTTTTATTCGTTTAATATTGGACCTGTAAACAAGTTTT TTGTCAAGACAATGTTGTCAAATTTCAAATGCCTTCGGATGTT AGTCTTGAACAATCTAGATCTTGAGGAGTTGCCAACTTCGATA |

TABLE 13-continued

Additional Sequences.

| Description | SEQ ID NO: | Sequence |
|---|---|---|
| | | GGTAACTTGAATGAATTAAGATACCTTAACCTTAGTGACAGT<br>GGTAATATCAAGTTTATTCCAAGGTCTATGAGCAAATTAGTA<br>AATTTGCACACCCTTAACCTCATTAACTGTGAACAGCTTAAGG<br>AGTTGCCAAGAGACTTTAGAAAGTTAATCAGCCTGAAGACCT<br>TGTATTTGACCACACATCAGATATTAGCAGGGATCAAGAATC<br>AACATTCTTTCACTTCTCTTCAATTTTTGCTTCTTTTCGAATGT<br>TGTTTCCCAAAATTGCAGCCAGAACTGGTGCAGCATTTTACTG<br>AACTTCGGTTGTTGCGTATCTACGAATGCCAAGTTTATGTTCT<br>CTTCCAAGAAGTATTAGATATCTTACTTCACTTGAAAAGCTAT<br>GGATCTGGAACTGTGAAGAACTTGATTTGATTGATAGAGAAG<br>GAATGTCAGGCCTAACAAGTCTTCAATCCTTGCTTCTAATGGG<br>GCTTCCTAAGTTGGTGACTCTACCATTGGAACTCAAAGATACC<br>GCTCCTACAACATTGAAGTACTTTAGAATCGCCGATTGTCCCT<br>ACCTGGTGGAGCTTCCAGAGTGGCTGCCGAATTGCTCCTCACT<br>TCAGAGACTGTATATAGAGGATTGTCCTGTTTTGGCATCGATA<br>CCTCAAGGAATCTACAACCACAATGCCAACGTCCATATAATC<br>GACTGTCCATTGCTAGGTGGATGA |
| SpPtr1 | 115 | ATGTAGATCCTTGAACGTGTTTTGGCGAAATCTTTCTTGTTCA<br>ATATCATTGAACGTGTTTTGGCTAAAGTTTCTTCAATTGCTAT<br>ATATGAGATCAGTCTAGCTTGGAATGTTAAGACAGAGCTAAG<br>GAAACTCCAAAGTACTCTATCCACCATCAAAGTTGTACTTCTA<br>GATGCAAACGAGCAGCAGGCGAAGAACCATGAAGTGAGAGA<br>TTGGCTGGAAAAGCTCAGAGATGTTGTTTATGATGTCGATGAT<br>TTGATGGGTGATTTATCAACACAACTGTTGCTGCGAATGCATT<br>TCCAGAAAAGCTTTAGGAAGAAGGCAAGGAAGTTCTTTTCAA<br>GTTCAAATCCAATTATATATCGATTCAAGATTGGCAGAAAAG<br>TAAAAGAAATCAAGGAGCTGCTGAATGAGATTGCAGATGATA<br>GGAGAAATTTCCACTTCACGGAACATACTTATGTAATTCCAGC<br>TGAAAATACGAGTAGAGAACAAACACACTCCTTTGTGAGGGC<br>ATCAGATATCATTGGTAGAGATGATGATCAAGAAAACATTGT<br>ATAACAGCTGATAGATTCTCATGATGAGGAAAATATTTTTGTG<br>ATTCCTATTGTTGGACTTAGAGGGCTTGGAAAAACCACACTTG<br>TTAAGTTGGTTTATAACAATAATAGGGTTGTTCAGAATTTCAA<br>CCTTAGATTGTGGGTTAGTATTTCTGAAGATTTTAGTCTGAGC<br>AAGGTAATTGAGAAAATTGTTAGGTCCGGAACAGGAGAGAGT<br>TTTGACCACCTAGATATGGACCAATTACAAGGTTGTTTGGGA<br>GAGGTTTTGCAACAGAAAAGGTATTTACTTGTGCTGGATGAT<br>GTGTGGAATGAAGATCAACACAAGTGGACAGATATGAGGGA<br>GTTGCTGATGAATTGTTCCAGAGGTAGTAAAATTGTTGTCACT<br>ACACGTAGTAAGATGGTTGCTTTGATTACTGGAACAGTTCCGC<br>CTTATTATTTGAGAGGCCTTGGTAATGATGACTGCTTATCTTA<br>TTTTTGAAATGTGCATTTGGAGGGCAGGACAATTTGTTTCCTA<br>ATCTAGTAGAAATAGGAAAAGAAATTGTGAAAAAGTGTGGA<br>GGAGTGCCTTTGGCTGTGAAAACCTTGGGAAGGTTGTTGTAC<br>ATGAAAACAGACAAGAACGAATGGTTGCAGATAAGAGACAA<br>TGAGATATGGGAAATCGAACAGAATAAATCTGACATCTTACC<br>AATATTGAGGTTGAGCTATGAACAGATGCCATCACATCTAAG<br>ACAGTGCTTTGCCTATTGCCCCATGTTACCCAAAGGTCAAGAA<br>ATTCCGAGGGAGGATTTTATCAATCGCTGGGCTCAAGGATTT<br>ATCCAGAGTTCAAACAGAAACAGGAAGTTGGAAGATATCGGT<br>AATCAGTACTTTGATGAGTTGCTATCAAGGTTTTGCTTCCTAG<br>ATGTGGTACAAGCTTTTGATGGAGAAATATTGGCTTGTAAGA<br>TACACAATCTTGTGCATGATCTTGCACAGTCAGTATCAGGTGC<br>AGAGTGCTTAAATGTGAAACCCAATGCTTTCGTGGTTTCTGAG<br>AGAGTTCGCCACTTATTCTTCCATGCAGAAGATATGTCTAGGA<br>AATACTTCCCCAGATTTTTGCTTCCTTTGCATAAGGTGAGGTC<br>TTTTTCTTATTCGTTTAACATTGGACCTGTAAACAAGTTTTTTG<br>TCAAGACAATGTTGTCAAATTTCAAATGCCTTCGGATGTTAGT<br>CTTGAACAATCTAGATCTTGAGGAGTTGCCAACTTCGATAGGT<br>AACTTGAATGAATTAAGATACCTTAACCTTAGTGACAGTGGT<br>AATATCAAGTTTCTTCCAAGGTCTATGAGCAAATTAGTAAATT<br>TGCACACCCTTAACCTCATTAACTGTGAACAGCTTAAGGAGTT<br>GCCAAGAGACTTTAGAAAGTTAATCAGCCTGAAGACCTTGTA<br>TTTGACCACACATCAGATATTTGCAGGGATCAAGAATCAACA<br>TTCTTTCACTTCTCTTCAATTTTGCTTCTTTTCAAATGTTGTTTC<br>CCAAAATTGCAGCCAGAACTGGTGCAGCATTTTACTGCACTTC<br>GGTTGTTGCGTATCTACGAATGCCAAGTTTATGTTCTCTTCC<br>AAGCAGTATTAGATATCTTACTTCACTTGAAAAGCTATGGATC<br>TGGAACTGTGAAGAACTTGATTTGA |
| *S. tuberosum* Ptr1 | 116 | MAESFLFNIIERVLAKVSSIAVYEITLAWNVKIELRKLQSTLSTIK<br>AVLLDANEQQAKNHEVRDWLEKLRDVVYDVDDLMDDLSTQLL<br>LQMHFQKSFRKKVRKFFSSSNPIIYRFKIGRKVKEIRELLNEIADD<br>RRNFHFTEHTFVISAENTSREQTHSFVRASDIIGRDDDQENIIKQLI |

TABLE 13-continued

Additional Sequences.

| Description | SEQ ID NO: | Sequence |
|---|---|---|
| | | GSHDEENISVIPIVGLGGLGKTTLVKLVYNNNRVVQNYDLRMW
VSISEDFNLSKVIEKILRSATGESFDHLDMDQLQGCLGEVLQQKR
YLLVLDDVWNEDQHKWTDLRELLMNCSRGSKIVVTTRSKMVA
LITGTVPPYYLGGLADDDCLSLFLKCAFGGQDNLFPNLVEIGKEI
VKKCGGVPLAVKTLGRLLYMKTDENEWLQIRDNEIWEIEQNKS
DILPILRLSYEQMPSHLRQCFAYCSMLSKGQEIPREDFINRWIAQG
FIQSSNRNRKLEDIGNQYFDELLSRFCFLDVVQAFDGEILACKIHN
LVHDLAQSVAGAECLNVKPNAFVVSERVRHLFFHAEDMSRKHF
PRILLLPLQKLRSFSYSFNIGPVNKFFVKTMLSNFKCLRMLVLNNL
DLEELPTSIGHLKELRYLNLSNSGNIKFLPRSMSKLVNLHTLNLIN
CEQLKELPRDFRKLISLKTLYLTTHQISAGIKNQHVFTSLQFLLLF
KCCFPKLQPELVQHFSALRVLRIYECPSLCSLPSSIRYLTSLEKLWI
WNCEELDLIDGEGMSGLTSLHSLLLMGLPKLVTLPLELKDTAPT
TLKYFRIADCPNLMELPEWLPNCSSLQRLYIEDCPVLASIPQGIYS
HNANLHIIDCPLLGG |
| C. annuum Ptr1 | 117 | MAESFLFNIIERVLAKVSSIAVYEISLAWNVKTDLRKLQSTLSTIK
AVLLDANEKQAKNHEVRDWLEKLRDVVYDVDDLMDDLSTQLL
LQMHFQKSFGKKVRRFFSSSNPIIYRFKIGRRVKEIRELLNEIADD
RKSFHFTEHNYLIPAENTSREQTHSSVRASDIIGRDADQENIVKQL
IDSHNEENISVIPIVGLGGLGKTTLVKLVYNDNRVVQNFDLRMW
VSISEDFSLRKIIEKILRSATGESFDHLDMDQLQGCLGNVLRLKRY
LLVLDDVWNEDQHKWTDLRELLMNCASGSKIVVTTRSKMAALI
TGTVPPYYLEGLANSDDCLSLFLKCAFGGQDNMFPNLVEIGKEI
VKKCGGVPLAVKTLGRLLYTKTDENEWLQIRDNEIWEIEQKESD
ILPILRLSYEQMPSHLRQCFAYCSMLSKGQEIPREDFINRWIAQGF
IQSSNRNSKLEDIGNQYFDELLSRFCFLDVVQAFDGEILACKIHSL
VHDLAQSVAGAECLNVKPNAFVVPERVRHLFFHAEDMSGKHFP
KFLLPLRKLRSFSYSFNVGPVNKFFVKTILSNFKRLRMLVLSNLD
LEELPTSIGHLKELRYLNLSGSGNIKFLPRSMSKLVNLQTLNLINC
EQLKELPRDFAKLISLKTLYLTTQQISVGIKCKNQHSFTSLQFLLL
FKCCFPKLQPELVQHFTALRVLRIYECPSLCSLPSSIRYLTSLEKL
WIWNCEELDLMDGEGMSGLSSLRSLLLMGLPKLVTLPLELKDT
APATSKYFRIADCPNLVELPEWLQNYSSLQRLYVEDCPALASIPP
GIYNHNVNVHIIDCPLLSGGC |
| C. baccatum Ptr1 | 118 | MAESFLFNIIERVLAKVSSIAVYEISLAWNVKTDLRKLQSTLSTIK
AVLLDANEKQAKNHEVRDWLEKLRDVVYDVDDLMDDLSTQLL
LQMHFQKSFGKKVRRFFSSSNPIIYRFKIGRRVKEIRELLNEIADD
RKSFHFTEHNYLIPAENTSREQTHSFVRASDIIGRDADQENIVKQL
IDSRNEENISVIPIVGLGGLGKTTLVKLVYNDNRVVQNFDLRMW
VSISEDFSLRKIIEKILRSATGESFDHLDMDQLQGCLGNVLQLKR
YLLVLDDVWNEDQHKWTDLRELLMNCARGSKIVVTTRSKMAA
LITGTVPPYYLEGLASDDCLSLFLKCAFGGQDNMFPNLVEIGKEI
VKKCGGVPLAVKTLGRLLYTKTDENEWLQIRDNEIWEIEQKESD
ILPILRLSYEQMPSHLRQCFAYCSMLSKGQEIPREDFINRWIAQGF
IQSSNRNSKLEDIGNQYFDELLSRFCFLDVVQAFDGEILACKIHSL
VHDLAQSVAGAECLNVKPNAFVVPERVRHLFFHAEDMSGKHFP
KFLLPLRKLRSFSYSFNVGPVNKFFVKTILSNFKRLRMLVLSNLD
LEELPTSIGHLKELRYLNLSGSGNIKFLPRSMSKLVNLQTLNLINC
EQLKELPRDFTKLISLKTLYLTTQQISVGIKFKNQHSFTSLQFLLLF
KCCFPKLQPELVQHFTALRVLRIYECPSLCSLPSSIRYLTSLEKLW
IWNCEELDLMDGEGMSGLSSLRSLLLMGLPKLVTLPLELKDTAP
ATSKYFRIADCPNLVELPEWLQNYSSLQRLYIEDCPALASIPPGIY
NHNVNVHIIDCPLLSGGC |
| C. chinense Ptr1 | 119 | MAESFLFNIIERVLAKVSSIAVYEISLAWNVKTDLRKLQSTLSTIK
AVLLDANEKQAKNHEVRDWLEKLRDVVYDVDDLMDDLSTQLL
LQMHFQKSFGKKVRRFFSSSNPIIYRFKIGRRVKEIRELLNEIADD
RRSFHFTEHNYLIPAENTSREQTHSSVRASDIIGRDADQENIVKQL
IDSHNEENISVIPIVGLGGLGKTTLVKLVYNDNRVVQNFDLRMW
VSISEDFSLRKIIEKILRSATGESFDHLDMDQLQGCLGNVLQLKR
YLLVLDDVWNEDQHKWTDLRELLMNCASGSKIVVTTRSKMAA
LITGTVPLYYLEGLASDDCLSLFLKCAFGGQDNMFPNLVEIGKEI
VKKCGGVPLAVKTLGRLLYTKTDENEWLQIRDNEIWEIEQKESD
ILPILRLSYEQMPSHLRQCFAYCSMLSKGQEIPREDFINRWIAQGF
IQSSNRNSKLEDIGNQYFDELLSRFCFLDVVQAFDGEILACKIHSL
VHDLAQSVAGAECLNVKPNAFVVPERVRHLFFHAEDMSGKHFP
KFLLPLRKLRSFSYSFNVGPVNKFFVKTILSNFKRLRMLVLSNLD
LEELPTSIGHLKELRYLNLSGSGNIKFLPRSMSKLVNLQTLNLINC
EQLKELPRDFAKLISLKTLYLTTQQISVGIKCKNQHSFTSLQFLLL
FKCCFPKLQPELVQHFTALRVLRIYECPSLCSLPSSIRYLTSLEKL
WIWNCEELDLMDGEGMSGLSSLRSLLLMGLPKLVTLPLELKDT
APATSKYFRIADCPNLVELPEWLQNYSSLQRLYIEDCPALASIPPG
IYNHNVNVHIIDCPLLSGGC |

TABLE 13-continued

Additional Sequences.

| Description | SEQ ID NO: | Sequence |
|---|---|---|
| N. attenuata Ptr1 | 120 | MAESFLFNIIERVLAKVSSVAVTEISLAWNVKTELRKLQSTLSTIK AVLLDANEQQAKNHEVRDWLEKLRDVVYDVDDVLDDLSTQLL LQIHFQKSLKKKVRKFFSSSNPIIYRFKIGRKVKEIRELLNEIADDR KSFHFTEHTCLNPVENICREQTHSFVRASDIIGRETDQENIVKQLI DARDEENISVIPIVGLGGLGKTTLVKLVYNYNTVVQNFDLRMW VSISEDFSLSKVIEKILRSATGESFGHLDMDQLQGHLSEVLRSKRY LLVLDDVWNEDQNKWTDLRELLMNCSKGSKIVVTTRSKMVALI TGTVAPYYLGGLTDDACLLLFLKCAFVGEDKLLPNLVEIGKEIV KKCGGVPLAVKTLGRLLYMKTDENEWLRIRDNEIWEIEQKQSDI LPILRLSYEQMPSHLRQCFAYCSMLSKGQEIPREDFINRWIAQGFI QSSNGSRKLEDIGNQYFDELLSRFCFLDVVQAFDGEILACKLHNL VHDLAQSVAGSECLNVKSNASVVSERVRHLFFHAEDMSRKHFP RFLLSLQKLRSFSYSFNIGPVNKFFVKTTLSNFKCLRVLVLNNLD FEELPTSIGHLKELRYLNLSDNGNIKFLPMSMSKLVNLQTFNLIN CEQLKELPRDFGKLICLKTLYLTTYKISAGKNQQSFPSLQFLLLFK CCFPKLQPELVQQFTALRVLRIYECPSLCSLPSSIRYLTSLEKLWI WNCEELDLMDGEGMVGLTSLRSLLLMGLPKLVTLPLGLKDAAH ATLKYFRVADCPNLVVLPEWLQNCSSLQRLYIEDCPVLATIPQGI YNHNANVHIIDCPLLSGGC |
| N. benthamiana (Nb) Ptr1a | 121 | MAEFFLFNIIERVLSKVSSVSVNEISLAWNVKTELRKLQSTLSTIK AVLLDANERQAKNHEVRDWLEKLRDVVYDVDDVLDDLSTQLL LQIHFQESLKKKVRKFFSSSNPIIYRFKIGRKIKEIRELLNDIADDR KSFHFTEHTCINPVENICREQTHSFVRASDIIGRETDQENIVKQLID SRDEENISVIPIVGLGGLGKTTLVKLVYNNNKVVQNFDLRMWVS ISEDFSLSKVIEKILRSATGESFGHLDMDQLQGHLSEVLRSKRYLL VLDDVWNEDQNRWTDLRELLMNCSRGSKIVVTTRSKMVALITG TVAPYYLGGLTDDACLSLFLKCAFVGEDKLLPNLVEIGKEIVKK CGGVPLAVKTLGRLLYMKTDENEWLRIRDNEIWEIEQKQSDILPI LRLSYEQMPSHLRQCFAYCSMLSKGQEIPREDFINRWIAQGFIQS SNGSRKLEDIGNQYFDELLSRFCFLDVVQAFDGEILACKLHNLV HDLAQSVAGSECSNVKSNASVVSERVRHLFFHAEDMSRKHFPRF LLSLQKLRSFSYAFNIGPANKFFVKTTLSNFKCLRVLVLNNLDFE ELPTSIGHLKELRYLNLSDNGNIKFLPRSMSKLVNLQTLNLINCE QLKELPRDFGKLICLKTLYLTTYKISAGKNQQSFPSLQFLLLLFKCC FPKLQPELVQQFTALRVLRIYECPSLCSLPSSIRYLTSLEKLWIWN CEELDLMDGEGMVGLTNLRSLLLMGLPKLVTLPLGLKDAAHAT LNYFRVADCPNLVVLPEWLQDCSSLQRLYIEDCPVLATVPQGIY NHNANVHIIDCPLLSGGC |
| N. tabacum Ptr1 | 122 | MLLQSMAETFLFNIIERVLAKVSSVAVYEISLAWNVKTELRKLQS TLSTIKAVLLDANEQQAKNHEVRDWLEKLRDVVYDVDDLLDDL STQLTLQMHFQKSLKKKVRKFFSSSNPIFYRFKIGRKVKEIRELLN EIAHDRKSFHFTEHTYLNPVENICREQTHSFVRASDIIGRETDQEN IVKQLIDAREEENISVIPIVGLGGLGKTTLVKLVVVQNFD LRMWVSISEDFSLSKVIEKILRSATGESFGHLDMDQLQSHLSEVL RSKRYLLVLDDVWNEDQNKWTDLRELLMNCSRGSKIVVTTRSK MVALITGTVAPYYLGGLADDECLSLFLKCAFVGEDKLLPNLVEI GKEIVKKCGGVPLAVKTLGRLLYMKTDENEWLRIRDNEIWEIEQ KQSDILPILRLSYEQMPSHLRQCFAYCSMLSKGQEIPREDFINRWI AQGFIQSSNGSRKLEDIGNQYFDELLSRFCFLDVVQAFDGEILAC KLHNLVHDLAQSVAGSECLNVKSNASVVSERVRHLFFHAEDMS RKHFPRFLLSLQKLRSFSYSFNIGPVNKFFVKTMLSNFKCLRVLV LNNLDFGELPTSIGHLKELRYLNLSDNGNIKFLPRSMSKLVNLQT LNLINCEQLKELPRDFEKLICLKTLYLTTYKISAGKNQQSFPSLQF LLLFKCCFPKLQPELVQQFTALRILRIYECRSLYSLPSSIRYLTSLE KLWIWNCEELDLMDGEGMVGLTSLRSLLLMGLPKLVTLPLGLK DTAHATLKYFRVADCPNLAVLPEWLQNCSSLQRLYIEDCPVLAS IPQGIYNHNAEVHIIDCPLLSGGC |
| N. tomentosiformis Ptr1 | 123 | MAETFLFNIIERVLAKVSSVAVYEISLAWNVKTELRKFQSTLSTIK AVLLDANEQQAKNHEVRDWLEKLRDVVYDVDDLLDDLSTQLT LQMHFQKSLKKKVRKFFSSSNPIIYRFKIGRKVKEIRELLNEIAHD RKSFHFTEHTYLNPVENICREQTHSFVRASDIIGRETDQENIVKQL IDAREEENISVIPIVGLGGLGKTTLVKLVYNNNKVVQNFDLRMW VSISEDFSLSKVIEKILRSATGESFGHLDMDQLQSHLSEVLRSKRY LLVLDDVWNEDQNKWTDLRELLMNCSRGSKIVVTTRSKMVALI TGTVAPYYLGGLADDECLSLFLKCAFVGEDKLLPNLVEIGKEIV KKCGGVPLAVKTLGRLLYMKTDENEWLRIRDNEIWEIEQKQSDI LPILRLSYEQMPSHLRQCFAYCSMLSKGQEIPREDFINRWIAQGFI QSSNGSRKLEDIGNQYFDELLSRFCFLDVVQAFDGEILACKLHNL VHDLAQSVAGSECLNVKSNASVVSERVRHLFFHAEDMSRKHFP RFLLSLQKLRSFSYSFNIGPVNKFFVKTMLSNFKCLRVLVLNNLD FGELPTSIGHLKELRYLNLSDNGNIKFLPRSMSKLVNLQTLNLINC |

TABLE 13-continued

Additional Sequences.

| Description | SEQ ID NO: | Sequence |
|---|---|---|
| | | EQLKELPRDFEKLICLKTLYLTTYKISAGKNQQSFPSLQFLLLFKC<br>CFPKLQPELVQQFTALRILRIYECRSLYSLPSSIRYLTSLEKLWIW<br>NCEELDLMDGEGMVGLTSLRSLLLMGLPKLVTLPLGLKDTAHA<br>TLKYFRVADCPNLAVLPEWLQNCSSLQRLYIEDCPVLASITQGIY<br>NHNAEVHIIDCPLLSGGC |
| NbPtr1a | 124 | ATGGCAGAATTTTCTTGTTCAACATCATTGAAAGAGTTTTGT<br>CAAAAGTTTCTTCAGTTTCTGTAAATGAGATCAGTTTAGCGTG<br>GAATGTTAAAACAGAGTTAAGAAAACTCCAGAGCACTTTATC<br>CACAATCAAAGCTGTACTTTTAGATGCAAATGAGCGGCAGGC<br>AAAGAACCATGAAGTGAGAGATTGGCTGGAAAAGCTAAGAG<br>ATGTTGTTTATGATGTCGATGATGTGCTCGATGATTTGTCAAC<br>ACAGCTATTACTACAAATACATTTTCAGGAAAGCCTTAAGAA<br>GAAGGTAAGAAAATTCTTTTCAAGTTCAAATCCAATTATTTAT<br>AGATTCAAGATTGGTAGAAAGATAAAAGAGATTAGGGAACT<br>ATTGAATGATATTGCAGATGATCGGAAAAGTTTCCACTTTACT<br>GAACATACTTGTATAAATCCAGTTGAAAATATTTGTAGAGAA<br>CAAACACATTCCTTTGTAAGGGCCTCTGATATTATTGGTAGAG<br>AAACTGATCAAGAAAACATAGTAAAACAGCTCATAGATTCTC<br>GCGATGAGGAAAATATTTCTGTGATTCCTATTGTTGGACTTGG<br>AGGGCTTGGAAAAACCACACTTGTTAAGTTGGTTTATAACAA<br>TAATAAGGTTGTTCAGAATTTTGACCTGAGAATGTGGGTGAG<br>TATTTCAGAAGATTTTAGTCTGAGTAAGGTAATTGAGAAAATT<br>CTGCGATCTGCAACAGGAGAGAGTTTTGGCCACCTAGATATG<br>GACCAATTACAAGGTCATTTGAGTGAGGTTTTGCGATCGAAA<br>AGGTATTTACTTGTACTGGATGATGTGTGGAATGAAGATCAA<br>AACAGGTGGACGGACTTGAGGGAGTTGCTGATGAATTGTTCT<br>AGAGGTAGTAAGATTGTTGTCACTACACGCAGTAAGATGGTT<br>GCTTTGATTACTGGAACAGTTGCACCTTACTATTTGGGTGGTC<br>TTACCGATGATGCGTGCTTATCGTTATTTTTGAAATGTGCATT<br>TGTAGGGGAGGACAAATTGTTGCCTAATCTAGTAGAAATAGG<br>AAAAGAGATTGTGAAAAAGTGTGGAGGAGTGCCTTTGGCTGT<br>GAAAACCTTGGGAAGGTTATTGTATATGAAAACAGACGAAAA<br>TGAATGGTTGCGGATAAGAGATAATGAGATATGGGAGATCGA<br>ACAGAAACAATCAGACATTTTACCAATATTGAGATTGAGCTA<br>TGAACAGATGCCATCTCATCTAAGACAGTGCTTTGCCTATTGC<br>TCCATGTTATCCAAAGGTCAAGAAATTCCGAGAGAGGACTTC<br>ATCAACCGGTGGATTGCTCAAGGATTTATACAGAGTTCTAAC<br>GGATCCAGGAAGTTGGAAGATATTGGTAATCAGTACTTTGAT<br>GAGTTGCTATCAAGGTTTTGCTTCCTTGATGTGGTACAAGCAT<br>TTGATGGAGAAATATTGGCTTGTAAGTTACACAATCTTGTGCA<br>TGATCTTGCACAGTCAGTGGCAGGTTCTGAATGTTCAAATGTG<br>AAATCTAATGCTTCTGTGGTTTCTGAAAGAGTTCGCCACTTAT<br>TTTTTCATGCAGAAGATATGTCTAGGAAACACTTCCCAAGATT<br>TTTACTTTCTTTGCAAAAGTTGAGGTCTTTTTCTTACGCATTTA<br>ACATTGGACCTGCAAACAAGTTCTTTGTCAAGACGACATTATC<br>AAATTTCAAATGCCTTCGGGTGTTAGTCTTGAACAATTTAGAT<br>TTTGAGGAGTTGCCAACTTCGATAGGTCACTTGAAGGAACTA<br>AGATATCTTAACCTCAGTGACAATGGTAACATCAAGTTTCTCC<br>CAAGGTCTATGAGCAAATTAGTAAATCTGCAGACTCTTAACC<br>TCATTAATTGTGAACAGCTTAAGGAGTTGCCGAGAGACTTTG<br>GAAAGTTAATCTGCTTGAAGACCTTGTATTTGACTACATATAA<br>GATATCAGCAGGGAAGAATCAACAATCTTTCCCTTCTCTTCAA<br>TTTTTGCTTCTTTTCAAGTGTTGTTTCCCAAAATTGCAGCCAGA<br>ACTGGTGCAGCAGTTTACTGCACTTCGGGTTTTGCGTATCTAT<br>GAATGCCCGAGTTTATGTTCTCTTCCAAGCAGTATTAGATACC<br>TGACTTCACTTGAAAAGCTATGATTTGGAACTGTGAAGAAC<br>TTGATTTGATGGATGGAGAGGGAATGGTAGGCCTAACAAATT<br>TACGGTCGTTGCTTCTAATGGGACTCCCTAAGTTGGTGACTCT<br>ACCATTGGGACTTAAAGATGCTGCTCATGCAACACTGAACTA<br>CTTTAGAGTTGCCGATTGTCCCAACCTAGTGGTGCTTCCAGAA<br>TGGCTGCAGGATTGCTCTTCCCTTCAGAGGCTGTATATAGAGG<br>ATTGTCCTGTATTGGCAACTGTACCTCAAGGAATCTACAACCA<br>TAATGCCAATGTCCATATAATCGACTGTCCATTGCTAAGTGGA<br>GGATGCTAA |
| NbPtr1b | 125 | ATGGCAGAATCTTTCTTGTTCAACATCATTGAAAGAGTTTTGG<br>CAAAAGTCTCTTCAGTTGCTGTAAATGAGATCAGTTTAGCTTG<br>GATTGTTAAAATTAAGAAAACTCCAGAGCACTTTATCCACAA<br>TCAAAGCTGTACTTTTAGATGCAAATGAGCAGTAGGCAAAGA<br>ACCATGAAGTGAGAGATTGGCTGGAAAAGCTAAGACATATTG<br>TTTATGATGTCGATGATCTGCTCGATGATTTGTCTACACAGTT<br>ATTACTACAAATACATTTTCAGAAAAGCCTTAAGAAGAAGGT<br>AAGAAAATTCTTTTCAAGTTCAAATCCAATTATTTATAGATTC<br>AAGATTGGTAGAAAGGTAAAAGAGATTAGGGAACTATTGAAT |

TABLE 13-continued

Additional Sequences.

| Description | SEQ ID NO: | Sequence |
|---|---|---|
| | | GAGATTGCAGATGATAGGAGAACTTTCCACTTTACTGAACAT<br>ACTTGTCTAAATCCAGTTGAGAATATTTGTAGAGAACAAACA<br>CATTCCTTTGTAAGGGCCTCCGATATTATTAGTAGAGAAACTG<br>ATCAAGAAAACATAGTAAAACAGCTCATAGATGCTCGTGACG<br>AGGAAAATATTTCTGTGATTCCTGTTGTTGGACTTGGTGGGCT<br>TGGAAAAACCACACTTGTTAAGTTGGTTTATAACAATAATAA<br>GGTTGTTCAGAATTTTGACCTGAGAATGTGGGTTAGTATTTCA<br>GAGGATTTTAGTCTGAGTAAGGTAATTGAGAAAATTCTGCGG<br>TCTGCAACAGGAGAGAGTTTTGGCCACCTTGATATGGATCAA<br>TTACAAGGTCATTTAAGTGAGGTTTTGCGATCAAAATGGTATT<br>TACTTGTACTGGATGATGTGTGGAATGAAGATCAAACAGGT<br>GGACGGACTTGAGGGAGTTGCTGATGAATTGTTCTAGAGGTA<br>GTACGATTGTTGTCACTACACGCAATAAGATGGTTGCTTTGAT<br>TACTGGAACAGTTGCACCTTACTATTTGGGTGGTCTTACTGAT<br>GTGCGTGCTTATCGTTATTTTTGAAATGTGCATTTGTAGGGGT<br>GGAAAAATTGTTGCCTAATCTAGTAGAAATAGGAAAAGAAAT<br>TGTGAAAAAGTGTGGAGGAGTGCCTTTGGCTGTGAAAACCTT<br>GGGAAGGTTGCTGTACATGAAAACAGACGAAAATGAATGGTT<br>GCGGATACGAGATAATGAGATATGGGAGATCGAACAGAAAC<br>AATCTGACATTTTGCCAATATTGAGATTGAGCTATGAACAGAT<br>GCCATCACATCTAAGACAGTGCTTTGCCTATTGCTCCATGTTA<br>TCCAAAGGTCAAGAAATTCCGAGAGAGGACTTCATCAACCGG<br>TGGATTGCTCAAGGATTTATACAGAGTTCAAACGGATCCAGG<br>AAGTTGGAAGATATTGGTAATCAGTACTTTGATGAGTTACTAT<br>CGAGGTTTTGCTTCCTTGATGTGGTACAAGCTTTTGATGGAGA<br>ATATTGGCTTGTAAGTTACACAATCTTGTGCATGATCTTGCA<br>CAGTCAGTGGCAGGTTCTGAATGTTAAATGTGAAATCTAAT<br>GCTTCTGTGGTTTCTGAAAGAGTTCGCCACTTATTTTTTCATGC<br>AGAAGATATGTCTAGGAAACACTTCCCAATATTTTTACTTTCT<br>TTGCAAAAGTTGAGGTCTTTTTCTTACTCATTTAACATTGGAC<br>CTGTAAACAAGTTCTTTGTCAAAACGACGTTATCAAATTTCAA<br>ATGCCTTCGGGTGTTAGTCTTGAACAATTTAGATTTTGAGGAG<br>TTGCCAACTTCGATAGGTCACTTGAAGGAATTAAGATATCTTA<br>ACCTTAGTGACAATGGCAACATCAAGTTTCTCCCAAGGTCTAT<br>GAGCAAATTAGTAAATCTGCAGACTTTTAACCTCATTAGTTGG<br>GAACAGCTTAAGGAGTTGCCAAGAGGCTTTGGAAAGTTAATC<br>TGTTTGAAGACCTTGTATTTGACTACATATAAGATACGGAAA<br>AGAGTCATATGTTCTACTAGTCAAAATAAGCTACATTTGTCCT<br>CCGTTATACTATTTGGCCATATATGTCCCTACCGTTCACATCT<br>CTGGCCATATATGTCCCTCTGACGTTAACTTTTTTAAAAAAAT<br>AATTAAAAGCCACGTGTCATAGTCCTATTGGTTAAACTAAAC<br>CCACTTCTTTTTTTTAATATTAAAACGAAAATATTTGTAAAAA<br>ATGTAAAAAAACTTGTAAAAAATGTGTCAAAAATAATTTTGT<br>CAAAAATAAAAATATTTTATTAAAAAAATTTTATTTTTGTTTT<br>TACAAGAAGAAAATCAGTTCATTTTCAAATTTGAAAAATATTT<br>CCAAAATGTGTTTTTGTTTTTAAAA |
| SynPtr1 | 126 | ATGGCAGAATCATTCCTTTTCAACATTATTGAGAGGGTTCTTG<br>CTAAGGTTTCATCAATCGCTGTGTATGAAATCTCACTAGCATG<br>GAACGTTAAAACAGAACTAAGAAAACTTCAATCTACTCTTTC<br>CACTATCAAGGCTGTTCTTCTTGATGCTAACGAACAAAAAGC<br>AAAAAACCACGAAGTTAGAGACTGGCTTGAAAAACTCAGGG<br>ATGTGGTTTACGATGTTGATGACCTTATGGACGATCTTTCAAC<br>TCAACTTTTGCTTCAGATGCACTTCCAAAAATCTTTTAGAAAG<br>AAAGTAAGGAGATTTTTTCTAGTTCTAATCCTATTATTTATA<br>GATTCAAAATTGGAAGAAAAGTAAAGGAAATTAGGGAACTG<br>CTTAATGAAATTGCTGATGACAGGAGGAATTTTCACTTTACGG<br>AGCATACATATGTTATTCCTGCTGAGAATACTAGTAGGGAAC<br>AGACACATTCCTTCGTGAGAGCCTCTGATATTATTGGAAGAG<br>ACGATGACCAAGAGAACATCGTAAAGCAGCTTATAGACTCTC<br>ACGATGAAGAAACATTTCAGTGATCCCTATCGTTGGTCTTGG<br>TGGGTTGGGAAAGACCACTCTTGTGAAGCTTGTTTACAACAA<br>CAATAGAGTTGTGCAGAACTTTGATCTTAGGATGTGGGTGAG<br>TATCTCAGAGGATTTTAGTCTTAGCAAAGTAATCGAGAAGAT<br>TCTTAGGTCTGCAACTGGAGAAAGTTTCGACCATCTAGACAT<br>GGATCAACTTCAATGCTGTCTTGGAGAAGTTCTTCAACAAAA<br>AAGATATCTTCTTGTTCTGGACGATGTGTGGAATGAAGACCA<br>ACATAAGTGGACAGATCTTAGAGAGCTTCTTATGAACTGTTCT<br>AGAGGAAGTAAGATTGTGGTCACAACAAGAAGTAAATGGT<br>GGCTCTTATTACAGGAACTGTTCCACCTTACTATCTTGGAGGA<br>CTTGCAAATGACGACTGTTTATCATTATTCTTGAAGTGTGCTT<br>TTGGTGGACAAGACAACTTGTTCCCTAACCTAGTTGAAATTGG<br>AAAGGAAATCGTGAAGAAGTGCGGAGGTGTGCCATTGGCAGT<br>GAAGACCCTTGGAAGATTGCTTATATGAAGACAGATGAGAA<br>CGAGTGGTTGCAAATAAGGGATAACGAGATTTGGGAGATCGA |

TABLE 13-continued

Additional Sequences.

| Description | SEQ ID NO: | Sequence |
|---|---|---|
| | | GCAGAACAAATCAGACATCTTACCTATACTTAGACTTAGCTA<br>CGAACAAATGCCTTCACACCTAAGGCAGTGTTTTGCTTATTGT<br>TCTATGTTGCCCAAGGGTCAGGAAATCCCGAGAGAGGACTTT<br>ATTAATAGATGGATCGCTCAGGGATTCATACAAAGTTCTAAC<br>AGGAACAGAAAGCTTGAAGACATCGGAAATCAATACTTCGAT<br>GAATTGCTTTCAAGATTTTGTTTCCTTGATGTTGTACAGGCTTT<br>CGATGGTGAAATTTTGGCATGTAAAATACATAATTTGGTGCA<br>CGATTTGGCACAATCAGTTTCAGGAGCAGAATGCCTTAATGTT<br>AAACCTAATGCATTCGTTGTCTCAGAAAGGGTTAGACACCTTT<br>TTTTTCATGCTGAAGACATGTCAAGGAAGCACTTTCCCAGGTT<br>TCTTCTTCCATTGCAGAAGCTTAGGTCATTCTCATATTCATTTA<br>ATATTGGTCCTGTTAACAAATTCTTCGTCAAAACTATGCTTTC<br>AAACTTCAAGTGCTTGAGAATGCTTGTCCTTAACAACCTAGAC<br>CTTGAAGAGCTTCCAACATCGATTGGTCATTTGAAAGAACTTA<br>GATATCTCAATCTTTCTGACTCTGGTAAAATCAAATTTTTGCC<br>AAGATCAATGTCTAAACTTGTAAACCTGCATACCCTAAATCTC<br>ATCAACTGCGAACAACTTAAAGAGCTTCCAAGGGATTTCAGA<br>AAATTAATTAGCCTTAAGACTTTGTACTTGACAACACACCAA<br>ATGTCTGCAGGTATCAAAAATCAGCATTCATTCACATCTTTGC<br>AATTCTTATTGCTTTTTAAATGCTGTTTTCCAAAGTTGCAACC<br>AGAGCTGGTTCAGCACTTTACTGCATTGCGGGTGTTGAGAATC<br>TACGAATGTCCATCATTATGCTCTTTGCCATCTAGTATCAGAT<br>ACCTGACATCATTGGAAAAACTTTGGATTTGGAATTGTGAGG<br>AATTGGATCTTATTGACGGAGAGGGAATGTCTGGCCTTACAT<br>CTCTTCAGTCCCTTCTTCTTATGGGACTTCCAAAGCTTGTGAC<br>ACTACCTTTGGAGCTTAAGGATACAGCTCCAACAACTTTAAA<br>ATACTTTAGAATTGCCGACTGTCCTAACCTTGTGGAACTTCCT<br>GAATGGCTTCCTAACTGCTCTTCATTGCAGAGGCTCTACATAG<br>AAGATTGCCCTGTGTTGGCTTCGATTCCTCAGGGAATTTACTC<br>TCACAACGCCAATGTCCACATAATTGACTGCCCACTTCTAGGA<br>GGATAA |
| RPS2 | 127 | ATGGATTTCATCTCATCTCTTATCGTTGGCTGTGCTCAGGTGTT<br>GTGTGAATCTATGAATATGGCGGAGAGAAGAGGACATAAGA<br>CTGATCTTAGACAAGCCATCACTGATCTTGAAACAGCCATCG<br>GTGACTTGAAGGCCATACGTGATGACCTGACTTTACGGATCC<br>AACAAGACGGTCTAGAGGGACGAAGCTGCTCAAATCGTGCCA<br>GAGAGTGGCTTAGTGCGGTGCAAGTAACGGAGACTAAAACA<br>GCCCTACTTTTAGTGAGGTTTAGGCGTCGGGAACAGAGGACG<br>CGAATGAGGAGGAGATACCTCAGTTGTTTCGGTTGTGCCGAC<br>TACAAACTGTGCAAGAAGGTTTCTGCCATATTGAAGAGCATT<br>GGTGAGCTGAGAGAACGCTCTGAAGCTATCAAAACAGATGGC<br>GGGTCAATTCAAGTAACTTGTAGAGAGATACCCATCAAGTCC<br>GTTGTCGGAAATACCACGATGATGGAACAGGTTTTGGAATTT<br>CTCAGTGAAGAAGAAGAAAGAGGAATCATTGGTGTTTATGGA<br>CCTGGTGGGGTTGGGAAGACAACGTTAATGCAGAGCATTAAC<br>AACGAGCTGATCACAAAAGGACATCAGTATGATGTACTGATT<br>TGGGTTCAAATGTCCAGAGAATTCGGCGAGTGTACAATTCAG<br>CAAGCCGTTGGAGCACGGTTGGGTTTATCTTGGGACGAGAAG<br>GAGACCGGCGAAAACAGAGCTTTGAAGATATACAGAGCTTTG<br>AGACAGAAACGTTTCTTGTTGTTGCTAGATGATGTCTGGGAA<br>GAGATAGACTTGGAGAAAACTGGAGTTCCTCGACCTGACAGG<br>GAAAACAAATGCAAGGTGATGTTCACGACACGGTCTATAGCA<br>TTATGCAACAATATGGGTGCGGAATACAAGTTGAGAGTGGAG<br>TTTCTGGAGAAGAAACACGCGTGGGAGCTGTTCTGTAGTAAG<br>GTATGGAGAAAAGATCTTTTAGAGTCATCATCAATTCGCCGG<br>CTCGCGGAGATTATAGTGAGTAAATGTGGAGGATTGCCACTA<br>GCGTTGATCACTTTAGGAGGAGCCATGGCTCATAGAGAGACA<br>GAAGAAGAGTGGATCCATGCTAGTGAAGTTCTGACTAGATTT<br>CCAGCAGAGATGAAGGGTATGAACTATGTATTTGCCCTTTTG<br>AAATTCAGCTACGACAACCTCGAGAGTGATCTGCTTCGGTCTT<br>GTTTCTTGTACTGCGCTTTATTCCCAGAAGAACATTCTATAGA<br>GATCGAGCAGCTTGTTGAGTACTGGGTCGGCGAAGGGTTTCT<br>CACCAGCTCCCATGGCGTTAACACCATTTACAAGGGATATTTT<br>CTCATTGGGGATCTGAAAGCGGCATGTTTGTTGGAAACCGGA<br>GATGAGAAAACACAGGTGAAGATGCATAATGTGGTCAGAAG<br>CTTTGCATTGTGGATGGCATCTGAACAGGGGACTTATAAGGA<br>GCTGATCCTAGTTGAGCCTAGCATGGGACATACTGAAGCTCC<br>TAAAGCAGAAAACTGGCGACAAGCGTTGGTGATCTCATTGTT<br>AGATAACAGAATCCAGACCTTGCCTGAAAAACTCATATGCCC<br>GAAACTGACAACACTGATGCTCAACAGAACAGCTCTTTGAA<br>GAAGATTCCAACAGGGTTTTTCATGCATATGCCTGTTCTCAGA<br>GTCTTGGACTTGTCGTTCACAAGTATCACTGAGATTCCGTTGT<br>CTATCAAGTATTTGGTGGAGTTGTATCATCTGTCTATGTCAGG<br>AACAAAGATAAGTGTATTGCCACAGGAGCTTGGGAATCTTAG |

TABLE 13-continued

Additional Sequences.

| Description | SEQ ID NO: | Sequence |
|---|---|---|
| | | AAAACTGAAGCATCTGGACCTACAAAGAACTCAGTTTCTTCA |
| | | GACGATCCCACGAGATGCCATATGTTGGCTGAGCAAGCTCGA |
| | | GGTTCTGAACTTGTACTACAGTTACGCCGGTTGGGAACTGCA |
| | | GAGCTTTGGAGAAGATGAAGCAGAAGAACTCGGATTCGCTGA |
| | | CTTGGAATACTTGGAAAACCTAACCACACTCGGTATCACTGTT |
| | | CTCTCATTGGAGACCCTAAAAACTCTCTTCGAGTTCGGTGCTT |
| | | TGCATAAACATATACAGCATCTCCACGTTGAAGAGTGCAATG |
| | | AACTCCTCTACTTCAATCTCCCATCACTCACTAACCATGGCAG |
| | | GAACCTGAGAAGACTTAGCATTAAAAGTTGCCATGACTTGGA |
| | | GTACCTGGTCACACCCGCAGATTTTGAAAATGATTGGCTTCCG |
| | | AGTCTAGAGGTTCTGACGTTACACAGCCTTCACAACTTAACCA |
| | | GAGTGTGGGAAATTCTGTAAGCCAAGATTGTCTGCGGAATA |
| | | TCCGTTGCATAAACATTTCACACTGCAACAAGCTGAAGAATG |
| | | TCTCATGGGTTCAGAAACTCCCAAAGCTAGAGGTGATTGAAC |
| | | TGTTCGACTGCAGAGAGATAGAGGAATTGATAAGCGAACACG |
| | | AGAGTCCATCCGTCGAAGATCCAACATTGTTCCCAAGCCTGA |
| | | AGACCTTGAGAACTAGGGATCTGCCAGAACTAAACAGCATCC |
| | | TCCCATCTCGATTTTCATTCCAAAAAGTTGAAACATTAGTCAT |
| | | CACAAATTGCCCCAGAGTTAAGAAACTGCCGTTTCAGGAGAG |
| | | GAGGACCCAGATGAACTTGCCAACAGTTTATTGTGAGGAGAA |
| | | ATGGTGGAAAGCACTGGAAAAAGATCAACCAAACGAAGAGC |
| | | TTTGTTATTTACCGCGCTTTGTTCCAAATTGA |
| Mr5 | 128 | ATGGGGGGAGAGGCTTTTCTTGTGGCATTCCTCCAAGTGCTGG |
| | | TTGACAAGTTGGCGCATCGCGAGGTCTTCAAGTACTTTGGACT |
| | | TGTAAAGGGCGTAGATCAAAAACTGAAGAAATGGAGTGCCA |
| | | CCTTGTCTGCGATTGGAGCGGTGCTGAATGACGCAGAGGAGA |
| | | GGCAACTGACGGCTAAGAACAACACACTGAAGCTCTGGCTCG |
| | | AAGATCTCAGGGACTTGGCTTTTGATGTGGAAGACGTGTTGG |
| | | ACAAATATGCTACTAAAATGTTGAAACGTCAGATACAACATG |
| | | CTCATTCCCGCACAACAAGCAAACTATGGAACTCAATTCCTG |
| | | ATGGTGTTTTCAACTTCAACATGAACTCGGAAATACAGAAGA |
| | | TTAGTGAGCGATTACAAGAGATATCTGAACAAAAAGACCAGC |
| | | TTAATTTGAAAATTGATACTGGGGCGTTGACTACAAGGGCAC |
| | | GCCGAAACATATCACCTAGTTCCAGTCAACCAGATGGACCTG |
| | | TGATTGGAAGGGATGAGGACAAAAGAAAGATTGTTGAGCTGC |
| | | TGTCGAAACAAGAGCATCGTACTGTCAATTTCGATGTAGTTGC |
| | | AATTGTTGGTATGGCTGGAGTCGGAAAGACAACACTTGCTGG |
| | | ACAAGTACTCAATGATATGGTTGCAACCCAAACGTTTCAACC |
| | | AGCTGTTTGGGCATGCGTATCTGACGACTTCAACCTTGAAAG |
| | | AGTGACAAAGCAAATTCTTGAATCAATCACATCTCGGCAATG |
| | | CACCACAGAAGATTACAATAAGGTTCAAGATTATCTGCATAA |
| | | GGAGTTAGCGGGGAAGAAGTTTTTAATTGTTTTAGATGATGT |
| | | GTGGAAAACGTGTAGCTACGGTGAATGGATGAAGTTGCAGTC |
| | | CCCTTTTCGTGACGGAGCACAAGGAAGCAAGATAATTGTGAC |
| | | AACACGTGATACAGATGTTTCAAAAATGATGGGAGCTGCCAC |
| | | GCTCGTTCACAATTTGGAGCCTATGGAAAGTAGTGTTTGTTTG |
| | | CAAGTATTTGAGCAGCATGCATTCTTAAATTCTAATGACGACA |
| | | AACCACCAAATTACGAGTTACTTAAGGAAAAAATTGCTGCCA |
| | | AGTGTAGGGGATTGCCTTTGGCCGCAAGGACCCTTGGTGGTG |
| | | TTCTACTTCGTAAAGATACATACGAATGGGAAGACATATTGA |
| | | ACAACAAACTGTGGAGTCTATCAAATGAGCACGACATACTTC |
| | | CAGTACTGAGATTAACCTACTTTTTATCTTCCTTCACATTTGAA |
| | | AAGATGCTTTGCCTATTGCTCAATACTTCCAAATGACTATGAA |
| | | TTTGAAGAGAAGCAAATGATCCTTCTATGGATGGCCGAGGGG |
| | | TTTATTCTTCCACGACCAGAAGATAAGAAGCAAATTGAAGAT |
| | | TTAGGTGCTGATTATTTTCGGGATCTCGTATCAAGGTCATTGT |
| | | TTCAAAAATCAACCAAATGTATTTCAAAATATGTGATGCATG |
| | | ACCTTATTGGTGATTTAGCACGGTGGGCAGCAGGAGAAATTT |
| | | GTTTTAGATTGGAGGATAAGCAAATGATGATGGTGAACAAC |
| | | TTAGATGTTTTCCCAAGGCACGCCATTCGTCTTACATCAGGGG |
| | | TCTGTCTGATGGGTCAAAAGATTTGAGGTATTTTCTGAACTG |
| | | AAATATTTGCGAACCTTCTTGCCACTAAGAAAGGATTCTTTCT |
| | | GGAATTATTTAAGTCGTCAGGTTGCTTTTGATTTATTGCCGAA |
| | | ATTGCAATATTTGCGGGTGCTCTCTTTCAATTGCTATAAAATA |
| | | ACTGAGCTTCCAGACTCAATCGGTGATTTAAGGTATCTACGGT |
| | | ATCTCGACCTTTCCTACACAGATATAACAAGTTTACCTAAATC |
| | | AACAAGCACTCTTTACAACTTGCAGACGTTGATATTGGAAGG |
| | | CTGTTCTAAATTGAAGGCATTGCCTATAGACATGAGTAATCTA |
| | | GTTAATTTGCGTCATCTCAACAACTCAAATGTATCTTTGTTGG |
| | | AAGACATGCCTCCACAACTAGGTCGATTGGTGAATCTCCAGT |
| | | CATTGACTAAGTTTGTGGTGAGTGGTGGTGGTGGTGATC |
| | | GATCAGGGATACGAGAGCTGGAGTTCCTAATGCATCTCCGAG |
| | | GAACATTGTGCATCTCAAGATTGGAGAATGTGACTGATGTCG |
| | | AGGATGCTCAGAGGGCCAACTTAAACTGCAAAGAGAGGCTTG |

TABLE 13-continued

Additional Sequences.

| Description | SEQ ID NO: | Sequence |
|---|---|---|
| | | ATTCGTTGGTGCTAGAATGGTCTCATTCAAGCGACACAAGAG<br>AAACAGAATCCGCTGTGCTTGACATGTTACAGCCTCATACAA<br>AGCTTAAGGAGCTCACCATCAAGAGTTATGCAGGAAAAGAAT<br>TTTCATCATGGGTTGGAGTTCCATTGTTCTCTAATATGGTGCT<br>CGTGCGCTTAGAGGAATGTAACAATTGTCTATCTCTACCACCT<br>CTCGGAAAATTGCCTCATCTCAAAGAACTTTATATTAGAGGA<br>ATGAATGCAGTGGAAAGTGTTGGAGCTGAGTTTTATGGAGAG<br>TGCTCCTTGCCTTTTCCGCTATTAGAGACTCTTGAGTTTGTGG<br>ATATGCAACATTGGAAAGTATGGCTTCCATTTCAAACGGATC<br>ACAGAGGTAGTGTTTTCCCTTGCCTGAAAACACTCTTAGTCAG<br>AAAATGTTCTAAACTGGAGGGTAAGCTGCCAGAGAACCTTGA<br>TTCGCTGGCATCGCTTGAAATTGTTAAATGTGAAGAATTATTG<br>GTTTCAATTGCCAATTACAAACAACTTCGTCAGTTAAACATTG<br>ACGGTTGTAAAGGGGTGGTGCATACAGCTGCTAAGGTTGAGT<br>TTGAGTTATTAGAGTCCTTGTACCTTTCAAATATTTCGGAGCT<br>GACGTCTCTACAAACAGGAGAATTGTGCAGAAATGGATTAAA<br>CATGGTCAGAGATTTGAAGATTAATGGATGTGAGGAGCTGAC<br>GTCTTCATTGAAGAATGAGGCAATATTATTGCAACAGTTGATT<br>TCTCTTGGCCGTTTAGAGATTGAAGACAACTCTCTCCTAGTTG<br>AAGAACTAGGAAAAGAAGCAGATGAGTTGTTGCAATTGCAA<br>ATATTGGGTGTAAGCTTGAATTTCTGAAGTTAAAGAAGTGC<br>AAAAATCTTTTGAAGCTACCAGAAGGGTTAAATCAGTTGTCG<br>TCACTTCAAGAGCTTCGCATACATGAATGTTCAAGTCTAGTTT<br>CTTTTCCAGATGTTGGTTTGCCCACCTTCTCTTAAAGACATCGA<br>GATTACAGAGTGCCACTCGTTGATATATTTTGCAAAATCCCAG<br>ATTCCCCAAAATCTCAGAAGAATACAGATAAGAGATTGCAGA<br>AGTTTGAGATCACTAGTAGACAATGAGGCTGTTGGTTCTTGTT<br>CTTCGTCTTCTCACAATTGTCTTGAGTACTTGAATATCGAGAG<br>ATGTCAATCTCTAACGTTGTTATCATTGAGTGACCAGCTTGTC<br>AGGGCACTTAGAGAACTTGACATATATGATTGTGAACAACTG<br>GAGTTTCTCGCACCGGACGGGTTGTTCTGCAACAACACTAATT<br>ACTTTCTCGAAAATTTTAGGATACGGAGGTGCCAAAATCTGA<br>AATCCTTACCGAGACTGAGTGGGGGGATAAGGGGCTCTAACC<br>TGAGAGAGATCCGGATCACCGATTGCGACAGATTGGAGGCCT<br>TGCCCGAAGACATGCACAATTTCAACTCTCTTGAGAAATTGAT<br>TATCGACTACCGTGAAGGTTTGACTTGCTCCTTTCCCGCCAAC<br>CTAACATCACTTATGATTTGGAAGGTCAAGAGCTGTAAGTCA<br>TTGTGGGAGTTGGAGTGGGGGTTACACAGACTCACCTCTCTTA<br>GATACTTGTGGATCGGTGGTGAAGACCCGGATATGGTATCGT<br>TTCCACCGGACATGGTCCGAATGGAGACGTTGCTCCCCAAAT<br>CTCTCACTGAACTCTCAATTGGTGGCTTCCCGAATCTGAAGAA<br>ACTGAGCAGCAAGGGCTTTCAATTCCTAACCTCCCTTGAATCT<br>TTGGAACTCTGGGATTGTCCAAAGCTAGCATCCATTCCAAAG<br>GAGGGACTGCCTCTTTCACTTACGGAACTTTGCATCTATGGGT<br>GTCCTGTTCTAAAAGAGAGATGTCAACCAGGAAAAGGACGCT<br>ACTGGCACAAAATATCCCACATCCCTTACATAGATATAGATT<br>GGAAGATGATTTGA |
| RPS2 | 129 | MDFISSLIVGCAQVLCESMNMAERRGHKTDLRQAITDLETAIGD<br>LKAIRDDLTLRIQQDGLEGRSCSNRAREWLSAVQVTETKTALLL<br>VRFRRREQRTRMRRRYLSCFGCADYKLCKKVSAILKSIGELRER<br>SEAIKTDGGSIQVTCREIPIKSVVGNTTMMEQVLEFLSEEEERGII<br>GVYGPGGVGKTTLMQSINNELITKGHQYDVLIWVQMSREFGEC<br>TIQQAVGARLGLSWDEKETGENRALKIYRALRQKRFLLLLDDV<br>WEEIDLEKTGVPRPDRENKCKVMFTTRSIALCNNMGAEYKLRV<br>EFLEKKHAWELFCSKVWRKDLLESSSIRRLAEIIVSKCGGLPLALI<br>TLGGAMAHRETEEEWIHASEVLTRFPAEMKGMNYVFALLKFSY<br>DNLESDLLRSCFLYCALFPEEHSIEIEQLVEYWVGEGFLTSSHGV<br>NTIYKGYFLIGDLKAACLLETGDEKTQVKMHNVVRSFALWMAS<br>EQGTYKELILVEPSMGHTEAPKAENWRQALVISLLDNRIQTLPEK<br>LICPKLTTLMLQQNSSLKKIPTGFFMHMPVLRVLDLSFTSITEIPLS<br>IKYLVELYHLSMSGTKISVLPQELGNLRKLKHLDLQRTQFLQTIP<br>RDAICWLSKLEVLNLYYSYAGWELQSFGEDEAEELGFADLEYLE<br>NLTTLGITVLSLETLKTLFEFGALHKHIQHLHVEECNELLYFNLPS<br>LTNHGRNLRRLSIKSCHDLEYLVTPADFENDWLPSLEVLTLHSLH<br>NLTRVWGNSVSQDCLRNIRCINISHCNKLKNVSWVQKLPKLEVI<br>ELFDCREIEELISEHESPSVEDPTLFPSLKTLRTRDLPELNSILPSRF<br>SFQKVETLVITNCPRVKKLPFQERRTQMNLPTVYCEEKWWKAL<br>EKDQPNEELCYLPRFVPN |
| Mr5 | 130 | MGGEAFLVAFLQVLVDKLAHREVFKYFGLVKGVDQKLKKWSA<br>TLSAIGAVLNDAEERQLTAKNNTLKLWLEDLRDLAFDVEDVLD<br>KYATKMLKRQIQHAHSRTTSKLWNSIPDGVFNFNMNSEIQKISE<br>RLQEISEQKDQLNLKIDTGALTTRARRNISPSSSQPDGPVIGRDED<br>KRKIVELLSKQEHRTVNFDVVAIVGMAGVGKTTLAGQVLNDMV |

TABLE 13-continued

Additional Sequences.

| Description | SEQ ID NO: | Sequence |
|---|---|---|
| | | ATQTFQPAVWACVSDDFNLERVTKQILESITSRQCTTEDYNKVQ<br>DYLHKELAGKKFLIVLDDVWKTCSYGEWMKLQSPFRDGAQGS<br>KIIVTTRDTDVSKMMGAATLVHNLEPMESSVCLQVFEQHAFLNS<br>NDDKPPNYELLKEKIAAKCRGLPLAARTLGGVLLRKDTYEWEDI<br>LNNKLWSLSNEHDILPVLRLTYFYLPSHLKRCFAYCSILPNDYEF<br>EEKQMILLWMAEGFILPRPEDKKQIEDLGADYFRDLVSRSLFQKS<br>TKCISKYVMHDLIGDLARWAAGEICFRLEDKQNDDGEQLRCFPK<br>ARHSSYIRGLSDGVKRFEVFSELKYLRTFLPLRKDSFWNYLSRQV<br>AFDLLPKLQYLRVLSFNCYKITELPDSIGDLRYLRYLDLSYTDITS<br>LPKSTSTLYNLQTLILEGCSKLKALPIDMSNLVNLRHLNNSNVSL<br>LEDMPPQLGRLVNLQSLTKFVVSGGGGGDRSGIRELEFLMHLRG<br>TLCISRLENVTDVEDAQRANLNCKERLDSLVLEWSHSSDTRETE<br>SAVLDMLQPHTKLKELTIKSYAGKEFSSWVGVPLFSNMVLVRLE<br>ECNNCLSLPPLGKLPHLKELYIRGMNAVESVGAEFYGECSLPFPL<br>LETLEFVDMQHWKVWLPFQTDHRGSVFPCLKTLLVRKCSKLEG<br>KLPENLDSLASLEIVKCEELLVSIANYKQLRQLNIDGCKGVVHTA<br>AKVEFELLESLYLSNISELTSLQTGELCRNGLNMVRDLKINGCEE<br>LTSSLKNEAILLQQLISLGRLEIEDNSLLVEELGKEADELLQLQIL<br>GCKLEFLKLKKCKNLLKLPEGLNQLSSLQELRIHECSSLVSFPDV<br>GLPPSLKDIEITECHSLIYFAKSQIPQNLRRIQIRDCRSLRSLVDNE<br>AVGSCSSSSHNCLEYLNIERCQSLTLLSLSDQLVRALRELDIYDCE<br>QLEFLAPDGLFCNNTNYFLENFRIRRCQNLKSLPRLSGGIRGSNL<br>REIRITDCDRLEALPEDMIHNFNSLEKLIIDYREGLTCSFPANLTSL<br>MIWKVKSCKSLWELEWGLHRLTSLRYLWIGGEDPDMVSFPPDM<br>VRMETLLPKSLTELSIGGFPNLKKLSSKGFQFLTSLESLELWDCP<br>KLASIPKEGLPLSLTELCIYGCPVLKERCQPGKGRYWHKISHIPYI<br>DIDWKMI |
| StPtr1 (GenBank Accession No. XP_006340095.1) | 131 | MAESFLFNIIERVLAKVSSIAVYEITLAWNVKIELRKLQSILSTIK<br>AVLLDANEQQAKNHEVRDWLEKLRDVVYDVDDLMDDLSTQLL<br>LQMHFQKSFRKKVRKFFSSSNPIIYRFKIGRKVKEIRELLNEIADD<br>RRNFHFTEHTYVIPAENTSREQTHSFVRASDIIGRDDDQENIVKQ<br>LIDSHDEENISVIPIVGLGGLGKTTLVKLVYNNNRVVQNFDLRM<br>WVSISEDFSLSKVIEKILRSATGESFDHLDMDQLQGCLGEVLQQK<br>RYLLVLDDVWNEDQHKWTDLRELLMNCSRGSKIVVTTRSKMA<br>ALITGTVPPYYLEGLADDDCLSLFLKCAFGGQDNLFPNLVEIGKE<br>IVKKCGGVPLAVKTLGRLLYMKTDENEWLQIRDNEIWEIEQNKS<br>DILPILRLSYEQMPSHLRQCFAYCSMLSKGQBPREDFINRWIAQG<br>FIQSSNRNRKLEDIGNQYFDELLSRFCFLDVVQAFDGEILACKIHN<br>LVHDLAQSVAGAECLNVKPNAFVVSERVRHLFFHAEDMSRKHF<br>PRFLLPLQKLRSFSYSFNIGPVNKFFVKTMLSNFKCLRMLVLNNL<br>DLEELPTSIGHLKELRYLNLSNSGNIKFLPRSMSKLVNLHTLNLIN<br>CRQLKELPRDERKLISLKTLYLTTHQISEGIKNQHSFTSLQFLLLF<br>KCCFPKLQPELVQHFTALRVLRIYECPSLCSLPSSIRYLTSLEKLW<br>IWNCEELDLIDGEGMSGLTSLQSLLIMGLPKLVTLPLELKDTAPT<br>TLKYFRIADCPNLMELPEWLPNCSSLQRLYIEDCPVLASIPQGIYS<br>HNANLHIIDCPLLGG |
| StPtr1 (coding sequence from GenBank Accession No. XM_006340033.2) | 132 | ATGGCGGAATCTTTCTTGTTCAATATCATTGAACGAGTTTTGG<br>CTAAAGTTTCTTCAATTGCTGTATATGAGATCACTCTAGCTTG<br>GAATGTTAAGATAGAGCTAAGGAAACTCCAAAGTACTCTATC<br>CACCATCAAAGCTGTACTTCTAGATGCAAACGAGCAACAGGC<br>AAAGAACCATGAAGTGAGAGATTGGCTGGAAAAGCTCAGAG<br>ATGTTGTTTATGATGTCGATGATTTGATGGATGATTTATCAAC<br>ACAACTGTTGCTGCAAATGCATTTCCAGAAAAGCTTTAGGAA<br>GAAGGTAAGAAAATTCTTTTCAAGTTCAAATCCAATTATATAT<br>CGATTCAAGATTGGCAGAAAGGTAAAAGAAATCAGGGAGCT<br>ACTGAATGAGATTGCAGATGATAGGAGAAATTTCCACTTCAC<br>GGAACATACGTATGTAATTCCAGCTGAGAATACGAGTAGAGA<br>ACAAACACACTCCTTTGTGAGGGCATCAGATATCATTGGTAG<br>AGATGATGATCAAGAAAACATTGTAAAACAGCTGATAGATTC<br>TCATGATGAGGAAATATTTCTGTGATTCCTATTGTTGGACTT<br>GGAGGGCTTGGAAAAACCACACTTGTTAAGTTGGTTTATAAC<br>AATAATAGGGTTGTTCAGAATTTTGACCTTAGAATGTGGGTTA<br>GTATTTCAGAAGATTTTAGTCTGAGCAAGGTAATTGAGAAAA<br>TTCTGAGGTCTGCAACGGGAGAGAGTTTTGACCACCTAGATA<br>TGGACCAATTACAAGGTTGTTTGGGAGAGGTTTTGCAACAGA<br>AAAGGTATTTACTTGTGCTGGATGATGTGTGGAATGAAGATC<br>AACACAAGTGGACAGATCTGAGGGAGTTGCTGATGAATTGTT<br>CCAGAGGTAGTAAAATTGTTGTCACTACACGTAGTAAGATGG<br>CTGCTTTGATTACTGGAACAGTTCCGCCTTATTATTTGGAAGG<br>CCCTTGCTGATGATGACTGCTTATCTTTATTTTTGAAATGTGCAT<br>TTGGAGGGCAGGACAATTTGTTTCCTAATCTAGTAGAAATAG<br>GAAAAGAAATTGTGAAAAGTGTGGAGGAGTGCCTTTGGCTG<br>TGAAAACCTTGGGAAGGTTATTGTACATGAAAACAGACGAGA |

TABLE 13-continued

Additional Sequences.

| Description | SEQ ID NO: | Sequence |
|---|---|---|
| | | ATGAATGGTTGCAAATAAGAGATAATGAGATATGGGAAATCG<br>AACAGAATAAATCTGACATTTTACCAATATTGAGATTGAGCT<br>ATGAACAGATGCCATCACATCTAAGACAGTGCTTTGCCTATTG<br>CTCCATGTTATCCAAAGGTCAAGAAATTCCGAGGGAGGATTT<br>TATCAATCGGTGGATTGCTCAAGGATTTATACAGAGTTCAAA<br>CAGAAACAGGAAGCTGGAAGATATAGGTAATCAGTACTTTGA<br>TGAGTTGCTATCAAGGTTTTGCTTCCTAGATGTGGTACAAGCT<br>TTTGATGGAGAAATATTGGCTTGTAAGATACACAATCTTGTGC<br>ATGATCTTGCACAGTCAGTAGCAGGTGCAGAATGCTTAAATG<br>TGAAACCCAATGCTTTCGTGGTTTCTGAAAGAGTTCGCCACTT<br>ATTCTTCCATGCAGAAGATATGTCTAGGAAACACTTCCCCAG<br>ATTTTTGCTTCCTTTGCAAAAGTTGAGGTCTTTCTCTTATTCTT<br>TTAACATTGGACCTGTAAACAAGTTCTTTGTCAAGACAATGTT<br>GTCAAATTTCAAATGCCTTCGGATGTTAGTCTTGAACAATCTA<br>GATCTTGAGGAGTTGCCAACTTCGATAGGTCACTTGAAGGAA<br>TTAAGATACCTTAACCTTAGCAACAGTGGTAATATCAAGTTTC<br>TTCCAAGGTCTATGAGCAAATTAGTAAATCTGCACACCCTAA<br>ACCTCATTAACTGTGAACAGCTTAAGGAGTTGCCAAGAGACT<br>TTAGAAAGTTAATCAGCCTAAAGACCTTGTATTTGACTACACA<br>TCAGATATCAGAAGGGATCAAGAATCAACATTCTTTCACTTCT<br>CTTCAATTTTTGCTTCTTTTCAAATGTTGTTTCCCAAAATTGCA<br>GCCAGAACTGGTGCAGCATTTTACTGCACTTCGGGTTTTGCGT<br>ATCTATGAATGCCCAAGTTTATGTTCTCTTCCAAGCAGTATTA<br>GATATCTGACTTCACTTGAAAAGCTATGGATCTGGAACTGTG<br>AAGAACTTGATTTGATAGATGGAGAAGGAATGTCAGGCCTAA<br>CAAGTCTTCAATCCTTGCTTCTAATGGGCTTCCTAAGTTGGT<br>GACTCTACCATTGGAACTTAAAGATACTGCTCCTACAACATTA<br>AAGTACTTCAGAATCGCCGATTGTCCCAACCTGATGGAGCTTC<br>CAGAGTGGCTGCCCAATTGCTCCTCACTTCAGAGACTGTATAT<br>AGAGGACTGTCCTGTTTTGGCATCGATACCTCAAGGAATCTAC<br>AGCCACAATGCCAATCTCCATATAATCGACTGTCCATTGCTAG<br>GTGGATGA |

Although certain embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A nucleic acid construct comprising:
   a nucleic acid molecule comprising a *Pseudomonas tomato* race 1 (Ptr1) polynucleotide encoding an amino acid sequence having at least 94% sequence identity to SEQ ID NO: 19, wherein the amino acid sequence confers disease resistance against *Pseudomonas syringae* tomato race 1 in a plant from the Solanaceae family;

a 5' DNA promoter sequence heterologous to the nucleic acid molecule; and a 3' terminator sequence, wherein the nucleic acid molecule, the DNA promoter sequence, and the terminator sequence are operatively coupled to permit transcription of the nucleic acid molecule.

2. The nucleic acid construct according to claim 1, wherein the nucleic acid molecule comprises the nucleotide sequence of SEQ ID NO: 18.

3. The nucleic acid construct according to claim 1, wherein the nucleic acid molecule encodes the amino acid sequence of SEQ ID NO:19.

4. The nucleic acid construct according to claim 1, wherein the nucleic acid molecule further comprises a *Pseudomonas tomato* (Pto) polynucleotide encoding the amino acid sequence of SEQ ID NO:17.

5. The nucleic acid construct according to claim 1, wherein the DNA promoter sequence is a constitutive, inducible, tissue-specific, or organ-specific plant promoter.

6. An expression vector comprising the nucleic acid construct according to claim 1.

7. A host cell transformed with the nucleic acid construct according to claim 1.

8. The host cell according to claim 7, wherein the host cell is a bacterial cell or a plant cell.

9. A plant transformed with the nucleic acid construct according to claim 1.

10. The plant transformed with the nucleic acid construct according to claim 9, wherein the plant is rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, Petunia, Pelargonium, Poinsettia, Chrysanthemum*, carnation, *Crocus*, marigold, daffodil, pine, *Medicago truncatula, Sandersonia aurantiaca, Zinnia*, or a dicot.

11. The plant according to claim 9, wherein the plant is *Solanum lycopersicum.*

12. A cell of the plant according to claim 9 comprising the nucleic acid construct.

13. A fruit comprising the nucleic acid construct, wherein the fruit is produced from the plant according to claim 9.

14. A plant seed comprising the nucleic acid construct, wherein the plant seed is produced from the plant according to claim 9.

15. A plant seed transformed with the nucleic acid construct according to claim 1.

16. A method of expressing a nucleic acid molecule in a plant, said method comprising:

transforming a plant, a plant seed, or a plant cell with a nucleic acid construct to produce a transgenic plant, a transgenic plant seed, or a transgenic plant cell comprising:

a nucleic acid molecule comprising a *Pseudomonas tomato* race 1 (Ptr1) polynucleotide encoding an amino acid sequence having at least 94% sequence identity to SEQ ID NO: 19, wherein the amino acid sequence confers disease resistance against *Pseudomonas syringae* tomato race 1 in a plant from the Solanaceae family;

a 5' DNA promoter sequence heterologous to the nucleic acid molecule; and a 3' terminator sequence, wherein the nucleic acid molecule, the DNA promoter sequence, and the terminator sequence are operatively coupled to permit transcription of the nucleic acid molecule, and wherein the plant, plant seed, or plant cell comprises the nucleic acid construct, and growing the transgenic plant or a plant grown from the transgenic plant seed or the transgenic plant cell under conditions effective to express the nucleic acid molecule in said transgenic plant or said plant grown from the transgenic plant seed or the transgenic plant cell.

17. A method of expressing a nucleic acid molecule comprising:
transforming or editing a plant or a plant cell from the Solanaceae family to comprise a nucleic acid molecule encoding an amino acid sequence having at least 94% sequence identity to SEQ ID NO: 19, wherein the amino acid sequence is expressed, and wherein the amino acid sequence confers disease resistance against *Pseudomonas syringae* tomato race 1.

18. A plant cell comprising:

a nucleic acid molecule comprising a *Pseudomonas tomato* race 1 (Ptr1) polynucleotide encoding an amino acid sequence having at least 94% sequence identity to SEQ ID NO: 19, wherein the nucleic acid molecule is heterologous to the plant cell, wherein the amino acid sequence is expressed, and wherein the amino acid sequence confers disease resistance against *Pseudomonas syringae* tomato race 1 in a plant from the Solanaceae family.

19. The plant cell according to claim 18, wherein the Ptr1 polynucleotide encodes the amino acid sequence of SEQ ID NO: 19.

20. The method according to claim 16, wherein the nucleic acid molecule encodes the amino acid sequence of SEQ ID NO: 19.

21. The method according to claim 16, wherein the nucleic acid molecule comprises the nucleotide sequence of SEQ ID NO:18.

22. The method according to claim 16, wherein the nucleic acid molecule further comprises a polynucleotide encoding the amino acid sequence of SEQ ID NO:17.

23. The method according to claim 16, wherein said transforming comprises *Agrobacterium*-mediated transformation, whisker method transformation, vacuum infiltration, biolistic transformation, electroporation, micro-injection, polyethylene-mediated transformation, or laser-beam transformation.

24. The method according to claim 17, wherein said transforming or editing a plant or a plant cell comprises transforming the plant or plant cell.

25. The method according to claim 24, wherein the transformed plant cell is a transformed seed cell and said method further comprises:

planting a transformed plant seed comprising the transformed seed cell under conditions effective for a plant to grow from the transformed plant seed.

26. The method according to claim 17, wherein the nucleic acid molecule encodes the amino acid sequence of SEQ ID NO:19.

27. The method according to claim 17, wherein the nucleic acid molecule comprises the nucleotide sequence of SEQ ID NO:18.

28. A plant produced by the method of claim 17.

29. The plant cell according to claim 18, wherein the Ptr1 polynucleotide comprises the nucleotide sequence of SEQ ID NO:18.

30. The plant cell according to claim 18, wherein the nucleic acid molecule further comprises a polynucleotide encoding the amino acid sequence of SEQ ID NO:17.

31. A plant comprising the plant cell of claim 18.

32. The plant according to claim 31, wherein the plant is tomato, potato, pepper, tobacco, eggplant, tomatillo, or *Petunia*.

33. The plant according to claim 31, wherein the plant is *S. lycopersicum, S. pennellii, S. tuberosum, Capsicum annuum, Capsicum baccatum, Capsicum chinense, Nicotiana attenuata, Nicotiana benthamiana, Nicotiana tabacum*, or *Nicotiana tomentosiformis*.

34. The plant according to claim 31, wherein the plant is *S. lycopersicum*.

35. The method according to claim 17, wherein said editing a plant or plant cell comprises performing site directed mutagenesis of the plant or plant cell.

36. The method according to claim 17, wherein said editing a plant or plant cell comprises performing genome editing of the plant or plant cell.

37. The method according to claim 17, wherein the nucleic acid molecule encodes an amino acid sequence having at least 95% sequence identity to SEQ ID NO: 19.

38. The plant cell according to claim 17, wherein the polynucleotide-encodes an amino acid sequence having at least 96% sequence identity to SEQ ID NO: 19.

39. The method according to claim 18, wherein the polynucleotide encodes an amino acid sequence having at least 95% sequence identity to SEQ ID NO: 19.

40. The plant cell according to claim 18, wherein the polynucleotide encodes an amino acid sequence having at least 96% sequence identity to SEQ ID NO: 19.

* * * * *